United States Patent
Buhr et al.

(10) Patent No.: US 9,102,688 B2
(45) Date of Patent: Aug. 11, 2015

(54) SULFONAMINOQUINOLINE HEPCIDIN ANTAGONISTS

(71) Applicant: Vifor (International) AG, St. Gallen (CH)

(72) Inventors: Wilm Buhr, Constance (DE); Susanna Burckhardt, Zürich (CH); Franz Dürrenberger, Dornach (CH); Felix Funk, Winterthur (CH); Peter O. Geisser, St. Gallen (CH); Vincent A. Corden, Stanford in the Vale (GB); Stephen M. Courtney, Stanford in the Vale (GB); Graham Dawson, Abingdon (GB); Tara Davenport, Abingdon (GB); Mark Slack, Hamburg (DE); Mark P. Ridgill, Horsham (GB); Christopher J. Yarnold, Didcot (GB); Susan Boyce, Pinneberg (DE); Albertus A. Ellenbroek, Weillington (NZ)

(73) Assignee: Vifor (International) AG, St. Gallen (CH)

( * ) Notice: Subject to any disclaimer, the term of this patent is extended or adjusted under 35 U.S.C. 154(b) by 0 days.

(21) Appl. No.: 14/310,254

(22) Filed: Jun. 20, 2014

(65) Prior Publication Data

US 2014/0364424 A1  Dec. 11, 2014

Related U.S. Application Data

(62) Division of application No. 13/364,566, filed on Feb. 2, 2012, now abandoned.

(60) Provisional application No. 61/473,223, filed on Apr. 8, 2011.

(30) Foreign Application Priority Data

Feb. 18, 2011 (EP) .................................... 11155103

(51) Int. Cl.
| | |
|---|---|
| A61K 31/542 | (2006.01) |
| A61K 45/06 | (2006.01) |
| C07D 513/04 | (2006.01) |
| C07D 215/40 | (2006.01) |
| C07D 215/42 | (2006.01) |
| C07D 215/46 | (2006.01) |
| C07D 401/12 | (2006.01) |
| C07D 409/12 | (2006.01) |
| C07D 417/12 | (2006.01) |
| C07D 333/34 | (2006.01) |
| C07D 215/50 | (2006.01) |

(52) U.S. Cl.
CPC .............. *C07D 513/04* (2013.01); *A61K 45/06* (2013.01); *C07D 215/40* (2013.01); *C07D 215/42* (2013.01); *C07D 215/46* (2013.01); *C07D 215/50* (2013.01); *C07D 333/34* (2013.01); *C07D 401/12* (2013.01); *C07D 409/12* (2013.01); *C07D 417/12* (2013.01)

(58) Field of Classification Search
CPC .. C07D 513/04; C07D 409/12; C07D 215/40; A61K 45/06
USPC ........................................... 514/222.8, 224.5
See application file for complete search history.

(56) References Cited

PUBLICATIONS

Xie et al. Bioorganic & Medicinal Chemistry Letters (2008), 18(1), 329-335.*
International Preliminary Report on Patentability for corresponding PCT/EP2012/052694 mailed Aug. 29, 2013, 12 pages.

* cited by examiner

*Primary Examiner* — Kahsay Habte
(74) *Attorney, Agent, or Firm* — Rankin, Hill & Clark LLP

(57) ABSTRACT

The present invention relates to novel hepcidin antagonists, pharmaceutical compositions comprising them and the use thereof as medicaments for the use in the treatment of iron metabolism disorders, such as, in particular, iron deficiency diseases and anemias, in particular anemias in connection with chronic inflammatory diseases.

16 Claims, 125 Drawing Sheets

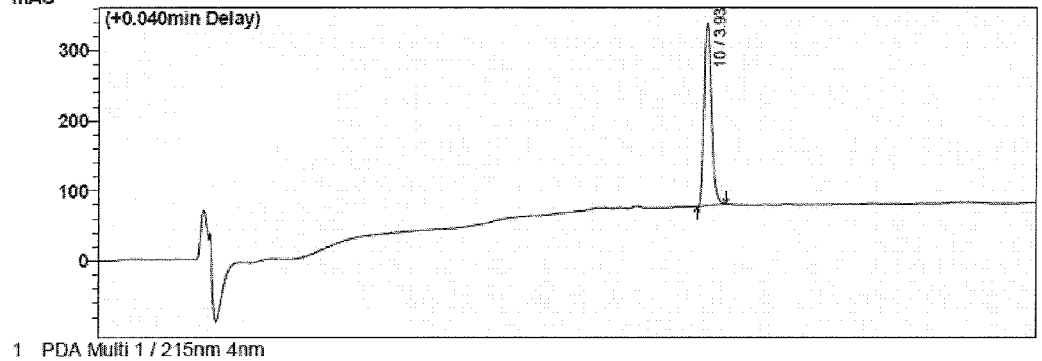
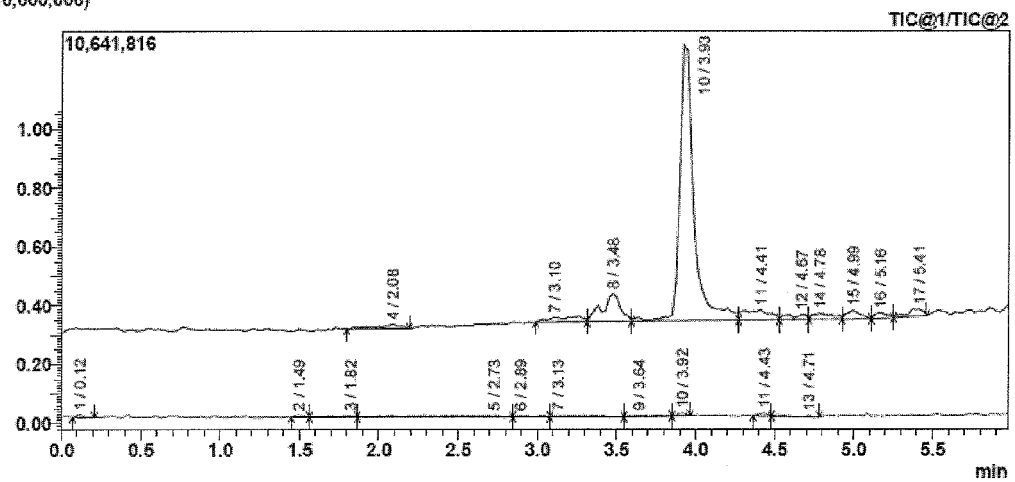
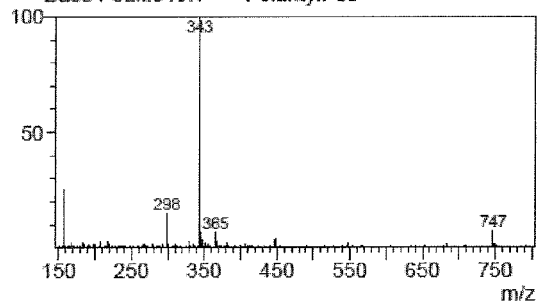
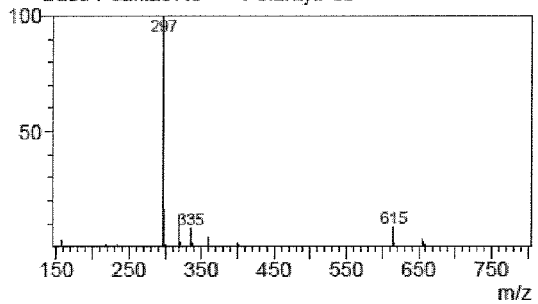
Fig. 3

Fig. 5.5

SULFONAMINOQUINOLINE HEPCIDIN ANTAGONISTS

INTRODUCTION

The invention relates to novel hepcidin antagonists of the general formula (I), pharmaceutical compositions comprising these and their use for treatment of iron metabolism disorders, in particular of anaemias in connection with chronic inflammatory diseases (anaemia of chronic disease (ACD) and anaemia of inflammation (AI)) or of iron deficiency symptoms and iron deficiency anaemias.

BACKGROUND

Iron is an essential trace element for almost all organisms and in this context is relevant in particular for growth and blood formation. The balance of iron metabolism in this context is primarily regulated at the level of recovery of iron from haemoglobin from ageing erythrocytes and duodenal absorption of iron bonded in food. The iron released is absorbed via the intestine, in particular by way of specific transport systems (DMT-1, ferroportin, transferrin, transferrin receptors), transported into the blood stream and passed on by this means into the corresponding tissue and organs.

The element iron is of great importance in the human body inter alia for oxygen transport, oxygen uptake, cell functions, such as mitochondrial electron transport, and finally for energy metabolism in total.

The body of a human contains on average 4 to 5 g of iron, this being present in enzymes, in haemoglobin and myoglobin and as depot or reserve iron in the form of ferritin and haemosiderin.

About half of this iron, approx. 2 g, is present as haem iron bonded in the haemoglobin of red blood corpuscles. Since these erythrocytes have only a limited life (75-150 days), new ones must constantly be formed and old ones eliminated (over 2 million new erythrocytes are formed per second). This high regeneration capacity is achieved by macrophages, in that these absorb the ageing erythrocytes by phagocytosis, lyse them and in this way can recycle the iron contained in them for the iron metabolism. The amount of iron required daily for erythropoiesis of approx. 25 mg is thus mostly provided.

The daily iron requirement of an adult human is between 0.5 and 1.5 mg per day, and for infants and women in pregnancy the iron requirement is 2 to 5 mg per day. Daily iron losses, e.g. by exfoliation of skin cells and epithelial cells, is comparatively low, but increased iron losses occur, for example, in women during menstrual bleeding. Blood losses generally can considerably reduce iron metabolism, since about 1 mg of iron is lost per 2 ml of blood. The normal daily iron loss of approx. 1 mg is conventionally replaced again by an adult, healthy human via the daily food intake. Iron metabolism is regulated via absorption, the absorption rate of the iron present in food being between 6 and 12%, and in the event of iron deficiency the absorption rate is up to 25%. The absorption rate is regulated by the organism as a function of iron requirement and the size of the iron store. In this context, the human organism uses both divalent and trivalent iron ions. Iron(III) compounds are conventionally dissolved in the stomach at a sufficiently acid pH and are thus made available for absorption. Absorption of the iron takes place in the upper small intestine by mucosa cells. In this context, for absorption trivalent non-haem iron is first reduced to $Fe^{2+}$ e.g. by ferrireductase (duodenal cytochrome b at the membrane) in the membrane of intestinal cells, so that it can then be transported by the transport protein DMT1 (divalent metal transporter 1) into the intestinal cells. On the other hand, haem iron enters into the enterocytes unchanged via the cell membrane. In the enterocytes, iron is either stored as depot iron in ferritin or released into the blood by the transport protein ferroportin, bonded to transferrin. Hepcidin plays a central role in this operation, since it is the essential regulation factor of iron uptake. The divalent iron transported into the blood by the ferroportin is converted into trivalent iron by oxidases (ceruloplasmin, hephaestin), which is then transported to the relevant places in the organism by means of transferrin (see for example: "Balancing acts: molecular control of mammalian iron metabolism". M. W. Hentze, *Cell* 117, 2004, 285-297.)

The regulation of the iron level in this context is controlled or regulated by hepcidin.

Hepcidin is a peptide hormone which is produced in the liver. The prevailing active form has 25 amino acids (see for example: "Hepcidin, a key regulator of iron metabolism and mediator of anemia of inflammation". T. Ganz *Blood* 102, 2003, 783-8), although two forms shortened at the amino end, hepcidin-22 and hepcidin-20, have been found. Hepcidin acts on iron uptake via the intestine, via the placenta and on the release of iron from the reticuloendothelial system. In the body, hepcidin is synthesized from so-called pro-hepcidin in the liver, pro-hepcidin being coded by the so-called HAMP gene. If the organism is adequately supplied with iron and oxygen, increased hepcidin is formed. In the mucosa cells of the small intestine and in the macrophages, hepcidin binds to ferroportin, by means of which iron is conventionally transported out of the cell interior into the blood.

The transport protein ferroportin is a membrane transport protein comprising 571 amino acids which is formed and located in the liver, spleen, kidneys, heart, intestine and placenta. In particular, in this context ferroportin is located in the basolateral membrane of intestinal epithelial cells. The ferroportin bound in this way effects export of iron into the blood here. In this context, ferroportin very probably transports iron as $Fe^{2+}$. If hepcidin is bound to ferroportin, ferroportin is transported into the cell interior and degraded, as a result of which the release of iron from the cells is then almost completely blocked. If the ferroportin is inactivated via hepcidin, the iron stored in the mucosa cells therefore cannot be transported away, and the iron is lost with the natural exfoliation of cells via the stool. As a result, absorption of iron in the intestine is reduced by hepcidin. On the other hand, if the iron content in the serum is lowered, hepcidin production in the hepatocytes of the liver is reduced, so that less hepcidin is released and therefore less ferroportin is inactivated, as a result of which an increased amount of iron can be transported into the serum.

Ferroportin is moreover located to a high degree in the reticuloendothelial system (RES), to which the macrophages also belong.

Hepcidin plays an important role here in the event of impaired iron metabolism in the context of chronic inflammations, since interleukin-6 in particular is increased with such inflammations, which leads to an increase in the hepcidin level. Increased hepcidin is bound to the ferroportin of the macrophages by this means, as a result of which release of iron is blocked here, which in the end then leads to an inflammation-related anaemia (ACD or AI).

Since the organism of mammals cannot actively excrete iron, iron metabolism is essentially controlled via cellular release of iron from macrophages, hepatocytes and enterocytes by way of hepcidin.

Hepcidin thus plays an important role in functional anaemia. In this case, in spite of a full iron store, the iron requirement of bone marrow for erythropoiesis is not met sufficiently. The reason for this is assumed to be an increased hepcidin concentration, which in particular limits the transport of iron from the macrophages by blocking the ferroportin and thus greatly reduces the release of iron recycled by phagocytosis.

In the event of a disturbance in the hepcidin regulation mechanism, a direct effect thus manifests itself on iron metabolism in the organism. For example, if hepcidin expression is prevented, for example by a genetic defect, this leads directly to an overloading of iron, which is known as the iron storage disease haemochromatosis.

On the other hand, overexpression of hepcidin, for example due to inflammation processes, for example with chronic inflammations, results directly in reduced serum iron levels. In pathological cases this can lead to a reduced content of haemoglobin, reduced erythrocyte production and therefore to an anaemia.

The duration of use of chemotherapeutics in carcinoma treatments can be significantly reduced by an existing anaemia, since the state of reduced formation of red blood corpuscles caused by the chemotherapeutics employed is intensified still further by an existing anaemia.

Further symptoms of anaemias include tiredness, pallor and reduced attention capacities. The clinical symptoms of anaemia include low serum iron contents (hypoferraemia), low haemoglobin contents, low haematocrit level and a reduced number of red blood corpuscles, reduced reticulocytes and increased values of soluble transferrin receptors.

Iron deficiency symptoms or iron anaemias are conventionally treated by supplying iron. In this context, substitution with iron takes place either by the oral route or by intravenous administration of iron. Erythropoietin and other erythropoiesis-stimulating substances can moreover also be employed in the treatment of anaemias to give a boost to the formation of red blood corpuscles.

Anaemias which are caused by chronic diseases, e.g. chronic inflammatory diseases, can be treated only inadequately with such conventional treatment methods. Cytokines, such as in particular inflammatory cytokine, in particular play a particular role in anaemias which are based on chronic inflammation processes. An overexpression of hepcidin occurs in particular with such chronic inflammatory diseases and is known to lead to a reduced availability of iron for the formation of the red blood corpuscles.

From this emerges the need for an effective treatment method for hepcidin-mediated or -imparted anaemias, in particular those which cannot be treated with conventional iron substitution, such as those anaemias which are caused by chronic inflammatory diseases (ACD and AI).

Anaemia is to be attributed inter alia to those chronic inflammatory diseases mentioned, and to malnutrition or low-iron diets or unbalanced, low-iron eating habits. Anaemias moreover occur due to reduced or poor absorption of iron, for example due to gastrectomies or diseases such as Crohn's disease. An iron deficiency can also occur as a result of an increased blood loss, e.g. due to an injury, heavy menstrual bleeding or blood donation. An increased iron requirement in the growth phase of adolescents and children and in pregnant women is also known. Since an iron deficiency leads not only to a reduced formation of red blood corpuscles but therefore also to a poor supply of oxygen to the organism, which can lead to the abovementioned symptoms, such as tiredness, pallor and lack of concentration and also precisely in adolescents to long-term negative effects on cognitive development, a particularly effective therapy in addition to the known conventional substitution therapy is also of particular interest for this sector.

Compounds which bind to hepcidin or to ferroportin and therefore inhibit the binding of hepcidin to ferroportin and therefore in turn prevent the inactivation of ferroportin by hepcidin, or compounds which, although hepcidin is bound to ferroportin, prevent the internalization of the hepcidin-ferroportin complex, and in this manner prevent the inactivation of the ferroportin by the hepcidin, can be called in general terms hepcidin antagonists.

By using such hepcidin antagonists, there is moreover also generally the possibility, for example by inhibiting hepcidin expression or by blocking the hepcidin-ferroportin interaction, of acting directly on the regulation mechanism of hepcidin and therefore of preventing via this route blocking of the iron transport pathway from tissue macrophages, liver cells and mucosa cells into the serum via the transport protein ferroportin. With such hepcidin antagonists or ferroportin expression inhibitors, substances are therefore available which are suitable for the preparation of pharmaceutical compositions or medicaments in the treatment of anaemias, in particular anaemias with chronic inflammatory diseases. These substances can be employed for treatment of such disorders and the resulting diseases, since these have a direct influence on the increase in the release of recycled haem iron by macrophages and effect an increase in the iron absorption of iron released from food in the intestinal tract. Such substances, inhibitors of hepcidin expression or hepcidin antagonists, can therefore be used for treatment of iron metabolism disorders, such as iron deficiency diseases, anaemias and anaemia-related diseases. In particular, this also includes those anaemias which are caused by acute or chronic inflammatory diseases, such as, for example, osteoarticular diseases, such as rheumatoid polyarthritis, or diseases which are associated with inflammatory syndromes. Such substances can therefore be of particular benefit in particular in the indications of cancer, in particular colorectal cancer, multiple myeloma, ovarian and endometrial cancer and prostate cancer, CKD 3-5 (chronic kidney disease stage 3-5) CHF (chronic heart failure), RA (rheumatoid arthritis), SLE (systemic lupus erythematosus) and IBD (inflammatory bowel disease).

Prior Art

Hepcidin antagonists or compounds which have an inhibiting or assisting action on the biochemical regulation pathways in iron metabolism are known in principle from the prior art.

Thus, for example, WO 2008/036933 describes double-stranded dsRNA which has an inhibiting action on the expression of human HAMP genes in cells and therefore already suppresses the formation of hepcidin, which is coded by the HAMP gene, at a very early stage in the iron metabolism signal pathway. As a result, less hepcidin is formed, so that hepcidin is not available for the inhibition of ferroportin, so that the transport of iron from the cell into the blood by ferroportin can take place unimpeded.

Further compounds which aim directly at reduction of hepcidin expression are known from US 2005/020487, which describes compounds which have an HIF-α stabilizing action and therefore lead to a reduction in hepcidin expression.

The subject matter of US 2007/004618 is siRNA, which has a directly inhibiting action on hepcidin mRNA expression.

All these compounds or methods are therefore those which start in the iron metabolism pathway before formation of the hepcidin and already regulate its general formation downwards. In addition, however, also such substances and compounds are known and described in the prior art which bind in the body to hepcidin which has already formed and therefore inhibit its binding action on the membrane transport protein ferroportin, so that an inactivation of ferroportin by hepcidin is no longer possible. Such compounds are therefore so-called hepcidin antagonists, those based on hepcidin antibodies being known in particular from this group. Such documents are furthermore known in the prior art which describe various mechanisms for action on hepcidin expression, for example by antisense RNA or DNA molecules, ribozymes and anti-hepcidin antibodies. Such mechanisms are described, for example, in EP 1 392 345.

WO2009/058797 furthermore discloses anti-hepcidin antibodies and the use thereof for specific binding to human hepcidin-25, and therefore the use thereof for therapeutic treatment of low iron contents, in particular of anaemias.

Further compounds which act as hepcidin antagonists and are formed from the group of hepcidin antibodies are known from EP 1 578 254, WO2008/097461, US2006/019339, WO2009/044284 or WO2009/027752.

In addition, antibodies which bind to ferroportin-1 and therefore activate ferroportin in order to assist in the iron transport from the cell into the serum by this means are also known. Such ferroportin-1 antibodies are known, for example, from US2007/218055.

All these compounds described which can act as hepcidin antagonists or can display an inhibiting action in hepcidin expression are compounds of higher molecular weight, in particular those which are chiefly obtainable by genetic engineering processes.

In addition, low molecular weight compounds which play a role in iron metabolism and which can have either an inhibiting or also an assisting action are also known.

WO2008/109840 thus describes certain tricyclic compounds which can be employed in particular for treatment of disorders in iron metabolism, such as, for example, ferroportin disorders, these compounds being able to act by regulation of DMT-1 in the form of inhibition or activation. In this context, the compounds of this WO08/109840 are described in particular as DMT-1 inhibitors, whereby they can preferably be employed on diseases with increased iron accumulation or iron storage diseases, such as haemochromatosis.

WO2008/121861 also discloses low molecular weight compounds which have a regulating action on the DMT-1 mechanism. Certain pyrazole and pyrrole compounds are dealt with here, treatment of iron overloading disorders, for example on the basis of ferroportin disorders, also being described here in particular.

The subject matter of US2008/234384 is furthermore certain diaryl and diheteroaryl compounds for treatment of disorders in iron metabolism, such as, for example, ferroportin disorders, which likewise by their action as DMT-1 inhibitors can be employed in particular for treatment of disorders on the basis of increased iron accumulation. In this document, however, possible DMT-1 regulatory mechanisms which can be employed for use on iron deficiency symptoms are also mentioned quite generally.

The same applies to WO2008/151288, which describes certain aromatic and heteroaromatic compounds with an action on DMT-1 regulation and therefore for treatment of disorders in iron metabolism.

The low molecular weight compounds described in the prior art which have an action on iron metabolism are therefore based on DMT-1 regulatory mechanisms and are disclosed in particular for use as agents for treatment of iron accumulation disorders or iron overloading syndromes, such as haemochromatosis.

"Role of STAT1, NF-kappaB, and C/EBPbeta in the macrophage transcriptional regulation of Hepcidin by mycobacterial infection and IFN-gamma" (Sow Fatoumata B. et al., Journal of of Leukocyte Biology, 86 (5), 2009) refers to the use of NFkB inhibitors as hepcidin antagonists but remains silent about the use of 8-sulfonaminoquinoline derivatives.

"Hepcidin in human iron disorders: Therapeutic implications" (Pietrangelo et al., Journal of Hepatology, 54 (1), 2011) refers to the use of hepcidin antagonists for treating iron metabolism disorders such as anaemia. Nevertheless, the publication remains silent about the use of 8-sulfonaminoquinoline derivatives in such indication.

"Hepcidin—Central-regulator of iron-metabolism" (Atanasiu Valeriu et al., European Journal of Haematology, 78 (1), 2007) gives an overview of hepcidin and its function. However, no indications of low molecular weight antagonists, in particular those with an sulfonaminoquinoline structure, emerge from this.

Several chemical compounds on the structural basis of sulfonaminoquinolines have been described to be used in the medical field e.g. in cancer or diabetes treatment, as anti malaria agent, antibacterial agent or as metalloproteinase inhibitors, kinase inhibitors or phosphatase inhibitors etc. For example, EP 726254 relates to N-(4-quinolylcarbonyl) guanidines as hydrogen ion-sodium antiporter inhibitors. Further documents, referring to 8-sulfonaminoquinoline derivatives for use in the medical field are e.g. WO2010/051064 A1, WO2008/074068 A1, US2007/254894 A1 or "Identification of N-(quinolin-8-yl)benzenesulfonamides as agents capable of down-regulating NfkappaB activity within two separate high-throughput screens of NfkappaB activation" (Xie et al., Bioorganic & Medical Chemistry Letters, 18 (1), 2007), "Convenient preparation of N-8-quinolinyl benzenesultams as novel NF-kappaB inhibitors" (Xie et al., Tetrahedron Letters, 49 (14), 2008) or "Synthesis and in vitro evaluation of leishmanicidal and trypanocidal activities of N-quinolin-8-yl-arylsulfonamides" (Da Silva et al., Bioorganic & Medical Chemistry, 15 (24), 2007).

WO2008/144011 A1 refers to the use of selected 8-sulfonaminoquinoline derivatives in the medical treatment of autoimmune deficiencies and inflammatory disorders such as e.g. aplastic anemia (automimmune attack on the bone marrow), pernicious anemia (anemia due to improper absorption of vitamin B12), systemic lupus erythematosus, or inflammatory bowel disease. Nevertheless, the document remains silent about the use of the selected 8-sulfonaminoquinoline derivatives in the treatment of iron metabolism disorders such as e.g. iron deficiency diseases or iron anaemia.

Further, WO2009/134973 A1 refers to the use of selected 8-sulfonaminoquinoline derivatives in the medical treatment of e.g. aplastic anemia but remains silent about any use thereof in the treatment of iron metabolism disorders, especially of iron deficiency diseases or iron anaemia.

Furthermore the use of sulfonaminoquinolines in the formation of metal complexes is known, such as e.g. iron (III) complexes as described in "Fluorometric determination of iron using 5-(4-methoxyphenylazo)-8-(4-toluenesulfonamido)quinoline" (Zeng Zuotao and Jewsbury Roger A., Analyst, 125 (9), 1661-1665, 2000).

Accordingly, chemical compounds on the structural basis of sulfonaminoquinoline have not yet hitherto been described in connection with treatment of disorders in iron metabolism. Furthermore, no low molecular weight chemical structures which display their action as hepcidin antagonists and as a result are suitable for treatment of disorders in iron metabolism have yet been described hitherto.

Object

The object of the present invention was to provide in particular such compounds which can be employed for use for iron deficiency disorders or anaemias, in particular ACD and AI and which act in iron metabolism in particular as hepcidin antagonists and therefore display an antagonistic and via this a regulating action in the hepcidin-ferroportin interaction in iron metabolism. It was furthermore in particular an object of the present invention to provide in this context such compounds which are chosen from the group of low molecular weight compounds and which generally can be prepared by simpler synthesis routes than the antagonistic or hepcidin-inhibiting compounds obtainable by genetic engineering processes, such as RNA, DNA or antibodies.

DESCRIPTION OF THE INVENTION

The inventors have found that certain compounds from the group of sulfonaminoquinolines have an action as hepcidin antagonists.

The invention provides compounds of the general structural formula (I)

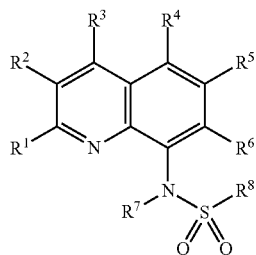

(I)

wherein
$R^1$, $R^2$, $R^3$, $R^4$, $R^5$ and $R^6$ are the same or different and are respectively selected from the group consisting of:
hydrogen,
hydroxyl,
carboxyl,
halogen,
cyano,
nitro,
carboxyl,
optionally substituted sulfonyl (—$SO_2R$),
optionally substituted aminocarbonyl,
optionally substituted aminosulfonyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted alkinyl,
optionally substituted aryl, and
optionally substituted heterocyclyl;
$R^7$ is selected from the group consisting of:
hydrogen,
optionally substituted sulfonyl (—$SO_2R$),
optionally substituted alkyl,
optionally substituted alkenyl,
optionally substituted alkinyl,
optionally substituted acyl,
optionally substituted aryl, and
optionally substituted heterocyclyl; and
$R^8$ is selected from the group consisting of:
hydroxyl,
optionally substituted amino,
optionally substituted alkyl,
optionally substituted alkoxy,
optionally substituted aryloxy,
optionally substituted alkenyl,
optionally substituted alkinyl,
optionally substituted aryl, and
optionally substituted heterocyclyl;
or wherein the substituents $R^1$ to $R^5$ and $R^7$ have one of the above meanings and $R^6$ and $R^8$ together form a residue of the formula

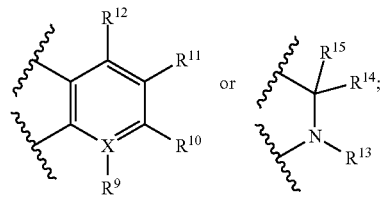

wherein
X is C or N (preferably C);
$R^9$, $R^{10}$, $R^{11}$ and $R^{12}$ are the same or different and are respectively selected from the group consisting of:
hydrogen,
hydroxyl,
halogen,
cyano,
nitro,
carboxyl,
optionally substituted sulfonyl (—$SO_2R$),
optionally substituted aminocarbonyl,
optionally substituted aminosulfonyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted alkinyl,
optionally substituted aryl, and
optionally substituted heterocyclyl;
$R^{13}$ is selected from the group consisting of:
hydrogen,
optionally substituted sulfonyl (—$SO_2R$),
optionally substituted alkyl,
optionally substituted alkinyl,
optionally substituted alkenyl,
optionally substituted acyl,
optionally substituted alkoxycarbonyl,
optionally substituted aryl, and
optionally substituted heterocyclyl; and
$R^{14}$ and $R^{15}$ are the same or different and are respectively selected from the group consisting of:
hydrogen, hydroxyl,
halogen,
cyano,
nitro,
carboxyl,
optionally substituted sulfonyl (—SO$_2$R),
optionally substituted aminocarbonyl,
optionally substituted aminosulfonyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted alkinyl,
optionally substituted aryl, and
optionally substituted heterocyclyl;
or pharmaceutically acceptable salts thereof;
for use in the treatment of iron metabolism disorders.

In the context of the entire invention, the abovementioned substituent groups are defined as follows:

In the context of the present invention the substituent X is preferably C.

Optionally substituted alkyl preferably includes: straight-chain or branched alkyl having preferably 1 to 8, more preferably 1 to 6, particularly preferably 1 to 4 carbon atoms. In one embodiment of the invention, optionally substituted straight-chain or branched alkyl can also include such alkyl groups in which preferably 1 to 3 carbon atom(s) are replaced by corresponding hetero-analogous groups which contain nitrogen, oxygen or sulfur. This means in particular that, for example, one or more methylene groups in the alkyl radicals mentioned can be replaced by NH, O or S.

Optionally substituted alkyl furthermore includes cycloalkyl having preferably 3 to 8, more preferably 5 or 6, particularly preferably 6 carbon atoms.

Substituents of the optionally substituted alkyl defined above preferably include 1 to 3 identical or different substituents which are chosen, for example, from the group which consists of: hydroxyl, halogen, cyano, alkoxy, as defined below, optionally substituted aryloxy, as defined below, optionally substituted heterocyclyloxy, as defined below, carboxyl, optionally substituted acyl, as defined below, optionally substituted aryl, as defined below, optionally substituted heterocyclyl, as defined below, optionally substituted amino, as defined below, mercapto, optionally substituted alkyl-, aryl- or heterocyclylsulfonyl (R—SO$_2$—), as defined below.

Examples of alkyl radicals having 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group etc. Those having 1 to 6 carbon atoms, in particular methyl, ethyl, n-propyl, i-propyl and butyl, are preferred. C$_1$ to C$_4$ alkyl, such as, in particular, methyl and ethyl and i-propyl, are most preferred.

Examples of alkyl groups which arise by replacement with one or more hetero-analogous groups, such as —O—, —S— or —NH—, are preferably those in which one or more methylene groups are replaced by —O— to form an ether group, such as methoxymethyl, ethoxymethyl, 2-methoxyethyl, 3-methoxypropyl, 2-ethoxyethyl etc., 2-methoxyethyl, 3-methoxypropyl and 2-ethoxyethyl being particularly preferred.

According to the invention, polyether groups, such as poly (ethylenoxy) groups, are also included in the definition of alkyl.

Cycloalkyl radicals having 3 to 8 carbon atoms preferably include: a cyclopropyl group, a cyclobutyl group, a cyclopentyl group, a cyclohexyl group, a cycloheptyl group and a cyclooctyl group. A cyclopropyl group, a cyclobutyl group, a cyclopentyl group and a cyclohexyl group are preferred. A cyclopentyl group and a cyclohexyl group are particularly preferred.

In the context of the present invention, halogen includes fluorine, chlorine, bromine and iodine, preferably fluorine or chlorine or bromine.

Examples of a linear or branched alkyl radical having 1 to 8 carbon atoms and substituted by halogen include:

a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc. A trifluoromethyl group is preferred.

Examples of a cycloalkyl radical having 3 to 8 carbon atoms and substituted by halogen include: a 2-fluorocyclopentyl group, a 2-chlorocyclopentyl group, a 2-bromocyclopentyl group, a 3-fluorocyclopentyl group, a 3-chlorocyclopentyl group, a 3-bromocyclopentyl group, a 2-fluorocyclohexyl group, a 2-chlorocyclohexyl group, a 2-bromocyclohexyl group, a 3-fluorocyclohexyl group, a 3-chlorocyclohexyl group, a 3-bromocyclohexyl group, a 4-fluorocyclohexyl group, a 4-chlorocyclohexyl group, a 4-bromocyclohexyl group, a di-fluorocyclopentyl group, a di-chlorocyclopentyl group, a di-bromocyclopentyl group, a di-fluorocyclohexyl group, a di-chlorocyclohexyl group, a di-bromocyclohexyl group, a tri-fluorocyclohexyl group, a tri-chlorocyclohexyl group, a tri-bromocyclohexyl group etc.

Examples of an alkyl radical substituted by hydroxyl include the abovementioned alkyl radicals which contain 1 to 3 hydroxyl radicals, such as, for example, hydroxymethyl, 2-hydroxyethyl, 3-hydroxypropyl etc. 2-hydroxyethyl being preferred.

Examples of an alkyl radical substituted by alkoxy include the abovementioned alkyl radicals which contain 1 to 3 alkoxy radicals, as defined below, such as, for example, methoxymethyl, ethoxymethyl, 2-methoxyethyl, 2-ethoxyethyl, 2-methoxypropyl, 3-methoxypropyl etc., 2-methoxyethylene etc. 2-Methoxyethyl, 2-ethoxyethyl and 3-methoxypropyl are preferred.

Examples of an alkyl radical substituted by aryloxy include the abovementioned alkyl radicals which contain 1 to 3 aryloxy radicals, as defined below, such as, for example, phenoxymethyl, 2-phenoxyethyl and 2or 3-phenoxypropyl etc. Phenoxymethyl is preferred.

Examples of an alkyl radical substituted by heterocyclyloxy include the abovementioned alkyl radicals which contain 1 to 3 heterocyclyloxy radicals, as defined below, such as, for example, pyridin-2-yloxymethyl, -ethyl or -propyl, pyridin-3-yloxymethyl, -ethyl or -propyl, thiophen-2-yloxymethyl, -ethyl or -propyl, thiophen-3-yloxymethyl, -ethyl or propyl, furan-2-yloxymethyl, -ethyl or -propyl, furan-3-yloxymethyl, -ethyl or -propyl etc.

Examples of an alkyl radical substituted by acyl include the abovementioned alkyl radicals which contain 1 to 3 acyl radicals, as defined below.

Examples of an alkyl group substituted by cycloalkyl include the abovementioned alkyl radicals which contain 1 to 3, preferably one (optionally substituted) cycloalkyl group, such as, for example: cyclohexylmethyl, 2-cyclohexylethyl, 2- or 3-cyclohexylpropyl etc.

Examples of an alkyl group substituted by aryl include the abovementioned alkyl radicals which contain 1 to 3, preferably one (optionally substituted) aryl group, as defined below, such as, for example, phenylmethyl, 2-phenylethyl, 2- or 3-phenylpropyl etc., phenylmethyl being preferred.

Examples of an alkyl group substituted by heterocyclyl include the abovementioned alkyl radicals which contain 1 to 3, preferably one (optionally substituted) heterocyclyl group, as defined below, such as, for example, 2-pyridin-2-yl-ethyl, 2-pyridin-3-yl-ethyl, pyridin-2-yl-methyl, pyridin-3-yl-methyl, 2-furan-2-yl-ethyl, 2-furan-3-yl-ethyl, furan-2-yl-methyl, furan-3-yl-methyl, 2-thiophen-2-yl-ethyl, 2-thiophen-3-yl-ethyl, thiophen-2-yl-methyl, thiophen-3-yl-methyl, imidazol-1-yl-methyl, imidazol-2-yl-methyl, 2-imidazol-1-yl-ethyl, 2-imidazol-2-yl-ethyl, 2-morpholinylethyl, such as 2-morpholin-4-yl-ethyl, morpholinylmethyl, such as morpholin-4-yl-methyl, 2-tetrahydrofuranylethyl, such as 2-tetrahydrofuran-2-yl-ethyl, tetrahydrofuranylmethyl, such as tetrahydrofuran-2-yl-methyl etc.

Examples of an alkyl radical substituted by amino include the abovementioned alkyl radicals which contain 1 to 3, preferably one (optionally substituted) amino group, as defined below, such as, for example, methyl amino methyl, methyl amino ethyl, methylaminopropyl, 2-methylaminomethyl (di-methylaminomethyl), 2-ethylaminomethyl (di-ethylaminomethyl), 3-ethylaminomethyl, 2-methylaminoethyl (dimethylaminoethyl), 2-ethylaminoethyl (di-ethylaminoethyl), 3-ethylaminoethyl etc. 2-methylaminomethyl (di-methylaminomethyl) being preferred.

Optionally substituted alkoxy includes an optionally substituted alkyl-O group, wherein reference may be made to the above definition with respect to the definition of the alkyl group. Preferred alkoxy groups are linear or branched alkoxy groups having up to 6 carbon atoms, such as a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, and cycloalkyloxy groups, such as a cyclopentyloxy group or a cyclohexyloxy group. A methoxy group, an ethoxy group, an n-propyloxy group, an i-propyloxy group, an n-butyloxy group, an i-butyloxy group, a sec-butyloxy group, a t-butyloxy group are preferred. The methoxy group, the ethoxy group and the i-propyloxy group are particularly preferred. The methoxy group is most preferred. Further preferred is a substituted alkyl-O group, in particular a difluoromethoxy (—OCHF$_2$) and a trifluoromethoxy group (—OCF$_3$) as well as a di-methylaminoethoxy group or a benzyloxy (Phenyl-CH$_2$—O—) group.

Optionally substituted aryloxy includes an optionally substituted aryl-O group, wherein reference may be made to the following definition of optionally substituted aryl with respect to the definition of the aryl group. Preferred aryloxy groups include 5- and 6-membered aryl groups, among which phenoxy, which can be optionally substituted, is preferred.

Optionally substituted heterocyclyloxy includes an optionally substituted heterocyclyl-O group, wherein reference may be made to the following definition of heterocyclyl with respect to the definition of the heterocyclyl group. Preferred heterocyclyloxy groups include 5- and 6-membered heterocyclyloxy groups, among which pyridin-2-yloxy, pyridin-3-yloxy, thiophen-2-yloxy, thiophen-3-yloxy, furan-2-yloxy, furan-3-yloxy are preferred.

Optionally substituted alkenyl in the entire context of the invention preferably includes:
straight-chain or branched-chain alkenyl having 2 to 8 carbon atoms and cycloalkenyl having 3 to 8 carbon atoms, which can optionally be substituted by preferably 1 to 3 identical or different substituents, such as hydroxyl, halogen or alkoxy. Examples include: vinyl, 1-methylvinyl, allyl, 1-butenyl, isopropenyl, cyclopropenyl, cyclobutenyl, cyclopentenyl, cyclohexenyl. Vinyl or allyl are preferred.

Optionally substituted alkynyl in the entire context of the invention preferably includes:
straight-chain or branched-chain alkynyl having 2 to 8 carbon atoms and cycloalkynyl having 5 to 8 carbon atoms, which can optionally be substituted by preferably 1 to 3 identical or different substituents. With respect to the definition of the optionally substituted alkynyl, reference is made to the above definition of the optionally substituted alkyl having more than one carbon atom, wherein the optionally substituted alkynes include at least one C≡C triple bond. Examples include: ethynyl, propynyl, butynyl, pentynyl and variants thereof optionally substituted as defined above. Ethynyl and optionally substituted ethynyl are preferred.

Optionally substituted aryl in the entire context of the invention preferably includes:

aromatic hydrocarbon radicals having 6 to 14 carbon atoms (the carbon atoms of the possible substituents not being included), which can be monoor bicyclic and which can be substituted by preferably 1 to 3 identical or different substituents chosen from hydroxyl, halogen, as defined above, nitro, cyano, optionally substituted amino, as defined below, mercapto, optionally substituted alkyl, as defined above, optionally substituted acyl, as defined below, and optionally substituted alkoxy, as defined above, optionally substituted aryloxy, as defined above, optionally substituted heterocyclyloxy, as defined above, optionally substituted alkoxycarbonyl as defined below, optionally substituted aryl, as defined here, optionally substituted heterocyclyl, as defined below. Aromatic hydrocarbon radicals having 6 to 14 carbon atoms include, for example: phenyl, naphthyl, phenanthrenyl and anthracenyl, which can optionally be substituted once or several times by identical or different radicals. Phenyl and optionally substituted phenyl, such as, in particular, halogen-, nitro, cyano-, (optionally substituted) alkyl-, (optionally substituted) alkoxy-, (optionally substituted) alkoxycarbonyl- and (optionally substituted) amino-substituted phenyl, are preferred.

Examples of an aryl group substituted by alkyl preferably include: aryl, as described above, which is substituted by straight-chain or branched alkyl having 1 to 8, preferably 1 to 4 carbon atoms, as described above. Preferred alkylaryl is toluyl (2-, 3- or 4-toluyl), trimethylphenyl and trifluoromethylbenzene (benzotrifluoride).

Examples of an aryl group substituted by halogen preferably include: aryl, as described above, which is substituted by one or more identical or different halogens, as described above.

Examples of an aryl radical having 3 to 8, preferably 6 carbon atoms in the aromatic ring system and substituted by halogen include: a 2-fluorophenyl group, a 2-chlorophenyl group, a 2-bromophenyl group, a 3-fluorophenyl group, a 3-chlorophenyl group, a 3-bromophenyl group, a 4-fluorophenyl group, a 4-chlorophenyl group, a 4-bromophenyl group, a 2,3-di-fluorophenyl group, a 2,3-di-chlorophenyl group, a 2,3-di-bromophenyl group, a 2,4-di-fluorophenyl group, a 2,4-di-chlorophenyl group, a 2,4-di-bromophenyl group, a 3,5-di-fluorophenyl group, a 3,5-di-chlorophenyl group, a 3,5-di-bromophenyl group, 2,6-di-fluorophenyl group, a 2,6-di-chlorophenyl group, a 2,6-di-bromophenyl group etc., a 2,4,6-tri-fluorophenyl group, a 2,4,6-tri-chlorophenyl group, a 2,4,6-tri-bromophenyl group etc. 2-fluorophenyl, 2-chlorophenyl, 3-fluorophenyl, 3-chlorophenyl, 4-fluorophenyl and 4-chlorophenyl, 2-,3-di-chlorophenyl, 2-,4-di-chlorophenyl, 2-,6-di-chlorophenyl, 2-,4,-6-tri-chlorophenyl, 3-,4-di-fluorophenyl, 2-,6-di-fluorophenyl, and 2-,4-,6-tri-fluorophenyl as well as 3-chloro-4-fluorophenyl, 2-fluoro-3-chlorophenyl and 2-fluoro-4-chlorophenyl are preferred.

Examples of an aryl group substituted by a nitro group preferably include: aryl, as described above, which is substituted by 1 to 3 nitro radicals, such as, preferably, nitrophenyl, in particular 2-, 3- or 4-nitrophenyl, 2-nitrophenyl being particularly preferred.

Examples of an aryl group substituted by cyano preferably include: aryl, as described above, which is substituted by 1 to 3 cyano radicals, such as, preferably, benzonitrile (2-, 3- or 4-benzonitrile), in particular 2- or 3-benzonitrile.

Examples of an aryl group substituted by hydroxyl preferably include: aryl, as described above, which is substituted by 1 to 3 hydroxyl radicals, such as, for example, 2-hydroxyphenyl, 3-hydroxyphenyl, 4-hydroxyphenyl, 2,4-di-hydroxyphenyl, 2,5-di-hydroxyphenyl, 2,6-di-hydroxyphenyl, 3,5-di-hydroxyphenyl, 3,6-di-hydroxyphenyl, 2,4,6-tri-hydroxyphenyl etc. 2-Hydroxyphenyl, 3-hydroxyphenyl and 2,4-di-hydroxyphenyl are preferred.

Examples of an aryl group substituted by alkoxy or a substituted alkoxy group preferably include:

aryl, as described above, which is substituted by 1 to 3 alkoxy radicals, as described above, such as, preferably, 2-methoxyphenyl, 3-methoxyphenyl, 4-methoxyphenyl, 2-ethoxyphenyl, 3-ethoxyphenyl, 4-ethoxyphenyl, 2-propyloxyphenyl, 3-propyloxyphenyl, 4-propyloxyphenyl, 2-i-propyloxyphenyl, 3-i-propyloxyphenyl, 4-i-propyloxyphenyl, 2,4-di-methoxyphenyl etc., as well as 2-, 3- or 4-di-fluoromethoxy, 2-, 3- or 4-tri-fluoromethoxy. 2-methoxyphenyl, 4-methoxyphenyl 2-trifluoromethoxy, 3-trifluoromethoxy and 4-trifluoromethoxy being particularly preferred.

Examples of an aryl group substituted by alkoxycarbonyl preferably include: aryl, as described above, which is substituted by 1 to 3 alkoxycarbonyl radicals, as described below, such as, preferably, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl etc., methoxycarbonylphenyl, in particular 2-methoxycarbonylphenyl and 3-methoxycarbonylphenyl, being preferred.

Examples of an aryl group substituted by amino preferably include: aryl, as described above, which is substituted by an optionally substituted amino group, as described below. Preferred aminoaryl is anilinyl (2-, 3- or 4-anilinyl), with 2-anilinyl and 3-anilinyl being preferred, and acylaminophenyl such as acetylaminophenyl, propionylaminophenyl, i-propionylaminophenyl and trifluoroacetylaminophenyl.

Further preferred are aryl groups substituted by at least two different substituents such as particularly 2-methyl-3-chlorophenyl, 2-methyl-3-fluorophenyl, 2-methyl-4-fluorophenyl, 2-nitro-4-fluorophenyl, 2-nitro-4-trifluoromethylphenyl, 2-nitro-4-methoxyphenyl, 4-methyl-2-anilinyl, 4-trifluoromethyl-2-anilinyl, 4-fluoro-2-anilinyl, 3-fluoro-4-methoxyphenyl, 4-methoxy-2-anilinyl, 3-carboxy-4-fluorophenyl, 2-acetylamino-4-trifluoromethylphenyl, 2-i-propionylamino-4-trifluoromethylphenyl, 2-trifluoroacetylamino-4-trifluoromethylphenyl, 3-dimethylaminoethylaminomethyl-4-fluoro-phenyl, 3-N-morpholinoethylaminomethyl-4-fluorophenyl, 3-piperazinmethyl-4-fluorophenyl, 3-N-morpholinoacetyl-4-fluorophenyl, 3-dimethylaminoethylaminoacyl-4-fluorophenyl.

Optionally substituted heterocyclyl in the entire context of the invention preferably includes:

aliphatic, saturated or unsaturated heterocyclic 5- to 8-membered cyclic radicals which contain 1 to 3, preferably 1 to 2 hetero atoms chosen from N, O or S, and which can optionally be substituted, preferably by 1 to 3 substituents, wherein reference may be made to the definition of the possible substituents of aryl with respect to possible substituents. 5- or 6-membered and 7-membered saturated or unsaturated, optionally substituted heterocyclic radicals are preferred, such as tetrahydrofuran-2-yl, tetrahydrofuran-3-yl, tetrahydro-thiophen-2-yl, tetrahydro-thiophen-3-yl, pyrrolidin-1-yl, pyrrolidin-2-yl, pyrrolidin-3-yl, morpholin-1-yl, morpholin-2-yl, morpholin-3-yl, morpholin-4-yl, piperidin-1-yl, piperidin-2-yl, piperidin-3-yl, piperidin-4-yl, piperazin-1-yl, piperazin-2-yl, tetrahydropyran-2-yl, tetrahydropyran-3-yl, tetrahydropyran-4-yl, azepan-2-yl, azepan-3-yl, azepan-4-yl, diazepan-1-yl, diazepan-2-yl, diazepan-3-yl, diazepan-5-yl, etc., which can optionally be fused with aromatic rings, etc. Most preferred are optionally substituted heterocyclic radicals such as pyrrolidinyl, morpholinyl, piperidinyl, piperazinyl, optionally substituted with e.g. an alkyl group as defined above preferably with an amino-substituted alkyl group such as e.g. a dimethylaminoethyl group as preferably dimethylaminoethyl-piperazin:

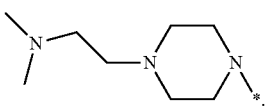

Optionally substituted heterocyclyl in the entire context of the invention moreover includes heteroaromatic hydrocarbon radicals having 4 to 9 ring carbon atoms, which additionally preferably contain 1 to 3 identical or different hetero atoms from the series S, O, N in the ring, and which therefore preferably form 5- to 12-membered heteroaromatic radicals, which can preferably be monocyclic, but also bicyclic. Preferred aromatic heterocyclic radicals include: pyridinyl, such as pyridin-2-yl, pyridin-3-yl and pyridin-4-yl, pyridyl N-oxide, pyrimidyl, pyridazinyl, pyrazinyl, thienyl (thiophenyl), furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. 5- or 6-membered aromatic heterocyclyls, such as e.g. pyridinyl, pyrimidyl, pyridazinyl, pyrazinyl, pyrazolyl, imidazolyl, furyl and thienyl, are preferred, as well as quinolyl. Most preferred are pyrazolyl, pyridinyl, thienyl and quinolyl.

The heterocyclyl radicals according to the invention can be substituted by preferably 1 to 3 identical or different substituents chosen, for example, from hydroxyl, halogen, as defined above, cyano, amino, as defined below, mercapto, alkyl, as defined above, acyl, as defined below, and alkoxy, as defined above, aryloxy, as defined above, heterocyclyloxy, as defined above, aryl, as defined above, heterocyclyl, as defined here.

Heterocyclyl preferably includes: tetrahydrofuranyl, pyrrolidinyl, morpholinyl, piperidinyl or tetrahydropyranyl, piperazinyl, diazepanyl, pyridinyl, pyridyl N-oxide, pyrimidyl, pyridazinyl, pyrazinyl, thienyl (thiophenyl), furanyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, quinoxalinyl. 5- or 6-membered aromatic heterocyclyls, such as e.g. pyridyl, pyridyl N-oxide, pyrimidyl, pyridazinyl, pyrazinyl, pyrazolyl, imidazolyl, furanyl and thienyl, as well as the bicyclyc aromatic heterocyclyl quinolyl are preferred. Particularly preferred heterocyclyl includes: pyridinyl, with pyridin-2-yl:

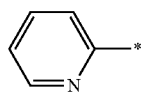 [SMILES: *c1ccccn1]

and
pyridin-3-yl:

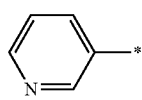

and
pyridin-4-yl:

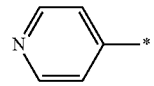

being particularly preferred,
pyrimidinyl, with pyrimidin-2-yl:

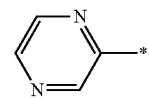

being particularly preferred,
thiazolyl, with thiazol-2-yl:

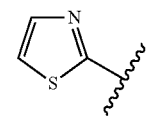 [SMILES: *c1nccs1]

being particularly preferred,
thienyl, with thien-2-yl:

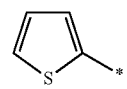

being particularly preferred,
and quinolyl, such as, preferably, quinol-3-yl:

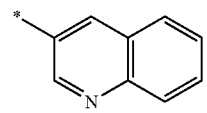 [SMILES: *c1cnc2ccccc2c1]

(* Bonding position to the base skeleton).

Examples of a heterocyclyl group substituted by alkyl preferably include: heterocyclyl, as described above, which is substituted by optionally substituted straight-chain or branched alkyl having 1 to 8, preferably 1 to 4 carbon atoms, as described above. Preferred alkylheterocyclyl are methylpyridinyl, ethylpyridinyl, methylthienyl, ethylthienyl, methylquinolyl, ethylquinolyl, trifluoromethylpyridinyl, trifluoromethylthienyl, and trifluoromethylquinolyl, with trifluoromethylpyridinyl, in particular 6-trifluoromethyl-pyridin-3-yl:

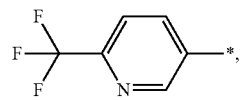

5-trifluoromethyl-pyridin-3-yl:

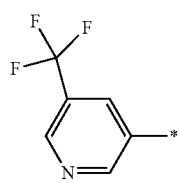 [SMILES: *c1cncc(C(F)(F)F)c1]

5-methyl-pyridin-2-yl:

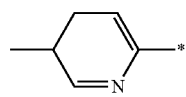

6-methyl-pyridin-2-yl:

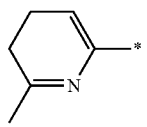 [SMILES: *C1=CCCC(C)=N1]

(* Bonding position to the base skeleton), being preferred.

Examples of a heterocyclyl group substituted by halogen preferably include: heterocyclyl, as described above, which is substituted by one or more identical or different halogens, as described above.

Examples of a heterocyclyl group substituted by cyano preferably include: heterocyclyl, as described above, which is substituted by a cyano group such as preferably 6-cyano-pyridin-3-yl:

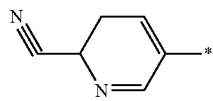

(* Bonding position to the base skeleton), being preferred.

Examples of a heterocyclyl group substituted by halogen preferably include: heterocyclyl, as described above, which is substituted by halogen as described above. Preferred halogen-substituted heterocyclyl groups are fluoropiperidinyl, chloropiperidinyl, bromopiperidinyl fluoropiperazinyl, chloropiperazinyl, bromopiperazinyl, fluoropyridinyl, chloropyridinyl, bromopyridinyl, fluorothienyl, chlorothienyl, bromothienyl fluoroquinolyl, chloroquinolyl, bromoquinolyl, etc., with 5-bromo-thien-2-yl:

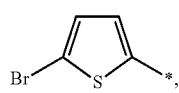

5-fluor-pyridin-2-yl:

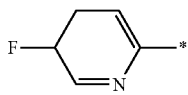

3-fluor-pyridin-4-yl:

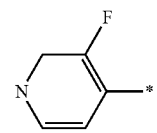

(* Bonding position to the base skeleton), being particularly preferred.

Examples of a heterocyclyl group substituted by hydroxyl preferably include: heterocyclyl, as described above, which is substituted by 1 to 3 hydroxyl radicals, such as, for example, 3-hydroxypyridyl, 4-hydroxypyridyl 3-hydroxythienyl, hydroxyquinolyl etc.

Examples of a heterocyclyl group substituted by alkoxy preferably include: heterocyclyl, as described above which is substituted by 1 to 3 alkoxy radicals, as described above, such as, preferably, 3-alkoxypyridyl, 4-alkoxypyridyl 3-alkoxythienyl, alkoxyquinolyl etc.

Examples of a heterocyclyl group substituted by acyl preferably include: heterocyclyl, as described above, which is substituted by 1 to 3 acyl radicals, as described below.

Optionally substituted acyl here and in the following includes: optionally substituted aliphatic acyl (alkanoyl=alkyl-CO—, wherein reference may be made to the above definition of optionally substituted alkyl with respect to the alkyl group), optionally substituted aromatic acyl (aroyl=aryl-CO—, wherein reference may be made to the above definition of optionally substituted aryl with respect to the aryl group) or heterocyclic acyl (heterocycloyl=heterocyclyl-CO—, wherein reference may be made to the above definition of optionally substituted heterocyclyl with respect to the heterocyclic group). Aliphatic acyl (alkyl-CO—) is preferred.

In this context, optionally substituted aliphatic acyl (alkanoyl) preferably includes: $C_1$ to $C_6$ alkanoyl, such as formyl, acetyl, propionyl, iso-propionyl (i-propionyl), butyryl, Isobutyryl, valeryl, isovaleryl, pivaloyl, hexanoyl, cyclohexanoyl etc. Formyl, acetyl and iso-propionyl are particularly preferred.

Examples of substituted aliphatic acyl include, for example: optionally halogen-substituted $C_2$ to $C_6$ alkanoyl and optionally heterocyclyl-substituted $C_2$ to $C_6$ alkanoyl, wherein reference may be made to the above definitions with respect to the definitions of halogen, heterocyclyl and $C_2$ to $C_6$ alkanoyl, such as particularly trifluoroacetyl and morpholinylacetyl:

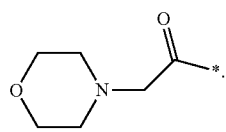

Optionally substituted aromatic acyl (aroyl) includes in particular: $C_6$ to $C_{10}$ aroyl, such as benzoyl, toluoyl, xyloyl, alkoxybenzoyl etc.

Optionally substituted heterocyclic acyl (heterocycloyl) includes in particular: $C_6$ to $C_{10}$ heterocycloyl, such as furanoyl, pyridinoyl, such as pyridin-2-oyl, pyrrolidinoyl, piperidinoyl, tetrahydrofuranoyl.

Optionally substituted amino in the entire context of the invention preferably includes: amino, mono- or dialkylamino, mono- or diarylamino, (N-alkyl)(N-aryl)amino, mono- or diheterocyclylamino, (N-alkyl)(N-heterocyclyl)amino, (N-aryl)(N-heterocyclyl)amino, mono- or diacylamino etc., wherein reference may be made to the corresponding above definition for optionally substituted alkyl, optionally substituted aryl, optionally substituted heterocyclyl and optionally substituted acyl with respect to alkyl, aryl, heterocyclyl and acyl.

Mono- or dialkylamino in this context includes in particular: straight-chain or branched mono- or dialkylamino having 1 to 8, preferably 1 to 6, more preferably 1 to 4 saturated or unsaturated carbon atoms, optionally substituted as described above, in each alkyl group, in particular methylamino, dimethylamino, ethylamino, diethylamino, wherein the alkyl groups can be substituted by preferably one substituent such as e.g. by amino, alkoxy or heterocyclyl as defined herein. Preferred is a mono- and dimethylamino group, a dieethylamino group, and an amino substituted alkyl-amino group such as dimethylaminoethylamino:

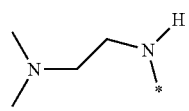

and
N-methyl-N-dimethylaminoethyl:

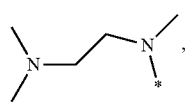

an alkoxy substituted alkyl-amino group such as methoxyethylamino:

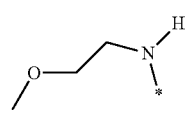

and
N-methyl-N-methoxyethylamino:

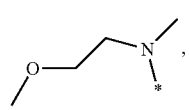

and
an heterocyclyl substituted alkyl-amino group such as morpholinylethylamino:

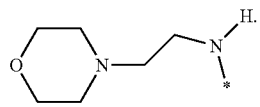

Mono- or diarylamino in this context includes in particular: mono- or diarylamino with 3- to 8-, preferably 5- to 6-membered aryl radicals which are optionally substituted as described above, in particular phenylamino or diphenylamino, wherein the aryl groups can be substituted by preferably one or two substituents.

(N-Alkyl)(N-aryl)amino describes in particular a substituted amino which is substituted in each case on the nitrogen atom by an alkyl radical and by an aryl radical.

Mono- or diheterocyclylamino includes in particular: mono- or diheterocyclylamino with 3- to 8-, preferably 5- to 6-membered heterocyclyl radicals which are optionally substituted as described above.

(N-Alkyl)(N-heterocyclyl)amino describes in particular a substituted amino which is substituted in each case on the nitrogen atom by an alkyl radical and by a heterocyclyl radical.

(N-Aryl)(N-heterocyclyl)amino describes in particular a substituted amino which is substituted in each case on the nitrogen atom by an aryl radical and by a heterocyclyl radical.

Mono- or diacylamino includes in particular a substituted amino which is substituted by one or two (optionally substituted) acyl radicals, as defined above, such as, in particular, acetylamino, propionylamino, iso-propionylamino, trifluoroacetylamino etc.

Optionally substituted aminocarbonyl in the context of the entire invention represents optionally substituted amino-CO, wherein reference may be made to the above definition with respect to the definition of optionally substituted amino. Optionally substituted aminocarbonyl preferably represents optionally substituted carbamoyl ($H_2NCO-$), such as $H_2NCO-$, mono- or dialkylaminocarbonyl (H(alkyl)N—CO— or (alkyl)$_2$N—CO—), mono- or diarylaminocarbonyl (H(aryl)N—CO— or (aryl)$_2$N—CO—) or mono- or diheterocyclylaminocarbonyl (H(heterocyclyl)N—CO— or (heterocyclyl)$_2$N—CO—), wherein reference may be made to the above explanations for optionally substituted alkyl, aryl or heterocyclyl with respect to the definition of alkyl, aryl or heterocyclyl. Preferred is aminocarbonyl ($H_2NCO-$) and alkylaminocarbonyl selected from monomethylaminocarbonyl (H(CH$_3$)NCO—), dimethylaminocarbonyl ((CH$_3$)$_2$NCO—), dimethylaminoethylaminocarbonyl:

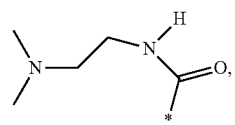 [SMILES: *C(=O)NCCN(C)C]

methoxyethylaminocarbonyl:

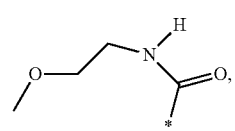 [SMILES: *C(=O)NCCOC]

2-hydroxy-1-hydroxymethyl-ethylaminocarbonyl:

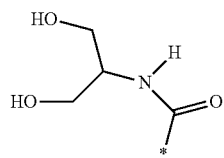

as well as piperidinylethylaminocarbonyl:

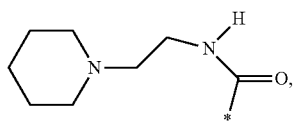 [SMILES: *C(=O)NCCN1CCCCC1]

4-hydroxy-piperidin-1-yl-carbonyl:

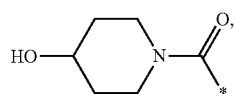 [SMILES: *C(=O)N1CCC(O)CC1]

3-hydroxy-pyrrolidin-1-yl-carbonyl:

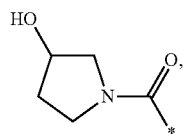

4-methyl-piperazin-1-yl-carbonyl:

and
morpholinyl-carbonyl:

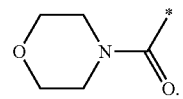

Optionally substituted aminosulfonyl in the context of the entire invention furthermore represents optionally substituted amino-SO$_2$—, wherein reference may be made to the above definition with respect to the definition of optionally substituted amino. Optionally substituted sulfamoyl (H$_2$N—SO$_2$—), such as sulfamoyl (H$_2$N—SO$_2$—) or mono- or dialkylaminosulfonyl (alkyl)$_2$N—SO$_2$, are preferred, wherein reference may be made to the above explanations for optionally substituted alkyl with respect to the definition of alkyl.

Optionally substituted Sulfonyl (—SO$_2$R), wherein R is a hydroxyl group (—OH or an optionally substituted alkyl, aryl or heterocyclyl as defined above) furthermore preferably represents a sulfonic acid residue, methylsulfonyl, ethylsulfonyl, phenylsulfonyl, tolylsulfonyl or benzylsulfonyl. Methylsulfonyl is preferred.

Optionally substituted alkoxycarbonyl (—(C=O)—O-alkyl; ester-group) includes the optionally substituted alkoxy (—O-alkyl) mentioned above with respect to the definition of alkoxy, and includes, for example, methoxycarbonyl, ethoxycarbonyl, cycloalkyloxycarbonyl, heterocyclyloxycarbonyl etc. Methoxycarbonyl, cyclopentyloxycarbonyl, piperidinyloxycarbonyl such as piperidin-4-yl-oxycarbonyl:

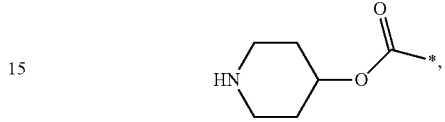

and
pyrrolidinyloxycarbonyl such as pyrrolidin-3-yl-oxycarbonyl:

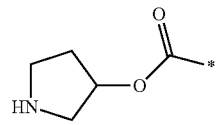 [SMILES: *C(=O)OC1CCNC1]

is preferred.

Optionally substituted acyloxy (—O—(C=O)-alkyl; —O—(C=O)-aryl; —O—(C=O)-heterocyclyl) includes the optionally substituted acyl mentioned above with respect to the definition of acyl.

Preferred Embodiments:

In a preferred embodiment, the compound of the formula (I) has the following substituent definitions:

$R^1$, $R^2$, $R^3$, $R^4$, $R^5$ and $R^6$ are the same or different and are respectively selected from the group consisting of:
hydrogen,
hydroxyl,
halogen,
cyano,
nitro,
carboxyl,
optionally substituted sulfonyl (—SO$_2$R),
optionally substituted aminocarbonyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted aryl, and
optionally substituted heterocyclyl;
$R^7$ is selected from the group consisting of:
hydrogen,
optionally substituted alkyl,
optionally substituted alkenyl,
optionally substituted aryl, and
optionally substituted heterocyclyl; and
$R^8$ is selected from the group consisting of:
hydroxyl,
optionally substituted amino,
optionally substituted alkyl, optionally substituted alkoxy,
optionally substituted aryloxy,
optionally substituted aryl, and
optionally substituted heterocyclyl;
or the substituents $R^1$ to $R^5$ and $R^7$ have one of the above meanings and $R^6$ and $R^8$ together form a residue of the formula

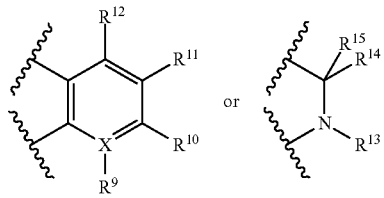

wherein
X is C or N (preferably C);
$R^9$, $R^{10}$, $R^{11}$ and $R^{12}$ are the same or different and are respectively selected from the group consisting of:
hydrogen,
hydroxyl,
carboxyl,
halogen,
cyano,
nitro,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted aryl, and
optionally substituted heterocyclyl;
$R^{13}$ is selected from the group consisting of:
hydrogen,
optionally substituted sulfonyl (—SO$_2$R),
optionally substituted alkyl,
optionally substituted acyl,
optionally substituted alkoxycarbonyl,
optionally substituted aryl, and
optionally substituted heterocyclyl; and
$R^{14}$ and $R^{15}$ are the same or different and are respectively selected
from the group consisting of:
hydrogen,
hydroxyl,
halogen,
cyano,
carboxyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted aryl, and
optionally substituted heterocyclyl.
In a further more preferred embodiment, the compound of the formula (I) has the following substituent definitions:
$R^1$, $R^2$, $R^3$, $R^4$, $R^5$ and $R^6$ are the same or different and are respectively selected from the group consisting of:
hydrogen,
hydroxyl,
halogen,
cyano,
optionally substituted aminocarbonyl,
optionally substituted amino,
optionally substituted alkyl,
optionally substituted acyl,
optionally substituted alkoxycarbonyl,
optionally substituted alkoxy, and
optionally substituted heterocyclyl;
$R^7$ is selected from the group consisting of:
hydrogen and
optionally substituted alkyl,
$R^8$ is selected from the group consisting of:
optionally substituted amino,
optionally substituted alkoxy,
optionally substituted aryloxy,
optionally substituted aryl, and
optionally substituted heterocyclyl;
or the substituents $R^1$ to $R^5$ and $R^7$ have one of the above meanings and $R^6$ and $R^8$ together form a residue of the formula

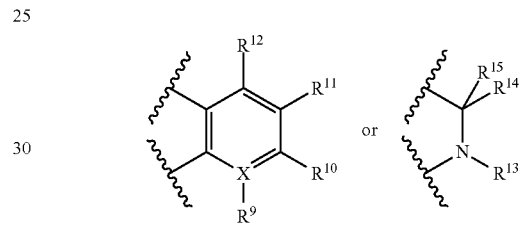

Wherein
X is C or N (preferably C);
$R^9$, $R^{10}$, $R^{11}$ and $R^{12}$ are the same or different and are respectively selected from the group consisting of:
hydrogen,
carboxyl,
halogen,
optionally substituted alkyl, and
optionally substituted alkoxy;
$R^{13}$ is selected from the group consisting of:
hydrogen,
optionally substituted alkyl, and
optionally substituted aryl; and
$R^{14}$ and $R^{15}$ are the same or different and are respectively selected from the group consisting of:
hydrogen,
optionally substituted alkyl,
optionally substituted aryl, and
optionally substituted heterocyclyl.
Further more preferred embodiments relate to:
1. Compounds of the Formula (I) with the Following Substituent Definitions:
$R^1$ is selected from
hydrogen,
halogen and
optionally substituted alkyl;
$R^2$ is selected from
hydrogen and
optionally substituted alkyl;
$R^3$ is selected from
hydrogen,
halogen,
optionally substituted aminocarbonyl, optionally substituted amino,
optionally substituted alkyl,
optionally substituted alkoxycarbonyl,
optionally substituted alkoxy, and
optionally substituted heterocyclyl;
$R^4$ is selected from
hydrogen,
halogen,
cyano,
optionally substituted aminocarbonyl,
optionally substituted amino,
optionally substituted alkyl,
optionally substituted acyl,
optionally substituted alkoxy, and
optionally substituted heterocyclyl;
$R^5$ is selected from
hydrogen,
halogen,
optionally substituted alkyl, and
optionally substituted alkoxy;
$R^6$ is selected from
hydrogen,
hydroxyl,
halogen,
optionally substituted alkyl, and
optionally substituted alkoxy;
$R^7$ is selected from
hydrogen and
optionally substituted alkyl; and
$R^8$ is selected from
optionally substituted amino,
optionally substituted alkoxy,
optionally substituted aryloxy,
optionally substituted aryl, and
optionally substituted heterocyclyl;

2. Compounds of the General Formula (Ia),

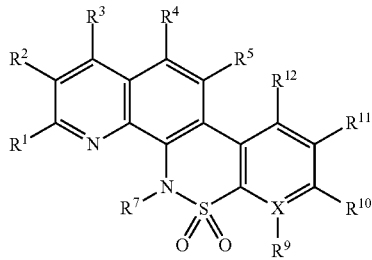

(Ia)

wherein the substituents $R^1$ to $R^5$ and $R^7$ have the meaning according to any one of the preceding embodiments and wherein
X is C or N (preferably C); and
$R^9$, $R^{10}$, $R^{11}$ and $R^{12}$ are the same or different and are respectively selected from the group consisting of:
hydrogen,
hydroxyl,
carboxyl,
halogen,
cyano,
nitro,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted aryl, and
optionally substituted heterocyclyl;

3. Compounds of the Formula (Ia) with the Following Substituent Definitions:
$R^1$ to $R^5$ and $R^7$ have the meaning according to any one of the preceding embodiments and
X is C or N (preferably C); and
$R^9$, $R^{10}$, $R^{11}$ and $R^{12}$ are the same or different and are respectively selected from the group consisting of:
hydrogen,
halogen,
optionally substituted alkyl,
optionally substituted alkoxy;

4. Compounds of the General Formula (Ib),

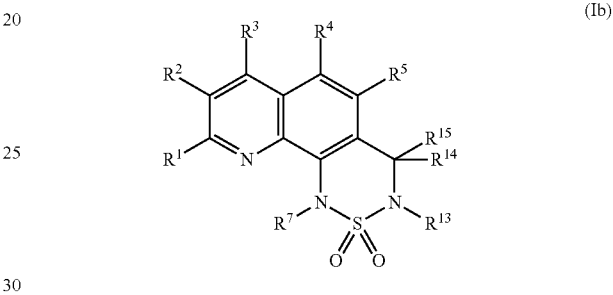

(Ib)

wherein the substituents $R^1$ to $R^5$ and $R^7$ have the meaning according to any one of the preceding embodiments and wherein
$R^{13}$ is selected from the group consisting of:
hydrogen,
optionally substituted sulfonyl (—$SO_2R$),
optionally substituted alkyl,
optionally substituted acyl,
optionally substituted alkoxycarbonyl,
optionally substituted aryl, and
optionally substituted heterocyclyl; and
$R^{14}$ and $R^{15}$ are the same or different and are respectively selected from the group consisting of:
hydrogen,
hydroxyl,
halogen,
cyano,
carboxyl,
optionally substituted amino,
optionally substituted alkyl,
optionally substituted acyl,
optionally substituted alkoxycarbonyl,
optionally substituted acyloxy,
optionally substituted alkoxy,
optionally substituted aryloxy,
optionally substituted alkenyl,
optionally substituted aryl, and
optionally substituted heterocyclyl.

5. Compounds of the Formula (Ib) with the Following Substituent Definitions:
$R^1$ to $R^5$ and $R^7$ have the meaning according to any one of the preceding embodiments and
$R^{13}$ is selected from the group consisting of:
hydrogen,
optionally substituted alkyl, and
optionally substituted aryl; and $R^{14}$ and $R^{15}$ are the same or different and are respectively selected from the group consisting of:
hydrogen,
optionally substituted alkyl,
optionally substituted aryl, and
optionally substituted heterocyclyl.

In preferred embodiments of the general formula (I) or (Ia) or (Ib), the individual substituents each have the following definitions:

$R^1$ is selected from
hydrogen,
halogen and
optionally substituted alkyl;
$R^2$ is selected from
hydrogen and
optionally substituted alkyl;
$R^3$ is selected from
hydrogen,
halogen,
optionally substituted aminocarbonyl,
optionally substituted amino,
optionally substituted alkyl,
optionally substituted alkoxycarbonyl,
optionally substituted alkoxy, and
optionally substituted heterocyclyl;
$R^4$ is selected from
hydrogen,
halogen,
cyano,
optionally substituted aminocarbonyl,
optionally substituted amino,
optionally substituted alkyl,
optionally substituted acyl,
optionally substituted alkoxy, and
optionally substituted heterocyclyl;
$R^5$ is selected from
hydrogen,
halogen,
optionally substituted alkyl, and
optionally substituted alkoxy;
$R^6$ is selected from
hydrogen,
hydroxyl,
halogen,
optionally substituted alkyl, and
optionally substituted alkoxy;
$R^7$ is selected from
hydrogen and
optionally substituted alkyl; and
$R^8$ is selected from
optionally substituted amino,
optionally substituted alkoxy,
optionally substituted aryloxy,
optionally substituted aryl, and
optionally substituted heterocyclyl;
$R^9$ is selected from
hydrogen
optionally substituted alkyl, preferably methyl;
$R^{10}$ is selected from
hydrogen,
halogen, preferably fluorine or chlorine
optionally substituted alkoxy, preferably methoxy and
optionally substituted alkyl, preferably methyl;
$R^{11}$ is selected from
hydrogen,
halogen, preferably fluorine and chlorine,
carboxyl,
cyano,
optionally substituted alkyl, preferably methyl, trifluoromethyl, and cyclopentyloxycarbonyl, and
optionally substituted alkoxy, preferably methoxy, ethoxy, cyclopentyloxy, trifluormethoxy, dimethylaminoethoxy, pyrrolidin-3-yloxy, piperidin-4-yloxy,
optionally substituted alkoxycarbonyl, preferably methoxycarbonyl, pyrrolidin-3-yl-oxycarbonyl, piperidin-4-yl-oxycarbonyl
optionally substituted aminocarbonyl, preferably aminocarbonyl, monomethylaminocarbonyl, dimethylaminocarbonyl, dimethylaminoethylaminocarbonyl, methoxyethylaminocarbonyl, 2-hydroxy-1-hydroxyethylaminocarbonyl, 3-hydroxy-pyrrolidinylcarbonyl, 4-hydroxy-piperidinylcarbonyl, morpholinylcarbonyl, 4-methyl-piperazinylcarbonyl,
optionally substituted amino, preferably amino, monomethylamino, dimethylamino, monoethylamino, diethylamino, methoxyethylamino, 2-hydroxy-1-hydroxyethylamino, morpholinylethylamino,
optionally substituted heterocycly, preferably pyrrolidin (such as 3-hydroxy-pyrrolidin), piperidin (such as e.g. 4-hydroxypiperidin), morpholin, piperazin (such as 4-methyl-piperazin), and
optionally substituted sulfonyl such as e.g. methylsulfonyl;
$R^{12}$ is selected from
hydrogen; and
$R^{13}$ is selected from
hydrogen,
optionally substituted alkyl, preferably methyl and dimethylaminoethyl, and
optionally substituted aryl, preferably phenyl;
$R^{14}$ and $R^{15}$ are the same or different and are respectively selected from
hydrogen,
optionally substituted alkyl, preferably methyl and ethyl, and
optionally substituted aryl, preferably phenyl which may be substituted by one or more same or different substituents selected from halogens, a carboxyl group, an (optionally substituted) alkyl group, an (optionally substituted) acyl group, an (optionally substituted) alkoxy group, an (optionally substituted) aminocarbonyl group, and
optionally substituted heterocyclyl, preferably an (optionally substituted) pyridine group.

It is further preferred that at least one of the substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ is defined as in any one of the aforementioned embodiments.

Particularly preferred compounds of the general formula (I) are shown in the following table:

| | Example Compound |
|---|---|
| 1 |  |

-continued
| Example Compound | |
|---|---|
| 2 | 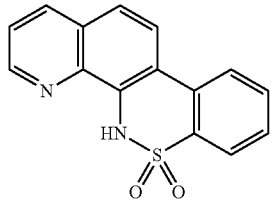 [SMILES: O=S1(=O)Nc2c(ccc3cccnc23)-c2ccccc21] |
| 3 | 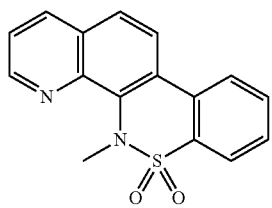 [SMILES: CN1c2c(ccc3cccnc23)-c2ccccc2S1(=O)=O] |
| 4 | 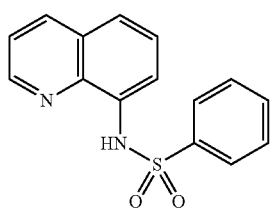 [SMILES: O=S(=O)(Nc1cccc2cccnc12)c1ccccc1] |
| 5 | 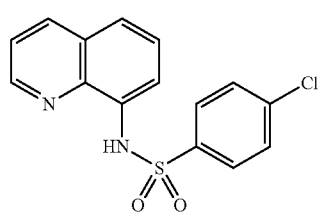 [SMILES: O=S(=O)(Nc1cccc2cccnc12)c1ccc(Cl)cc1] |
| 6 | 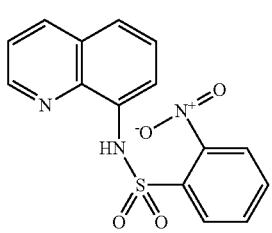 |
| 7 | 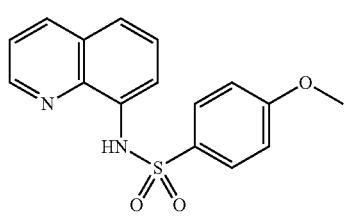 [SMILES: COc1ccc(S(=O)(=O)Nc2cccc3cccnc23)cc1] |
| 8 | 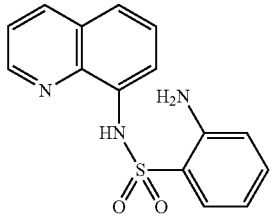 [SMILES: Nc1ccccc1S(=O)(=O)Nc1cccc2cccnc12] |
-continued
| Example Compound | |
|---|---|
| 9 | 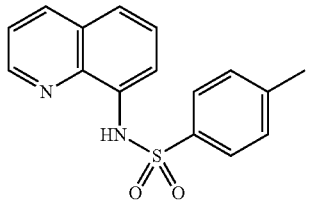 [SMILES: Cc1ccc(S(=O)(=O)Nc2cccc3cccnc23)cc1] |
| 10 | 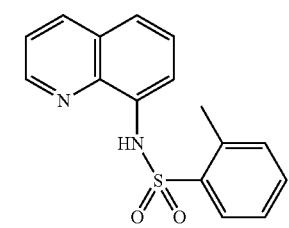 [SMILES: Cc1ccccc1S(=O)(=O)Nc1cccc2cccnc12] |
| 11 | 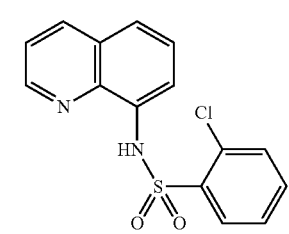 [SMILES: O=S(=O)(Nc1cccc2cccnc12)c1ccccc1Cl] |
| 12 | 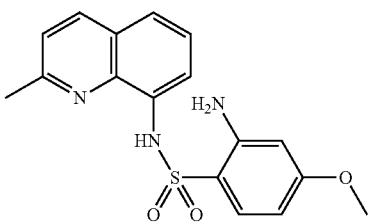 |
| 13 | 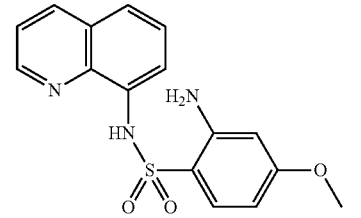 [SMILES: COc1ccc(S(=O)(=O)Nc2cccc3cccnc23)c(N)c1] |
| 14 | 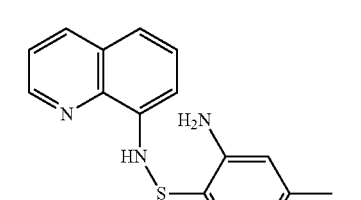 |
| 15 | 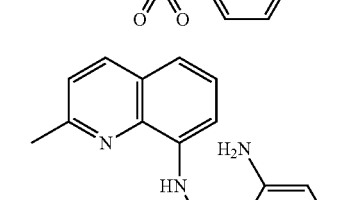 |

-continued
Example Compound
16 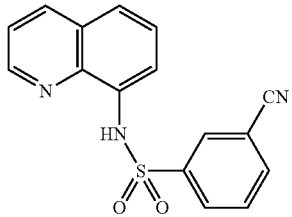 [SMILES: N#Cc1cccc(S(=O)(=O)Nc2cccc3cccnc23)c1]
17 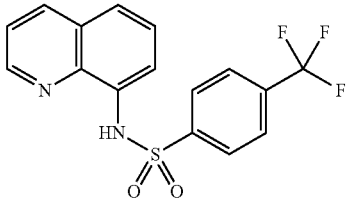 [SMILES: O=S(=O)(Nc1cccc2cccnc12)c1ccc(C(F)(F)F)cc1]
18 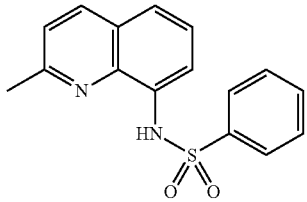 [SMILES: Cc1ccc2cccc(NS(=O)(=O)c3ccccc3)c2n1]
19 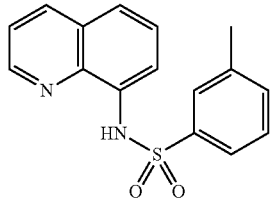
20 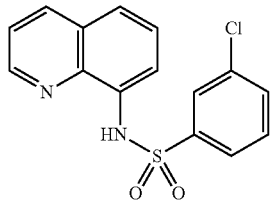 [SMILES: O=S(=O)(Nc1cccc2cccnc12)c1cccc(Cl)c1]
21 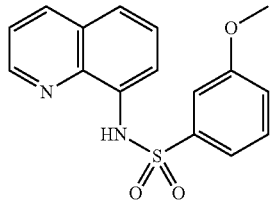 [SMILES: COc1cccc(S(=O)(=O)Nc2cccc3cccnc23)c1]
22 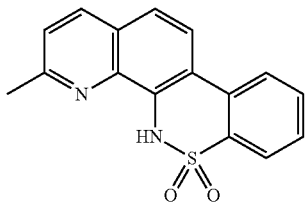
-continued
Example Compound
23 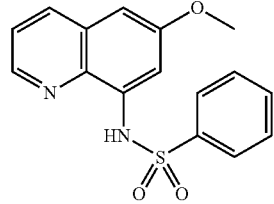 [SMILES: COc1cc(NS(=O)(=O)c2ccccc2)c2ncccc2c1]
24 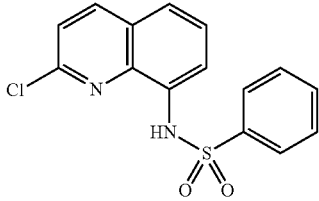 [SMILES: O=S(=O)(Nc1cccc2ccc(Cl)nc12)c1ccccc1]
25 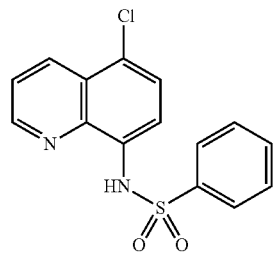 [SMILES: O=S(=O)(Nc1ccc(Cl)c2cccnc12)c1ccccc1]
26 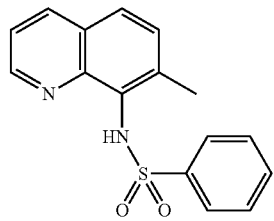 [SMILES: Cc1ccc2cccnc2c1NS(=O)(=O)c1ccccc1]
27 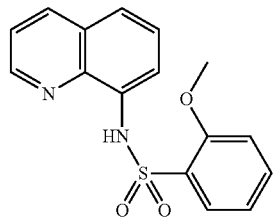 [SMILES: COc1ccccc1S(=O)(=O)Nc1cccc2cccnc12]
28 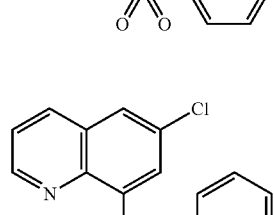

| Example Compound | | Example Compound | |
|---|---|---|---|
| 29 | 5-bromo-N-(quinolin-8-yl)benzenesulfonamide | 36 | N-(quinolin-8-yl)-2-(trifluoromethoxy)benzenesulfonamide |
| 30 | 4-fluoro-2-nitro-N-(quinolin-8-yl)benzenesulfonamide | 37 | 2-cyano-N-(quinolin-8-yl)benzenesulfonamide |
| 31 | 2-amino-4-fluoro-N-(quinolin-8-yl)benzenesulfonamide | 38 | N-(quinolin-8-yl)-3-(trifluoromethoxy)benzenesulfonamide |
| 32 | 2-nitro-N-(quinolin-8-yl)-4-(trifluoromethyl)benzenesulfonamide | 39 | methyl 2-(N-(quinolin-8-yl)sulfamoyl)benzoate |
| 33 | N-(quinolin-8-yl)pyridine-3-sulfonamide | 40 | methyl 3-(N-(quinolin-8-yl)sulfamoyl)benzoate |
| 34 | 4-methoxy-2-nitro-N-(quinolin-8-yl)benzenesulfonamide | 41 | 2,4-dichloro-N-(quinolin-8-yl)benzenesulfonamide |
| 35 | 2-amino-N-(quinolin-8-yl)-4-(trifluoromethyl)benzenesulfonamide | 42 | 4-chloro-2-fluoro-N-(quinolin-8-yl)benzenesulfonamide |

| Example Compound | |
|---|---|
| 43 | 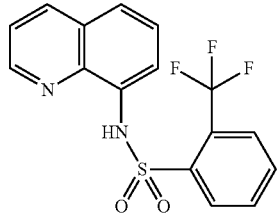 [SMILES: O=S(=O)(Nc1cccc2cccnc12)c1ccccc1C(F)(F)F] |
| 44 | 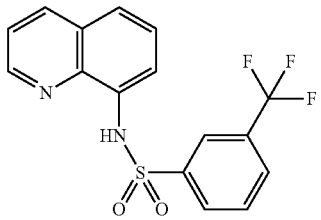 [SMILES: O=S(=O)(Nc1cccc2cccnc12)c1cccc(C(F)(F)F)c1] |
| 45 | 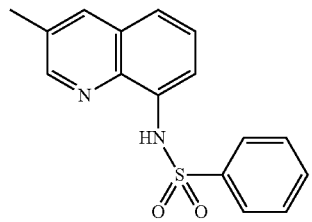 [SMILES: Cc1cnc2c(NS(=O)(=O)c3ccccc3)cccc2c1] |
| 46 | 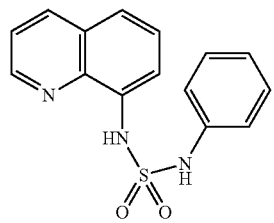 [SMILES: O=S(=O)(Nc1ccccc1)Nc1cccc2cccnc12] |
| 47 | 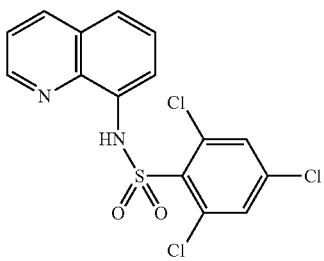 [SMILES: O=S(=O)(Nc1cccc2cccnc12)c1c(Cl)cc(Cl)cc1Cl] |
| 48 | 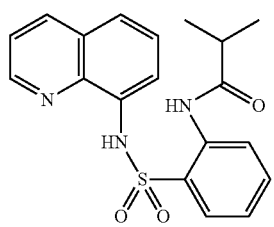 [SMILES: CC(C)C(=O)Nc1ccccc1S(=O)(=O)Nc1cccc2cccnc12] |
| 49 | 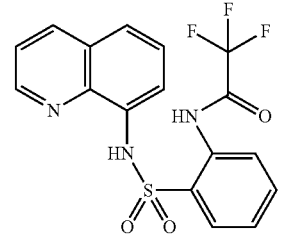 [SMILES: O=C(Nc1ccccc1S(=O)(=O)Nc1cccc2cccnc12)C(F)(F)F] |
| 50 | 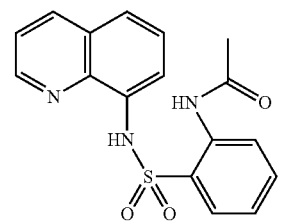 [SMILES: CC(=O)Nc1ccccc1S(=O)(=O)Nc1cccc2cccnc12] |
| 51 | 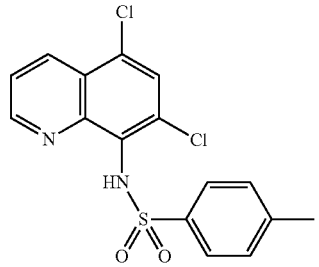 [SMILES: Cc1ccc(S(=O)(=O)Nc2c(Cl)cc(Cl)c3cccnc23)cc1] |
| 52 | 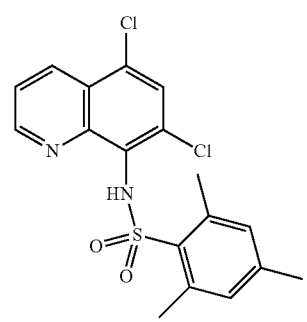 [SMILES: Cc1cc(C)c(S(=O)(=O)Nc2c(Cl)cc(Cl)c3cccnc23)c(C)c1] |
| 53 | 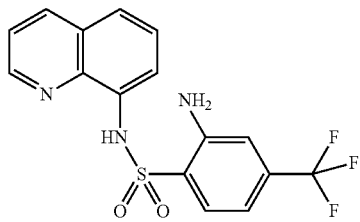 [SMILES: Nc1cc(C(F)(F)F)ccc1S(=O)(=O)Nc1cccc2cccnc12] |
| 54 | 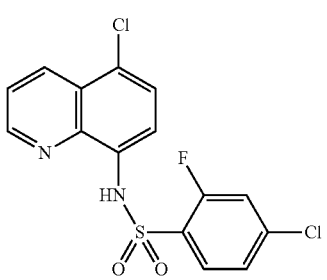 [SMILES: O=S(=O)(Nc1ccc(Cl)c2cccnc12)c1ccc(Cl)cc1F] |

| Example Compound | | Example Compound | |
|---|---|---|---|
| 55 | 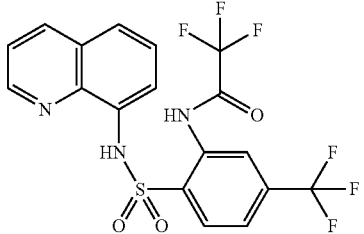 [SMILES: O=C(Nc1cc(C(F)(F)F)ccc1S(=O)(=O)Nc1cccc2cccnc12)C(F)(F)F] | 61 | 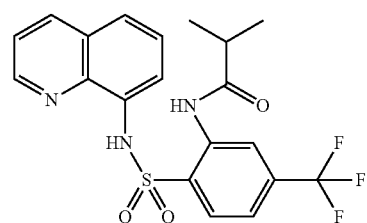 |
| 56 | 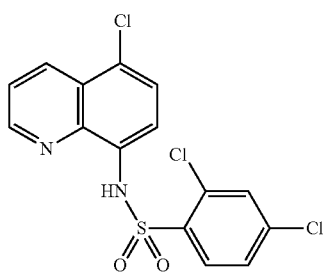 [SMILES: O=S(=O)(Nc1ccc(Cl)c2cccnc12)c1ccc(Cl)cc1Cl] | 62 | 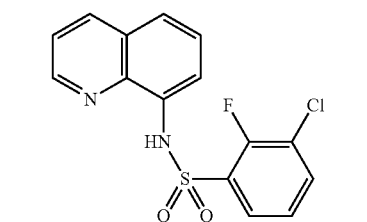 |
| 57 | 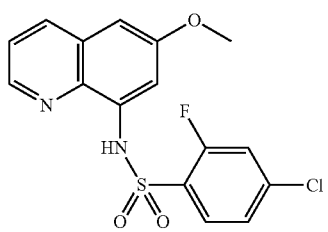 [SMILES: COc1cc(NS(=O)(=O)c2ccc(Cl)cc2F)c2ncccc2c1] | 63 | 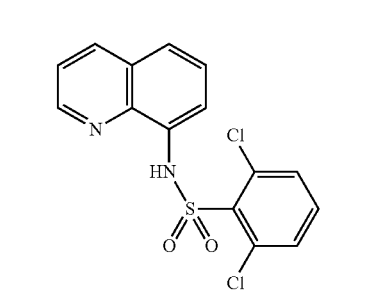 |
| 58 | 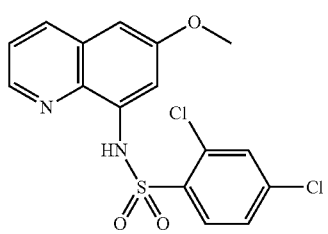 [SMILES: COc1cc(NS(=O)(=O)c2ccc(Cl)cc2Cl)c2ncccc2c1] | 64 | 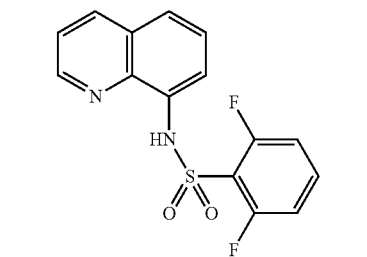 |
| 59 | 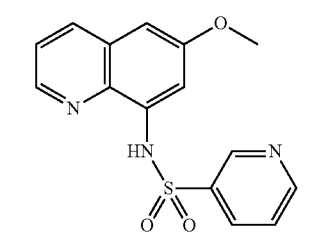 [SMILES: COc1cc(NS(=O)(=O)c2cccnc2)c2ncccc2c1] | 65 | 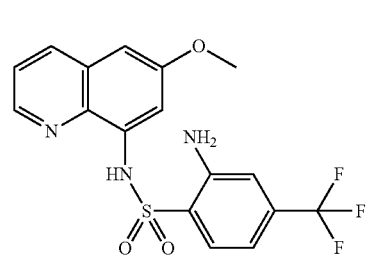 [SMILES: COc1cc(NS(=O)(=O)c2ccc(C(F)(F)F)cc2N)c2ncccc2c1] |
| 60 | 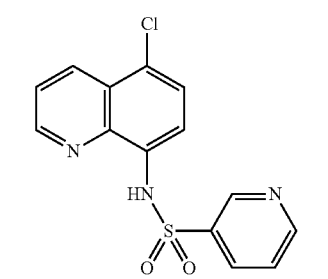 | 66 | 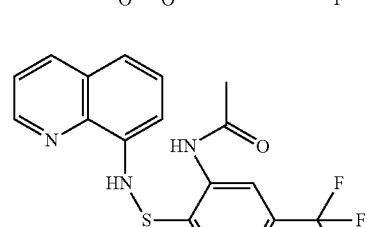 |

| Example Compound | |
|---|---|
| 67 | 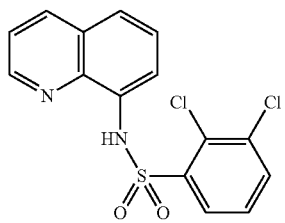 [SMILES: O=S(=O)(Nc1cccc2cccnc12)c1cccc(Cl)c1Cl] |
| 68 | 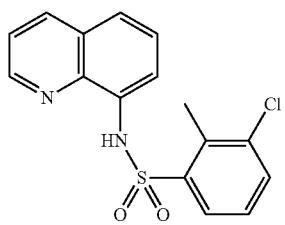 [SMILES: Cc1c(Cl)cccc1S(=O)(=O)Nc1cccc2cccnc12] |
| 69 | 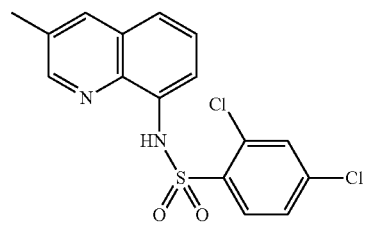 [SMILES: Cc1cnc2c(NS(=O)(=O)c3ccc(Cl)cc3Cl)cccc2c1] |
| 70 | 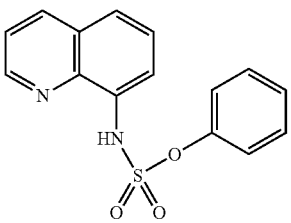 [SMILES: O=S(=O)(Nc1cccc2cccnc12)Oc1ccccc1] |
| 71 | 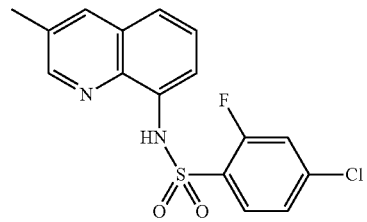 [SMILES: Cc1cnc2c(NS(=O)(=O)c3ccc(Cl)cc3F)cccc2c1] |
| 72 | 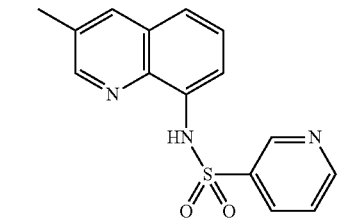 [SMILES: Cc1cnc2c(NS(=O)(=O)c3cccnc3)cccc2c1] |
| 73 | 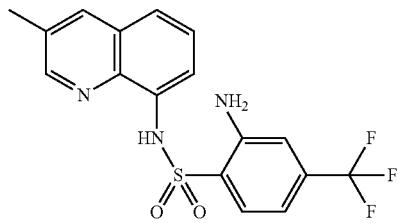 [SMILES: Cc1cnc2c(NS(=O)(=O)c3ccc(C(F)(F)F)cc3N)cccc2c1] |
| Example Compound | |
|---|---|
| 74 | 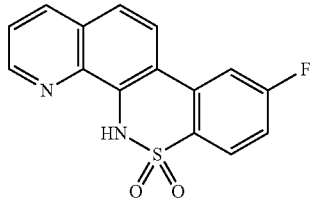 [SMILES: O=S1(=O)Nc2c(ccc3cccnc23)-c2cc(F)ccc21] |
| 75 | 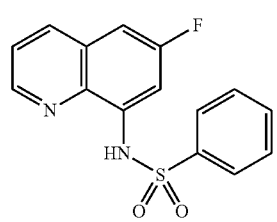 |
| 76 | 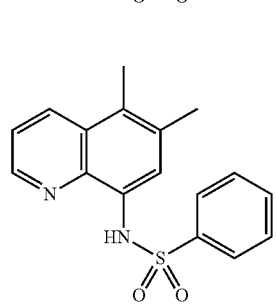 |
| 77 | 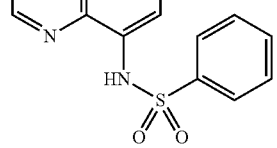 |
| 78 | 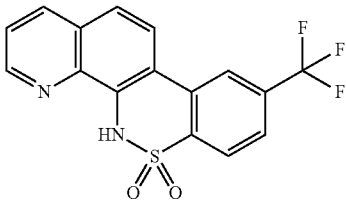 [SMILES: O=S1(=O)Nc2c(ccc3cccnc23)-c2cc(C(F)(F)F)ccc21] |
| 79 | 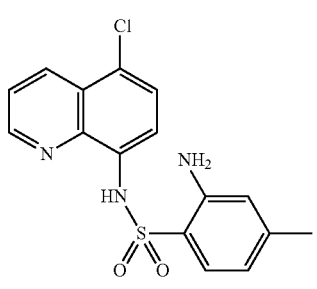 [SMILES: Cc1ccc(S(=O)(=O)Nc2ccc(Cl)c3cccnc23)c(N)c1] |

-continued
| Example Compound | |
|---|---|
| 80 | 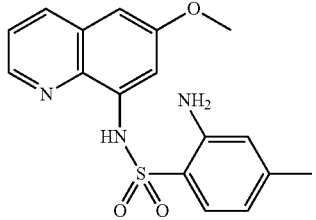 [SMILES: COc1cc(NS(=O)(=O)c2ccc(C)cc2N)c2ncccc2c1] |
| 81 | 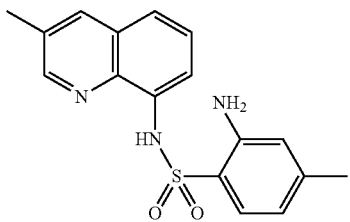 |
| 82 | 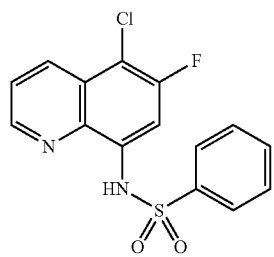 [SMILES: O=S(=O)(Nc1cc(F)c(Cl)c2cccnc12)c1ccccc1] |
| 83 | 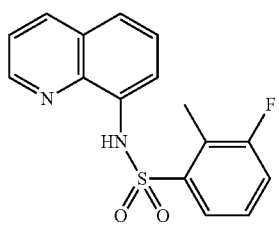 [SMILES: Cc1c(F)cccc1S(=O)(=O)Nc1cccc2cccnc12] |
| 84 | 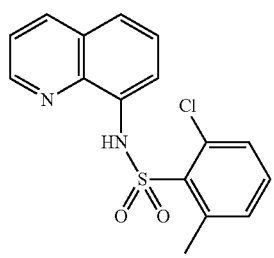 [SMILES: Cc1cccc(Cl)c1S(=O)(=O)Nc1cccc2cccnc12] |
| 85 | 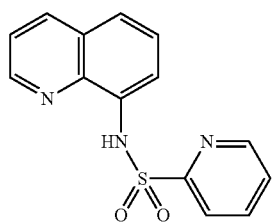 [SMILES: O=S(=O)(Nc1cccc2cccnc12)c1ccccn1] |
-continued
| Example Compound | |
|---|---|
| 86 | 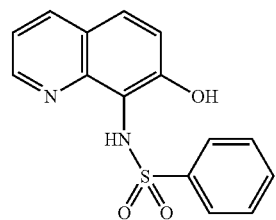 [SMILES: O=S(=O)(Nc1c(O)ccc2cccnc12)c1ccccc1] |
| 87 | 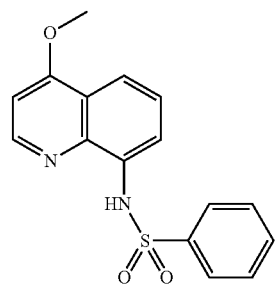 [SMILES: COc1ccnc2c(NS(=O)(=O)c3ccccc3)cccc12] |
| 88 | 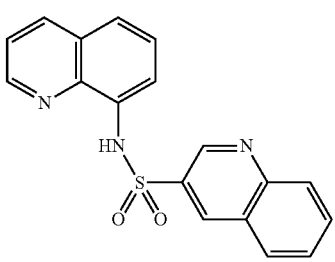 [SMILES: O=S(=O)(Nc1cccc2cccnc12)c1cnc2ccccc2c1] |
| 89 | 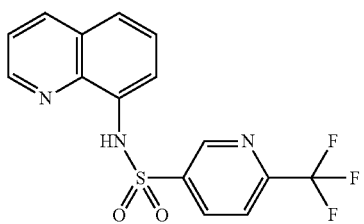 [SMILES: O=S(=O)(Nc1cccc2cccnc12)c1ccc(C(F)(F)F)nc1] |
| 90 | 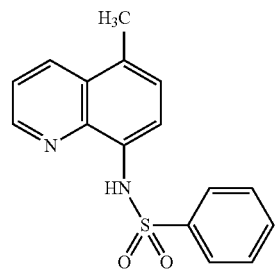 [SMILES: Cc1ccc(NS(=O)(=O)c2ccccc2)c2ncccc12] |
| 91 | 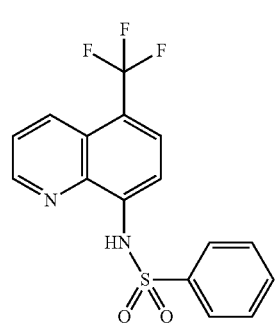 [SMILES: O=S(=O)(Nc1ccc(C(F)(F)F)c2cccnc12)c1ccccc1] |

| Example Compound | |
|---|---|
| 92 | 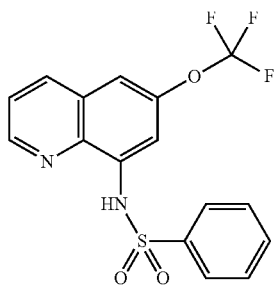 [SMILES: O=S(=O)(Nc1cc(OC(F)(F)F)cc2cccnc12)c1ccccc1] |
| 93 | 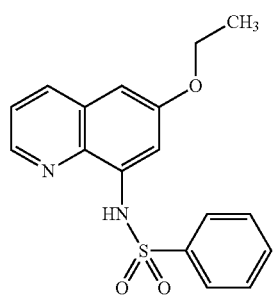 [SMILES: CCOc1cc(NS(=O)(=O)c2ccccc2)c2ncccc2c1] |
| 94 | 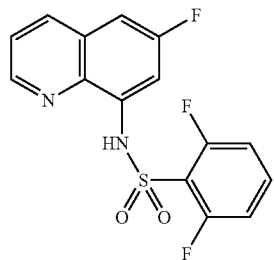 [SMILES: O=S(=O)(Nc1cc(F)cc2cccnc12)c1c(F)cccc1F] |
| 95 | 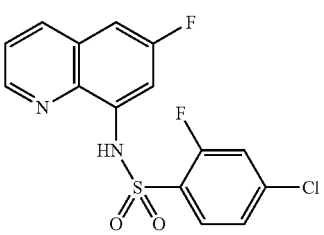 [SMILES: O=S(=O)(Nc1cc(F)cc2cccnc12)c1ccc(Cl)cc1F] |
| 96 | 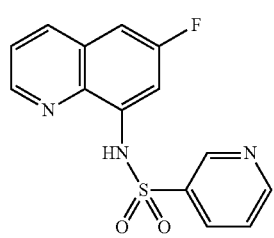 [SMILES: O=S(=O)(Nc1cc(F)cc2cccnc12)c1cccnc1] |
| Example Compound | |
|---|---|
| 97 | 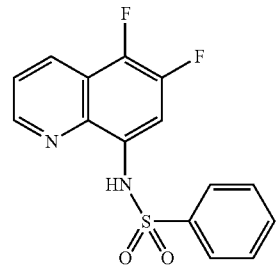 [SMILES: O=S(=O)(Nc1cc(F)c(F)c2cccnc12)c1ccccc1] |
| 98 | 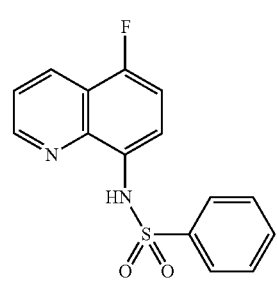 [SMILES: O=S(=O)(Nc1ccc(F)c2cccnc12)c1ccccc1] |
| 99 | 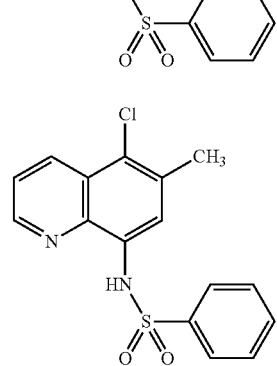 |
| 100 | 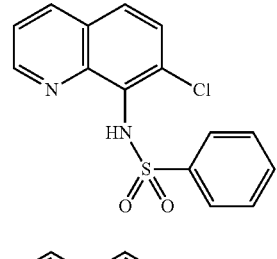 |
| 101 | 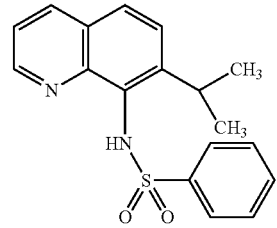 [SMILES: CC(C)c1ccc2cccnc2c1NS(=O)(=O)c1ccccc1] |
| 102 | 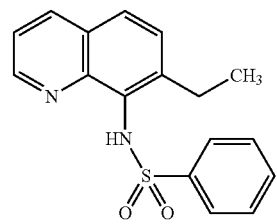 [SMILES: CCc1ccc2cccnc2c1NS(=O)(=O)c1ccccc1] |

-continued
Example Compound
103 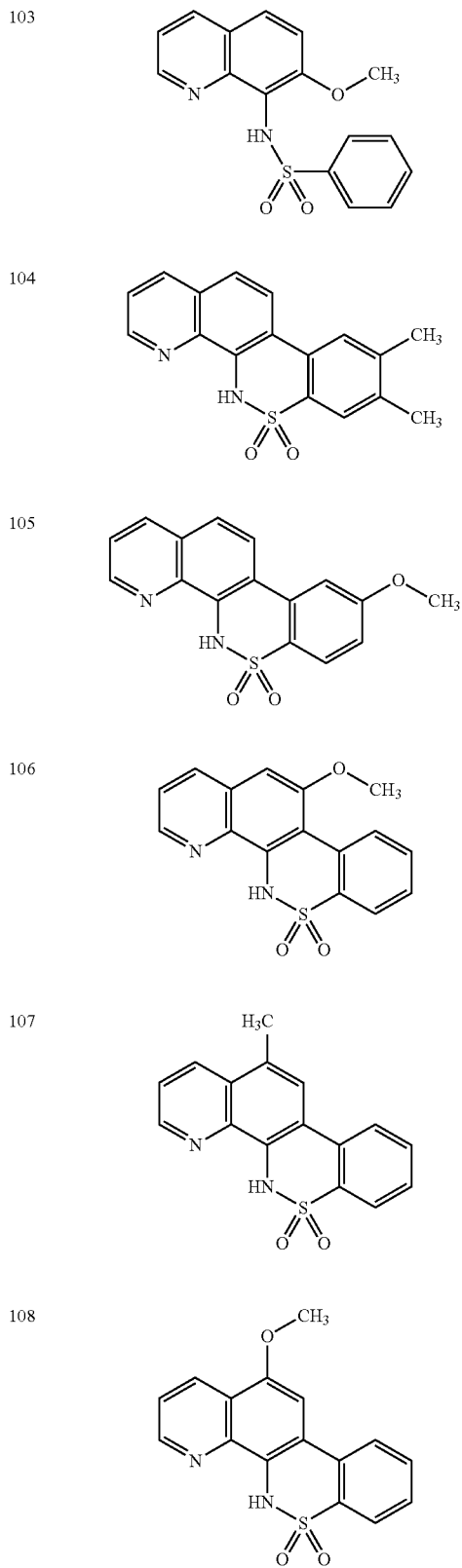
104
105
106
107
108
-continued
Example Compound
109 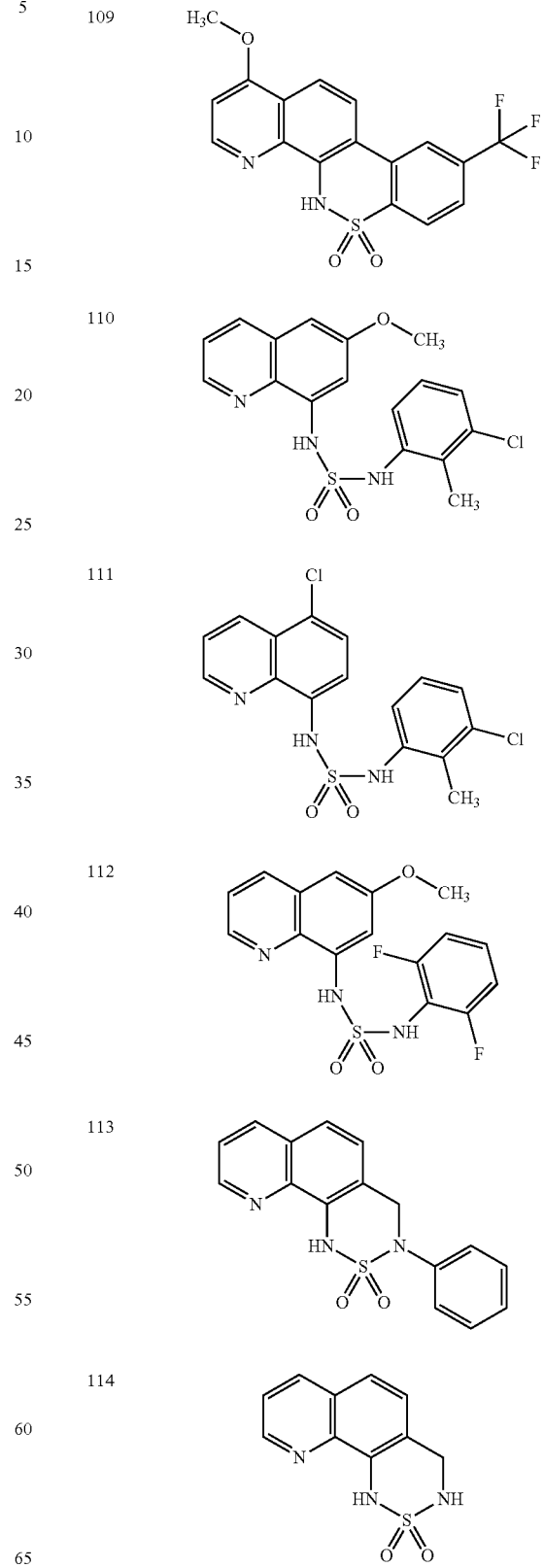
110
111
112
113
114

| Example Compound | | Example Compound | |
|---|---|---|---|
| 115 | 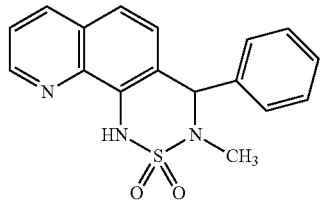 [SMILES: CN1C(c2ccccc2)c2ccc3cccnc3c2NS1(=O)=O] | 227 | 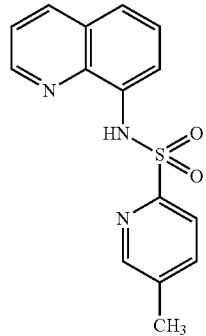 |
| 116 | 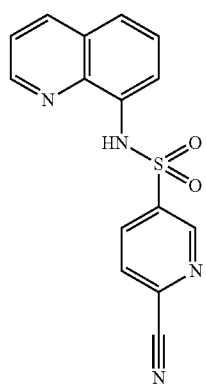 [SMILES: N#Cc1ccc(S(=O)(=O)Nc2cccc3cccnc23)cn1] | 228 | 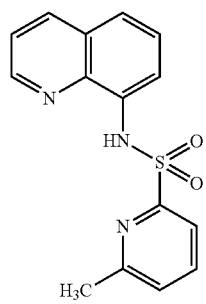 |
| 225 | 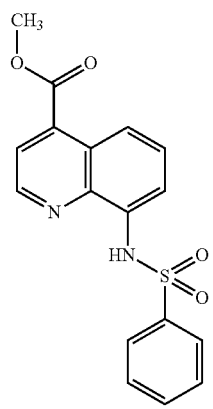 [SMILES: COC(=O)c1ccnc2c(NS(=O)(=O)c3ccccc3)cccc12] | 229 | 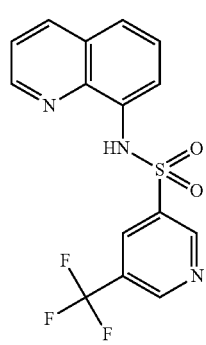 |
| 226 | 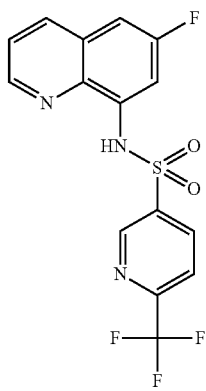 [SMILES: O=S(=O)(Nc1cc(F)cc2cccnc12)c1ccc(C(F)(F)F)nc1] | 230 | 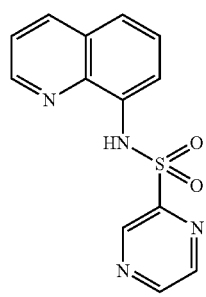 [SMILES: O=S(=O)(Nc1cccc2cccnc12)c1cnccn1] |
| | | 231 | 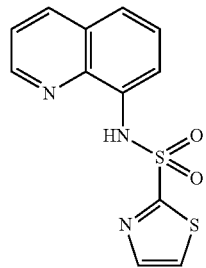 |

-continued
| Example Compound | |
|---|---|
| 232 | 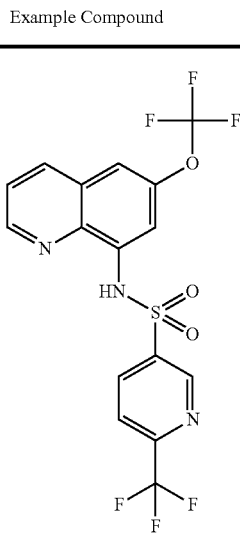 |
| 233 | 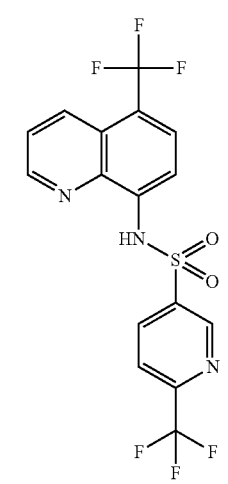 [SMILES: O=S(=O)(Nc1ccc(C(F)(F)F)c2cccnc12)c1ccc(C(F)(F)F)nc1] |
| 234 | 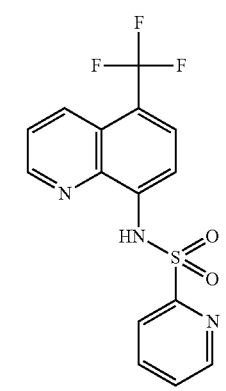 |
-continued
| Example Compound | |
|---|---|
| 235 | 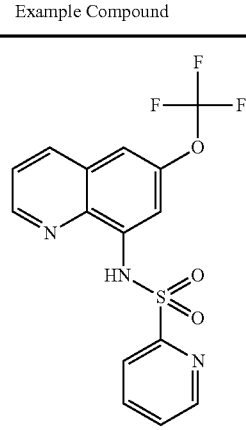 |
| 236 | 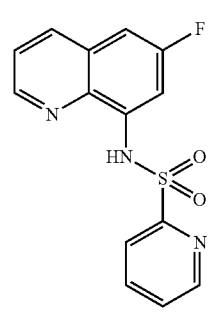 [SMILES: O=S(=O)(Nc1cc(F)cc2cccnc12)c1ccccn1] |
| 237 | 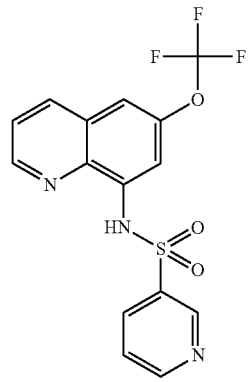 [SMILES: O=S(=O)(Nc1cc(OC(F)(F)F)cc2cccnc12)c1cccnc1] |
| 238 | 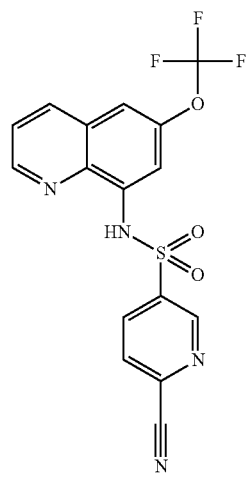 [SMILES: N#Cc1ccc(S(=O)(=O)Nc2cc(OC(F)(F)F)cc3cccnc23)cn1] |

TABLE -continued
| Example Compound | |
|---|---|
| 239 | 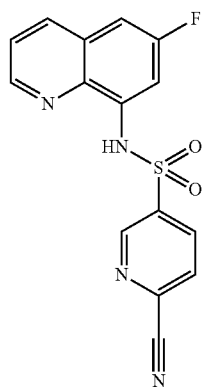 |
| 240 | 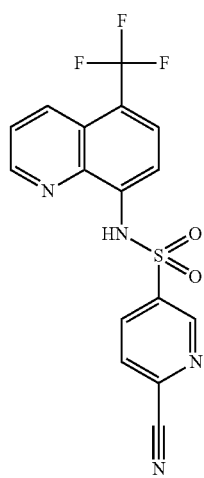 [SMILES: N#Cc1ccc(S(=O)(=O)Nc2ccc(C(F)(F)F)c3cccnc23)cn1] |
| 305 | 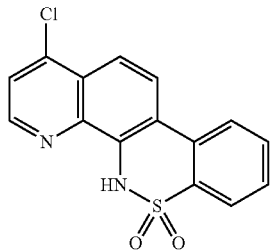 [SMILES: O=S1(=O)Nc2c(ccc3c(Cl)ccnc23)-c2ccccc21] |
| 306 | 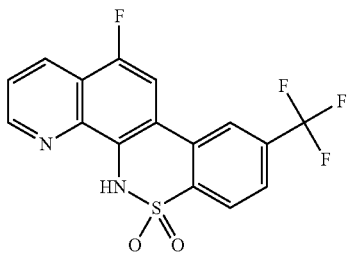 |
| 307 | 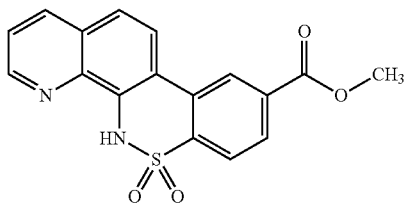 [SMILES: COC(=O)c1ccc2c(c1)-c1ccc3cccnc3c1NS2(=O)=O] |
| 308 | 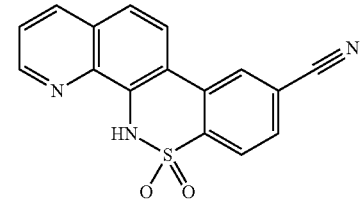 |
| 309 | 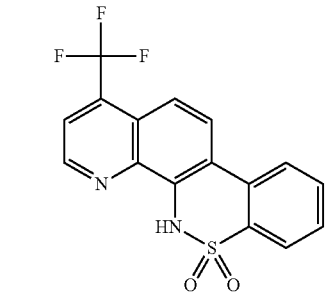 [SMILES: O=S1(=O)Nc2c(ccc3c(C(F)(F)F)ccnc23)-c2ccccc21] |
| 310 | 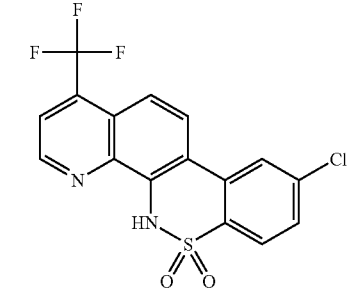 [SMILES: O=S1(=O)Nc2c(ccc3c(C(F)(F)F)ccnc23)-c2cc(Cl)ccc21] |
| 311 | 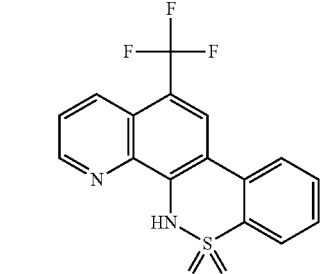 |
| 312 | 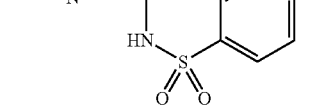 |

-continued
| Example Compound | | Example Compound | |
|---|---|---|---|
| 313 | 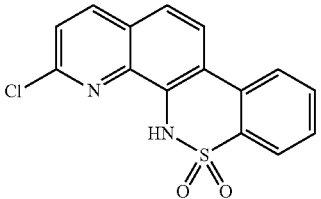 [SMILES: O=S1(=O)Nc2c(ccc3ccc(Cl)nc23)-c2ccccc21] | 319 | 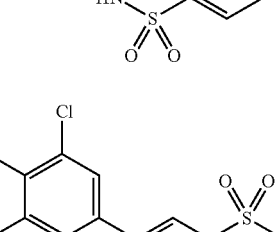 |
| 314 | 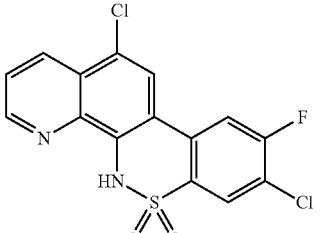 | 321 | 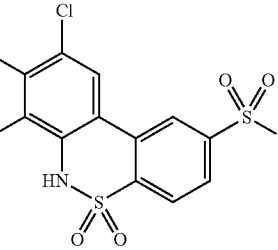 |
| 315 | 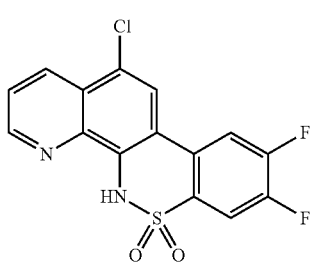 | 323 | 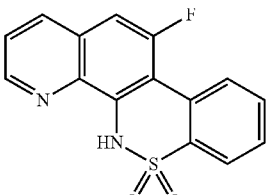 |
| 316 | 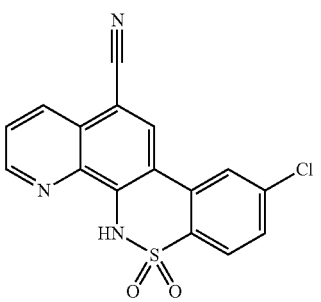 [SMILES: N#Cc1cc2c(c3ncccc13)NS(=O)(=O)c1ccc(Cl)cc1-2] | 324 | 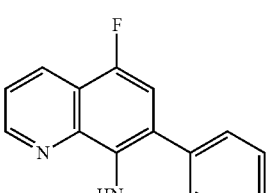 |
| 317 | 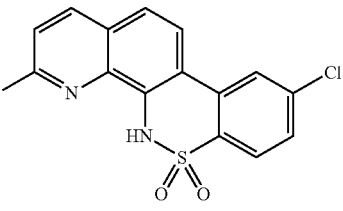 | 325 | 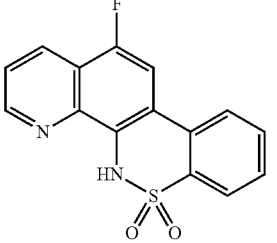 |
| 318 | 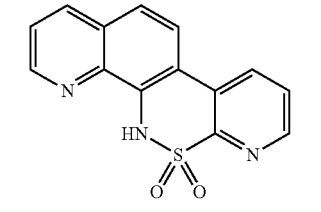 [SMILES: O=S1(=O)Nc2c(ccc3cccnc23)-c2cccnc21] | 326 | 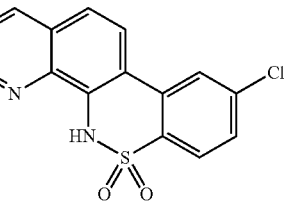 |

| Example Compound | | Example Compound | |
|---|---|---|---|
| 327 | 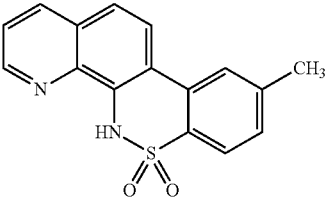 [SMILES: Cc1ccc2c(c1)-c1ccc3cccnc3c1NS2(=O)=O] | 334 | 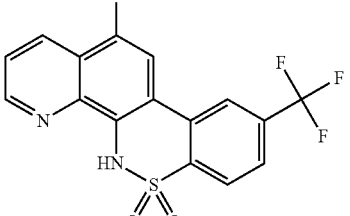 |
| 328 | 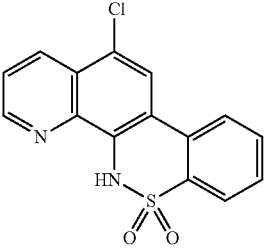 [SMILES: O=S1(=O)Nc2c(cc(Cl)c3cccnc23)-c2ccccc21] | 335 | 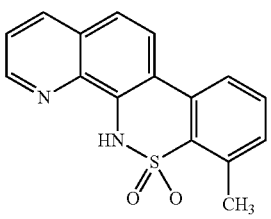 |
| 329 | 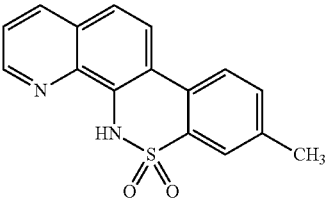 [SMILES: Cc1ccc2c(c1)S(=O)(=O)Nc1c-2ccc2cccnc12] | 382 | 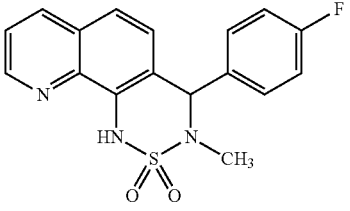 |
| 330 | 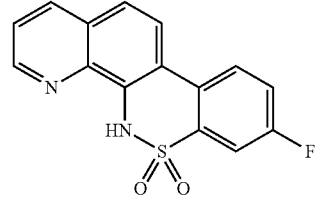 [SMILES: O=S1(=O)Nc2c(ccc3cccnc23)-c2ccc(F)cc21] | 383 | 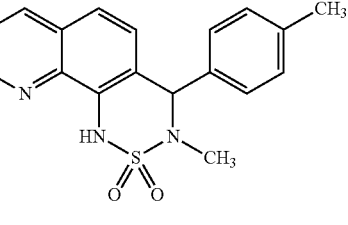 |
| 331 | 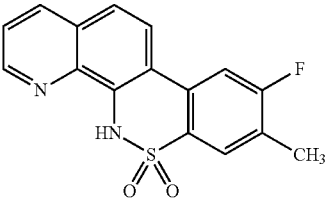 [SMILES: Cc1cc2c(cc1F)-c1ccc3cccnc3c1NS2(=O)=O] | 384 | 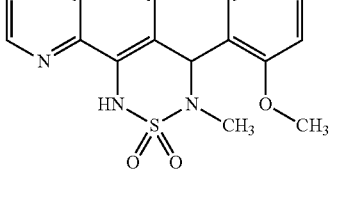 |
| 332 | 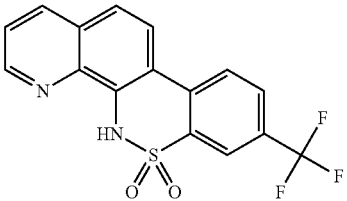 [SMILES: O=S1(=O)Nc2c(ccc3cccnc23)-c2ccc(C(F)(F)F)cc21] | 385 | 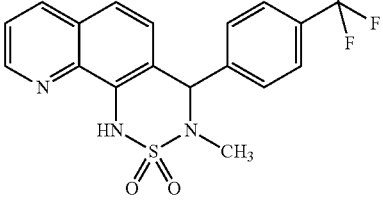 |
| 333 | 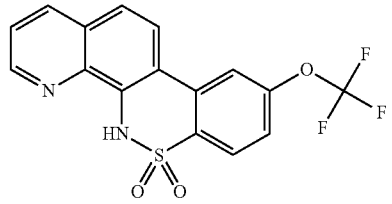 [SMILES: O=S1(=O)Nc2c(ccc3cccnc23)-c2cc(OC(F)(F)F)ccc21] | | |

TABLE -continued

| Example Compound |
|---|
| 386 |
| 387 |
| 388 |
| 389 |
| 390 |
| 391 |
| 392 |
| 393 |
| 394 |
| 395 |
| 396 |
| 398 |

TABLE-continued
Example Compound
399 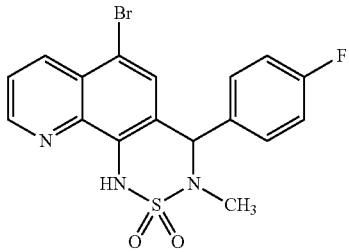 [SMILES: CN1C(c2ccc(F)cc2)c2cc(Br)c3cccnc3c2NS1(=O)=O]
401 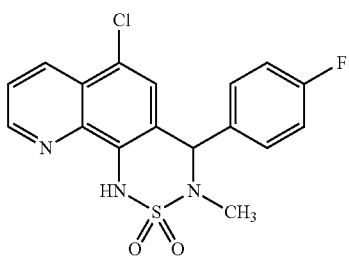 [SMILES: CN1C(c2ccc(F)cc2)c2cc(Cl)c3cccnc3c2NS1(=O)=O]
402 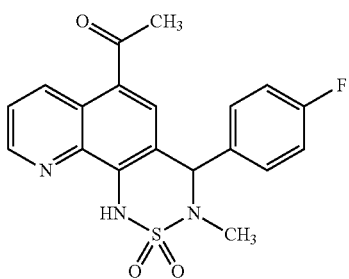 [SMILES: CC(=O)c1cc2c(c3ncccc13)NS(=O)(=O)N(C)C2c1ccc(F)cc1]
403 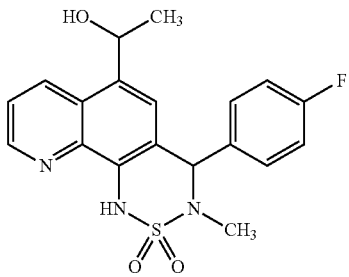 [SMILES: CC(O)c1cc2c(c3ncccc13)NS(=O)(=O)N(C)C2c1ccc(F)cc1]
405 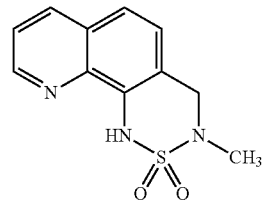 [SMILES: CN1Cc2ccc3cccnc3c2NS1(=O)=O]
407 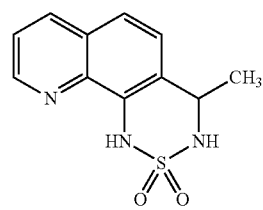 [SMILES: CC1NS(=O)(=O)Nc2c1ccc1cccnc21]
412 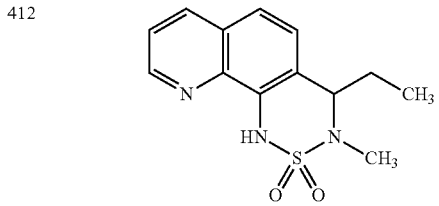
413 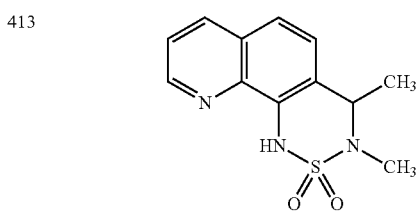
416 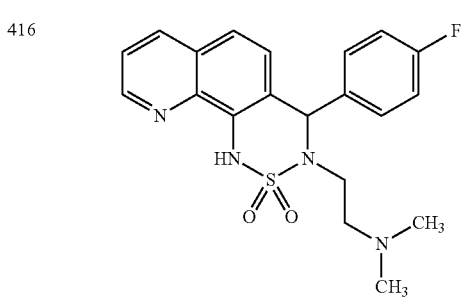
424 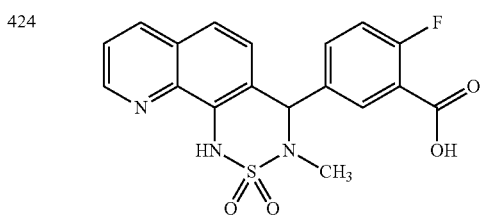
425 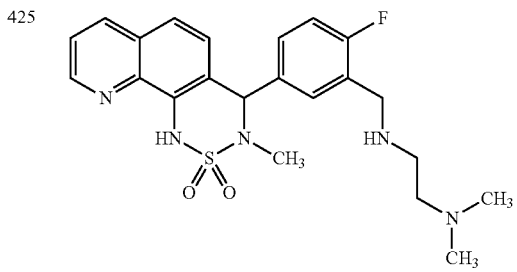
426 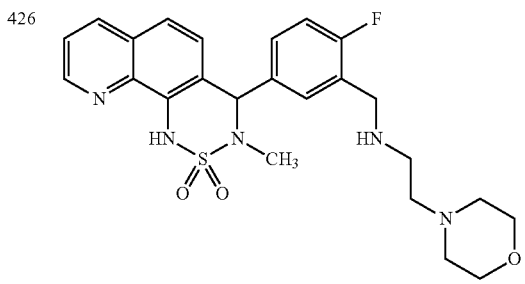

TABLE-continued
| Example Compound | | Example Compound | |
|---|---|---|---|
| 427 | 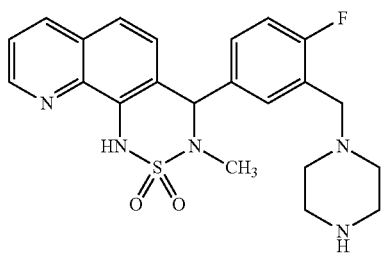 [SMILES: CN1C(c2ccc(F)c(CN3CCNCC3)c2)c2ccc3cccnc3c2NS1(=O)=O] | 492 | 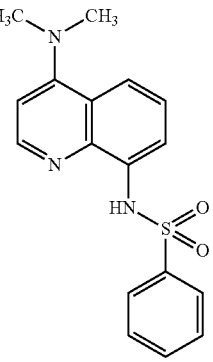 |
| 428 | 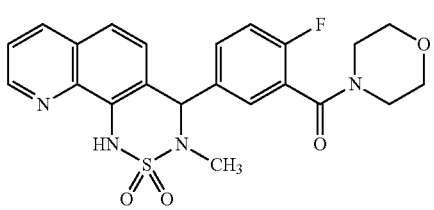 [SMILES: CN1C(c2ccc(F)c(C(=O)N3CCOCC3)c2)c2ccc3cccnc3c2NS1(=O)=O] | 493 | 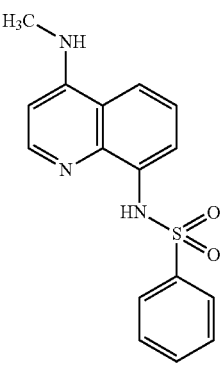 |
| 429 | 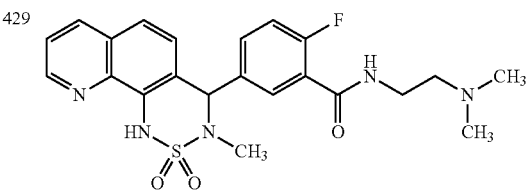 | 494 | 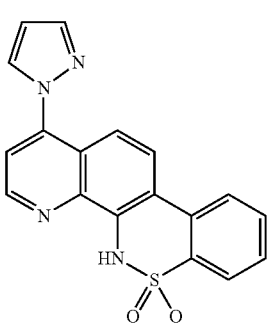 |
| 490 | 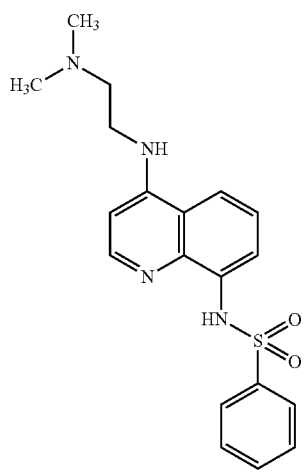 [SMILES: CN(C)CCNc1ccnc2c(NS(=O)(=O)c3ccccc3)cccc12] | 495 | 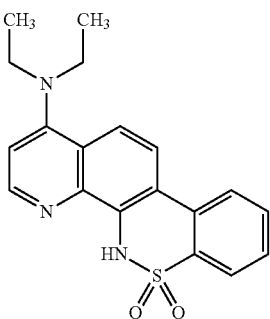 [SMILES: CCN(CC)c1ccnc2c3c(ccc12)-c1ccccc1S(=O)(=O)N3] |
| 491 | 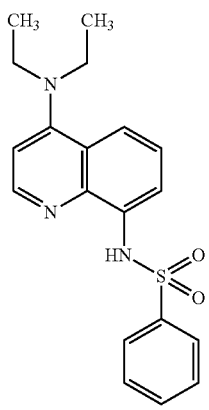 | | |

-continued

| Example Compound | | Example Compound |
|---|---|---|
| 496 | | 504 |
| 497 | | 505 |
| 498 | | 506 |
| 499 | | 507 |
| 502 | | 508 |
| | | 509 |

-continued
Example Compound
510 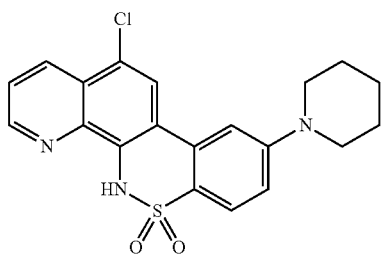 [SMILES: O=S1(=O)Nc2c(cc(Cl)c3cccnc23)-c2cc(N3CCCCC3)ccc21]
511 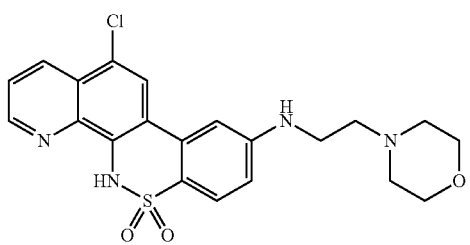 [SMILES: O=S1(=O)Nc2c(cc(Cl)c3cccnc23)-c2cc(NCCN3CCOCC3)ccc21]
512 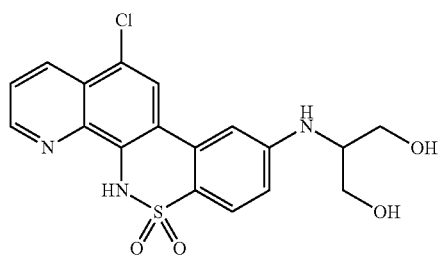 [SMILES: O=S1(=O)Nc2c(cc(Cl)c3cccnc23)-c2cc(NC(CO)CO)ccc21]
514 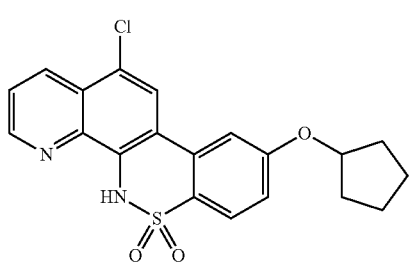 [SMILES: O=S1(=O)Nc2c(cc(Cl)c3cccnc23)-c2cc(OC3CCCC3)ccc21]
515 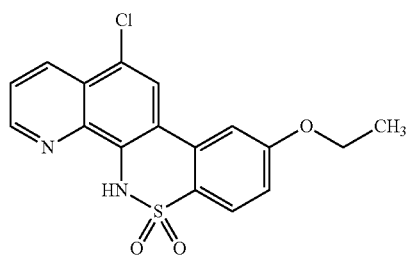 [SMILES: CCOc1ccc2c(c1)-c1cc(Cl)c3cccnc3c1NS2(=O)=O]
516 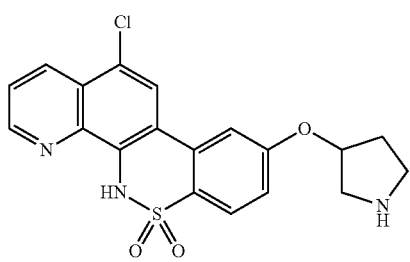 [SMILES: O=S1(=O)Nc2c(cc(Cl)c3cccnc23)-c2cc(OC3CCNC3)ccc21]
-continued
Example Compound
517 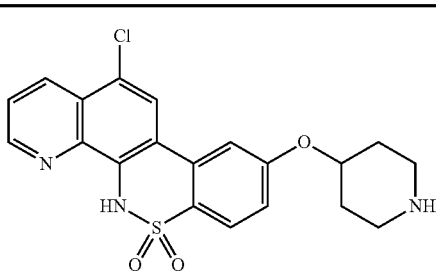
518 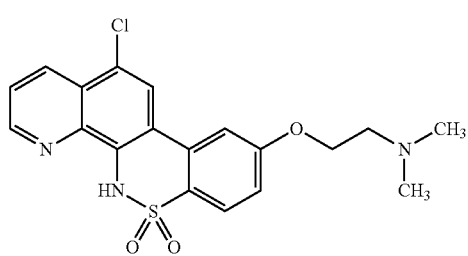 [SMILES: CN(C)CCOc1ccc2c(c1)-c1cc(Cl)c3cccnc3c1NS2(=O)=O]
519 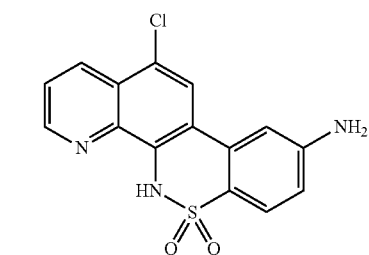 [SMILES: Nc1ccc2c(c1)-c1cc(Cl)c3cccnc3c1NS2(=O)=O]
520 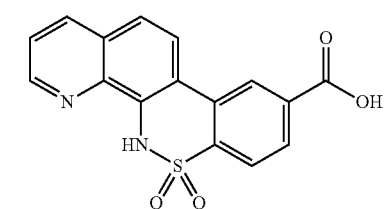 [SMILES: O=C(O)c1ccc2c(c1)-c1ccc3cccnc3c1NS2(=O)=O]
521 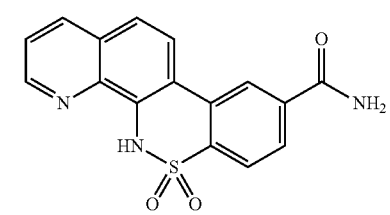 [SMILES: NC(=O)c1ccc2c(c1)-c1ccc3cccnc3c1NS2(=O)=O]
522 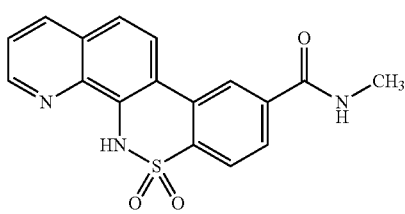

-continued
| Example Compound | | Example Compound | |
|---|---|---|---|
| 525 | 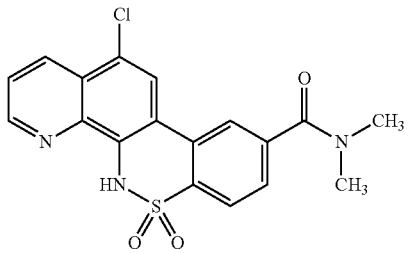 | 531 | 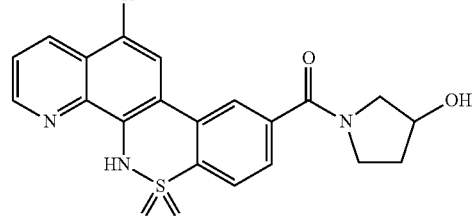 |
| 526 | 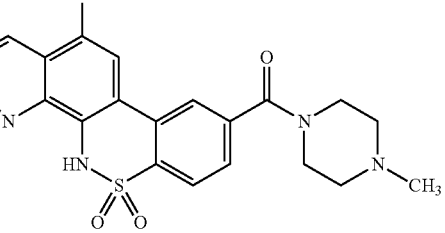 | 562 | 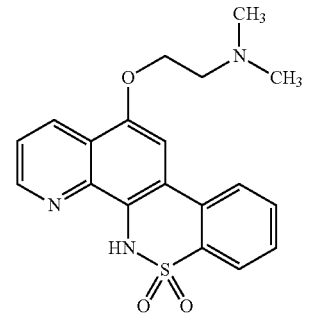 [SMILES: CN(C)CCOc1cc2c(c3ncccc13)NS(=O)(=O)c1ccccc1-2] |
| 527 | 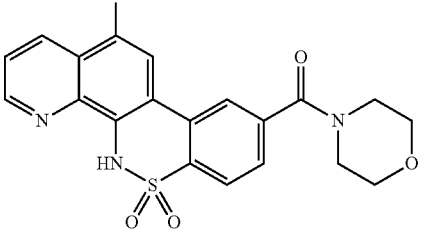 | 532 | 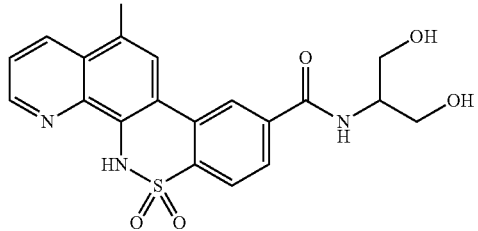 |
| 528 | 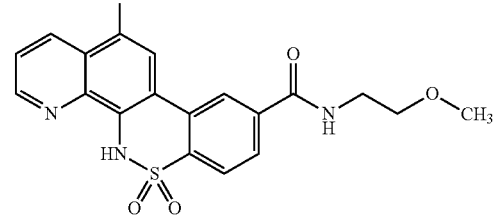 | 533 | 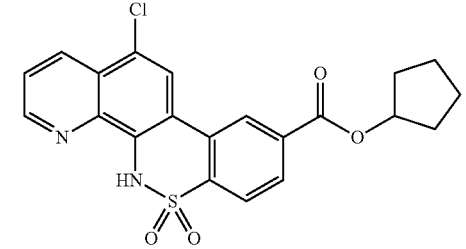 [SMILES: O=C(OC1CCCC1)c1ccc2c(c1)-c1cc(Cl)c3cccnc3c1NS2(=O)=O] |
| 529 | 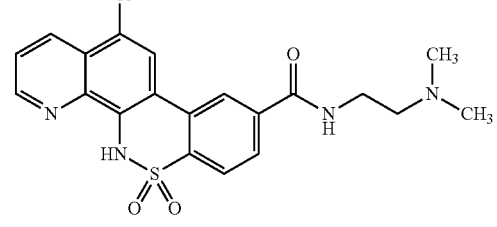 | 536 | 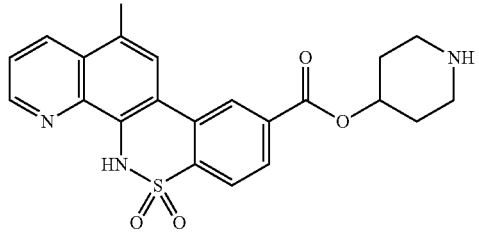 |
| 530 | 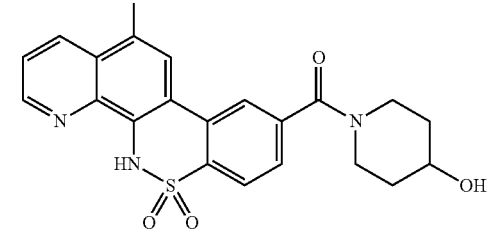 | | |

-continued

| Example Compound |
|---|
| 537 (chemical structure) |
| 538 (chemical structure) |
| 539 (chemical structure) |
| 541 (chemical structure) |

-continued

| Example Compound |
|---|
| 542 (chemical structure) |
| 543 (chemical structure) |
| 544 (chemical structure) |
| 545 (chemical structure) |

-continued
Example Compound
546
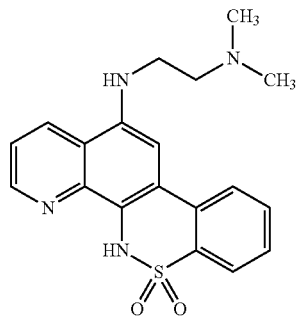 [SMILES: CN(C)CCNc1cc2c(c3ncccc13)NS(=O)(=O)c1ccccc1-2]
547
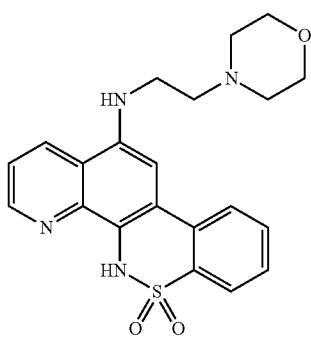 [SMILES: O=S1(=O)Nc2c(cc(NCCN3CCOCC3)c3cccnc23)-c2ccccc21]
548
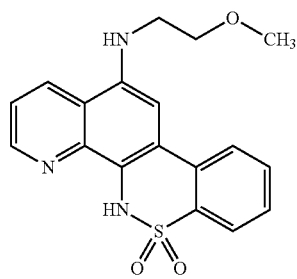
549
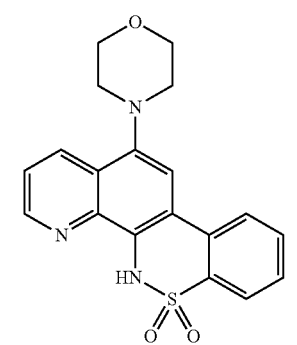
-continued
Example Compound
550
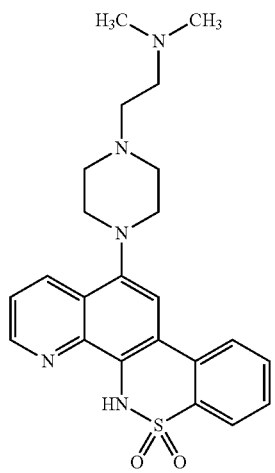
551
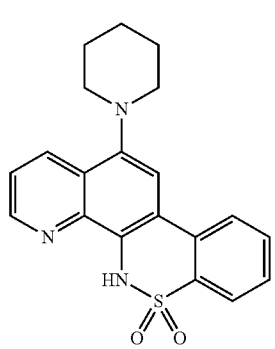 [SMILES: O=S1(=O)Nc2c(cc(N3CCCCC3)c3cccnc23)-c2ccccc21]
552
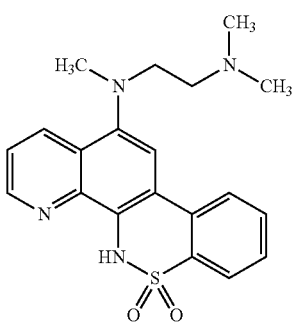 [SMILES: CN(C)CCN(C)c1cc2c(c3ncccc13)NS(=O)(=O)c1ccccc1-2]
553
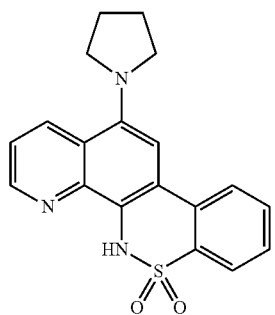 [SMILES: O=S1(=O)Nc2c(cc(N3CCCC3)c3cccnc23)-c2ccccc21]

| Example Compound | | Example Compound | |
|---|---|---|---|
| 554 | 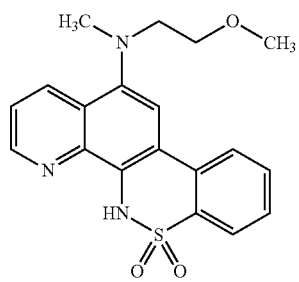 [SMILES: COCCN(C)c1cc2c(c3ncccc13)NS(=O)(=O)c1ccccc1-2] | 561 | 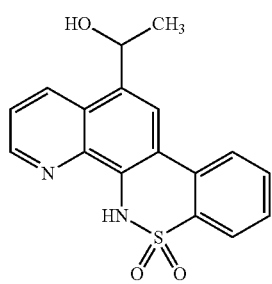 |
| 555 | 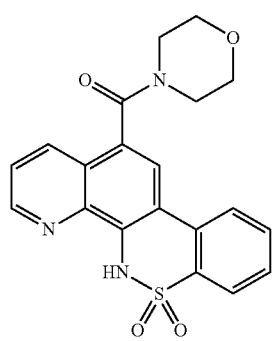 [SMILES: O=C(c1cc2c(c3ncccc13)NS(=O)(=O)c1ccccc1-2)N1CCOCC1] | 568 | 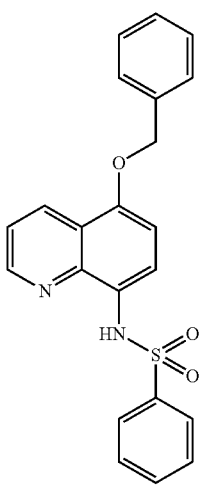 |
| 556 | 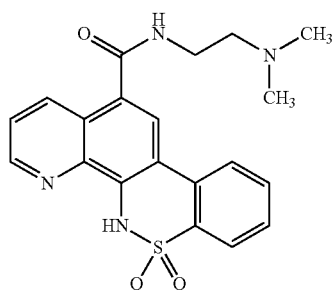 | 572 | 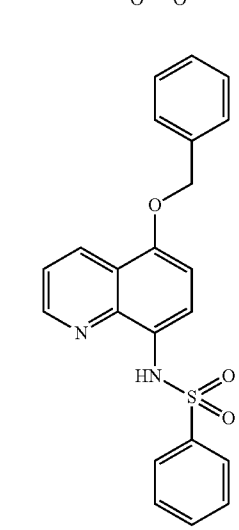 |
| 557 | 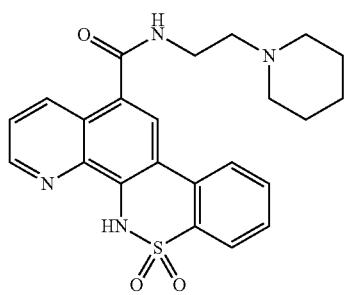 [SMILES: O=C(NCCN1CCCCC1)c1cc2c(c3ncccc13)NS(=O)(=O)c1ccccc1-2] | 584 | 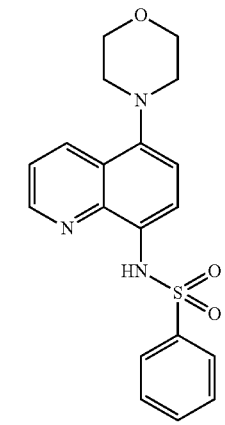 |
| 560 | 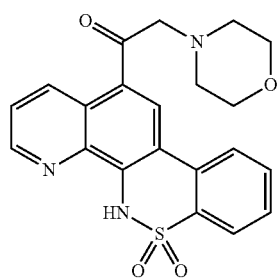 [SMILES: O=C(CN1CCOCC1)c1cc2c(c3ncccc13)NS(=O)(=O)c1ccccc1-2] | | |

| Example Compound | |
|---|---|
| 589 | 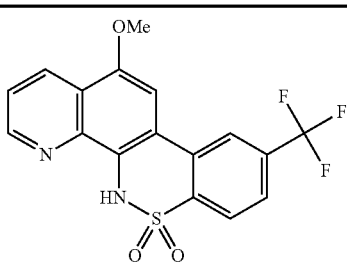 |

The compounds of the general structural formula (I), (Ia) and (Ib) respectively, according to the present invention, comprise pharmaceutically acceptable salts thereof.

A further aspect of the present invention is directed to the new compounds according to the general formula (Ib)

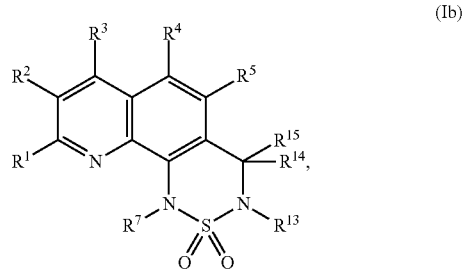

(Ib)

with the substituent definition according to one or more of the aforementioned embodiments. Preferably such new compounds are selected from the compounds as defined in the aforementioned table with the example compounds Nos.: 113, 114, 115, 382, 383, 384, 385, 386, 387, 388, 389, 390, 391, 392, 393, 394, 395, 396, 398, 399, 401, 402, 403, 405, 407, 412, 413, 416, 424, 425, 426, 427, 428, and 429.

A further aspect of the present invention relates to the new compounds according to the generals formula (Ib) and preferably of the new compounds Nos.: 113, 114, 115, 382, 383, 384, 385, 386, 387, 388, 389, 390, 391, 392, 393, 394, 395, 396, 398, 399, 401, 402, 403, 405, 407, 412, 413, 416, 424, 425, 426, 427, 428, and 429 as described herein for the use as a medicament.

In principle, in the context of the present invention it is possible to combine the individual preferred, more preferred or particularly preferred meanings for the substituents $R^1$ to $R^{15}$ and X with one another. That is to say that the present invention includes compounds of the general formula (I), (Ia) and (Ib) respectively in which, for example, the substituents $R^1$ to $R^5$ and $R^7$ have the general meaning and the substituents $R^6$ and $R^8$ and X have a preferred meaning or the substituents $R^1$ to $R^5$ and $R^7$ have a preferred meaning and the substituents $R^6$ and $R^8$ and X have the general meaning etc.

Depending on their structure, if asymmetric carbon atoms are present the compounds according to the invention can exist in stereoisomeric forms (enantiomers, diastereomers). The invention therefore includes the use of the enantiomers or diastereomers and their particular mixtures. The enantiomerically pure forms can optionally be obtained by conventional processes of optical resolution, such as by fractional crystallization of diastereomers therefrom by reaction with optically active compounds. If the compounds according to the invention can occur in tautomeric forms, the present invention includes the use of all the tautomeric forms.

The compounds provided according to the invention can be present as mixtures of various possible isomeric forms, in particular of stereoisomers, such as e.g. E and Z, syn and anti, and optical isomers. Both the E and the Z isomers and the optical isomers, and any desired mixtures of these isomers are claimed.

The compounds according to the invention of the general structural formula (I) can in principle be obtained by the processes explained in the following synthesis routes with preferred process parameters and the definition of the abbreviations being presented in the examples below.

The numbering of the "general procedures" as described herein is not applied continuously and thus e.g. general procedures nos. 1, 2, 6 and 7 do not exist herein. The same holds true for the numbering of the "synthesis routes" nos. 23 to 26, which are not presented herein.

The meaning of the substituents $R^1$ to $R^{15}$ as far as mentioned herein is consistent with the meaning according to the present invention. Concrete embodiments comprising compounds with selected substituents are presented in the examples below.

Synthesis Route 1:

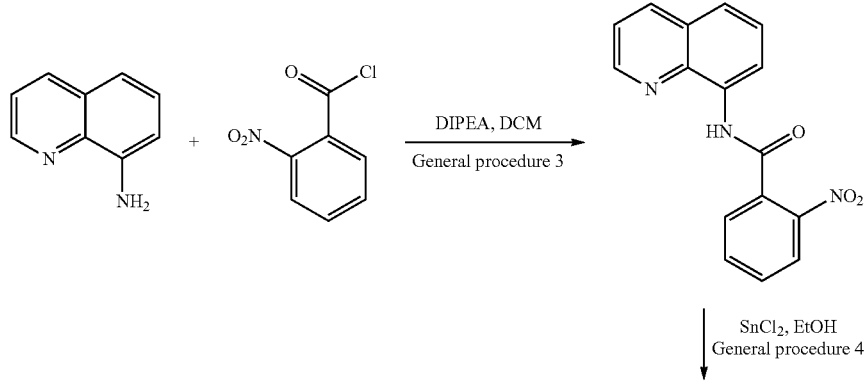

-continued
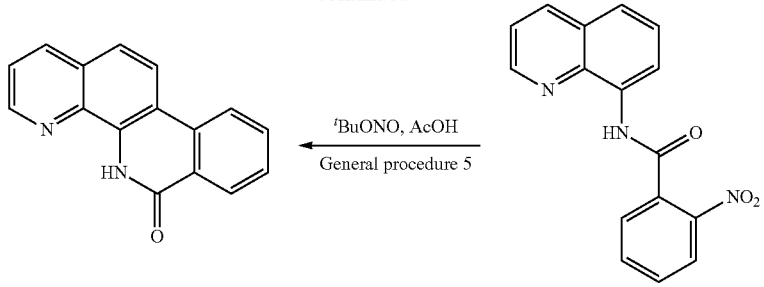
Synthesis Route 2:
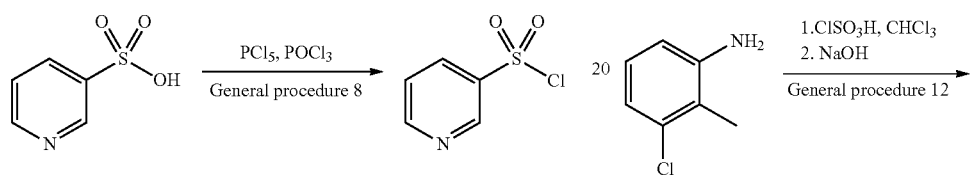
Synthesis Route 3:
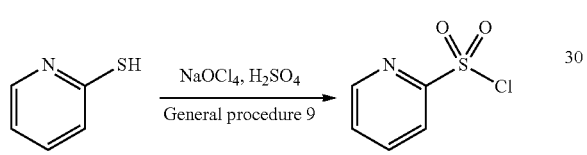
Synthesis Route 3a:
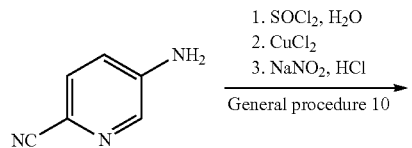
Synthesis Route 4:
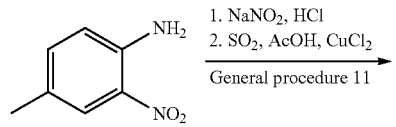
Synthesis Route 5:
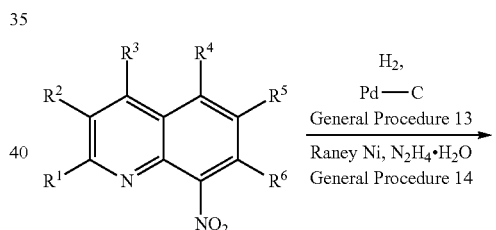
Synthesis Route 6:
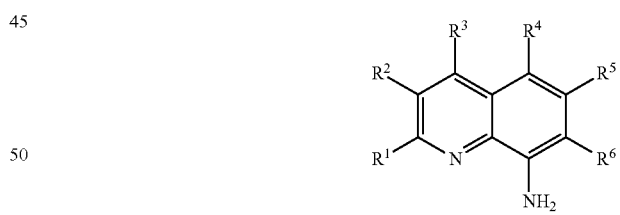
with the meaning of $R^1$ to $R^6$ as defined in the present invention
Synthesis Route 7:
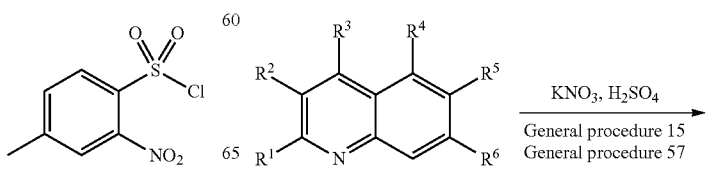

-continued
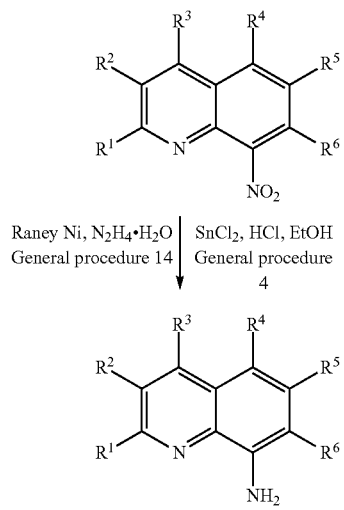
with the meaning of $R^1$ to $R^6$ as defined in the present invention
Synthesis Route 8:
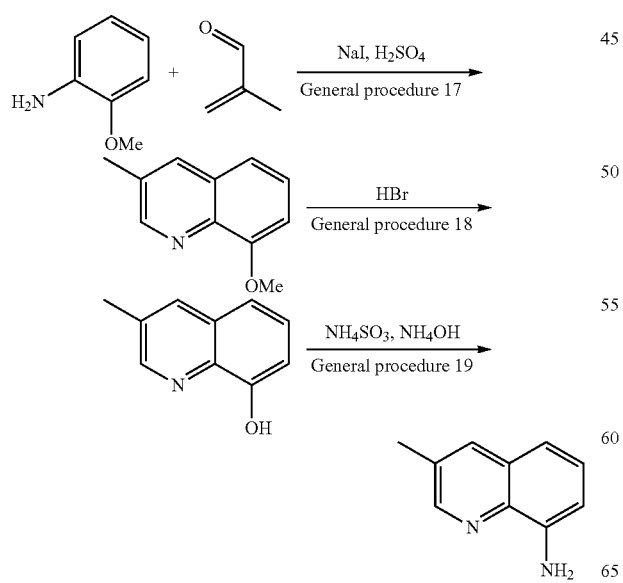
Synthesis Route 9:
Synthesis Route 10:
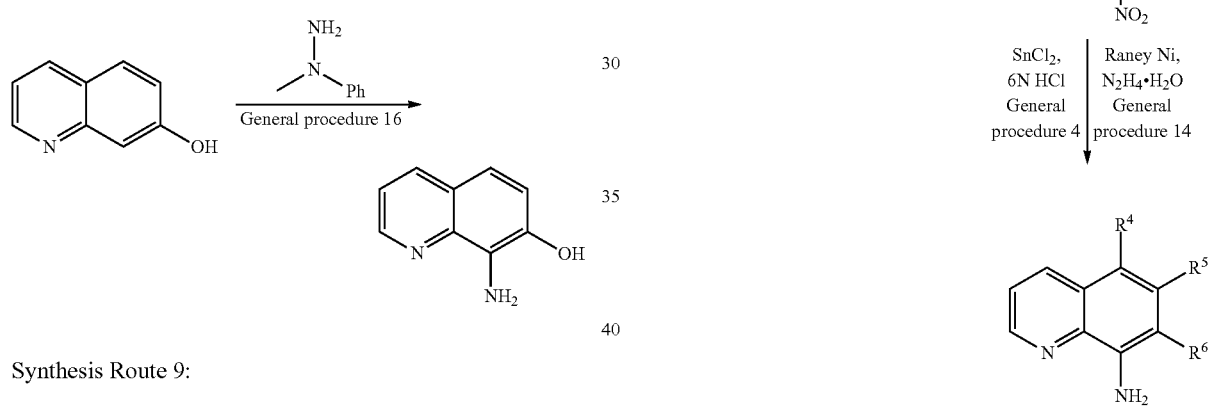
with the meaning of $R^4$ to $R^6$ as defined in the present invention
Synthesis Route 11:
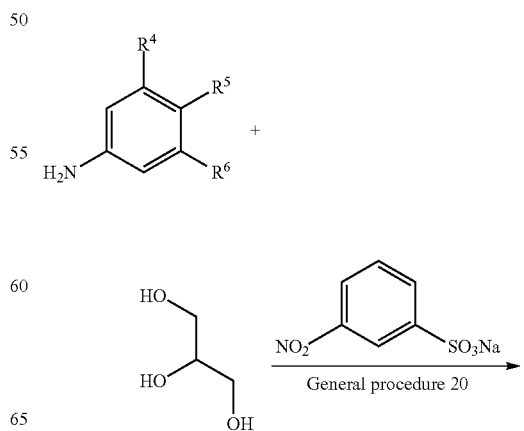

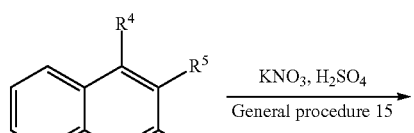
Synthesis Route 13:
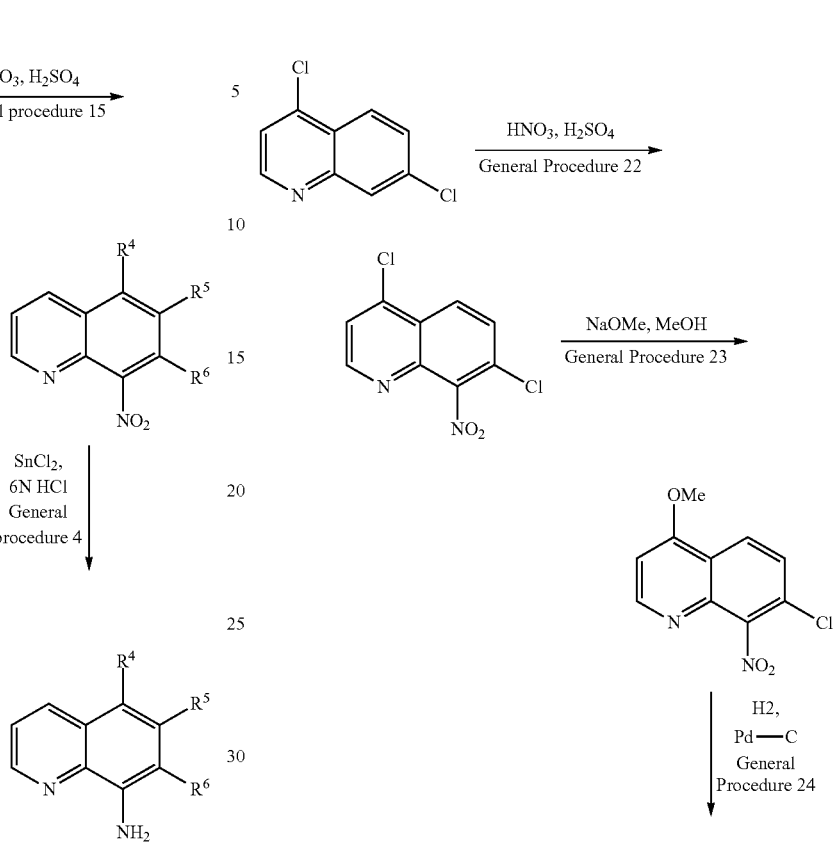
with the meaning of $R^4$ to $R^6$ as defined in the present invention
Synthesis Route 12:
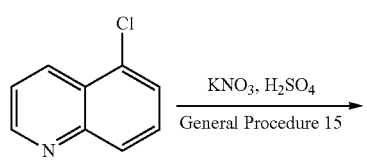
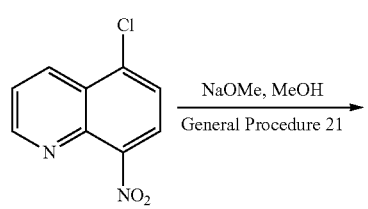
Synthesis Route 14:
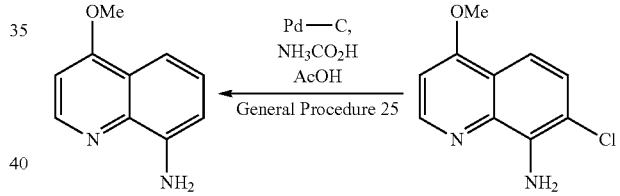
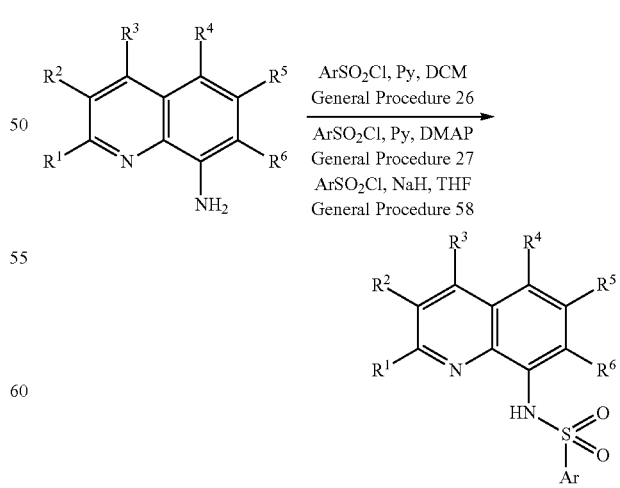
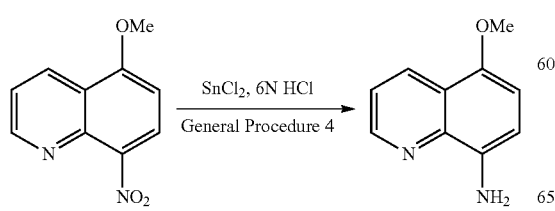
with the meaning of $R^1$ to $R^6$ as defined in the present invention.

Synthesis Route 15:

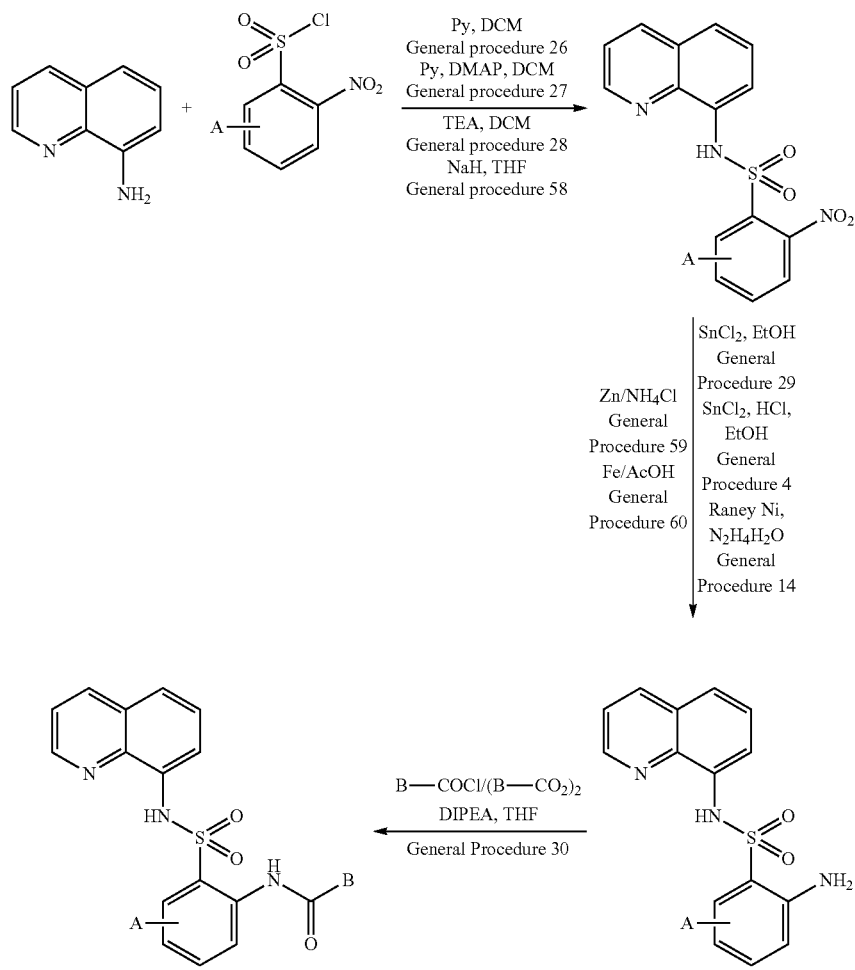

with the substituent A being selected from a suitable aryl-substituent as defined in the present invention and with the substituent B being particularly selected from an alkyl-group to form a suitable acyl-, particularly a suitable acyl-amino group as defined in the present invention.

Synthesis Route 16:

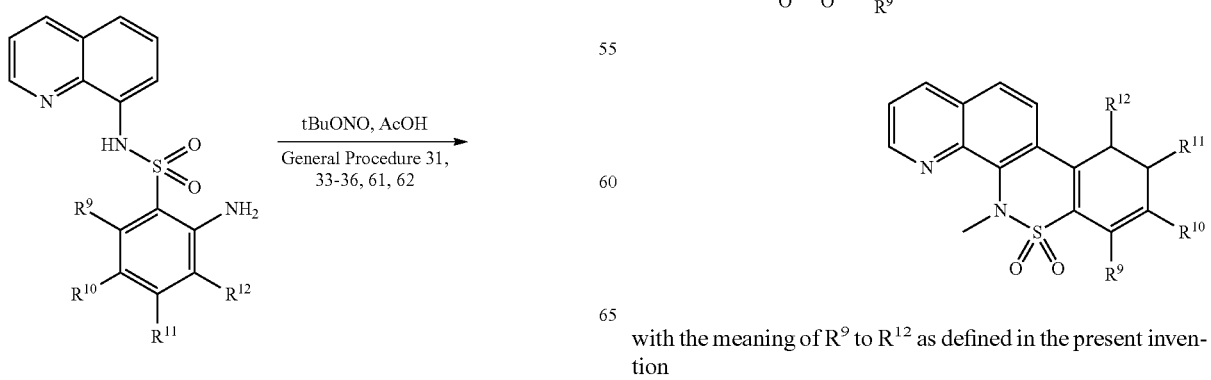

with the meaning of $R^9$ to $R^{12}$ as defined in the present invention

Synthesis Route 17:
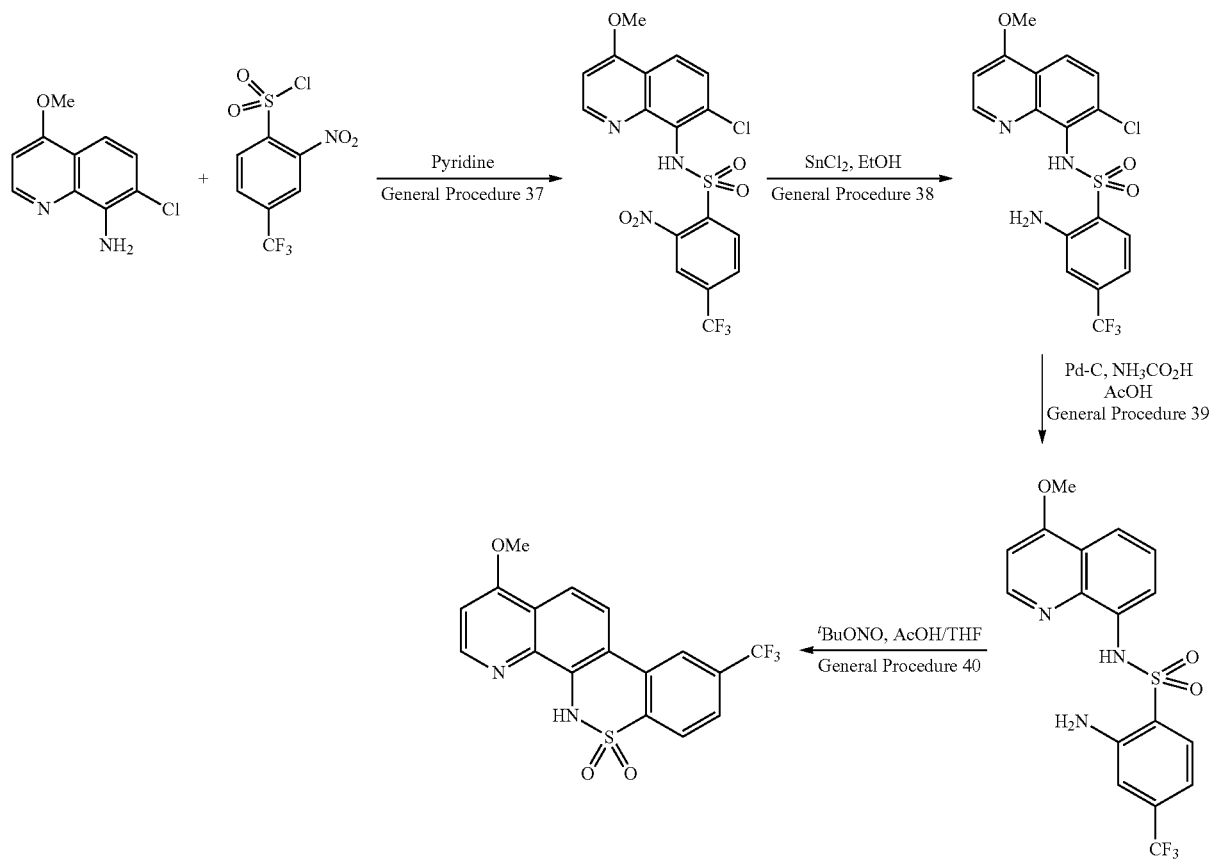 [SMILES: COc1ccnc2c(N)c(Cl)ccc12 ; O=[N+]([O-])c1cc(C(F)(F)F)ccc1S(=O)(=O)Cl ; COc1ccnc2c(NS(=O)(=O)c3ccc(C(F)(F)F)cc3[N+](=O)[O-])c(Cl)ccc12 ; COc1ccnc2c(NS(=O)(=O)c3ccc(C(F)(F)F)cc3N)c(Cl)ccc12 ; COc1ccnc2c3c(ccc12)-c1cc(C(F)(F)F)ccc1S(=O)(=O)N3 ; COc1ccnc2c(NS(=O)(=O)c3ccc(C(F)(F)F)cc3N)cccc12]
Synthesis Route 18:
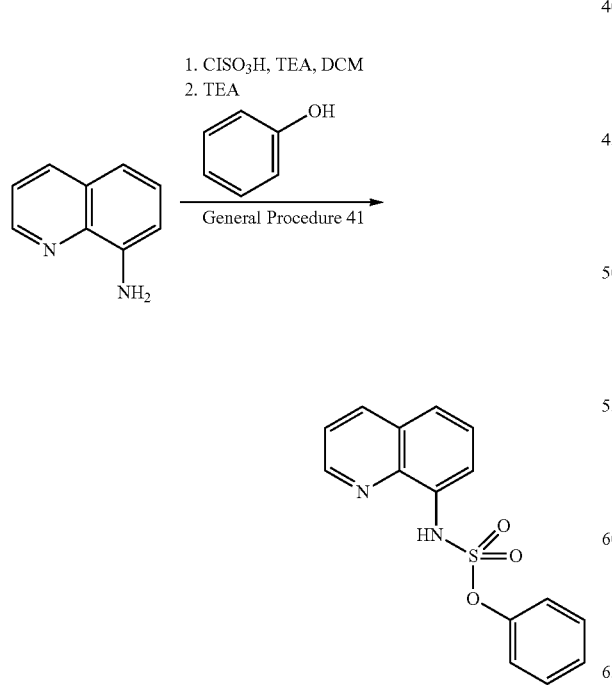
Synthesis Route 19:
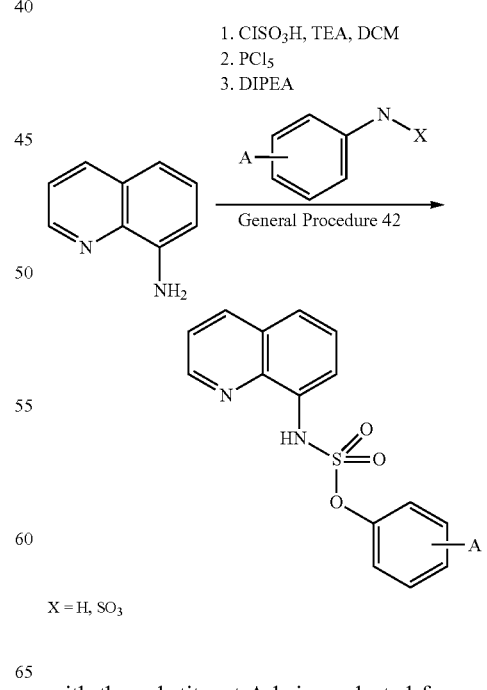
X = H, SO₃
with the substituent A being selected from a suitable aryl-substituent as defined in the present invention and Synthesis Route 20:
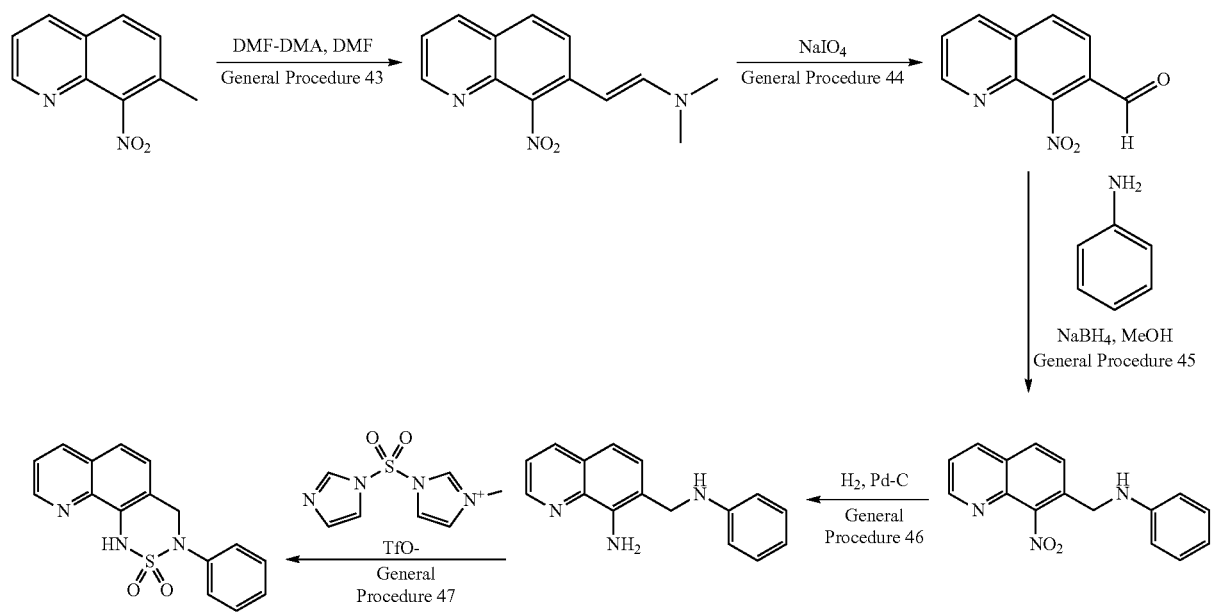
Synthesis Route 21:
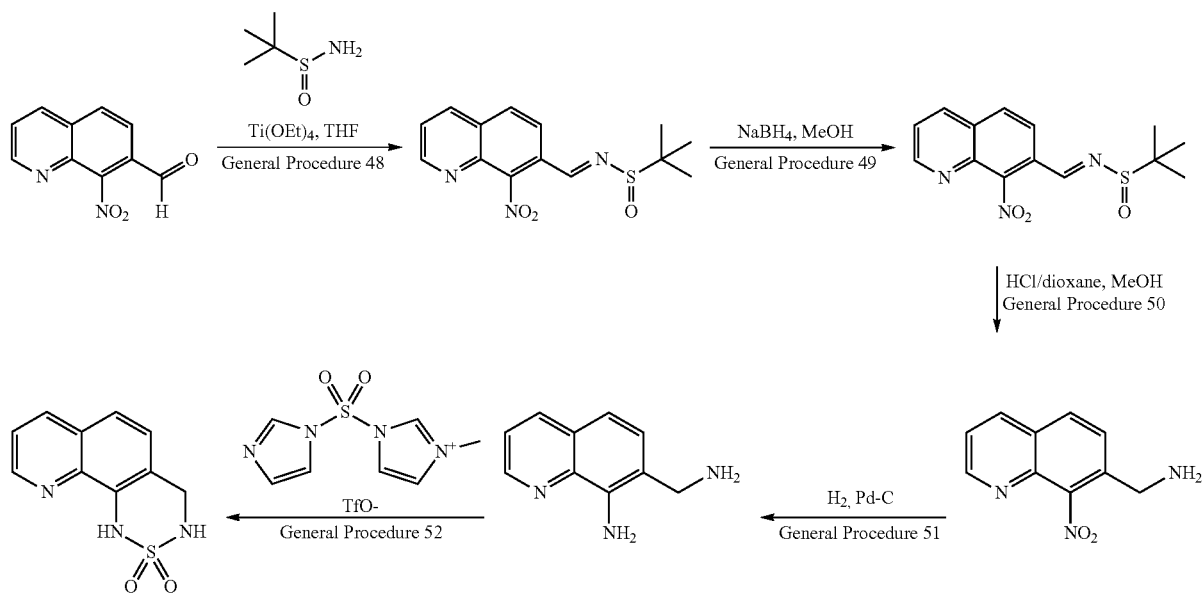
Synthesis Route 22:
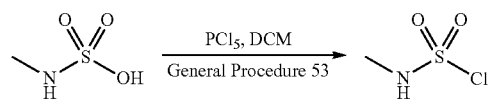

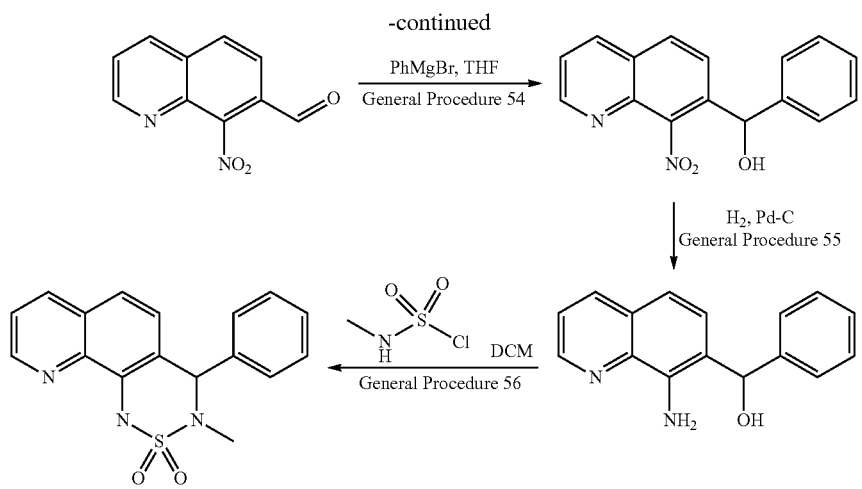
Synthesis Route 27:
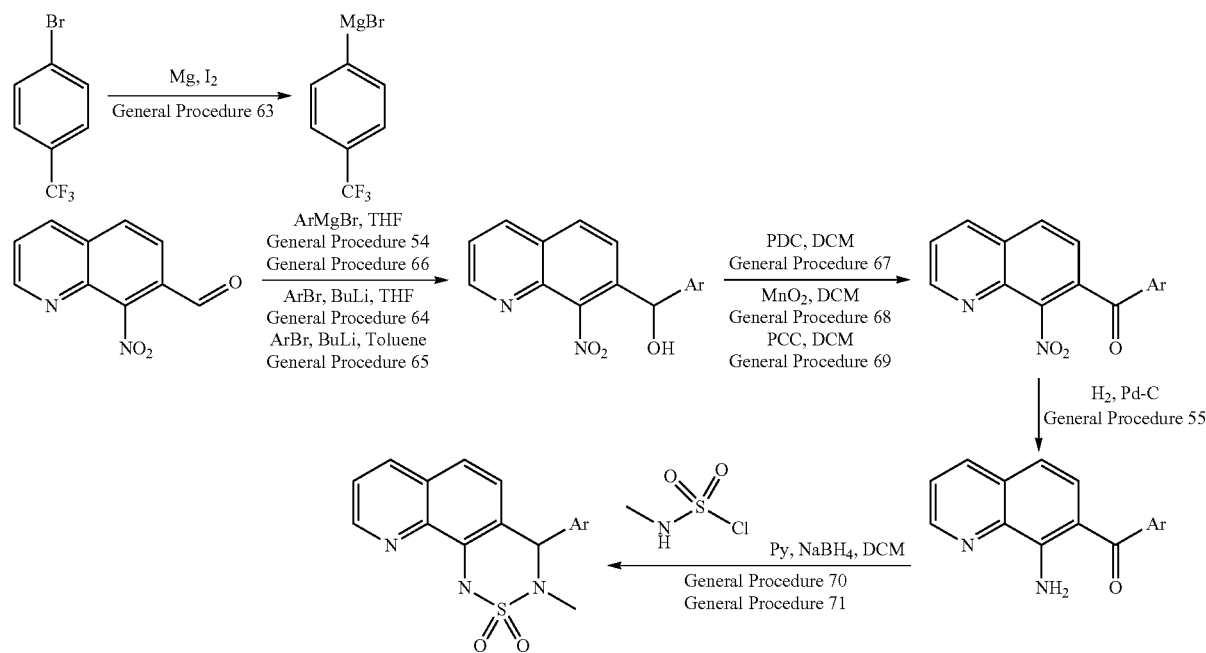
Synthesis Route 28:
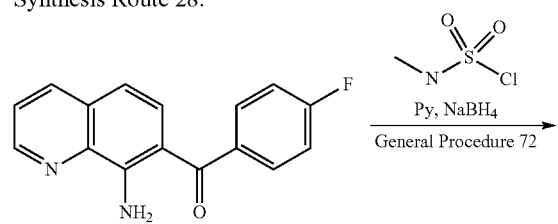
Synthesis Route 29:
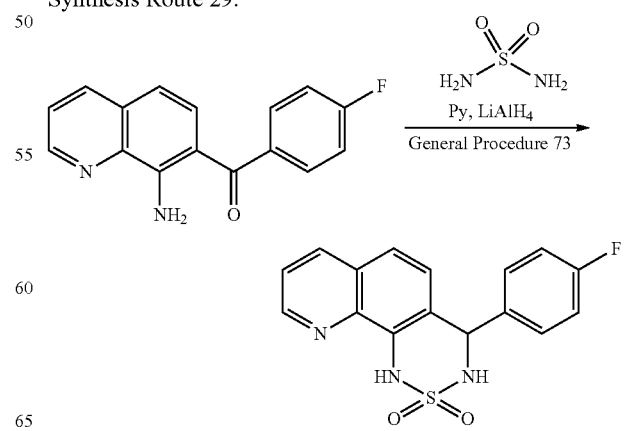

Synthesis Route 30:
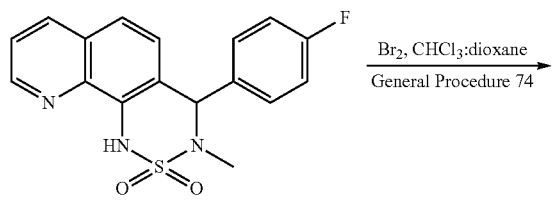
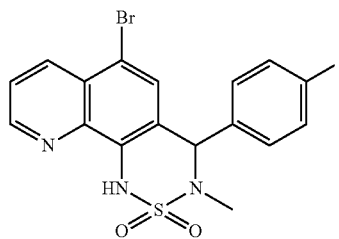
Synthesis Route 31:
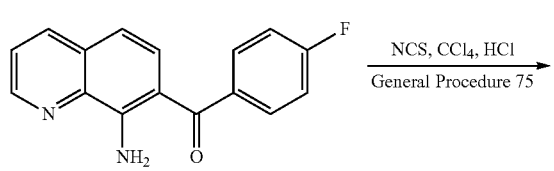
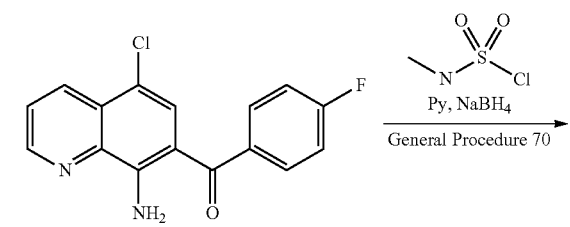
Synthesis Route 32:
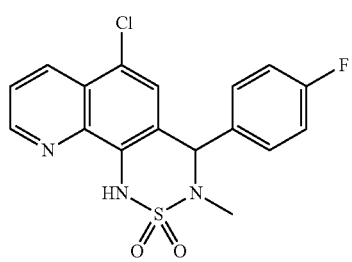
-continued
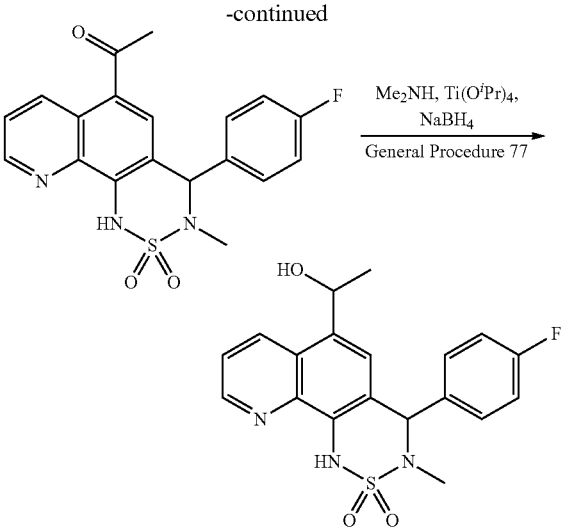
Synthesis Route 33:
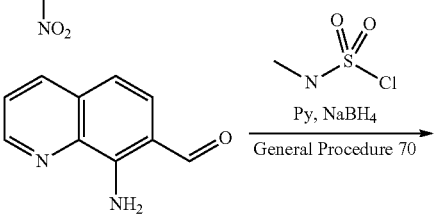
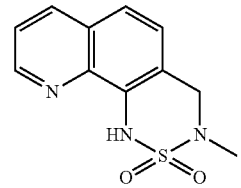
Synthesis Route 34:
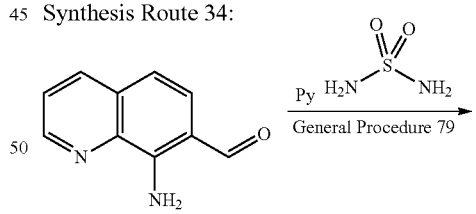
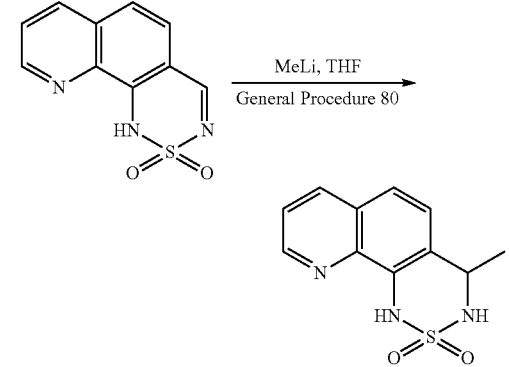

Synthesis Route 35:
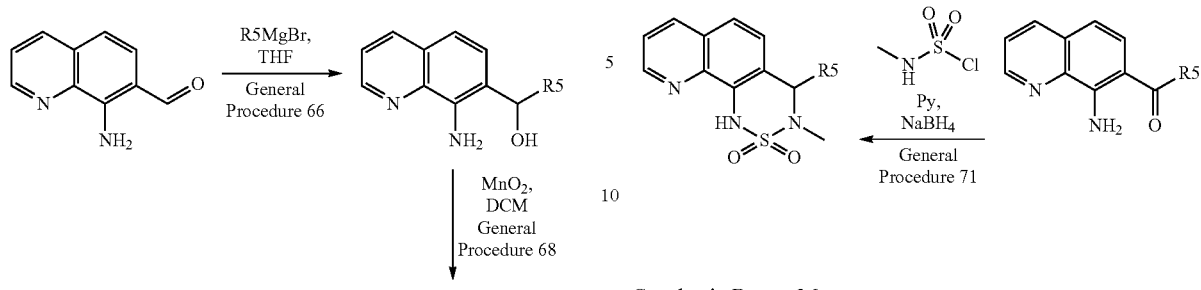
Synthesis Route 36:
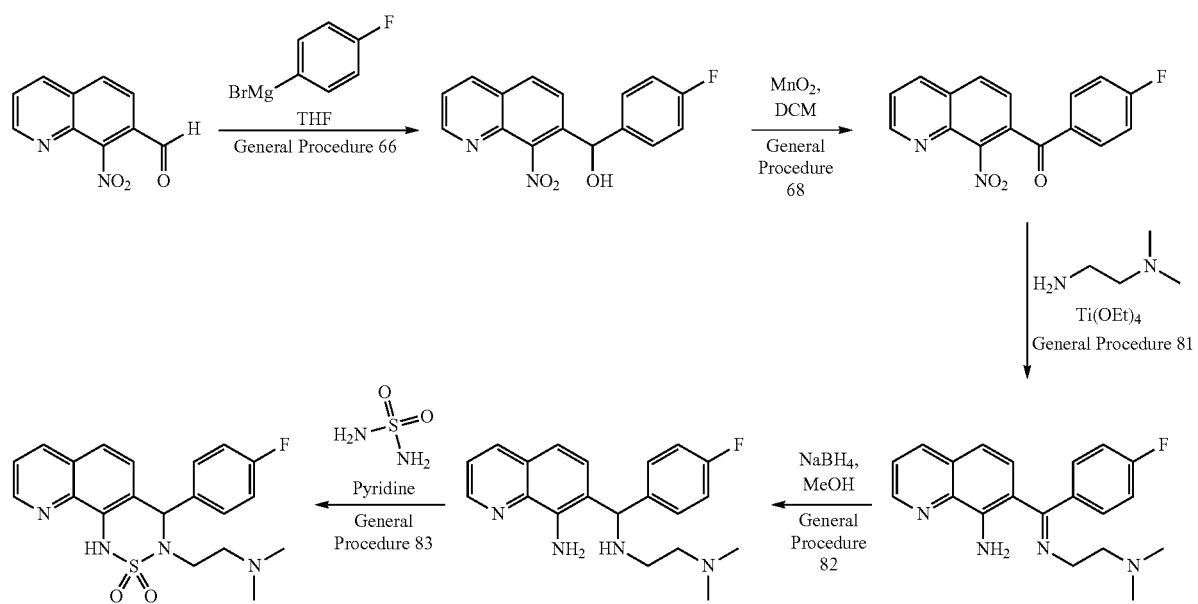
Synthesis Route 37:

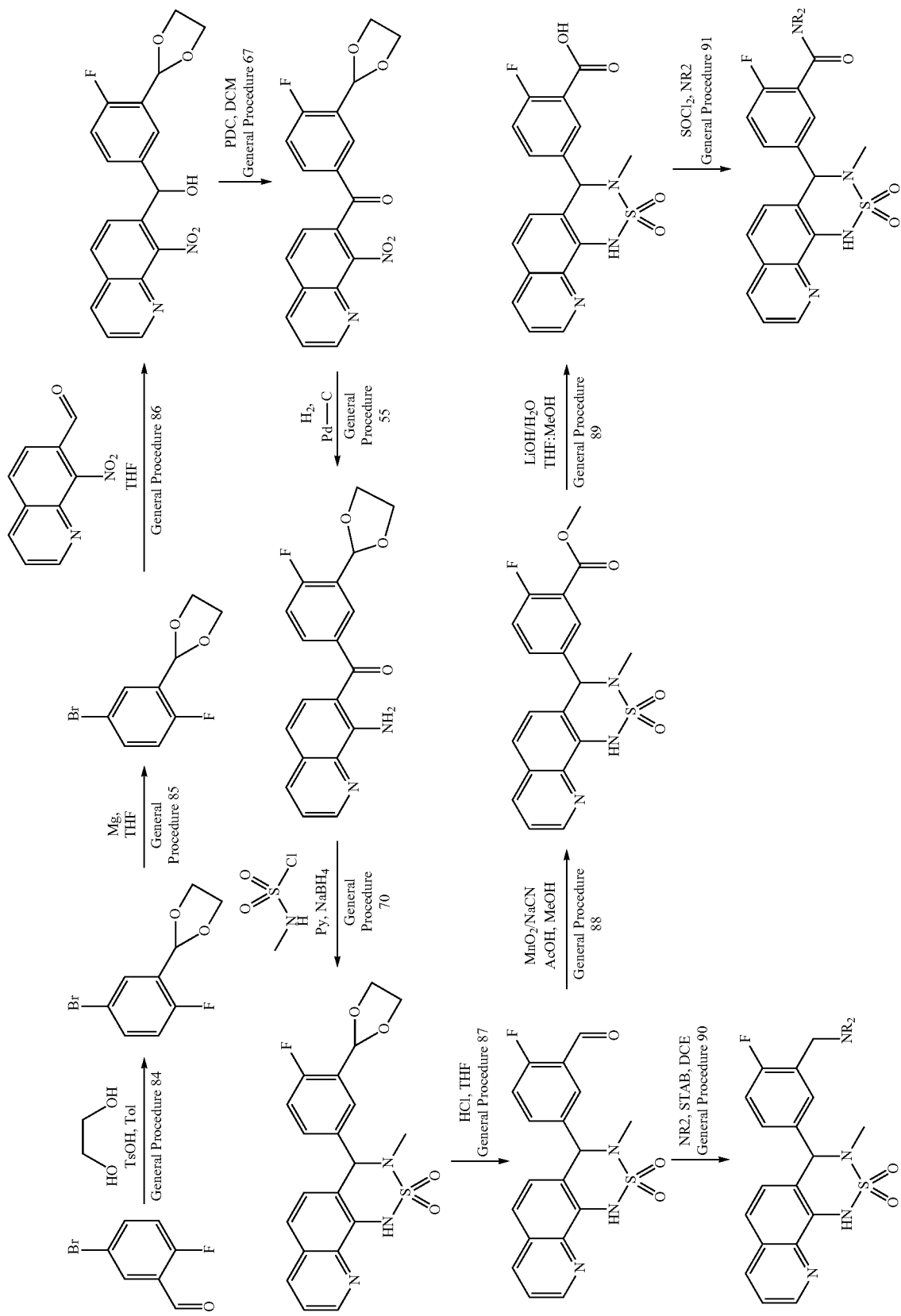

Synthesis Route 38:
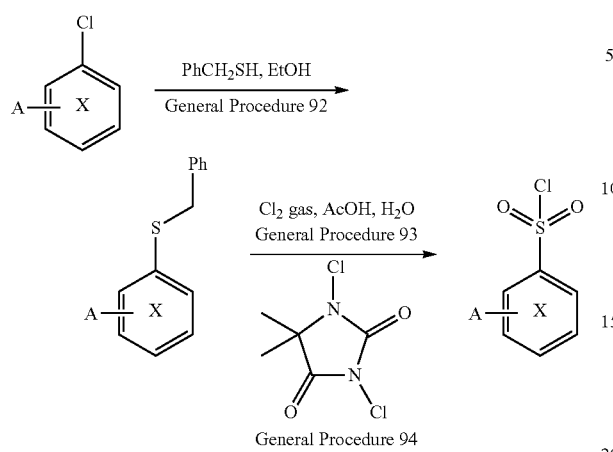
X = C, N
with the substituent A being selected from a suitable aryl-substituent as defined in the present invention,
Synthesis Route 39:
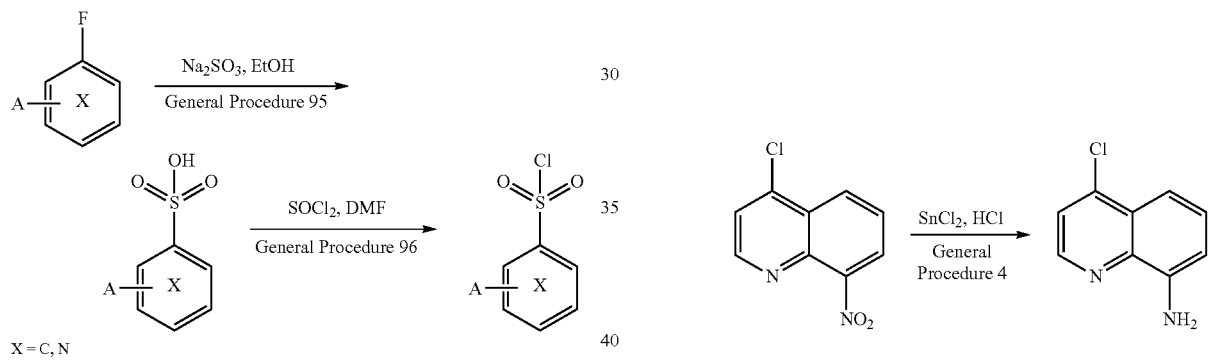
X = C, N
with the substituent A being selected from a suitable aryl-substituent as defined in the present invention
Synthesis Route 40:
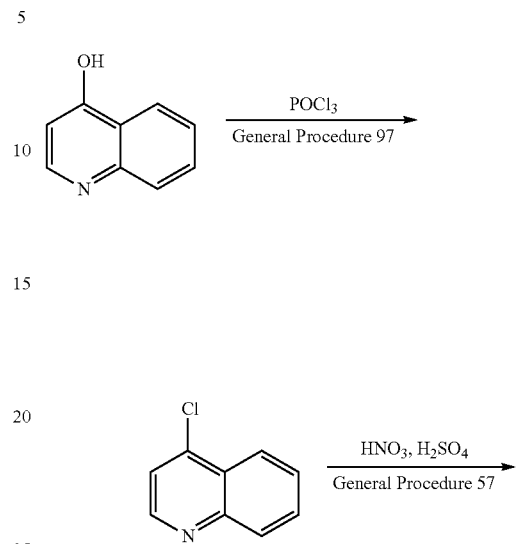
Synthesis Route 41:
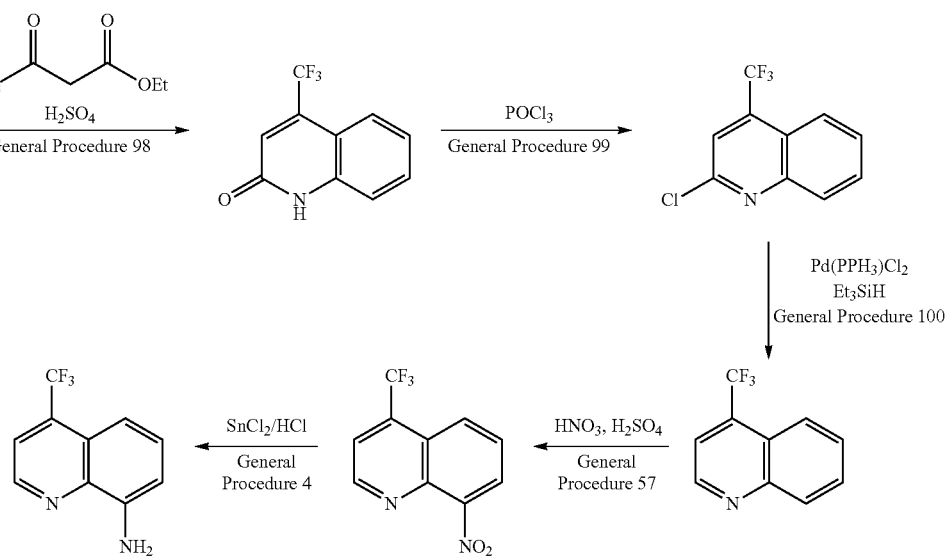

Synthesis Route 42:
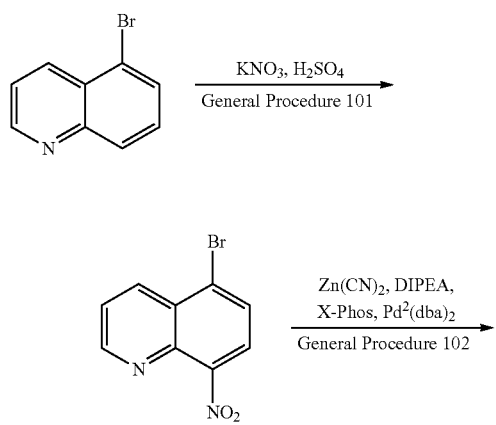
-continued
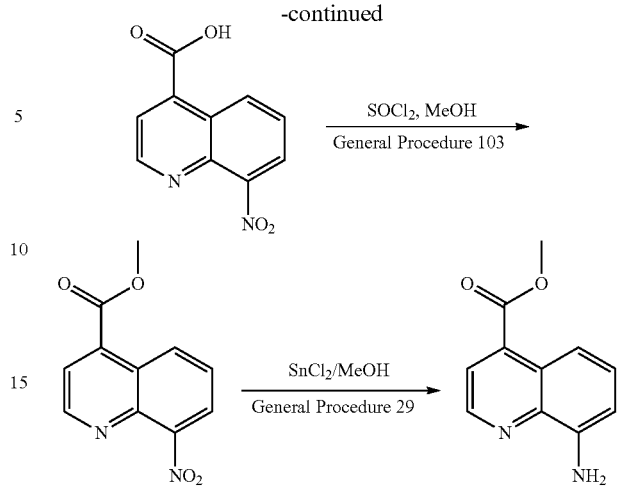
Synthesis Route 44:
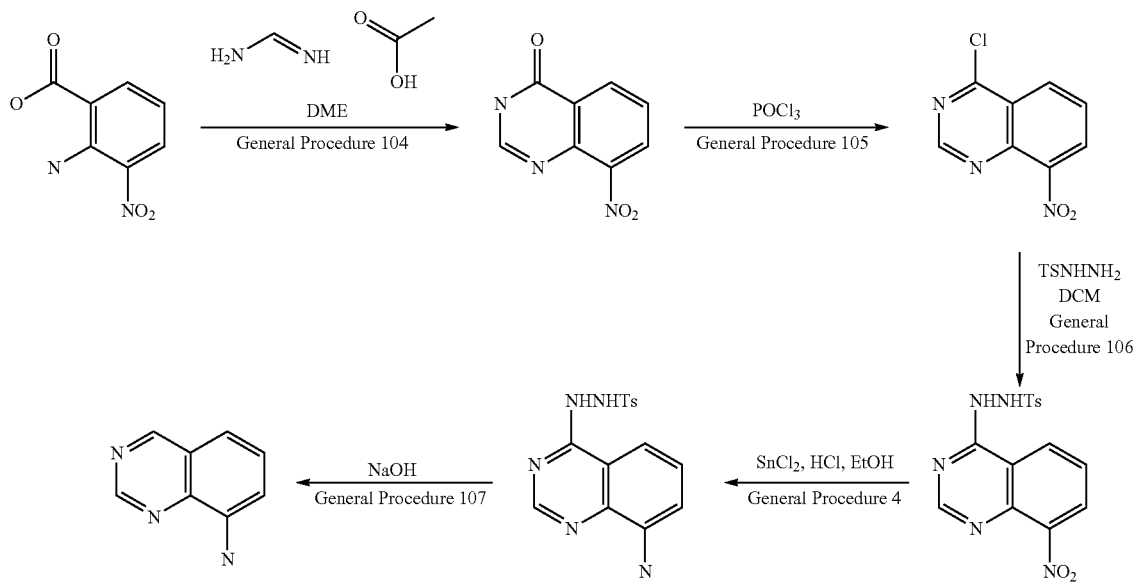
-continued
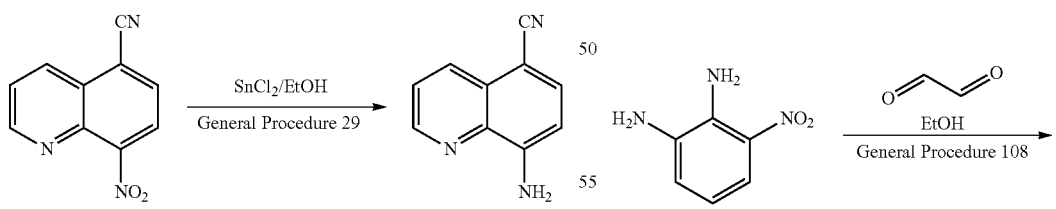
Synthesis Route 43:
Synthesis Route 45:
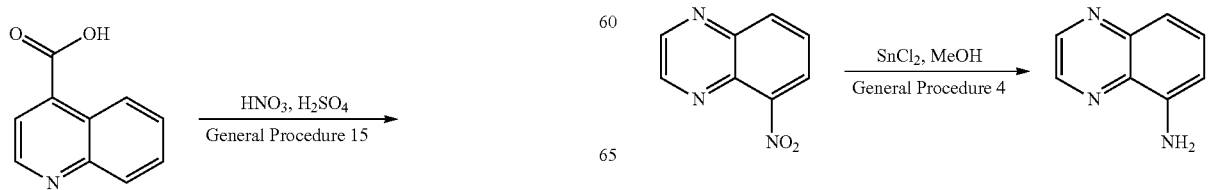

Synthesis Route 46:
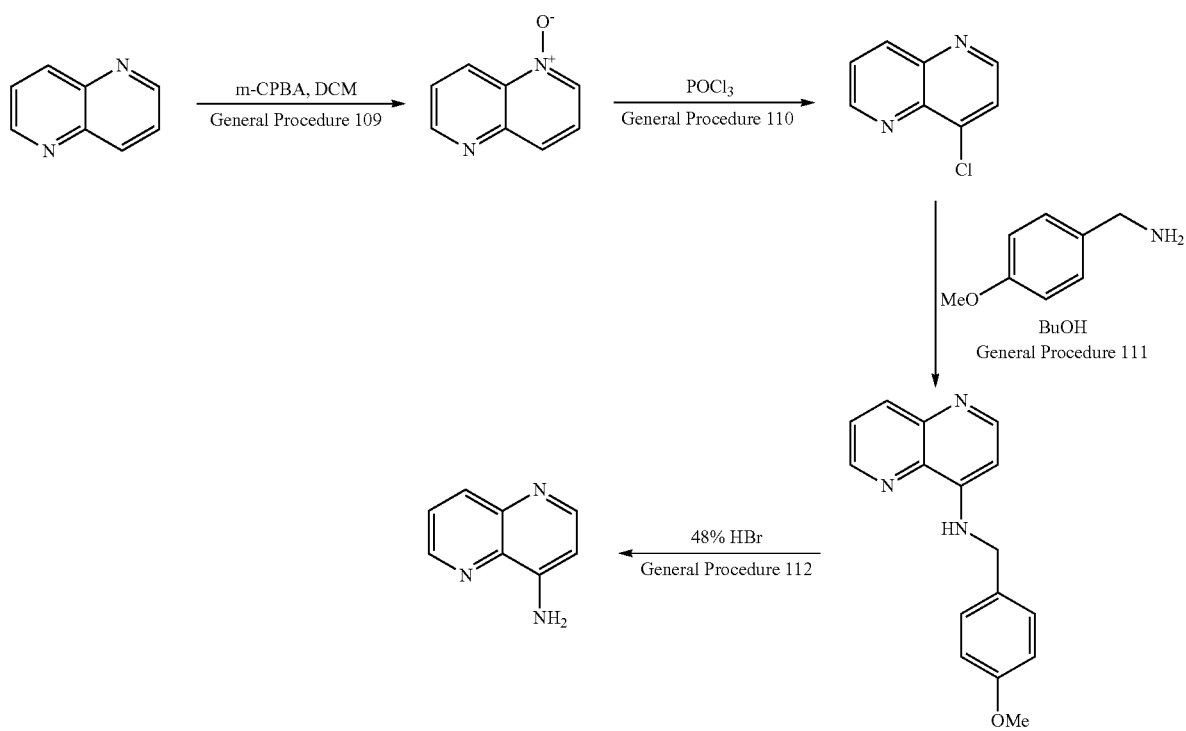
Synthesis Route 47:
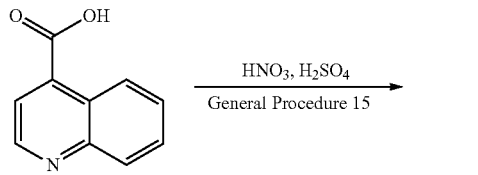
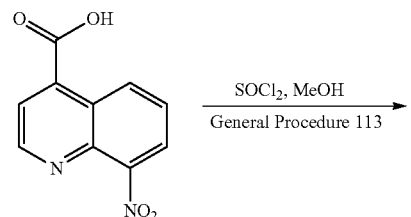
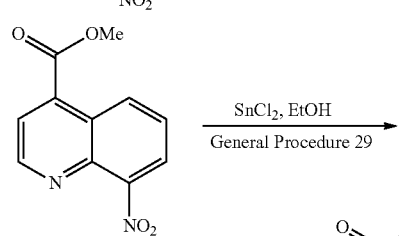
Synthesis Route 48:
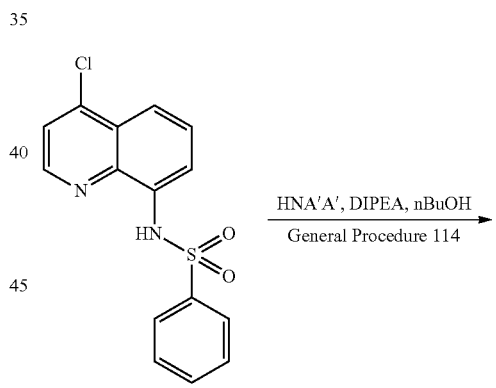
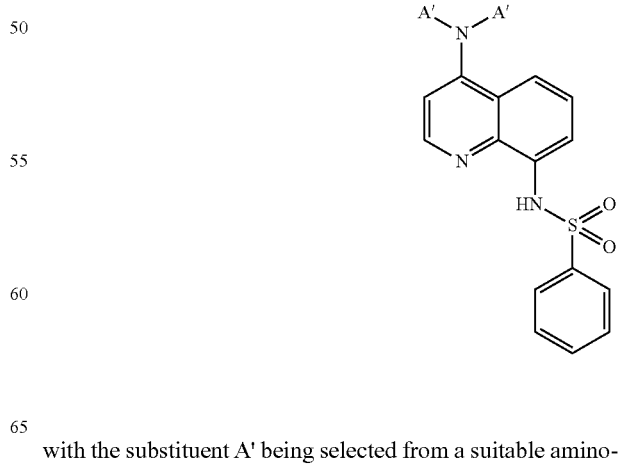
with the substituent A' being selected from a suitable amino-substituent as defined in the present invention Synthesis Route 49:
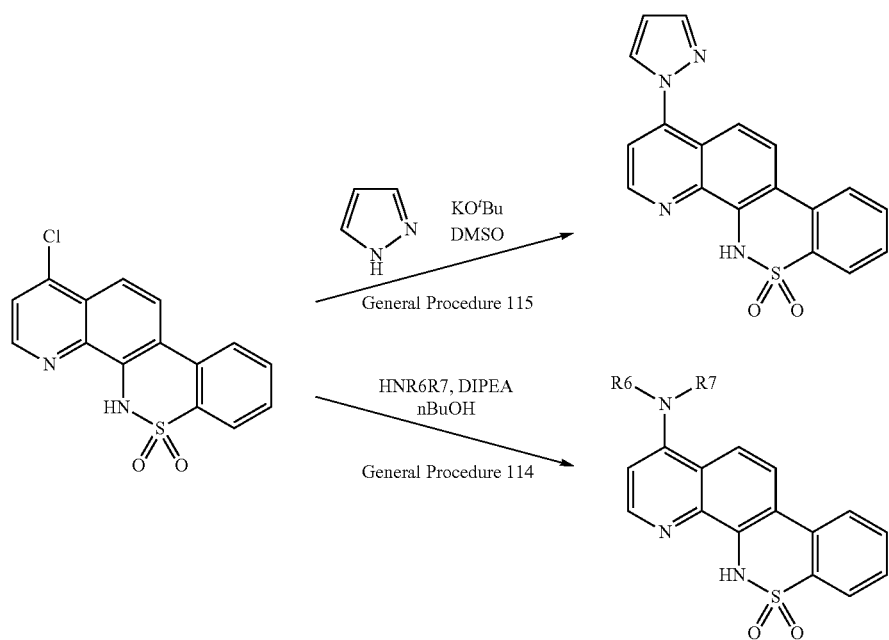
Synthesis Route 50:
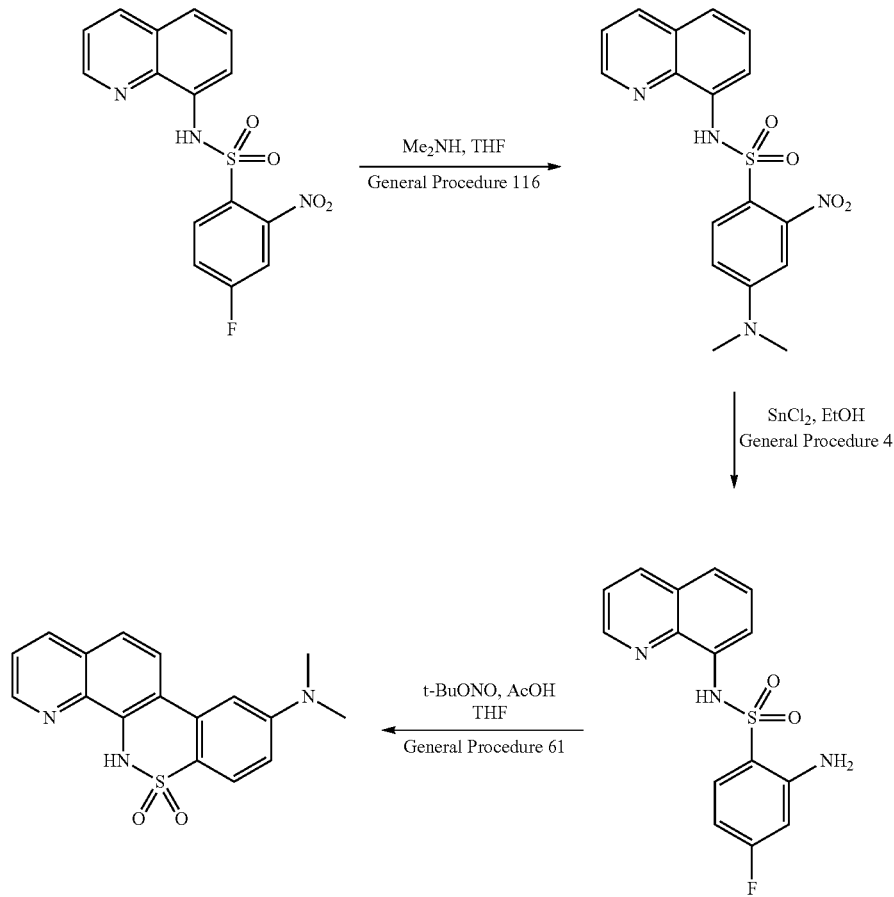 [SMILES: O=[N+]([O-])c1cc(F)ccc1S(=O)(=O)Nc1cccc2cccnc12 ; CN(C)c1ccc(S(=O)(=O)Nc2cccc3cccnc23)c([N+](=O)[O-])c1 ; CN(C)c1ccc2c(c1)-c1ccc3cccnc3c1NS2(=O)=O ; Nc1cc(F)ccc1S(=O)(=O)Nc1cccc2cccnc12]

Synthesis Route 51:

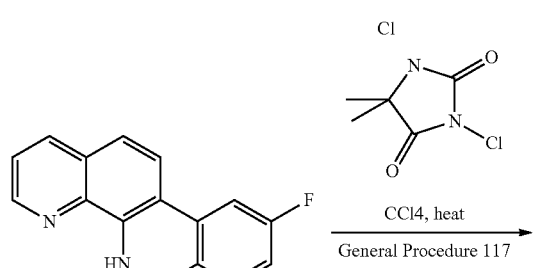

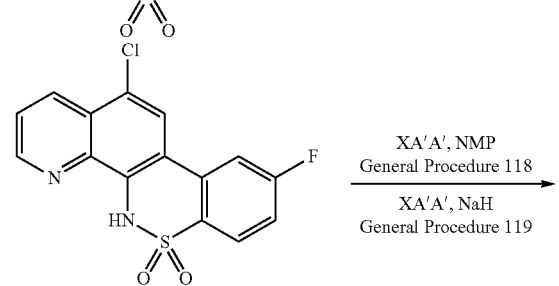

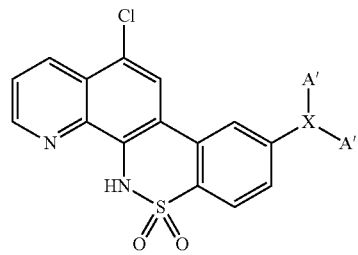

with the substituent X being C or preferably N with the substituent A' being selected from a suitable alkyl- or amino-substituent, respectively, each as defined in the present invention Synthesis Route 52:

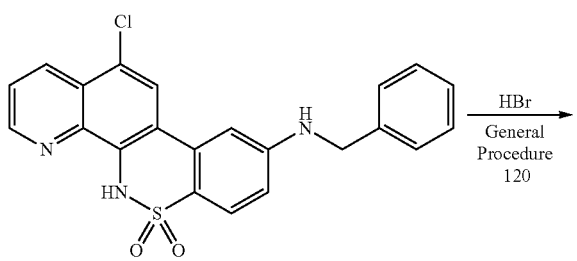

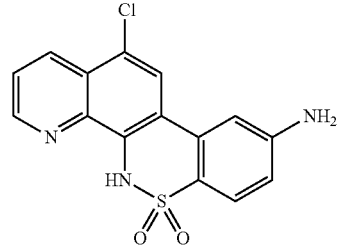

Synthesis Route 53:

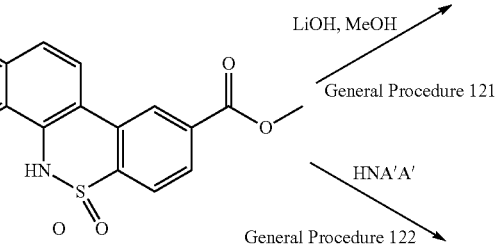

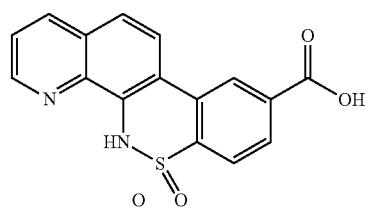

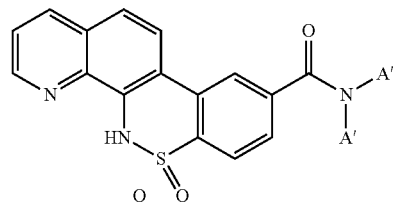

with the substituent A' being selected from a suitable amino-substituent as defined in the present invention Synthesis Route 54:

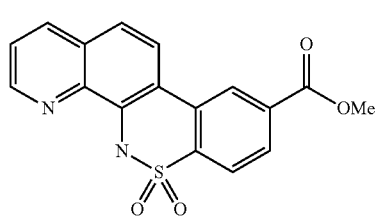 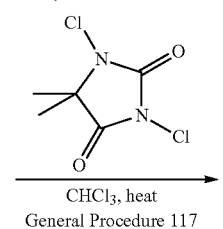 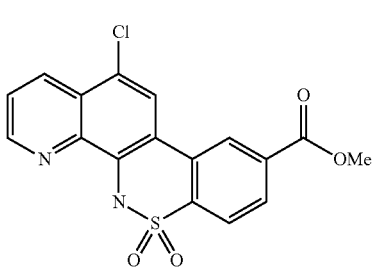

LiOH
General Procedure 121

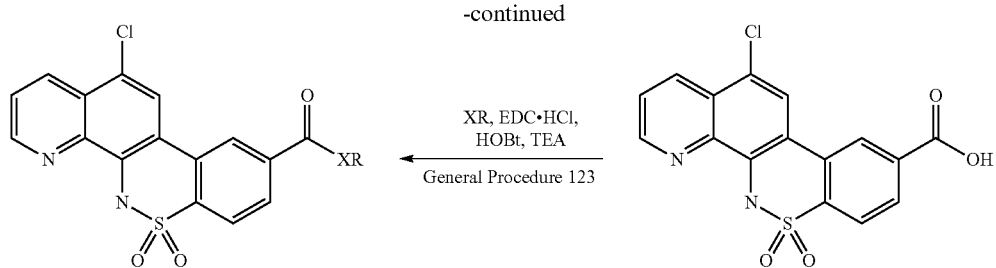
Synthesis Route 55:
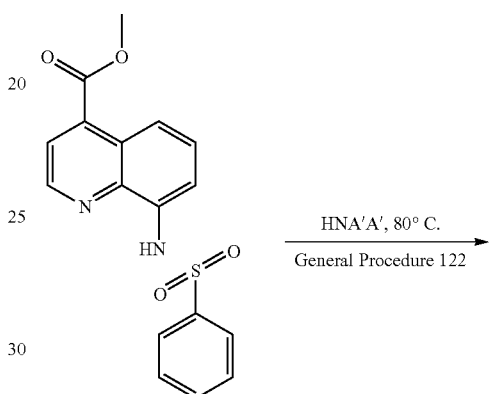
Synthesis Route 56:
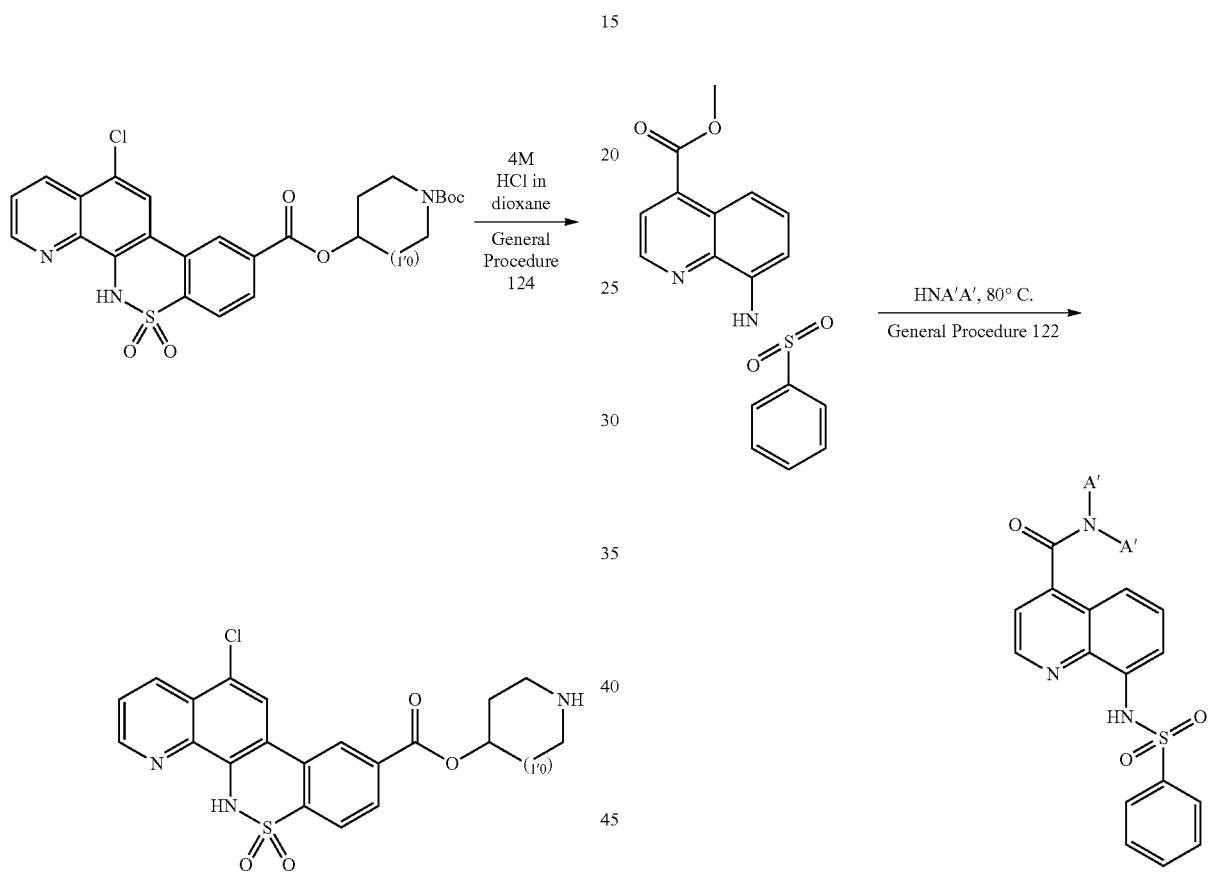
with the substituent A' being selected from a suitable amino-substituent as defined in the present invention
Synthesis Route 57:
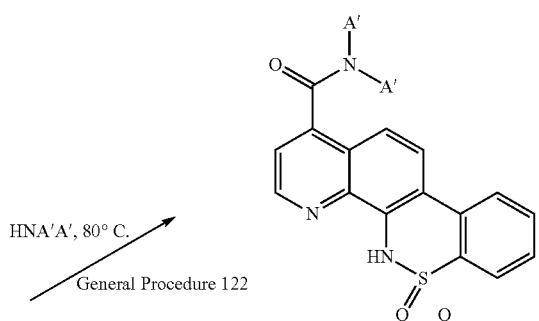

-continued
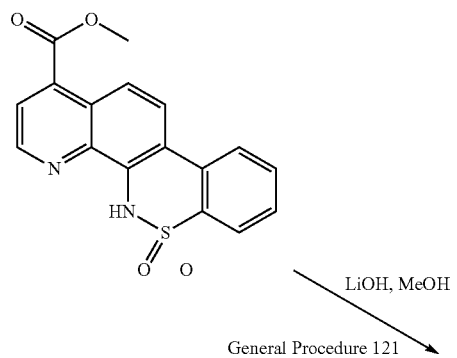
LiOH, MeOH
General Procedure 121
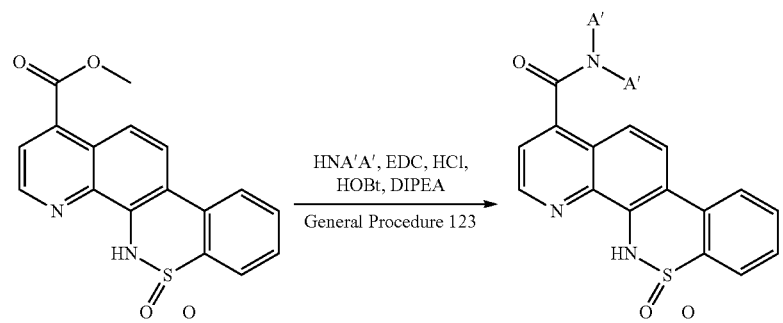
with the substituent A' being selected from a suitable amino-substituent as defined in the present invention
Synthesis Route 58:
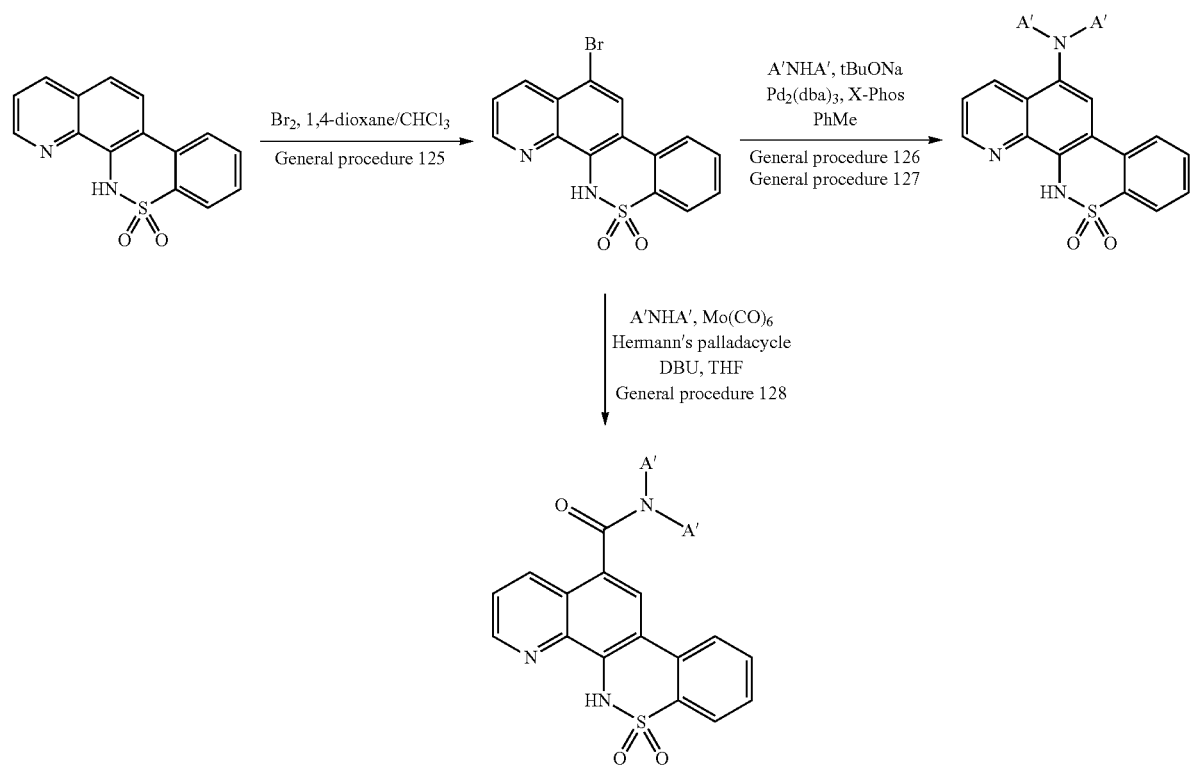
with the substituent A' being selected from a suitable amino-substituent as defined in the present invention Synthesis Route 59:
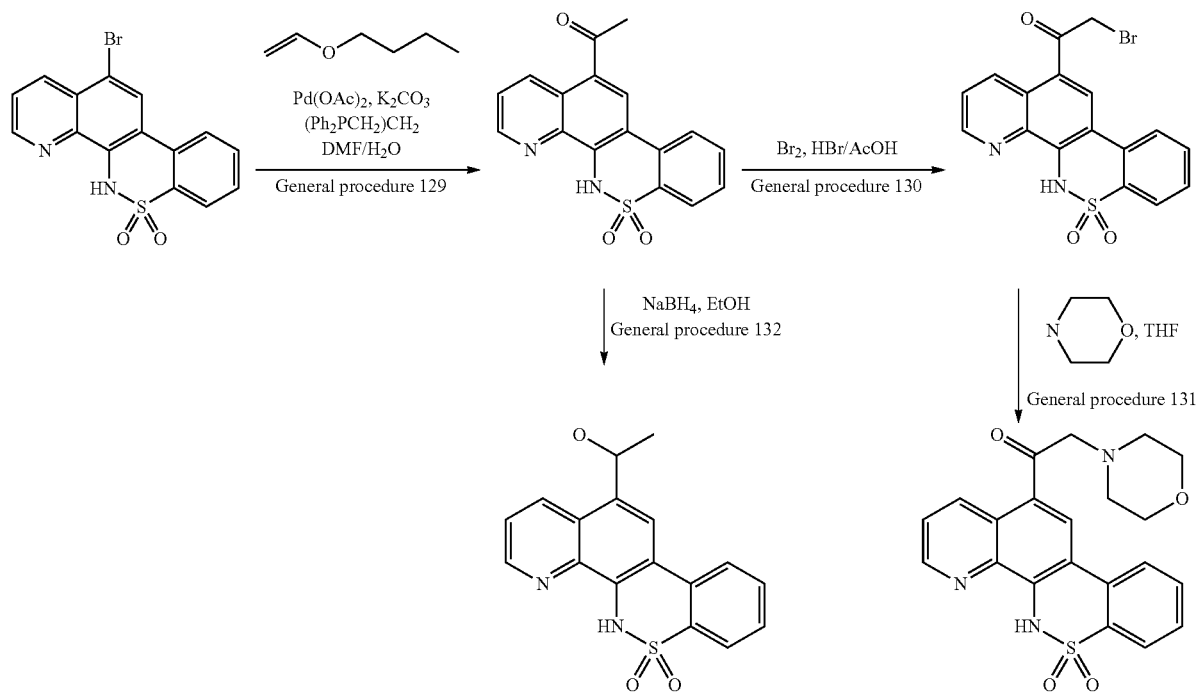
Synthesis Route 60:
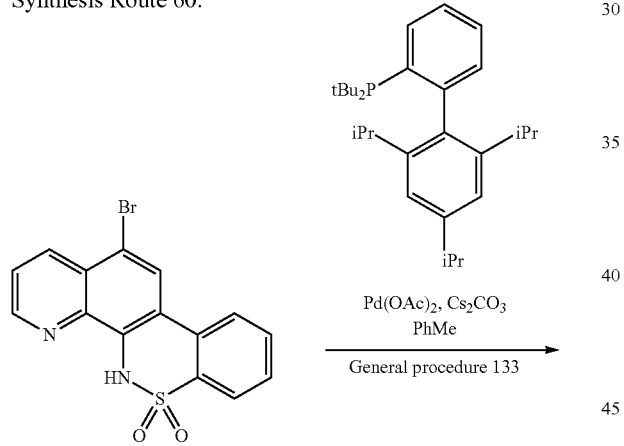
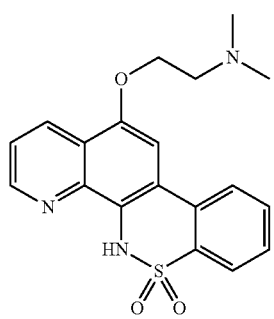
-continued
Synthesis Route 61:
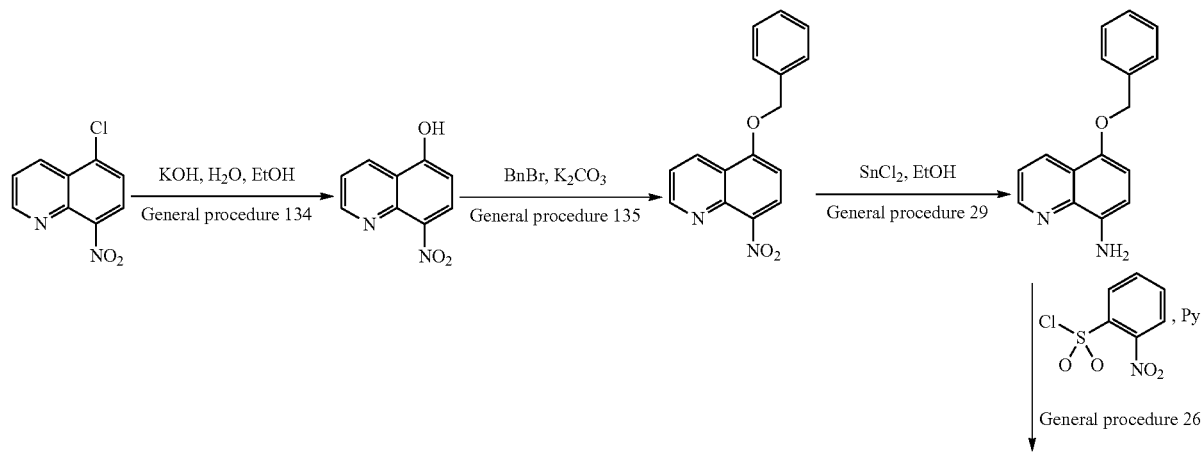

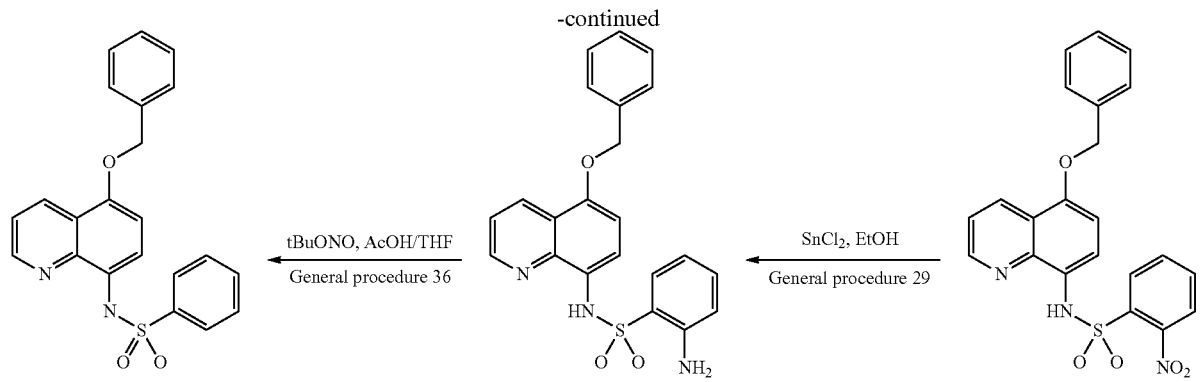
Synthesis Route 62:
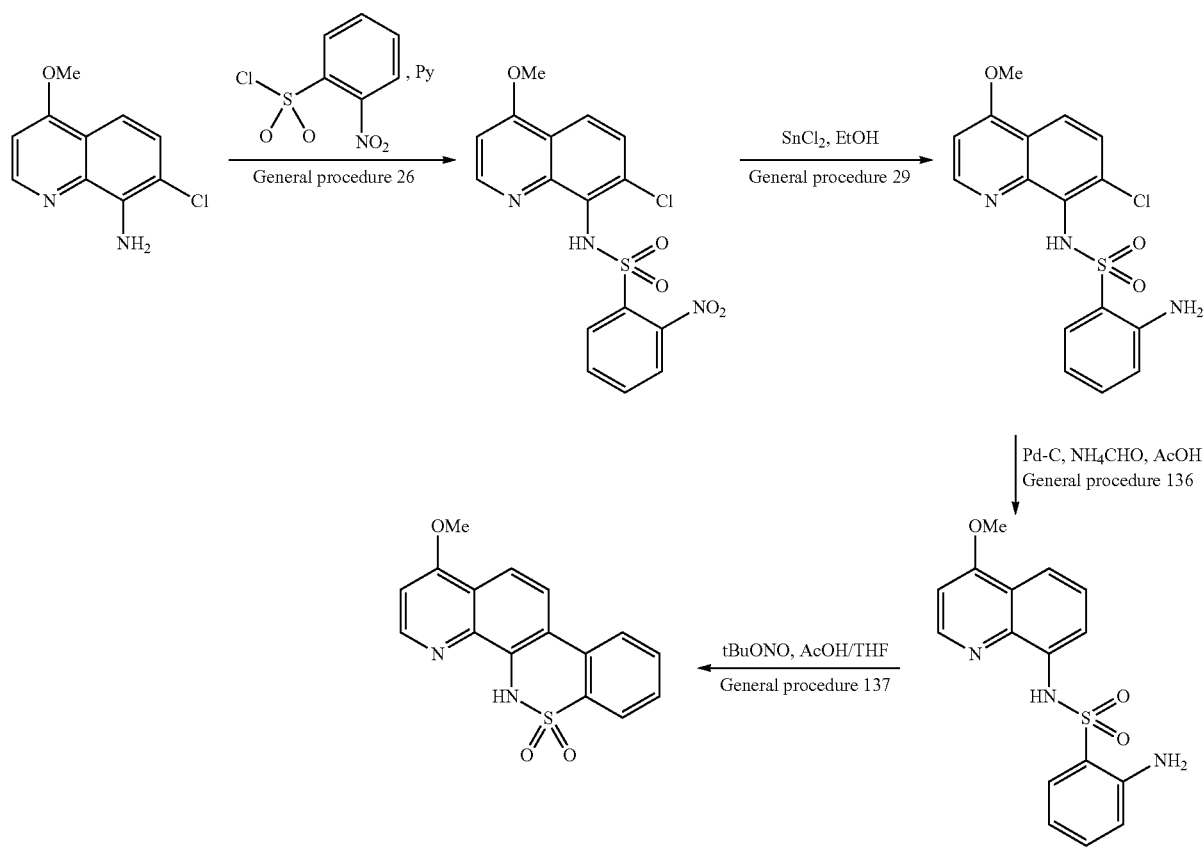
Synthesis Route 63:
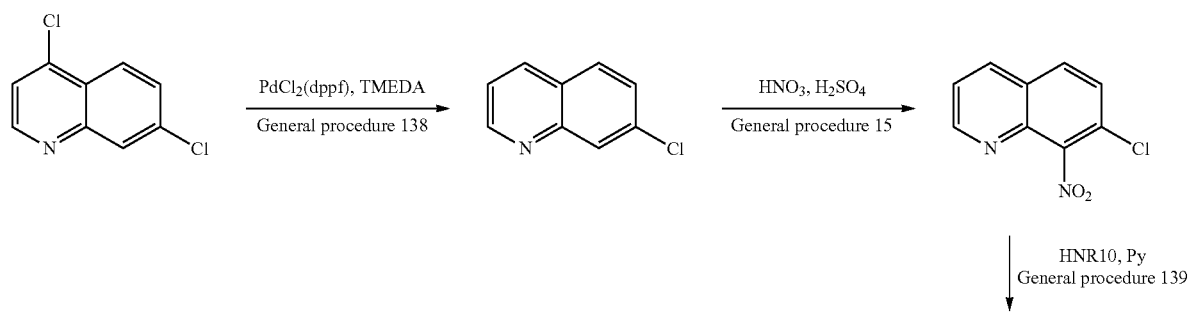

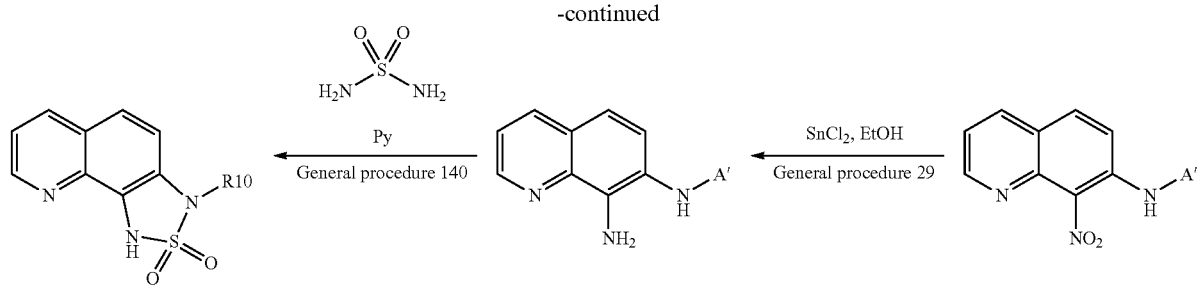
with the substituent A' being selected from a suitable amino-substituent as defined in the present invention
Synthesis Route 64:
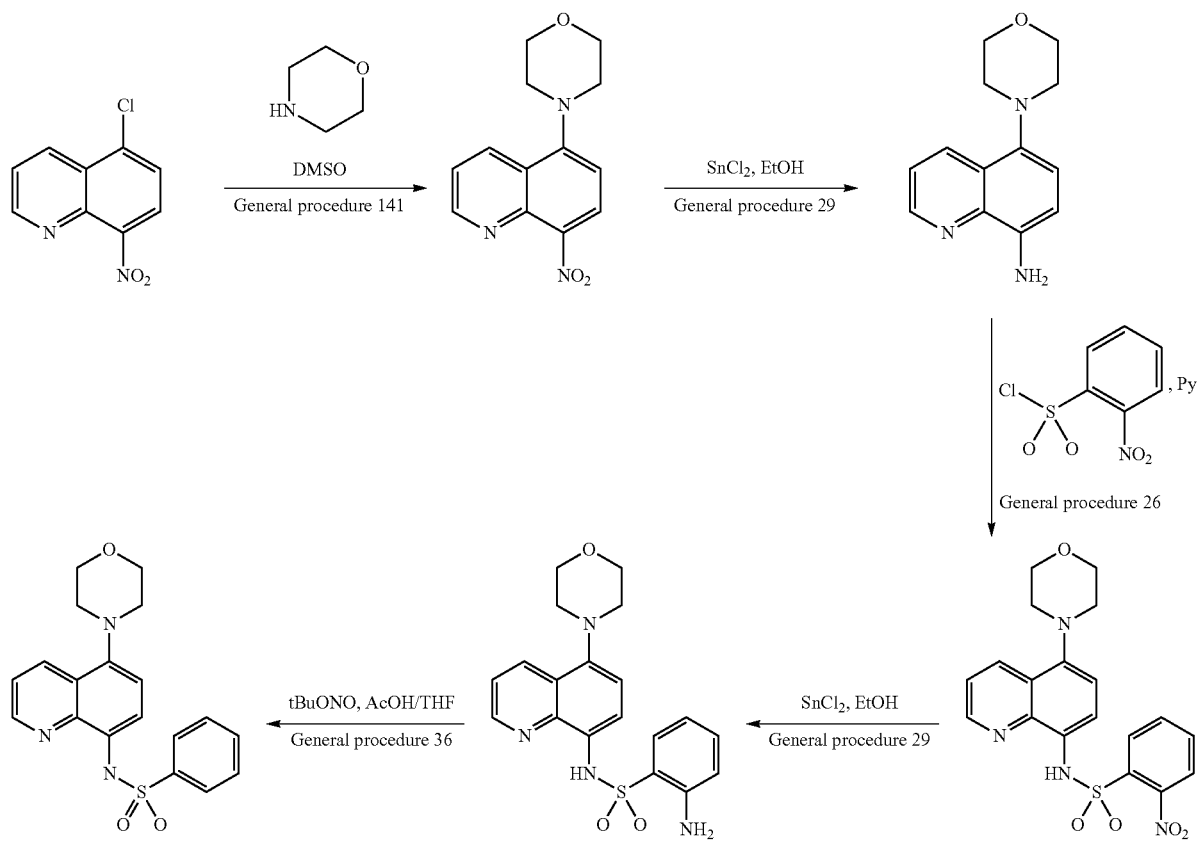
Synthesis Route 65:
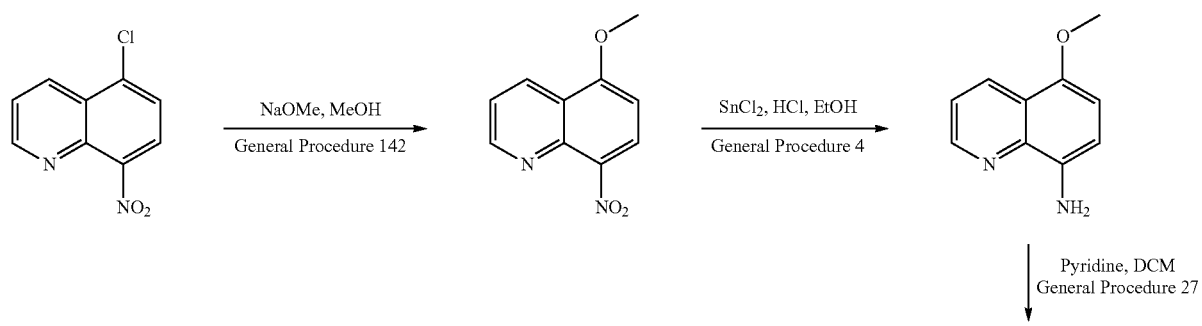

-continued

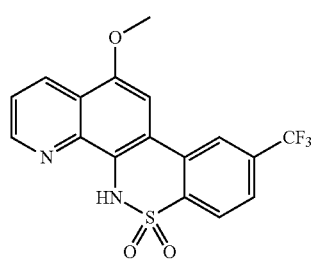 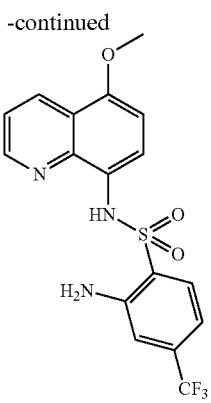 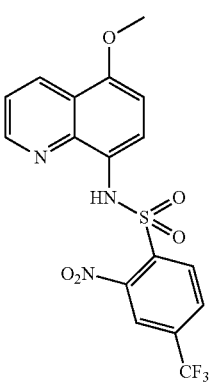

tBuONO, AcOH
General Procedure 61

SnCl₂, HCl, EtOH
General Procedure 4

The reaction paths shown here are reaction types which are known per se and which can be carried out in a manner known per se. By reaction with a pharmaceutical acceptable base or acid, corresponding salts are obtained.

The reaction of the various reaction partners can be carried out in various solvents, and in this respect is not subject to a particular limitation. Corresponding examples of suitable solvents are thus water, methanol, ethanol, acetone, dichloromethane, dichloroethane, methylene chloride, dimethoxyethane, diglyme, acetonitrile, butyronitrile, THF, dioxane, ethyl acetate, butyl acetate, dimethylacetamide, toluene, chlorobenzene, dimethylsulfoxice (DMSO) etc. Methanol, ethanol, acetone and methylene chloride are preferred, and in particular the solvents used in the preferred processes according to synthesis routes 1 to 65 as described herein.

It is moreover possible to carry out the reaction in an essentially homogeneous mixture of water and solvents if the organic solvent is miscible with water.

The reaction according to the invention of the reaction partners is carried out, for example, at room temperature. However, temperatures above room temperature, for example up to 80 or 90° C., and temperatures below room temperature, for example down to −20° C. or less, can also be used.

The pH at which the reaction according to the invention of the reaction partners is carried out is suitably adjusted.

The pH adjustment is preferably carried out by addition of a base. Both organic and inorganic bases can be used as bases. Preferably, inorganic bases, such as, for example, LiOH, NaOH, KOH, Ca(OH)$_2$, Ba(OH)$_2$, Li$_2$CO$_3$, K$_2$CO$_3$, Na$_2$CO$_3$, NaHCO$_3$, or organic bases, such as amines (such as, for example, preferably triethylamine (TEA, NEt$_3$), N,N-diisoproylethylamine (diethylisopropylamine), Bu$_4$NOH, piperidine, morpholine, pyridine and alkylpyridines (4-Dimethylaminopyridine), are used. Particularly preferably, NaOH or organic bases, very particularly preferably triethylamine, and in particular the bases as mentioned in the preferred processes according to synthesis routes 1 to 65 as described herein, are used.

The pH adjustment can optionally also be carried out by means of acids. Both organic and inorganic acids can be used as acids. Preferably, inorganic acids, such as, for example, HCl, HBr, HF, H$_2$SO$_4$, H$_3$PO$_4$, or organic acids, such as CF$_3$COOH, acetic acid (CH$_3$COOH, AcOH), p-toluenesulfonic acid, and salts thereof are used. HCl, H$_2$SO$_4$, Organic acids, such as acetic acid (CH$_3$COOH, AcOH), are particularly preferably used.

The pH adjustment is particularly preferably carried out by means of the pH-adjusting agents used in the preferred processes described herein according to synthesis routes 1 to 65.

A person skilled in the art is in a position here to choose the most suitable solvent and the optimum reaction conditions, in particular with respect to temperature, pH, catalyst and solvent, for the corresponding synthesis route or for the corresponding reaction step. In any case, the parameters as provided in the above presented synthesis routes 1 to 65 are preferred.

The present invention thus also provides novel intermediate products in accordance with the present invention, which are accessible with the preparation processes as described herein, such as, in particular, the intermediate products as described in the examples below and which are obtainable from the synthesis routes 1 to 65 as described herein.

The inventors have found, surprisingly, that the compounds provided by the present invention and represented by the general structural formula (I), (Ia) and (Ib) respectively show an action as a hepcidin antagonist and are therefore suitable for use as medicaments for treatment of hepcidin-mediated diseases and the symptoms accompanied by these or associated with these. In particular, the compounds according to the invention are suitable in use for treatment of disorders in iron metabolism, in particular for treatment of iron deficiency diseases and/or anaemias, in particular ACD and AI.

The medicaments containing the compounds of the general structural formula (I), (Ia) and (Ib) respectively are suitable in this context for use in human and veterinary medicine.

The present invention thus provides new compounds according to the general structural formula (Ib) as well as the compounds of the general structural formula (I), (Ia) and (Ib) respectively according to the invention, each with the above substituent meanings, for use as medicaments, in particular for the use in the treatment of iron metabolism disorders.

The compounds according to the invention are therefore also suitable for the preparation of a medicament for treatment of patients suffering from symptoms of iron metabolism disorders, such as e.g. from an iron deficiency anaemia, such as, for example: tiredness, lack of drive, lack of concentration, low cognitive efficiency, difficulties in finding the correct words, forgetfulness, unnatural pallor, irritability, accelerated heart rate (tachycardia), sore or swollen tongue, enlarged spleen, pregnancy cravings (pica), headaches, loss of appetite, increased susceptibility to infections, depressive moods or suffering from ACD or AL.

The compounds according to the invention are therefore also suitable for the preparation of a medicament for treatment of patients suffering from symptoms of an iron deficiency anaemia.

Administration can take place over a period of several months until the iron status improves, reflected, for example, by the haemoglobin value, the transferrin saturation and the ferritin value of the patient, or until the desired improvement is achieved in an impairment of the state of health caused by iron deficiency anaemia or by ACD or AI.

The preparation according to the invention can be taken by children, adolescents and adults.

The compounds of the present invention can furthermore also be used in combination with further active compounds or medicaments known in the treatment of disorders in iron metabolism and/or with active compounds or medicaments which are administered concomitantly with agents for treatment of diseases which are associated with disorders in iron metabolism, in particular with iron deficiency and/or anaemias. Examples of such agents for treatment of disorders in iron metabolism and further diseases associated with iron deficiency and/or anaemias which can be used in combination can include, for example, iron-containing compounds, such as e.g. iron salts, iron-carbohydrate complex compounds, such as iron-maltose or iron-dextrin complex compounds, vitamin D and/or derivatives thereof.

The compounds used in combination with the compounds according to the invention can be administered in this context either orally or parenterally, or the administration of the compounds according to the invention and of the compounds used in combination can take place by combination of the administration possibilities mentioned.

The compounds according to the invention and the combinations of the compounds according to the invention with further active compounds or medicaments can be employed in the treatment of disorders in iron metabolism, such as, in particular, iron deficiency diseases and/or anaemias, in particular anaemias with cancer, anaemia induced by chemotherapy, anaemia induced by inflammation (AI), anaemias with congestive cardiac insufficiency (CHF; congestive heart failure), anaemia with chronic renal insufficiency stage 3-5 (CKD 3-5; chronic kidney diseases stage 3-5), anaemia induced by chronic inflammation (ACD), anaemia with rheumatic arthritis (RA; rheumatoid arthritis), anaemia with systemic lupus erythematosus (SLE) and anaemia with inflammatory intestinal diseases (IBD; inflammatory bowel disease) or used for the preparation of medicaments for treatment of these diseases.

The compounds according to the invention and the above-mentioned combinations of the compounds according to the invention with further active compounds or medicaments can be used in particular for the preparation of medicaments for treatment of iron deficiency anaemia, such as iron deficiency anaemias in pregnant women, latent iron deficiency anaemia in children and adolescents, iron deficiency anaemia as a result of gastrointestinal abnormalities, iron deficiency anaemia as a result of blood losses, such as by gastrointestinal haemorrhages (e.g. as a result of ulcers, carcinomas, haemorrhoids, inflammatory disorders, intake of acetylsalicylic acid), menstruation, injuries, iron deficiency anaemia as a result of psilosis (sprue), iron deficiency anaemia as a result of reduced uptake of iron from the diet, in particular in selectively eating children and adolescents, weak immune system caused by iron deficiency anaemia, impaired cerebral performance caused by iron deficiency anaemia, restless leg syndrome.

The use according to the invention leads to an improvement in the iron, haemoglobin, ferritin and transferrin values which, especially in adolescents and children, but also in adults, are accompanied by an improvement in the short term memory test (STM), in the long term memory test (LTM), in the Raven's progressive matrices test, in the Wechsler adult intelligence scale (WAIS) and/or in the emotional coefficient (Baron EQ-i, YV test; youth version), or to an improvement in neutrophile levels, antibody levels and/or lymphocyte function.

The present invention furthermore relates to pharmaceutical compositions comprising one or more compounds of the formula (I) according to the invention and optionally one or more further pharmaceutically active compounds and optionally one or more pharmacologically acceptable carriers and/or auxiliary substances and/or solvents.

In this context, the pharmaceutical carriers, auxiliary substances or solvents are conventional substances. The pharmaceutical compositions mentioned are suitable, for example, for intravenous, intraperitoneal, intramuscular, intravaginal, intrabuccal, percutaneous, subcutaneous, mucocutaneous, oral, rectal, transdermal, topical, intradermal, intragastral or intracutaneous administration and are present, for example, in the form of pills, tablets, tablets resistant to gastric juice, film-coated tablets, layered tablets, sustained release formulations for oral, subcutaneous or cutaneous administration (in particular as patches), depot formulation, sugar-coated tablets, small suppositories, gels, ointments, syrup, granules, suppositories, emulsions, dispersions, microcapsules, microformulations, nanoformulations, liposomal formulations, capsules, capsules resistant to gastric juice, powders, powders for inhalation, microcrystalline formulations, sprays for inhalation, dusting powders, drops, nasal drops, nasal sprays, aerosols, ampoules, solutions, juices, suspensions, infusion solutions or injection solutions etc.

Preferably, the compounds according to the invention and pharmaceutical compositions comprising such compounds are administered orally and/or parenterally, in particular intravenously.

For this, the compounds according to the invention are preferably present in pharmaceutical compositions in the form of pills, tablets, tablets resistant to gastric juice, film-coated tablets, layered tablets, sustained release formulations for oral administration, depot formulations, sugar-coated tablets, granules, emulsions, dispersions, microcapsules, microformulations, nanoformulations, liposomal formulations, capsules, capsules resistant to gastric juice, powders, microcrystalline formulations, dusting powders, drops, ampoules, solutions, suspensions, infusion solutions or injection solutions.

The compounds according to the invention can be administered in a pharmaceutical composition which can comprise various organic or inorganic carrier materials and/or auxiliary materials such as are conventionally used for pharmaceutical purposes, in particular for solid medicament formulations. such as, for example, excipients (such as sucrose, starch, mannitol, sorbitol, lactose, glucose, cellulose, talc, calcium phosphate, calcium carbonates), binders (such as cellulose, methylcellulose, hydroxypropylcellulose, polypropylpyrrolidone, gelatine, gum arabic, polyethylene glycol, sucrose, starch), disintegrating agents (such as starch, hydrolysed starch, carboxymethylcellulose, calcium salt of carboxymethylcellulose, hydroxypropyl-starch, sodium glycol starch, sodium bicarbonate, calcium phosphate, calcium citrate), lubricants and slip agents (such as magnesium stearate, talc, sodium lauryl sulfate), a flavouring agent (such as citric acid, menthol, glycine, orange powder), preservatives (such as sodium benzoate, sodium bisulfite, methylparaben, propylparaben), stabilizers (such as citric acid, sodium citrate, acetic acid, and multicarboxylic acids from the Titriplex series, such as e.g. diethylenetriaminepentaacetic acid (DTPA)), suspending agents (such as methylcellulose, polyvinylpyrrolidone, aluminium stearate), dispersing agents, diluents (such as water, organic solvents), beeswax, cacao butter, polyethylene glycol, white petrolatum etc.

Liquid medicament formulations, such as solutions, suspensions and gels, conventionally contain a liquid carrier, such as water and/or pharmaceutically acceptable organic solvents. Such liquid formulations can furthermore also contain pH-adjusting agents, emulsifiers or dispersing agents, buffering agents, preservatives, wetting agents, gelling agents (for example methylcellulose), colouring agents and/or aroma substances. The compositions can be isotonic, that is to say these can have the same osmotic pressure as blood. The isotonicity of the composition can be adjusted using sodium chloride or other pharmaceutically acceptable agents, such as, for example, dextrose, maltose, boric acid, sodium tartrate, propylene glycol or other inorganic or organic soluble substances. The viscosity of the liquid compositions can be adjusted using a pharmaceutically acceptable thickening agent, such as methylcellulose. Other suitable thickening agents include, for example, xanthan, carboxymethylcellulose, hydroxypropylcellulose, carbomer and the like. The preferred concentration of the thickening agent will depend on the agent chosen. Pharmaceutically acceptable preservatives can be used to increase the life of the liquid composition. Benzyl alcohol may be suitable, although a large number of preservatives, including, for example, paraben, thimerosal, chlorobutanol or benzalkonium chloride, can likewise be used.

The active compound can be administered, for example, with a unit dose of from 0.001 mg/kg to 500 mg/kg of body weight, for example up to 1 to 4 times a day. However, the dosage can be increased or reduced, depending on the age, weight, condition of the patient, severity of the disease or nature of the administration.

A preferred embodiment relates to the use of the compounds according to the invention and of the compositions according to the invention comprising the compounds according to the invention and of the combination preparations according to the invention comprising the compounds and compositions according to the invention for the preparation of a medicament for oral or parenteral administration.

The invention is illustrated in more detail by the following examples. The examples are given merely by way of example and the person skilled in the art is in a position to extend the specific examples to further compounds claimed.

EXAMPLES

Pharmacological Action Studies
The following materials were used:

| Reagents | Batch no. | Comments |
| --- | --- | --- |
| MDCK-FPN-HaloTag clone 7 | | |
| Hepcidin 100 µM stock solution in water | Lot# 571007 | Peptides International |
| HaloTag ®TMR ligand | Lot# 257780 | Promega, cat# G8251 |
| Opera confocal plate imager | | PerkinElmer |
| Perkin Elmer 384 Cell carrier plates | | cat# 6007430 |
| Paraformaldehyde | Lot# 080416 | Electron Microscopy Sciences |
| | | cat# 15710-S |
| Draq5 | | Biostatus, cat no: DR51000 |

The hepcidin-antagonistic action of the sulfonaminoquinoline compounds of the present invention was determined by means of the "ferroportin internalization assay" described in the following.

Principle of the "Ferroportin Internalization Assay"

Organic compounds of low molecular weight which counteract the biological actions of hepcidin on its receptor, the iron exporter ferroportin (Fpn), were identified on the basis of their ability to inhibit hepcidin-induced internalization of Fpn in living cells. For this purpose, a stable cell line (Madin-Darby canine kidney, MDCK) was produced which constitutively expresses human ferroportin fused recombinantly at its C terminus with a fluorescent reporter protein (HaloTag®, Promega Corp.). The internalization of Fpn was monitored by labelling these cells with fluorescent ligands (HaloTag®-TMR, tetramethylrhodamine) which join covalently on to the HaloTag reporter gene fused with the Fpn. Imaging by confocal fluorescence microscopy showed a cell surface location of Fpn in the absence of hepcidin and the absence of Fpn surface staining in the presence of hepcidin. Optimized image analysis algorithms were used to ascertain the cell surface and to quantify the corresponding membrane fluorescence associated with the Fpn-HaloTag fusion protein. This assay allows a quantitative image-based analysis in order to quickly evaluate compounds which can block hepcidin-induced internalization of Fpn. This assay is a direct in vitro pendant of the in vivo action mechanism proposed for medicament candidates and is therefore suitable as an initial assay with a high throughput for identifying compounds which counteract the action of hepcidin on its receptor ferroportin.

Detailed Assay Procedure 7,500 cells per well (MDCK-FPN-HaloTag) were transinoculated in 50 µl of DMEM medium (Dulbeccos Modified Eagle Medium with 10% foetal bovine serum (FBS), which contained 1% penicillin, 1% streptomycin and 450 µg/ml of G-418) in microtitre plates with 384 wells (384 Cell carrier plates, Perkin Elmer, cat. no. 6007430), followed by incubation overnight at 37° C./5% $CO_2$.

The volume of the medium was reduced to 10 µl, and 10 µl of 5 µM HaloTag-TMR ligands (Promega, cat. no. G 8251) were added in DMEM medium in order to stain the Fpn-HaloTag fusion protein.

15 min incubation at 37° C./5% $CO_2$

The HaloTag-TMR ligand was removed and the cells were washed with fresh DMEM medium and the volume was reduced to 20 µl of DMEM medium.

3 µl per well of a solution of the test compound (dissolved DMSO) were added (10 µl final volume).

7 µl of 43 µM hepcidin (Peptides International, cat. no. PLP-4392-s, 100 µM stock solution diluted in water in DMEM medium) were added per well up to a final hepcidin concentration of 100 nM.

The cells were incubated overnight at 37° C./5% $CO_2$.

The cells were fixed by adding paraformaldehyde (PFA, Electron Microscopy Sciences, cat. no. 15710-S) directly to the cells up to a final concentration of 4%, followed by incubation at room temperature for 15-20 minutes.

The PFA solution was removed and the cells were washed with PBS (phosphate-buffered saline solution), in each case 30 µl remaining in the plate.

20 µl of Draq5 (Biostatus, cat. no. DR 51000) were added up to a final concentration of 2.5 µM in order to stain the cell nuclei, and the plates were sealed with a foil plate seal.

The plates were analysed with the Opera Plate Imager (Opera Confocal Plate Imager, Perkin Elmer) with 7 images per well; 440 ms exposure time per image, 1 µM focal point height.

Analysis of the Data

Optimized algorithms were used for the image analysis to ascertain and quantify the fluorescence associated with the cell surface as a measure of the cell surface location of Fpn-HaloTag.

The final display corresponded to the percentage content of cells which showed membrane fluorescence: wells treated with 100 nM hepcidin gave the lowest values (negative control display=0% inhibition of the Fpn internalization) and wells which were not treated with hepcidin resulted in the maximum percentage content of cells with membrane fluorescence (positive control display 100% inhibition of the Fpn internalization).

On each plate, the median value of the 6 positive and 6 negative control values was used to calculate the percentage inhibition of the compounds tested according to the following formula:

$$I = 100 \times \frac{R_{neg} - R_{compound}}{R_{neg} - R_{pos}}$$

where: $R_{pos}$ positive control display value (median)
$R_{neg}$ negative control display value (median)
$R_{compound}$ display value of the compound investigated
I percentage inhibition by the particular compound In dose/effect studies, dilution series (11 concentrations, 1:2 dilution steps) of the compounds were tested (concentration range from 0.04 to 40 µM), and standardized signal values of replicated tests (average of 6 titrations on independent plates) were used to fit the curves by a robust standard dose/effect model with four parameters (lower asymptote, upper asymptote, IC50, gradient).

The following results were obtained:

| Example Number | Compound Name | Structure | Ferroportin/IC50 µM |
|---|---|---|---|
| 1 | 5-Bromo-thiophene-2-sulfonic acid naphthalene-1-yl-amide | 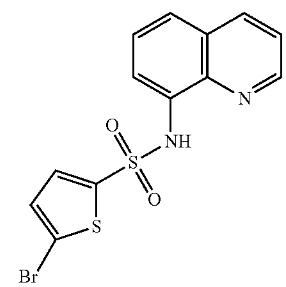 [SMILES: O=S(=O)(Nc1cccc2cccnc12)c1ccc(Br)s1] | 6.8 |
| 2 | 5H-6-Thia-4,5-diaza-chrysene 6,6-dioxide | 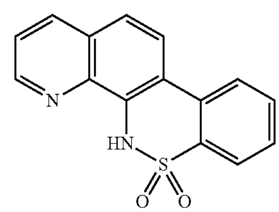 [SMILES: O=S1(=O)Nc2c(ccc3cccnc23)-c2ccccc21] | 2.9 |
| 3 | 5-Methyl-5H-6-thia-4,5-diaza-chrysene 6,6-dioxide | 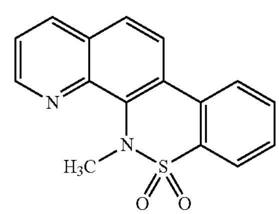 [SMILES: CN1c2c(ccc3cccnc23)-c2ccccc2S1(=O)=O] | 100 |
| 4 | N-Quinolin-8-yl-benzenesulfonamide | 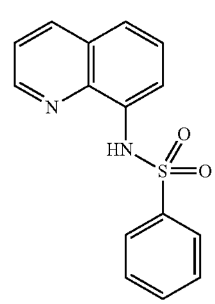 [SMILES: O=S(=O)(Nc1cccc2cccnc12)c1ccccc1] | 4.59 |

-continued

| Example Number | Compound Name | Structure | Ferroportin/ IC50 μM |
|---|---|---|---|
| 5 | 4-Chloro-N-quinolin-8-yl-benzenesulfonamide | 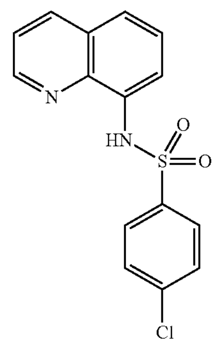 [SMILES: O=S(=O)(Nc1cccc2cccnc12)c1ccc(Cl)cc1] | 3.2 |
| 6 | 2-Nitro-N-quinolin-8-yl-benzenesulfonamide | 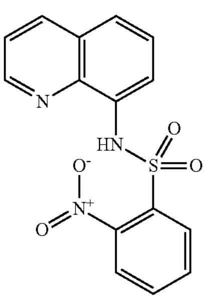 [SMILES: O=[N+]([O-])c1ccccc1S(=O)(=O)Nc1cccc2cccnc12] | 2.9 |
| 7 | 4-Methoxy-N-quinolin-8-yl-benzenesulfonamide | 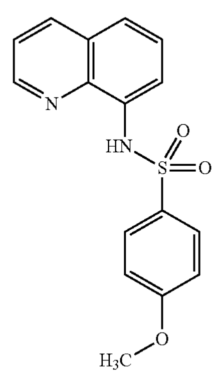 [SMILES: COc1ccc(S(=O)(=O)Nc2cccc3cccnc23)cc1] | 100 |
| 8 | 2-Amino-N-quinolin-8-yl-benzenesulfonamide | 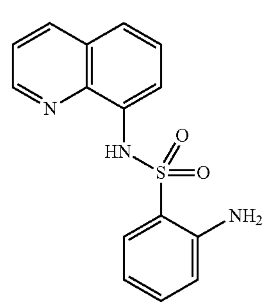 [SMILES: Nc1ccccc1S(=O)(=O)Nc1cccc2cccnc12] | 20.8 |

-continued

| Example Number | Compound Name | Structure | Ferroportin/ IC50 μM |
|---|---|---|---|
| 9 | 4-Methyl-N-quinolin-8-yl-benzenesulfonamide | 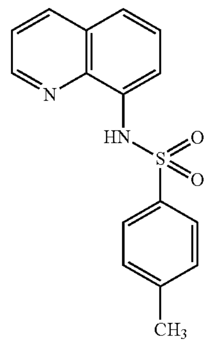 [SMILES: Cc1ccc(S(=O)(=O)Nc2cccc3cccnc23)cc1] | 49.9 |
| 10 | 2-Methyl-N-quinolin-8-yl-benzenesulfonamide | 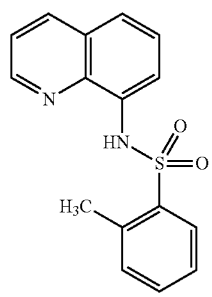 [SMILES: Cc1ccccc1S(=O)(=O)Nc1cccc2cccnc12] | 100 |
| 11 | 2-Chloro-N-quinolin-8-yl-benzenesulfonamide | 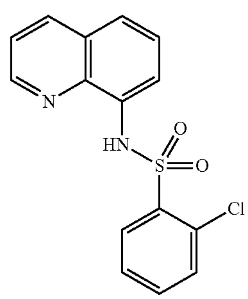 [SMILES: O=S(=O)(Nc1cccc2cccnc12)c1ccccc1Cl] | 8 |
| 12 | 2-Amino-4-methoxy-N-(2-methyl-quinolin-8-yl)-benzenesulfonamide | 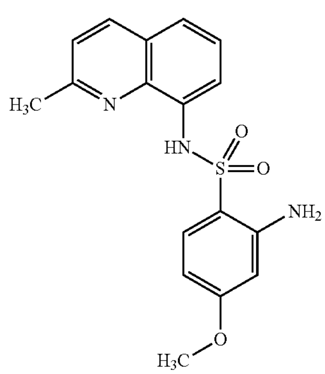 [SMILES: COc1ccc(S(=O)(=O)Nc2cccc3ccc(C)nc23)c(N)c1] | 100 |

-continued
| Example Number | Compound Name | Structure | Ferroportin/ IC50 μM |
|---|---|---|---|
| 13 | 2-Amino-4-methoxy-N-quinolin-8-yl-benzenesulfonamide | 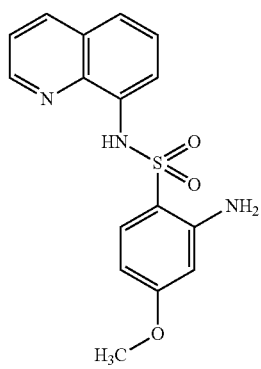 [SMILES: COc1ccc(S(=O)(=O)Nc2cccc3cccnc23)c(N)c1] | 100 |
| 14 | 2-Amino-4-methyl-N-quinolin-8-yl-benzenesulfonamide | 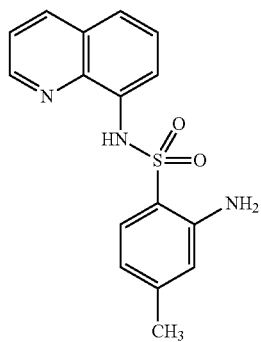 [SMILES: Cc1ccc(S(=O)(=O)Nc2cccc3cccnc23)c(N)c1] | 0.3 |
| 15 | 2-Amino-N-(2-methyl-quinolin-8-yl)-benzenesulfonamide | 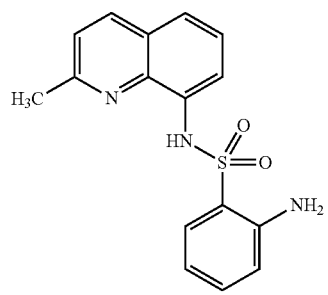 [SMILES: Cc1ccc2cccc(NS(=O)(=O)c3ccccc3N)c2n1] | 100 |
| 16 | 3-Cyano-N-quinolin-8-yl-benzenesulfonamide | 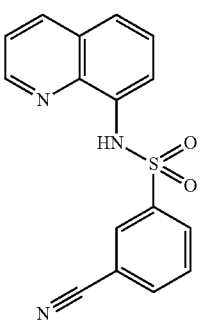 [SMILES: N#Cc1cccc(S(=O)(=O)Nc2cccc3cccnc23)c1] | 0.413 |

| Example Number | Compound Name | Structure | Ferroportin/ IC50 μM |
|---|---|---|---|
| 17 | N-Quinolin-8-yl-4-trifluoromethyl-benzenesulfonamide | 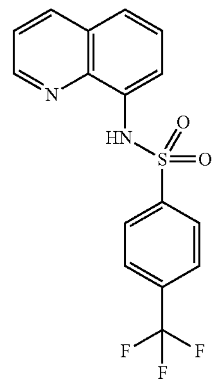 [SMILES: O=S(=O)(Nc1cccc2cccnc12)c1ccc(C(F)(F)F)cc1] | 1 |
| 18 | N-(2-Methyl-quinolin-8-yl)-benzenesulfonamide | 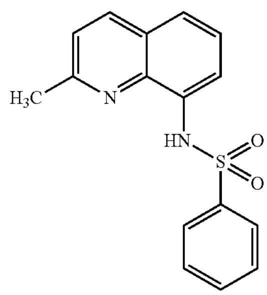 [SMILES: Cc1ccc2cccc(NS(=O)(=O)c3ccccc3)c2n1] | 100 |
| 19 | 3-Methyl-N-quinolin-8-yl-benzenesulfonamide | 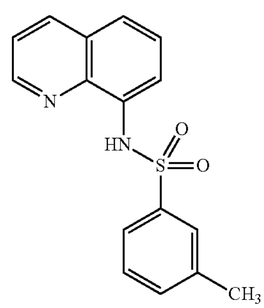 [SMILES: Cc1cccc(S(=O)(=O)Nc2cccc3cccnc23)c1] | 2.09 |
| 20 | 3-Chloro-N-quinolin-8-yl-benzenesulfonamide | 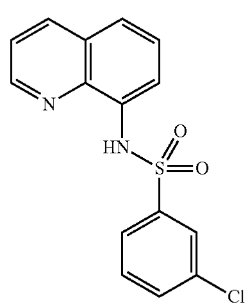 [SMILES: O=S(=O)(Nc1cccc2cccnc12)c1cccc(Cl)c1] | 0.985 |

-continued

| Example Number | Compound Name | Structure | Ferroportin/ IC50 μM |
|---|---|---|---|
| 21 | 3-Methoxy-N-quinolin-8-yl-benzenesulfonamide | 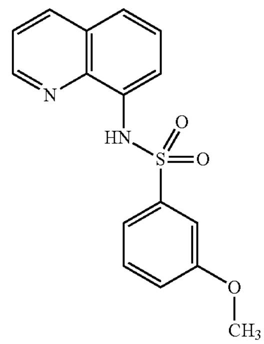 [SMILES: COc1cccc(S(=O)(=O)Nc2cccc3cccnc23)c1] | 1.5 |
| 22 | 3-Methyl-5H-6-thia-4,5-diaza-chrysene 6,6-dioxide | 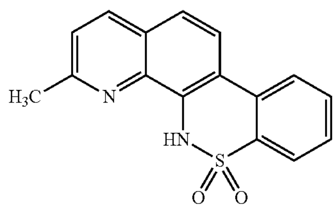 [SMILES: Cc1ccc2ccc3c(c2n1)NS(=O)(=O)c1ccccc1-3] | 100 |
| 23 | N-(6-Methoxy-quinolin-8-yl)-benzenesulfonamide | 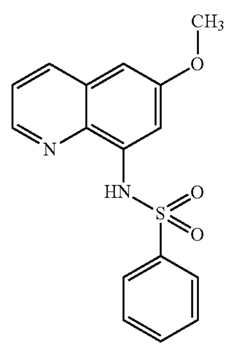 [SMILES: COc1cc(NS(=O)(=O)c2ccccc2)c2ncccc2c1] | 6.4 |
| 24 | N-(2-Chloro-quinolin-8-yl)-benzenesulfonamide | 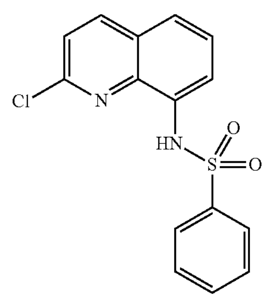 [SMILES: O=S(=O)(Nc1cccc2ccc(Cl)nc12)c1ccccc1] | 100 |
| 25 | N-(5-Chloro-quinolin-8-yl)-benzenesulfonamide | 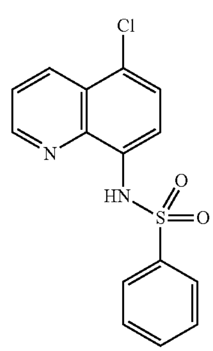 [SMILES: O=S(=O)(Nc1ccc(Cl)c2cccnc12)c1ccccc1] | 1.67 |

-continued

| Example Number | Compound Name | Structure | Ferroportin/ IC50 μM |
|---|---|---|---|
| 26 | N-(7-Methyl-quinolin-8-yl)-benzenesulfonamide | 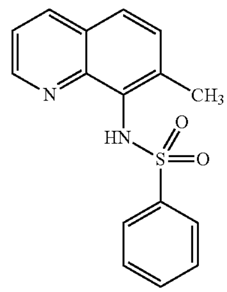 [SMILES: Cc1ccc2cccnc2c1NS(=O)(=O)c1ccccc1] | 100 |
| 27 | 2-Methoxy-N-quinolin-8-yl-benzenesulfonamide | 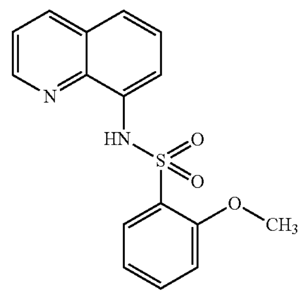 [SMILES: COc1ccccc1S(=O)(=O)Nc1cccc2cccnc12] | 100 |
| 28 | N-(6-Chloro-quinolin-8-yl)-benzenesulfonamide | 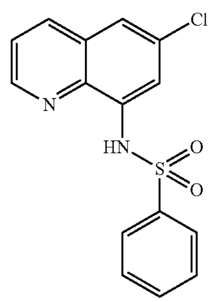 [SMILES: O=S(=O)(Nc1cc(Cl)cc2cccnc12)c1ccccc1] | 100 |
| 29 | N-(5-Bromo-quinolin-8-yl)-benzenesulfonamide | 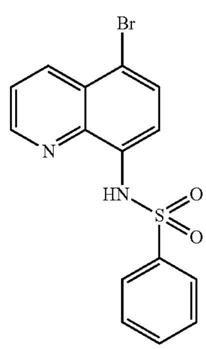 [SMILES: O=S(=O)(Nc1ccc(Br)c2cccnc12)c1ccccc1] | 100 |
| 30 | 4-Fluoro-2-nitro-N-quinolin-8-yl-benzenesulfonamide | 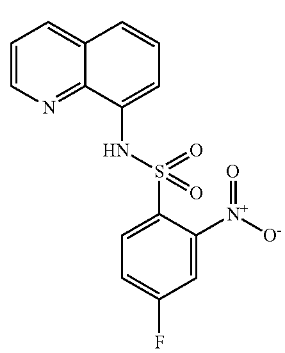 [SMILES: O=[N+]([O-])c1cc(F)ccc1S(=O)(=O)Nc1cccc2cccnc12] | 0.92 |

-continued

| Example Number | Compound Name | Structure | Ferroportin/ IC50 μM |
|---|---|---|---|
| 31 | 2-Amino-4-fluoro-N-quinolin-8-yl-benzenesulfonamide | 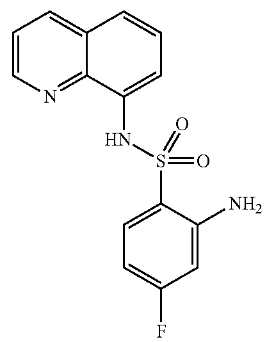 [SMILES: Nc1cc(F)ccc1S(=O)(=O)Nc1cccc2cccnc12] | 3.94 |
| 32 | 2-Nitro-N-quinolin-8-yl-4-trifluoromethyl-benzenesulfonamide | 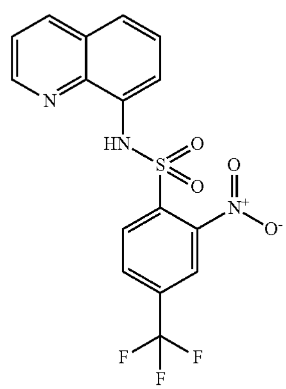 [SMILES: O=[N+]([O-])c1cc(C(F)(F)F)ccc1S(=O)(=O)Nc1cccc2cccnc12] | 100 |
| 33 | Pyridine-3-sulfonic acid quinolin-8-ylamide | 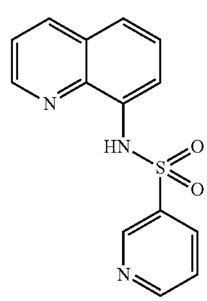 [SMILES: O=S(=O)(Nc1cccc2cccnc12)c1cccnc1] | 3.64 |
| 34 | 4-Methoxy-2-nitro-N-quinolin-8-yl-benzenesulfonamide | 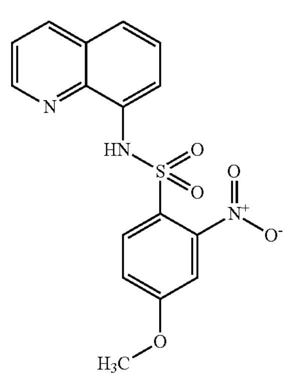 [SMILES: COc1ccc(S(=O)(=O)Nc2cccc3cccnc23)c([N+](=O)[O-])c1] | 1.81 |

-continued

| Example Number | Compound Name | Structure | Ferroportin/ IC50 μM |
|---|---|---|---|
| 35 | 2-Amino-N-quinolin-8-yl-4-trifluoromethyl-benzenesulfonamide | 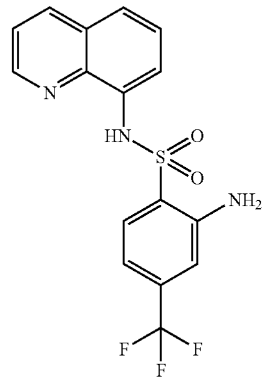 [SMILES: Nc1cc(C(F)(F)F)ccc1S(=O)(=O)Nc1cccc2cccnc12] | 0.76 |
| 36 | N-Quinolin-8-yl-2-trifluoromethoxy-benzenesulfonamide | 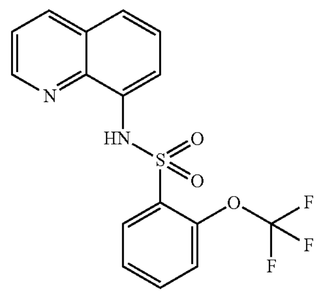 [SMILES: O=S(=O)(Nc1cccc2cccnc12)c1ccccc1OC(F)(F)F] | 2.5 |
| 37 | 2-Cyano-N-quinolin-8-yl-benzenesulfonamide | 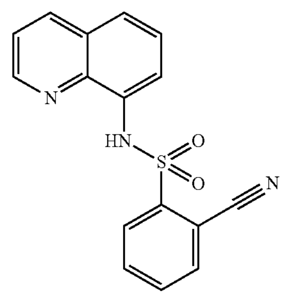 [SMILES: N#Cc1ccccc1S(=O)(=O)Nc1cccc2cccnc12] | 0.815 |
| 38 | N-Quinolin-8-yl-3-trifluoromethoxy-benzenesulfonamide | 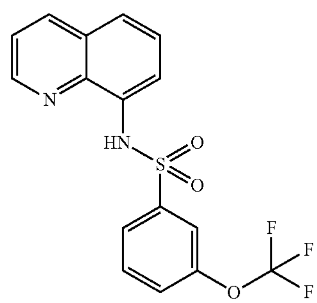 [SMILES: O=S(=O)(Nc1cccc2cccnc12)c1cccc(OC(F)(F)F)c1] | 1.2 |
| 39 | 2-(Quinolin-8-ylsulfamoyl)-benzoic acid methyl ester | 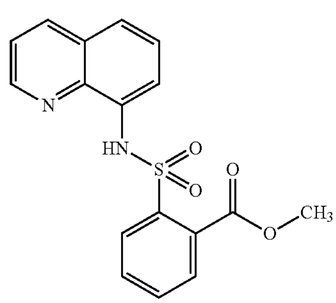 [SMILES: COC(=O)c1ccccc1S(=O)(=O)Nc1cccc2cccnc12] | 58.1 |

-continued

| Example Number | Compound Name | Structure | Ferroportin/ IC50 μM |
|---|---|---|---|
| 40 | 3-(Quinolin-8-ylsulfamoyl)-benzoic acid methyl ester | 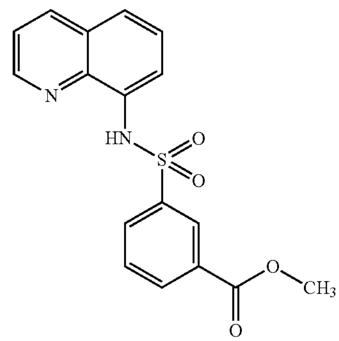 [SMILES: COC(=O)c1cccc(S(=O)(=O)Nc2cccc3cccnc23)c1] | 1.42 |
| 41 | 2,4-Dichloro-N-quinolin-8-yl-benzenesulfonamide | 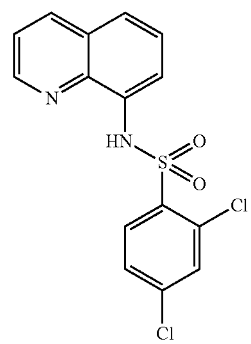 [SMILES: O=S(=O)(Nc1cccc2cccnc12)c1ccc(Cl)cc1Cl] | 0.989 |
| 42 | 4-Chloro-2-fluoro-N-quinolin-8-yl-benzenesulfonamide | 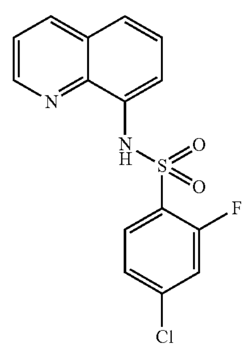 [SMILES: O=S(=O)(Nc1cccc2cccnc12)c1ccc(Cl)cc1F] | 0.873 |
| 43 | N-Quinolin-8-yl-2-trifluoromethyl-benzenesulfonamide | 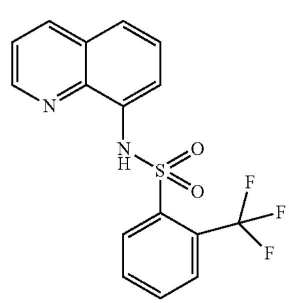 [SMILES: O=S(=O)(Nc1cccc2cccnc12)c1ccccc1C(F)(F)F] | 0.419 |

-continued
| Example Number | Compound Name | Structure | Ferroportin/ IC50 μM |
|---|---|---|---|
| 44 | N-Quinolin-8-yl-3-trifluoromethyl-benzenesulfonamide | 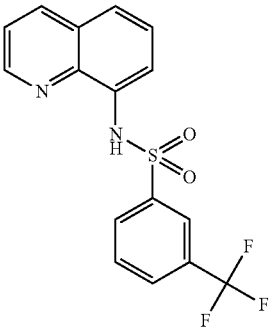 [SMILES: O=S(=O)(Nc1cccc2cccnc12)c1cccc(C(F)(F)F)c1] | 0.72 |
| 45 | N-(3-Methyl-quinolin-8-yl)-benzenesulfonamide | 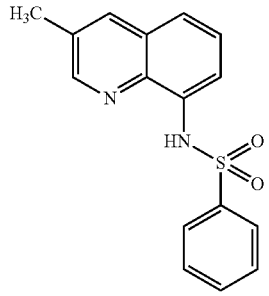 [SMILES: Cc1cnc2c(NS(=O)(=O)c3ccccc3)cccc2c1] | 0.61 |
| 46 | N-phenyl(quinolin-8-ylamino)sulfonamide | 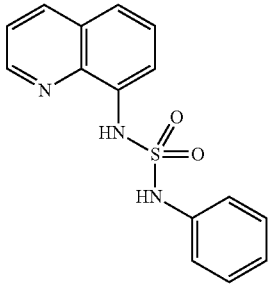 [SMILES: O=S(=O)(Nc1ccccc1)Nc1cccc2cccnc12] | 2.3 |
| 47 | 2,4,6-Trichloro-N-quinolin-8-yl-benzenesulfonamide | 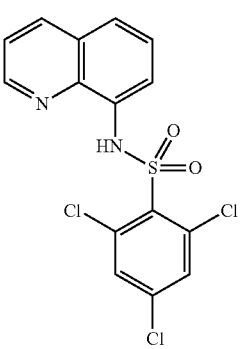 [SMILES: O=S(=O)(Nc1cccc2cccnc12)c1c(Cl)cc(Cl)cc1Cl] | 0.857 |
| 48 | N-[2-(Quinolin-8-ylsulfamoyl)-phenyl]-isobutyramide | 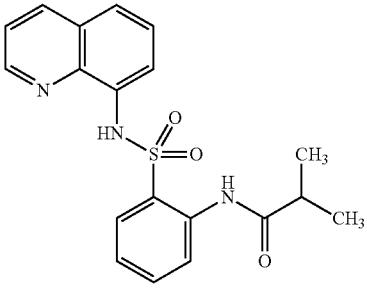 [SMILES: CC(C)C(=O)Nc1ccccc1S(=O)(=O)Nc1cccc2cccnc12] | 24.6 |

-continued

| Example Number | Compound Name | Structure | Ferroportin/ IC50 μM |
|---|---|---|---|
| 49 | 2,2,2-Trifluoro-N-[2-(quinolin-8-ylsulfamoyl)-phenyl]-acetamide | 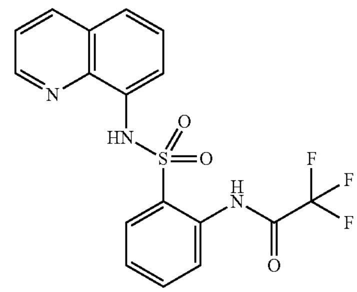 [SMILES: O=C(Nc1ccccc1S(=O)(=O)Nc1cccc2cccnc12)C(F)(F)F] | 0.307 |
| 50 | N-[2-(Quinolin-8-ylsulfamoyl)-phenyl]-acetamide | 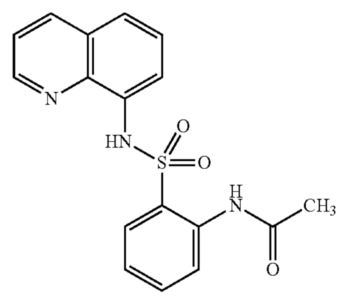 [SMILES: CC(=O)Nc1ccccc1S(=O)(=O)Nc1cccc2cccnc12] | 1.37 |
| 51 | N-(5,7-Dichloro-quinolin-8-yl)-4-methyl-benzenesulfonamide | 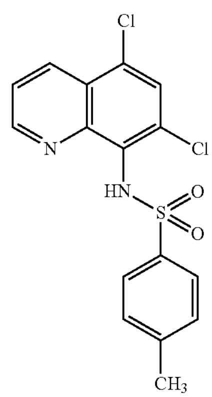 [SMILES: Cc1ccc(S(=O)(=O)Nc2c(Cl)cc(Cl)c3cccnc23)cc1] | 79 |
| 52 | N-(5,7-Dichloro-quinolin-8-yl)-2,4,6-trimethyl-benzenesulfonamide | 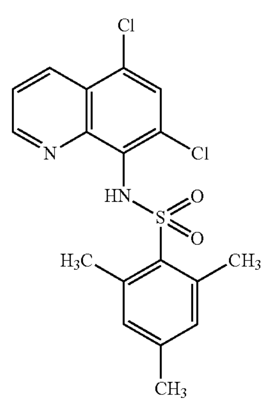 [SMILES: Cc1cc(C)c(S(=O)(=O)Nc2c(Cl)cc(Cl)c3cccnc23)c(C)c1] | 100 |

-continued

| Example Number | Compound Name | Structure | Ferroportin/ IC50 μM |
|---|---|---|---|
| 53 | 2-Amino-N-(5-chloro-quinolin-8-yl)-4-trifluoromethyl-benzenesulfonamide | 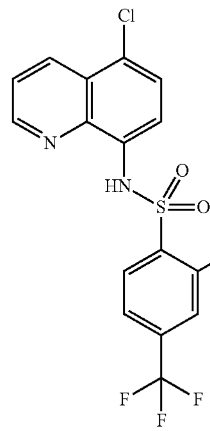 | 100 |
| 54 | 4-Chloro-N-(5-chloro-quinolin-8-yl)-2-fluoro-benzenesulfonamide | 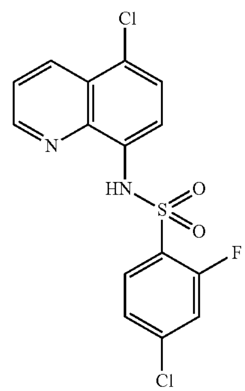 [SMILES: O=S(=O)(Nc1ccc(Cl)c2cccnc12)c1ccc(Cl)cc1F] | 1.38 |
| 55 | 2,2,2-Trifluoro-N-[2-(quinolin-8-ylsulfamoyl)-5-trifluoromethyl-phenyl]-acetamide | 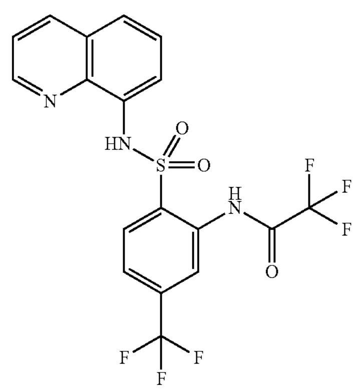 [SMILES: O=C(Nc1cc(C(F)(F)F)ccc1S(=O)(=O)Nc1cccc2cccnc12)C(F)(F)F] | 25 |
| 56 | 2,4-Dichloro-N-(5-chloro-quinolin-8-yl)-benzenesulfonamide | 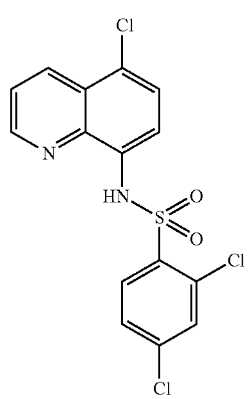 [SMILES: O=S(=O)(Nc1ccc(Cl)c2cccnc12)c1ccc(Cl)cc1Cl] | 100 |

-continued

| Example Number | Compound Name | Structure | Ferroportin/IC50 μM |
|---|---|---|---|
| 57 | 4-Chloro-2-fluoro-N-(6-methoxy-quinolin-8-yl)-benzenesulfonamide | 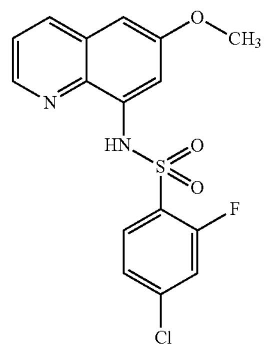 [SMILES: COc1cc(NS(=O)(=O)c2ccc(Cl)cc2F)c2ncccc2c1] | 1.75 |
| 58 | 2,4-Dichloro-N-(6-methoxy-quinolin-8-yl)-benzenesulfonamide | 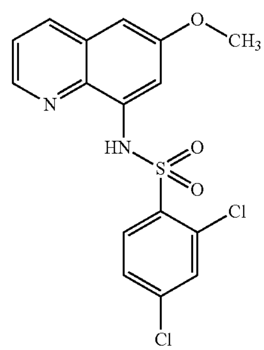 [SMILES: COc1cc(NS(=O)(=O)c2ccc(Cl)cc2Cl)c2ncccc2c1] | 100 |
| 59 | Pyridine-3-sulfonic acid (6-methoxy-quinolin-8-yl)-amide | 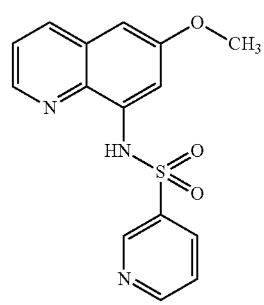 [SMILES: COc1cc(NS(=O)(=O)c2cccnc2)c2ncccc2c1] | 2.8 |
| 60 | Pyridine-3-sulfonic acid (5-chloro-quinolin-8-yl)-amide | 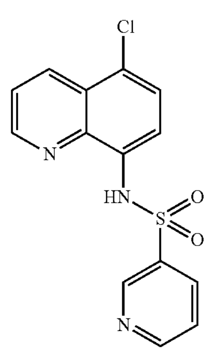 [SMILES: O=S(=O)(Nc1ccc(Cl)c2cccnc12)c1cccnc1] | 1.78 |

-continued

| Example Number | Compound Name | Structure | Ferroportin/ IC50 μM |
|---|---|---|---|
| 61 | N-[2-(Quinolin-8-ylsulfamoyl)-5-trifluoromethyl-phenyl]-isobutyramide | 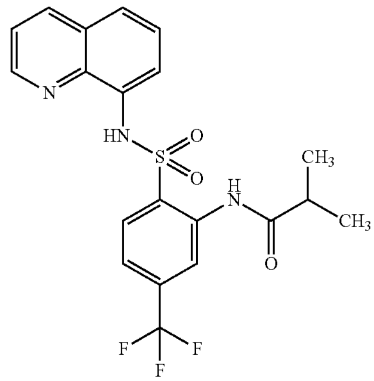 [SMILES: CC(C)C(=O)Nc1cc(C(F)(F)F)ccc1S(=O)(=O)Nc1cccc2cccnc12] | 10 |
| 62 | 3-Chloro-2-fluoro-N-quinolin-8-yl-benzenesulfonamide | 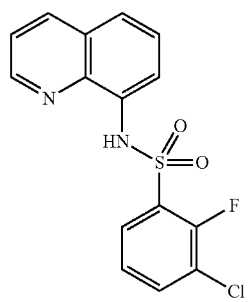 [SMILES: O=S(=O)(Nc1cccc2cccnc12)c1cccc(Cl)c1F] | 1.71 |
| 63 | 2,6-Dichloro-N-quinolin-8-yl-benzenesulfonamide | 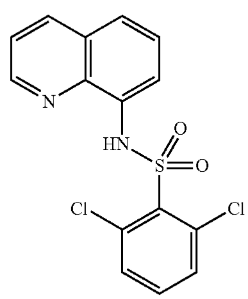 [SMILES: O=S(=O)(Nc1cccc2cccnc12)c1c(Cl)cccc1Cl] | 100 |
| 64 | 2,6-Difluoro-N-quinolin-8-yl-benzenesulfonamide | 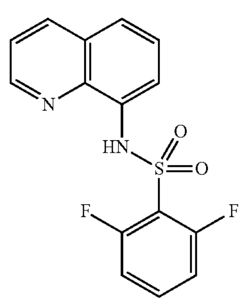 [SMILES: O=S(=O)(Nc1cccc2cccnc12)c1c(F)cccc1F] | 1.14 |

-continued

| Example Number | Compound Name | Structure | Ferroportin/ IC50 μM |
|---|---|---|---|
| 65 | 2-Amino-N-(6-methoxy-quinolin-8-yl)-4-trifluoromethyl-benzenesulfonamide | 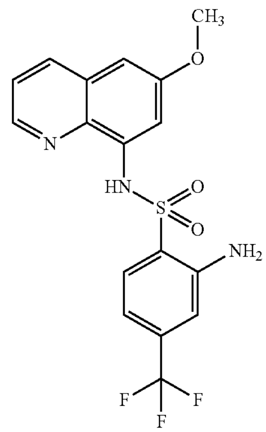 [SMILES: COc1cc(NS(=O)(=O)c2ccc(C(F)(F)F)cc2N)c2ncccc2c1] | 1 |
| 66 | N-[2-(Quinolin-8-ylsulfamoyl)-5-trifluoromethyl-phenyl]-acetamide | 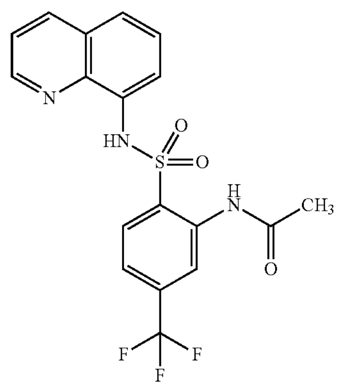 [SMILES: CC(=O)Nc1cc(C(F)(F)F)ccc1S(=O)(=O)Nc1cccc2cccnc12] | 100 |
| 67 | 2,3-Dichloro-N-quinolin-8-yl-benzenesulfonamide | 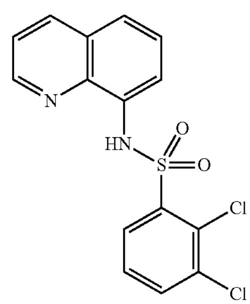 [SMILES: O=S(=O)(Nc1cccc2cccnc12)c1cccc(Cl)c1Cl] | 7.09 |
| 68 | 3-Chloro-2-methyl-N-quinolin-8-yl-benzenesulfonamide | 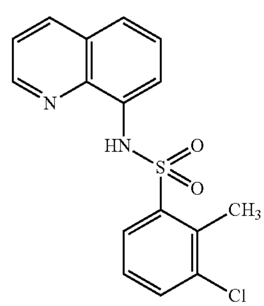 [SMILES: Cc1c(Cl)cccc1S(=O)(=O)Nc1cccc2cccnc12] | 4 |

| Example Number | Compound Name | Structure | Ferroportin/ IC50 μM |
|---|---|---|---|
| 69 | 2,4-Dichloro-N-(3-methyl-quinolin-8-yl)-benzenesulfonamide | 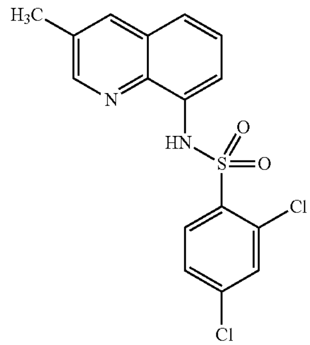 [SMILES: Cc1cnc2c(NS(=O)(=O)c3ccc(Cl)cc3Cl)cccc2c1] | 100 |
| 70 | Quinolin-8-yl-sulfamic acid phenyl ester | 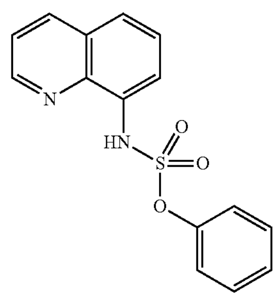 [SMILES: O=S(=O)(Nc1cccc2cccnc12)Oc1ccccc1] | 3.25 |
| 71 | 4-Chloro-2-fluoro-N-(3-methyl-quinolin-8-yl)-benzenesulfonamide | 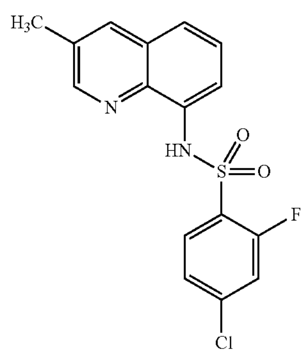 [SMILES: Cc1cnc2c(NS(=O)(=O)c3ccc(Cl)cc3F)cccc2c1] | 1.3 |
| 72 | Pyridine-3-sulfonic acid (3-methyl-quinolin-8-yl)-amide | 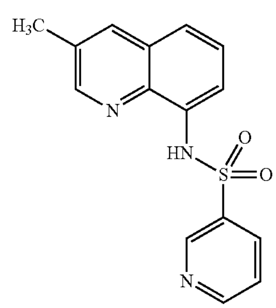 [SMILES: Cc1cnc2c(NS(=O)(=O)c3cccnc3)cccc2c1] | 1.39 |

-continued

| Example Number | Compound Name | Structure | Ferroportin/ IC50 μM |
|---|---|---|---|
| 73 | 2-Amino-N-(3-methyl-quinolin-8-yl)-4-trifluoromethyl-benzenesulfonamide | 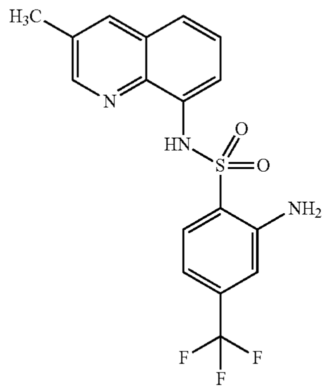 [SMILES: Cc1cnc2c(NS(=O)(=O)c3ccc(C(F)(F)F)cc3N)cccc2c1] | 3 |
| 74 | 9-Fluoro-5H-6-thia-4,5-diaza-chrysene 6,6-dioxide | 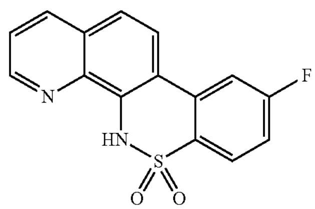 [SMILES: O=S1(=O)Nc2c(ccc3cccnc23)-c2cc(F)ccc21] | 1.56 |
| 75 | N-(6-Fluoro-quinolin-8-yl)-benzenesulfonamide | 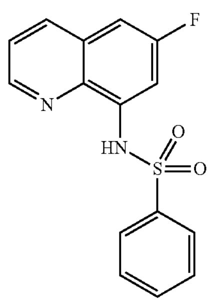 [SMILES: O=S(=O)(Nc1cc(F)cc2cccnc12)c1ccccc1] | 0.78 |
| 76 | N-(5,6-Dimethyl-quinolin-8-yl)-benzenesulfonamide | 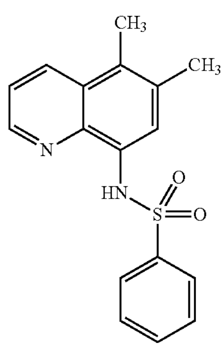 [SMILES: Cc1cc(NS(=O)(=O)c2ccccc2)c2ncccc2c1C] | 100 |
| 77 | N-(6-Methyl-quinolin-8-yl)-benzenesulfonamide | 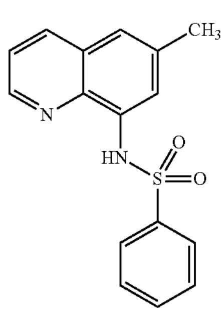 [SMILES: Cc1cc(NS(=O)(=O)c2ccccc2)c2ncccc2c1] | 2.18 |

-continued

| Example Number | Compound Name | Structure | Ferroportin/ IC50 μM |
|---|---|---|---|
| 78 | 9-Trifluoromethyl-5H-6-thia-4,5-diaza-chrysene 6,6-dioxide | 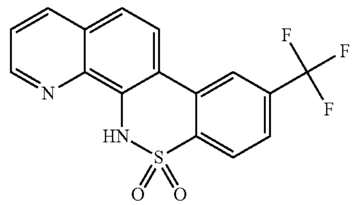 [SMILES: O=S1(=O)Nc2c(ccc3cccnc23)-c2cc(C(F)(F)F)ccc21] | 0.13 |
| 79 | 2-Amino-N-(5-chloro-quinolin-8-yl)-4-methyl-benzenesulfonamide | 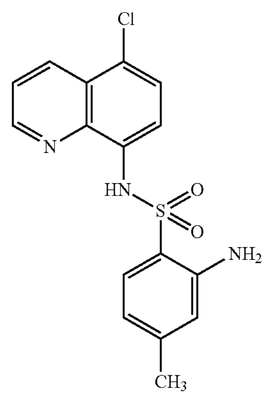 [SMILES: Cc1ccc(S(=O)(=O)Nc2ccc(Cl)c3cccnc23)c(N)c1] | 1.22 |
| 80 | 2-Amino-N-(6-methoxy-quinolin-8-yl)-4-methyl-benzenesulfonamide | 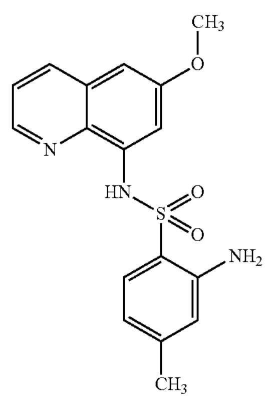 [SMILES: COc1cc(NS(=O)(=O)c2ccc(C)cc2N)c2ncccc2c1] | 0.585 |
| 81 | 2-Amino-4-methyl-N-(3-methyl-quinolin-8-yl)-benzenesulfonamide | 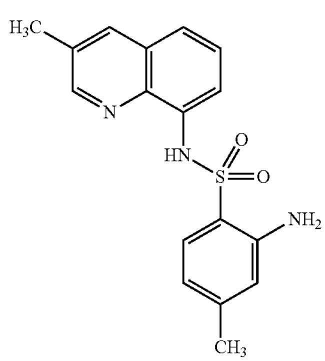 [SMILES: Cc1ccc(S(=O)(=O)Nc2cccc3cc(C)cnc23)c(N)c1] | 100 |

-continued

| Example Number | Compound Name | Structure | Ferroportin/ IC50 μM |
|---|---|---|---|
| 82 | N-(5-Chloro-6-fluoro-quinolin-8-yl)-benzenesulfonamide | 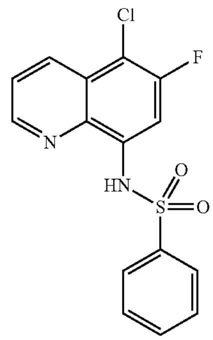 [SMILES: O=S(=O)(Nc1cc(F)c(Cl)c2cccnc12)c1ccccc1] | 1.5 |
| 83 | 3-Fluoro-2-methyl-N-quinolin-8-yl-benzenesulfonamide | 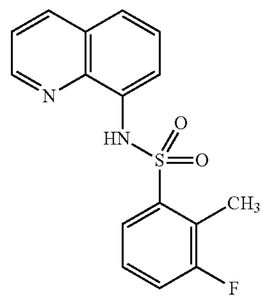 [SMILES: Cc1c(F)cccc1S(=O)(=O)Nc1cccc2cccnc12] | 1.5 |
| 84 | 2-Chloro-6-methyl-N-quinolin-8-yl-benzenesulfonamide | 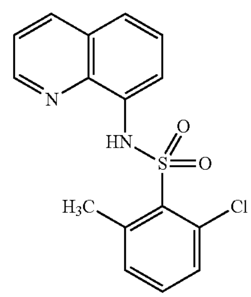 [SMILES: Cc1cccc(Cl)c1S(=O)(=O)Nc1cccc2cccnc12] | 100 |
| 85 | Pyridine-2-sulfonic acid quinolin-8-ylamide | 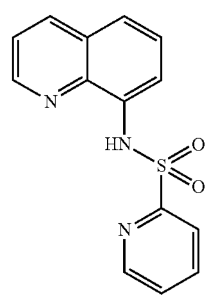 [SMILES: O=S(=O)(Nc1cccc2cccnc12)c1ccccn1] | 1.89 |
| 86 | N-(7-Hydroxy-quinolin-8-yl)-benzenesulfonamide | 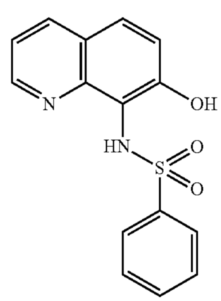 [SMILES: O=S(=O)(Nc1c(O)ccc2cccnc12)c1ccccc1] | 100 |

-continued

| Example Number | Compound Name | Structure | Ferroportin/ IC50 μM |
|---|---|---|---|
| 87 | N-(4-Methoxy-quinolin-8-yl)-benzenesulfonamide | 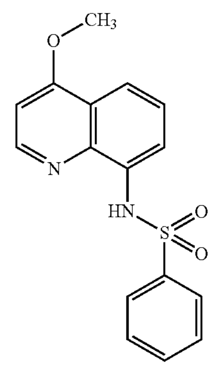 [SMILES: COc1ccnc2c(NS(=O)(=O)c3ccccc3)cccc12] | 100 |
| 88 | Quinoline-3-sulfonic acid quinolin-8-ylamide | 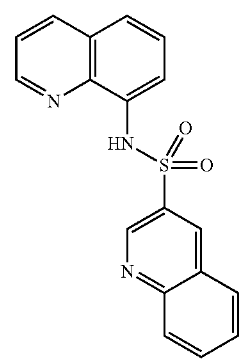 [SMILES: O=S(=O)(Nc1cccc2cccnc12)c1cnc2ccccc2c1] | 2.06 |
| 89 | 6-Trifluoromethyl-pyridine-3-sulfonic acid quinolin-8-ylamide | 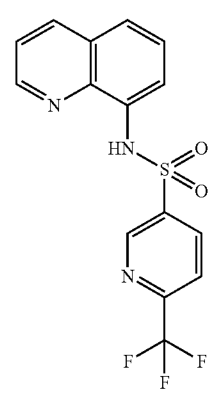 [SMILES: O=S(=O)(Nc1cccc2cccnc12)c1ccc(C(F)(F)F)nc1] | 3.69 |
| 90 | N-(5-Methyl-quinolin-8-yl)-benzenesulfonamide | 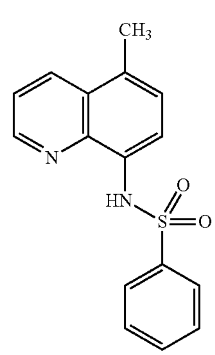 [SMILES: Cc1ccc(NS(=O)(=O)c2ccccc2)c2ncccc12] | 1.1 |

-continued
| Example Number | Compound Name | Structure | Ferroportin/ IC50 μM |
|---|---|---|---|
| 91 | N-(5-Trifluoromethyl-quinolin-8-yl)-benzenesulfonamide | 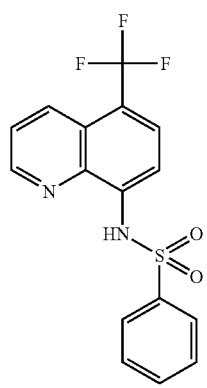 | 1.05 |
| 92 | N-(6-Trifluoromethoxy-quinolin-8-yl)-benzenesulfonamide | 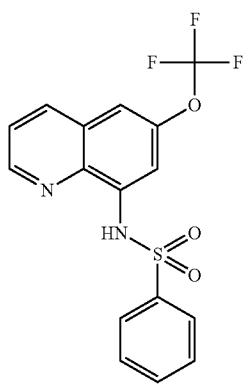 | 9 |
| 93 | N-(6-Ethoxy-quinolin-8-yl)-benzenesulfonamide | 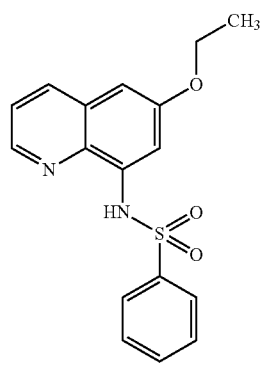 [SMILES: CCOc1cc(NS(=O)(=O)c2ccccc2)c2ncccc2c1] | 100 |
| 94 | 2,6-Difluoro-N-(6-fluoro-quinolin-8-yl)-benzenesulfonamide | 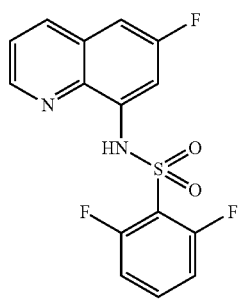 [SMILES: O=S(=O)(Nc1cc(F)cc2cccnc12)c1c(F)cccc1F] | 1 |

-continued
| Example Number | Compound Name | Structure | Ferroportin/ IC50 μM |
|---|---|---|---|
| 95 | 4-Chloro-2-fluoro-N-(6-fluoro-quinolin-8-yl)-benzenesulfonamide | 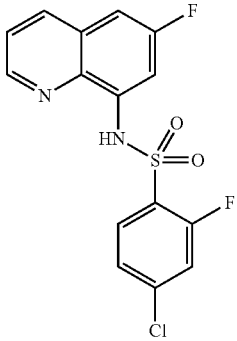 [SMILES: O=S(=O)(Nc1cc(F)cc2cccnc12)c1ccc(Cl)cc1F] | 0.69 |
| 96 | Pyridine-3-sulfonic acid (6-fluoro-quinolin-8-yl)-amide | 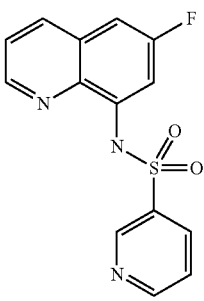 [SMILES: O=S(=O)(Nc1cc(F)cc2cccnc12)c1cccnc1] | 5.87 |
| 97 | N-(5,6-Difluoro-quinolin-8-yl)-benzenesulfonamide | 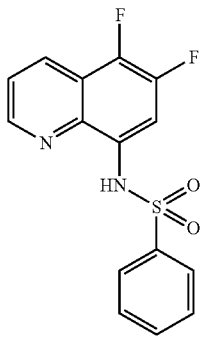 [SMILES: O=S(=O)(Nc1cc(F)c(F)c2cccnc12)c1ccccc1] | 8 |
| 98 | N-(5-Fluoro-quinolin-8-yl)-benzenesulfonamide | 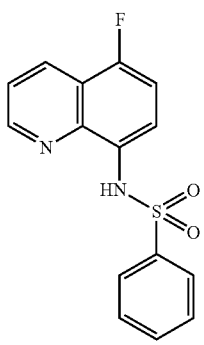 [SMILES: O=S(=O)(Nc1ccc(F)c2cccnc12)c1ccccc1] | 0.988 |

-continued

| Example Number | Compound Name | Structure | Ferroportin/ IC50 μM |
|---|---|---|---|
| 99 | N-(5-Chloro-6-methyl-quinolin-8-yl)-benzenesulfonamide | 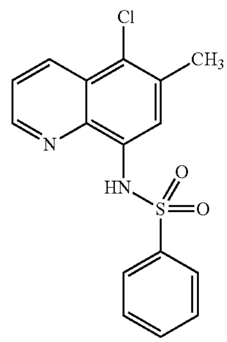 [SMILES: Cc1cc(NS(=O)(=O)c2ccccc2)c2ncccc2c1Cl] | 100 |
| 100 | N-(7-Chloro-quinolin-8-yl)-benzenesulfonamide | 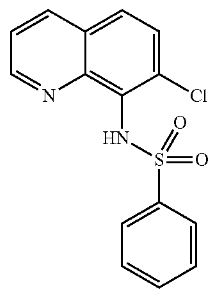 [SMILES: O=S(=O)(Nc1c(Cl)ccc2cccnc12)c1ccccc1] | 100 |
| 101 | N-(7-Isopropyl-quinolin-8-yl)-benzenesulfonamide | 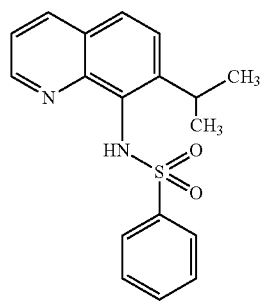 [SMILES: CC(C)c1ccc2cccnc2c1NS(=O)(=O)c1ccccc1] | 100 |
| 102 | N-(7-Ethyl-quinolin-8-yl)-benzenesulfonamide | 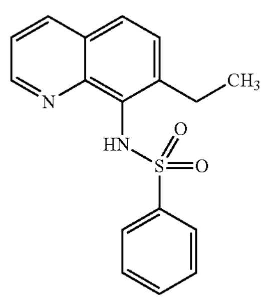 [SMILES: CCc1ccc2cccnc2c1NS(=O)(=O)c1ccccc1] | 100 |
| 103 | N-(7-Methoxy-quinolin-8-yl)-benzenesulfonamide | 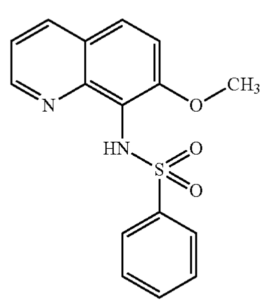 [SMILES: COc1ccc2cccnc2c1NS(=O)(=O)c1ccccc1] | 100 |

-continued

| Example Number | Compound Name | Structure | Ferroportin/ IC50 μM |
|---|---|---|---|
| 104 | 8,9-Dimethyl-5H-6-thia-4,5-diaza-chrysene 6,6-dioxide | 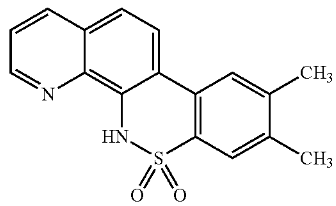 [SMILES: Cc1cc2c(cc1C)S(=O)(=O)Nc1c-2ccc2cccnc12] | 4.02 |
| 105 | 9-Methoxy-5H-6-thia-4,5-diaza-chrysene 6,6-dioxide | 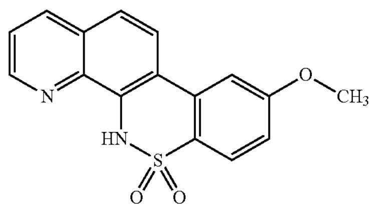 [SMILES: COc1ccc2c(c1)-c1ccc3cccnc3c1NS2(=O)=O] | 1.58 |
| 106 | 11-Methoxy-5H-6-thia-4,5-diaza-chrysene 6,6-dioxide | 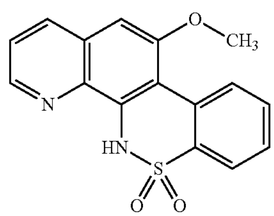 [SMILES: COc1cc2cccnc2c2c1-c1ccccc1S(=O)(=O)N2] | 100 |
| 107 | 12-Methyl-5H-6-thia-4,5-diaza-chrysene 6,6-dioxide | 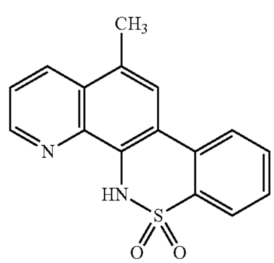 [SMILES: Cc1cc2c(c3ncccc13)NS(=O)(=O)c1ccccc1-2] | 0.599 |
| 108 | 12-Methoxy-5H-6-thia-4,5-diaza-chrysene 6,6-dioxide | 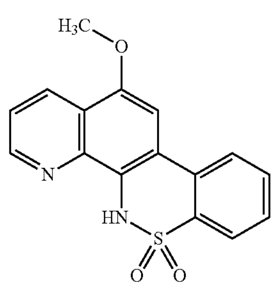 [SMILES: COc1cc2c(c3ncccc13)NS(=O)(=O)c1ccccc1-2] | 0.99 |
| 109 | 1-Methoxy-9-trifluoromethyl-5H-6-thia-4,5-diaza-chrysene 6,6-dioxide | 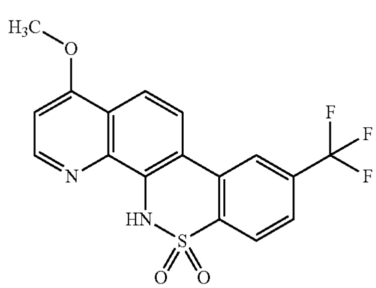 [SMILES: COc1ccnc2c3c(ccc12)-c1cc(C(F)(F)F)ccc1S(=O)(=O)N3] | 0.979 |

-continued

| Example Number | Compound Name | Structure | Ferroportin/ IC50 μM |
|---|---|---|---|
| 110 | N-(3-chloro-2-methylphenyl)[(6-methoxyquinolin-8-yl)amino]sulfonamide | 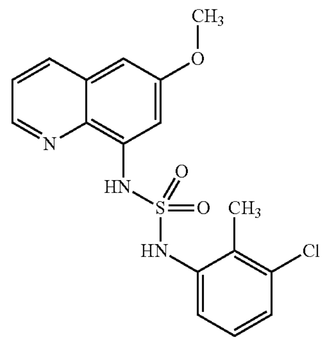 [SMILES: COc1cc(NS(=O)(=O)Nc2cccc(Cl)c2C)c2ncccc2c1] | 100 |
| 111 | N-(3-chloro-2-methylphenyl)[(5-chloroquinolin-8-yl)amino]sulfonamide | 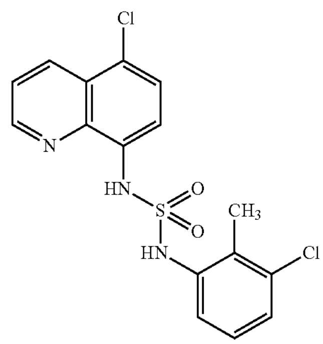 [SMILES: Cc1c(Cl)cccc1NS(=O)(=O)Nc1ccc(Cl)c2cccnc12] | 100 |
| 112 | N-(2,6-difluorophenyl)[(6-methoxyquinolin-8-yl)amino]sulfonamide | 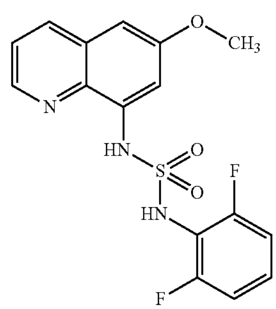 [SMILES: COc1cc(NS(=O)(=O)Nc2c(F)cccc2F)c2ncccc2c1] | 100 |
| 113 | 2-Phenyl-1,4-dihydro-2H-3-thia-2,4,5-triaza-phenanthrene 3,3-dioxide | 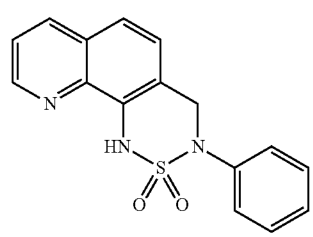 [SMILES: O=S1(=O)Nc2c(ccc3cccnc23)CN1c1ccccc1] | 0.46 |
| 114 | 1,4-Dihydro-2H-3-thia-2,4,5-triaza-phenanthrene 3,3-dioxide | 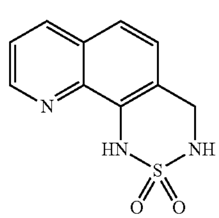 [SMILES: O=S1(=O)NCc2ccc3cccnc3c2N1] | 39.5 |

-continued

| Example Number | Compound Name | Structure | Ferroportin/ IC50 μM |
|---|---|---|---|
| 115 | 2-Methyl-1-phenyl-1,4-dihydro-2H-3-thia-2,4,5-triaza-phenanthrene 3,3-dioxide | 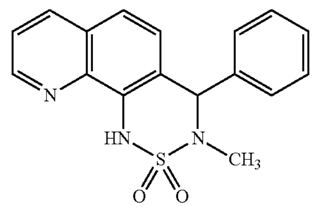 [SMILES: CN1C(c2ccccc2)c2ccc3cccnc3c2NS1(=O)=O] | 0.87 |
| 116 | 6-Cyano-pyridine-3-sulfonic acid quinolin-8-ylamide | 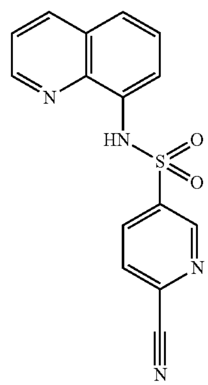 [SMILES: N#Cc1ccc(S(=O)(=O)Nc2cccc3cccnc23)cn1] | 4.26 |
| 225 | 8-Benzenesulfonylamino-quinoline-4-carboxylic acid methyl ester | 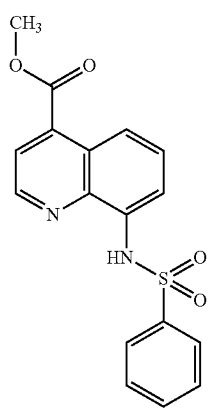 [SMILES: COC(=O)c1ccnc2c(NS(=O)(=O)c3ccccc3)cccc12] | 50 |
| 226 | 6-Trifluoromethyl-pyridine-3-sulfonic acid (6-fluoro-quinolin-8-yl)-amide | 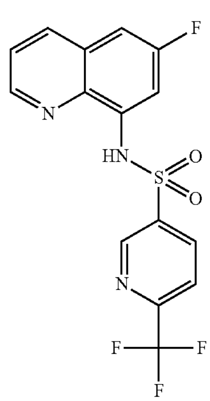 [SMILES: O=S(=O)(Nc1cc(F)cc2cccnc12)c1ccc(C(F)(F)F)nc1] | 25 |

-continued

| Example Number | Compound Name | Structure | Ferroportin/ IC50 μM |
|---|---|---|---|
| 227 | 5-Methyl-pyridine-2-sulfonic acid quinolin-8-ylamide | 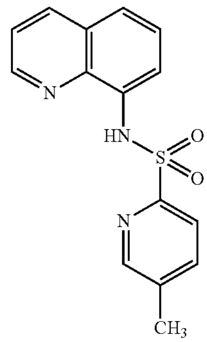 [SMILES: Cc1ccc(S(=O)(=O)Nc2cccc3cccnc23)nc1] | 0.38 |
| 228 | 6-Methyl-pyridine-2-sulfonic acid quinolin-8-ylamide | 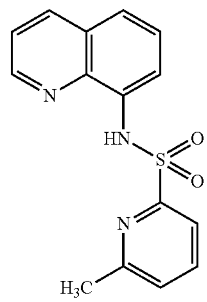 [SMILES: Cc1cccc(S(=O)(=O)Nc2cccc3cccnc23)n1] | 15.4 |
| 229 | 5-Trifluoromethyl-pyridine-3-sulfonic acid quinolin-8-ylamide | 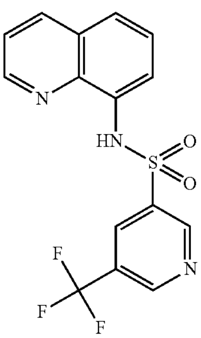 [SMILES: O=S(=O)(Nc1cccc2cccnc12)c1cncc(C(F)(F)F)c1] | 3.98 |
| 230 | Pyrazine-2-sulfonic acid quinolin-8-ylamide | 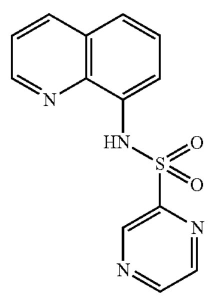 [SMILES: O=S(=O)(Nc1cccc2cccnc12)c1cnccn1] | 1.91 |
| 231 | Thiazole-2-sulfonic acid quinolin-8-ylamide | 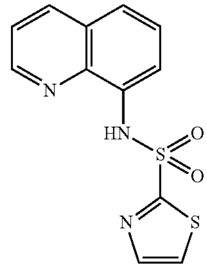 [SMILES: O=S(=O)(Nc1cccc2cccnc12)c1nccs1] | 4.58 |

| Example Number | Compound Name | Structure | Ferroportin/ IC50 μM |
|---|---|---|---|
| 232 | 6-Trifluoromethyl-pyridine-3-sulfonic acid (6-trifluoromethoxy-quinolin-8-yl)-amide | 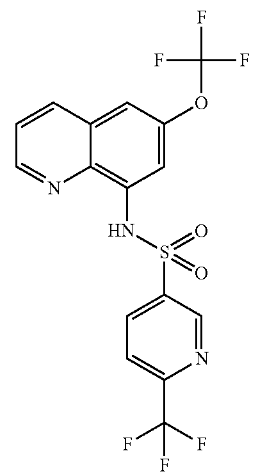 [SMILES: O=S(=O)(Nc1cc(OC(F)(F)F)cc2cccnc12)c1ccc(C(F)(F)F)nc1] | 12.5 |
| 233 | 6-Trifluoromethyl-pyridine-3-sulfonic acid (5-trifluoromethyl-quinolin-8-yl)-amide | 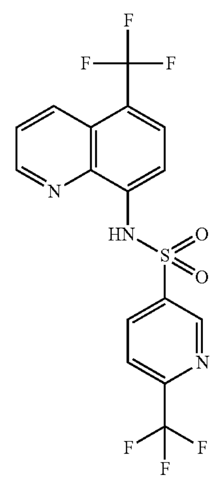 [SMILES: O=S(=O)(Nc1ccc(C(F)(F)F)c2cccnc12)c1ccc(C(F)(F)F)nc1] | 25 |
| 234 | Pyridine-2-sulfonic acid (5-trifluoromethyl-quinolin-8-yl)-amide | 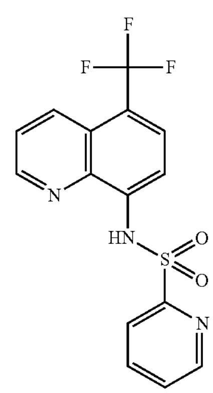 [SMILES: O=S(=O)(Nc1ccc(C(F)(F)F)c2cccnc12)c1ccccn1] | 0.46 |

| Example Number | Compound Name | Structure | Ferroportin/ IC50 μM |
|---|---|---|---|
| 235 | Pyridine-2-sulfonic acid (6-trifluoromethoxy-quinolin-8-yl)-amide | 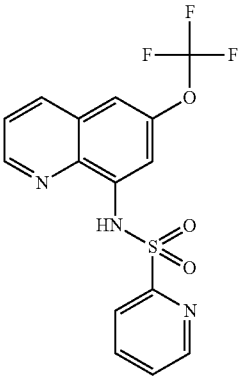 [SMILES: O=S(=O)(Nc1cc(OC(F)(F)F)cc2cccnc12)c1ccccn1] | 1.09 |
| 236 | Pyridine-2-sulfonic acid (6-fluoro-quinolin-8-yl)-amide | 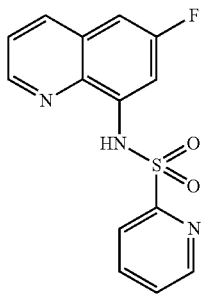 [SMILES: O=S(=O)(Nc1cc(F)cc2cccnc12)c1ccccn1] | 2.37 |
| 237 | Pyridine-3-sulfonic acid (6-trifluoromethoxy-quinolin-8-yl)-amide | 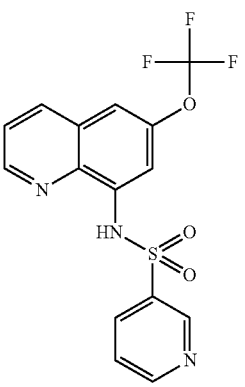 [SMILES: O=S(=O)(Nc1cc(OC(F)(F)F)cc2cccnc12)c1cccnc1] | 3.84 |
| 238 | 6-Cyano-pyridine-3-sulfonic acid (6-trifluoromethoxy-quinolin-8-yl)-amide | 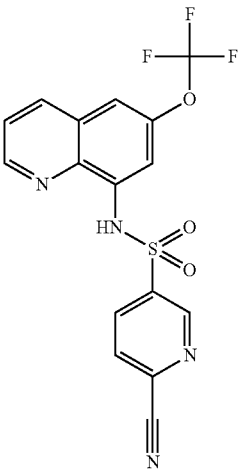 [SMILES: N#Cc1ccc(S(=O)(=O)Nc2cc(OC(F)(F)F)cc3cccnc23)cn1] | 2.11 |

| Example Number | Compound Name | Structure | Ferroportin/ IC50 μM |
|---|---|---|---|
| 239 | 6-Cyano-pyridine-3-sulfonic acid (6-fluoro-quinolin-8-yl)-amide | 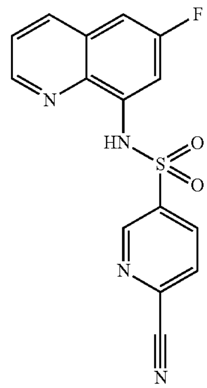 [SMILES: N#Cc1ccc(S(=O)(=O)Nc2cc(F)cc3cccnc23)cn1] | 3.75 |
| 240 | 6-Cyano-pyridine-3-sulfonic acid (5-trifluoromethyl-quinolin-8-yl)-amide | 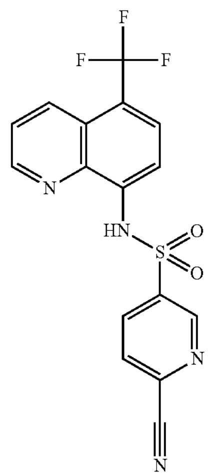 [SMILES: N#Cc1ccc(S(=O)(=O)Nc2ccc(C(F)(F)F)c3cccnc23)cn1] | 2.6 |
| 305 | 1-Chloro-5H-6-thia-4,5-diaza-chrysene 6,6-dioxide | 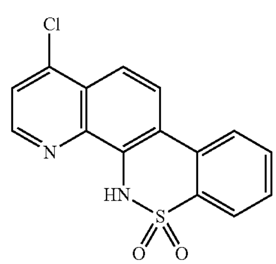 [SMILES: O=S1(=O)Nc2c(ccc3c(Cl)ccnc23)-c2ccccc21] | 12.5 |
| 306 | 12-Fluoro-9-trifluoromethyl-5H-6-thia-4,5-diaza-chrysene 6,6-dioxide | 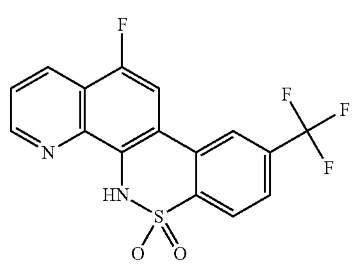 | 4.19 |

-continued
| Example Number | Compound Name | Structure | Ferroportin/ IC50 μM |
|---|---|---|---|
| 307 | 6,6-Dioxo-5,6-dihydro-6λ*6*-thia-4,5-diaza-chrysene-9-carboxylic acid methyl ester | 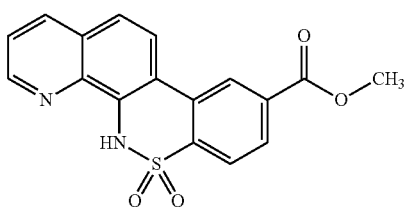 [SMILES: COC(=O)c1ccc2c(c1)-c1ccc3cccnc3c1NS2(=O)=O] | 4.18 |
| 308 | 6,6-Dioxo-5,6-dihydro-6λ*6*-thia-4,5-diaza-chrysene-9-carbonitrile | 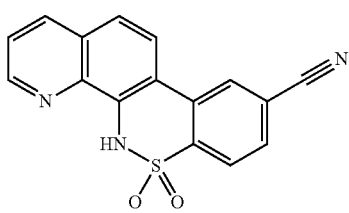 | 2.83 |
| 309 | 1-Trifluoromethyl-5H-6-thia-4,5-diaza-chrysene 6,6-dioxide | 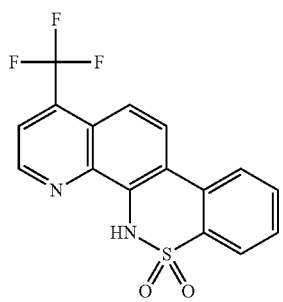 [SMILES: O=S1(=O)Nc2c(ccc3c(C(F)(F)F)ccnc23)-c2ccccc21] | 25 |
| 310 | 9-Chloro-1-trifluoromethyl-5H-6-thia-4,5-diaza-chrysene 6,6-dioxide | 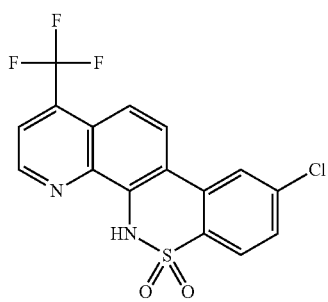 [SMILES: O=S1(=O)Nc2c(ccc3c(C(F)(F)F)ccnc23)-c2cc(Cl)ccc21] | 25 |
| 311 | 12-Trifluoromethyl-5H-6-thia-4,5-diaza-chrysene 6,6-dioxide | 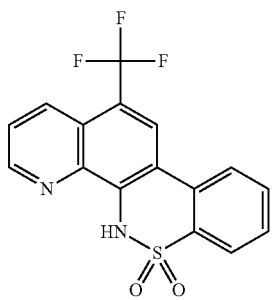 [SMILES: O=S1(=O)Nc2c(cc(C(F)(F)F)c3cccnc23)-c2ccccc21] | 14.1 |

-continued

| Example Number | Compound Name | Structure | Ferroportin/ IC50 μM |
|---|---|---|---|
| 312 | 9-Chloro-12-trifluoromethyl-5H-6-thia-4,5-diaza-chrysene 6,6-dioxide | 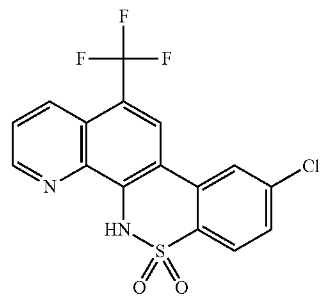 [SMILES: O=S1(=O)Nc2c(cc(C(F)(F)F)c3cccnc23)-c2cc(Cl)ccc21] | 8.51 |
| 313 | 3-Chloro-5H-6-thia-4,5-diaza-chrysene 6,6-dioxide | 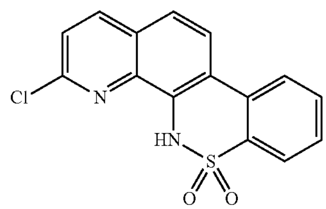 [SMILES: O=S1(=O)Nc2c(ccc3ccc(Cl)nc23)-c2ccccc21] | 25 |
| 314 | 8,12-Dichloro-9-fluoro-5H-6-thia-4,5-diaza-chrysene 6,6-dioxide | 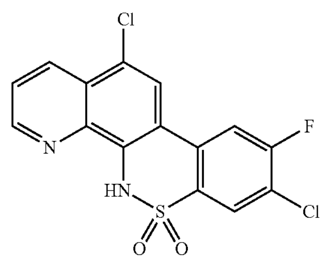 [SMILES: O=S1(=O)Nc2c(cc(Cl)c3cccnc23)-c2cc(F)c(Cl)cc21] | 25 |
| 315 | 12-Chloro-8,9-difluoro-5H-6-thia-4,5-diaza-chrysene 6,6-dioxide | 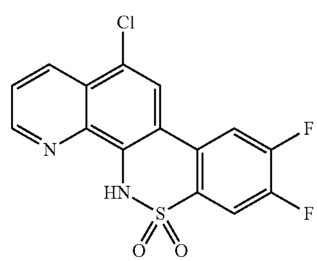 [SMILES: O=S1(=O)Nc2c(cc(Cl)c3cccnc23)-c2cc(F)c(F)cc21] | 25 |
| 316 | 9-Chloro-6,6-dioxo-5,6-dihydro-6λ*6*-thia-4,5-diaza-chrysene-12-carbonitrile | 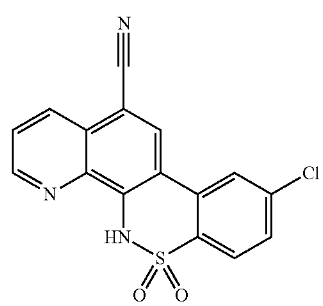 [SMILES: N#Cc1cc2c(c3ncccc13)NS(=O)(=O)c1ccc(Cl)cc1-2] | 25 |
| 317 | 3,9-Dichloro-5H-6-thia-4,5-diaza-chrysene 6,6-dioxide | 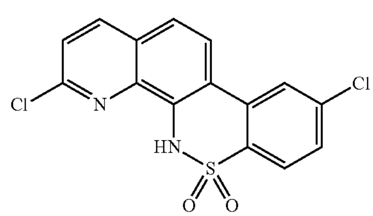 [SMILES: O=S1(=O)Nc2c(ccc3ccc(Cl)nc23)-c2cc(Cl)ccc21] | 25 |

-continued

| Example Number | Compound Name | Structure | Ferroportin/ IC50 μM |
|---|---|---|---|
| 318 | 11H-12-Thia-1,10,11-triaza-chrysene 12,12-dioxide | 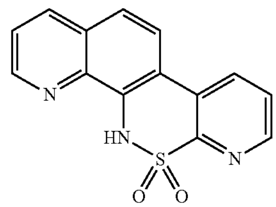 [SMILES: O=S1(=O)Nc2c(ccc3cccnc23)-c2cccnc21] | 6.15 |
| 319 | 6,6-Dioxo-5,6-dihydro-6λ*6*-thia-4,5-diaza-chrysene-1-carboxylic acid methyl ester | 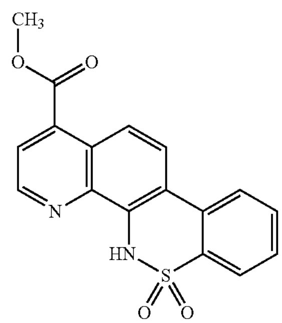 [SMILES: COC(=O)c1ccnc2c3c(ccc12)-c1ccccc1S(=O)(=O)N3] | 2.94 |
| 321 | 12-Chloro-9-methanesulfonyl-5H-6-thia-4,5-diaza-chrysene 6,6-dioxide | 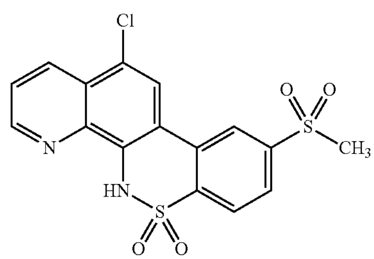 [SMILES: CS(=O)(=O)c1ccc2c(c1)-c1cc(Cl)c3cccnc3c1NS2(=O)=O] | 25 |
| 323 | 11-Fluoro-5H-6-thia-4,5-diaza-chrysene 6,6-dioxide | 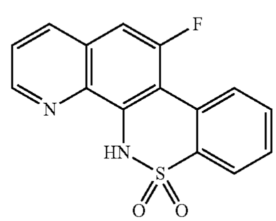 [SMILES: O=S1(=O)Nc2c(c(F)cc3cccnc23)-c2ccccc21] | 3.57 |
| 324 | 12-Fluoro-5H-6-thia-4,5-diaza-chrysene 6,6-dioxide | 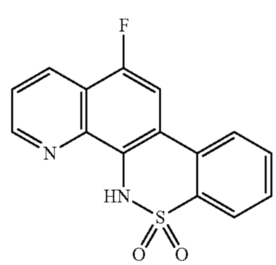 [SMILES: O=S1(=O)Nc2c(cc(F)c3cccnc23)-c2ccccc21] | 1.39 |
| 325 | 9-Chloro-5H-6-thia-4,5-diaza-chrysene 6,6-dioxide | 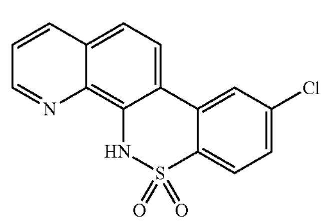 [SMILES: O=S1(=O)Nc2c(ccc3cccnc23)-c2cc(Cl)ccc21] | 0.77 |

-continued

| Example Number | Compound Name | Structure | Ferroportin/ IC50 μM |
|---|---|---|---|
| 326 | 8-Methoxy-5H-6-thia-4,5-diaza-chrysene 6,6-dioxide | 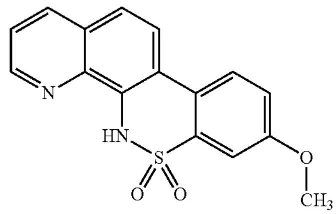 [SMILES: COc1ccc2c(c1)S(=O)(=O)Nc1c-2ccc2cccnc12] | 2.11 |
| 327 | 9-Methyl-5H-6-thia-4,5-diaza-chrysene 6,6-dioxide | 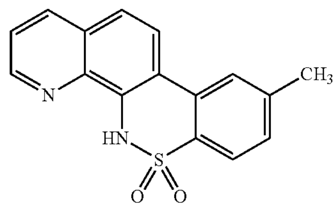 [SMILES: Cc1ccc2c(c1)-c1ccc3cccnc3c1NS2(=O)=O] | 3.2 |
| 328 | 12-Chloro-5H-6-thia-4,5-diaza-chrysene 6,6-dioxide | 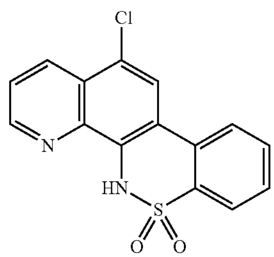 [SMILES: O=S1(=O)Nc2c(cc(Cl)c3cccnc23)-c2ccccc21] | 0.32 |
| 329 | 8-Methyl-5H-6-thia-4,5-diaza-chrysene 6,6-dioxide | 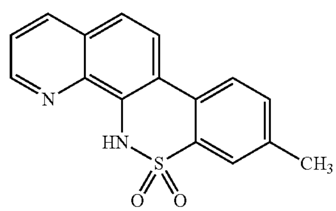 [SMILES: Cc1ccc2c(c1)S(=O)(=O)Nc1c-2ccc2cccnc12] | 0.36 |
| 330 | 8-Fluoro-5H-6-thia-4,5-diaza-chrysene 6,6-dioxide | 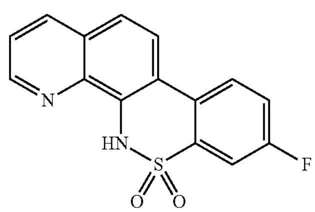 [SMILES: O=S1(=O)Nc2c(ccc3cccnc23)-c2ccc(F)cc21] | 1.62 |
| 331 | 9-Fluoro-8-methyl-5H-6-thia-4,5-diaza-chrysene 6,6-dioxide | 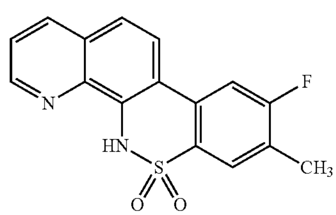 [SMILES: Cc1cc2c(cc1F)-c1ccc3cccnc3c1NS2(=O)=O] | 3.24 |
| 332 | 8-Trifluoromethyl-5H-6-thia-4,5-diaza-chrysene 6,6-dioxide | 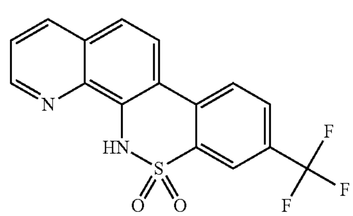 [SMILES: O=S1(=O)Nc2c(ccc3cccnc23)-c2ccc(C(F)(F)F)cc21] | 2.34 |

-continued

| Example Number | Compound Name | Structure | Ferroportin/ IC50 μM |
|---|---|---|---|
| 333 | 9-Trifluoromethoxy-5H-6-thia-4,5-diaza-chrysene 6,6-dioxide | 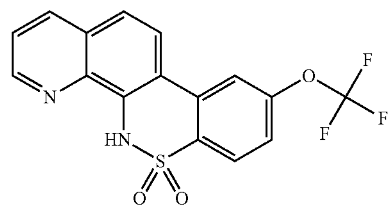 [SMILES: O=S1(=O)Nc2c(ccc3cccnc23)-c2cc(OC(F)(F)F)ccc21] | 1.17 |
| 334 | 12-Chloro-9-trifluoromethyl-5H-6-thia-4,5-diaza-chrysene 6,6-dioxide | 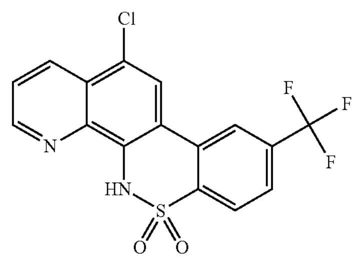 [SMILES: O=S1(=O)Nc2c(cc(Cl)c3cccnc23)-c2cc(C(F)(F)F)ccc21] | 6.25 |
| 335 | 7-Methyl-5H-6-thia-4,5-diaza-chrysene 6,6-dioxide | 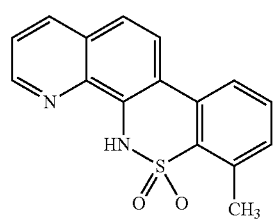 | 3.88 |
| 382 | 1-(4-Fluoro-phenyl)-2-methyl-1,4-dihydro-2H-3-thia-2,4,5-triaza-phenanthrene 3,3-dioxide | 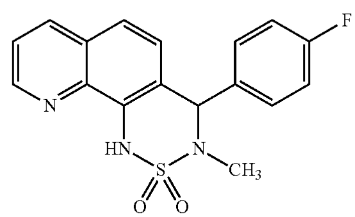 [SMILES: CN1C(c2ccc(F)cc2)c2ccc3cccnc3c2NS1(=O)=O] | 0.34 |
| 383 | 2-Methyl-1-p-tolyl-1,4-dihydro-2H-3-thia-2,4,5-triaza-phenanthrene 3,3-dioxide | 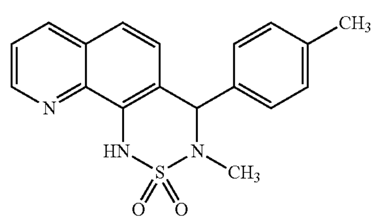 [SMILES: Cc1ccc(C2c3ccc4cccnc4c3NS(=O)(=O)N2C)cc1] | 0.6 |
| 384 | 1-(2-Methoxy-phenyl)-2-methyl-1,4-dihydro-2H-3-thia-2,4,5-triaza-phenanthrene 3,3-dioxide | 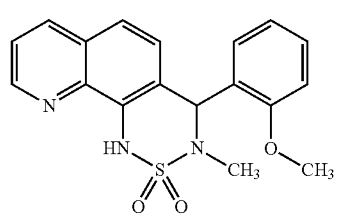 [SMILES: COc1ccccc1C1c2ccc3cccnc3c2NS(=O)(=O)N1C] | 1.87 |

-continued

| Example Number | Compound Name | Structure | Ferroportin/ IC50 μM |
|---|---|---|---|
| 385 | 2-Methyl-1-(4-trifluoromethyl-phenyl)-1,4-dihydro-2H-3-thia-2,4,5-triaza-phenanthrene 3,3-dioxide | 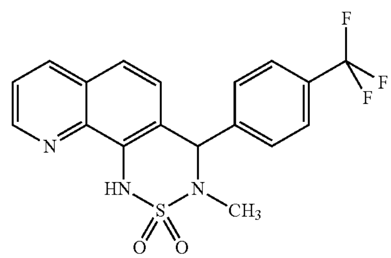 [SMILES: CN1C(c2ccc(C(F)(F)F)cc2)c2ccc3cccnc3c2NS1(=O)=O] | 1.37 |
| 386 | 2-Methyl-1-(6-trifluoromethyl-pyridin-3-yl)-1,4-dihydro-2H-3-thia-2,4,5-triaza-phenanthrene 3,3-dioxide | 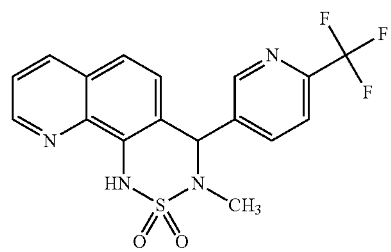 [SMILES: CN1C(c2ccc(C(F)(F)F)nc2)c2ccc3cccnc3c2NS1(=O)=O] | 0.96 |
| 387 | 1-(3-Fluoro-pyridin-4-yl)-2-methyl-1,4-dihydro-2H-3-thia-2,4,5-triaza-phenanthrene 3,3-dioxide | 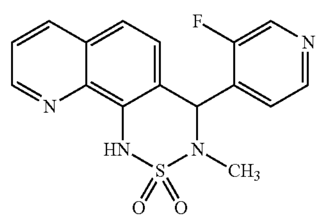 [SMILES: CN1C(c2ccncc2F)c2ccc3cccnc3c2NS1(=O)=O] | 1.6 |
| 388 | 1-(5-Fluoro-pyridin-2-yl)-2-methyl-1,4-dihydro-2H-3-thia-2,4,5-triaza-phenanthrene 3,3-dioxide | 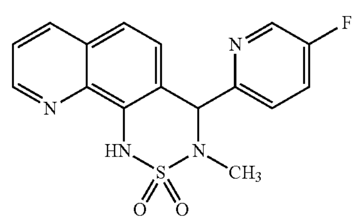 [SMILES: CN1C(c2ccc(F)cn2)c2ccc3cccnc3c2NS1(=O)=O] | 1.57 |
| 389 | 1-(3-Fluoro-phenyl)-2-methyl-1,4-dihydro-2H-3-thia-2,4,5-triaza-phenanthrene 3,3-dioxide | 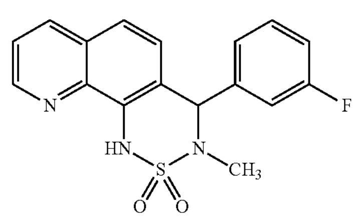 [SMILES: CN1C(c2cccc(F)c2)c2ccc3cccnc3c2NS1(=O)=O] | 0.72 |
| 390 | 1-(4-Methoxy-phenyl)-2-methyl-1,4-dihydro-2H-3-thia-2,4,5-triaza-phenanthrene 3,3-dioxide | 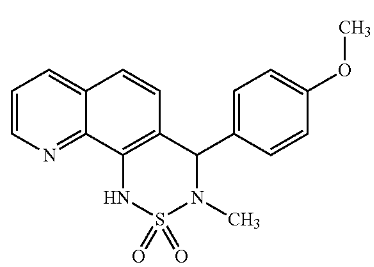 [SMILES: COc1ccc(C2c3ccc4cccnc4c3NS(=O)(=O)N2C)cc1] | 2.24 |

-continued

| Example Number | Compound Name | Structure | Ferroportin/ IC50 μM |
|---|---|---|---|
| 391 | 1-(3-Chloro-4-fluoro-phenyl)-2-methyl-1,4-dihydro-2H-3-thia-2,4,5-triaza-phenanthrene 3,3-dioxide | 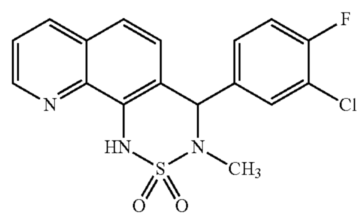 [SMILES: CN1C(c2ccc(F)c(Cl)c2)c2ccc3cccnc3c2NS1(=O)=O] | 3.7 |
| 392 | 1-(3,4-Difluoro-phenyl)-2-methyl-1,4-dihydro-2H-3-thia-2,4,5-triaza-phenanthrene 3,3-dioxide | 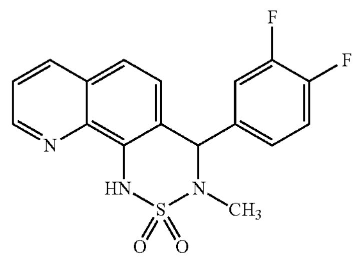 [SMILES: CN1C(c2ccc(F)c(F)c2)c2ccc3cccnc3c2NS1(=O)=O] | 0.25 |
| 393 | 2-Methyl-1-(4-trifluoromethoxy-phenyl)-1,4-dihydro-2H-3-thia-2,4,5-triaza-phenanthrene 3,3-dioxide | 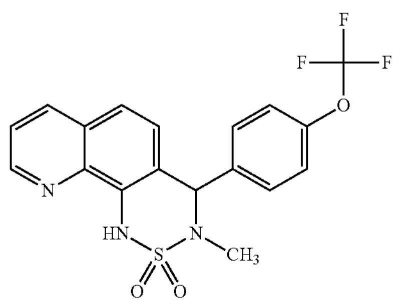 [SMILES: CN1C(c2ccc(OC(F)(F)F)cc2)c2ccc3cccnc3c2NS1(=O)=O] | 1.15 |
| 394 | 1-(2,4-Dimethoxy-phenyl)-2-methyl-1,4-dihydro-2H-3-thia-2,4,5-triaza-phenanthrene 3,3-dioxide | 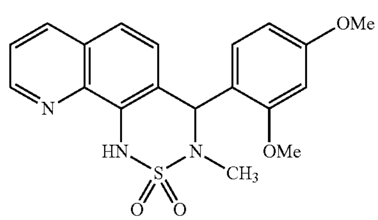 [SMILES: COc1ccc(C2c3ccc4cccnc4c3NS(=O)(=O)N2C)c(OC)c1] | 1.07 |
| 395 | 1-(4-Fluoro-2-methyl-phenyl)-2-methyl-1,4-dihydro-2H-3-thia-2,4,5-triaza-phenanthrene 3,3-dioxide | 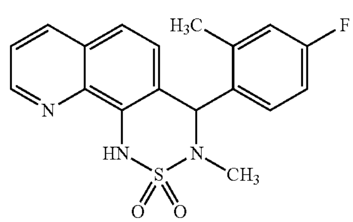 [SMILES: Cc1cc(F)ccc1C1c2ccc3cccnc3c2NS(=O)(=O)N1C] | 1.5 |
| 396 | 1-(3-Fluoro-4-methoxy-phenyl)-2-methyl-1,4-dihydro-2H-3-thia-2,4,5-triaza-phenanthrene 3,3-dioxide | 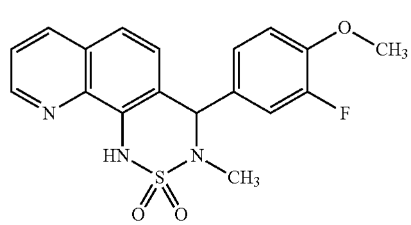 [SMILES: COc1ccc(C2c3ccc4cccnc4c3NS(=O)(=O)N2C)cc1F] | 1.48 |

-continued

| Example Number | Compound Name | Structure | Ferroportin/ IC50 μM |
|---|---|---|---|
| 398 | 1-(4-Fluoro-phenyl)-1,4-dihydro-2H-3-thia-2,4,5-triaza-phenanthrene 3,3-dioxide | 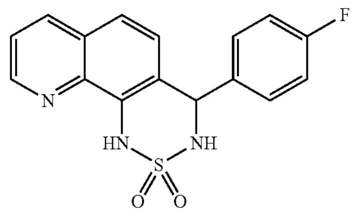 [SMILES: O=S1(=O)Nc2c(ccc3cccnc23)C(c2ccc(F)cc2)N1] | 2.78 |
| 399 | 9-Bromo-1-(4-fluoro-phenyl)-2-methyl-1,4-dihydro-2H-3-thia-2,4,5-triaza-phenanthrene 3,3-dioxide | 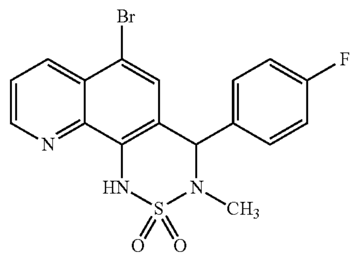 [SMILES: CN1C(c2ccc(F)cc2)c2cc(Br)c3cccnc3c2NS1(=O)=O] | 25 |
| 401 | 9-Chloro-1-(4-fluoro-phenyl)-2-methyl-1,4-dihydro-2H-3-thia-2,4,5-triaza-phenanthrene 3,3-dioxide | 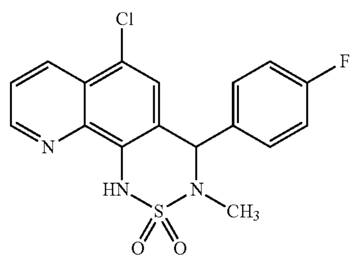 [SMILES: CN1C(c2ccc(F)cc2)c2cc(Cl)c3cccnc3c2NS1(=O)=O] | 12.5 |
| 402 | 1-[1-(4-Fluoro-phenyl)-2-methyl-3,3-dioxo-1,2,3,4-tetrahydro-3λ*6*-thia-2,4,5-triaza-phenanthren-9-yl]-ethanone | 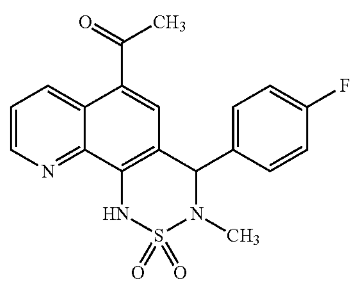 [SMILES: CC(=O)c1cc2c(c3ncccc13)NS(=O)(=O)N(C)C2c1ccc(F)cc1] | 0.25 |
| 403 | 1-[1-(4-Fluoro-phenyl)-2-methyl-3,3-dioxo-1,2,3,4-tetrahydro-3λ*6*-thia-2,4,5-triaza-phenanthren-9-yl]-ethanol | 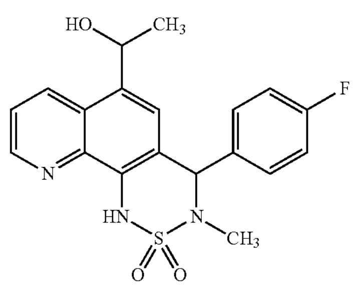 [SMILES: CC(O)c1cc2c(c3ncccc13)NS(=O)(=O)N(C)C2c1ccc(F)cc1] | 2.37 |
| 405 | 2-Methyl-1,4-dihydro-2H-3-thia-2,4,5-triaza-phenanthrene 3,3-dioxide | 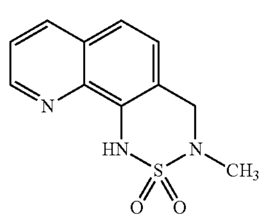 [SMILES: CN1Cc2ccc3cccnc3c2NS1(=O)=O] | 6.5 |

-continued

| Example Number | Compound Name | Structure | Ferroportin/ IC50 μM |
|---|---|---|---|
| 407 | 1-Methyl-1,4-dihydro-2H-3-thia-2,4,5-triaza-phenanthrene 3,3-dioxide | 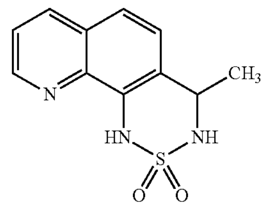 [SMILES: CC1NS(=O)(=O)Nc2c1ccc1cccnc21] | 25 |
| 412 | 1-Ethyl-2-methyl-1,4-dihydro-2H-3-thia-2,4,5-triaza-phenanthrene 3,3-dioxide | 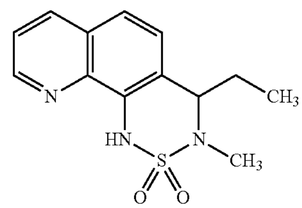 [SMILES: CCC1c2ccc3cccnc3c2NS(=O)(=O)N1C] | 2.22 |
| 413 | 1,2-Dimethyl-1,4-dihydro-2H-3-thia-2,4,5-triaza-phenanthrene 3,3-dioxide | 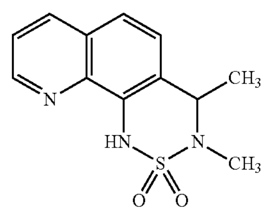 [SMILES: CC1c2ccc3cccnc3c2NS(=O)(=O)N1C] | 4.69 |
| 416 | {2-[1-(4-Fluoro-phenyl)-3,3-dioxo-3,4-dihydro-1H-3λ*6*-thia-2,4,5-triaza-phenanthren-2-yl]-ethyl}-dimethyl-amine | 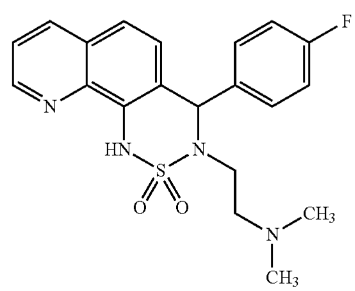 [SMILES: CN(C)CCN1C(c2ccc(F)cc2)c2ccc3cccnc3c2NS1(=O)=O] | 25 |
| 424 | 2-Fluoro-5-(2-methyl-3,3-dioxo-1,2,3,4-tetrahydro-3λ*6*-thia-2,4,5-triaza-phenanthren-1-yl)-benzoic acid | 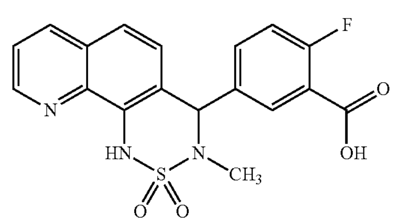 [SMILES: CN1C(c2ccc(F)c(C(=O)O)c2)c2ccc3cccnc3c2NS1(=O)=O] | 5.43 |
| 425 | N'-[2-Fluoro-5-(2-methyl-3,3-dioxo-1,2,3,4-tetrahydro-3λ*6*-thia-2,4,5-triaza-phenanthren-1-yl)-benzyl]-N,N-dimethyl-ethane-1,2-diamine | 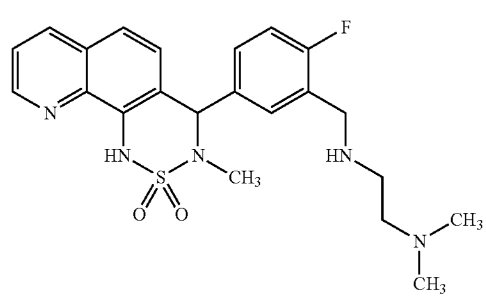 [SMILES: CN(C)CCNCc1cc(C2c3ccc4cccnc4c3NS(=O)(=O)N2C)ccc1F] | 7.41 |

-continued

| Example Number | Compound Name | Structure | Ferroportin/ IC50 μM |
|---|---|---|---|
| 426 | [2-Fluoro-5-(2-methyl-3,3-dioxo-1,2,3,4-tetrahydro-3λ*6*-thia-2,4,5-triaza-phenanthren-1-yl)-benzyl]-(2-morpholin-4-yl-ethyl)-amine | 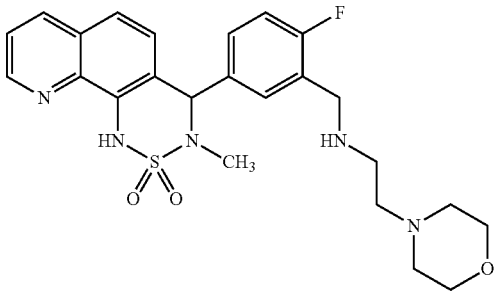 [SMILES: CN1C(c2ccc(F)c(CNCCN3CCOCC3)c2)c2ccc3cccnc3c2NS1(=O)=O] | 8.56 |
| 427 | 1-(4-Fluoro-3-piperazin-1-ylmethyl-phenyl)-2-methyl-1,4-dihydro-2H-3-thia-2,4,5-triaza-phenanthrene 3,3-dioxide | 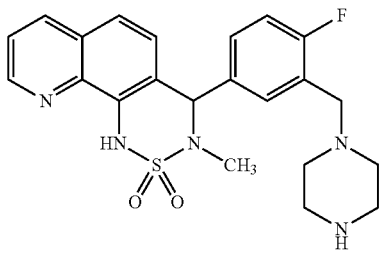 [SMILES: CN1C(c2ccc(F)c(CN3CCNCC3)c2)c2ccc3cccnc3c2NS1(=O)=O] | 4.49 |
| 428 | [2-Fluoro-5-(2-methyl-3,3-dioxo-1,2,3,4-tetrahydro-3λ*6*-thia-2,4,5-triaza-phenanthren-1-yl)-phenyl]-morpholin-4-yl-methanone | 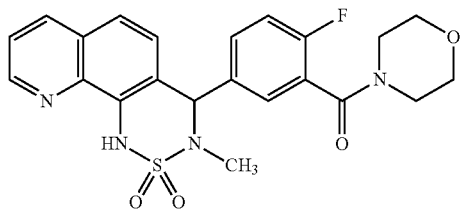 [SMILES: CN1C(c2ccc(F)c(C(=O)N3CCOCC3)c2)c2ccc3cccnc3c2NS1(=O)=O] | 2.62 |
| 429 | N-(2-Dimethylamino-ethyl)-2-fluoro-5-(2-methyl-3,3-dioxo-1,2,3,4-tetrahydro-3λ*6*-thia-2,4,5-triaza-phenanthren-1-yl)-benzamide | 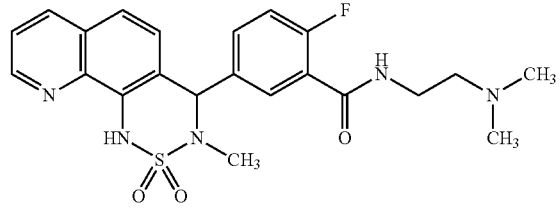 [SMILES: CN(C)CCNC(=O)c1cc(C2c3ccc4cccnc4c3NS(=O)(=O)N2C)ccc1F] | 7.46 |
| 490 | N-[4-(2-Dimethylamino-ethylamino)-quinolin-8-yl]-benzenesulfonamide | 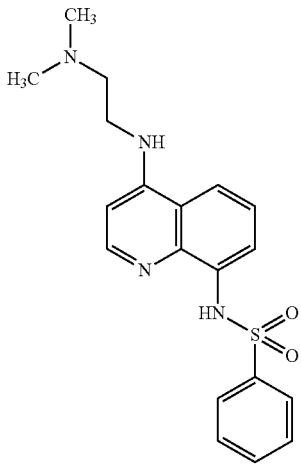 [SMILES: CN(C)CCNc1ccnc2c(NS(=O)(=O)c3ccccc3)cccc12] | 25 |

-continued

| Example Number | Compound Name | Structure | Ferroportin/ IC50 μM |
|---|---|---|---|
| 491 | N-(4-Diethylamino-quinolin-8-yl)-benzenesulfonamide | 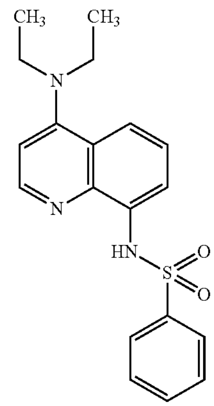 [SMILES: CCN(CC)c1ccnc2c(NS(=O)(=O)c3ccccc3)cccc12] | 25 |
| 492 | N-(4-Dimethylamino-quinolin-8-yl)-benzenesulfonamide | 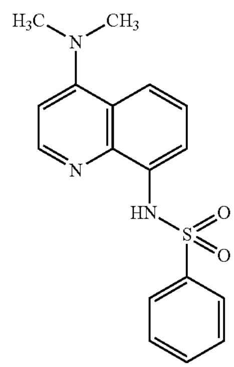 [SMILES: CN(C)c1ccnc2c(NS(=O)(=O)c3ccccc3)cccc12] | 25 |
| 493 | N-(4-Methylamino-quinolin-8-yl)-benzenesulfonamide | 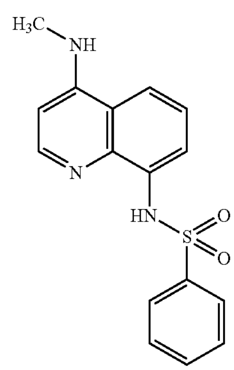 [SMILES: CNc1ccnc2c(NS(=O)(=O)c3ccccc3)cccc12] | 25 |
| 494 | 1-Pyrazol-1-yl-5H-6-thia-4,5-diaza-chrysene 6,6-dioxide | 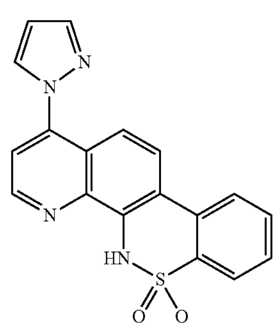 | 3.53 |

| Example Number | Compound Name | Structure | Ferroportin/ IC50 μM |
|---|---|---|---|
| 495 | (6,6-Dioxo-5,6-dihydro-6λ*6*-thia-4,5-diaza-chrysen-1-yl)-diethyl-amine | 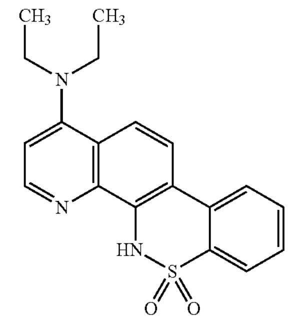 [SMILES: CCN(CC)c1ccnc2c3c(ccc12)-c1ccccc1S(=O)(=O)N3] | 25 |
| 496 | N'-(6,6-Dioxo-5,6-dihydro-6λ*6*-thia-4,5-diaza-chrysen-1-yl)-N,N-dimethyl-ethane-1,2-diamine | 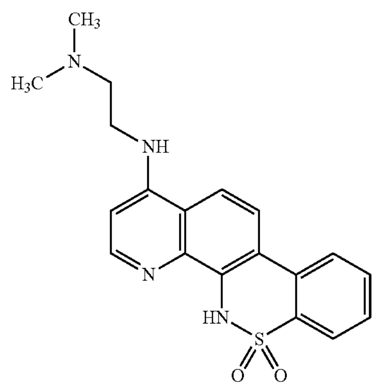 [SMILES: CN(C)CCNc1ccnc2c3c(ccc12)-c1ccccc1S(=O)(=O)N3] | 25 |
| 497 | (6,6-Dioxo-5,6-dihydro-6λ*6*-thia-4,5-diaza-chrysen-1-yl)-dimethyl-amine | 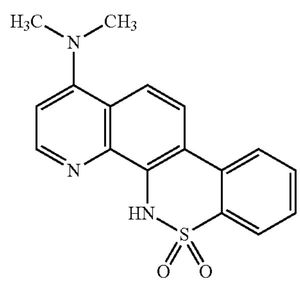 [SMILES: CN(C)c1ccnc2c3c(ccc12)-c1ccccc1S(=O)(=O)N3] | 25 |
| 498 | (6,6-Dioxo-5,6-dihydro-6λ*6*-thia-4,5-diaza-chrysen-1-yl)-methyl-amine | 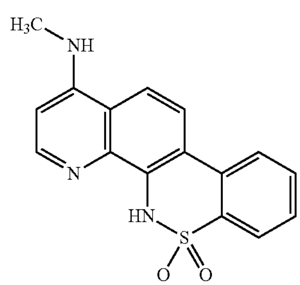 | 25 |
| 499 | 6,6-Dioxo-5,6-dihydro-6λ*6*-thia-4,5-diaza-chrysen-1-ylamine | 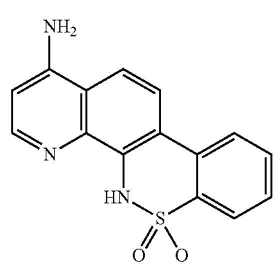 | 25 |

-continued

| Example Number | Compound Name | Structure | Ferroportin/ IC50 μM |
|---|---|---|---|
| 502 | (6,6-Dioxo-5,6-dihydro-6λ*6*-thia-4,5-diaza-chrysen-9-yl)-dimethyl-amine | 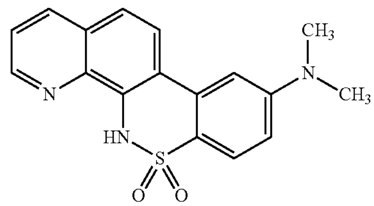 [SMILES: CN(C)c1ccc2c(c1)-c1ccc3cccnc3c1NS2(=O)=O] | 0.91 |
| 504 | 1-(12-Chloro-6,6-dioxo-5,6-dihydro-6λ*6*-thia-4,5-diaza-chrysen-9-yl)-piperidin-4-ol | 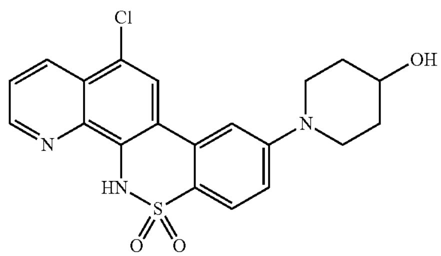 [SMILES: O=S1(=O)Nc2c(cc(Cl)c3cccnc23)-c2cc(N3CCC(O)CC3)ccc21] | 1.1 |
| 505 | (12-Chloro-6,6-dioxo-5,6-dihydro-6λ*6*-thia-4,5-diaza-chrysen-9-yl)-diethyl-amine | 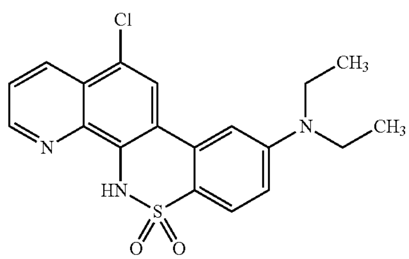 [SMILES: CCN(CC)c1ccc2c(c1)-c1cc(Cl)c3cccnc3c1NS2(=O)=O] | 2.19 |
| 506 | 1-(6,6-Dioxo-5,6-dihydro-6λ*6*-thia-4,5-diaza-chrysen-9-yl)-pyrrolidin-3-ol | 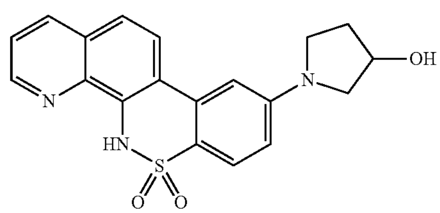 [SMILES: O=S1(=O)Nc2c(ccc3cccnc23)-c2cc(N3CCC(O)C3)ccc21] | 2.01 |
| 507 | (12-Chloro-6,6-dioxo-5,6-dihydro-6λ*6*-thia-4,5-diaza-chrysen-9-yl)-(2-methoxy-ethyl)-amine | 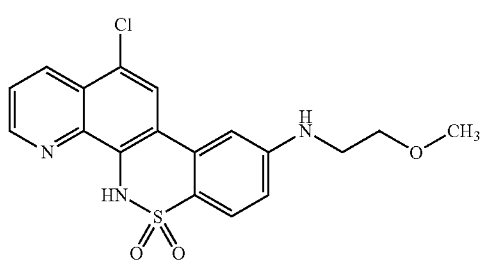 [SMILES: COCCNc1ccc2c(c1)-c1cc(Cl)c3cccnc3c1NS2(=O)=O] | 1.98 |
| 508 | 12-Chloro-9-(4-methyl-piperazin-1-yl)-5H-6-thia-4,5-diaza-chrysene 6,6-dioxide | 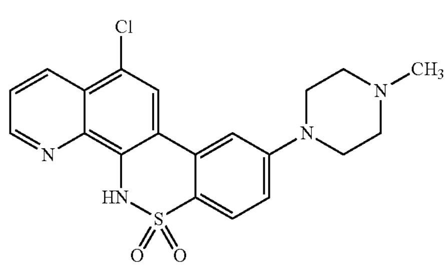 [SMILES: CN1CCN(c2ccc3c(c2)-c2cc(Cl)c4cccnc4c2NS3(=O)=O)CC1] | ND |

-continued

| Example Number | Compound Name | Structure | Ferroportin/ IC50 μM |
|---|---|---|---|
| 509 | 12-Chloro-9-morpholin-4-yl-5H-6-thia-4,5-diaza-chrysene 6,6-dioxide | 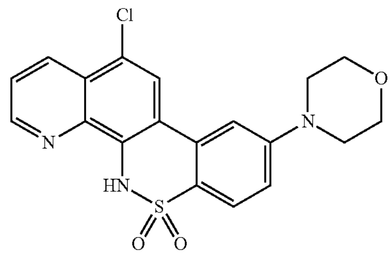 [SMILES: O=S1(=O)Nc2c(cc(Cl)c3cccnc23)-c2cc(N3CCOCC3)ccc21] | 1.62 |
| 510 | 12-Chloro-9-piperidin-1-yl-5H-6-thia-4,5-diaza-chrysene 6,6-dioxide | 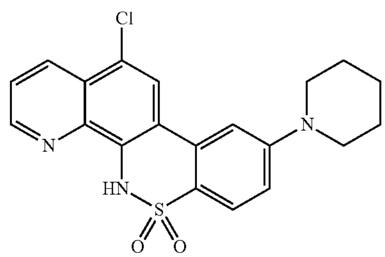 [SMILES: O=S1(=O)Nc2c(cc(Cl)c3cccnc23)-c2cc(N3CCCCC3)ccc21] | ND |
| 511 | (12-Chloro-6,6-dioxo-5,6-dihydro-6$\lambda$*6*-thia-4,5-diaza-chrysen-9-yl)-(2-morpholin-4-yl-ethyl)-amine | 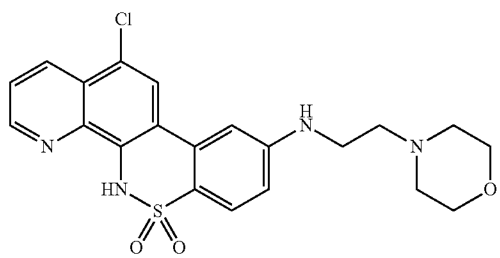 [SMILES: O=S1(=O)Nc2c(cc(Cl)c3cccnc23)-c2cc(NCCN3CCOCC3)ccc21] | 0.62 |
| 512 | 2-(12-Chloro-6,6-dioxo-5,6-dihydro-6$\lambda$*6*-thia-4,5-diaza-chrysen-9-ylamino)-propane-1,3-diol | 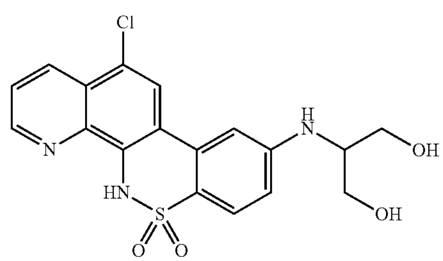 [SMILES: O=S1(=O)Nc2c(cc(Cl)c3cccnc23)-c2cc(NC(CO)CO)ccc21] | 13.4 |
| 514 | 12-Chloro-9-cyclopentyloxy-5H-6-thia-4,5-diaza-chrysene 6,6-dioxide | 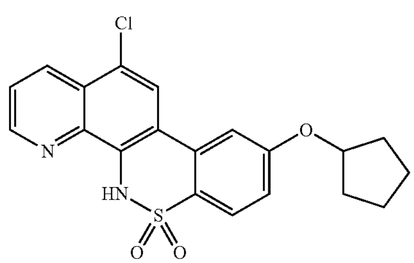 [SMILES: O=S1(=O)Nc2c(cc(Cl)c3cccnc23)-c2cc(OC3CCCC3)ccc21] | 0.42 |
| 515 | 12-Chloro-9-ethoxy-5H-6-thia-4,5-diaza-chrysene 6,6-dioxide | 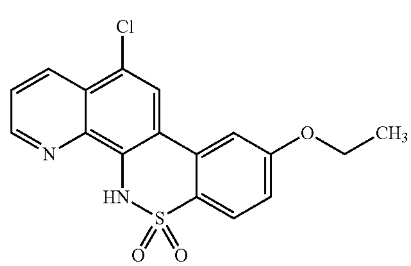 [SMILES: CCOc1ccc2c(c1)-c1cc(Cl)c3cccnc3c1NS2(=O)=O] | 25 |

-continued

| Example Number | Compound Name | Structure | Ferroportin/ IC50 μM |
|---|---|---|---|
| 516 | 12-Chloro-9-(pyrrolidin-3-yloxy)-5H-6-thia-4,5-diaza-chrysene 6,6-dioxide | 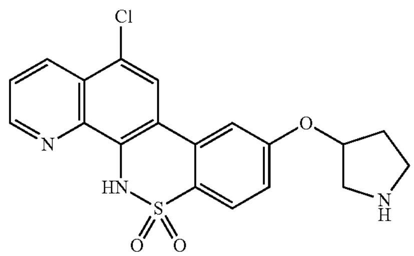 [SMILES: O=S1(=O)Nc2c(cc(Cl)c3cccnc23)-c2cc(OC3CCNC3)ccc21] | ND |
| 517 | 12-Chloro-9-(piperidin-4-yloxy)-5H-6-thia-4,5-diaza-chrysene 6,6-dioxide | 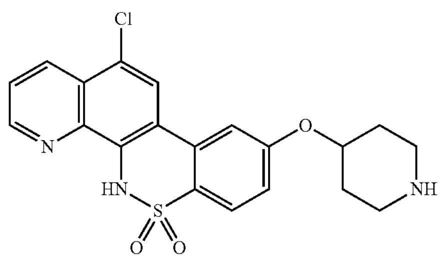 [SMILES: O=S1(=O)Nc2c(cc(Cl)c3cccnc23)-c2cc(OC3CCNCC3)ccc21] | ND |
| 518 | [2-(12-Chloro-6,6-dioxo-5,6-dihydro-6λ*6*-thia-4,5-diaza-chrysen-9-yloxy)-ethyl]-dimethyl-amine | 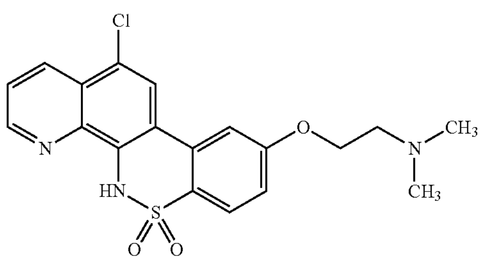 [SMILES: CN(C)CCOc1ccc2c(c1)-c1cc(Cl)c3cccnc3c1NS2(=O)=O] | ND |
| 519 | 12-Chloro-6,6-dioxo-5,6-dihydro-6λ*6*-thia-4,5-diaza-chrysen-9-ylamine | 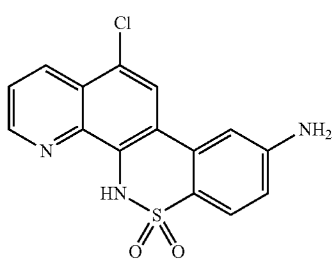 [SMILES: Nc1ccc2c(c1)-c1cc(Cl)c3cccnc3c1NS2(=O)=O] | 3.57 |
| 520 | 6,6-Dioxo-5,6-dihydro-6λ*6*-thia-4,5-diaza-chrysene-9-carboxylic acid | 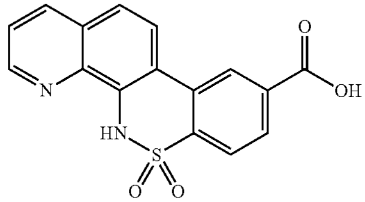 [SMILES: O=C(O)c1ccc2c(c1)-c1ccc3cccnc3c1NS2(=O)=O] | 25 |
| 521 | 6,6-Dioxo-5,6-dihydro-6λ*6*-thia-4,5-diaza-chrysene-9-carboxylic acid amide | 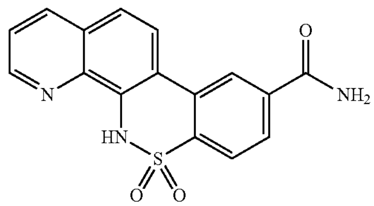 [SMILES: NC(=O)c1ccc2c(c1)-c1ccc3cccnc3c1NS2(=O)=O] | 25 |

-continued

| Example Number | Compound Name | Structure | Ferroportin/ IC50 μM |
|---|---|---|---|
| 522 | 6,6-Dioxo-5,6-dihydro-6λ*6*-thia-4,5-diaza-chrysene-9-carboxylic acid methylamide | 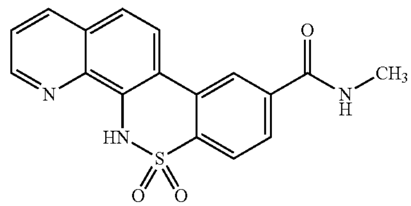 [SMILES: CNC(=O)c1ccc2c(c1)-c1ccc3cccnc3c1NS2(=O)=O] | 13.2 |
| 525 | 12-Chloro-6,6-dioxo-5,6-dihydro-6λ*6*-thia-4,5-diaza-chrysene-9-carboxylic acid dimethylamide | 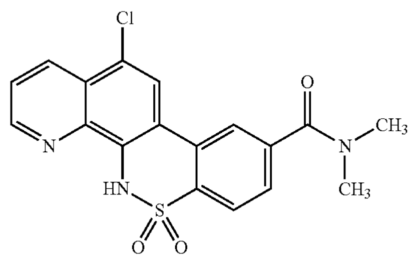 [SMILES: CN(C)C(=O)c1ccc2c(c1)-c1cc(Cl)c3cccnc3c1NS2(=O)=O] | 4.06 |
| 526 | (12-Chloro-6,6-dioxo-5,6-dihydro-6λ*6*-thia-4,5-diaza-chrysen-9-yl)-(4-methyl-piperazin-1-yl)-methanone | 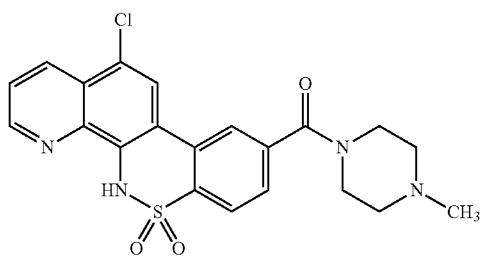 [SMILES: CN1CCN(C(=O)c2ccc3c(c2)-c2cc(Cl)c4cccnc4c2NS3(=O)=O)CC1] | ND |
| 527 | (12-Chloro-6,6-dioxo-5,6-dihydro-6λ*6*-thia-4,5-diaza-chrysen-9-yl)-morpholin-4-yl-methanone | 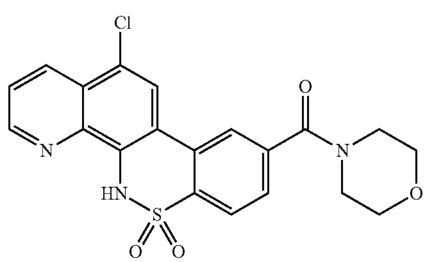 [SMILES: O=C(c1ccc2c(c1)-c1cc(Cl)c3cccnc3c1NS2(=O)=O)N1CCOCC1] | 2.74 |
| 528 | 12-Chloro-6,6-dioxo-5,6-dihydro-6λ*6*-thia-4,5-diaza-chrysene-9-carboxylic acid (2-methoxy-ethyl)-amide | 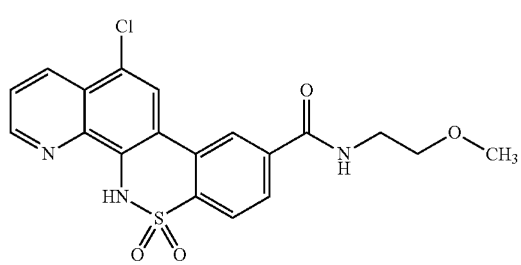 [SMILES: COCCNC(=O)c1ccc2c(c1)-c1cc(Cl)c3cccnc3c1NS2(=O)=O] | 3.9 |
| 529 | 12-Chloro-6,6-dioxo-5,6-dihydro-6λ*6*-thia-4,5-diaza-chrysene-9-carboxylic acid (2-dimethylamino-ethyl)-amide | 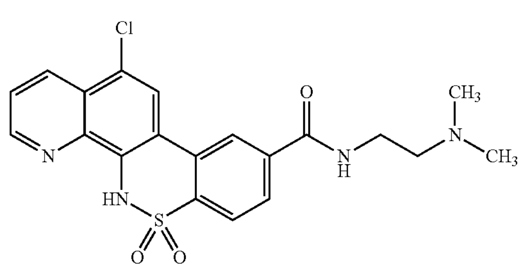 [SMILES: CN(C)CCNC(=O)c1ccc2c(c1)-c1cc(Cl)c3cccnc3c1NS2(=O)=O] | ND |

-continued

| Example Number | Compound Name | Structure | Ferroportin/ IC50 μM |
|---|---|---|---|
| 530 | (12-Chloro-6,6-dioxo-5,6-dihydro-6λ*6*-thia-4,5-diaza-chrysen-9-yl)-(4-hydroxy-piperidin-1-yl)-methanone | 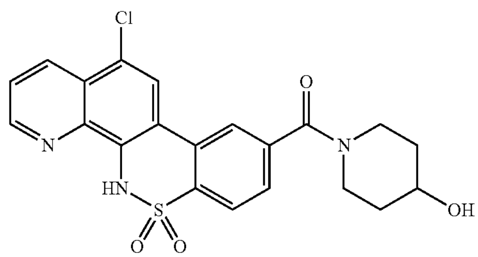 [SMILES: O=C(c1ccc2c(c1)-c1cc(Cl)c3cccnc3c1NS2(=O)=O)N1CCC(O)CC1] | 25 |
| 531 | (12-Chloro-6,6-dioxo-5,6-dihydro-6λ*6*-thia-4,5-diaza-chrysen-9-yl)-(3-hydroxy-pyrrolidin-1-yl)-methanone | 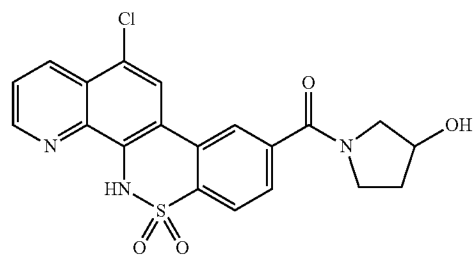 [SMILES: O=C(c1ccc2c(c1)-c1cc(Cl)c3cccnc3c1NS2(=O)=O)N1CCC(O)C1] | 15 |
| 562 | [2-(6,6-Dioxo-5,6-dihydro-6λ*6*-thia-4,5-diaza-chrysen-12-yloxy)-ethyl]-dimethyl-amine | 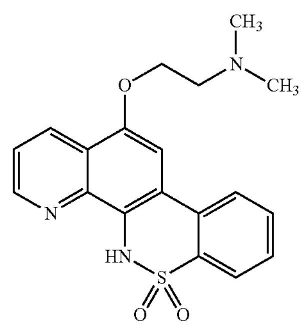 [SMILES: CN(C)CCOc1cc2c(c3ncccc13)NS(=O)(=O)c1ccccc1-2] | 2.76 |
| 532 | 12-Chloro-6,6-dioxo-5,6-dihydro-6λ*6*-thia-4,5-diaza-chrysene-9-carboxylic acid (2-hydroxy-1-hydroxymethyl-ethyl)-amide | 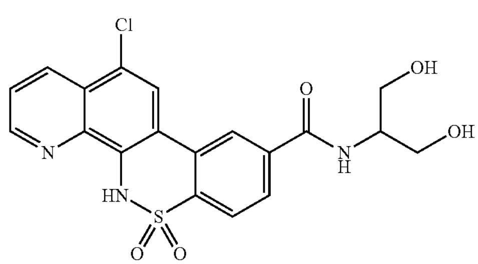 [SMILES: O=C(NC(CO)CO)c1ccc2c(c1)-c1cc(Cl)c3cccnc3c1NS2(=O)=O] | 25 |
| 533 | 12-Chloro-6,6-dioxo-5,6-dihydro-6λ*6*-thia-4,5-diaza-chrysene-9-carboxylic acid cyclopentyl ester | 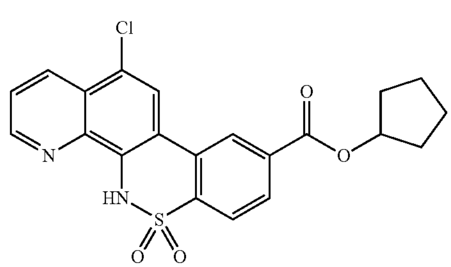 [SMILES: O=C(OC1CCCC1)c1ccc2c(c1)-c1cc(Cl)c3cccnc3c1NS2(=O)=O] | 0.99 |

| Example Number | Compound Name | Structure | Ferroportin/ IC50 μM |
|---|---|---|---|
| 536 | 12-Chloro-6,6-dioxo-5,6-dihydro-6λ*6*-thia-4,5-diaza-chrysene-9-carboxylic acid piperidin-4-yl ester | 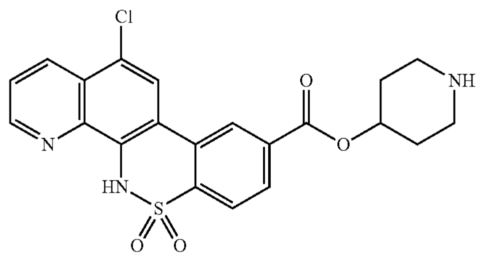 [SMILES: O=C(OC1CCNCC1)c1ccc2c(c1)-c1cc(Cl)c3cccnc3c1NS2(=O)=O] | 25 |
| 537 | 12-Chloro-6,6-dioxo-5,6-dihydro-6λ*6*-thia-4,5-diaza-chrysene-9-carboxylic acid pyrrolidin-3-yl ester | 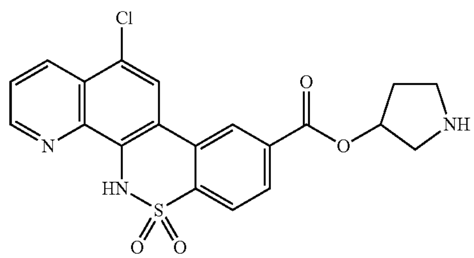 [SMILES: O=C(OC1CCNC1)c1ccc2c(c1)-c1cc(Cl)c3cccnc3c1NS2(=O)=O] | 25 |
| 538 | 8-Benzenesulfonylamino-quinoline-4-carboxylic acid methylamide | 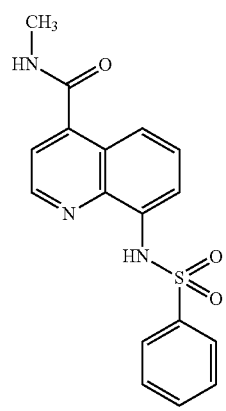 [SMILES: CNC(=O)c1ccnc2c(NS(=O)(=O)c3ccccc3)cccc12] | 6.24 |
| 539 | 8-Benzenesulfonylamino-quinoline-4-carboxylic acid amide | 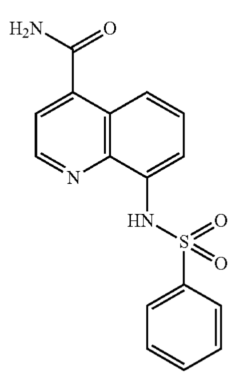 [SMILES: NC(=O)c1ccnc2c(NS(=O)(=O)c3ccccc3)cccc12] | 10.4 |

-continued

| Example Number | Compound Name | Structure | Ferroportin/ IC50 μM |
|---|---|---|---|
| 541 | 6,6-Dioxo-5,6-dihydro-6λ*6*-thia-4,5-diaza-chrysene-1-carboxylic acid dimethylamide | 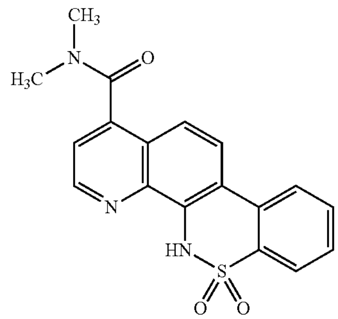 [SMILES: CN(C)C(=O)c1ccnc2c3c(ccc12)-c1ccccc1S(=O)(=O)N3] | 21 |
| 542 | 6,6-Dioxo-5,6-dihydro-6λ*6*-thia-4,5-diaza-chrysene-1-carboxylic acid methylamide | 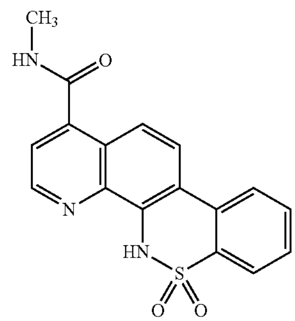 [SMILES: CNC(=O)c1ccnc2c3c(ccc12)-c1ccccc1S(=O)(=O)N3] | 4.77 |
| 543 | 6,6-Dioxo-5,6-dihydro-6λ*6*-thia-4,5-diaza-chrysene-1-carboxylic acid amide | 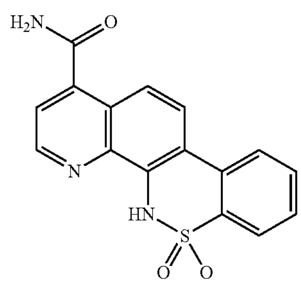 | 25 |
| 544 | 6,6-Dioxo-5,6-dihydro-6λ*6*-thia-4,5-diaza-chrysene-1-carboxylic acid (2-piperidin-1-yl-ethyl)-amide | 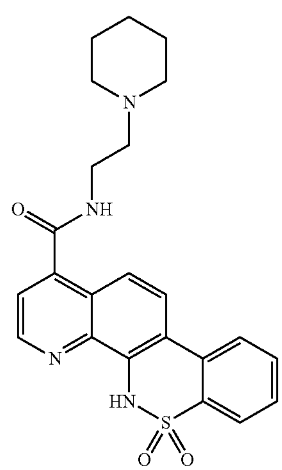 [SMILES: O=C(NCCN1CCCCC1)c1ccnc2c3c(ccc12)-c1ccccc1S(=O)(=O)N3] | 2 |

-continued

| Example Number | Compound Name | Structure | Ferroportin/ IC50 μM |
|---|---|---|---|
| 545 | 12-Bromo-5H-6-thia-4,5-diaza-chrysene 6,6-dioxide | 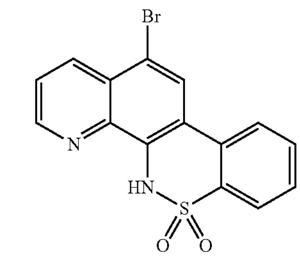 [SMILES: O=S1(=O)Nc2c(cc(Br)c3cccnc23)-c2ccccc21] | 12.6 |
| 546 | N'-(6,6-Dioxo-5,6-dihydro-6λ*6*-thia-4,5-diaza-chrysen-12-yl)-N,N-dimethyl-ethane-1,2-diamine | 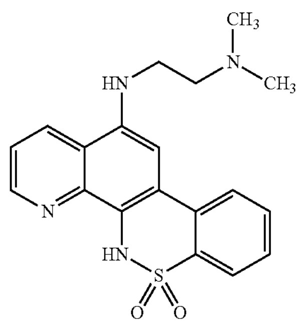 [SMILES: CN(C)CCNc1cc2c(c3ncccc13)NS(=O)(=O)c1ccccc1-2] | 9.98 |
| 547 | (6,6-Dioxo-5,6-dihydro-6λ*6*-thia-4,5-diaza-chrysen-12-yl)-(2-morpholin-4-yl-ethyl)-amine | 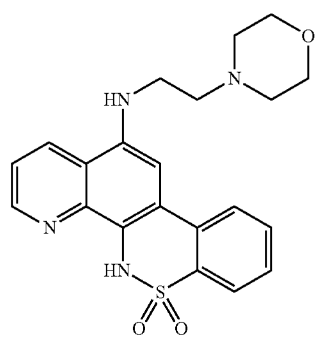 [SMILES: O=S1(=O)Nc2c(cc(NCCN3CCOCC3)c3cccnc23)-c2ccccc21] | 22 |
| 548 | (6,6-Dioxo-5,6-dihydro-6λ*6*-thia-4,5-diaza-chrysen-12-yl)-(2-methoxy-ethyl)-amine | 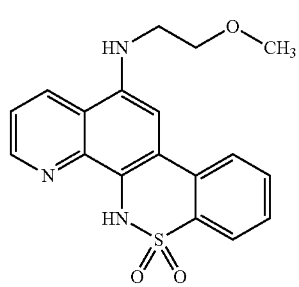 [SMILES: COCCNc1cc2c(c3ncccc13)NS(=O)(=O)c1ccccc1-2] | 2.83 |
| 549 | 12-Morpholin-4-yl-5H-6-thia-4,5-diaza-chrysene 6,6-dioxide | 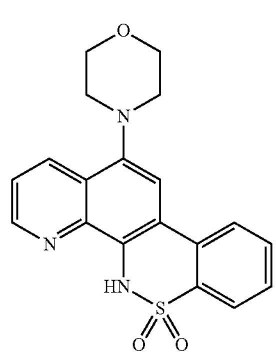 [SMILES: O=S1(=O)Nc2c(cc(N3CCOCC3)c3cccnc23)-c2ccccc21] | 1.14 |

-continued

| Example Number | Compound Name | Structure | Ferroportin/ IC50 μM |
|---|---|---|---|
| 550 | {2-[4-(6,6-Dioxo-5,6-dihydro-6λ*6*-thia-4,5-diaza-chrysen-12-yl)-piperazin-1-yl]-ethyl}-dimethyl-amine | 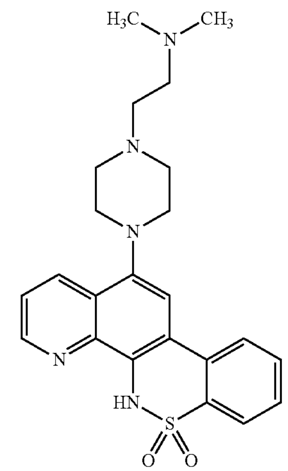 [SMILES: CN(C)CCN1CCN(c2cc3c(c4ncccc24)NS(=O)(=O)c2ccccc2-3)CC1] | 25 |
| 551 | 12-Piperidin-1-yl-5H-6-thia-4,5-diaza-chrysene 6,6-dioxide | 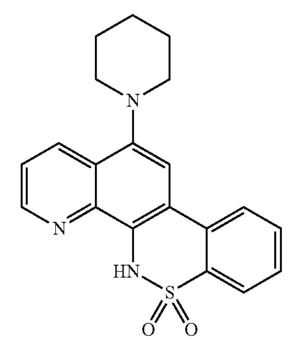 [SMILES: O=S1(=O)Nc2c(cc(N3CCCCC3)c3cccnc23)-c2ccccc21] | 1.56 |
| 552 | N-(6,6-Dioxo-5,6-dihydro-6λ*6*-thia-4,5-diaza-chrysen-12-yl)-N,N',N'-trimethyl-ethane-1,2-diamine | 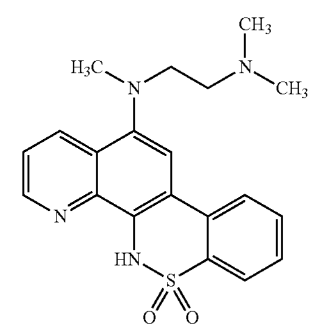 [SMILES: CN(C)CCN(C)c1cc2c(c3ncccc13)NS(=O)(=O)c1ccccc1-2] | 5 |
| 553 | 12-Pyrrolidin-1-yl-5H-6-thia-4,5-diaza-chrysene 6,6-dioxide | 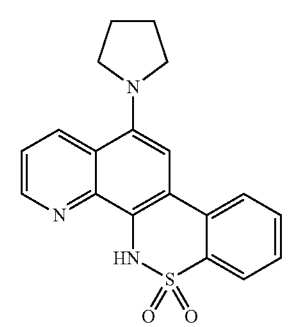 [SMILES: O=S1(=O)Nc2c(cc(N3CCCC3)c3cccnc23)-c2ccccc21] | 4.36 |

-continued

| Example Number | Compound Name | Structure | Ferroportin/ IC50 μM |
|---|---|---|---|
| 554 | (6,6-Dioxo-5,6-dihydro-6λ*6*-thia-4,5-diaza-chrysen-12-yl)-(2-methoxy-ethyl)-methyl-amine | 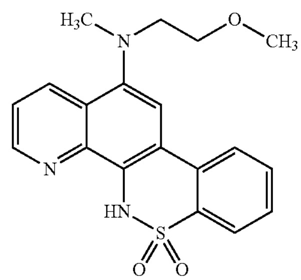 [SMILES: COCCN(C)c1cc2c(c3ncccc13)NS(=O)(=O)c1ccccc1-2] | 0.55 |
| 555 | (6,6-Dioxo-5,6-dihydro-6λ*6*-thia-4,5-diaza-chrysen-12-yl)-morpholin-4-yl-methanone | 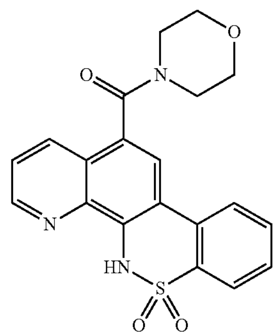 [SMILES: O=C(c1cc2c(c3ncccc13)NS(=O)(=O)c1ccccc1-2)N1CCOCC1] | 25 |
| 556 | 6,6-Dioxo-5,6-dihydro-6λ*6*-thia-4,5-diaza-chrysene-12-carboxylic acid (2-dimethylamino-ethyl)-amide | 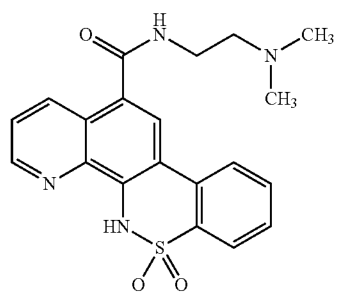 | 25 |
| 557 | 6,6-Dioxo-5,6-dihydro-6λ*6*-thia-4,5-diaza-chrysene-12-carboxylic acid (2-piperidin-1-yl-ethyl)-amide | 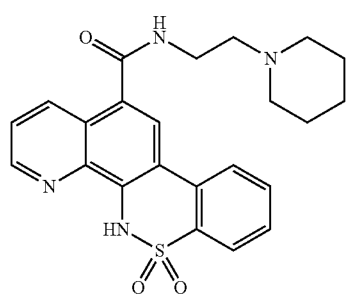 [SMILES: O=C(NCCN1CCCCC1)c1cc2c(c3ncccc13)NS(=O)(=O)c1ccccc1-2] | 25 |
| 560 | 1-(6,6-Dioxo-5,6-dihydro-6λ*6*-thia-4,5-diaza-chrysen-12-yl)-2-morpholin-4-yl-ethanone | 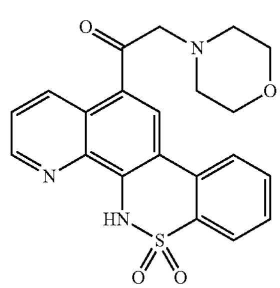 [SMILES: O=C(CN1CCOCC1)c1cc2c(c3ncccc13)NS(=O)(=O)c1ccccc1-2] | ND |

-continued
| Example Number | Compound Name | Structure | Ferroportin/ IC50 μM |
|---|---|---|---|
| 561 | 1-(6,6-Dioxo-5,6-dihydro-6λ*6*-thia-4,5-diaza-chrysen-12-yl)-ethanol | 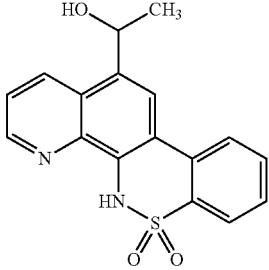 [SMILES: CC(O)c1cc2c(c3ncccc13)NS(=O)(=O)c1ccccc1-2] | 25 |
| 568 | N-(5-Benzyloxy-quinolin-8-yl)-benzenesulfonamide | 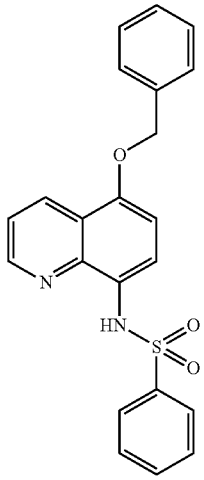 [SMILES: O=S(=O)(Nc1ccc(OCc2ccccc2)c2cccnc12)c1ccccc1] | 25 |
| 572 | 1-Methoxy-5H-6-thia-4,5-diaza-chrysene 6,6-dioxide | 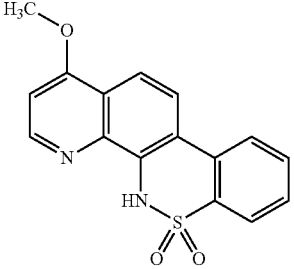 [SMILES: COc1ccnc2c3c(ccc12)-c1ccccc1S(=O)(=O)N3] | 100 |
| 584 | N-(5-Morpholin-4-yl-quinolin-8-yl)-benzenesulfonamide | 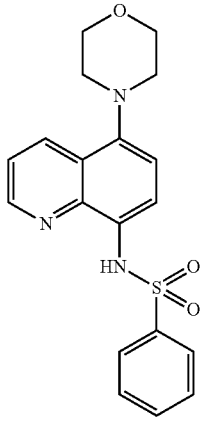 [SMILES: O=S(=O)(Nc1ccc(N2CCOCC2)c2cccnc12)c1ccccc1] | 25 |

| Example Number | Compound Name | Structure | Ferroportin/ IC50 μM |
|---|---|---|---|
| 589 | 12-Methoxy-9-trifluoromethyl-5H-6-thia-4,5-diaza-chrysene 6,6-dioxide | 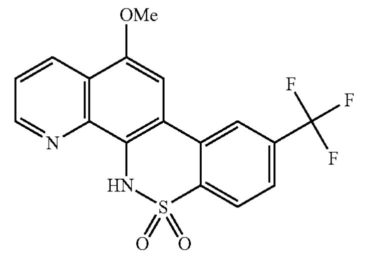 [SMILES: COc1cc2c(c3ncccc13)NS(=O)(=O)c1ccc(C(F)(F)F)cc1-2] | 0.96 |

Preparation Examples

I. Purification by Means of Preparative HPLC and Column Chromatography

The following preparation examples were carried out according to the preparation process according to the invention optionally with subsequent purification by means of preparative HPLC and/or by means of column chromatography under the following conditions:

I.I Preparative HPLC (Acidic Conditions)

Column: Waters SunFire Prep C18 OBD (5 μm 19×100 mm)
Flow rate: 26 ml/min
Solvent A: 0.1% TFA/water
Solvent B: 0.1% TFA/acetonitrile
Injection Volume: 1000 μl
Column Temperature: room temperature
Detection: Mass directed
Eluent:
0 mins to 1 min, 90% solvent A+10% solvent B;
1 minute to 7.5 min, constant gradient from 90% solvent A+10% solvent B to 100% solvent B;
7.5 min to 9 min, 100% solvent B;
9 mins to 9.1 min, constant gradient from 100% solvent B to 90% solvent A+10% solvent B;
9.1 min to 10 min, 90% solvent A+10% solvent B.
Waters Micromass Platform LCZ single quadrupole mass spectrometer
Waters 600 solvent delivery module
Waters 515 ancillary pumps
Waters 2487 UV detector
Gilson 215 autosampler and fraction collector
A) Preparative HPLC—Acidic Conditions 1
Column: Waters SunFire Prep C18 OBD (5 μm 19×100 mm)
Flow rate: 20 ml/min
Solvent A: 0.1% Formic acid/acetonitrile
Solvent B: 0.1% Formic acid/water
Injection Volume: 1000 μl
Column Temperature: room temperature
Detection: UV @ 215 nm
Eluent: 0 mins to 2 min, 95% solvent A+5% solvent B; 2 minute to 2.5 min, constant gradient from 95% solvent A+5% solvent B to 90% solvent A+10% solvent B; 2.5 min to 14.5 min, constant gradient from 90% solvent A+10% solvent B to 0% solvent A+100% solvent B; 14.5 mins to 16.5 min, 100% solvent B; 16.6 mins to 17 mins, constant gradient from 100% solvent B to 95% solvent A+5% solvent B; 17 min to 19 min, 95% solvent A+5% solvent B.
Waters Micromass Platform LCZ single quadrupole mass spectrometer
Waters 600 solvent delivery module
Waters 515 ancillary pumps
Waters 2487 UV detector
Gilson 215 autosampler and fraction collector
B) Preparative HPLC—Acidic Conditions 2
Column: Waters SunFire Prep C18 OBD (5 μm 19×100 mm)
Flow rate: 15 ml/min
Solvent A: 0.1% Formic acid/water
Solvent B: 0.1% Formic acid/acetonitrile
Injection Volume: 1000 μl
Column Temperature: room temperature
Detection: Mass directed
Eluent: 0 min 85% solvent A+15% solvent B, constant gradient 0 min to 8 min to 60% solvent A+40% solvent B; 8 min to 9 min, gradient to 100% solvent B; 9 mins to 11 mins 100% solvent B; 11.1 mins to 11.3 min, constant gradient to 15% solvent B+85% solvent A.
Waters Micromass Platform LCZ single quadrupole mass spectrometer
Waters 600 solvent delivery module
Waters 515 ancillary pumps
Waters 2487 UV detector
Gilson 215 autosampler and fraction collector I.II Preparative HPLC (Neutral Conditions)

Column: Sunfire C18 100 mm×19 mm, 5 μ (with a Sunfire guard column)
Flow rate: 20 ml/min
Solvent A: Water
Solvent B: Acetonitrile
Detection: UV directed 215 and 254 nm
Eluent:
0 min, 40% solvent B+60% solvent A;
0.1 min to 10 min constant gradient to 100% solvent B+0% solvent A, 10 min to 10.5 min 100% solvent B+0% solvent A;
10.5 min to 10.6 min 40% solvent B+60% solvent A.

I.III Preparative HPLC (Basic Conditions)

Column: XBridge Prep C18 OBD (5 μm 19×100 mm)
Flow rate: 20 ml/min
Solvent A: Water+0.2% Ammonium hydroxide
Solvent B: Acetonitrile+0.2% Ammonium hydroxide
Injection Volume: 1000 μl
Column Temperature: room temperature
Detection: UV directed Eluent:

0 min to 2 min, 5% solvent B+95% solvent A;
2 min to 2.5 min constant gradient to 10% solvent B+90% solvent A, 2.5 min to 14.5 min constant gradient to 100% solvent B;
14.5 min to 16.5 min 100% solvent B;
16.5 to 16.7 min constant gradient to 5% B+95% A;
16.7 min to 17.2 min 5% solvent B+95% solvent A.

Gilson semi-prep HPLC modules with 119 UV detector and 5.11 Unipoint control software

I.IV Column Chromatography

Flash silica gel chromatography was carried out on silica gel 230-400 mesh or on pre-packed silica cartridges.

II. Analytical HPLC-MS

II.I Method A

Column: Waters Atlantis dC18 (2.1×100 mm, 3 µm column)
Flow rate: 0.6 ml/min
Solvent A: 0.1% Formic acid/water
Solvent B: 0.1% Formic acid/acetonitrile
Injection Volume: 3 µl
Column temperature: 40° C.
UV Detection wavelength: 215 nm
Eluent:
0 min to 5 min, constant gradient from 95% solvent A+5% solvent B to 100% solvent B;
5 mins to 5.4 min, 100% solvent B;
5.4 min to 5.42 min, constant gradient from 100% solvent B to 95% solvent A+5% solvent B;
5.42 min to 7.00 min, 95% solvent A+5% solvent B

II.II Method B

Column: Waters Atlantis dC18 (2.1×50 mm, 3 µm)
Solvent A: 0.1% Formic acid/water
Solvent B: 0.1% Formic acid/acetonitrile
Flow rate: 1 ml/min
Injection volume: 3 µl
UV Detection wavelength: 215 nm
Eluent:
0 to 2.5 min, constant gradient from 95% solvent A+5% solvent B to 100% solvent B;
2.5 min to 2.7 min, 100% solvent B;
2.71 to 3.0 min, 95% solvent A+5% solvent B.

II.III Method C

Column: Waters Atlantis dC18 (50 mm×30 mm, 3 µm column)
Flow rate: 1.2 ml/min
Solvent A: 0.1% Formic acid/water
Solvent B: 0.1% Formic acid/acetonitrile
Injection volume: 5 µl
UV Detection wavelength: 215 nm
UV detection diode array or UV
Eluent:
0 min to 3.5 min, constant gradient from 95% solvent A+5% solvent B to 100% solvent B;
3.5 min to 3.8 min, 100% solvent B;
3.8 min to 3.9 min, constant gradient from 100% solvent B to 95% solvent A+5% solvent B;
3.9 min to 4.5 min, 95% solvent A+5% solvent B.

II.IV Method D

Column: Atlantis dC18 (50 mm×3 mm; 3 µm column)
Mobile phase A: 0.1% Formic acid/Water
Mobile phase B: 0.1% Formic acid/Acetonitrile
Flow rate: 0.8 ml/min.
Detection wavelength: Diode array Spectrum I max (with scan in the region 210-350 nm)
Sampling rate: 5
Column temperature: 35° C.
Injection volume: 5 µl
Eluent:
0 min 95% solvent A+5% solvent B, 0.2 min 95% solvent A+5% solvent B;
0.2 min to 3.2 min constant gradient from 95% solvent A+5% solvent B to 5% solvent A and 95% solvent B;
5 min 5% solvent A and 95% solvent B;
5 min to 5.2 min constant gradient from 5% solvent A and 95% solvent B to 95% solvent A+5% solvent B;
5.5 min 95% solvent A and 5% solvent B.

MS detection using Waters LCT or LCT Premier, or ZQ or ZMD

UV detection using Waters 2996 photodiode array or Waters 2787 UV or Waters 2788 UV

II.V Method E

Column: Waters Atlantis dC18 (3.0×50 mm, 3 µm)
Solvent A: 0.1% Formic acid/water
Solvent B: 0.1% Formic acid/acetonitrile
Flow rate: 1.2 ml/min
Injection volume: 5 µl
Column temperature: 35° C.
UV Detection wavelength: 215 nm
Eluent:
0 to 6.30 mins, constant gradient from 95% solvent A+5% solvent B to 100% solvent B;
6.30 mins to 6.70 mins, 100% solvent B;
6.70 to 6.80 mins, constant gradient from 100% solvent B to 95% solvent A+5% solvent B; 6.80 to 7.50 mins, 95% solvent A+5% solvent B.

II.VI Method F

Column: Waters Atlantis dC18 (3.0×50 mm, 3 µm)
Solvent A: 0.1% Formic acid/water
Solvent B: 0.1% Formic acid/acetonitrile
Flow rate: 1.0 ml/min
Injection volume: 5 µl
Column temperature: 35° C.
UV Detection wavelength: 215 nm
Eluent:
0.00 to 1.00 mins, 95% solvent A+5% solvent B; 1.00 to 6.50 mins, constant gradient from 95% solvent A+5% solvent B to 5% solvent A+95% solvent B; 6.50 mins to 9.00 mins, 5% solvent A+95% solvent B; 9.00 mins to 9.50 mins, constant gradient from 5% solvent A+95% solvent B to 95% solvent A+5% solvent B; 9.50 mins to 10.00 mins, 95% solvent A+5% solvent B

III. Microwave Treatment

Microwave reactions were carried out using a CEM Discover or Explorer focussed microwaves apparatus.

IV. Designation of the Compounds

Some compounds are isolated as TFA or HCl salts, which are not reflected by the chemical name. Within the meaning of the present invention the chemical name represents the compound in neutral form as well as its TFA salt or any other salt, especially pharmaceutically acceptable salt, if applicable.

V. Abbreviations

AcOH Acetic acid
Aq. Aqueous
BuLi Butyl lithium
cat. Catalytic
conc. Concentrated
dba dibenzylideneacetone
DCE 1,2-Dichloroethane
DCM Dichloromethane
DBU 1,8-Diazabicycloundec-7-ene
DIPEA N,N-diisoproylethylamine
DMAP 4-Dimethylaminopyridine
DME 1,2-Dimethoxyethane
DMF N,N-dimethylformamide
DMF-DMA N,N-dimethylformamidedimethyl acetal
DMSO Dimethyl sulfoxide
dppf 1,1'-Bisdiphenylphosphino ferrocene
EDC.HCl 1-Ethyl-3-(3-dimethyllaminopropyl)carbodiimide hydrochloride
EtOAc Ethyl acetate
EtOH Ethanol
h Hour(s)
HOBt Hydroxybenzotriazole
HPLC High Performance Liquid Chromatography
MeCN Acetonitrile
MeOH Methanol
min Minute(s)
MW Molecular weight
PCC Pyridinium chlorochromate
PDC Pyridinium dichromate
Pd—C Palladium on Carbon
Py Pyridine
sat. Saturated
STAB Sodium triacetoxyborohydride
TBAF Tetrabutyammonium fluoride
PS TBTU O-(Benzotriazol-1-yl)-N,N,N',N'-tetramethyluronium tetrafluoroborate
TEA Triethylamine
THF Tetrahydrofuran
TMEDA Tetramethylethylenediamine
X-Phos (9,9-dimethyl-9H-xanthene-4,5-diyl)bis(diphenylphosphane)

VI. Preparation Examples According to Synthesis Routes 1 to 65

The following examples refer to the preparation of selected compounds (Example Compounds 1 to 589) according to formula (I) of the present invention and further comprises methods for the preparation of numerous intermediate products, deriving from such manufacturing processes.

In this context, numbering of the example compounds and intermediates is not applied continuously and thus some compound nos. do not exist herein.

In principle, the same holds true for the numbering of the "general procedures" as described in the synthesis routes of the present invention.

The meaning of the substituents $R^1$ to $R^{15}$ (and A or B) as far as mentioned in the description of the synthesis routes 1 to 65 is consistent with the meaning as defined in the present invention. Examples 1 to 589 refer to selected embodiments, with specific substituents selected from preferred substituents as defined according to the present invention.

Route 1 and Route 2 (See Above)

General Procedure 8: Pyridine-3-Sulfonyl Chloride (Intermediate 17)

Phosphorus pentachloride (3.0 g, 14.6 mmol) was added to a solution of 3-pyridinesulfonic acid (1.5 g, 9.42 mmol) dissolved in phosphoryl trichloride (2.45 g, 16.0 mmol) and the mixture heated to 130° C. for 3 h under argon. The mixture was concentrated in vacuo, the residue was quenched over ice and extracted with ether. The organic phase was washed with a saturated sodium bicarbonate solution and concentrated in vacuo to give the crude title compound (0.6 g, 36%) which was used immediately without purification.

Route 3 (See Above)

General Procedure 9: Pyridine-2-Sulfonyl Chloride (Intermediate 18)

Sodium hypochlorite solution (conc., 62 ml) was added dropwise to a stirred solution of pyridine-2-thiol (1.0 g, 8.995 mmol) dissolved in $H_2SO_4$ (25 ml) at 0° C. The mixture was stirred for 30 min, water (15 ml) added and the mixture extracted with DCM. The organic phases were combined, dried (MgSO$_4$) and concentrated in vacuo gave the title compound (800 mg, 50%) which was used in the next step without purification. The structure was confirmed by $^1$H NMR.

Route 3a (See Above)

General Procedure 10: 6-Cyanopyridine-3-sulfonyl chloride (Intermediate 19)

SOCl$_2$ (1.8 ml, 24.8 mmol) was added dropwise to ice water and stirred for 18 h at room temperature. CuCl$_2$ (22 mg, 0.22 mmol) was added at 0° C. and the mixture was stirred for 15 min. In a separate flask, a solution of NaNO$_2$ (450 mg, 6.52 mmol) in water (4.5 ml) was added to a stirred solution of 5-amino-pyridine-2-carbonitrile (534 mg, 4.5 mmol) in conc. HCl (4.5 ml) at 0° C., over 15 min. The diazonium salt solution was added dropwise to the thionyl chloride/CuCl$_2$ solution at 0° C. and stirring was continued for 1 h. The reaction mixture was extracted with DCM and the combined organic phases were dried (Na$_2$SO$_4$) and concentrated in vacuo to give the title compound (620 mg) which was used in the next step without purification. The structure was confirmed by $^1$H NMR.

4-Cyano-2-nitro-benzenesulfonyl chloride (Intermediate 217)

In a similar fashion using route 3a general procedure 10, SOCl$_2$ (2.5 ml, 33.7 mmol), CuCl (30 mg, 0.30 mmol), 4-amino-3-nitrobenzonitrile (1 g, 6.13 mmol), NaNO$_2$ (0.61 g, 8.83 mmol) and conc. HCl (6.2 ml) gave the title compound (1.5 g) which was used in the next step without further purification. The structure was confirmed by $^1$H NMR.

5-Chloro-4-fluoro-2-nitro-benzenesulfonyl chloride (Intermediate 218)

In a similar fashion using route 3a general procedure 10, SOCl$_2$ (2.8 ml, 28.8 mmol) in water (15 ml), CuCl (26 mg, 0.26 mmol), 5-chloro-4-fluoro-2-nitroaniline (1 g, 5.2 mmol), NaNO$_2$ (522 mg, 7.5 mmol) and conc. HCl (10 ml)

gave the title compound (1.5 g) which was used in the next step without further purification. The structure was confirmed by $^1$H NMR.

4,5-Difluoro-2-nitro-benzenesulfonyl chloride (Intermediate 219)

In a similar fashion using route 3a general procedure 10, $SOCl_2$ (1.15 ml, 15.7 mmol) in water (6 ml), CuCl (14 mg, 0.14 mmol), 4,5-difluoro-2nitroaniline (500 mg, 2.8 mmol), $NaNO_2$ (285 mg, 7.5 mmol) and conc. HCl (5 ml) gave the title compound (1.5 g) which was used in the next step without further purification. The structure was confirmed by $^1$H NMR.

4-Fluoro-2-nitro-benzenesulfonyl chloride (Intermediate 220)

In a similar fashion using route 3a general procedure 10, $SOCl_2$ (51.4 g, 704 mmol) in water (260 ml), CuCl (0.65 g, 6.4 mmol), 2-nitro 4-fluro-aniline (20 g, 128 mmol), $NaNO_2$ (12.7 g, 184 mmol) and conc. HCl (200 ml) gave the title compound (25 g, 81%) which was used in the next step without further purification. The structure was confirmed by $^1$H NMR.

2-Nitro-4-trifluoromethoxy-benzenesulfonyl chloride (Intermediate 221)

In a similar fashion using route 3a general procedure 10, $SOCl_2$ (0.36 ml, 4.95 mmol) in cold water (2 ml), CuCl (5 mg, 0.05 mmol), 2-nitro-4-(trifluoromethoxy)aniline (200 mg, 0.90 mmol), conc. HCl (2 ml), $NaNO_2$ (90 mg, 1.3 mmol) in water (2 ml) gave the title compound (290 mg) which was used in the next step without further purification. The structure was confirmed by $^1$H NMR.
Route 4 (See Above)

General Procedure 11: 4-Methyl-2-nitrobenzene-1-sulfonyl chloride (Intermediate 20)

Aqueous $NaNO_2$ (2.0 g, 29.5 mmol) was added dropwise to 4-methyl-2-nitroaniline (3.0 g, 19.7 mmol) dissolved in conc. HCl (15 ml) at 0° C. and the mixture was stirred for 45 min. The mixture was filtered and the filtrate added to a saturated solution of $SO_2$ gas in AcOH (10 ml), in the presence of $CuCl_2$ (800 mg, 6.0 mmol) at 50° C. The reaction was stirred for 5 h and the precipitate formed collected by filtration, dissolved in DCM, dried ($Na_2SO_4$) and concentrated in vacuo to give the title compound (950 mg, 67%). The structure was confirmed by $^1$H NMR.
Route 5 (See Above)

General Procedure 12: Sodium (2-methyl-3-chlorophenyl)sulfamate (Intermediate 21)

Chlorosulfonic acid (516 µl, 7.77 mmol) in chloroform (5 ml) was added dropwise to a solution of 3-chloro-2-methylaniline (844 µl, 6.98 mmol) and TEA (7.8 ml, 56.54 mmol) in chloroform (20 ml) at 0° C. The mixture was stirred for 90 min, concentrated in vacuo and a solution of NaOH (848 mg, 21.2 mmol) in water (10 ml) was added and the mixture stirred for 30 min at room temperature. The reaction was concentrated in vacuo and azeotroped with toluene. The solid obtained was heated in EtOH (50 ml) at 60° C. for 15 min, concentrated in vacuo and EtOAc (50 ml) added. The resulting solid was collected by filtration and the filtrate allowed to stand at room temperature for 4 h. The crystals formed were filtered, washed with EtOAc, and the solids combined to give the title compound (1.44 g, 84%).
MW: 243.65 (sodium salt)
HPLCMS (Method C): [m/z] ES–: 219.97
Route 6 (See Above)

General procedure 13: 2-Methyl-quinolin-8-ylamine (Intermediate 22)

Palladium on carbon (10%, 50 mg) was added to a solution of 2-methyl-8-nitroquinoline (500 mg, 2.66 mmol) in EtOH (40 ml) and the mixture was stirred under an atmosphere of hydrogen for 2 h. The mixture was diluted with MeOH (40 ml), filtered through celite and the filtrate was concentrated in vacuo to give the title compound (417 mg, 99%).
MW: 158.20
HPLCMS (Method B): [m/z]: 159

General Procedure 14: 6-Methoxyquinolin-8-amine (Intermediate 23)

Raney Nickel (60 mg, 20% wt) was added portionwise to a solution of 6-methoxy-8-nitroquinoline (300 mg, 1.40 mmol) in MeOH (10 ml), under argon. Hydrazine hydrate (270 µl, 5.6 mmol) was added and the reaction stirred at room temperature for 1 h. The mixture was filtered through celite and washed with MeOH. The filtrate was concentrated in vacuo, re-dissolved in DCM and washed with water. The organic phase was dried ($Na_2SO_4$) and concentrated in vacuo to give the title compound (250 mg, 100%) which was used in the next step without purification.
MW: 174.20
HPLCMS (Method C): [m/z]: 175
Route 7 (See Above)

General Procedure 15: 2-Chloro-8-nitroquinoline (Intermediate 24)

Conc. $H_2SO_4$ was added slowly to 2-chloroquinoline (1.0 g, 6.13 mmol), followed by portionwise addition of potassium nitrate (800 mg, 7.97 mmol) at 0° C. The mixture was allowed to warm to room temperature overnight. After completion of the reaction (monitored by TLC and HPLCMS), the solution was poured slowly over ice, and the precipitate was extracted with EtOAc. The organic phase was washed with brine and concentrated in vacuo. The crude residue was purified by column chromatography with n-hexane/EtOAC (17:3) as the eluent to give the title compound (450 mg, 38%).
MW: 208.61
HPLCMS (4.5 min): [m/z]: 209

5-Chloro-8-nitroquinoline (Intermediate 25)

In a similar fashion using route 7 general procedure 15, 5-chloroquinoline (1.0 g, 6.13 mmol), potassium nitrate (0.8 g, 7.98 mmol) and $H_2SO_4$ (3 ml) gave the title compound (630 mg, 51%) after trituration from DCM/n-pentane.
MW: 208.61
HPLCMS (4.5 min): [m/z]: 209

General Procedure 57: 4-Nitro-benzothiazole (Intermediate 222)

$KNO_3$ (1.95 g, 19.3 mmol) was added portionwise to an ice-cold solution of 1,3-benzothiazole (2.0 g, 14.8 mmol) in H$_2$SO$_4$ (5 ml) while maintaining the temperature below 10° C. and the mixture was stirred at 0° C. for 2 h. The mixture was poured onto ice and the aqueous phase was extracted with DCM. The organic phase was washed with sat NaHCO$_3$ solution and brine, dried (Na$_2$SO$_4$) and concentrated in vacuo. The residue was diluted with MeOH (15 ml) and heated under stirring at 65° C. for 1 h, on cooling the resulting precipitate was collected by filtered and washed with MeOH to give the title compound (500 mg, 38%).
MW: 180.19
HPLCMS: (Method C): [m/z]:181

2-Chloroquinolin-8-amine (Intermediate 26)

In the similar fashion using route 6 general procedure 14, 2-chloro-8-nitroquinoline (Intermediate 24) (100 mg, 0.48 mmol), Raney nickel (20 mg, 20% wt), hydrazine hydrate (96 mg, 1.92 mmol) and MeOH (10 ml) gave the crude title compound (70 mg, 82%) which was used in the next step without purification.
MW: 178.62
HPLCMS (Method C): [m/z]: 179

5-Chloroquinolin-8-amine (Intermediate 27)

In the similar fashion using route 6 general procedure 14, 5-chloro-8-nitroquinoline (Intermediate 25) (500 mg, 2.40 mmol), Raney nickel (100 mg, 20% wt), hydrazine hydrate (0.5 ml, 9.62 mmol) and MeOH/THF (10 ml, 4:1), gave the title compound (420 mg, 98%) which was used in the next step without purification.
MW: 178.62
HPLCMS (Method C): [m/z]: 179
Route 8 (See Above)

General Procedure 16: 7-Hydroxyquinolin-8-amine (Intermediate 28)

7-Hydroxyquinoline (1.1 g, 7.5 mmol) and 1-phenyl-1-methylhydrazine (0.92 g, 7.5 mmol) were combined and heated at 130° C. under nitrogen for 16 h. After cooling the solvent was partially evaporated, the crude product was purified by column chromatography with heptane/EtOAc (1:1) as the eluent to give the title compound (370 mg, 31%).
MW: 160.18
HPLCMS (Method B):[m/z]: 160.95
Route 9 (See Above)

General Procedure 17: 8-Methoxy-3-methylquinoline (Intermediate 29)

Methacrolein (1.86 g, 26.0 mmol) was added dropwise to a stirred solution of o-ansidine (2.0 g, 16.0 mmol) and NaI (21 mg, 0.14 mmol) in H$_2$SO$_4$ (6 ml) at 110° C. for 1 h. The reaction was cooled to room temperature and stirring continued for 18 h. The reaction was poured over sodium carbonate, the pH adjusted with sat. sodium carbonate solution to pH=7 and extracted with DCM. The organic phase was dried (Na$_2$SO$_4$) and concentrated in vacuo. The crude residue was purified by column chromatography with DCM/MeOH/NH$_3$ (199:1:1) as eluent to give the title compound (500 mg, 18%).
MW: 173.20
HPLCMS (Method C): [m/z]: 174

General Procedure 18: 3-Methylquinolin-8-ol (Intermediate 30)

47% HBr (10 ml) was added to 8-methoxy-3-methylquinoline (Intermediate 29) (500 mg, 2.80 mmol) and heated at 122° C. for 18 h. The reaction was cooled to room temperature, the pH adjusted with sodium carbonate solution to pH=7 and extracted with DCM. The organic phase was dried (Na$_2$SO$_4$) and concentrated in vacuo to give the title compound (150 mg, 83%).
MW: 159.19
HPLCMS (Method C): [m/z]: 160

General Procedure 19: 3-Methylquinolin-8-amine (Intermediate 31)

3-methylquinolin-8-ol (Intermediate 30) (150 mg, 0.9 mmol) and ammonium sulphite (250 mg, 1.8 mmol) were added to aqueous ammonia (3 ml) and heated for 48 h. After cooling, water was added and the mixture was extracted with DCM. The organic phase was dried (Na$_2$SO$_4$) and concentrated in vacuo to give the title compound (130 mg, 86%).
MW: 158.20
HPLCMS (Method C): [m/z]: 159
Route 10 (See Above)

General Procedure 20: 5-Methyl-8-nitroquinoline (Intermediate 32)

5-methyl-2-nitroaniline (1.0 g, 6.57 mmol), glycerol (1.88 g, 20.4 mmol), 3-nitrobenzenesulfonic acid sodium salt (1.92 g, 8.54 mmol) were added to H$_2$SO$_4$/H$_2$O (6 ml, 7:5) solution and heated at 105° C. for 48 h. After completion of the reaction (monitored by LCMS), the mixture was cooled to 45° C. and poured slowly onto ice water (50 ml) and the mixture was extracted with DCM. The combined organic phases were dried (Na$_2$SO$_4$) and concentrated in vacuo to give the title compound (950 mg, 77%) which was used in the next step without purification.
MW: 188.19
HPLCMS (Method C): [m/z]: 189

8-Nitro-5-(trifluoromethyl)quinoline (Intermediate 33)

In a similar fashion using route 10 general procedure 20, 2-nitro-5-(trifluoromethyl)aniline (1.0 g, 4.85 mmol), glycerol (1.4 g, 15.0 mmol) and 3-nitrobenzenesulfonic acid sodium salt (1.42 g, 6.31 mmol) gave the title compound (820 mg, 80%) which was used in the next step without purification. The structure was confirmed by $^1$H NMR.

8-Nitro-6-(trifluoromethoxy)quinoline (Intermediate 34)

In a similar fashion using route 10 general procedure 20, 2-nitro-4-(trifluoromethoxy)aniline (1.0 g, 4.50 mmol), glycerol (1.3 g, 13.96 mmol) and 3-nitrobenzenesulfonic acid sodium salt (1.32 g, 5.85 mmol), gave the title compound (1.1 g, 95%) which was used in the next step without purification.
MW: 258.16
HPLCMS (Method C): [m/z]: 259

6-Ethoxy-8-nitroquinoline (Intermediate 35)

In a similar fashion using route 10 general procedure 20, 4-ethoxy-2-nitroaniline (1.0 g, 5.49 mmol), glycerol (1.6 g, 17.0 mmol) and 3-nitrobenzenesulfonic acid sodium salt (1.6 g, 7.14 mmol) gave the title compound (900 mg, 75%) which was used in the next step without purification.
MW: 218.21
HPLCMS (Method C): [m/z] ES–: 218

6-Fluoro-8-nitroquinoline (Intermediate 36)

In a similar fashion using route 10 general procedure 20, 4-fluoro-2-nitroaniline (1.0 g, 6.41 mmol), glycerol (1.83 g, 19.9 mmol), 3-nitrobenzenesulfonic acid sodium salt (1.8 g, 8.33 mmol) and $H_2SO_4/H_2O$ (6 ml, 7:5) gave the title compound (1.04 g, 84%) which was used in the next step without purification.
MW: 192.15
HPLCMS (Method C): [m/z]: 193

5,6-Difluoro-8-nitroquinoline (Intermediate 37)

In a similar fashion using route 10 general procedure 20, 4,5-difluoro-2-nitroaniline (200 mg, 1.15 mmol), glycerol (330 mg, 3.56 mmol), 3-nitrobenzenesulfonic acid sodium salt (336 mg, 1.49 mmol) and $H_2SO_4/H_2O$ (1.2 ml, 7:5) gave the title compound (200 mg, 83%) after purification by column chromatography with DCM as the eluent.
MW: 210.14
HPLCMS (Method C): [m/z]: 211

5-Fluoro-8-nitroquinoline (Intermediate 38)

In a similar fashion using route 10 general procedure 20, 5-fluoro-2-nitroaniline (1.0 g, 6.4 mmol), glycerol (1.83 g, 19.86 mmol), 3-nitrobenzenesulfonic acid sodium salt (1.8 g, 8.33 mmol) and $H_2SO_4/H_2O$ (1.2 ml, 7:5) gave the title compound (500 mg, 60%) after purification by column chromatography with DCM as the eluent.
MW: 192.15
HPLCMS (Method C): [m/z]: 192.99

5-Chloro-6-methyl-8-nitroquinoline (Intermediate 39)

In a similar fashion using route 10 general procedure 20, 5-chloro-4-methyl-2-nitroaniline (1.0 g, 5.3 mmol), glycerol (1.52 g, 16.6 mmol), 3-nitrobenzensulfonic acid sodium salt (1.55 g, 6.8 mmol) and $H_2SO_4/H_2O$ (6 ml, 7:5) gave the title compound (350 mg, 30%) which was used in the next step without purification.
MW: 222.63
HPLCMS (Method C): [m/z]: 223

7-Chloro-8-nitroquinoline (Intermediate 40)

In a similar fashion using route 10 general procedure 20, 3-chloro-2-nitroaniline (1.0 g, 5.8 mmol), glycerol (1.65 g, 18.0 mmol), 3-nitrobenzensulfonic acid sodium salt (1.66 g, 7.5 mmol) and $H_2SO_4/H_2O$ (12 ml, 7:5) gave the title compound (490 mg, 40%) which was used in the next step without purification.
MW: 208.61
HPLCMS (Method C): [m/z]: 211

5-Chloro-6-fluoro-8-nitroquinoline (Intermediate 41)

In a similar fashion using route 10 general procedure 20, 5-chloro-4-fluoro-2-nitroaniline (1.0 g, 5.2 mmol), glycerol (1.5 g, 16.2 mmol), 3-nitrobenzensulfonic acid sodium salt (1.52 g, 6.7 mmol) and $H_2SO_4/H_2O$ (6 ml, 7:5) gave the title compound (790 mg, 67%) which was used in the next step without purification.
MW: 226.60
HPLCMS (Method C): [m/z]: 227

5,6-Dimethyl-8-nitroquinoline (Intermediate 43)

In a similar fashion using route 10 general procedure 20, 4,5-dimethyl-2-nitroaniline (1.0 g, 6.0 mmol), glycerol (1.0 g, 11.4 mmol), 3-nitrobenzenesulfonic acid sodium salt (2.2 g, 9.6 mmol) and $H_2SO_4/H_2O$ (3 ml, 7:1), further reagents added over 4 days, gave the title compound (200 mg, 16%) which was used in the next step without purification.
MW: 202.21
HPLCMS (Method C): [m/z]: 203

5-Methylquinolin-8-amine (Intermediate 44)

In a similar fashion using route 1 general procedure 4, 5-methyl-8-nitroquinoline (Intermediate 32) (950 mg, 5.05 mmol), tin (II) chloride (2.87 g, 15.1 mmol) and 6 N HCl (5 drops) gave the title compound (950 mg, >100% crude) which was used in the next step without purification. The structure was confirmed by $^1$H NMR.

5-(Trifluoromethyl)quinolin-8-amine (Intermediate 45)

In a similar fashion using route 1 general procedure 4, 8-nitro-5-(trifluoromethyl)quinoline (Intermediate 33) (820 mg, 3.39 mmol), tin (II) chloride (1.93 g, 10.2 mmol) and 6 N HCl (10 drops) gave the title compound (615 mg, 85%) which was used in the next step without purification.
MW: 212.18
HPLCMS (Method C): [m/z]: 213

6-(Trifluoromethoxy)quinolin-8-amine (Intermediate 46)

In a similar fashion using route 1 general procedure 4, 8-nitro-6-(trifluoromethoxy)quinolone (Intermediate 34) (1.1 g, 4.26 mmol), tin (II) chloride (2.42 g, 12.8 mmol) and 6 N HCl (13 drops) gave the title compound (820 mg, 84%) which was used in the next step without purification.
MW: 228.18
HPLCMS (Method C): [m/z]: 229

6-Ethoxyquinolin-8-amine (Intermediate 47)

In a similar fashion using route 1 general procedure 4, 6-ethoxy-8-nitroquinoline (Intermediate 35) (900 mg, 4.12 mmol), tin (II) chloride (2.4 g, 12.4 mmol) and 6 N HCl (10 drops) gave the title compound (700 mg, 90%) which was used in the next step without purification.
MW: 188.23
HPLCMS (Method C): [m/z]: 189

6-Fluoroquinolin-8-amine (Intermediate 48)

In a similar fashion using route 1 general procedure 4, 6-fluoro-8-nitroquinoline (Intermediate 36) (1.0 g, 5.41 mmol), tin (II) chloride (3.08 g, 16.2 mmol) and 6N HCl (5 drops) gave the title compound (650 mg, 74%) which was used in the next step without further purification.
MW: 162.17
HPLCMS (Method C): [m/z]: 163

5,6-Difluoroquinolin-8-amine (Intermediate 49)

In a similar fashion using route 1 general procedure 4,5,6-difluoro-8-nitroquinoline (Intermediate 37) (200 mg, 0.95 mmol), tin (II) chloride (540 mg, 2.85 mmol) and 6N HCl (2

5-Fluoroquinolin-8-amine (Intermediate 50)

In a similar fashion using route 1 general procedure 4, 5-fluoro-8-nitroquinoline (Intermediate 38) (500 mg, 2.60 mmol), tin (II) chloride (1.48 mg, 7.80 mmol) and 6N HCl (4 drops) gave the title compound (450 mg, >100% crude) which was used in the next step without purification. The structure was confirmed by $^1$H NMR.

5-Chloro-6-methylquinolin-8-amine (Intermediate 51)

In a similar fashion using route 1 general procedure 4, 5-chloro-6-methyl-8-nitroquinoline (Intermediate 39) (300 mg, 1.35 mmol), tin (II) chloride (760 mg, 4.05 mmol) and 6N HCl (4 drops) gave the title compound (160 mg, 62%) after purification by column chromatography with n-hexane/EtOAc (9:1) as the eluent.
MW: 192.65
HPLCMS (Method C): [m/z]: 193

7-Chloroquinolin-8-amine (Intermediate 52)

In a similar fashion using route 1 general procedure 4, 7-chloroquinolin-8-amine (Intermediate 40) (300 mg, 1.4 mmol), tin (II) chloride (810 mg, 4.3 mmol) and 6N HCl (4 drops) gave the title compound (110 mg, 44%) after purification by column chromatography with n-hexane/EtOAc (19:1) as the eluent.
MW: 178.62
HPLCMS (Method C): [m/z]: 179

5-Chloro-6-fluoroquinolin-8-amine (Intermediate 53)

In a similar fashion using route 6 general procedure 14, 5-chloro-6-fluoro-8-nitroquinoline (Intermediate 41) (300 mg, 1.34 mmol), Raney nickel (60 mg, 20% wt), hydrazine hydrate (270 mg, 5.40 mmol) and MeOH (5 ml) gave the title compound (130 mg, 49%) which was used in the next step without purification.
MW: 196.61
HPLCMS (Method C): [m/z]: 197

6-Methylquinolin-8-amine (Intermediate 54)

In a similar fashion using route 6 general procedure 14, 6-methyl-8-nitroquinoline (Intermediate 42) (300 mg, 1.6 mmol), Raney nickel (60 mg, 20% wt) hydrazine hydrate (0.32 ml, 6.30 mmol) and MeOH (8 ml) gave the title compound (159 mg) which was used in the next step without purification.
MW: 158.20
HPLCMS (Method C): [m/z]: 159

5,6-Dimethylquinolin-8-amine (Intermediate 55)

In a similar fashion using route 6 general procedure 14, 5,6-dimethyl-8-nitroquinoline (Intermediate 43) (200 mg, 0.9 mmol), Raney nickel (40 mg, 20 wt), hydrazine hydrate (200 µl, 3.9 mmol) and MeOH (5 ml) gave the title compound (120 mg, 77%) which was used in the next step without purification.
MW: 172.23
HPLCMS (Method C): [m/z]: 173
Route 11 (See Above)

7-Isopropylquinoline (Intermediate 56)

In a similar fashion using route 10 general procedure 20, 3-isopropylaniline (1 g, 7.4 mmol), glycerol (2.11 g, 22.9 mmol) and 3-nitro benzenesulfonic acid sodium salt (2.2 g, 9.61 mmol) gave the title compound (1.3 g, 100%) which was used in the next step without purification.
MW: 171.24
HPLCMS (Method C): [m/z]: 172

7-Ethylquinoline (Intermediate 57)

In a similar fashion using route 10 general procedure 20, 3-ethylaniline (1 g, 8.25 mmol), glycerol (2.35 g, 25.6 mmol), 3-nitro benzenesulfonic acid sodium salt (2.42 g, 10.7 mmol), $H_2SO_4$:$H_2O$ (3.5 ml:2.5 ml) gave the title compound (1.21 g, 93%) which was used in the next step without purification. The structure was confirmed by $^1$H NMR.

7-Methoxyquinoline (Intermediate 58)

In a similar fashion using route 10 general procedure 20, 3-methoxyaniline (1.0 g, 8.12 mmol), glycerol (2.32 g, 25.2 mmol), 3-nitrobenzenesulfonic acid sodium salt (2.4 g, 10.6 mmol) and $H_2SO_4$/$H_2O$ (6 ml, 7:5) gave the title compound (170 mg, 14%) after purification by column chromatography with n-hexane/EtOAc (17:3) as the eluent.
MW: 159.19
HPLCMS (Method C): [m/z]: 160

7-Isopropyl-8-nitroquinoline (Intermediate 59)

In a similar fashion using route 7 general procedure 15, 7-isopropylquinoline (Intermediate 56) (1.36 g, 7.94 mmol), potassium nitrate (1.04 g, 10.3 mmol) and $H_2SO_4$ (4.2 ml) gave the title compound (670 mg, 39%) after purification by column chromatography with n-hexane/EtOAc (9:1-22:3) as the eluent.
MW: 216.24
HPLCMS (Method C): [m/z]: 217

7-Ethyl-8-nitroquinoline (Intermediate 60)

In a similar fashion using route 7 general procedure 15, 7-ethylquinoline (Intermediate 57) (1.21 g, 7.7 mmol), potassium nitrate (1.01 g, 10.0 mmol) and $H_2SO_4$ (3.6 ml) gave the title compound (170 mg, 12%) after purification by column chromatography with n-hexane/EtOAc (23:2-17:3) gradient elution.
MW: 202.21
HPLCMS (Method C): [m/z]: 203

7-Methoxy-8-nitroquinoline (Intermediate 61)

In a similar fashion using route 7 general procedure 15, 7-methoxyquinoline (Intermediate 58) (400 mg, 2.51 mmol), potassium nitrate (330 mg, 3.26 mmol) and conc. $H_2SO_4$ (1.2 ml) gave the title compound (250 mg, 50%) after purification by column chromatography with n-hexane/EtOAc (3:1) as the eluent.
MW: 204.19
HPLCMS (Method C): [m/z]: 205

7-Isopropylquinolin-8-amine (Intermediate 62)

In a similar fashion using route 1 general procedure 4, 7-isopropyl-8-nitroquinoline (Intermediate 59) (670 mg, 3.09 mmol), tin (II) chloride (1.8 g, 9.3 mmol) and 6 N HCl (6 drops) gave the title compound (420 mg, 73%) which was used in the next step without purification.

MW: 186.26

HPLCMS (Method C): [m/z]:187

7-Ethylquinolin-8-amine (Intermediate 63)

In a similar fashion using route 1 general procedure 4, 7-ethyl-8-nitroquinoline (Intermediate 60) (170 mg, 0.84 mmol), tin (II) chloride (500 mg, 2.52 mmol) and 6 N HCl (2 drops) gave the title compound (144 mg, 100%) which was used in the next step without purification.

MW: 172.23

HPLCMS (Method C): [m/z]: 173

7-Methoxyquinolin-8-amine (Intermediate 64)

In a similar fashion using route 1 general procedure 4, 7-methoxy-8-nitroquinoline (Intermediate 61) (250 mg, 1.22 mmol), tin (II) chloride (700 mg, 3.67 mmol) and 6N HCl (3 drops) gave the title compound (150 mg, 71%) which was used in the next step without purification.

MW: 174.20

HPLCMS (Method C): [m/z]: 175

Route 12 (See Above)

5-Chloro-8-nitroquinoline (Intermediate 65)

In a similar fashion using route 7 general procedure 15, 5-chloroquinoline (1 g, 6.13 mmol), potassium nitrate (800 mg, 7.98 mmol) and $H_2SO_4$ (3 ml) and gave the title compound (926 mg, 73%). The structure was confirmed by $^1H$ NMR.

General Procedure 21: 5-Methoxy-8-nitroquinoline (Intermediate 66)

Sodium methoxide (571 mg, 1.05 mmol) was added to a solution of 5-chloro-8-nitroquinoline (Intermediate 65) (550 mg, 2.64 mmol) in MeOH (15 ml) and heated to 81° C. for 2 h. After cooling, the mixture was concentrated in vacuo, water was added and the mixture was extracted with DCM. The organic phase was dried ($Na_2SO_4$) and concentrated in vacuo gave the title compound (500 mg, 93%). The structure was confirmed by $^1H$ NMR.

5-Methoxyquinolin-8-amine (Intermediate 67)

In a similar fashion using route 2 general procedure 4, 5-methoxy-8-nitroquinoline (Intermediate 66) (550 mg, 2.69 mmol), tin (II) chloride (1.53 mg, 8.07 mmol) and 6 N HCl (3 drops) gave the title compound (430 mg, 91%).

MW: 176.22

HPLCMS (Method C): [m/z]:ES−: 175

Route 13 (See Above)

General Procedure 22: 4,7-Dichloro-8-nitro-quinoline (Intermediate 68)

Fuming nitric acid (8 ml) and concentrated sulfuric acid (16 ml) were combined cautiously at −10° C. 4,7-dichloroquinoline (5 g, 25 mmol) was added portionwise at −10° C. and after complete addition the mixture was allowed to warm to room temperature and stirring continued for 18 h. The reaction mixture was poured onto ice and the resulting solid removed by filtration washed with water (100 ml) to give the title compound (5.7 g, 94%).

MW:243.05

HPLCMS (Method B):[m/z]: 242.80.

General Procedure 23: 7-Chloro-4-methoxy-8-nitro-quinoline (Intermediate 69)

Sodium methoxide (2.0 g, 37.0 mmol) was added to a solution of 4,7-dichloro-8-nitro-quinoline (Intermediate 68) (3.0 g, 12.3 mmol) in MeOH (20 ml) and the reaction was heated under reflux for 24 h. The solvent was removed in vacuo. The residue was dissolved in EtOAc (150 ml) and washed with water, dried ($MgSO_4$) and concentrated in vacuo. The crude residue was purified by column chromatography with EtOAc/heptane (4:1) to give the title compound (2.54 g, 83%).

MW:238.63

HPLCMS (Method B):[m/z]: 239

General Procedure 24: 7-Chloro-4-methoxy-quinolin-8-ylamine (Intermediate 70)

7-Chloro-4-methoxy-8-nitro-quinoline (Intermediate 69) (261 mg, 1.1 mmol) was treated with 10% palladium on carbon (11.6 mg, cat) in EtOH (20 ml) in a Parr pressure reaction system and placed under a hydrogen atmosphere at 5 Barr pressure whilst stirring overnight. The pressure was released and the catalyst removed by filtration through celite. The solvent was removed in vacuo to give the title compound (246 mg, 100%).

MW:208.65

HPLCMS (Method B):[m/z]: 208.95.

General Procedure 25: 4-Methoxy-quinolin-8-ylamine (Intermediate 71)

10% palladium on carbon (125 mg, 1.1 mmol) was added to a solution of 7-chloro-4-methoxy-quinolin-8-ylamine (Intermediate 70) (246 mg, 1.1 mmol), and ammonium formate (365 mg, 5.8 mmol) in 50% acetic acid (5 ml) and the reaction was heated under reflux for 30 min. After cooling the solvent was removed in vacuo. The residue was dissolved in EtOAc (100 ml) and washed with sat sodium bicarbonate solution, dried ($MgSO_4$) and concentrated in vacuo to give the title compound (124 mg, 65%).

MW:174.20

HPLCMS (Method B):[m/z]: 174.95

Route 14 (See Above)

General Procedure 26: N-(5-Bromo-quinolin-8-yl)-benzenesulfonamide (Example Compound 29)

Benzenesulfonyl chloride (72 µl, 0.57 mmol) was added to a solution of 5-bromoquinolin-8-ylamine hydrochloride (84 mg, 0.38 mmol) in pyridine (150 µl, 1.89 mmol) and DCM (5 ml) and the mixture was stirred at room temperature for 20 h. Water (5 ml) was added and the organic phase was separated. The aqueous phase was extracted with DCM and the combined organic phases were dried ($MgSO_4$) and concentrated in vacuo. The crude residue was purified by trituration from DMSO/MeOH (1:2) to give the title compound (60 mg, 44%).

EOAI3334934 VIT-1320
MW: 363.23
HPLCMS (Method A):[m/z]: 364
The result is shown in FIG. 29.

N-(6-Chloro-quinolin-8-yl)-benzenesulfonamide (Example Compound 28)

In a similar fashion using route 14 general procedure 26, benzenesulfonyl chloride (72 μl, 0.57 mmol), 6-chloroquinolin-8-ylamine (67 mg, 0.38 mmol) in pyridine (150 μl, 1.89 mmol) gave the title compound (73 mg, 61%) after trituration from DMSO/MeOH (1:2).
EOAI3334935 VIT-1319
MW: 318.78
HPLCMS (Method A):[m/z]: 320
The result is shown in FIG. 28.

Pyridine-3-sulfonic acid quinolin-8-ylamide (Example Compound 33)

In a similar fashion using route 14 general procedure 26, pyridine-3-sulfonyl chloride hydrochloride (0.30 g, 1.39 mmol), 8-aminoquinoline (0.20 g, 1.39 mmol) in pyridine (0.56 ml, 6.94 mmol) gave the title compound (70 mg, 18%) after trituration from MeOH.
EOAI3335060 VIT-1337
MW: 285.32
HPLCMS (Method A):[m/z]: 285
The result is shown in FIG. 33.

Pyridine-2-sulfonic acid quinolin-8-ylamide (Example Compound 85)

In a similar fashion using route 14 general procedure 26, 8-aminoquinoline (100 mg, 0.69 mmol), pyridine-2-sulfonyl chloride (Intermediate 18) (196 mg, 1.107 mmol) gave the title compound (130 mg, 65%) after purification by column chromatography with n-hexane/EtOAc (17:3) as the eluent.
EOAI3344526 VIT-1723
MW: 285.32
HPLCMS (Method D): [m/z]: 286
The result is shown in FIG. 85.

4-Chloro-2-fluoro-N-(6-methoxyquinolin-8-yl)benzenesulfonamide (Example Compound 57)

In a similar fashion using route 14 general procedure 26, 6-methoxyquinolin-8-amine (Intermediate 23) (60 mg, 0.35 mmol), 2-fluoro-4-chlorobenzenesulfonyl chloride (100 mg, 0.45 mmol) gave the title compound (70 mg, 56%) after purification by column chromatography with DCM as the eluent.
EOAI3335730 VIT-1418
MW: 366.79
HPLCMS (Method A): [m/z]: 367
The result is shown in FIG. 57.

2,4-Dichloro-N-(6-methoxyquinolin-8-yl)benzenesulfonamide (Example Compound 58)

In a similar fashion using route 14 general procedure 26, 6-methoxyquinolin-8-amine (Intermediate 23) (60 mg, 0.35 mmol), 2,4-dichlorobenzenesulfonyl chloride (110 mg, 0.45 mmol) gave the title compound (70 mg, 53%) after purification by column chromatography with DCM as the eluent.
EOAI3335731 VIT-1419
MW: 383.25
HPLCMS (Method A): [m/z]: 384
The result is shown in FIG. 58.

Pyridine-3-sulfonic acid (6-methoxy-quinolin-8-yl)-amide (Example Compound 59)

In a similar fashion using route 14 general procedure 26, 6-methoxyquinolin-8-amine (Intermediate 23) (50 mg, 0.29 mmol), pyridine-3-sulfonyl chloride (Intermediate 17) (76 mg, 0.43 mmol) gave the title compound (35 mg, 39%) after purification by column chromatography with DCM as the eluent.
EOAI3335732 VIT-1420
MW: 315.35
HPLCMS (Method A): [m/z]: 316
The result is shown in FIG. 59.

4-Chloro-N-(5-chloro-quinolin-8-yl)-2-fluoro-benzenesulfonamide (Example Compound 54)

In a similar fashion using route 14 general procedure 26, 5-chloroquinolin-8-amine (Intermediate 27) (50 mg, 0.28 mmol), 4-chloro-2-fluorobenzenesulfonyl chloride (96 mg, 0.42 mmol) gave the title compound (35 mg, 35%) after purification by column chromatography with DCM as the eluent.
EOAI3335670 VIT-1404
MW: 371.21
HPLCMS (Method A): [m/z]: 370.85
The result is shown in FIG. 54.

2,4-Dichloro-N-(5-chloro-quinolin-8-yl)-benzenesulfonamide (Example Compound 56)

In a similar fashion using route 14 general procedure 26, 5-chloroquinolin-8-amine (Intermediate 27) (50 mg, 0.28 mmol), 2,4-dichlorobenzenesulfonyl chloride (103 mg, 0.42 mmol) gave the title compound (40 mg, 40%) after purification by column chromatography with DCM as the eluent.
EOAI3335729 VIT-1417
MW: 387.67
HPLCMS (Method A): [m/z]: 388
The result is shown in FIG. 56.

Pyridine-3-sulfonic acid (5-chloro-quinolin-8-yl)-amide (Example Compound 60)

In a similar fashion using route 14 general procedure 26, 5-chloroquinolin-8-amine (Intermediate 27) (50 mg, 0.28 mmol), pyridine-3-sulfonyl chloride (Intermediate 17) (74 mg, 0.42 mmol) gave the title compound (38 mg, 43%) after purification by column chromatography with DCM as the eluent.
EOAI3335733 VIT-1421
MW: 319.77
HPLCMS (Method A): [m/z]: 320
The result is shown in FIG. 60.

N-(7-Hydroxy-quinolin-8-yl)-benzenesulfonamide (Example Compound 86)

In a similar fashion using route 14 general procedure 26, 8 amino-7-hydroxyquinoline (Intermediate 28) (250 mg, 1.5 mmol), benzenesulfonyl chloride (303 mg, 1.7 mmol) gave the title compound (21 mg, 5%) after purification by column chromatography with heptane/EtOAc (1:1) as the eluent.
EOAI3344338 VIT-1685
MW: 300.34
HPLCMS (Method A):[m/z]: 300.95
The result is shown in FIG. 86.

N-(6-Methyl-quinolin-8-yl)-benzenesulfonamide (Example Compound 77)

In a similar fashion using route 14 general procedure 26, 6-methylquinolin-8-amine (Intermediate 31) (70 mg, 0.44 mmol), benzenesulfonyl chloride (0.07 ml, 0.53 mmol) gave the title compound (30 mg, 23%) after purification by column chromatography with DCM as the eluent.
EOAI3336593 VIT-1482
MW: 298.36
HPLCMS (Method A): [m/z]: 299
The result is shown in FIG. 77.

N-(4-Methoxy-quinolin-8-yl)-benzenesulfonamide (Example Compound 87)

In a similar fashion using route 14 general procedure 26, 4-methoxy-quinolin-8-ylamine (Intermediate 71) (71 mg, 0.41 mmol), benzenesulfonyl chloride (79 mg, 0.44 mmol) gave the title compound (22 mg, 17%) after purification by column chromatography with DCM as the eluent.
EOAI3345271 VIT-1733
MW:314.37
HPLCMS (Method A):[m/z]: 315.
The result is shown in FIG. 87.

N-(4-Chloro-quinolin-8-yl)-benzenesulfonamide (Intermediate 224)

In a similar fashion using route 14 general procedure 26, 4-chloro-quinolin-8-ylamine 464 (228 mg, 1.28 mmol), benzenesulfonyl chloride (0.2 ml, 1.53 mmol) pyridine (0.21 ml, 2.56 mmol) in DCM (10 ml) gave the title compound (250 mg, 61%) after purification by column chromatography with DCM/MeOH (99:1) as the eluent.
MW: 318.78
HPLCMS (Method C): [m/z]: 319

8-Benzenesulfonylamino-quinoline-4-carboxylic acid methyl ester (Example Compound 225)

In a similar fashion using route 14 general procedure 26, 8-Amino-quinoline-4-carboxylic acid methyl ester 489 (56 mg, 0.27 mmol), benzenesulfonyl chloride (54 mg, 0.30 mmol) and pyridine (5 ml) gave the title compound (61 mg, 64%) after purification by column chromatography with DCM/EtOAc (90:10 as the eluent.
EOAI3349511 VIT-1875
MW: 342.38
HPLCMS (Method B):[m/z]: 343

General procedure 27:
4-Chloro-N-quinolin-8-yl-benzenesulfonamide (Example Compound 5)

4-Chlorobenzenesulfonyl chloride (300 mg, 1.38 mmol) was added to a stirred solution of 8-aminoquinoline (200 mg, 1.38 mmol) in pyridine (2 ml). DMAP (cat.) was added and the reaction was stirred at room temperature for 4 h. After no further progress of the reaction was observed (monitored by TLC and LCMS), water was added and the mixture was extracted with DCM. The organic phase was washed with a sat. $KHSO_4$ solution, dried ($Na_2SO_4$) and concentrated in vacuo. The crude residue was triturated with n-hexane to give the title compound (270 mg, 61%).
EOAI3334107 VIT-1247
MW: 318.78
HPLCMS (Method A): [m/z]: 318.90
The result is shown in FIG. 5.

4-Methoxy-N-quinolin-8-yl-benzenesulfonamide (Example Compound 7)

In the similar fashion using route 14 general procedure 27, 8-aminoquinoline (200 mg, 1.38 mmol), 4-methoxybenzenesulfonyl chloride (300 mg, 1.3 mmol) and DMAP (cat.) gave the title compound (250 mg, 58%) after purification by column chromatography with $DCM/MeOH/NH_3$ (100-100:1:1 drop).
EOAI3334109 VIT-1249
MW: 314.36
HPLCMS (Method A): [m/z]: 314.95
The result is shown in FIG. 7.

4-Methyl-N-quinolin-8-yl-benzenesulfonamide (Example Compound 9)

In the similar fashion using route 14 general procedure 27, 8-aminoquinoline (200 mg, 1.38 mmol), p-toluenesulfonyl chloride (260 mg, 1.3 mmol) and DMAP (cat.) gave the title compound (250 mg, 60%) after trituration from n-hexane.
EOAI3334326 VIT-1255
MW: 298.36
HPLCMS (Method A): [m/z]: 299
The result is shown in FIG. 9

2-Methyl-N-quinolin-8-yl-benzenesulfonamide (Example Compound 10)

In the similar fashion using route 14 general procedure 27, 8-aminoquinoline (200 mg, 1.38 mmol), o-toluenesulfonyl chloride (260 mg, 1.3 mmol) and DMAP (cat.) gave the title compound (250 mg, 60%) after trituration from n-hexane.
EOAI3334327 VIT-1256
MW: 298.36
HPLCMS (Method A): [m/z]: 299
The result is shown in FIG. 10.

2-Chloro-N-quinolin-8-yl-benzenesulfonamide (Example Compound 11)

In the similar fashion using route 14 general procedure 27, 8-aminoquinoline (200 mg, 1.38 mmol), 2-chlorobenzenesulfonyl chloride (300 mg, 1.3 mmol) and DMAP (cat.) gave the title compound (250 mg, 58%) after trituration from n-hexane.
EOAI3334328 VIT-1257
MW: 318.78
HPLCMS (Method A): [m/z]: 318.9
The result is shown in FIG. 11.

3-Cyano-N-quinolin-8-yl-benzenesulfonamide (Example Compound 16) In the similar fashion using route 14 general procedure 27, 8-aminoquinoline (200 mg, 1.38 mmol), 2-cyanobenzenesulfonyl chloride (277 mg, 1.38 mmol) and DMAP (cat.) gave the title compound (65 mg, 15%) after recrystalization from DCM/n-pentane.

EOAI3334561 VIT-1285
MW: 309.34
HPLCMS (Method A): [m/z]: 309.9
The result is shown in FIG. 16.

N-Quinolin-8-yl-4-trifluoromethyl-benzenesulfonamide (Example Compound 17)

In the similar fashion using route 14 general procedure 27, 8-aminoquinoline (200 mg, 1.38 mmol), 2-trifluorobenzenesulfonyl chloride (336 mg, 1.38 mmol) and DMAP (cat.) gave the title compound (400 mg, 82%) after recrystalisation from DCM/n-pentane.
EOAI3334562 VIT-1286
MW: 352.33
HPLCMS (Method A): [m/z]: 353
The result is shown in FIG. 17.

3-Methyl-N-quinolin-8-yl-benzenesulfonamide (Example Compound 19)

In the similar fashion using route 14 general procedure 27, 8-aminoquinoline (200 mg, 1.38 mmol), m-toluenesulfonyl chloride (260 mg, 1.3 mmol) and DMAP (cat.) gave the title compound (250 mg, 60%) after purification by column chromatography with DCM as the eluent.
EOAI3334564 VIT-1288
MW: 298.36
HPLCMS (Method A): [m/z]: 298.95
The result is shown in FIG. 19

3-Chloro-N-quinolin-8-yl-benzenesulfonamide (Example Compound 20)

In the similar fashion using route 14 general procedure 27, 8-aminoquinoline (200 mg, 1.38 mmol), 3-chlorobenzenesulfonyl chloride (270 mg, 1.3 mmol) and DMAP (cat.) gave the title compound (250 mg, 59%) after purification by column chromatography with DCM as the eluent.
EOAI3334565 VIT-1289
MW: 318.78
HPLCMS (Method A): [m/z]: 318.9
The result is shown in FIG. 20

3-Methoxy-N-quinolin-8-yl-benzenesulfonamide (Example Compound 21)

In the similar fashion using route 14 general procedure 27, 8-aminoquinoline (200 mg, 1.38 mmol), 3-methoxybenzenesulfonyl chloride (260 mg, 1.3 mmol) and DMAP (cat.) gave the title compound (250 mg, 56%) after purification by column chromatography with DCM as the eluent.
EOAI3334566 VIT-1290
MW: 314.36
HPLCMS (Method A): [m/z]: 314.95
The result is shown in FIG. 21

2-Methoxy-N-quinolin-8-yl-benzenesulfonamide (Example Compound 27)

In the similar fashion using route 14 general procedure 27, 8-aminoquinoline (200 mg, 1.38 mmol), 2-methoxybenzenesulfonyl chloride (280 mg, 1.38 mmol) and DMAP (cat.) gave the title compound (250 mg, 58%) after purification by column chromatography with DCM as the eluent.
EOAI3334931 VIT-1316
MW: 314.36
HPLCMS (Method A): [m/z]: 315
The result is shown in FIG. 27

N-Quinolin-8-yl-2-trifluoromethoxy-benzenesulfonamide (Example Compound 36)

In the similar fashion using route 14 general procedure 27, 8-aminoquinoline (100 mg, 0.69 mmol), 2-trifluoromethoxybenzenesulfonyl chloride (200 mg, 0.69 mmol) and DMAP (cat.) gave the title compound (150 mg, 60%) after column purification with DCM elution.
EOAI3335291 VIT-1349
MW: 368.33
HPLCMS (Method A): [m/z]: 369
The result is shown in FIG. 36

2-Cyano-N-quinolin-8-yl-benzenesulfonamide (Example Compound 37)

In the similar fashion using route 14 general procedure 27, 8-aminoquinoline (100 mg, 0.69 mmol), 2-cyanobenzenesulfonyl chloride (140 mg, 0.69 mmol) and DMAP (cat.) gave the title compound (100 mg, 50%) after purification by column chromatography with DCM as the eluent.
EOAI3335292 VIT-1350
MW: 309.34
HPLCMS (Method A): [m/z]: 310
The result is shown in FIG. 37

N-Quinolin-8-yl-3-trifluoromethoxy-benzenesulfonamide (Example Compound 38)

In the similar fashion using route 14 general procedure 27, 8-aminoquinoline (100 mg, 0.69 mmol), 3-trifluoromethoxybenzenesulfonyl chloride (200 mg, 0.69 mmol) and DMAP (cat.) gave the title compound (150 mg, 60%) after purification by column chromatography with DCM as the eluent.
EOAI3335293 VIT-1351
MW: 368.33
HPLCMS (Method A): [m/z]: 369
The result is shown in FIG. 38

2-(Quinolin-8-ylsulfamoyl)-benzoic acid methyl ester (Example Compound 39)

In the similar fashion using route 14 general procedure 27, 8-aminoquinoline (100 mg, 0.69 mmol), methyl 2-chlorosulfonylbenzoate (160 mg, 0.69 mmol) and DMAP (cat.) gave the title compound (80 mg, 35%) after purification by column chromatography with DCM as the eluent.
EOAI3335294 VIT-1352
MW: 342.37
HPLCMS (Method A): [m/z]: 343
The result is shown in FIG. 39

3-(Quinolin-8-ylsulfamoyl)-benzoic acid methyl ester (Example Compound 40)

In the similar fashion using route 14 general procedure 27, 8-aminoquinoline (100 mg, 0.69 mmol), methyl 3-chlorosulfonylbenzoate (160 mg, 0.69 mmol) and DMAP (cat.) gave the title compound (150 mg, 64%) after purification by column chromatography with DCM as the eluent.
EOAI3335295 VIT-1353
MW: 342.37
HPLCMS (Method A): [m/z]: 343
The result is shown in FIG. 40

2,4-Dichloro-N-quinolin-8-yl-benzenesulfonamide (Example Compound 41)

In the similar fashion using route 14 general procedure 27, 8-aminoquinoline (100 mg, 0.69 mmol), 2,4-dichlorobenzenesulfonyl chloride (200 mg, 0.83 mmol) and DMAP (cat.) gave the title compound (252 mg, 100%) after purification by column chromatography with DCM as the eluent.
EOAI3335305 VIT-1363
MW: 353.22
HPLCMS (Method A): [m/z]: 352.85
The result is shown in FIG. 41

4-Chloro-2-fluoro-N-quinolin-8-yl-benzenesulfonamide (Example Compound 42)

In the similar fashion using route 14 general procedure 27, 8-aminoquinoline (100 mg, 0.69 mmol), 4-chloro-2-fluorobenzenesulfonyl chloride (200 mg, 0.83 mmol) and DMAP (cat.) gave the title compound (190 mg, 82%) after purification by column chromatography with DCM as the eluent.
EOAI3335306 VIT-1364
MW: 336.77
HPLCMS (Method A): [m/z]: 336.9
The result is shown in FIG. 42

N-Quinolin-8-yl-2-trifluoromethyl-benzenesulfonamide (Example Compound 43)

In the similar fashion using route 14 general procedure 27, 8-aminoquinoline (100 mg, 0.69 mmol), 2-(trifluoromethyl)sulfonyl chloride (200 mg, 0.81 mmol) and DMAP (cat.) gave the title compound (230 mg, 94%) after purification by column chromatography with DCM as the eluent.
EOAI3335307 VIT-1365
MW: 352.33
HPLCMS (Method A): [m/z]: 352.95
The result is shown in FIG. 43

N-Quinolin-8-yl-3-trifluoromethyl-benzenesulfonamide (Example Compound 44)

In the similar fashion using route 14 general procedure 27, 8-aminoquinoline (100 mg, 0.69 mmol), 3-trifluoromethyl-benzenesulfonyl chloride (200 mg, 0.83 mmol) and DMAP (cat.) gave the title compound (244 mg, 100%) after purification by column chromatography with DCM as the eluent.
EOAI3335308 VIT-1366
MW: 352.33
HPLCMS (Method A): [m/z]: 353
The result is shown in FIG. 44

2,4,6-Trichloro-N-quinolin-8-yl-benzenesulfonamide (Example Compound 47)

In the similar fashion using route 14 general procedure 27, 8-aminoquinoline (100 mg, 0.69 mmol), 2,4,6 trichlorobenzenesulfonyl chloride (280 mg, 1.03 mmol) and DMAP (cat.) gave the title compound (200 mg, 76%) after purification by column chromatography with DCM as the eluent.
EOAI3335380 VIT-1371
MW: 387.67
HPLCMS (Method A): [m/z]: 388
The result is shown in FIG. 47

3-Chloro-2-fluoro-N-quinolin-8-yl-benzenesulfonamide (Example Compound 62)

In a similar fashion using route 14 general procedure 27, 8-aminoquinoline (100 mg, 0.70 mmol), 3-chloro-2-fluorobenzenesulfonyl chloride (180 mg, 0.83 mmol) and DMAP (cat.) gave the title compound (80 mg, 35%) after purification by column chromatography with DCM as the eluent followed by trituration from EtOAc/n-hexane.
EOAI3335950 VIT-1425
MW: 336.77
HPLCMS (Method A): [m/z]: 336.95
The result is shown in FIG. 62

2,6-Dichloro-N-quinolin-8-yl-benzenesulfonamide (Example Compound 63)

In a similar fashion using route 14 general procedure 27, 8-aminoquinoline (100 mg, 0.70 mmol), 2,6-dichlorobenzenesulfonyl chloride (190 mg, 0.83 mmol) and DMAP (cat.) gave the title compound (100 mg, 41%) after purification by column chromatography with DCM as the eluent.
EOAI3335951 VIT-1426
MW: 353.23
HPLCMS (Method A): [m/z]: 352.9
The result is shown in FIG. 63

2,6-Difluoro-N-quinolin-8-yl-benzenesulfonamide (Example Compound 64)

In a similar fashion using route 14 general procedure 27, 8-aminoquinoline (100 mg, 0.70 mmol), 2,6-difluorobenzenesulfonyl chloride (170 mg, 0.83 mmol) and DMAP (cat.) gave the title compound (100 mg, 45%) after purification by column chromatography with DCM as the eluent followed by trituration from EtOAc/n-hexane.
EOAI3335952 VIT-1427
MW: 320.31
HPLCMS (Method A): [m/z]: 321
The result is shown in FIG. 64

2,3-Dichloro-N-quinolin-8-yl-benzenesulfonamide (Example Compound 67)

In a similar fashion using route 14 general procedure 27, 8-aminoquinoline (100 mg, 0.7 mmol), 2,3-dichlorobenzenesulfonyl chloride (190 mg, 0.8 mmol) and DMAP (cat.) gave the title compound (150 mg, 63%) after purification by column chromatography with DCM as the eluent.
EOAI3336270 VIT-1450
MW: 353.22
HPLCMS (Method A): [m/z]: 352.95
The result is shown in FIG. 67

3-Chloro-2-methyl-N-quinolin-8-yl-benzenesulfonamide (Example Compound 68)

In a similar fashion using route 14 general procedure 27, 8-aminoquinoline (100 mg, 0.7 mmol), 2-methyl-3-chlorobenzenesulfonyl chloride (180 mg, 0.8 mmol) and DMAP (cat.) gave the title compound (150 mg, 65%) after purification by column chromatography with DCM as the eluent.
EAOI3336271 VIT-1451
MW: 332.81
HPLCMS (Method A): [m/z]: 333
The result is shown in FIG. 68

3-Fluoro-2-methyl-N-quinolin-8-yl-benzenesulfonamide (Example Compound 83)

In a similar fashion using route 14 general procedure 27, 8-aminoquinoline (100 mg, 0.69 mmol), 3-fluoro-2-methylbenzenesulfonyl chloride (210 mg, 1.04 mmol) and DMAP (cat.) gave the title compound (120 mg, 57%) after purification by column chromatography with DCM eluent.
EOAI3336898 VIT-1500
MW: 316.35
HPLCMS (Method A): [m/z]: 317
The result is shown in FIG. 83

2-Chloro-6-methyl-N-quinolin-8-yl-benzenesulfonamide (Example Compound 84)

In a similar fashion using route 14 general procedure 27, using 8-aminoquinoline (100 mg, 0.69 mmol), 2-chloro-6-methylbenzenesulfonyl chloride (230 mg, 1.04 mmol) and DMAP (cat.) gave the title compound (110 mg, 48%) after purification by column chromatography with DCM as the eluent.
EOAI3336899 VIT-1501
MW: 332.81
HPLCMS (Method A): [m/z]: 333
The result is shown in FIG. 84

Quinoline-3-sulfonic acid quinolin-8-ylamide (Example Compound 88)

In a similar fashion using route 14 general procedure 27, 8-aminoquinoline (57 mg, 0.40 mmol), quinoline-3-sulfonyl chloride (10 mg, 0.44 mmol) and DMAP (cat.) gave the title compound (28 mg, 21%).
EOAI3343683 VIT-1614
MW: 335.38
HPLCMS (Method C): [m/z]: 336
The result is shown in FIG. 88

6-Cyano-pyridine-3-sulfinic acid quinolin-8-ylamide (Example Compound 116)

In a similar fashion using route 18 general procedure 27, 8-aminoquinoline (200 mg, 1.39 mmol), 6-cyanopyridine-3-sulfonyl chloride 19 (337 mg, 1.66 mmol) and DMAP (cat.) gave the title compound (110 mg, 25%) after purification by column chromatography with n-hexane/EtOAc (4:1) as the eluent.
EOAI3344197 VIT-1657
MW: 310.33
HPLCMS (Method C): [m/z]: 311

6-Trifluoromethyl-pyridine-3-sulfonic acid quinolin-8-ylamide (Example Compound 89)

In a similar fashion using route 14 general procedure 27, 8-aminoquinoline (200 mg, 1.38 mmol), 6-(trifluoromethyl) pyridine-3-sulfonyl chloride (0.31 g, 1.25 mmol) and DMAP (cat) gave the title compound (250 mg, 58%) after purification by column chromatography with DCM as the eluent.
EOAI3346325 VIT-1833
MW: 353.32
HPLCMS (Method C): [m/z]: 354
The result is shown in FIG. 89

N-(7-Methylquinolin-8-yl)-benzenesulfonamide (Example Compound 26)

In the similar fashion using route 14 general procedure 27, 7-methyl-8-aminoquinoline (200 mg, 1.26 mmol), benzenesulfonyl chloride (260 mg, 1.5 mmol) and DMAP (cat.) gave the title compound (250 mg, 67%) after purification by column chromatography with DCM as the eluent.
EOAI3334930 VIT-1315
MW: 298.36
HPLCMS (Method A): [m/z]: 298.9
The result is shown in FIG. 26

N-(2-Methylquinolin-8-yl)-benzenesulfonamide (Example Compound 18)

In the similar fashion using route 14 general procedure 27, 2-methyl-8-aminoquinoline (Intermediate 22) (200 mg, 1.2 mmol), benzenesulfonyl chloride (230 mg, 1.2 mmol) and DMAP (cat.) gave the title compound (150 mg, 43%) after purification by column chromatography with DCM as the eluent.
EOAI3334563 VIT-1287
MW: 298.36
HPLCMS (Method A): [m/z]: 299
The result is shown in FIG. 18

N-(6-Methoxyquinolin-8-yl)-benzenesulfonamide (Example Compound 23)

In the similar fashion using route 14 general procedure 27, 6-methoxyquinolin-8-amine (Intermediate 23) (250 mg, 1.43 mmol), benzenesulfonyl chloride (220 µl, 1.3 mmol) and DMAP (cat.) gave the title compound (260 mg, 57%) after purification by column chromatography with DCM as the eluent.
EOAI3334774 VIT-1308
MW: 314.36
HPLCMS (Method A): [m/z]: 315
The result is shown in FIG. 23

N-(2-Chloroquinolin-8-yl)-benzenesulfonamide (24)

In the similar fashion using route 14 general procedure 27, 2-chloroquinolin-8-amine (Intermediate 26) (70 mg, 0.39 mmol), benzenesulfonyl chloride (83 mg, 0.42 mmol) and DMAP (cat.) gave the title compound (110 mg, 88%) after purification by column chromatography with DCM as the eluent.
EOAI3334775 VIT-1309
MW: 318.78
HPLCMS (Method A): [m/z]: 318.85
The result is shown in FIG. 24

N-(5-Chloroquinolin-8-yl)-benzenesulfonamide (Example Compound 25)

In the similar fashion using route 14 general procedure 27, 5-chloroquinolin-8-amine (Intermediate 27) (70 mg, 0.39 mmol), benzenesulfonyl chloride (83 mg, 0.42 mmol) and DMAP (cat.) gave the title compound (80 mg, 64%) after purification by column chromatography with DCM as the eluent.
EOAI3334776 VIT-1310
MW: 318.78
HPLCMS (Method A): [m/z]: 318.9
The result is shown in FIG. 25

N-(3-Methylquinolin-8-yl)-benzenesulfonamide (Example Compound 45)

In the similar fashion using route 14 general procedure 27, 3-methylquinoline (Intermediate 31) (130 mg, 0.82 mmol), benzenesulfonyl chloride (170 mg, 0.9 mmol) and DMAP (cat.) gave the title compound (150 mg, 61%) after tituration from n-hexane.
EOAI3335309 VIT-1367
MW: 298.36
HPLCMS (Method A): [m/z]: 299
The result is shown in FIG. 45

2,4-Dichloro-N-(3-methylquinolin-8-yl)-benzenesulfonamide (Example Compound 69)

In a similar fashion using route 14 general procedure 27, 3-methyl-8-aminoquinoline (Intermediate 31) (40 mg, 0.25 mmol), 2,4-dichlorobenzenesulfonyl chloride (74 mg, 0.30 mmol) and DMAP (cat.) gave the title compound (30 mg, 33%) after purification by column chromatography with DCM as the eluent.
EOAI3336272 VIT-1452
MW: 367.25
HPLCMS (Method A): [m/z]: 366.95
The result is shown in FIG. 69

4-Chloro-2-fluoro-N-(3-methylquinolin-8-yl)-benzenesulfonamide (Example Compound 71)

In a similar fashion using route 14 general procedure 27, 3-methyl-8-aminoquinoline (Intermediate 31) (40 mg, 0.25 mmol), 2-fluoro-4-chlorobenzenesulfonyl chloride (70 mg, 0.30 mmol) and DMAP (cat.) gave the title compound (40 mg, 50%) after purification by column chromatography with DCM as the eluent.
EOAI3336404 VIT-1464
MW: 350.8
HPLCMS (Method A): [m/z]: 351
The result is shown in FIG. 71

Pyridine-3-sulfonic acid (3-methyl-quinolin-8-yl)-amide (Example Compound 72)

In a similar fashion using route 14 general procedure 27, 3-methyl-8-aminoquinoline (Intermediate 31) (40 mg, 0.25 mmol), pyridine-3-sulfonyl chloride (Intermediate 17) (53 mg, 0.30 mmol) and DMAP (cat.) gave the title compound (40 mg, 50%) after purification by column chromatography with DCM/MeOH (1:0-99:1) gradient elution.
EOAI3336405 VIT-1465
MW: 299.35
HPLCMS (Method A): [m/z]: 300
The result is shown in FIG. 72

N-5-Methylquinolin-8-yl-benzenesulfonamide (Example Compound 90)

In a similar fashion using route 14 general procedure 27, 5-methylquinolin-8-amine (Intermediate 44) (150 mg, 0.95 mmol) and benzenesulfonyl chloride (200 mg, 1.14 mmol) gave the title compound (80 mg, 28%) after column chromatography with DCM as the eluent.
EOAI3338242 VIT-1580
MW: 298.36
HPLCMS (Method A): [m/z]: 299
The result is shown in FIG. 90

N-(5-(Trifluoromethyl-quinolin-8-yl)-benzenesulfonamide (Example Compound 91)

In a similar fashion using route 14 general procedure 27, 5-(trifluoromethyl)quinolin-8-amine (Intermediate 45) (320 mg, 1.51 mmol), benzenesulfonyl chloride (320 mg, 1.81 mmol) and DMAP (cat.) gave the title compound (21 mg, 4%) after purification by column chromatography with DCM/n-hexane (0:1-3:2) as the eluent followed by recrystallisation from DCM/n-pentane.
EOAI3344021 VIT-1655
MW: 352.33
HPLCMS (Method C): [m/z]: 353
The result is shown in FIG. 91

N-(6-(Trifluoromethoxy-quinolin-8-yl)-benzenesulfonamide (Example Compound 92)

In a similar fashion using route 14 general procedure 27, 6-(trifluoromethoxy)quinolin-8-amine (Intermediate 46) (150 mg, 0.66 mmol), benzenesulfonyl chloride (140 mg, 0.79 mmol) and DMAP (cat.) gave the title compound (140 mg, 58%) after purification by column chromatography with n-hexane/EtOAc (1:0-0:1) as the eluent.
EOAI3343905 VIT-1648
MW: 368.33
HPLCMS (Method C): [m/z]: 369
The result is shown in FIG. 92

N-(6-Ethoxy-quinolin-8-yl)-benzenesulfonamide (Example Compound 93)

In a similar fashion using route 14 general procedure 27, 6-ethoxyquinolin-8-amine (Intermediate 47) (150 mg, 0.8 mmol), benzenesulfonyl chloride (170 mg, 0.96 mmol) and DMAP (cat.) gave the title compound (85 mg, 33%) after purification by column chromatography with n-hexane/DCM (1:0-0:1) as the eluent and recrystallisation from DCM/n-pentane.
EOAI3343904 VIT-1647
MW: 328.39
HPLCMS (Method C): [m/z]: 329
The result is shown in FIG. 93

N-(6-Fluoro-quinolin-8-yl)benzenesulfonamide (Example Compound 75)

In a similar fashion using route 14 general procedure 27, 6-fluoroquinolin-8-amine (Intermediate 48) (60 mg, 0.37 mmol), benzenesulfonyl chloride (78 mg, 0.44 mmol) and DMAP (cat.) gave the title compound (40 mg, 36%) after purification by column chromatography with DCM as the eluent.
EOAI3336591 VIT-1480
MW: 302.32
HPLCMS (Method A): [m/z]: 303
The result is shown in FIG. 75

2,6-Difluoro-N-(6-fluoro-quinolin-8-yl)-benzenesulfonamide (Example Compound 94)

In a similar fashion using route 14 general procedure 27, 6-fluoroquinolin-8-amine (Intermediate 48) (140 mg, 0.86 mmol), 2,6-difluorobenzenesulfonyl chloride (220 mg, 1.04 mmol) and DMAP (cat.) gave the title compound (160 mg, 55%) after purification by column chromatography with DCM as the eluent followed by recrystallisation with DCM/n-pentane.
EOAI3343714 VIT-1604
MW: 338.30
HPLCMS (Method C): [m/z]: 339
The result is shown in FIG. 94

4-Chloro-2-fluoro-N-(6-fluoroquinolin-8-yl)-benzenesulfonamide (Example Compound 95)

In a similar fashion using route 14 general procedure 27, 6-fluoroquinolin-8-amine (Intermediate 48) (150 mg, 0.93 mmol), 4-chloro-2-fluorobenzenesulfonyl chloride (250 mg, 1.11 mmol) and DMAP (cat.) gave the title compound (140 mg, 43%) after purification by column chromatography with DCM/n-hexane (4:1) as the eluent.
EOAI3343682 VIT-1615
MW: 354.76
HPLCMS (Method C): [m/z]: 355
The result is shown in FIG. 95

Pyridine-3-sulfonic acid (6-fluoro-quinolin-8-yl)-amide (Example Compound 96)

In a similar fashion using route 14 general procedure 27, 6-fluoroquinolin-8-amine (Intermediate 48) (100 mg, 0.62 mmol), pyridine 3-sulfonyl chloride (Intermediate 17) (130 mg, 0.74 mmol) and DMAP (cat.) gave the title compound (60 mg, 32%) after purification by column chromatography with n-hexane/DCM (1:0-0:1) gradient elution followed by recrystallisation from DCM/n-pentane.
EOAI3343903 VIT-1642
MW: 303.31
HPLCMS (Method C): [m/z]: 304
The result is shown in FIG. 96

N-(5,6-Difluoro-quinolin-8-yl)-benzenesulfonamide (Example Compound 97)

In a similar fashion using route 14 general procedure 27, 5,6-difluoroquinolin-8-amine (Intermediate 49) (120 mg, 0.67 mmol), benzenesulfonyl chloride (141 mg, 0.78 mmol) and DMAP (cat.) gave the title compound (73 mg, 35%) after purification by column chromatography with n-hexane/EtOH (1:1) as the eluent.
EOAI3343715 VIT-1602
MW: 320.31
HPLCMS (Method C): [m/z]: 321
The result is shown in FIG. 97

N-(5-Fluoro-quinolin-8-yl)-benzenesulfonamide (Example Compound 98)

In a similar fashion using route 14 general procedure 27, 5-fluoroquinolin-8-amine (Intermediate 50) (150 mg, 0.93 mmol), benzenesulfonyl chloride (196 mg, 1.11 mmol) and DMAP (cat) gave the title compound (170 mg, 61%) after column chromatography with DCM eluent.
EOAI3338241 VIT-1579
MW: 302.32
HPLCMS (Method A): [m/z]: 303
The result is shown in FIG. 98

N-(5-Chloro-6-methyl-quinolin-8-yl)-benzenesulfonamide (Example Compound 99)

In a similar fashion using route 14 general procedure 27, 5-chloro-6-methylquinolin-8-amine (Intermediate 51) (160 mg, 0.83 mmol), benzenesulfonyl chloride (175 mg, 0.99 mmol) and DMAP (cat.) gave the title compound (110 mg, 40%) after purification by column chromatography with n-hexane/EtOAc (1:1), followed by DCM/MeOH (99:1) as the eluent.
EOAI3338240 VIT-1578
MW: 332.81
HPLCMS (Method A): [m/z]: 332.95
The result is shown in FIG. 99

N-(7-Chloro-quinolin-8-yl)-benzenesulfonamide (Example Compound 100)

In a similar fashion using route 14 general procedure 27, 7-chloroquinolin-8-amine (Intermediate 52) (100 mg, 0.56 mmol), benzenesulfonyl chloride (110 mg, 0.67 mmol) and DMAP (cat.) gave the title compound (110 mg, 56%) after trituration from n-pentane.
EOAI3337853 VIT-1516
MW: 318.78
HPLCMS (Method A): [m/z]: 319
The result is shown in FIG. 100

N-(5-Chloro-6-fluoro-quinolin-8-yl)-benzenesulfonamide (Example Compound 82)

In a similar fashion using route 14 general procedure 27, 5-chloro-6-fluoroquinolin-8-amine (Intermediate 53) (100 mg, 0.51 mmol), benzenesulfonyl chloride (100 mg, 0.61 mmol) and DMAP (cat.) gave the title compound (27 mg, 16%) after purification by column chromatography with DCM as the eluent followed by preparative HPLC (neutral conditions).
EOAI3336897 VIT-1499
MW: 336.77
HPLCMS (Method A): [m/z]: 337
The result is shown in FIG. 82

N-(5,6-Dimethyl-quinolin-8-yl)-benzenesulfonamide (Example Compound 76)

In a similar fashion using route 14 general procedure 27, 5,6-dimethylquinolin-8-amine (Intermediate 55) (60 mg, 0.38 mmol), benzenesulfonyl chloride (72 mg, 0.41 mmol) and DMAP (cat.) gave the title compound (10 mg, 10%) after purification by column chromatography with DCM as the eluent.
EOAI3336592 VIT-1481
MW: 312.39
HPLCMS (Method A): [m/z]: 313
The result is shown in FIG. 76

N-(7-Isopropyl-quinolin-8-yl)-benzenesulfonamide (Example Compound 101)

In a similar fashion using route 14 general procedure 27, 7-isopropylquinolin-8-amine (Intermediate 62) (150 mg, 0.81 mmol), bezenesulfonyl chloride (170 mg, 1.0 mmol) and DMAP (cat.) gave the title compound (105 mg, 40%) after purification by column chromatography with n-hexane/EtOAc (17:3-4:1) gradient elution.
EOAI3343688 VIT-1613
MW: 326.41
HPLCMS (Method C): [m/z]: 327
The result is shown in FIG. 101

N-(7-Ethyl-quinolin-8-yl)-benzenesulfonamide (Example Compound 102)

In a similar fashion using route 14 general procedure 27, 7-ethylquinolin-8-amine (Intermediate 63) (144 mg, 0.84 mmol), benzenesulfonyl chloride (170 mg, 1.01 mmol) and DMAP (cat.) gave the title compound (40 mg, 15%) after purification by column chromatography with n-hexane/EtOAc (17:3) as the eluent.
EOAI3343687 VIT-1612
MW: 312.39
HPLCMS (Method C): [m/z]: 313
The result is shown in FIG. 102

N-(7-Methoxy-quinolin-8-yl)-benzenesulfonamide (Example Compound 103)

In a similar fashion using route 14 general procedure 27, 7-methoxyquinolin-8-amine (Intermediate 64) (150 mg, 0.86 mmol), benzenesulfonyl chloride (130 μl, 1.03 mmol) and DMAP (cat.) gave the title compound (90 mg, 33%) after recrystallisation from DCM/n-pentane.
EOAI3343902 VIT-1649
MW: 314.36
HPLCMS (Method C): [m/z]: 315
The result is shown in FIG. 103

6-Trifluoromethyl-pyridine-3-sulfonic acid (6-fluoro-quinolin-8-yl)-amide (Example Compound 226)

In a similar fashion using route 14 general procedure 27, 6-fluoroquinolin-8-ylamine (Intermediate 48) (150 mg, 0.92 mmol), 6-(trifluoromethyl)pyridine-3-sulfonyl chloride (250 mg, 1.01 mmol) in DCM (2 ml), DMAP (cat), pyridine (146 mg, 1.84 mmol) and DCM (5 ml) gave the title compound (90 mg, 26%) after purification by column chromatography with n-hexane/EtOAc (90:10) as the eluent.
EOAI3356104 VIT-2020
MW: 371.30
HPLCMS (Method C): [m/z]: 372.0

5-Methyl-pyridine-2-sulfonic acid quinolin-8-ylamide (Example Compound 227)

In a similar fashion using route 14 general procedure 27, 8-aminoqunoline (40 mg, 0.27 mmol), 5-methyl-pyridine-2-sulfonyl chloride 440 (79 mg, 0.41 mmol), pyridine (1.5 ml) DMAP (cat.) and DCM (2 ml) gave the title compound (21 mg, 25%) after purification by column chromatography with n-hexane/EtOAc (93:7) as the eluent.
EOAI3348280 VIT-1849
MW: 299.35
HPLCMS (Method C): [m/z]: 300

6-Methyl-pyridine-2-sulfonic acid quinolin-8-ylamide (228)

In a similar fashion using route 14 general procedure 27, 8-aminoquinoline (250 mg, 1.73 mmol), 6-methyl-pyridine-2-sulfonyl chloride 441 (530 mg, 2.77 mmol), DMAP (cat.), pyridine (3 ml) and DCM (2 ml) gave the title compound (115 mg, 22%) after purification by column chromatography with n-hexane/EtOAc (90:10) as the eluent.
EOAI3348281 VIT-1850
MW: 299.35
HPLCMS (Method C):[m/z]: 300.35

5-Trifluoromethyl-pyridine-3-sulfonic acid quinolin-8-ylamide (Example Compound 229)

In a similar fashion using route 14 general procedure 27, 8-aminoquinoline (70 mg, 0.48 mmol), 5-trifluoromethyl-pyridine-3-sulfonyl chloride (Intermediate 442) (153 mg, 0.63 mmol), DMAP (cat.), pyridine (1.5 ml) and DCM (2 ml) gave the title compound (30 mg, 11%) after purification by column chromatography with n-hexane/EtOAc (85:15) as the eluent.
EOAI3351195 VIT-1939
MW: 353.33
HPLCMS (Method C): [m/z]: 353.98

Pyrazine-2-sulfonic acid quinolin-8-ylamide (Example Compound 230)

In a similar fashion using route 18 general procedure 27, 8-aminoqunoline (300 mg, 2.08 mmol), pyrazine-2-sulfonyl chloride 443 (482 mg, 2.7 mmol), pyridine (3 ml), DMAP (cat.) and DCM (2 ml) gave the title compound (102 mg, 13%) after purification by column chromatography with n-hexane/EtOAc (90:10) as the eluent.
EOAI3351196 VIT-1940
MW: 286.31
HPLCMS (Method C): [m/z]: 286.99

Thiazole-2-sulfonic acid quinolin-8-ylamide (231)

In a similar fashion using route 14 general procedure 27, 8-aminoqunoline (250 mg, 1.73 mmol), thiazole-2-sulfonyl chloride (Intermediate 444) (413 mg, 2.25 mmol), pyridine (2 ml), DMAP (cat.) and DCM (2 ml) gave the title compound (110 mg, 15%), after purification by column chromatography with n-hexane/EtOAc (90:10) as the eluent.
EOAI3351375 VIT-1951
MW: 290.96
HPLCMS (Method C): [m/z]: 291.96

6-Trifluoromethyl-pyridine-3-sulfonic acid (6-trifluoromethoxy-quinolin-8-yl)-amide (Example Compound 232)

In a similar fashion using route 14 general procedure 27, 6-trifluoromethoxy-quinolin-8-ylamine (Intermediate 46) (75 mg, 0.32 mmol), 6-(trifluoromethyl)pyridine-3-sulfonyl chloride (96 mg, 0.39 mmol), DMAP (cat.), pyridine (0.05 ml, 0.65 mmol) and DCM (2 ml) gave the title compound (60 mg, 42%) after purification by column chromatography with n-hexane/EtOAc (90:10) as the eluent.
EOAI3356105 VIT-2021
MW: 437.31
HPLCMS (Method C): [m/z]: 438

6-Trifluoromethyl-pyridine-3-sulfonic acid (5-trifluoromethyl-quinolin-8-yl)-amide (Example Compound 233)

In a similar fashion using route 14 general procedure 27, 5-trifluoromethyl-quinolin-8-ylamine (Intermediate 45) (100 mg, 0.47 mmol), 6-(trifluoromethyl)pyridine-3-sulfonyl chloride (138 mg, 0.56 mmol), pyridine (0.08 ml, 0.94 mmol), DMAP (cat.) and DCM (5 ml) gave the title compound (25 mg, 13%) after purification by column chromatography with n-hexane/DCM (50:50) as the eluent.
EOAI3356956 VIT-2035
MW: 421.31
HPLCMS (Method C): [m/z]: 421.9

Pyridine-2-sulfonic acid (5-trifluoromethyl-quinolin-8-yl)-amide (Example Compound 234)

In a similar fashion using route 14 general procedure 27, 5-trifluoromethyl-quinolin-8-ylamine (Intermediate 45) (125 mg, 0.58 mmol), pyridine-2-sulfonyl chloride (Intermediate 18) (125 mg, 0.70 mmol), pyridine (0.09 ml, 1.17 mmol), DMAP (cat.) and DCM (5 ml) gave the title compound (65 mg, 31%) after purification by column chromatography with n-hexane/DCM (50:50) as the eluent.
EOAI3356957 VIT-2034
MW: 353.31
HPLCMS (Method C): [m/z]: 354

Pyridine-2-sulfonic acid (6-trifluoromethoxy-quinolin-8-yl)-amide (Example Compound 235)

In a similar fashion using route 14 general procedure 27, 6-trifluoromethoxy-quinolin-8-ylamine (Intermediate 46) (110 mg, 0.48 mmol), pyridine-2-sulfonyl chloride (Intermediate 18) (102 mg, 0.57 mmol), pyridine (0.08 ml, 0.96 mmol), DMAP (cat.) and DCM (5 ml) gave the title compound (100 mg, 56%) after purification by column chromatography with n-hexane/DCM (50:50) as the eluent.
EOAI3356958 VIT-2033
MW: 369.31
HPLCMS (Method C): [m/z]: 370

Pyridine-2-sulfonic acid (6-fluoro-quinolin-8-yl)-amide (Example Compound 236)

In a similar fashion using route 14 general procedure 27, 6-fluoroquinolin-8-ylamine (Intermediate 48) (125 mg, 0.77 mmol), pyridine-2-sulfonyl chloride Intermediate 18) (163 mg, 0.92 mmol), pyridine (0.12 ml, 1.54 mmol), DMAP (cat.) and DCM (5 ml) gave the title compound (100 mg, 43%) after purification by column chromatography with n-hexane/DCM (50:50) as the eluent.
EOAI3357160 VIT-2054
MW: 303.31
HPLCMS (Method C): [m/z]: 304

Pyridine-3-sulfonic acid (6-trifluoromethoxy-quinolin-8-yl)-amide (Example Compound 237)

In a similar fashion using route 14 general procedure 27, 6-(trifluoromethoxy)quinolin-8-ylamine (Intermediate 46) (110 mg, 0.48 mmol), pyridine-3-sulfonyl chloride (Intermediate 17) (102 mg, 0.57 mmol), pyridine (0.08 ml, 0.96 mmol), DMAP (cat.) and DCM (5 ml) gave the title compound (150 mg, 85%) after purification by column chromatography with n-hexane/DCM (50:50) as the eluent.
EOAI3357161 VIT-2056
MW: 369.31
HPLCMS (Method C): [m/z]: 370

6-Cyano-pyridine-3-sulfonic acid (6-trifluoromethoxy-quinolin-8-yl)-amide (Example Compound 238)

In a similar fashion using route 14 general procedure 27, 6-(trifluoromethoxy)quinolin-8-ylamine (Intermediate 46) (125 mg, 0.54 mmol), 6-cyano-pyridine-3-sulfonyl chloride (Intermediate 19) (132 mg, 0.65 mmol), pyridine (0.09 ml, 1.09 mmol), DMAP (cat.) and DCM (10 ml) gave the title compound (75 mg, 35%) after purification by column chromatography with n-hexane/DCM (50:50) as the eluent.
EOAI3357162 VIT-2057
MW: 394.32
HPLCMS (Method C): [m/z]: 394.9

6-Cyano-pyridine-3-sulfonic acid (6-fluoro-quinolin-8-yl)-amide (239)

In a similar fashion using route 14 general procedure 27, 6-fluoroquinolin-8-ylamine (Intermediate 48) (125 mg, 0.77 mmol), 6-cyano-pyridine-3-sulfonyl chloride (Intermediate 19) (187 mg, 0.92 mmol), pyridine (121 mg, 1.54 mmol), DMAP (cat.) and DCM (10 ml) gave the title compound (67 mg, 26%) after purification by column chromatography with n-hexane/DCM (50:50) as the eluent.
EOAI3357163 VIT-2055
MW: 328.32
HPLCMS (Method C): [m/z]: 329

5-Cyano-pyridine-2-sulfonic acid (5-trifluoromethyl-quinolin-8-yl)-amide (Example Compound 240)

In a similar fashion using route 14 general procedure 27, 5-(trifluoromethyl)quinolin-8-ylamine (Intermediate 45) (125 mg, 0.58 mmol), 6-cyano-pyridine-3-sulfonyl chloride (Intermediate 19) (142 mg, 0.70 mmol), pyridine (0.09 ml, 1.17 mmol), DMAP (cat.) and DCM (10 ml) gave the title compound (115 mg, 52%) after purification by column chromatography with n-hexane/DCM (50:50) as the eluent.
EOAI3357164 VIT-2058
MW: 378.32
HPLCMS (Method C): [m/z]: 379

N-Quinazolin-8-yl-benzenesulfonamide (Example Compound 241)

In a similar fashion using route 14 general procedure 27, quinazolin-8-ylamine (Intermediate 480) (60 mg, 0.41 mmol), benzene sulfonyl chloride (94 mg, 0.53 mmol), DMAP (cat.) and pyridine (1 ml) at 150° C. for 2.5 h, gave title compound (30 mg, 54%) after purification by column chromatography with DCM as the eluent.
EOAI3366418 VIT-2354
MW: 285.33
HPLCMS: (Method E): [m/z]: 286

General Procedure 58:
N-[1,5]Naphthyridin-4-yl-benzenesulfonamide (Example Compound 242)

[1,5]Naphthyridin-4-ylamine (Intermediate 486) (60 mg, 0.41 mmol) was added to a suspension of NaH (60% in mineral oil; 25 mg, 0.53 mmol) in THF (2 ml) at 0° C. followed by a solution of benzenesulfonyl chloride (95 mg, 0.53 mmol) in THF (1 ml). The mixture was stirred at room temperature for 12 h. After completion, the reaction was quenched with water (5 ml) and the aqueous phase was extracted with EtOAc (30 ml). The organic phase was washed with brine, dried ($Na_2SO_4$) and concentrated in vacuo. The crude residue was purified by column chromatography with DCM/MeOH (98:2) as the eluent to give the title compound (30 mg, 30%).
EOAI3366688 VIT-2366
MW: 285.33
HPLCMS (Method E): [m/z]: 286.30
Route 15 (See Above)

General procedure 28:
2-Nitro-N-quinolin-8-yl-benzenesulfonamide (Example Compound 6)

2-Nitrobenzenesulfonyl chloride (1.15 g, 5.21 mmol) was added to a stirred solution of 8-aminoquinoline (500 mg, 3.47 mmol) and TEA (0.72 ml, 5.21 mmol) in DCM (5 ml), at 0° C., under argon. The reaction was allowed to warm to room temperature and was stirred for 5 h. The mixture was concentrated in vacuo. The residue was dissolved in EtOAc, washed with water and a sat. sodium bicarbonate solution. The organic phase was dried (Na$_2$SO$_4$) and concentrated in vacuo to give the title compound (980 mg, 86%).

EOAI3334108 VIT-1248
MW: 329.33
HPLCMS (Method A): [m/z]: 329.95
The result is shown in FIG. 6

4-Fluoro-2-nitro-N-quinolin-8-yl-benzenesulfonamide (Example Compound 30)

In a similar fashion using route 14 general procedure 26, 8-aminoquinoline (500 mg, 3 mmol) and 2-nitro-4-fluorobenzenesulfonyl chloride (Intermediate 220) (914 mg, 4 mmol) gave the title compound (1.10 g, 91%).

EOAI3335057 VIT-1334
MW: 347.32
HPLCMS (Method A): [m/z]: 347.90
The result is shown in FIG. 30

2-Nitro-N-quinolin-8-yl-4-trifluoromethyl-benzenesulfonamide (Example Compound 32)

In a similar fashion using route 14 general procedure 26, 8-aminoquinoline (500 mg, 3 mmol) and 2-nitro-4-(trifluoromethyl)benzene-1-sulfonyl chloride (990 mg, 3 mmol) gave the title compound (1.22 g, 99%).

EOAI3335059 VIT-1336
MW: 397.34
HPLCMS (Method A): [m/z]: 397.90
The result is shown in FIG. 32

4,5-Dimethyl-2-nitro-N-quinolin-8-yl-benzenesulfonamide (Intermediate 147)

In a similar fashion using route 14 general procedure 26, 8-aminoquinoline (0.25 g, 1.73 mmol) and dimethyl-2-nitrobenzenesulfonyl chloride (0.47 g, 1.9 mmol) gave the title compound (0.54 g, 80%).

MW: 357.38
HPLCMS (Method B): [m/z]: 358

4-Methoxy-2-nitro-N-quinolin-8-yl-benzenesulfonamide (Example Compound 34)

In a similar fashion using route 14 general procedure 26, 8-aminoquinoline (220 mg, 2 mmol) and 4-methoxy-2-nitrobenzene-1-sulfonyl chloride (420 mg, 2 mmol) gave the title compound (406 mg, 74%) after purification by column chromatography with heptane/EtOAc (50:50-0:100) gradient elution.

EOAI3335137 VIT-1344
MW: 359.36
HPLCMS (Method A): [m/z]: 360
The result is shown in FIG. 34

N-(2-Methyl-quinolin-8-yl)-2-nitro-benzenesulfonamide (Intermediate 149)

In a similar fashion using route 14 general procedure 26, 2-methyl-quinolin-8-ylamine (Intermediate 22) (417 mg, 2.64 mmol) and 2-nitrobenzensulfonyl chloride (643 mg, 2.64 mmol) gave the title compound (423 mg, 47%).

MW: 343.36
HPLCMS (Method B): [m/z]: 344

2-Nitro-4-methoxy-N-(2-methyl-quinolin-8-yl)-benzenesulfonamide (Intermediate 150)

In a similar fashion using route 14 general procedure 27, 2-methyl-quinolin-8-ylamine (Intermediate 22) (500 mg, 3.1 mmol) and 4-methoxy-2-nitrobenzenesulfonyl chloride (826 mg, 3.4 mmol) and DMAP (19 mg, 1.5 mmol) gave the title compound (600 mg, 51%).

MW: 373.39
HPLCMS (Method C): [m/z]: ES−:372

4-Methyl-2-nitro-N-quinolin-8-yl-benzenesulfonamide (Intermediate 151)

In the similar using route 15 general procedure 28, 8-aminoquinoline (1.89 g 13.0 mmol), 2-nitro-4-methylbenzenesulfonyl chloride (Intermediate 20) (3.1 g, 13.0 mmol) and TEA (2.75 ml, 19.7 mmol) gave the title compound (3.2 g, 71%) after trituration from pentane.

MW: 343.36
HPLCMS (Method C): [m/z]: 344

N-(6-Methoxyquinolin-8-yl)-2-nitrobenzenesulfonamide (Intermediate 152)

In a similar fashion using route 14 general procedure 26, 6-methoxyquinolin-8-amine (Intermediate 23) (350 mg, 2.01 mmol) and 2-nitrobenzenesulfonyl chloride (533 mg, 2.41 mmol) gave the title compound (460 mg, 64%).

MW: 359.36
HPLCMS (Method C): [m/z]: ES−:358

N-(6-Methoxyquinolin-8-yl)-4-methyl-2-nitrobenzenesulfonamide (Intermediate 153)

In a similar fashion using route 14 general procedure 26, 6-methoxyquinolin-8-amine (Intermediate 23) (120 mg, 0.69 mmol) and 4-methyl-2-nitrobenzenesulfonyl chloride (Intermediate 20) (186 mg, 1.03 mmol) gave the title compound (150 mg, 58%) after purification by column chromatography with DCM as the eluent.

MW: 373.39
HPLCMS (Method C): [m/z]: 374

N-(6-Methoxyquinolin-8-yl)-2-nitro-4-trifluoromethylbenzenesulfonamide (Intermediate 154)

In a similar fashion using route 14 general procedure 26, 6-methoxyquinolin-8-amine (Intermediate 23) (150 mg, 0.86 mmol), 2-nitro-(4-trifluoromethyl)benzenesulfonyl chloride (373 mg, 0.13 mmol) gave the title compound (200 mg, 54%) after purification by column chromatography with DCM as the eluent.

MW: 427.36
HPLCMS (Method C): [m/z]: 428

N-(5-Chloroquinolin-8-yl)-4-methyl-2-nitrobenzenesulfonamide (Intermediate 155)

In a similar fashion using route 14 general procedure 26, 5-chloro-8-aminoquinoline (Intermediate 27) (150 mg, 0.84 mmol), 2-nitro-4-methylbenzenesulfonyl chloride (Intermediate 20) (228 mg, 1.26 mmol) gave the title compound (170 mg, 54%) after purification by column chromatography with DCM as the eluent.
MW: 377.81
HPLCMS (Method C): [m/z]: 378

N-(5-Chloroquinolin-8-yl)-2-nitro-4-trifluoromethyl-benzenesulfonamide (Intermediate 156)

In a similar fashion using route 14 general procedure 26, 5-chloroquinolin-8-amine (Intermediate 27) (50 mg, 0.28 mmol), 2-nitro-4-(trifluoromethyl)benzene-1-sulfonyl chloride (162 mg, 0.56 mmol) gave the title compound (120 mg, 50%) after purification by column chromatography with DCM as the eluent.
MW: 431.78
HPLCMS (Method C): [m/z]: 432

2-Nitro-N-quinoxalin-5-yl-benzenesulfonamide (Intermediate 243)

In a similar fashion using route 14 general procedure 26, quinoxalin-5-ylamine (Intermediate 482) (540 mg, 3.7 mmol), 2-nitro-benzenesulfonyl chloride (986 mg, 4.46 mmol), pyridine (0.9 ml, 7.44 mmol) and DCM (10 ml) gave the title compound (679 mg, 56%) after purification by column chromatography with DCM as the eluent.
MW: 330.32
HPLCMS: (Method C): [m/z]: 331

N-(6-Fluoro-quinolin-8-yl)-2-nitro-benzenesulfonamide (Intermediate 244)

In a similar fashion using route 14 general procedure 26, 6-fluoroquinolin-8-ylamine (Intermediate 48) (320 mg, 1.97 mmol), 2-nitro-benzenesulfonyl chloride (523 mg, 2.37 mmol), pyridine (2 ml) for 16 h gave the title compound (520 mg, 76%) which was used in the next step without further purification.
MW: 347.33
HPLCMS (Method C): [m/z]: 348

N-(5-Fluoro-quinolin-8-yl)-2-nitro-benzenesulfonamide (Intermediate 245)

In a similar fashion using route 14 general procedure 26, 5-fluoro-quinolin-8-ylamine (Intermediate 50) (350 mg, 2.0 mmol), 2-nitro-benzenesulfonyl chloride (575 mg, 2.59 mmol), pyridine (0.35 ml, 4.3 mmol) and DCM (12 ml) gave the title compound (470 mg, 63%) after purification by column chromatography with DCM as the eluent.
MW: 347.33
HPLCMS (Method C): [m/z]: 348

N-(5-Chloro-quinolin-8-yl)-2-nitro-benzenesulfonamide (Intermediate 246)

In a similar fashion using route 14 general procedure 26, 5-chloro-quinolin-8-ylamine (Intermediate 27) (380 mg, 2.13 mmol), 2-nitrobenzene-1-sulfonyl chloride (566 mg, 2.56 mmol), pyridine (0.34 ml, 4.26 mmol) and DCM (12 ml) gave the title compound (610 mg, 79%) after purification by column chromatography with n-hexane/DCM (1:1) as the eluent.
MW: 363.77
HPLCMS (Method C): [m/z]: 364

4-Methyl-N-(3-methylquinolin-8-yl)-2-nitrobenzene-sulfonamide (Intermediate 157)

In a similar fashion using route 14 general procedure 27, 3-methylquinolin-8-amine (Intermediate 31) (80 mg, 0.50 mmol), 4-methyl-2-nitrobenzenesulfonyl chloride (Intermediate 20) (140 mg, 0.60 mmol) and DMAP (cat.) gave the title compound (145 mg, 80%) after purification by column chromatography with DCM as the eluent.
MW: 357.39
HPLCMS (Method C): [m/z]: 358

N-(3-Methylquinolin-8-yl)-2-nitro-4-trifluoromethylbenzenesulfonamide (Intermediate 158)

In a similar fashion using route 14 general procedure 27, 3-methyl-8-aminoquinoline (Intermediate 31) (70 mg, 0.44 mmol), 2-nitro-4-(trifluoromethane)benzenesulfonyl chloride (150 mg, 0.53 mmol) and DMAP (cat.) gave the title compound (120 mg, 66%) after purification by column chromatography with DCM as the eluent.
MW: 411.36
HPLCMS (Method C): [m/z]: 412.50

N-(5-Methylquinolin-8-yl)-2-nitrobenzenesulfonamide (Intermediate 159)

In a similar fashion using route 14 general procedure 27, 5-methylquinolin-8-amine (Intermediate 44) (690 mg, 4.38 mmol) and 2-nitrobenzenesulfonyl chloride (1.15 g, 5.24 mmol) gave the title compound (820 mg, 57%). The structure was confirmed by $^1$H NMR.

N-(5-Methoxyquinolin-8-yl)-2-nitrobenzenesulfonamide (Intermediate 160)

In a similar fashion using route 14 general procedure 27, 6-methoxyquinolin-8-amine (Intermediate 67) (350 mg, 2.01 mmol) and 2-nitrobenzenesulfonyl chloride (533 mg, 2.41 mmol) gave the title compound (460 mg, 64%) after purification by column chromatography with DCM as the eluent.
MW: 359.36
HPLCMS (Method C): [m/z]: 360

N-(4-Chloro-quinolin-8-yl)-2-nitro-benzenesulfonamide (Intermediate 247)

In a similar fashion using route 14 general procedure 27, 4-chloro-quinolin-8-ylamine (Intermediate 464) (1.5 g, 8.43 mmol), 2-nitrobenzene-1-sulfonyl chloride (2.43 g, 11.0 mmol), DMAP (cat), pyridine (2 ml, 25.28 mmol) in DCM (70 ml) for 3 h at room temperature gave the title compound (2.3 g, 74%) after purification by column chromatography with DCM as the eluent.
MW: 363.78
HPLCMS: (Method C): [m/z]: 363.92

N-(5-Fluoro-quinolin-8-yl)-2-nitro-4-trifluoromethyl-benzenesulfonamide (Intermediate 248)

In a similar fashion using route 14 general procedure 27, 5-fluoro-quinolin-8-ylamine (Intermediate 50) (280 mg, 1.73 mmol), 2-nitro-4-trifluoromethylbenzenesulfonyl chloride (0.6 g, 2.07 mmol), DMAP (cat), pyridine (0.42 ml, 5.19 mmol) and DCM (5 ml) gave the title compound (420 mg, 59%) after purification by column chromatography with DCM/MeOH (98:2) as the eluent.
MW: 412.33
HPLCMS (Method C): [m/z]: 415.93

3-Nitro-4-(quinolin-8-ylsulfamoyl)-benzoic acid methyl ester (Intermediate 249)

In a similar fashion using route 14 general procedure 27, 8-aminoqunoline (0.60 g, 4.16 mmol), 4-chlorosulfonyl-3-nitro-benzoic acid methyl ester (Intermediate 438) (1.5 g, 5.41 mmol), DMAP (cat), pyridine (6 ml) and DCM (3 ml) gave the title compound (0.65 g, 40%) after purification by column chromatography with n-hexane/EtOAc (80:20) as the eluent.
MW: 387.0
HPLCMS (Method C): [m/z]: 388

4-Cyano-2-nitro-N-quinolin-8-yl-benzenesulfonamide (Intermediate 250)

In a similar fashion using route 14 general procedure 27, 8-aminoqunoline (0.60 g, 4.16 mmol), 4-cyano-2-nitro-benzenesulfonyl chloride (Intermediate 217) (1.33 g, 5.41 mmol), DMAP (cat), pyridine (5 ml) and DCM (3 ml) gave the title compound (0.65 g, 46%) after purification by column chromatography with n-hexane/EtOAc (90:10) as the eluent.
MW: 354.0
HPLCMS (Method C): [m/z]: 355

2-Nitro-N-(4-trifluoromethyl-quinolin-8-yl)-benzenesulfonamide (Intermediate 251)

In a similar fashion using route 14 general procedure 27, 4-trifluoromethyl-quinolin-8-ylamine (Intermediate 469) (350 mg, 1.65 mmol), 2-nitrobenzenesulfonyl chloride (474 mg, 12.1 mmol), DMAP (cat), pyridine (2 ml) and DCM (5 ml) gave the title compound (400 mg, 60%) after purification by column chromatography with n-hexane/EtOAc (80:20) as the eluent.
MW: 397.34
HPLCMS (Method C):[m/z]: 398

4-Chloro-2-nitro-N-(4-trifluoromethyl-quinolin-8-yl)-benzenesulfonamide (Intermediate 252)

In a similar fashion using route 14 general procedure 27, 4-trifluoromethyl-quinolin-8-ylamine (Intermediate 469) (325 mg, 1.53 mmol), 4-chloro-2-nitrobenzenesulfonylchloride (Intermediate 454) (507 mg, 1.99 mmol), DMAP (cat.), pyridine (0.5 ml), and DCM (5 ml) gave the title compound (400 mg, 60%) after purification by column chromatography with DCM as the eluent.
MW: 431.78
HPLCMS (Method C): [m/z]: 432

2-Nitro-N-(5-trifluoromethyl-quinolin-8-yl)-benzenesulfonamide (Intermediate 253)

In a similar fashion using route 14 general procedure 27, 5-trifluoromethyl-quinolin-8-ylamine (Intermediate 45) (260 mg, 1.2 mmol), 2-nitrobenzene-1-sulfonyl chloride (597 mg, 2.69 mmol), DMAP (cat) and pyridine (0.3 ml, 3.67 mmol) in DCM (5 ml) gave the title compound (275 mg, 56%) after purification by column chromatography with n-hexane/EtOAc (90:10) as the eluent.
MW: 397.0
HPLCMS (Method C): [m/z]: 398

4-Chloro-2-nitro-N-(5-trifluoromethyl-quinolin-8-yl)-benzenesulfonamide (Intermediate 254)

In a similar fashion using route 14 general procedure 27, 5-trifluoromethyl-quinolin-8-ylamine (Intermediate 45) (390 mg, 1.83 mmol), 4-chloro-2-nitrobenzene-1-sulfonyl chloride (Intermediate 454) (565 mg, 2.22 mmol), DMAP(cat) and pyridine (0.3 ml, 5.55 mmol) in DCM (7 ml) gave the title compound (370 mg, 46%) after purification by column chromatography with n-hexane/EtOAc (90:10) as the eluent.
MW: 431.0
HPLCMS (Method C): [m/z]: 431.9

N-(2-Chloro-quinolin-8-yl)-2-nitro-benzenesulfonamide (Intermediate 255)

In a similar fashion using route 14 general procedure 27, 2-nitrobenzene-1-sulfonyl chloride (800 mg, 3.65 mmol), 2-chloro-quinolin-8-ylamine (Intermediate 26), pyridine (0.67 ml, 0.8 mmol) and DMAP (cat.) in DCM (30 ml) gave the title compound (800 mg, 80%) after purification by column chromatography with DCM as the eluent.
MW: 363.78
HPLCMS: (Method C): [m/z]: 363.9

5-Chloro-N-(5-chloro-quinolin-8-yl)-4-fluoro-2-nitro-benzenesulfonamide (Intermediate 256)

In a similar fashion using route 14 general procedure 27, using 5-chloro-quinolin-8-ylamine (Intermediate 27) (750 mg, 4.2 mmol), 5-chloro-4-fluoro-2-nitro-benzenesulfonyl chloride (Intermediate 218) (1.5 g, 5.4 mmol), DMAP (cat), pyridine (8 ml) and DCM (15 ml) gave the title compound (210 mg, 12%) after purification by column chromatography with DCM as the eluent.
MW: 416
HPLCMS (Method C): [m/z]: 416.9

N-(5-Chloro-quinolin-8-yl)-4,5-difluoro-2-nitro-benzenesulfonamide (Intermediate 257)

In the similar fashion using route 14 general procedure 27, 5-chloro-quinolin-8-ylamine (Intermediate 27) (400 mg, 2.2 mmol), 4,5-difluoro-2-nitro-benzenesulfonyl chloride (Intermediate 219) (750 mg, 2.9 mmol), DMAP (cat.) and pyridine (5 ml) and DCM (5 ml) gave the title compound (125 mg, 14%) after purification by column chromatography with DCM as the eluent.
MW: 399.76
HPLCMS (Method C): [m/z]: 400.1

4-Chloro-N-(2-chloro-quinolin-8-yl)-2-nitro-benzenesulfonamide (Intermediate 258)

In a similar fashion using route 14 general procedure 27, 4-chloro-2-nitrobenzene-1-sulfonyl chloride (Intermediate 454) (0.86 g, 3.37 mmol), 2-chloro-quinolin-8-ylamine (Intermediate 26) (0.5 g, 2.80 mmol), DMAP (cat), pyridine (0.68 ml, 8.42 mmol) and DCM (10 ml) gave the title compound (0.25 g, 23%) after purification by column chromatography DCM/MeOH (99:1) as the eluent.

MW: 398.23
HPLCMS: (Method C): [m/z]: 398

3-Nitro-pyridine-2-sulfonic acid quinolin-8-ylamide (Intermediate 259)

In a similar fashion using route 14 general procedure 27, 8-aminoquinoline (1.3 g, 9.36 mmol), 3-nitro-pyridine-2-sulfonyl chloride 445 (2.7 g, 12.2 mmol), pyridine (2.25 ml, 28.1 mmol), DMAP (cat.) and DCM (100 ml) gave the title compound (1.3 g, 42%) after purification by column chromatography with DCM as the eluent.
MW: 330.32
LCMS: (Method C): [m/z]: 331.2

8-(2-Nitro-benzenesulfonylamino)-quinoline-4-carboxylic acid methyl ester (Intermediate 260)

In a similar fashion using route 14 general procedure 27, 8-amino-quinoline-4-carboxylic acid methyl ester (Intermediate 475) (370 mg, 1.38 mmol), 2-nitrobenzenesulfonyl chloride (530 mg, 2.3 mmol), DMAP (cat.), pyridine (0.44 ml, 5.4 mmol) and DCM (15 ml) gave the title compound (500 mg, 70%) after purification by column chromatography with DCM/MeOH (99:1) as the eluent.
MW: 387.37
HPLCMS (Method C): [m/z]: 388

N-Benzothiazol-4-yl-2-nitro-benzenesulfonamide (Intermediate 261)

In a similar fashion using route 14 general procedure 27, 2-nitrobenzenesulfonyl chloride (1.7 g, 7.9 mmol), benzothiazol-4-ylamine (Intermediate 222) (1.0 g, 6.6 mmol), DMAP (cat), pyridine (2 ml, 24.8 mmol) and DCM (10 ml) at 0° C. for 5 h, gave the title compound (1.0 g, 45%) which was used in the next step without further purification.
MW: 335.36
HPLCMS (Method C): [m/z]: 336

N-(5-Chloro-quinolin-8-yl)-4-methanesulfonyl-2-nitro-benzenesulfonamide (Intermediate 262)

In the similar fashion using route 14 general procedure 27, 5-chloro-quinolin-8-ylamine (Intermediate 27) (200 mg, 1.12 mmol), 4-methanesulfonyl-2-nitro-benzenesulfonyl chloride (Intermediate 439) (456 mg, 1.46 mmol), DMAP (cat.) and pyridine (5 ml) gave the title compound (350 mg, 60%) after purification by column chromatography with DCM/MeOH (99:1) as the eluent.
MW: 441.87
HPLCMS: (Method E): [m/z]: 442

4-Chloro-2-nitro-N-quinolin-8-yl-benzenesulfonamide (Intermediate 263)

In a similar fashion using route 18 general procedure 27, 8-aminoquinoline (420 mg, 2.91 mmol), 4-chloro-2-nitro-benzenesulfonyl chloride (Intermediate 454) (1.1 g, 4.37 mmol), pyridine (1.5 ml), DMAP (cat.) and DCM (10 ml) gave the title compound (280 mg, 16%) after purification by column chromatography with n-hexane/EtOAc (90:10) elution.
MW: 363.78
HPLCMS: (Method C):[m/z]: 364

5-Methoxy-2-nitro-N-quinolin-8-yl-benzenesulfonamide (Intermediate 264)

In a similar fashion using route 14 general procedure 27, 8-aminoquinoline (950 mg, 6.59 mmol), 5-methoxy-2-nitro-benzenesulfonyl chloride (Intermediate 447) (2.15 g, 8.57 mmol), pyridine (4 ml), DMAP (cat.) and DCM (8 ml) gave the title compound (690 mg, 30%) after purification by column chromatography with n-hexane/EtOAc (80:20) as the eluent.
MW: 359.36
HPLCMS (Method C): [m/z]: 359.90

4-Methyl-2-nitro-N-quinolin-8-yl-benzenesulfonamide (Intermediate 265)

In a similar fashion using route 14 general procedure 27, 8-aminoquinoline (1.4 g, 9.72 mmol), 4-methyl-2-nitro-benzenesulfonyl chloride (Intermediate 448) (2.97 g, 12.6 mmol), pyridine (7 ml) DMAP (cat.) and DCM (30 ml) gave the title compound (1.5 g, 45%), after purification by column chromatography with n-hexane/EtOAc (90:10) as the eluent.
MW: 343.36
HPLCMS (Method C): [m/z]: 344

5-Methyl-2-nitro-N-quinolin-8-yl-benzenesulfonamide (Intermediate 266)

In a similar fashion using route 14 general procedure 27, 8-aminoquinoline (0.350 g, 2.4 mmol), 5-methyl-2-nitro-benzenesulfonyl chloride (Intermediate 449) (0.86 g, 3.6 mmol), pyridine (1 ml) DMAP (cat) and DCM (5 ml) gave the title compound (100 mg, 12%) after purification by column chromatography with n-hexane/EtOAc (10:90) as the eluent. The structure was confirmed by 1H NMR.

5-Fluoro-2-nitro-N-quinolin-8-yl-benzenesulfonamide (Intermediate 267)

In a similar fashion using route 18 general procedure 27, 8-aminoquinoline (1.6 g, 11.1 mmol), 5-fluoro-2-nitro-benzenesulfonyl chloride (Intermediate 450) (3.4 g, 14.4 mmol), pyridine (4.48 ml, 55.5 mmol), DMAP (cat.) and DCM (6 ml) gave the title compound (0.95 g, 25%) after purification by column chromatography with n-hexane/DCM (50:50) as the eluent. The structure was confirmed by 1H NMR.

2-Methyl-6-nitro-N-quinolin-8-yl-benzenesulfonamide (Intermediate 268)

In a similar fashion using route 14 general procedure 27, 8-aminoqunoline (1.6 g, 11.1 mmol), 2-methyl-6-nitro-benzenesulfonyl chloride (Intermediate 451) (3.5 g, 14.4 mmol), pyridine (10 ml), DMAP (cat.) and DCM (5 ml) gave the title compound (1.5 g, 39%) after purification by column chromatography with n-hexane/EtOAc (85:15) as the eluent.
MW: 343.36
HPLCMS (Method C): [m/z]: 344

4-Fluoro-5-methyl-2-nitro-N-quinolin-8-yl-benzenesulfonamide (Intermediate 269)

In a similar fashion using route 14 general procedure 27, 4-fluoro-5-methyl-2-nitro-benzenesulfonyl chloride (Intermediate 452) (1.6 g, 6.3 mmol), 8-aminoquinoline (700 mg, 4.86 mmol), DMAP (cat.), pyridine (5 ml) and DCM (5 ml)

gave the title compound (520 mg, 52%) after purification by column chromatography with DCM/MeOH (99:1) as the eluent.
MW: 361.35
HPLCMS (Method C): [m/z]: 362

2-Nitro-N-quinolin-8-yl-5-trifluoromethyl-benzenesulfonamide (Intermediate 270)

In a similar fashion using route 14 general procedure 27, 8-aminoqunoline (550 mg, 3.8 mmol), 2-nitro-5-trifluoromethyl-benzenesulfonyl chloride (Intermediate 453) (1.43 g, 4.9 mmol), DMAP (cat.), pyridine (4 ml) and DCM (5 ml) gave the title compound (490 mg, 32%) after purification by column chromatography with n-hexane/EtOAc (90:10) as the eluent.
MW: 397.34
HPLCMS (Method C): [m/z]: 398.34

2-Nitro-N-quinolin-8-yl-4-trifluoromethoxy-benzenesulfonamide (Intermediate 271)

In a similar fashion using route 14 general procedure 27, 8-aminoqunoline (500 mg, 3.47 mmol), 2-nitro-4-trifluoromethoxy-benzenesulfonyl chloride (Intermediate 221) (1.4 g, 4.51 mmol), pyridine (5 ml), DMAP (cat.) and DCM (3 ml) gave the title compound (500 mg, 35%) after purification by column chromatography with n-hexane/EtOAc (90:10) as the eluent.
MW: 413.33
HPLCMS (Method C):[m/z]: 414

N-(5-Chloro-quinolin-8-yl)-2-nitro-4-trifluoromethyl-benzenesulfonamide (Intermediate 272)

In a similar fashion using route 14 general procedure 27, 2-nitro-4-trifluoromethylbenzenesulfonyl chloride (Intermediate 461) (1.24 g, 4.29 mmol), 5-chloro-quinolin-8-ylamine (Intermediate 27) (0.64 g, 3.58 mmol), DMAP (cat.), pyridine (0.86 ml, 10.7 mmol) and DCM (5 ml) gave the title compound (700 mg, 45%) after purification by column chromatography with DCM as the eluent.
MW: 431.78
HPLCMS: (Method C):[m/z]: 432.9

4-Chloro-N-(5-cyano-quinolin-8-yl)-2-nitro-benzenesulfonamide (Intermediate 273)

In a similar fashion using route 14 general procedure 58, 8-aminoquinoline-5-carbonitrile (Intermediate 472) (100 mg, 0.5 mmol), 4-chloro-2-nitrobenzenesulfonyl chloride (Intermediate 454) (166 mg, 0.65 mmol), NaH (60% dispersion in mineral oil, 26 mg, 0.65 mmol) and THF (2 ml) gave the title compound (60 mg, 26%) after purification by column chromatography with n-hexane/DCM (50:50) as the eluent.
MW: 388.79
HPLCMS: (Method C): [m/z]: 389.30

General procedure 29:
2-Amino-N-quinolin-8-yl-benzenesulfonamide (Example Compound 8)

Tin (II) chloride dihydrate (4.11 g, 18.2 mmol) was added to a solution of 2-nitro-N-quinolin-8-yl-benzenesulfonamide (Example Compound 6) (2.0 g, 6.07 mmol) in EtOH (50 ml) and the mixture was heated under reflux for 2 h. After cooling, the mixture was concentrated in vacuo. The crude residue was dissolved in EtOAc (40 ml) and cooled in an ice bath, the mixture was basified with aqueous ammonia. The resulting white precipitate was collected by filtration, washed with EtOAc and discarded. The organic combined organic filtrates were washed with brine, dried ($Na_2SO_4$) and concentrated in vacuo to give the title compound (1.82 g, 53%).
EOAI3334101 VIT-1250
MW: 299.35
HPLCMS (Method A): [m/z]: 299.95
The result is shown in FIG. 8

2-Amino-4-fluoro-N-quinolin-8-yl-benzenesulfonamide (Example Compound 31)

In a similar fashion using route 15 general procedure 29, 4-fluoro-2-nitro-N-quinolin-8-yl-benzenesulfonamide (Example Compound 30) (1.1 g, 3.17 mmol) and tin (II) chloride dihydrate (4.29 g, 19 mmol) gave the title compound (900 mg, 90%).
EOAI3335058 VIT-1335
MW: 317.34
HPLCMS (Method A): [m/z]: 317.95
The result is shown in FIG. 31

2-Amino-N-quinolin-8-yl-4-trifluoromethyl-benzenesulfonamide (Example Compound 35)

In a similar fashion using route 15 general procedure 29, 2-nitro-N-quinolin-8-yl-4-trifluoromethyl-benzenesulfonamide (Example Compound 32) (1.22 g, 3.07 mmol) and tin (II) chloride dihydrate (3.46 g, 15.4 mmol) gave the title compound (797 mg, 71%).
EOAI3335138 VIT-1345
MW: 367.35
HPLCMS (Method A): [m/z]: 368
The result is shown in FIG. 35

2-Amino-4,5-dimethyl-N-quinolin-8-yl-benzenesulfonamide (Intermediate 164)

In a similar fashion using route 15 general procedure 29, 4,5-dimethyl-2-nitro-N-quinolin-8-yl-benzenesulfonamide (Intermediate 147) (0.52 g, 1.45 mmol) and tin (II) chloride dihydrate (1.37 g, 7.26 mmol) gave the title compound (0.31 g, 66%).
MW: 327.4
HPLCMS (Method B): [m/z]: 328

2-Amino-4-methoxy-N-quinolin-8-yl-benzenesulfonamide (Example Compound 13)

In the similar fashion using route 1 general procedure 4, 4-methoxy-2-nitro-N-quinolin-8-yl-benzenesulfonamide (Example Compound 34) (600 mg, 1.6 mmol), tin (II) chloride (950 mg, 5.0 mmol) and 6N HCl (2 drops) gave the title compound (300 mg, 54%).
EOAI3334330 VIT-1259
MW: 329.37
HPLCMS (Method A): [m/z]: 330
The result is shown in FIG. 13

2-Amino-N-(2-methyl-quinolin-8-yl)-benzenesulfonamide (Example Compound 15)

In a similar fashion using route 15 general procedure 29, N-(2-methyl-quinolin-8-yl)-2-nitro-benzenesulfonamide (Intermediate 149) (423 mg, 1.23 mmol) and tin (II) chloride dihydrate (701 mg, 3.70 mmol) gave the title compound (182 mg, 47%) after purification by column chromatography with DCM/MeOH (99:1-95:5) gradient elution.
EOAI3334315 VIT-1264
MW: 313.37
HPLCMS (Method A): [m/z]: 313.90
The result is shown in FIG. 15

2-Amino-N-(5-chloro-quinolin-8-yl)-4-methanesulfonyl-benzenesulfonamide (Intermediate 274)

In the similar fashion using route 15 general procedure 29, N-(5-chloro-quinolin-8-yl)-4-methanesulfonyl-2-nitro-benzenesulfonamide (Intermediate 262 (350 mg, 0.79 mmol), $SnCl_2$ (399 mg, 4.76 mmol) and EtOH (12 ml) gave the title compound (205 mg, 63%) after trituration from DCM: pentane
MW: 411.89
HPLCMS: (Method C): [m/z]: 412

2-Amino-4-methoxy-N-(2-methyl-quinolin-8-yl)-benzenesulfonamide (Example Compound 12)

In the similar fashion using route 1 general procedure 4, 2-nitro-4-methoxy-N-(2-methyl-quinolin-8-yl)-benzenesulfonamide (Intermediate 150) (550 mg, 1.4 mmol), tin (II) chloride (838 mg, 4.4 mmol) and 6N HCl (2 drops) gave the title compound (350 mg, 70%).
EOAI3334329 VIT-1258
MW: 343.40
HPLCMS (Method A): [m/z]: 344
The result is shown in FIG. 12

2-Amino-4-methyl-N-quinolin-8-yl-benzenesulfonamide (Example Compound 14)

In the similar fashion using route 1 general procedure 4, 4-methyl-2-nitro-N-quinolin-8-yl-benzenesulfonamide (Intermediate 151) (3.2 g, 9.3 mmol), tin (II) chloride (5.3 g, 2.79 mmol) and 6N HCl (2 ml) gave the title compound (500 mg, 17%).
EOAI3334331 VIT-1260
MW: 313.37
HPLCMS (Method A): [m/z]: 313.95
The result is shown in FIG. 14

2-Amino-N-(6-methoxyquinolin-8-yl)-benzenesulfonamide (Intermediate 169)

In a similar fashion using route 1 general procedure 4, N-(6-methoxyquinolin-8-yl)-2-nitrobenzenesulfonamide (Intermediate 152) (460 mg, 1.17 mmol), tin (II) chloride (886 mg, 4.68 mmol) and 6 N HCl (3 drops) gave the title compound (260 mg, 68%). The structure was confirmed by $^1$H NMR.

2-Amino-N-(4-chloro-quinolin-8-yl)-benzenesulfonamide (Intermediate 275)

In a similar fashion using route 1 general procedure 4, N-(4-chloro-quinolin-8-yl)-2-nitro-benzenesulfonamide (Intermediate 246) (2.3 g, 6.32 mmol), $SnCl_2$ (5.99 g, 31.6 mmol) and 6N HCl (cat.) in EtOH (30 ml) at 90° C. for 22 h gave the title compound (1.35 g, 64%) which was used in the next step without further purification.
MW: 333.80
HPLCMS (Method C): [m/z]: 335.1

2-Amino-N-(5-fluoro-quinolin-8-yl)-4-trifluoromethyl-benzenesulfonamide (Intermediate 276)

In a similar fashion using route 1 general procedure 4, N-(5-fluoro-quinolin-8-yl)-2-nitro-4-trifluoromethyl-benzenesulfonamide (Intermediate 248) (0.42 g, 1.01 mmol), $SnCl_2$ (0.96 g, 5.06 mmol), 6N HCl (cat.) and EtOH (6 ml) at 85° C. for 24 h gave the title compound (200 mg, 52%).
MW: 385.34
HPLCMS (Method C): [m/z]: 385.98

3-Amino-4-(quinolin-8-ylsulfamoyl)-benzoic acid methyl ester (Intermediate 277)

In a similar fashion using route 1 general procedure 4, 3-nitro-4-(quinolin-8-ylsulfamoyl)-benzoic acid methyl ester (Intermediate 249) (0.65 g, 1.67 mmol), $SnCl_2$ (1.6 g, 8.3 mmol), 4-5 drops of conc. HCl and EtOH (15 ml) at 85° C. for 5 h gave the title compound (0.53 g, 88%).
MW: 357.0
HPLCMS (Method C): [m/z]: 358

2-Amino-4-cyano-N-quinolin-8-yl-benzenesulfonamide (Intermediate 278)

In a similar fashion using route 1 general procedure 4, 4-cyano-2-nitro-N-quinolin-8-yl-benzenesulfonamide (Intermediate 250) (0.63 g, 1.77 mmol), $SnCl_2$ (2.0 g, 10.6 mmol), conc.HCl (5 drops) and EtOH (15 ml) gave the title compound (0.36 g, 61%) which was used in the next step without further purification.
MW: 324.36
HPLCMS (Method C):[m/z]: 325

2-Amino-N-(4-trifluoromethyl-quinolin-8-yl)-benzenesulfonamide (Intermediate 279)

In a similar fashion using route 1 general procedure 4, 2-nitro-N-(4-trifluoromethyl-quinolin-8-yl)-benzenesulfonamide (Intermediate 251) (0.4 g, 1.0 mmol), $SnCl_2$ (0.76 g, 4.03 mmol), 6N HCl (2 drops) and EtOH (15 ml) gave the title compound (300 mg, 81%) which was used in the next step without further purification.
MW: 367.35
HPLCMS (Method C): [m/z]: 368

2-Amino-4-chloro-N-(4-trifluoromethyl-quinolin-8-yl)-benzenesulfonamide (Intermediate 280)

In a similar fashion using route 1 general procedure 4, 4-chloro-2-nitro-N-(4-trifluoromethyl-quinolin-8-yl)-benzenesulfonamide (Intermediate 252) (365 mg, 0.84 mmol), $SnCl_2$ (637 mg, 3.37 mmol), 6N HCl (2 drops) and EtOH (15 ml) gave the title compound (340 mg, 100%).
MW: 401.80
HPLCMS (Method C): [m/z]: 401.9

2-Amino-N-(5-trifluoromethyl-quinolin-8-yl)-benzenesulfonamide (Intermediate 281)

In a similar fashion using route 1 general procedure 4, 2-nitro-N-(5-trifluoromethyl-quinolin-8-yl)-benzenesulfonamide (Intermediate 253) (275 mg, 0.69 mmol), $SnCl_2$ (526 mg, 3.46 mmol), conc.HCl (5 drops) and EtOH (10 ml) gave the title compound (230 mg, 90%) which was used in the next step without further purification.
MW: 367.0
HPLCMS: (Method C): [m/z]:368

2-Amino-4-chloro-N-(5-trifluoromethyl-quinolin-8-yl)-benzenesulfonamide (Intermediate 282)

In a similar fashion using route 1 general procedure 4, 4-chloro-2-nitro-N-(5-trifluoromethyl-quinolin-8-yl)-benzenesulfonamide (Intermediate 254) (370 mg, 0.86 mmol), $SnCl_2$ (967 mg, 5.15 mmol), conc.HCl (4-5 drops) and EtOH (15 ml) gave the title compound (340 mg, 98%) which was used in the next step without further purification.
MW: 401.0
HPLCMS (Method C): [m/z]: 411

2-Amino-N-(2-chloro-quinolin-8-yl)-benzenesulfonamide (Intermediate 283)

In a similar fashion using route 1 general procedure 4, N-(2-chloro-quinolin-8-yl)-2-nitro-benzenesulfonamide (Intermediate 255) (0.80 g, 2.2 mmol), $SnCl_2$ (1.7 g, 8.8 mmol), 6N HCl (2 drops) and EtOH (15 ml) gave the title compound (0.59 g, 80%) which was used in the next steps without further purification.
MW: 333.80
HPLCMS (Method C): [m/z]: 334

2-Amino-5-chloro-N-(5-chloro-quinolin-8-yl)-4-fluoro-benzenesulfonamide (Intermediate 284)

In a similar fashion using route 1 general procedure 4, 5-chloro-N-(5-chloro-quinolin-8-yl)-4-fluoro-2-nitro-benzenesulfonamide (Intermediate 285) (210 mg, 5.0 mmol), $SnCl_2$ (382 mg, 2.0 mmol), 6N HCl (4 drops) and EtOH (5 ml) for 30 h at 90° C. gave the title compound (150 mg, 77%) after purification by column chromatography with DCM as the eluent.
MW: 386.23
HPLCMS (Method C): [m/z]: 387

2-Amino-N-(5-chloro-quinolin-8-yl)-4,5-difluoro-benzenesulfonamide (Intermediate 285)

In a similar fashion using route 1 general procedure 4, N-(5-chloro-quinolin-8-yl)-4,5-difluoro-2-nitro-benzenesulfonamide (Intermediate 257) (125 mg, 0.31 mmol), $SnCl_2$ (238 mg, 1.25 mmol), 6N HCl (3 drops) and EtOH (3 ml) for 3.5 h at 85° C. gave the title compound (95 mg, 72%) which was used in the next step without further purification.
MW: 369.78
HPLCMS (Method C): [m/z]: 370

2-Amino-4-chloro-N-(5-cyano-quinolin-8-yl)-benzenesulfonamide (Intermediate 286)

In a similar fashion using route 1 general procedure 4, 4-chloro-N-(5-cyano-quinolin-8-yl)-2-nitro-benzenesulfonamide (Intermediate 273) (90 mg, 0.2 mmol), $SnCl_2$ (28 mg, 1.3 mmol), 6N HCl (cat) and EtOH (6 ml) at 85° C. for 3 h gave the title compound (100 mg) which was used in the next step without further purification.
MW: 358.81
HPLCMS: (Method C): [m/z]: 359.30

2-Amino-4-chloro-N-(2-chloro-quinolin-8-yl)-benzenesulfonamide (Intermediate 287)

In a similar fashion using route 1 general procedure 4, 4-chloro-N-(2-chloro-quinolin-8-yl)-2-nitro-benzenesulfonamide (Intermediate 258) (0.36 g, 0.63 mmol), $SnCl_2$ (0.36 g, 1.88 mmol) and EtOH (10 ml) at 90° C. for 4 h gave the title compound (0.11 g, 46%) after purification by column chromatography with DCM/MeOH (99.5:0.5) as the eluent.
MW: 368.24
LCMS: (Method C): [m/z]: 369

8-(2-Amino-benzenesulfonylamino)-quinoline-4-carboxylic acid methyl ester (Intermediate 288)

In a similar fashion using route 1 general procedure 4, 8-(2-nitro-benzenesulfonylamino)-quinoline-4-carboxylic acid methyl ester (Intermediate 260) (0.62 g, 1.6 mmol), $SnCl_2$ (1.3 g, 6.4 mmol), 6N HCl (2 drops) and MeOH (15 ml) at 80° C. for 48 h gave the title compound (270 mg, 50%) which was used in the next step without further purification.
MW: 357.39
HPLCMS (Method C): [m/z]: 358

2-Amino-N-benzothiazol-4-yl-benzenesulfonamide (Intermediate 289)

In a similar fashion using route 1 general procedure 4, of N-benzothiazol-4-yl-2-nitro-benzenesulfonamide (Intermediate 261) (375 mg, 1.1 mmol), $SnCl_2$ (847 mg, 4.5 mmol), 6N HCl (1.3 ml) and EtOH (4 ml) gave the title compound (240 mg, 70.4%) which was used in the next step without further purification.
MW: 305.38
HPLCMS: (Method C): [m/z]: 306.2

2-Amino-N-(6-fluoro-quinolin-8-yl)-benzenesulfonamide (Intermediate 290)

In a similar fashion using route 1 general procedure 4, N-(6-fluoro-quinolin-8-yl)-2-nitro-benzenesulfonamide (Intermediate 244) (520 mg, 1.49 mmol), $SnCl_2$ (983 mg, 5.99 mmol), 6N HCl (3 drops) and EtOH (10 ml) for 4 h at 80° C. gave the title compound (410 mg, 86%) which was used in the next step without further purification. The structure was confirmed by 1H NMR.

2-Amino-N-(5-fluoro-quinolin-8-yl)-benzenesulfonamide (Intermediate 291)

In a similar fashion using route 1 general procedure 4, N-(5-Fluoro-quinolin-8-yl)-2-nitro-benzenesulfonamide (Intermediate 245) (470 mg, 1.35 mmol), $SnCl_2$ (770 mg, 4.06 mmol), 6N HCl (6 drops) and EtOH (10 ml) for 6 h at 85° C. gave the title compound (350 mg, 82%) which was used in the next step without further purification.
MW: 317.34
HPLCMS (Method C): [m/z]: 318

2-Amino-4-chloro-N-quinolin-8-yl-benzenesulfonamide (Intermediate 292)

In a similar fashion using route 1 general procedure 4, 4-chloro-2-nitro-N-quinolin-8-yl-benzenesulfonamide (Intermediate 263) (280 mg, 0.77 mmol), $SnCl_2$ (383 mg, 3.08 mmol), 6N HCl (2 drops) and EtOH (4 ml) for 6 h at 85° C. gave the title compound (152 mg, 59%) after purification by column chromatography with DCM/MeOH (97:3) as the eluent.
MW: 333.80
HPLCMS (Method C):[m/z]: 334

2-Amino-5-methoxy-N-quinolin-8-yl-benzenesulfonamide (Intermediate 293)

In a similar fashion using route 1 general procedure 4, 5-methoxy-2-nitro-N-quinolin-8-yl-benzenesulfonamide (Intermediate 264) (690 mg, 1.9 mmol), $SnCl_2$ (1.45 g, 7.68 mmol), 6N HCl (2 drops) and EtOH (12 ml) at 85° C. for 6 h gave the title compound (450 mg, 71%) which was used in the next step without further purification.
MW: 329.38
HPLCMS (Method C): [m/z]: 330

2-Amino-4-methyl-N-quinolin-8-yl-benzenesulfonamide (Intermediate 294)

In a similar fashion using route 1 general procedure 4, 4-methyl-2-nitro-N-quinolin-8-yl-benzenesulfonamide (Intermediate 265) (1.3 g, 3.79 mmol), $SnCl_2$ (2.87 g, 15.1 mmol), 6N HCl (2 drops) and EtOH (10 ml) at 85° C. for 6 h gave the title compound (540 mg, 45%) which was used in the next step without further purification.
MW: 313.38
HPLCMS (Method C): [m/z]: 314

2-Amino-N-(5-chloro-quinolin-8-yl)-benzenesulfonamide (Intermediate 295)

In a similar fashion using route 1 general procedure 4, N-(5-chloro-quinolin-8-yl)-2-nitro-benzenesulfonamide (Intermediate 246) (600 mg, 1.64 mmol), $SnCl_2$ (940 mg, 4.94 mmol), 6N HCl (5-6 drops) and EtOH (12 ml) at 80° C. for 3 h, gave the title compound (375 mg, 55%) which was used in the next step without further purification.
MW: 333.79
HPLCMS (Method C): [m/z]: 334

2-Amino-5-methyl-N-quinolin-8-yl-benzenesulfonamide (Intermediate 296)

In a similar fashion using route 1 general procedure 4, 5-methyl-2-nitro-N-quinolin-8-yl-benzenesulfonamide (Intermediate 266) (350 mg, 1.02 mmol), $SnCl_2$ (773 mg, 4.08 mmol), 6N HCl (5 drops) and EtOH (5 ml), at 80° C. for 2 h gave the title compound (160 mg, 50%) after purification by column chromatography with n-hexane/EtOAc (98:2) as the eluent.
MW: 313.37
HPLCMS (Method C): [m/z]: 314

2-Amino-5-fluoro-N-quinolin-8-yl-benzenesulfonamide (Intermediate 297)

In a similar fashion using route 1 general procedure 4, 5-fluoro-2-nitro-N-quinolin-8-yl-benzenesulfonamide (Intermediate 267) (0.60 g, 1.72 mmol), $SnCl_2$ (1.31 g, 6.91 mmol), 6N HCl (6 drops) and EtOH (7 ml) gave the title compound (610 mg) which was used in the next step without further purification.
MW: 317.33
HPLCMS (Method C): [m/z]:318

2-Amino-6-methyl-N-quinolin-8-yl-benzenesulfonamide (Intermediate 298)

In a similar fashion using route 1 general procedure 4, 2-methyl-6-nitro-N-quinolin-8-yl-benzenesulfonamide (Intermediate 268) (1.5 g, 4.3 mmol), $SnCl_2$ (3.3 g, 17.5 mmol), 6N HCl (5 drops) and EtOH (15 ml) gave the title compound (530 mg, 38%), after purification by column chromatography with DCM/MeOH (99:1) as the eluent.
MW: 313.18
HPLCMS (Method C): [m/z]: 314.18

2-Amino-4-fluoro-5-methyl-N-quinolin-8-yl-benzenesulfonamide (Intermediate 299)

In a similar fashion using route 1 general procedure 4, 4-fluoro-5-methyl-2-nitro-N-quinolin-8-yl-benzenesulfonamide (Intermediate 269) (520 mg, 1.44 mmol), $SnCl_2$ (1.08 g, 5.76 mmol), 6N HCl (2 drops) and EtOH (5 ml) gave the title compound after purification by column chromatography with DCM/MeOH (98:2) (340 mg, 71%).
MW: 331.37
HPLCMS (Method C): [m/z]: 332.10

2-Amino-N-quinolin-8-yl-5-trifluoromethyl-benzenesulfonamide (Intermediate 300)

In a similar fashion using route 1 general procedure 4, 2-nitro-N-quinolin-8-yl-5-trifluoromethyl-benzenesulfonamide (Intermediate 270) (490 mg, 1.2 mmol), $SnCl_2$ (936 mg, 4.93 mmol), 6N HCl (5 drops) and EtOH (10 ml) gave the title compound (330 mg, 73%) which was used in the next step without further purification.
MW: 367.35
HPLCMS (Method C): [m/z]: 368.35

2-Amino-N-quinolin-8-yl-4-trifluoromethoxy-benzenesulfonamide (Intermediate 301)

In a similar fashion using route 1 general procedure 4, 2-nitro-N-quinolin-8-yl-4-trifluoromethoxy-benzenesulfonamide (Intermediate 271) (500 mg, 1.21 mmol), $SnCl_2$ (918 mg, 4.84 mmol), 6N HCl (5 drops) and EtOH (10 ml) gave the title compound (350 mg, 75%) which was used in the next step without further purification.
MW: 383.35
HPLCMS (Method C): [m/z]: 384

2-Amino-N-(5-chloro-quinolin-8-yl)-4-trifluoromethyl-benzenesulfonamide (Intermediate 302)

In a similar fashion using route 1 general procedure 4, N-(5-chloro-quinolin-8-yl)-2-nitro-4-trifluoromethyl-benzenesulfonamide (Intermediate 272) (0.7 g, 1.62 mmol), $SnCl_2$ (0.92 g, 4.86 mmol) and EtOH (15 ml) gave the title compound (0.6 g, 92%) which was used in the next step without further purification.
MW: 401.79
HPLCMS (Method C):[m/z]: 403.2

2-Amino-N-(6-methoxy-quinolin-8-yl)-4-methyl-benzenesulfonamide (Example Compound 80)

In a similar fashion using route 6 general procedure 14, N-(6-methoxyquinolin-8-yl)-4-methyl-2-nitro-benzenesulfonamide (Intermediate 153) (150 mg, 0.40 mmol), Raney nickel (30 mg, 20% wt) and hydrazine hydrate (64 mg, 1.21 mmol) gave title compound (60 mg, 44%) after purification by column chromatography with DCM as the eluent.
EOAI3336894 VIT-1496
MW: 343.4
HPLCMS (Method A): [m/z]: 344
The result is shown in FIG. 80

2-Amino-N-(6-methoxyquinolin-8-yl)-4-trifluoromethyl-benzenesulfonamide (Example Compound 65)

In a similar fashion using route 6 general procedure 14, N-(6-methoxyquinolin-8-yl)-2-nitro-4-(trifluoromethyl) benzenesulfonamide (Intermediate 154) (200 mg, 0.47 mmol), Raney nickel (40 mg, 20% wt), hydrazine hydrate (70 µl, 1.41 mmol) gave the title compound (110 mg, 59%) after purification by column chromatography with DCM as the eluent.
EOAI3335956 VIT-1431
MW: 397.37
HPLCMS (Method A): [m/z]: 398
The result is shown in FIG. 65

2-Amino-N-(5-chloroquinolin-8-yl)-4-methyl-benzenesulfonamide (Example Compound 79)

In a similar fashion using route 6 general procedure 14, N-(5-chloroquinolin-8-yl)-4-methyl-2-nitrobenzenesulfonamide (Intermediate 155) (160 mg, 0.42 mmol), Raney nickel (32 mg, 20% wt), hydrazine hydrate (63 mg, 1.27 mmol) and MeOH (10 ml) gave the title compound (40 mg, 27%) after purification by column chromatography with DCM as the eluent followed by recrystallisation from DCM/n-pentane.
EOAI3336893 VIT-1495
MW: 347.82
HPLCMS (Method A): [m/z]: 348
The result is shown in FIG. 79

2-Amino-N-(5-chloroquinolin-8-yl)-4-trifluoromethyl-benzenesulfonamide (Example Compound 53)

In the similar fashion using route 6 general procedure 14, N-(5-chloroquinolin-8-yl)-2-nitro-4-trifluoromethylbenzenesulfonamide (Intermediate 156) (120 mg, 0.28 mmol), Raney nickel (24 mg, 20% wt), hydrazine hydrate (40 µl, 0.84 mmol), MeOH (3 ml) gave the title compound (30 mg, 27%) after purification by column chromatography with DCM/MeOH (199:1) as the eluent.
EOAI3335669 VIT-1403
MW: 401.79
HPLCMS (Method A): [m/z]: 401.9
The result is shown in FIG. 53

2-Amino-4-methyl-N-(3-methylquinolin-8-yl)-benzenesulfonamide (Example Compound 81)

In a similar fashion using route 6 general procedure 14, 4-methyl-N-(3-methylquinolin-8-yl)-2-nitrobenzenesulfonamide (Intermediate 157) (100 mg, 0.28 mmol), Raney nickel (20 mg, 20% wt), hydrazine hydrate (42 mg, 0.84 mmol) and MeOH/THF (4:1, 5 ml) gave the title compound (20 mg, 22%) after purification by column chromatography with n-hexane/EtOAc (1:0-4:1) gradient elution.
EOAI3336895 VIT-1497
MW: 327.40
HPLCMS (Method A): [m/z]: 328
The result is shown in FIG. 81

2-Amino-N-(3-methylquinolin-8-yl)-4-trifluoromethyl-benzenesulfonamide (Example Compound 73)

In a similar fashion using route 6 general procedure 14, N-(3-Methylquinolin-8-yl)-2-nitro-4-trifluoromethylbenzenesulfonamide (Intermediate 158) (60 mg, 0.14 mmol), Raney nickel (10 mg, 20% wt) and hydrazine hydrate (20 mg, 0.43 mmol) gave the title compound (12 mg, 22%) after purification by column chromatography with DCM as the eluent.
EOAI3336493 VIT-1472
MW: 381.37
HPLCMS (Method A): [m/z]: 382
The result is shown in FIG. 73

2-Amino-N-(5-methylquinolin-8-yl)-benzenesulfonamide (Intermediate 176)

In a similar fashion using route 1 general procedure 4, N-(5-methylquinolin-8-yl)-2-nitrobenzenesulfonamide (Intermediate 159) (830 mg, 2.42 mmol), tin (II) chloride (1.83 g, 9.68 mmol) and 6 N HCl (3 drops) gave the title compound (430 mg, 58%).
MW: 313.38
HPLCMS (Method C): [m/z]: 314

2-Amino-N-(5-methoxyquinolin-8-yl)-benzenesulfonamide (Intermediate 177)

In a similar fashion using route 1 general procedure 4, N-(6-methoxyquinolin-8-yl)-2-nitrobenzenesulfonamide (Intermediate 160) (460 mg, 1.17 mmol), tin (II) chloride (1.55 mg, 8.15 mmol) and 6N HCl (3 drops) gave the title compound (260 mg, 68%). The structure was confirmed by $^1$H NMR.

General Procedure 59: 3-Amino-pyridine-2-sulfonic acid quinolin-8-ylamide (Intermediate 303)

Sat. NH$_4$Cl (0.49 g, 9.09 mmol) was added to a solution of 3-nitro-pyridine-2-sulfonic acid quinolin-8-ylamide (Intermediate 259) (0.3 g, 0.91 mmol) in MeOH:THF(10 ml, 1:1) followed by zinc powder (0.48 g, 7.27 mmol) and the mixture was stirred at room temperature for 18 h. The mixture was filtered through celite and washed with THF. The filtrate was concentrated in vacuo and the residue was diluted with EtOAc. The organic phase was dried (Na$_2$SO$_4$) and concentrated in vacuo. The crude residue was purified by column chromatography with DCM/MeOH as the eluent to give the title compound (0.26 g, 95%)
MW: 300.34
HPLCMS: (Method C): [m/z]: 301.10

General Procedure 60: 2-Amino-N-quinoxalin-5-yl-benzenesulfonamide (Intermediate 304)

Iron powder (455 mg, 8.14 mmol) was added to a solution of 2-nitro-N-quinoxalin-5-yl-benzenesulfonamide (Intermediate 243) (673 mg, 2.08 mmol) in AcOH (15 ml) and the mixture was heated at 80° C. for 2 h. After cooling, the mixture was concentrated in vacuo. The residue was diluted with EtOAc and the mixture was filtered through celite. The filtrate was washed with sat. NaHCO$_3$ solution, dried (Na2SO4) and concentrated in vacuo to give the title compound (440 mg, 72%) which was used in the next step without further purification.
MW: 300.34
HPLCMS: (Method C): [m/z]: 301

General Procedure 30: N-[2-(Quinolin-8-ylsulfamoyl)-phenyl]-isobutyramide (Example Compound 48)

Isobutyryl chloride (42 mg, 0.40 mmol) and DIPEA (100 mg, 0.83 mmol) were added to a solution of 2-amino-N- quinolin-8-yl-benzenesulfonamide (Example Compound 8) (100 mg, 0.33 mmol) in THF (3 ml) at 0° C. The reaction was stirred at room temperature for 1 h. The reaction was quenched water and extracted with DCM. The organic phase was dried (Na$_2$SO$_4$) and concentrated in vacuo. The crude residue was purified by column chromatography with DCM/MeOH (49:1) as the eluent to give the title compound (43 mg, 36%).
EOAI3335390 VIT-1381
MW: 369.44
HPLCMS (Method A): [m/z]: 370
The result is shown in FIG. 48

2,2,2-Trifluoro-N-[2-(quinolin-8-ylsulfamoyl)-phenyl]-acetamide (Example Compound 49)

In the similar fashion using route 15 general procedure 20, 2-amino-N-(quinolin-8-yl)benzenesulfonamide (Example Compound 8) (100 mg, 0.33 mmol), DIPEA (100 mg, 0.83 mmol), trifluoroacetic anhydride (100 mg, 0.50 mmol) gave the title compound (50 mg, 39%) after purification by column chromatography with DCM as the eluent.
EOAI3335391 VIT-1382
MW: 395.36
HPLCMS (Method A): [m/z]: 396
The result is shown in FIG. 49

N-[2-(Quinolin-8-ylsulfamoyl)-phenyl]-acetamide (Example Compound 50)

In the similar fashion using route 15 general procedure 30, 2-amino-N-(quinolin-8-yl)benzenesulfonamide (Example Compound 8) (100 mg, 0.33 mmol), DIPEA (140 µl, 0.83 mmol), acetic anhydride (23 µl, 0.49 mmol), THF (3 ml) gave the title compound (20 mg, 18%) after purification by column chromatography with DCM/MeOH/NH$_3$ (49:1:1) as the eluent.
EOAI3335392 VIT-1383
MW: 341.38
HPLCMS (Method A): [m/z]: 342
The result is shown in FIG. 50

N-[2-(Quinolin-8-ylsulfamoyl)-5-trifluoromethyl-phenyl]-isobutyramide (Example Compound 61)

In a similar fashion using route 15 general procedure 30, 2-amino-N-(quinolin-8-yl)-4-trifluoromethyl-benzenesulfonamide (Example Compound 35) (40 mg, 0.11 mmol), isobutyryl chloride (11 µl, 0.11 mmol) and DIPEA (47 µl, 0.27 mmol) gave the title compound (20 mg, 43%) after purification by column chromatography with DCM/n-hexane (4:1) as the eluent.
EOAI3335734 VIT-1422
MW: 437.44
HPLCMS (Method A): [m/z]: 438
The result is shown in FIG. 61

2,2,2-Trifluoro-N-[2-(quinolin-8-ylsulfamoyl)-5-trifluoromethyl-phenyl]-acetamide (Example Compound 55)

In a similar fashion using route 15 general procedure 30, 2-amino-N-(quinolin-8-yl)-4-trifluoromethyl-benzenesulfonamide (Example Compound 35) (100 mg, 0.27 mmol), trifluoroacetic anhydride (56 µl, 0.41 mmol) and DIPEA (119 µl, 0.68 mmol) gave the title compound (66 mg, 41%) after purification by column chromatography with DCM as the eluent.
EOAI3335671 VIT-1406
MW: 463.35
HPLCMS (Method A): [m/z]: 464
The result is shown in FIG. 55

N-[2-(Quinolin-8-ylsulfamoyl)-5-trifluoromethyl-phenyl]-acetamide (Example Compound 66)

In a similar fashion using route 15 general procedure 30, 2-amino-N-(quinolin-8-yl)-4-trifluoromethyl-benzenesulfonamide (Example Compound 35) (50 mg, 0.14 mmol), acetyl chloride (9 µl, 0.14 mmol) and DIPEA (59 µl, 0.34 mmol) gave the title compound (20 mg, 36%) after purification by column chromatography with DCM/n-hexane (4:1) as the eluent.
EOAI3335957 VIT-1432
MW: 409.38
HPLCMS (Method A): [m/z]: 410
The result is shown in FIG. 66
Route 16 (See Above)

General procedure 31: 5H-6-Thia-4,5-diaza-chrysene 6,6-dioxide (Example Compound 2)

2-Amino-N-(quinolin-8-yl)-benzenesulfonamide (Example Compound 8) (100 mg, 0.32 mmol) was dissolved in acetic acid (2 ml) and stirred at 10° C. for 5 min. The solution was cooled to −10° C. before tert-butyl nitrite (36 µl, 0.08 mmol) was added dropwise, the mixture was allowed to warm to room temperature and stirred for 10 minutes. The reaction was quenched with water and extracted with EtOAc. The organic phase was washed with a sat. sodium bicarbonate solution, brine, dried (Na$_2$SO$_4$) and concentrated in vacuo. The crude residue was purified by column chromatography with MeOH/DCM/NH$_3$ (1:100:2 drops) as the eluent to give the title compound (50 mg, 53%).
EOAI3330060 VIT-1085
MW: 282.31
HPLCMS (Method A): [m/z]: 283
The result is shown in FIG. 2

General Procedure 32:
5-Methyl-5H-6-thia-4,5-diaza-chrysene 6,6-dioxide (Example Compound 3)

5H-6-Thia-4,5-diaza-chrysene 6,6-dioxide (Example Compound 2) (50 mg, 0.18 mmol) was added to solution of NaH (60% dispersion in mineral oil; 11 mg, 0.27 mmol) dissolved in dry THF (3 ml), under argon, at 0° C., and the mixture was stirred for 15 min. Methyliodide (29 mg, 0.22 mmol) was added and the reaction was allowed to warm to room temperature and stirring continued for 12 h. After completion of the reaction (monitored by TLC), the solvent was removed in vacuo. The residue was dissolved in EtOAc, washed with water and brine. The organic phase was dried (Na$_2$SO$_4$) and concentrated in vacuo. The crude residue was purified by column chromatography with n-hexane/EtOAc (3:1) as the eluent to give the title compound (27 mg, 52%).
EOAI3333477 VIT-1190
MW: 296.34
HPLCMS (Method A): [m/z]: 297
The result is shown in FIG. 3

General Procedure 33:
3-Methyl-5H-6-thia-4,5-diaza-chrysene 6,6-dioxide (Example Compound 22)

2-Amino-N-(2-methyl-quinolin-8-yl)-benzenesulfonamide (Example Compound 15) (164 mg, 0.52 mmol) was suspended in acetic acid (3 ml) and cooled to 10° C. Tert-butylnitrite (93 µl, 0.79 mmol) was added and the reaction was slowly warmed to room temperature over 1 h. The reaction was then quenched with water (4 ml) and the resulting solution was concentrated in vacuo. The crude residue was purified by column chromatography with DCM as the eluent to give the title compound (7 mg, 5%).
EOAI3334539 VIT-1296
MW: 296.34
HPLCMS (Method A): [m/z]: 297
The result is shown in FIG. 22

General Procedure 34:
9-Fluoro-5H-6-thia-4,5-diaza-chrysene 6,6-dioxide (Example Compound 74)

2-Amino-4-fluoro-N-quinolin-8-yl-benzenesulfonamide (Example Compound 31) (315 mg, 0.99 mmol) was suspended in acetic acid (4 ml) and cooled to 10° C. Tert-butylnitrite (177 µl, 1.49 mmol) was added and the reaction was warmed to room temperature over 10 min. The reaction was quenched water (5 ml) and the resulting solution was concentrated in vacuo. The crude residue was dissolved in acetic acid (2 ml) and irradiated at 120° C. for 10 mins in the microwave. After cooling, the reaction was concentrated in vacuo. The crude residue was purified by preparative HPLC (acidic conditions) to give the title compound (7 mg, 2%).
EOAI3336487 VIT-1474
MW: 300.31
HPLCMS (Method A): [m/z]: 301
The result is shown in FIG. 74

General Procedure 35:
9-Trifluoromethyl-5H-6-thia-4,5-diaza-chrysene 6,6-dioxide (Example Compound 78)

2-Amino-N-quinolin-8-yl-4-trifluoromethyl-benzenesulfonamide (Example Compound 35) (50 mg, 0.14 mmol) was dissolved in acetic acid/THF (1:1; 2 ml) and cooled to 0° C. Tert-butylnitrite (16.2 µl, 0.14 mmol) was added and the mixture was stirred for 1 h keeping the temperature between 0° C. -5° C. The reaction was quenched with water (3 ml), while keeping the temperature between 0° C. -5° C., and the organic phase was extracted with EtOAc (10 ml). The combined organic phases were washed with sat. sodium bicarbonate and concentrated in vacuo. The crude residue was purified by column chromatography with DCM as the eluent to give the title compound (11 mg, 23%)
EOAI3336680 VIT-1486
MW: 350.32
HPLCMS (Method A): [m/z]: 350.90
The result is shown in FIG. 78

General Procedure 36:
8,9-Dimethyl-5H-6-thia-4,5-diaza-chrysene 6,6-dioxide (Example Compound 104)

2-Amino-4,5-dimethyl-N-quinolin-8-yl-benzenesulfonamide (Intermediate 164) (100 mg, 0.31 mmol) was suspended in acetic acid: THF (1:1) (2 ml) and cooled to 0° C. Tert-butylnitrite (54 µl, 0.46 mmol) was added and the reaction was slowly warmed to 5° C. over 3 h. The reaction was quenched with water (4 ml) and the resulting solution was concentrated in vacuo. The residue was dissolved in EtOAc (10 ml) and washed with brine, dried ($Na_2SO_4$) and concentrated in vacuo. The crude residue was purified by column chromatography with DCM as the eluent to give the title compound (7 mg, 7%).
EOAI3337848 VIT-1518
MW: 310.37
HPLCMS (Method A): [m/z]: 311
The result is shown in FIG. 104

9-Methoxy-5H-6-thia-4,5-diaza-chrysene 6,6-dioxide (Example Compound 105)

In a similar fashion using route 16 general procedure 36, 2-amino-4-methoxy-N-quinolin-8-yl-benzenesulfonamide (Example Compound 13) (60 mg, 0.18 mmol) and tert-butylnitrite (32 µl, 0.27 mmol) gave the title compound (7 mg, 10%) after purification by column chromatography with DCM as the eluent followed by a further column with heptane/EtOAC (9:1-0:1) gradient elution and then preparative HPLC (acidic conditions).
EOAI3338092 VIT-1532
MW: 312.34
HPLCMS (Method B): [m/z]: 313
The result is shown in FIG. 105

11-Methoxy-5H-6-thia-4,5-diaza-chrysene 6,6-dioxide (Example Compound 106)

In a similar fashion using route 16 general procedure 31, 2-amino-N-(6-methoxyquinolin-8-yl)-benzenesulfonamide (Intermediate 169) (100 mg, 0.30 mmol), acetic acid (0.02 ml, 0.32 mmol) and tert-butyl nitrite (60 mg, 0.61 mmol) gave the title compound (19 mg, 36%) after purification by column chromatography with DCM/n-hexane (9:1-1:0) followed by DCM/MeOH (199:1) gradient elution.
EOAI3344425 VIT-1730
MW: 312.34
HPLCMS (Method D): [m/z]: 313
The result is shown in FIG. 106

12-Methyl-5H-6-thia-4,5-diaza-chrysene 6,6-dioxide (Example Compound 107)

In a similar fashion using route 16 general procedure 31, 2-amino-N-(5-methylquinolin-8-yl)-benzenesulfonamide (Intermediate 176) (150 mg, 0.48 mmol), tert-butyl nitrite (0.12 ml, 0.88 mmol), acetic acid (28 µl, 0.48 mmol) and THF (5 ml), at 0° C. for 2 h then at room temperature for 2 h, gave the title compound (50 mg, 53%) after purification by column chromatography using silica basified with TEA with n-hexane/EtOAc (1:1) followed by DCM/MeOH (1:0-199:1) gradient elution.
EOAI3344424 VIT-1729
MW: 296.34
HPLCMS (Method A): [m/z]: 296.95
The result is shown in FIG. 107

12-Methoxy-5H-6-thia-4,5-diaza-chrysene 6,6-dioxide (Example Compound 108)

In a similar fashion using route 16 general procedure 31, 2-amino-N-(5-methoxyquinolin-8-yl)-benzenesulfonamide (Intermediate 177) (200 mg, 0.61 mmol), acetic acid (36 mg, 0.61 mmol), tert-butyl nitrite (93 mg, 0.91 mmol) gave the title compound (25 mg, 13%) after purification by column chromatography using silica basified by TEA with DCM/MeOH (1:0-499:1) as the eluent.
EOAI3346091 VIT-1807
MW: 312.34
HPLCMS (Method C): [m/z]: 313
The result is shown in FIG. 108

General procedure 61:
1-Chloro-5H-6-thia-4,5-diaza-chrysene 6,6-dioxide (Example Compound 305)

2-Amino-N-(4-chloro-quinolin-8-yl)-benzenesulfonamide (Intermediate 275) (1.3 g, 3.89 mmol) was dissolved in AcOH (13 ml) and the mixture was stirred at 0° C. for 5 min. The solution was cooled to −10° C. and t-butyl nitrite (0.7 ml, 5.83 mmol) was added dropwise and the mixture was stirred at room temperature 30 min. The mixture was quenched with sat. $NaHCO_3$ solution and the aqueous phase was extracted with EtOAc. The organic phase was washed with brine, dried ($Na_2SO_4$) and concentrated in vacuo to give the title compound (400 mg, 33%) after the purification by column chromatography with DCM/MeOH (90:10) as the eluent.
EOAI3359236 VIT-2106
MW: 316.77
HPLCMS (Method C): [m/z]: 316.91

12-Fluoro-9-trifluoromethyl-5H-6-thia-4,5-diaza-chrysene 6,6-dioxide (Example Compound 306)

In a similar fashion using route 16 general procedure 61, 2-amino-N-(5-fluoro-quinolin-8-yl)-4-trifluoromethyl-benzenesulfonamide (Intermediate 276) (200 mg, 0.52 mmol), t-butyl nitrite (0.09 ml, 0.78 mmol) and AcOH (2 ml) gave the title compound (20 mg, 11%) after purification by column chromatography with DCM/MeOH (98:2) as the eluent.
EOAI3359137 VIT-2094
MW: 368.31
HPLCMS (Method C): [m/z]: 368

6,6-Dioxo-5,6-dihydro-6λ*6*-thia-4,5-diaza-chrysene-9-carboxylic acid methyl ester (Example Compound 307)

In a similar fashion using route 16 general procedure 61, 3-amino-4-(quinolin-8-ylsulfamoyl)-benzoic acid methyl ester (Intermediate 277) (340 mg, 0.95 mmol), t-butyl nitrite (0.17 ml, 1.4 mmol), AcOH (3.4 ml) and THF (3.4 ml), gave the title compound (60 mg, 18%) after purification by column chromatography with DCM/MeOH (99.8:0.2) as the eluent.
EOAI3358946 VIT-2078
MW: 340.36
HPLCMS (Method C): [m/z]: 340.96

6,6-Dioxo-5,6-dihydro-6λ*6*-thia-4,5-diaza-chrysene-9-carbonitrile (Example Compound 308)

In a similar fashion using route 16 general procedure 61, 2-amino-4-cyano-N-quinolin-8-yl-benzenesulfonamide (Intermediate 278) (350 mg, 1.08 mmol), t-butyl nitrite (0.19 ml, 1.62 mmol), AcOH (3.5 ml) and THF (3.5 ml) gave the title compound (15 mg, 4%) after purification by column chromatography with DCM/MeOH (99:1) as the eluent.
EOAI3359535 VIT-2119
MW: 307.33
HPLCMS (Method C): [m/z]: 307.98

1-Trifluoromethyl-5H-6-thia-4,5-diaza-chrysene 6,6-dioxide (Example Compound 309)

In a similar fashion using route 16 general procedure 61, 2-amino-N-(4-trifluoromethyl-quinolin-8-yl)-benzenesulfonamide (Intermediate 279) (300 mg, 0.82 mmol), t-butyl nitrite (0.14 ml, 1.22 mmol) and AcOH (4 ml) gave the title compound (60 mg, 16%) after purification by column chromatography with DCM/MeOH: aq.NH3 (99:1:2 drops) as the eluent.
EOAI3360393 VIT-2151
MW: 350
HPLCMS (Method C): [m/z]: 351

9-Chloro-1-trifluoromethyl-5H-6-thia-4,5-diaza-chrysene 6,6-dioxide (Example Compound 310)

In a similar fashion using route 16 general procedure 61, 2-amino-4-chloro-N-(4-trifluoromethyl-quinolin-8-yl)-benzenesulfonamide (Intermediate 280) (340 mg, 0.85 mmol), t-butyl nitrite (0.15 ml, 1.27 mmol), AcOH (4 ml), THF (4 ml) gave the title compound (60 mg, 18%) after purification by column chromatography with DCM/MeOH (98:2) as the eluent.
EOAI3361124 VIT-2178
MW: 384.77
HPLCMS (Method C): [m/z]: 384.9

12-Trifluoromethyl-5H-6-thia-4,5-diaza-chrysene 6,6-dioxide (Example Compound 311)

In a similar fashion using route 16 general procedure 61, 2-amino-N-(5-trifluoromethyl-quinolin-8-yl)-benzenesulfonamide (Intermediate 281) (230 mg, 0.63 mmol), t-butyl nitrile (111 mg, 0.94 mmol) and AcOH:THF (2.3 ml: 2.3 ml) gave the title compound (27 mg, 12%) after purification by column chromatography with DCM/MeOH (99.7:0.3) as the eluent.
EOAI3360059 VIT-2131
MW: 350.0
HPLCMS (Method C): [m/z]: 350.96

9-Chloro-12-trifluoromethyl-5H-6-thia-4,5-diaza-chrysene 6,6-dioxide (Example Compound 312)

In a similar fashion using route 16 general procedure 61, 2-amino-4-chloro-N-(5-trifluoromethyl-quinolin-8-yl)-benzenesulfonamide (Intermediate 282) (340 mg, 0.85 mmol), t-butyl nitrile (0.15 ml, 1.27 mmol) and AcOH:THF (3.4 ml: 3.4 ml) gave the title compound (28 mg, 9%) after purification by column chromatography with DCM/MeOH (99.5:0.5) as the eluent.
EOAI336112 VIT-2177
MW: 384.0
HPLCMS (Method C): [m/z]: 384.9

3-Chloro-5H-6-thia-4,5-diaza-chrysene 6,6-dioxide (Example Compound 313)

In a similar fashion using route 16 general procedure 61, 2-amino-N-(2-chloro-quinolin-8-yl)-benzenesulfonamide (Intermediate 283) (590 mg, 1.77 mmol), t-butyl nitrite (0.32 ml, 2.65 mmol) and AcOH:THF (5.9 ml: 5.9 ml) gave the title compound (80 mg, 16%) after purification by column chromatography with DCM/MeOH (99:1) as the eluent.
EOAI3360060 VIT-2132
MW: 316
HPLCMS (Method C): [m/z]: 316.9

8,12-Dichloro-9-fluoro-5H-6-thia-4,5-diaza-chrysene 6,6-dioxide Example Compound (314)

In the similar fashion using route 16 general procedure 61, 2-amino-5-chloro-N-(5-chloro-quinolin-8-yl)-4-fluoro-benzenesulfonamide (Intermediate 284) (150 mg, 0.38 mmol), t-butyl nitrite (0.07 ml, 0.58 mmol) and AcOH:THF (1.5 ml:1.5 ml) gave the title compound (22 mg, 16%) after purification by column chromatography with chloroform/MeOH (99:1) as the eluent.
EOAI3361828 VIT-2204
MW: 369.20
HPLCMS (Method F): [m/z]: 368.96

12-Chloro-8,9-difluoro-5H-6-thia-4,5-diaza-chrysene 6,6-dioxide (Example Compound 315)

In a similar fashion using route 16 general procedure 61, 2-amino-N-(5-chloro-quinolin-8-yl)-4,5-difluoro-benzenesulfonamide (Intermediate 285) (95 mg, 0.25 mmol), t-butyl nitrite (0.05 ml, 0.38 mmol), AcOH:THF (1 ml:1 ml) gave the title compound (16 mg, 17%) after purification by column chromatography with DCM/MeOH (99:1) as the eluent.
EOAI3362522 VIT-2208
MW: 352.75
HPLCMS (Method C): [m/z]: 353

9-Chloro-6,6-dioxo-5,6-dihydro-6$\lambda$*6*-thia-4,5-diaza-chrysene-12-carbonitrile (Example Compound 316)

In a similar fashion using route 16 general procedure 61, 2-amino-4-chloro-N-(5-cyano-quinolin-8-yl)-benzenesulfonamide (Intermediate 286) (100 mg, 0.27 mmol), t-butyl nitrite (0.047 ml, 0.41 mmol) and AcOH: THF (2 ml: 1 ml) gave the title compound (40 mg, 42%) after purification by column chromatography with chloroform/MeOH (99.5:0.5) as the eluent.
EOAI3365877 VIT-2323
MW: 341.78
LCMS: (Method F): [m/z]: 342.30

3,9-Dichloro-5H-6-thia-4,5-diaza-chrysene 6,6-dioxide (Example Compound 317)

In a similar fashion using route 16 general procedure 61, 2-amino-4-chloro-N-(2-chloro-quinolin-8-yl)-benzenesulfonamide (Intermediate 287) (0.1 g, 0.27 mmol), t-butyl nitrite (0.05 ml, 0.41 mmol) and AcOH:THF (1 ml: 2 ml), gave the title compound (0.04 g, 45%) after purification by column chromatography with DCM/MeOH (90:10) as the eluent.
EOAI3361212 VIT-2189
MW: 351.21
HPLCMS: (Method F): [m/z]: 350, 352

11H-12-Thia-1,10,11-triaza-chrysene 12,12-dioxide (Example Compound 318)

In a similar fashion using route 16 general procedure 61, using 3-amino-pyridine-2-sulfonic acid quinolin-8-ylamide (Intermediate 303) (180 mg, 0.6 mmol), t-butyl nitrite (0.11 ml, 0.9 mmol), AcOH (1.8 ml) and THF(1.8 ml) gave the title compound (12 mg, 7%) after purification with prep HPLC (neutral conditions).
EOAI3362772 VIT-2222
MW: 283.31
HPLCMS: (Method E): [m/z]: 284.1

6,6-Dioxo-5,6-dihydro-6$\lambda$*6*-thia-4,5-diaza-chrysene-1-carboxylic acid methyl ester (Example Compound 319)

In a similar fashion using route 16 general procedure 61, 8-(2-amino-benzenesulfonylamino)-quinoline-4-carboxylic acid methyl ester (Intermediate 288) (270 mg, 0.75 mmol), t-butyl nitrite (0.14 ml, 1.13 mmol), AcOH (2.7 ml) and THF (2.7 ml) gave the title compound (60 mg, 23%) after purification by column chromatography with DCM/MeOH (99:1) as the eluent.
EOAI3355289 VIT-1995
MW: 340.36
HPLCMS (Method C): [m/z]: 341

7H-6,17-Dithia-7,15-diaza-cyclopenta[a]phenanthrene 6,6-dioxide (Example Compound 320)

In a similar fashion using route 16 general procedure 61, 2-amino-N-benzothiazol-4-yl-benzenesulfonamide (Intermediate 289) (190 mg, 0.62 mmol), t-butyl nitrite (96 mg, 0.93 mmol), AcOH (1.9 ml) and THF (4 ml) gave the title compound (35 mg, 19.5%) after purification by column chromatography with DCM/MeOH (99:1) as the eluent.
EOAI3365236 VIT-2288
MW: 288.35
HPLCMS (Method E): [m/z]: 289.20

12-Chloro-9-methanesulfonyl-5H-6-thia-4,5-diaza-chrysene 6,6-dioxide (Example Compound 321)

In a similar fashion using route 16 general procedure 61, 2-amino-N-(5-chloro-quinolin-8-yl)-4-methanesulfonyl-benzenesulfonamide (Intermediate 274) (205 mg, 0.5 mmol), t-butyl nitrite (0.09 ml, 0.75 mmol), AcOH (4 ml) and THF (4 ml) gave the title compound (22 mg, 16%) after purification by column chromatography with DCM as the eluent.
EOAI3363913 VIT-2254
MW: 394.86
HPLCMS: (Method E): [m/z]: 395.1

5H-6-Thia-1,4,5-triaza-chrysene 6,6-dioxide (Example Compound 322)

In a similar fashion using route 16 general procedure 61, 2-amino-N-quinoxalin-5-yl-benzenesulfonamide (Intermediate 304) (440 mg, 1.4 mmol), t-butyl nitrite (0.27 ml, 2.19 mmol), AcOH (4.5 ml) and THF (4.5 ml) gave the title compound (65 mg, 16%) after purification by column chromatography with DCM/MeOH (99:1) as the eluent.
EOAI3348432 VIT-1861
MW: 283.31
HPLCMS (Method C): [m/z]: 284

11-Fluoro-5H-6-thia-4,5-diaza-chrysene 6,6-dioxide (Example Compound 323)

In a similar fashion using route 16 general procedure 61, 2-amino-N-(6-fluoro-quinolin-8-yl)-benzenesulfonamide (Intermediate 290) (200 mg, 0.63 mmol), t-butyl nitrite (0.11 ml, 0.94 mmol), AcOH (2 ml) and THF (2 ml) gave the title compound (35 mg, 19%) after purification by column chromatography with DCM/MeOH (99:1) as the eluent.
EOAI3349343 VIT-1876
MW: 300.31
HPLCMS (Method C): [m/z]: 300.98

12-Fluoro-5H-6-thia-4,5-diaza-chrysene 6,6-dioxide (Example Compound 324)

In a similar fashion using route 16 general procedure 61, 2-amino-N-(5-fluoro-quinolin-8-yl)-benzenesulfonamide (Intermediate 291) (350 mg, 1.1 mmol), t-butyl nitrite (0.2 ml, 1.65 mmol), AcOH (3.5 ml) and THF (3.5 ml) gave the title compound (33 mg, 10%) after purification by column chromatography with DCM/MeOH (99:1) as the eluent followed by recrystallisation with DCM/pentane.
EOAI3349344 VIT-1877
MW: 300.31
HPLCMS (Method C): [m/z]: 300.96

9-Chloro-5H-6-thia-4,5-diaza-chrysene 6,6-dioxide (Example Compound 325)

In the similar fashion using route 16 general procedure 61, using 2-amino-4-chloro-N-quinolin-8-yl-benzenesulfonamide (Intermediate 292) (150 mg, 0.45 mmol), t-butyl nitrite (0.08 ml, 0.67 mmol), AcOH (1.5 ml) and THF (1.5 ml) gave the title compound (20 mg, 14%) after purification by column chromatography with DCM/MeOH (99.7:0.3) as the eluent.
EOAI3350532 VIT-1909
MW: 316.77
HPLCMS (Method C): [m/z]: 316.94

8-Methoxy-5H-6-thia-4,5-diaza-chrysene 6,6-dioxide (Example Compound 326)

In a similar fashion using route 16 general procedure 61, 2-amino-5-methoxy-N-quinolin-8-yl-benzenesulfonamide (Intermediate 293) (450 mg, 1.36 mmol), t-butyl nitrite (0.24 ml, 2.04 mmol), AcOH (4.5 ml) and THF (4.5 ml) gave the title compound (19 mg, 4%) after purification by column chromatography with DCM/MeOH (99.7:0.3) as the eluent.
EOAI3354630 VIT-1987
MW: 312.35
HPLCMS (Method C): [m/z]: 313

9-Methyl-5H-6-thia-4,5-diaza-chrysene 6,6-dioxide (Example Compound 327)

In a similar fashion using route 16 general procedure 61, 2-amino-4-methyl-N-quinolin-8-yl-benzenesulfonamide (Intermediate 294) (520 mg, 1.67 mmol), t-butyl nitrite (0.29 ml, 2.5 mmol), AcOH (5.2 ml) and THF (5.2 ml) gave the title compound (20 mg, 5%) after purification by column chromatography with DCM/MeOH (99.7:0.3) as the eluent.
EOAI3354631 VIT-1984
MW: 296.35
HPLCMS (Method C): [m/z]: 297

12-Chloro-5H-6-thia-4,5-diaza-chrysene 6,6-dioxide (Example Compound 328)

In a similar fashion using route 16 general procedure 61, 2-amino-N-(5-chloro-quinolin-8-yl)-benzenesulfonamide (Intermediate 295) (370 mg, 1.10 mmol), t-butyl nitrite (171 mg, 1.66 mmol), AcOH (3.7 ml) and THF (3.7 ml) gave the title compound (60 mg, 17%) after purification by column chromatography with n-hexane/DCM (1:1) as the eluent.
EOAI3349345 VIT-1878
MW: 316.76
HPLCMS (Method C): [m/z]: 317.22

8-Methyl-5H-6-thia-4,5-diaza-chrysene 6,6-dioxide (Example Compound 329)

In a similar fashion using route 16 general procedure 61, 2-amino-5-methyl-N-quinolin-8-yl-benzenesulfonamide (Intermediate 296) (160 mg, 0.51 mmol), t-butyl nitrite (80 mg, 0.76 mmol), AcOH (1.6 ml) and THF (1.6 ml) gave the title compound (20 mg, 13%) after purification by column chromatography with n-hexane/DCM (1:1) as the eluent.
EOAI3350623 VIT-1921
MW: 296.34
HPLCMS (Method C): [m/z]: 297

8-Fluoro-5H-6-thia-4,5-diaza-chrysene 6,6-dioxide Example Compound (330)

In a similar fashion using route 16 general procedure 61, 2-amino-5-fluoro-N-quinolin-8-yl-benzenesulfonamide (Intermediate 297) (250 mg, 0.78 mmol), t-butyl nitrite (121 mg, 1.18 mmol), AcOH (2.5 ml) and THF (2.5 ml) gave the title compound (21 mg, 8%) after purification by column chromatography (×2) with n-hexane/DCM (50:50) as the eluent followed by recrystallisation.
EOAI3351376 VIT-1952
MW: 300.30
HPLCMS (Method C): [m/z]: 301

9-Fluoro-8-methyl-5H-6-thia-4,5-diaza-chrysene 6,6-dioxide (Example Compound 331)

In a similar fashion using route 16 general procedure 61, 2-amino-4-fluoro-5-methyl-N-quinolin-8-yl-benzenesulfonamide (Intermediate 299) (340 mg, 1.03 mmol), t-butyl nitrite (0.18 ml, 1.54 mmol), AcOH (3.4 ml) and THF (3.4 ml) gave the title compound (50 mg, 15%) after purification by column chromatography with DCM/MeOH (90:10) as the eluent.
EOAI3356106 VIT-2018
MW: 314.34
HPLCMS: (Method C): [m/z]:315

8-Trifluoromethyl-5H-6-thia-4,5-diaza-chrysene 6,6-dioxide (Example Compound 332)

In a similar fashion using route 16 general procedure 61, 2-amino-N-quinolin-8-yl-5-trifluoromethyl-benzenesulfonamide (Intermediate 300) (330 mg, 0.9 mmol), t-butyl nitrite (0.16 ml, 1.3 mmol), AcOH (3.3 ml) and THF (3.3 ml) gave the title compound (25 mg, 7%) after purification by column chromatography with DCM/MeOH (99.8:0.2) as the eluent.
EOAI3356107 VIT-2019
MW: 350.32
HPLCMS: (Method C):[m/z]: 351

9-Trifluoromethoxy-5H-6-thia-4,5-diaza-chrysene 6,6-dioxide (Example Compound 333)

In a similar fashion using route 16 general procedure 61, 2-amino-N-quinolin-8-yl-4-trifluoromethoxy-benzenesulfonamide (Intermediate 301) (350 mg, 0.91 mmol), t-butyl nitrite (0.16 ml, 1.37 mmol), AcOH (3.5 ml) and THF (3.5 ml) gave the title compound (27 mg, 8%) after purification by column chromatography with DCM/MeOH (99.8:0.2) as the eluent.
EOAI3356959 VIT-2030
MW 366.32
HPLCMS (Method C): [m/z]: 366.94

12-Chloro-9-trifluoromethyl-5H-6-thia-4,5-diaza-chrysene 6,6-dioxide (Example Compound 334)

In a similar fashion using route 16 general procedure 61, 2-amino-N-(5-chloro-quinolin-8-yl)-4-trifluoromethyl-benzenesulfonamide (Intermediate 302) (350 mg, 0.87 mmol), t-butyl nitrite (0.16 ml, 1.30 mmol) and AcOH (3.5 ml) gave the title compound (110 mg, 33%) after purification by column chromatography with DCM/MeOH/NH3 (99:1:2 drops) as the eluent.
EOAI3358948 VIT-2079
MW: 384.79
HPLCMS (Method C): [m/z]: 384.9

General Procedure 62: 7-Methyl-5H-6-thia-4,5-diaza-chrysene 6,6-dioxide (Example Compound 335)

2-Amino-6-methyl-N-quinolin-8-yl-benzenesulfonamide (Intermediate 298) (525 mg, 1.6 mmol) was dissolved in AcOH (5.2 ml) and THF (5.2 ml) and the mixture was stirred at 0° C. for 5 min. The solution was cooled to −10° C. and t-butyl nitrite (0.3 ml, 2.5 mmol) was added dropwise and the mixture was stirred at room temperature to give the intermediate diazonium salt (90 mg) after purification by column chromatography with DCM/MeOH (99:1) as the eluent. The diazonium salt was heated in MeCN at 80° C. for 18 h. After cooling, the mixture was concentrated in vacuo. The crude residue was purified by column chromatography with DCM as the eluent to give the title compound (24 mg, 5%).
EOAI3355977 VIT-2004
MW: 296.35
HPLCMS (Method C): [m/z]: 297
Route 17 (See Above)

General Procedure 37: N-(7-Chloro-4-methoxy-quinolin-8-yl)-2-nitro-4-trifluoromethyl-benzenesulfonamide (Intermediate 194)

2-Nitro-4-(trifluoromethyl)benzenesulfonyl chloride (839 mg, 2.9 mmol) was added to a solution of 7-chloro-4-methoxy-quinolin-8-ylamine (Intermediate 70) (550 mg, 2.6 mmol) in pyridine(10 ml) and the mixture was stirred at room temperature for 18 h. The solvent was removed in vacuo. The residue was dissolved EtOAc (100 ml), washed sat. sodium bicarbonate solution, dried (MgSO$_4$) and concentrated in vacuo to give the title compound (830 mg, 69%).
MW:461.81
HPLCMS (Method B):[m/z]: 463

General Procedure 38: 2-Amino-N-(7-chloro-4-methoxy-quinolin-8-yl)-4-trifluoromethyl-benzenesulfonamide (Intermediate 195)

Tin (II) chloride (2.0 g, 9.0 mmol) was added to a solution of N-(7-chloro-4-methoxy-quinolin-8-yl)-2-nitro-4-trifluoromethyl-benzenesulfonamide (Intermediate 194) (830 mg, 1.8 mmol)) in EtOH (20 ml) and the mixture was heated at 95° C. for 2 h. After cooling the solvent was removed in vacuo. EtOAc (100 ml) was added and the solution cooled in an ice bath whilst aqueous NH$_3$ was added until the solution was basic, the white precipitate formed was filtered and washed with EtOAc (100 ml). The combined organics were washed with brine (100 ml), dried (MgSO$_4$) and concentrated in vacuo to give the title compound (670 mg, 86%).
MW:431.82
HPLCMS (Method B):[m/z]: 432

General Procedure 39: 2-Amino-N-(4-methoxy-quinolin-8-yl)-4-trifluoromethyl-benzenesulfonamide (Intermediate 196)

10% palladium on carbon (82 mg) was added to a solution of 2-amino-N-(7-chloro-4-methoxy-quinolin-8-yl)-4-trifluoromethyl-benzenesulfonamide (Intermediate 195) (670 mg, 1.5 mmol) and ammonium formate (481 mg, 7.5 mmol) in 50% acetic acid (5 ml) and the reaction was heated under reflux for 30 min. After cooling the mixture was diluted with EtOAc (100 ml), washed sat sodium bicarbonate solution, dried (MgSO$_4$) concentrated in vacuo. The crude residue was purified by column chromatography with DCM/MeOH (98:2) as the eluent to give the title compound (604 mg, 100%).
MW: 397.38
HPLCMS (Method B):[m/z]: 398

General Procedure 40: 1-Methoxy-9-trifluoromethyl-5H-6-thia-4,5-diaza-chrysene 6,6-dioxide (Example Compound 109)

A solution of 2-amino-N-(4-methoxy-quinolin-8-yl)-4-trifluoromethyl-benzenesulfonamide (Intermediate 196) (454 mg, 1.1 mmol) in AcOH/THF (1:1, 10 ml) was cooled to 0° C. and tert-butylnitrite (235 mg, 2.2 mmol) was added. The reaction was stirred at 0-5° C. for 2 h. The reaction was quenched water (5 ml) and the solvent partially evaporated. The residue was dissolved in EtOAc (150 ml), washed with sat. sodium bicarbonate solution, dried (MgSO$_4$) and concentrated in vacuo. The crude residue was purified by column chromatography with DCM/MeOH (1:0-99:1) gradient elution followed by recrystallisation from $^i$PA/MeCN to give the title compound (45 mg, 11%).
EOAI3346046 VIT-1766
MW: 380.35
HPLCMS (Method A):[m/z]: 381
The result is shown in FIG. 109
Route 18 (See Above)

General Procedure 41: Quinolin-8-yl-sulfamic acid phenyl ester (Example Compound 70)

Chlorosulfonic acid (210 mg, 1.8 mmol) in DCM was added dropwise to solution of 8-aminoquinoline (250 mg, 1.7 mmol) and TEA (260 mg, 2.6 mmol) in DCM (5 ml) at 0° C. and the mixture was stirred for 30 min. The reaction was allowed to warm to room temperature and stirring was continued for 1 h. PCl$_5$ (370 mg, 1.8 mmol) was added and the mixture was heated at 50° C. for 1 h. The reaction was cooled to room temperature, phenol (310 mg, 3.4 mmol) and TEA (340 mg, 3.4 mmol) were added and the reaction was stirred at room temperature overnight. Water was added and the mixture was extracted with DCM, the organic phase dried (Na$_2$SO$_4$) and concentrated in vacuo. The crude residue was purified by column chromatography with n-hexane/EtOAc (4:1) as the eluent to give the title compound (40 mg, 8%).
EOAI3336273 VIT-1453
MW: 300.33
HPLCMS (Method A): [m/z]: 301
The result is shown in FIG. 70
Route 19 (See Above)

General Procedure 42: N-Phenyl(quinolin-8-ylamino)sulfonamide (Example Compound 46)

Chlorosulfonic acid (260 mg, 2.2 mmol) in DCM was added to a solution of 8-aminoquinoline (300 mg, 2.08 mmol)

and TEA (310 mg, 3.12 mmol) in dry DCM (10 ml) at 0° C. and the mixture was stirred for 30 min. The reaction was allowed to warm to room temperature and stirring was continued for 1 h. PCl$_5$ (460 mg, 2.20 mmol) was added to the reaction and the mixture was heated under reflux for 1 h, then allowed to cool to room temperature. Aniline (770 mg, 8.3 mmol) and DIPEA (0.72 ml, 4.16 mmol) were added and the reaction stirred at room temperature for 2.5 h. The reaction was quenched with water and extracted with DCM. The organic phase was washed with water, brine, dried (Na$_2$SO$_4$) and concentrated in vacuo. The crude residue was purified by column chromatography with DCM as the eluent to give the title compound (70 mg, 11%).
EOAI3335379 VIT-1370
MW: 299.35
HPLCMS (Method A): [m/z]: 300
The result is shown in FIG. 46

N-(3-Chloro-2-methylphenyl)[(6-methoxyquinolin-8-yl)amino]sulfonamide (Example Compound 110)

In a similar fashion using route 19 general procedure 42, 6-methoxyquinolin-8-amine (Intermediate 23) (300 mg, 1.7 mmol), chlorosulfonic acid (120 µl, 1.8 mmol), PCl$_5$ (370 mg, 1.8 mmol), TEA (360 µl, 2.5 mmol), 3-chloro-2-methylaniline (810 µl, 6.8 mmol) and DIPEA (600 µl, 3.4 mmol) gave the title compound (15 mg, 2%) after purification by column chromatography with DCM/n-hexane (1:1) as the eluent, followed by recrystallisation from EtOAc/n-hexane and then further purification by column chromatography with n-hexane/EtOAc (4:1) as the eluent.
EOAI3337854 VIT-1517
MW: 377.85
HPLCMS (Method A): [m/z]: 378
The result is shown in FIG. 110

N-(3-Chloro-2-methylphenyl)[(5-chloroquinolin-8-yl)amino]sulfonamide (Example Compound 111)

In the similar fashion using route 19 general procedure 42, 5-chloroquinolin-8-amine (Intermediate 27) (155 mg, 1.15 mmol), sodium (2,3-dimethylphenyl)sulfamate (Intermediate 21) (300 mg, 1.23 mmol), PCl$_5$ (771 mg, 3.70 mmol), TEA (1.67 ml, 12.3 mmol) and toluene (10 ml) gave the title compound (24 mg, 7%) after purification by column chromatography with n-hexane/EtOAc (1:0-17:3) as the eluent followed by trituration from n-pentane.
EAOI3346097 VIT-1806
MW: 382.26
HPLCMS (Method C): [m/z] 382
The result is shown in FIG. 111

N-(2,6-Difluorophenyl)[(6-methoxyquinolin-8-yl)amino]sulfonamide (Example Compound 112)

In the similar fashion using route 19 general procedure 42, 6-methoxyquinolin-8-amine (Intermediate 23) (200 mg, 1.15 mmol), TEA (170 mg, 1.72 mmol), chlorosulfonic acid (150 mg, 1.27 mmol), PCl$_5$ (260 mg, 1.72 mmol), DIPEA (300 mg, 2.23 mmol), 2,6-difluoroaniline (600 mg, 4.6 mmol) gave the title compound (15 mg, 4%) after purification by column chromatography with DCM/MeOH (1:0-97:3) as the eluent.
EOAI3343713 VIT-1603
MW: 365.36
HPLCMS (Method C): [m/z]: 366
The result is shown in FIG. 112
Route 20 (See Above)

General Procedure 43: Dimethyl-[(E)-2-(8-nitro-quinolin-7-yl)-vinyl]-amine (Intermediate 203)

A solution of 7-methyl-8-nitroquinoline (6 g, 31.9 mmol) and 1,1-dimethoxy-N,N-dimethylmethanamine (4.27 ml, 31.9 mmol) in DMF (15 ml) was heated at 140° C., under nitrogen, for 16 h. After cooling to room temperature, water (15 ml) was added and the resulting precipitate was collected by filtration, washed with EtOAc and dried to give the title compound (4.4 g, 57%). The compound could not be detected by HPLCMS therefore structure was confirmed by $^1$H NMR.

General Procedure 44:
8-Nitro-quinoline-7-carbaldehyde (Intermediate 204)

NaIO$_4$ (11.71 g, 54.76 mmol) was added portionwise to a solution of dimethyl-[(E)-2-(8-nitro-quinolin-7-yl)-vinyl]-amine (Intermediate 203) (4.44 g, 18.3 mmol) in THF/water (1:1, 70 ml). The mixture was stirred at room temperature for 16 h. The insoluble material was removed by filtration and washed with EtOAc (60 ml). The combined organic phases were washed with sat. sodium bicarbonate solution, brine, dried (Na$_2$SO$_4$) and concentrated in vacuo to give the title compound (3.24 g, 71%).
MW: 202.17
HPLCMS (Method B): [m/z]: 202.95

General Procedure 45:
(8-Nitro-quinolin-7-ylmethyl)-phenyl-amine (Intermediate 205)

A solution of 8-nitro-quinoline-7-carbaldehyde (Intermediate 204) (500 mg, 2.4 mmol) and aniline (270 µl, 2.9 mmol) in MeOH (20 ml) under a nitrogen atmosphere was stirred at room temperature for 16 hours. Sodium borohydride (269 mg, 7.1 mmol) was added and stirring continued at room temperature for 1 h. The reaction mixture was concentrated in vacuo and residue was diluted with sat. NaHCO$_3$ solution (30 ml) and was extracted with DCM. The organic phases were dried (MgSO$_4$) and concentrated in vacuo. The crude residue was purified by column chromatography with heptane/EtOAc gradient elution to give the title compound (0.48 g, 69%).
MW: 279.29
HPLCMS (Method B): [m/z]: 279.95

General Procedure 46:
7-Phenylaminomethyl-quinolin-8-ylamine (Intermediate 206)

Palladium on Carbon (10%, 36 mg) was added to a solution of (8-nitro-quinolin-7-ylmethyl)-phenyl-amine (Intermediate 205) (478 mg, 1.69 mmol) in EtOH (10 ml) and the mixture was stirred under an atmosphere of hydrogen for 4 h. The mixture was diluted with MeOH (40 ml), filtered through celite and the filtrate was concentrated in vacuo to give the title compound (428 mg, 89%).
MW: 249.31
HPLCMS (Method B): [m/z]: 250

General Procedure 47: 2-Phenyl-1,4-dihydro-2H-3-thia-2,4,5-triaza-phenanthrene 3,3-dioxide (Example Compound 113)

A solution of 7-phenylaminomethyl-quinolin-8-ylamine (Intermediate 206) (350 mg, 1.4 mmol) and 1-(1H-imidazole-1-sulfonyl)-3-methyl-1H-imidazol-3-ium; trifluoromethanesulfonate (762 mg, 2.1 mmol) in MeCN (10 ml) was stirred at 0° C. then allowed to warm to room temperature overnight. The reaction mixture was concentrated in vacuo and the crude residue was purified by preparative HPLC (basic conditions) to give the title compound (18 mg, 4%).

EOAI3343970 VIT-1622-A
MW: 311.36
HPLCMS (Method A): [m/z]: 312
The result is shown in FIG. 113
Route 21 (See Above)

General Procedure 48: 2-Methyl-propane-2-sulfinic acid 1-(8-nitro-quinolin-7-yl)-meth-(E)-ylideneamide (Intermediate 208)

Titanium tetra-ethoxide (1.2 ml, 4.95 mmol) was added to a solution of 8-nitro-quinoline-7-carbaldehyde (Intermediate 204) (0.5 g, 2.47 mmol) and 2-methylpropane-2-sulfinamide (660 mg, 5.4 mmol) in THF (20 ml) under a nitrogen atmosphere and the mixture was heated under reflux for 17 h. The solution was cooled to room temperature and poured into rapidly stirring brine (40 ml) and stirred for 30 min. EtOAc (40 ml) was added and the mixture was filtered through Celite and washed with EtOAc (40 ml). The aqueous phase was extracted with EtOAc. The organic phases were dried ($MgSO_4$) and concentrated in vacuo. The solid was purified by column chromatography using heptane/EtOAc (1:1) to give the title compound (577 mg, 76%). The compound could not be detected by HPLCMS therefore structure was confirmed by $^1$H NMR.

General Procedure 49: 2-Methyl-propane-2-sulfinic acid (8-nitro-quinolin-7-ylmethyl)-amide (Intermediate 209)

A solution of 2-methyl-propane-2-sulfinic acid 1-(8-nitro-quinolin-7-yl)-meth-(E)-ylideneamide (Intermediate 208) (400 mg, 1.3 mmol) in MeOH (8 ml) under a nitrogen atmosphere was cooled to 0° C. Sodium borohydride (1.24 g, 3.3 mmol) was added and the mixture was allowed to warm to room temperature while stirring for 16 h. The reaction mixture was concentrated in vacuo and the residue was diluted with sat. sodium bicarbonate solution (15 ml), extracted with EtOAc followed by 10% MeOH/DCM. The combined organic phases were washed with brine, dried ($MgSO_4$) and concentrated in vacuo to give the title compound (411 mg, 100%). The material was used in the next step without purification.

MW: 307.37
HPLCMS (Method B): [m/z]: 308

General Procedure 50:
C-(8-Nitro-quinolin-7-yl)-methylamine (Intermediate 210)

A solution of 2-methyl-propane-2-sulfinic acid (8-nitroquinolin-7-ylmethyl)-amide (Intermediate 209) (402 mg, 1.31 mmol) in dry MeOH (10 ml) under a nitrogen atmosphere was cooled to 0° C. HCl in dioxane (4M, 1.7 ml, 6.9 mmol) was added and the mixture was stirred at 0° C. for 1 h and allowed to warm to room temperature overnight. The mixture was concentrated in vacuo and the residue was triturated with dry ether (10 ml). The solid was collected by filtration, washed with dry ether and dried at room temperature to give the title compound as an HCl salt (180 mg, 100%).
MW: 276.12

HCGeneral Procedure 51: 7-Aminomethyl-quinolin-8-ylamine (Intermediate 211)

Palladium on Carbon (5%, 25 mg) was added to a solution of C-(8-nitroquinolin-7-yl)-methylamine dihydrochloride (Intermediate 210) (180 mg, 1.09 mmol) in EtOH (10 ml) and the mixture was stirred under an atmosphere of hydrogen for 5 h. The mixture was diluted with MeOH (10 ml), filtered through celite and the filtrate was concentrated in vacuo to give the title compound (5 mg, 31%).

MW: 173.22
HPLCMS high pH (Method A): [m/z]: 174

General Procedure 52:
1,4-Dihydro-2H-3-thia-2,4,5-triaza-phenanthrene 3,3-dioxide (Example Compound 114)

7-Aminomethyl-quinolin-8-amine (Intermediate 211) (50 mg, 0.29 mmol) and 1-(1H-imidazole-1-sulfonyl)-3-methyl-1H-imidazol-3-ium; trifluoromethanesulfonate (157 mg, 0.43 mmol) in MeCN (5 ml) was stirred at room temperature for 18 h. The reaction mixture was concentrated in vacuo. The crude residue was purified by preparative HPLC (basic conditions) to give the title compound (4.5 mg, 6%).

EOAI3343971 VIT-1621
MW: 235.36
HPLCMS (Method A): [m/z]: 236
The result is shown in FIG. 114
Route 22 (See Above)

General Procedure 53: N-Methylsulfamoyl Chloride (Intermediate 213)

Phosphorus pentachloride (5.62 g, 27 mmol) was added portionwise to a solution of methyl sulfamic acid (3.00 g, 27 mmol) in anhydrous toluene (30 ml) under a nitrogen atmosphere. The resulting solution was slowly heated to 85° C. and left to stir for 1 h. After cooling, the reaction was concentrated in vacuo to give the title compound (2.50 g, 71%). The compound could not be detected by HPLCMS therefore structure was confirmed by 1H NMR.

General Procedure 54:
(8-Nitro-quinolin-7-yl)-phenyl-methanol (Intermediate 214)

A solution of 8-nitro-quinoline-7-carbaldehyde (Intermediate 204) (1.14 g, 5.64 mmol) in dry THF (10 ml) was cooled to 0° C. in an ice bath. Bromo(phenyl)magnesium (1 M in THF; 5.64 ml) was added and the reaction mixture was stirred at room temperature for 30 min. The reaction was quenched with sat. ammonium chloride (10 ml) and the resulting organic phase was extracted with EtOAc (20 ml). The combined organic phases were washed with brine (10 ml), dried ($Na_2SO_4$) and concentrated in vacuo. The crude residue was purified by column chromatography with heptane/EtOAc (60:40) as the eluent, to give the title compound (1.09 g, 60%).

MW: 280.28
HPLCMS (Method B): [m/z]: 281

General Procedure 55:
(8-Amino-quinolin-7-yl)-phenyl-methanol (Intermediate 215)

Palladium on Carbon (10%, 38 mg) was added to a solution of (8-nitro-quinolin-7-yl)-phenyl-methanol (Intermediate 214) (500 mg, 1.78 mmol) in EtOH (20 ml) and the mixture was stirred under an atmosphere of hydrogen for 1.5 h. The mixture was diluted with MeOH (40 ml), filtered through celite and the filtrate was concentrated in vacuo to give the title compound (443 mg, 99%).
MW: 250.30
HPLCMS (Method B): [m/z]: 251

General Procedure 56: 2-Methyl-1-phenyl-1,4-dihydro-2H-3-thia-2,4,5-triaza-phenanthrene 3,3-dioxide (Example Compound 115)

N-Methylsulfamoyl chloride (414 mg, 3.2 mmol) was added to a suspension of (8-amino-quinolin-7-yl)-phenyl-methanol (Intermediate 215) (200 mg, 0.8 mmol) in pyridine (5 ml) and the reaction was stirred at room temperature for 16 h. The solution was concentrated in vacuo. The crude residue was purified by column chromatography, with heptane/EtOAc (90:10-50:50) gradient elution to give the title compound (20 mg, 8%).
EOAI3348392 VIT-1841
MW: 325.39
HPLCMS (Method A): [m/z]: 326
The result is shown in FIG. 115
Route 23 (See Above)

General Procedure 63: Bromo[4-(trifluoromethyl)phenyl]magnesium (Intermediate 336)

Iodine (56.4 mg, 0.22 mmol) was added to a solution of magnesium (0.22 g, 0.01 mol) and 1-bromo-4-(trifluoromethyl)benzene (0.62 ml, 4.44 mmol) in THF (20 ml) under nitrogen. The mixture was allowed to stir until the solution went clear yielding the title compound (1.11 g, 100%).

4-Fluoro-phenyl)-(8-nitro-quinolin-7-yl)-methanol (Intermediate 337

In a similar fashion using route 22 general procedure 54, 8-nitroquinoline-7-carbaldehyde (Intermediate 204) (0.5 g, 2.47 mmol), bromo(4-fluorophenyl)magnesium (1M in THF; 2.47 mmol, 2.47 ml) in THF (10 ml) gave the title compound (214 mg, 29%) after purification by column chromatography with DCM as the eluent.
MW: 298.27
HPLCMS (Method B): [m/z]: 298.95

8-Nitro-quinolin-7-yl)-p-tolyl-methanol (Intermediate 338

In a similar fashion using route 22 general procedure 54, 8-nitroquinoline-7-carbaldehyde (Intermediate 204) (0.5 g, 2.47 mmol) and bromo(4-methylphenyl)magnesium (1M in THF; 2.47 ml, 2.47 mmol)) in THF (10 ml) gave the title compound (490 mg, 67%) after purification by column chromatography with DCM/MeOH (100:0-90:10 gradient) as the eluent.
MW: 294.3
HPLCMS (Method B): [m/z]: 294.95

2-Methoxy-phenyl)-(8-nitro-quinolin-7-yl)-methanol (Intermediate 339)

In a similar fashion using route 22 general procedure 54, 8-nitroquinoline-7-carbaldehyde (Intermediate 204) (0.5 g, 2.47 mmol) and bromo(2-methoxyphenyl)magnesium (1M in THF; 2.47 ml, 2.47 mmol) in THF (10 ml) gave the title compound (434 mg, 57%) after purification by trituration from MeOH.
MW: 310.3
HPLCMS (Method B): [m/z]: 311.40

8-Nitro-quinolin-7-yl)-(4-trifluoromethyl-phenyl)-methanol (Intermediate 340)

In a similar fashion using route 22 general procedure 54, 8-nitroquinoline-7-carbaldehyde (Intermediate 204) (0.5 g, 2.47 mmol) and bromo[4-(trifluoromethyl)phenyl]magnesium (Intermediate 336) (0.45M in THF; 8.24 ml, 3.71 mmol) in THF (10 ml) gave the title compound (214 mg, 25%) after purification by column chromatography with heptane/EtOAc (70:30) as the eluent.
MW: 348.28
HPLCMS (Method B): [m/z]: 349

General Procedure 64: (8-Nitro-quinolin-7-yl)-(6-trifluoromethyl-pyridin-3-yl)-methanol (Intermediate 341)

n-BuLi (1.6M in hexane; 2.77 ml, 4.43 mmol) was added dropwise to a solution of 5-bromo-2-(trifluoromethyl)pyridine (1 g, 4.42 mmol) in THF (5 ml) at −78° C. The mixture was stirred at −78° C. for 30 min before 8-nitroquinoline-7-carbaldehyde (Intermediate 204) (0.89 g, 4.42 mmol) in THF (10 ml) was added and the mixture was stirred at −78° C. for 10 min. The mixture was quenched with sat. NH$_4$Cl (5 ml) at −78° C. and allowed to warm to room temperature. The resulting mixture was extracted with EtOAc (50 ml, ×2), the organic phase was washed with brine (20 ml), dried (Na$_2$SO$_4$) and concentrated in vacuo. The crude residue was purified by column chromatography with heptane/EtOAc (50:50) as the eluent to give the title compound (350 mg, 23%).
MW: 349.26
HPLCMS (Method B): [m/z]: 350.30

3-Fluoro-pyridin-4-yl)-(8-nitro-quinolin-7-yl)-methanol (Intermediate 342

In a similar fashion route 27 using general procedure 64, n-BuLi (1.6M in hexane; 3.55 ml, 5.68 mmol), 2-bromo-5-fluoropyridine (1 g, 5.68 mmol) and 8-nitroquinoline-7-carbaldehyde (Intermediate 204) (1.15 g, 5.68 mmol) in THF (30 ml) gave the title compound (141 mg, 8%) after purification by column chromatography with heptane/EtOAc (20:80) as the eluent.
MW: 299.26
HPLCMS (Method B): [m/z]: 300.25

General Procedure 65: (5-Fluoro-pyridin-2-yl)-(8-nitro-quinolin-7-yl)-methanol (Intermediate 343)

n-BuLi (1.6M in hexane; 5.5 ml, 8.9 mmol) was added to anhydrous toluene (35 ml) at −78° C. under an N$_2$ atmosphere followed by dropwise addition of a solution 2-bromo-5-fluoropyridine (1.56 g, 8.9 mmol) in anhydrous toluene (10 ml). The mixture was stirred at −78° C. for 45 min. The mixture was added to a solution of 8-nitroquinoline-7-carbaldehyde (Intermediate 204) (1 g, 5.0 mmol) in THF (50 ml) at −78° C. over 10 min. The mixture was stirred at −78° C. for a further 1 h. NH$_4$Cl solution (10 ml) was added at −78° C. and the mixture was warmed to room temperature. The solvent was removed in vacuo. The residue was dissolved in DCM (50 ml) and the organic phase was washed with sat. NaHCO$_3$ solution, dried (Na2SO4) and concentrated in vacuo. The crude residue was purified by column chromatography DCM/MeOH (99:1) as the eluent to give the title compound (700 mg, 46%).
MW: 299.26
HPLCMS (Method B):[m/z]: 299.95

General Procedure 66: (3-Fluoro-phenyl)-(8-nitro-quinolin-7-yl)-methanol (Intermediate 344)

3-Fluorophenyl magnesium bromide (1 M solution in THF; 0.86 ml, 4.33 mmol) was added dropwise to a solution of 8-nitroquinoline-7-carbaldehyde (Intermediate 204) (0.35 g, 1.73 mmol) in dry THF (5 ml) at −78° C. and the mixture was stirred at −78° C. for 1 h. The reaction was quenched with saturated NH$_4$Cl solution and the aqueous phase was extracted with EtOAc. The organic phase was washed with brine, dried (Na2SO4) and concentrated in vacuo. The crude residue was purified by column chromatography with DCM as the eluent to give the title compound (0.3 g, 58%).
MW: 297.28
HPLCMS (Method D): [m/z]: 298.28

4-Methoxy-phenyl)-(8-nitro-quinolin-7-yl)-methanol (Intermediate 345

In a similar fashion using route 27 general procedure 66, 8-nitroquinoline-7-carbaldehyde (Intermediate 204) (0.3 g, 1.48 mmol), 4-methoxy phenyl magnesium bromide (0.5 M solution in THF; 1.7 ml, 7.40 mmol) and dry THF (5 ml) gave the title compound (0.2 g, 45%) after purification by column chromatography with DCM as the eluent.
MW: 310.3
HPLCMS (Method D): [m/z]: 311.3

3-Chloro-4-fluoro-phenyl)-(8-nitro-quinolin-7-yl)-methanol (Intermediate 346)

In a similar fashion using route 27 general procedure 66, 8-nitroquinoline-7-carbaldehyde (Intermediate 204) (0.4 g, 1.9 mmol), 3-chloro-4-fluorophenyl magnesium bromide (0.5 M solution in THF; 3.1 ml, 13.3 mmol) and dry THF (10 ml) gave the title compound (0.2 g, 33%) after purification by column chromatography with DCM as the eluent.
MW: 332.7
HPLCMS (Method D): [m/z]: 333.7

3,4-Difluoro-phenyl)-(8-nitro-quinolin-7-yl)-methanol (Intermediate 347

In a similar fashion using route 27 general procedure 66, 8-nitroquinoline-7-carbaldehyde (Intermediate 204) (0.4 g, 1.9 mmol), 3,4-difluorophenyl magnesium bromide (0.5 M solution in THF; 3.12 ml, 13.9 mmol) and dry THF (10 ml) gave the title compound (0.4 g, 67%) after purification by column chromatography with DCM as the eluent.
MW: 316.3
HPLCMS (Method D): [m/z]: 317.3

8-Nitro-quinolin-7-yl)-(4-trifluoromethoxy-phenyl)-methanol (Intermediate 348

In a similar fashion using route 27 general procedure 66, 8-nitroquinoline-7-carbaldehyde (Intermediate 204) (0.4 g, 1.9 mmol), (4-trifluoromethoxy)phenyl magnesium bromide (0.5 M solution in THF; 3.10 ml, 13.3 mmol) and dry THF (10 ml) gave the title compound (0.2 g, 33%) after purification by column chromatography with DCM as the eluent.
MW: 348.3
HPLCMS (Method D): [m/z]: 349.3

2,4-Dimethoxy-phenyl)-(8-nitro-quinolin-7-yl)-methanol (Intermediate 349)

In a similar fashion using route 27 general procedure 66, 8-nitro-quinoline-7-carbaldehyde (Intermediate 204) (600 mg, 0.29 mmol), 2,4-dimethoxy phenyl magnesium bromide (0.5 M solution in THF; 41.6 ml, 20 mmol) and THF (15 ml) gave the title compound (700 mg, 59%) after purification by column chromatography with DCM as the eluent.
MW: 340.34
HPLCMS (Method F) [m/z]: 341.30

4-Fluoro-2-methyl-phenyl)-(8-nitro-quinolin-7-yl)-methanol (Intermediate 350)

In a similar fashion using route 27 general procedure 66, 8-nitro-quinoline-7-carbaldehyde (Intermediate 204) (700 mg, 3.47 mmol), 4-fluoro-2-methylphenyl magnesium bromide (0.5 M solution in THF; 13.9 ml, 6.93 mmol) and dry THF (70 ml) gave the title compound (610 mg, 56%) after purification by column chromatography with n-hexane/DCM (30:70) as the eluent.
MW: 312.3
HPLCMS (Method C) [m/z]: 313.3

3-Fluoro-4-methoxy-phenyl)-(8-nitro-quinolin-7-yl)-methanol (Intermediate 351

In a similar fashion using route 27 general procedure 66, 8-nitro-quinoline-7-carbaldehyde (Intermediate 204) (1.0 g, 4.9 mmol), 3-fluoro-4-methoxyphenyl magnesium bromide (0.5 M in THF; 2.2 g, 9.9 mmol) and THF (100 ml) at -50° C. for 1 h. gave the title compound (800 mg, 56%) after purification by column chromatography with n-hexane: DCM (30:70) as the eluent.
MW: 328.3
HPLCMS (Method C): [m/z]: 329.3

General Procedure 67: (4-Fluoro-phenyl)-(8-nitro-quinolin-7-yl)-methanone (Intermediate 352)

PDC (404 mg, 1.08 mmol) was added to a solution of (4-fluoro-phenyl)-(8-nitro-quinolin-7-yl)-methanol (Intermediate 337) (214 mg, 0.72 mmol) in DCM (10 ml). The mixture was heated to 30° C. and stirring was continued for 18 h. After cooling, the mixture was concentrated in vacuo. The crude residue was dissolved in toluene, filtered and concentrated in vacuo to give the title compound (160 mg, 75%).
MW: 296.25
HPLCMS (Method B): [m/z]: 296.95

8-Nitro-quinolin-7-yl)-p-tolyl-methanone (Intermediate 353

In a similar fashion using route 27 general procedure 67, (8-nitro-quinolin-7-yl)-p-tolyl-methanol (Intermediate 338) (490 mg, 1.66 mmol) and PDC (939 mg, 2.5 mmol) in DCM (20 ml) gave the title compound (269 mg, 55%) which was used in the next step without further purification.
MW: 292.29
HPLCMS (Method B): [m/z]: 293.35

2-Methoxy-phenyl)-(8-nitro-quinolin-7-yl)-methanone (Intermediate 354

In a similar fashion using route 27 general procedure 67, (2-methoxy-phenyl)-(8-nitro-quinolin-7-yl)-methanol (Intermediate 339) (434 mg, 1.4 mmol) and PDC (789 mg, 2.1 mmol) in DCM (20 ml) gave the title compound (296 mg, 69%) which was used in the next step without further purification.
MW: 308.29
HPLCMS (Method B): [m/z]: 308.95

8-Nitro-quinolin-7-yl)-(4-trifluoromethyl-phenyl)-methanone (Intermediate 355

In a similar fashion using route 27 general procedure 67, (8-nitro-quinolin-7-yl)-(4-trifluoromethyl-phenyl)-methanol (Intermediate 340) (214 mg, 0.61 mmol) and PDC (346.74 mg, 0.92 mmol) in DCM (10 ml) gave the title compound (140 mg, 66%) which was used in the next step without further purification.
MW: 346.26
HPLCMS (Method B): [m/z]: 346.95

8-Nitro-quinolin-7-yl)-(6-trifluoromethyl-pyridin-3-yl)-methanone (Intermediate 356

In a similar fashion using route 27 general procedure 67, (8-nitro-quinolin-7-yl)-(6-trifluoromethyl-pyridin-3-yl)-methanol 341 (350 mg, 1 mmol) and PDC (565.49 mg, 1.5 mmol) in DCM (30 ml) gave the title compound (296 mg, 85%) which was used in the next step without further purification.
MW: 347.25
HPLCMS (Method B): [m/z]: 347.95

3-Fluoro-pyridin-4-yl)-(8-nitro-quinolin-7-yl)-methanone (Intermediate 357

In a similar fashion using route 27 general procedure 67, (3-fluoro-pyridin-4-yl)-(8-nitro-quinolin-7-yl)-methanol (Intermediate 342) (141 mg, 0.47 mmol) and PDC (265 mg, 0.71 mmol) in DCM (10 ml) gave the title compound (100 mg, 71%) which was used in the next step without further purification.
MW: 297.24
HPLCMS (Method B): [m/z]: 297.90

5-Fluoro-pyridin-2-yl)-(8-nitro-quinolin-7-yl)-methanone (Intermediate 358

In a similar fashion using route 27 general procedure 67, (5-fluoro-pyridin-2-yl)-(8-nitro-quinolin-7-yl)-methanol (Intermediate 343) (900 mg, 3.0 mmol) and PDC (1.69 g, 4.5 mmol) in DCM (10 ml) gave the title compound (646 mg, 70%) which was used in the next step without further purification.
MW: 297.25
HPLCMS (Method B):[m/z]: 297.95

General Procedure 68: (3-Fluoro-phenyl)-(8-nitro-quinolin-7-yl)-methanone (Intermediate 359)

$MnO_2$ powder (0.87 g, 10 mmol) was added to a solution of (3-fluoro-phenyl)-(8-nitro-quinolin-7-yl)-methanol (Intermediate 344) (0.3 g, 1.01 mmol) in DCM (20 ml) and the mixture was stirred at room temperature for 18 h. The mixture was filtered through celite and the filtrate was concentrated in vacuo to give the title compound (0.25 g, 85%) which was used in the next step without further purification.
MW: 296.0
HPLCMS (Method C): [m/z]: 297.10

4-Methoxy-phenyl)-(8-nitro-quinolin-7-yl)-methanone (Intermediate 360

In a similar fashion using route 27 general procedure 68, (4-methoxy-phenyl)-(8-nitro-quinolin-7-yl)-methanol (Intermediate 345) (0.2 g, 0.65 mmol), $MnO_2$ powder (0.87 g, 3.22 mmol) and DCM (20 ml) gave the title compound (0.19 g, 97%) which was used in the next step without further purification.
MW: 308.28
HPLCMS (Method C): [m/z]: 309.28

3-Chloro-4-fluoro-phenyl)-(8-nitro-quinolin-7-yl)-methanone (Intermediate 361

In a similar fashion using route 27 general procedure 68, (3-chloro-4-fluoro-phenyl)-(8-nitro-quinolin-7-yl)-methanol (Intermediate 346) (0.2 g, 1.20 mmol), $MnO_2$ powder (1.05 g, 6.33 mmol) and DCM (20 ml) gave the title compound (0.2 g, 50%) which was used in the next step without further purification.
MW: 330.7
HPLCMS (Method C): [m/z]: 331.7

3,4-Difluoro-phenyl)-(8-nitro-quinolin-7-yl)-methanone (Intermediate 362)

In a similar fashion using route 27 general procedure 68, (3,4-difluoro-phenyl)-(8-nitro-quinolin-7-yl)-methanol (Intermediate 347) (0.4 g, 0.63 mmol), $MnO_2$ powder (1.56 g, 6.33 mmol) and DCM (20 ml) gave the title compound (0.4 g, 90%) which was used in the next step without further purification.
MW: 314.24
HPLCMS (Method C): [m/z]: 315.24

8-Nitro-quinolin-7-yl)-(4-trifluoromethoxy-phenyl)-methanone (Intermediate 363

In a similar fashion using route 27 general procedure 68, (8-nitro-quinolin-7-yl)-(4-trifluoromethoxy-phenyl)-methanol (Intermediate 348) (0.2 g, 1.20 mmol), $MnO_2$ powder (1.05 g, 6.33 mmol) and DCM (20 ml) gave the title compound (0.2 g, 50%) which was used in the next step without further purification.
MW: 349.3
HPLCMS (Method C): [m/z]: 350.3

2,4-Dimethoxy-phenyl)-(8-nitro-quinolin-7-yl)-methanone (Intermediate 364)

In a similar fashion using route 27 general procedure 68, (2,4-dimethoxy-phenyl)-(8-nitro-quinolin-7-yl)-methanol (Intermediate 349) (700 mg, 2.09 mmol), $MnO_2$ (1.78 g, 20 mmol) and DCM (15 ml) gave the title compound (550 mg, 79%) which was used in the next step without further purification.
MW: 338.32
HPLCMS (Method C) [m/z]: 339.3

General Procedure 69: (4-Fluoro-2-methyl-phenyl)-(8-nitro-quinolin-7-yl)-methanone (Intermediate 365)

PCC (667 mg, 3.1 mmol) was added to a solution of (4-fluoro-2-methyl-phenyl)-(8-nitro-quinolin-7-yl)-methanol (Intermediate 350) (690 mg, 2.21 mmol) in DCM (700 ml) and the mixture was stirred at room temperature for 2 h. The mixture was filtered through celite and the filtrate was concentrated in vacuo. The crude residue was purified by column chromatography with n-hexane/DCM (30:70) as the eluent to give the title compound (600 mg, 87%).
MW: 310.29
HPLCMS (Method C) [m/z]: 311.3

3-Fluoro-4-methoxy-phenyl)-(8-nitro-quinolin-7-yl)-methanone (Intermediate 366

In a similar fashion using route 27 general procedure 69, (3-fluoro-4-methoxy-phenyl)-(8-nitro-quinolin-7-yl)-methanol (Intermediate 351) (700 mg, 2.1 mmol), PCC (640 mg, 2.9 mmol) and DCM (700 ml) gave the title compound (600 mg, 85%) after purification by column chromatography with n-hexane: DCM (30:70) as the eluent.
MW: 326.2
HPLCMS (Method C): [m/z]: 327.5

8-Amino-quinolin-7-yl)-(4-fluoro-phenyl)-methanone (Intermediate 367

In a similar fashion using route 22 general procedure 55, (4-fluoro-phenyl)-(8-nitro-quinolin-7-yl)-methanone 352 (160 mg, 0.54 mmol) and 10% Pd—C (12 mg) in THF (10 ml) gave the title compound (115 mg, 80%) which was used in the next step without further purification.
MW: 266.27
HPLCMS (Method B): [m/z]: 267

8-Amino-quinolin-7-yl)-p-tolyl-methanone (Intermediate 368

In a similar fashion using route 22 general procedure 55, (8-nitro-quinolin-7-yl)-p-tolyl-methanone (Intermediate 353) (260 mg, 0.89 mmol) and 10% Pd—C (12 mg) in THF (15 ml) gave the title compound (180 mg, 77%) which was used in the next step without further purification.
MW: 262.31
HPLCMS (Method B): [m/z]: 263

8-Amino-quinolin-7-yl)-(2-methoxy-phenyl)-methanone (Intermediate 369

In a similar fashion using route 22 general procedure 55, (2-methoxy-phenyl)-(8-nitro-quinolin-7-yl)-methanone 354 (296 mg, 0.96 mmol) and 10% Pd—C (20 mg) in THF (15 ml) gave the title compound (152 mg, 57%) after purification by column chromatography with heptane/EtOAc (80:20) as the eluent.
MW: 278.31
HPLCMS (Method B): [m/z]: 279

8-Amino-quinolin-7-yl)-(4-trifluoromethyl-phenyl)-methanone (Intermediate 370

In a similar fashion using route 22 general procedure 55, (8-nitro-quinolin-7-yl)-(4-trifluoromethyl-phenyl)-methanone 355 (140 mg, 0.4 mmol) and 10% Pd—C (10 mg) in THF (10 ml) gave the title compound (40 mg, 31%) after purification by column chromatography with heptane/EtOAc (80:20) as the eluent.
MW: 316.28
HPLCMS (Method B): [m/z]: 317

8-Amino-quinolin-7-yl)-(6-trifluoromethyl-pyridin-3-yl)-methanone (Intermediate 371

In a similar fashion using route 22 general procedure 55, (8-nitro-quinolin-7-yl)-(6-trifluoromethyl-pyridin-3-yl)-methanone (Intermediate 356) (296 mg, 0.85 mmol) and 10% Pd—C (36 mg) in THF (10 ml) gave the title compound (100 mg, 37%) after purification by column chromatography with heptane/EtOAc (80:20) as the eluent.
MW: 317.27
HPLCMS (Method B): [m/z]: 317.95

8-Amino-quinolin-7-yl)-(3-fluoro-pyridin-4-yl)-methanone (Intermediate 372)

In a similar fashion using route 22 general procedure 55, (3-fluoro-pyridin-4-yl)-(8-nitro-quinolin-7-yl)-methanone (Intermediate 357) (100 mg, 0.34 mmol) and 10% Pd—C (20 mg) in THF (10 ml) gave the title compound (60 mg, 67%) after purification by column chromatography with heptane/EtOAc (70:30) as the eluent.
MW: 267.26
HPLCMS (Method B): [m/z]: 268.05

7-[(5-fluoropyridin-2-yl)carbonyl]-8-aminoquinoline (Intermediate 373)

In a similar fashion using route 22 general procedure 55, 7-[(5-fluoropyridin-2-yl)carbonyl]-8-nitroquinoline (Intermediate 358) (1.43 g, 4.9 mmol) and 10% Pd—C (200 mg) in THF (60 ml) gave the title compound (648 mg, 43%) which was used in the next step without further purification.
MW: 267.26
HPLCMS (Method B):[m/z]: 267.95

8-Amino-quinolin-7-yl)-(3-fluoro-phenyl)-methanone (Intermediate 374

In a similar fashion using route 22 general procedure 55, (3-fluoro-phenyl)-(8-nitro-quinolin-7-yl)-methanone (Intermediate 359) (0.25 g, 0.85 mmol) and 10% Pd—C (30 mg) in THF (15 ml) gave the title compound (0.11 g, 48%) after purification by column chromatography with hexane/DCM (30:70) as the eluent.
MW: 266.27
HPLCMS (Method C) [m/z]: 267.3

8-Amino-quinolin-7-yl)-(4-methoxy-phenyl)-methanone (Intermediate 375)

In a similar fashion using route 22 general procedure 55, (4-methoxy-phenyl)-(8-nitro-quinolin-7-yl)-methanone 360 (200 mg, 0.65 mmol), 10% Pd—C (25 mg) and THF(10 ml) gave the title compound (105 mg, 60%) after purification by column chromatography with hexane/DCM (30:70) as the eluent.
MW: 278.3
HPLCMS (Method C) [m/z]: 279.3

8-Amino-quinolin-7-yl)-(3-chloro-4-fluoro-phenyl)-methanone (Intermediate 376

In a similar fashion using route 22 general procedure 55, (3-chloro-4-fluoro-phenyl)-(8-nitro-quinolin-7-yl)-methanone (Intermediate 361) (150 mg, 0.45 mmol), 10% Pd—C (20 mg) and THF (10 ml) gave the title compound (90 mg, 66%) after purification by column chromatography with hexane/DCM (30:70) as the eluent.
MW: 300.7
HPLCMS (Method C) [m/z]: 301.7

8-Amino-quinolin-7-yl)-(3,4-difluoro-phenyl)-methanone (Intermediate 377)

In a similar fashion using route 22 general procedure 55, (3,4-difluoro-phenyl)-(8-nitro-quinolin-7-yl)-methanone (Intermediate 362) (400 mg, 0.64 mmol) 10% Pd—C (45 mg) and THF(10 ml) gave the title compound (210 mg, 65%) after purification by column chromatography with hexane/DCM (30:70) as the eluent.
MW: 284.3
HPLCMS (Method C) [m/z]: 285.3

8-Amino-quinolin-7-yl)-(4-trifluoromethoxy-phenyl)-methanone (Intermediate 378

In a similar fashion using route 22 general procedure 55, (8-nitro-quinolin-7-yl)-(4-trifluoromethoxy-phenyl)-methanone (Intermediate 363) (400 mg, 0.45 mmol), 10% Pd—C (40 mg) and THF (10 ml) gave the title compound (300 mg, 88%) after purification by column chromatography with hexane/DCM (30:70) as the eluent.
MW: 320.3
HPLCMS (Method C) [m/z]: 320.3

8-Amino-quinolin-7-yl)-(2,4-dimethoxy-phenyl)-methanone (Intermediate 379)

In a similar fashion using route 22 general procedure 55, (2,4-dimethoxy-phenyl)-(8-nitro-quinolin-7-yl)-methanone (Intermediate 364) (150 mg, 0.44 mmol) 10% Pd/C (15 mg) in MeOH:THF (3 ml:3 ml) gave the title compound (110 mg, 80%) which was used in the next step without further purification.
MW: 309.84
HPLCMS (Method C): [m/z]: 310

8-Amino-quinolin-7-yl)-(4-fluoro-2-methyl-phenyl)-methanone (Intermediate 380

In a similar fashion using route 22 general procedure 55, (4-fluoro-2-methyl-phenyl)-(8-nitro-quinolin-7-yl)-methanone (Intermediate 365) (600 mg, 1.94 mmol), 10% palladium on carbon (60 mg) and THF (30 ml) gave the title compound (400 mg, 73%) after purification by column chromatography with n-hexane/DCM (30:70) as the eluent.
MW: 280.3
HPLCMS (Method C) [m/z]: 281.3

8-Amino-quinolin-7-yl)-(3-fluoro-4-methoxy-phenyl)-methanone (Intermediate 381

In a similar fashion using route 22 general procedure 55, (3-fluoro-4-methoxy-phenyl)-(8-nitro-quinolin-7-yl)-methanone (Intermediate 366) (600 mg, 1.84 mmol), 10% palladium on carbon (60 mg) and THF(10 ml) gave the title compound (400 mg, 80%) after purification by column chromatography with n-hexane/DCM (40:60) as the eluent.
MW: 296.3
HPLCMS (Method C) [m/z]: 297.3

General Procedure 70: 1-(4-Fluoro-phenyl)-2-methyl-1,4-dihydro-2H-3-thia-2,4,5-triaza-phenanthrene 3,3-dioxide (Example Compound 382)

N-Methylsulfamoyl chloride (Intermediate 213) (161 mg, 1.24 mmol) was added to suspension of (8-amino-quinolin-7-yl)-(4-fluoro-phenyl)-methanone (Intermediate 367) (110 mg, 0.41 mmol) in pyridine (10 ml) and the mixture was stirred room temperature for 18 h. $NaBH_4$ (16 mg, 0.41 mmol) was added and the mixture was stirred at room temperature for a further 18 h. The reaction was quenched with water (20 ml) and the aqueous phase was extracted with EtOAc (30 ml). The organic phase was washed with brine (15 ml), dried ($Na_2SO_4$) and concentrated n vacuo. The crude residue was purified by column chromatography heptane/EtOAc (80:20-50:50 gradient) as the eluent to give the title compound (20 mg, 14%).
EOAI3350579 VIT-1895
MW: 343.38
HPLCMS (Method A): [m/z]: 344.10

2-Methyl-1-p-tolyl-1,4-dihydro-2H-3-thia-2,4,5-triaza-phenanthrene 3,3-dioxide (Example Compound 383)

In a similar fashion using route 27 general procedure (Intermediate 70), (8-amino-quinolin-7-yl)-p-tolyl-methanone (Intermediate 368) (180 mg, 0.69 mmol), N-methylsulamoyl chloride (Intermediate 213) (267 mg, 2.06 mmol) and $NaBH_4$ (26 mg, 0.69 mmol) in pyridine (10 ml) gave the title compound (12 mg, 5%) after purification by column chromatography with heptane/EtOAc (80:20-50:50) as the eluent.
EOAI3351292 VIT-1934
MW: 339.41
HPLCMS (Method A): [m/z]: 340

1-(2-Methoxy-phenyl)-2-methyl-1,4-dihydro-2H-3-thia-2,4,5-triaza-phenanthrene 3,3-dioxide (Example Compound 384)

In a similar fashion using route 27 general procedure 70, (8-amino-quinolin-7-yl)-(2-methoxy-phenyl)-methanone (Intermediate 369) (152 mg, 0.55 mmol), N-methylsulamoyl chloride (Intermediate 213) (212 mg, 1.64 mmol) and $NaBH_4$ (21 mg, 0.55 mmol) in pyridine (10 ml) gave the title compound (85 mg, 44%) after trituration from MeOH.
EOAI3352086 VIT-1942
MW: 355.41
HPLCMS (Method A): [m/z]: 356.40

2-Methyl-1-(4-trifluoromethyl-phenyl)-1,4-dihydro-2H-3-thia-2,4,5-triaza-phenanthrene 3,3-dioxide (Example Compound 385)

In a similar fashion using route 27 general procedure (Intermediate 70), (8-amino-quinolin-7-yl)-(4-trifluoromethyl-phenyl)-methanone (Intermediate 370) (40 mg, 0.13 mmol), N-methylsulamoyl chloride (Intermediate 213) (49 mg, 0.38 mmol) and $NaBH_4$ (4.8 mg, 0.13 mmol) in pyridine (5 ml) gave the title compound (34 mg, 68%) after purification by preparative HPLC (acidic conditions 1).
EOAI3358830 VIT-2063
MW: 393.38
HPLCMS (Method A): [m/z]: 394.10

2-Methyl-1-(6-trifluoromethyl-pyridin-3-yl)-1,4-dihydro-2H-3-thia-2,4,5-triaza-phenanthrene 3,3-dioxide (Example Compound 386)

In a similar fashion using route 27 general procedure 70, (8-amino-quinolin-7-yl)-(6-trifluoromethyl-pyridin-3-yl)-methanone (Intermediate 371) (100 mg, 0.32 mmol), N-methylsulfamoyl chloride (Intermediate 213) (49 mg, 0.38 mmol) and NaBH$_4$ (12 mg, 0.315 mmol) in pyridine (5 ml) gave the title compound (65 mg, 52%) after purification by preparative HPLC (acidic conditions 1).
EOAI3360126 VIT-2115
MW: 394.37
HPLCMS (Method A): [m/z]: 395.20

1-(3-Fluoro-pyridin-4-yl)-2-methyl-1,4-dihydro-2H-3-thia-2,4,5-triaza-phenanthrene 3,3-dioxide (Example Compound 387)

In a similar fashion using route 27 general procedure 70, (8-amino-quinolin-7-yl)-(3-fluoro-pyridin-4-yl)-methanone (Intermediate 372) (60 mg, 0.22 mmol), N-methylsulfamoyl chloride (Intermediate 213) (87 mg, 0.67 mmol) and NaBH4 (8.5 mg, 0.22 mmol) in pyridine (5 ml) gave the title compound (24 mg, 31%).
EOAI3363869 VIT-2128
MW: 344.36
HPLCMS (Method A): [m/z]: 345.30

1-(5-Fluoro-pyridin-2-yl)-2-methyl-1,4-dihydro-2H-3-thia-2,4,5-triaza-phenanthrene 3,3-dioxide (Example Compound 388)

In a similar fashion using route 27 general procedure 70, 7-[(5-fluoropyridin-2-yl)carbonyl]-8-aminoquinoline (Intermediate 373) (648 mg, 2.4 mmol), N-methylsulfamoyl chloride (Intermediate 213) (942 mg, 7.2 mmol) and NaBH4 (92 mg, 2.4 mmol) in pyridine (10 ml) gave the title compound (57 mg, 2.2%) after purification by preparative HPLC (acidic conditions).
EOAI3363829 VIT-2241
MW: 344.37
HPLCMS (Method A):[m/z]: 344.95

1-(3-Fluoro-phenyl)-2-methyl-1,4-dihydro-2H-3-thia-2,4,5-triaza-phenanthrene 3,3-dioxide (Example Compound 389)

In a similar fashion using route 27 general procedure 70, (8-amino-quinolin-7-yl)-(3-fluoro-phenyl)-methanone (Intermediate 374) (100 mg, 0.38 mmol), N-methylsulfamoyl chloride (Intermediate 213) (146 mg, 1.13 mmol) and NaBH4 (14 mg, 0.38 mmol) in pyridine (3 ml) gave the title compound (50 mg, 39%) after purification by preparative HPLC (acidic conditions 1).
EOAI3362738 VIT-2211
MW: 343.38
HPLCMS (Method A): [m/z]: 344

1-(4-Methoxy-phenyl)-2-methyl-1,4-dihydro-2H-3-thia-2,4,5-triaza-phenanthrene 3,3-dioxide (Example Compound 390)

In a similar fashion using route 27 general procedure 70, (8-amino-quinolin-7-yl)-(4-methoxy-phenyl)-methanone (Intermediate 375) (95 mg, 0.34 mmol), N-methylsulfamoyl chloride (Intermediate 213) (133 mg, 1.02 mmol) and NaBH4 (13 mg, 0.34 mmol) in pyridine (5 ml) gave the title compound (8 mg, 7%) after purification by preparative HPLC (acidic conditions 1).
EOAI3362737 VIT-2210
MW: 355.41
HPLCMS (Method A): [m/z]: 356

1-(3-Chloro-4-fluoro-phenyl)-2-methyl-1,4-dihydro-2H-3-thia-2,4,5-triaza-phenanthrene 3,3-dioxide (Example Compound 391)

In a similar fashion using route 27 general procedure 70, (8-amino-quinolin-7-yl)-(3-chloro-4-fluoro-phenyl)-methanone (Intermediate 376) (80 mg, 0.27 mmol), N-methylsulfamoyl chloride (Intermediate 213) (103 mg, 0.8 mmol) and NaBH4 (10 mg, 0.27 mmol) in pyridine (3 ml) gave the title compound (35 mg, 35%) after purification by preparative HPLC (acidic conditions 1).
EOAI3363443 VIT-2228
MW: 377.82
HPLCMS (Method A): [m/z]: 377.95

1-(3,4-Difluoro-phenyl)-2-methyl-1,4-dihydro-2H-3-thia-2,4,5-triaza-phenanthrene 3,3-dioxide (Example Compound 392)

In a similar fashion using route 27 general procedure 70, 7-[(3, 4difluorophenyl)carbonyl]-8-aminoquinoline (Intermediate 377) (100 mg, 0.35 mmol), N-methylsulfamoyl chloride (Intermediate 213) (105 mg, 1.0 mmol) and NaBH4 (14 mg, 0.34 mmol) in pyridine (4 ml) gave the title compound (62 mg, 47%) after purification by preparative HPLC (acidic conditions 1).
EOAI3363827 VIT-2242
MW: 361.37
HPLCMS (Method A):[m/z]: 361.95

2-Methyl-1-(4-trifluoromethoxy-phenyl)-1,4-dihydro-2H-3-thia-2,4,5-triaza-phenanthrene 3,3-dioxide (Example Compound 393)

In a similar fashion using route 27 general procedure 70, 7[(4-trifluoromethoxyphenyl)carbonyl]-8-aminoquinoline (Intermediate 378) (100 mg, 0.31 mmol), N-methylsulfamoyl chloride (Intermediate 213) (105 mg, 1.0 mmol) and NaBH4 (14 mg, 0.34 mmol) in pyridine (4 ml) gave the title compound (70 mg, 56%) after purification by preparative HPLC (acidic conditions 1).
EOAI3363828 VIT-2243
MW: 409.39
HPLCMS (Method A):[m/z]: 410

General Procedure 71: 1-(2,4-Dimethoxy-phenyl)-2-methyl-1,4-dihydro-2H-3-thia-2,4,5-triaza-phenanthrene 3,3-dioxide (Example Compound 394)

N-methylsulfamyl chloride (Intermediate 213) (504 mg, 3.88 mmol) was added dropwise to a solution of (8-amino-quinolin-7-yl)-(2,4-dimethoxy-phenyl)-methanone (Intermediate 379) (200 mg, 0.65 mmol) in dry pyridine (10 ml) at 0° C. and the mixture was stirred at room temperature for 36 h (additional equivalents of methylsulfamyl choride were added as required after 24 h). After completion of the reaction (monitored by LCMS), NaBH4 (95 mg, 2.58 mmol) was added and reaction was stirred at room temperature for 18 h. The reaction was quenched with water, concentrated in vacuo and the residue was extracted with EtOAc. The organic phase was washed with brine, dried (Na2SO4) and concentrated in vacuo. The crude residue was purified by column chromatography with DCM/MeOH (99:1) as the eluent to give the title compound (40 mg, 16%).
EOAI3366421 VIT-2356
MW: 385.44
HPLCMS (Method F):[m/z]: 386.4

1-(4-Fluoro-2-methyl-phenyl)-2-methyl-1,4-dihydro-2H-3-thia-2,4,5-triaza-phenanthrene 3,3-dioxide (Example Compound 395)

In a similar fashion using route 27 general procedure 71, (8-amino-quinolin-7-yl)-(4-fluoro-2-methyl-phenyl)-methanone (Intermediate 380) (200 mg, 0.71 mmol), N-methylsulfamyl chloride (Intermediate 213) (700 mg, 5.4 mmol), NaBH4 (81 mg, 2.14 mmol) and pyridine (6 ml) gave the title compound (40 mg, 16%) after purification by preparative HPLC (neutral conditions).
EOAI3366861 VIT-2375
MW: 357.4
HPLCMS (Method F) [m/z]: 358.3

1-(3-Fluoro-4-methoxy-phenyl)-2-methyl-1,4-dihydro-2H-3-thia-2,4,5-triaza-phenanthrene 3,3-dioxide (Example Compound 396)

In a similar fashion using route 27 general procedure 71, (8-amino-quinolin-7-yl)-(3-fluoro-4-methoxy-phenyl)-methanone (Intermediate 381) (200 mg, 0.6 mmol), N-methylsulfamyl chloride (Intermediate 213) (260 mg, 2.0 mmol), NaBH4 (76 mg, 2.0 mmol) and pyridine (2 ml) gave the title compound (130 mg, 52%) after purification by column chromatography with n-hexane/EtOAc (50:50) as the eluent.
EOAI3366690 VIT-2363
MW: 373.4
HPLCMS (Method F) [m/z]: 374.4
Route 24 (See Above)

General Procedure 72: 1-(4-Fluoro-phenyl)-2-methyl-1,4,5,6,7,8-hexahydro-2H-3-thia-2,4,5-triaza-phenanthrene 3,3-dioxide (Example Compound 397)

N-methylsulfamoyl chloride 213 (729.9 mg, 5.63 mmol) was added to a solution of (8-amino-quinolin-7-yl)-(4-fluoro-phenyl)-methanone 367 (500 mg, 1.88 mmol) in pyridine (20 ml) and the mixture was stirred at room temperature for 18 h. NaBH4 (213 mg, 5.63 mmol) was added and stirring was continued at room temperature for 16 h. The reaction was quenched by the addition of water (20 ml) and the aqueous phase was extracted with EtOAc (30 ml). The organic phase was washed with brine (15 ml), dried (Na2SO4) and concentrated n vacuo. The crude residue was purified by column chromatography with heptane/EtOAc as the eluent to give the title compound (12 mg, 2%).
EOAI3356906 VIT-2013
MW: 347.41
HPLCMS (Method A): [m/z]: 348.05
Route 29 (See Above)

General Procedure 73: 1-(4-Fluoro-phenyl)-1,4-dihydro-2H-3-thia-2,4,5-triaza-phenanthrene 3,3-dioxide (Example Compound 398)

(8-Amino-quinolin-7-yl)-(4-fluoro-phenyl)-methanone 367 (100 mg, 0.38 mmol) and sulfamide (361 mg, 3.76 mmol) in pyridine (3 ml) and were heated in a microwave at 140° C. for 2 h. After cooling, the mixture was concentrated in vacuo. The residue was dissolved in anhydrous THF (5 ml). LiAlH4 (26 mg, 0.75 mmol) was added and the mixture was stirred at room temperature for 18 h. The reaction was quenched with water (5 ml) and the resulting precipitate was collected by filtration and dried. The crude solid was purified by preparative HPLC (acidic conditions 1) to give the title compound (27 mg, 22%).
EOAI3359191 VIT-2087
MW: 329.35
HPLCMS (Method A): [m/z]: 330
Route 30 (See Above)

General Procedure 74: 9-Bromo-1-(4-fluoro-phenyl)-2-methyl-1,4-dihydro-2H-3-thia-2,4,5-triaza-phenanthrene 3,3-dioxide (Example Compound 399)

Bromine (7.48 µl, 0.15 mmol) was added to a solution of 1-(4-fluoro-phenyl)-2-methyl-1,4-dihydro-2H-3-thia-2,4,5-triaza-phenanthrene 3,3-dioxide 382 (50 mg, 0.15 mmol) in dioxane:chloroform (1:1, 4 ml) at 0° C. and the mixture was stirred at 0° C. for 1 h. The resulting precipitate was collected by filtration and dried. The resulting solid was triturated from MeOH to give the title compound (17 mg, 28%).
EOAI3360128 VIT-2129
MW: 422.27
HPLCMS (Method A): [m/z]: 423.75
Route 31 (See Above)

General Procedure 75: (8-Amino-5-chloro-quinolin-7-yl)-(4-fluoro-phenyl)-methanone (Intermediate 400)

N-Chlorosuccinimide (0.12 g, 0.93 mmol) was added to a solution of (8-amino-quinolin-7-yl)-(4-fluoro-phenyl)-methanone 367 (0.25 g, 0.93 mmol) in CCl4 (3 ml) followed by HCl (cat) and the mixture was heated at 80° C. for 4 h. After cooling, the mixture was quenched with water and the aqueous phase was extracted with EtOAc. The organic phase was washed with brine, dried (Na2SO4) and concentrated in vacuo. The crude residue was purified by column chromatography with DCM as the eluent to give the title compound (0.1 g, 43%).
MW: 300.72
HPLCMS (Method D): [m/z]: 300.72

9-Chloro-1-(4-fluoro-phenyl)-2-methyl-1,4-dihydro-2H-3-thia-2,4,5-triaza-phenanthrene 3,3-dioxide (Example Compound 401)

In a similar fashion using route 27 general procedure 70, (8-amino-5-chloro-quinolin-7-yl)-(4-fluoro-phenyl)-methanone 400 (105 mg, 0.34 mmol), N-methylsulfamoyl chloride 213 (135 mg, 1.0 mmol) and NaBH4 (14 mg, 0.34 mmol) in pyridine (4 ml) gave the title compound (57 mg, 44%) after purification by preparative HPLC (acidic conditions 1).
EOAI3362468 VIT-2202
MW: 377.83
HPLCMS (7 min):[m/z]: 377.95, 4.67 min.
Route 32 (See Above)

General Procedure 76: 1-[1-(4-Fluoro-phenyl)-2-methyl-3,3-dioxo-1,2,3,4-tetrahydro-3λ*6*-thia-2,4,5-triazaphenanthren-9-yl]-ethanone (Example Compound 402)

DMF (2.6 ml) and water (0.6 ml) in a microwave tube were degassed with N2. 9-Bromo-1-(4-fluoro-phenyl)-2-methyl- 1,4-dihydro-2H-3-thia-2,4,5-triaza-phenanthrene 3,3-dioxide 399 (100 mg, 0.27 mmol), Pd(OAc)2 (10.6 mg, 0.047 mmol), 1,3-bis(diphenylphosphino)propane (39 mg, 0.09 mmol) and K2CO3 (39 mg, 0.28 mmol) and n-butyl vinylether (154 µl, 1.1 mmol). The mixture was heated in a microwave at 100° C. (200 W, <250 PSi) for 40 min. After cooling, the mixture was diluted with THF (5 ml), acidified with conc. HCl (1 ml) and the mixture was stirred at room temperature for 14 h. The organic phase was diluted with DCM (30 ml), and washed with HCl solution at pH=5-6 (20 ml). The organic phase was dried (Na2SO4) and concentrated in vacuo. The crude residue was purified by column chromatography with DCM/EtOAc (95:5) to give the title compound (17 mg, 15%).
EOAI3361317 VIT-2187
MW: 385.42
HPLCMS (Method A):[m/z]: 386

General Procedure 77: 1-[1-(4-Fluoro-phenyl)-2-methyl-3,3-dioxo-1,2,3,4-tetrahydro-3λ*6*-thia-2,4,5-triazaphenanthren-9-yl]-ethanol (Example Compound 403)

Dimethylamine (2.0M in THF; 65 µl, 0.13 mmol) was added to a solution of 1-(6,6-dioxo-5,6-dihydro-6λ*6*-thia-4,5-diaza-chrysen-12-yl)-ethanone 402 (50 mg, 0.13 mmol) in EtOH (2 ml) followed by Ti(OiPr)4 (37 µl, 0.13 mmol) and the mixture was stirred at room temperature for 18 h. The mixture was cooled to 0° C. and NaBH4 (5 mg, 0.13 mmol) was added. After 1 hr, additional NaBH4 (5 mg, 0.13 mmol) was added at 0° C. and the mixture was stirred at room temperature for 18 h. Further NaBH4 (10 mg, 0.26 mmol) was added at 0° C. and stirring continued at room temperature 24 h. The reaction was quenched with sat. NH4Cl solution (5 ml) and the aqueous phase was extracted with DCM and concentrated in vacuo. The crude residue was purified by preparative HPLC (acidic conditions 1) to give the title compound (14 mg, 27%).
EOAI3362736 VIT-2212
MW: 387.44
HPLCMS (Method A):[m/z]: 388.05
Route 33 (See Above)

General Procedure 78:
8-Amino-quinoline-7-carbaldehyde (Intermediate 404)

8-nitroquinoline-7-carbaldehyde 204 (100 mg, 0.49 mmol), iron powder (0.02 ml, 4.95 mmol) and conc. HCl (2 drops) was suspended in a mixture of EtOH/AcOH/water (2:2:1) and the mixture was heated under reflux for 15 min and then stirred at room temperature for 25 min. The mixture was filtered and the filtrate was concentrated in vacuo. The residue was diluted with EtOAc and washed with sat. NaHCO3 solution until the pH remained neutral. The organic phase was purified by column chromatography with heptane/EtOAc (80:20) as the eluent to yield the title compound (650 mg, 38%).
MW: 172.18
HPLCMS (Method B): [m/z]: 172.95

2-Methyl-1,4-dihydro-2H-3-thia-2,4,5-triaza-phenanthrene 3,3-dioxide (Example Compound 405)

In a similar fashion using route 27 general procedure 70, 8-amino-quinoline-7-carbaldehyde (100 mg, 0.58 mmol), N-methylsulfamoyl chloride (226 mg, 1.74 mmol), NaBH4 (22 mg, 0.58 mmol) and pyridine (1 ml) gave the title compound (20 mg, 14%) after purification by column chromatography with heptane/EtOAc (90:10) as the eluent.
EOAI3365608 VIT-2304
MW: 249.29
HPLCMS (Method A): [m/z]: 250
Route 34 (See Above)

General Procedure 79:
4H-3-Thia-2,4,5-triaza-phenanthrene 3,3-dioxide (Intermediate 406)

8-Amino-quinoline-7-carbaldehyde 404 (100 mg, 0.58 mmol) and sulfamide (558 mg, 5.81 mmol) in pyridine (2 ml) was heated in a microwave at 140° C. for 2 h. After cooling, the mixture was concentrated in vacuo. The crude residue was dissolved in DCM and neutralised with citric acid. The resulting precipitate was collected by filtration and dried to give the title compound (111 mg, 82%) which was used in the next step without further purification.
MW: 233.25
HPLCMS (Method B): [m/z]: 233.90

General Procedure 80: 1-Methyl-1,4-dihydro-2H-3-thia-2,4,5-triaza-phenanthrene 3,3-dioxide (Example Compound 407)

Ethoxyethane—trifluoroborane (1:1; 32.3 µl, 0.26 mmol) was added dropwise to a solution of 4H-3-thia-2,4,5-triaza-phenanthrene 3,3-dioxide 406 (60 mg, 0.26 mmol) in dry THF (3 ml) under an atmosphere of N2. The mixture was stirred at room temperature for 1 h and then cooled to −78° C. Methyllithium (1.6M in Et2O; 1.61 ml, 2.57 mmol) was added dropwise and the mixture was stirred −78° C. for 1 h. The reaction was quenched with sat NH4Cl (2 ml) at -78° C. and the mixture was warmed to room temperature. The mixture was extracted with EtOAc and the residue was purified by preparative HPLC (acidic conditions 1) to give the title compound (18 mg, 28%).
EOAI3366613 VIT-2362
MW: 249.29
HPLCMS (Method A): [m/z]: 250
Route 35 (See Above)

1-(8-Amino-quinolin-7-yl)-propan-1-ol (Intermediate 408)

In a similar fashion using route 27 general procedure 66, 8-amino-quinoline-7-carbaldehyde 404 (1 g, 5.83 mmol), ethyl magnesium bromide (3M in THF; 5.81 ml, 17.44 mmol) and THF (30 ml) gave the title compound (900 mg, 91%) after purification by column chromatography with DCM/MeOH (99:1) as the eluent.
MW: 202.26
HPLCMS (Method F) [m/z]: 203.2

1-(8-Nitro-quinolin-7-yl)-ethanol (Intermediate 409)

In a similar fashion using route 27 general procedure 66, 8-amino-quinoline-7-carbaldehyde 404 (350 mg, 2.03 mmol), methyl magnesium bromide (3M solution in THF; 2.03 ml, 6.10 mmol) and dry THF (10 ml) gave the title compound (200 mg, 52%) which was used in the next step without further purification.
MW: 188.23
HPLCMS (Method C) [m/z]: 189.2

1-(8-Amino-quinolin-7-yl)-propan-1-one (Intermediate 410)

In a similar fashion using route 27 general procedure 68, 1-(8-amino-quinolin-7-yl)-propan-1-ol 408 (1.0 g, 4.95 mmol), MnO2 powder (4.3 g, 49.5 mmol) and DCM (10 ml) gave the title compound (800 mg, 80%) which was used in the next step without further purification.
MW: 200.24
HPLCMS (Method C) [m/z]: 201.2

1-(8-Amino-quinolin-7-yl)-ethanone (Intermediate 411)

In a similar fashion using route 27 general procedure 68, 1-(8-nitro-quinolin-7-yl)-ethanol 409 (200 mg, 1.06 mmol), MnO2 (925 mg, 10.63 mmol) and DCM (5 ml) gave the title compound (150 mg, 78%) which was used in the next step without further purification.
MW: 186.22
HPLCMS (Method C) [m/z]: 187.2

1-Ethyl-2-methyl-1,4-dihydro-2H-3-thia-2,4,5-triaza-phenanthrene 3,3-dioxide (Example Compound 412)

In a similar fashion using route 27 general procedure 71, 1-(8-amino-quinolin-7-yl)-propan-1-one 410 (300 mg, 1.6 mmol), N-methylsulfamyl chloride 213 (1 g, 7.7 mmol) and NaBH4 (20 mg, 0.54 mmol) gave the title compound (40 mg, 10%) after purification by column chromatography with DCM/MeOH (99:1) as the eluent.
EOAI3366144 VIT-2348
MW: 277.35
HPLCMS (Method E) [m/z]: 278.3

1,2-Dimethyl-1,4-dihydro-2H-3-thia-2,4,5-triaza-phenanthrene 3,3-dioxide (Example Compound 413)

In a similar fashion using route 27 general procedure 71, 1-(8-amino-quinolin-7-yl)-ethanone 411 (200 mg, 1.07 mmol), N-methylsulfamyl chloride 213 (700 mg, 5.40 mmol), NaBH4 (79 mg, 2.13 mmol) and pyridine (10 ml) gave the title compound (40 mg, 13%) after purification by column chromatography with DCM/MeOH (99:1) as the eluent.
EOAI3366420 VIT-2355
MW: 263.32
HPLCMS (Method E) [m/z]: 264.3
Route 36 (See Above)

4-Fluoro-phenyl)-(8-nitro-quinolin-7-yl)-methanol (Intermediate 337

In a similar fashion using route 27 general procedure 66, 8-nitro-quinoline-7-carbaldehyde 204 (12 g, 59.4 mmol), 4-fluorophenyl magnesium bromide (1 M solution in THF; 58.2 ml, 297 mmol) and dry THF (50 ml) gave the title compound (10 g, 45%) after purification by column chromatography with n-hexane/EtOAc as the eluent.
MW: 297.28
HPLCMS (Method C): [m/z]: 298.28

4-Fluoro-phenyl)-(8-nitro-quinolin-7-yl)-methanone (Intermediate 352

In a similar fashion using route 27 general procedure 68, (4-fluoro-phenyl)-(8-nitro-quinolin-7-yl)-methanol 337 (1.6 g, 5.36 mmol), MnO2 powder (4.67 g, 53.7 mmol) and DCM (20 ml) gave the title compound (7.8 g, 98%) which was used in the next step without further purification.
MW: 296.0
HPLCMS (Method C): [m/z]: 297.0

General Procedure 81: N-[1-(8-Amino-quinolin-7-yl)-1-(4-fluoro-phenyl)-meth-(E)-ylidene]-N',N'-dimethyl-ethane-1,2-diamine (Intermediate 414)

N,N dimethylethylenediamine (2.5 ml, 3.37 mmol) and Ti(OEt)4 (1.16 ml, 5.46 mmol) were added to a solution of (4-fluoro-phenyl)-(8-nitro-quinolin-7-yl)-methanone 352 (400 mg, 1.35 mmol) in DCM/THF(10 ml:40 ml) under an argon atmosphere and the mixture was stirred at room temperature for 18 h. The mixture was poured into EtOAc/brine and the resulting solution was filtered through celite. The solid residue was washed with EtOAc. The combined organic phases were washed with brine, dried (Na2SO4) and concentrated in vacuo to give the title compound (414 mg, 91%) which was used in the next step without further purification.
MW: 336.4
HPLCMS (Method C):[m/z]: 338.37

General Procedure 82: N-[(8-Amino-quinolin-7-yl)-(4-fluoro-phenyl)-methyl]-N',N'-dimethyl-ethane-1,2-diamine (Intermediate 415)

NaBH4 (181 mg, 4.9 mmol) was added to a solution of N-[1-(8-amino-quinolin-7-yl)-1-(4-fluoro-phenyl)-meth-(E)-ylidene]-N',N'-dimethyl-ethane-1,2-diamine 414 (550 mg, 1.63 mmol) in EtOH (12 ml) at 0° C. and the mixture was heated at 80° C. for 4 h. After cooling, the reaction was quenched with water and the aqueous phase was extracted with EtOAc. The organic phase was washed with brine, dried (Na2SO4) and concentrated in vacuo. The crude residue was purified by column chromatography with DCM/MeOH (97:3) to give the title compound (420 mg, 75%).
MW: 338.4
HPLCMS (Method C): [m/z]: 340.40

General Procedure 83: {2-[1-(4-Fluoro-phenyl)-3,3-dioxo-3,4-dihydro-1H-3λ*6*-thia-2,4,5-triaza-phenanthren-2-yl]-ethyl}-dimethyl-amine (Example Compound 416)

Sulfamide (272 mg, 2.84 mmol) was added to a solution of N-[(8-amino-quinolin-7-yl)-(4-fluoro-phenyl)-methyl]-N',N'-dimethyl-ethane-1,2-diamine 415 (160 mg, 0.47 mmol) in pyridine (1.5 ml) and the mixture was heated at 120° C. for 1.5 h in a sealed tube. After cooling, the solvent was removed in vacuo. The crude residue was purified by column chromatography with DCM/MeOH (98:2) to give the title compound (35 mg, 18%).
EOAI3366860 VIT-2374
MW: 400.48
HPLCMS (Method E): [m/z]: 401.40
Route 37 (See Above)

General Procedure 84: 2-(5-Bromo-2-fluoro-phenyl)-[1,3]dioxolane (Intermediate 417)

To a 3 neck round bottom flask, fitted with a Dean-Stark apparatus, was added 5-bromo-2-fluorobenzaldehyde (5 g, 24.6 mmol), ethane-1,2-diol (4.12 ml, 73.9 mmol), and p-toluenesulfonic acid (424 mg, 2.46 mmol). The resulting mixture was placed under nitrogen, dissolved in anhydrous toluene (100 ml) and heated under reflux for 18 h. After cooling, the mixture was concentrated in vacuo. The residue was diluted with EtOAc (50 ml) and the organic phase was washed with sat. NaHCO3 solution (30 ml), brine (30 ml), dried (Na2SO4) and concentrated in vacuo. The crude residue was purified by column chromatography with heptane/EtOAc (95:5) as the eluent to give the title compound (4.69 g, 77%). The structure was confirmed by 1H NMR.

General Procedure 85 and 86: (3-[1,3]Dioxolan-2-yl-4-fluoro-phenyl)-(8-nitro-quinolin-7-yl)-methanol (Intermediate 418)

Magnesium (983 mg, 40.5 mmol) was suspended in anhydrous THF (30 ml). 1,2-dibromoethane (0.17 ml, 2.02 mmol) was added and the solution was stirred at room temperature for 20 min. 2-(5-bromo-2-fluoro-phenyl)-[1,3]dioxolane 417 (3.2 g, 12.95 mmol) was added dropwise and the mixture was heated at 40° C. for 2 h. The mixture was allowed to cool to room temperature. The Grignard reagent (0.43M; 28.6 ml) was added to a suspension of 8-nitroquinoline-7-carbaldehyde 204 (2.5 g, 12.4 mmol) in dry THF (30 ml) at 0° C. under a nitrogen atmosphere. The mixture was stirred at room temperature for 30 min. The mixture was quenched with sat. NH4Cl (10 ml) and the aqueous phase was extracted with EtOAc (20 ml). The organic phase was washed with brine (10 ml), dried (Na2SO4) and concentrated in vacuo. The crude residue was purified by column chromatography with heptane/EtOAc (50:50) as the eluent to give the title compound (3.39 g, 74%).
MW: 370.33
HPLCMS (Method B): [m/z]: 371.30

3-[1,3]Dioxolan-2-yl-4-fluoro-phenyl)-(8-nitro-quinolin-7-yl)-methanone (Intermediate 419

In a similar fashion, using route 27 general procedure 67, (3-[1,3]dioxolan-2-yl-4-fluoro-phenyl)-(8-nitro-quinolin-7-yl)-methanol 418 (3.39 g, 9.15 mmol) and PDC (5.17 g, 13.73 mmol) in DCM (50 ml) gave the title compound (2.65 g, 79%) which was used in the next step without further purification.
MW: 368.32
HPLCMS (Method B): [m/z]: 369.35

8-Amino-quinolin-7-yl)-(3-[1,3]dioxolan-2-yl-4-fluoro-phenyl)-methanone (Intermediate 420

In a similar fashion, using route 26 general procedure 55, (3-[1,3]dioxolan-2-yl-4-fluoro-phenyl)-(8-nitro-quinolin-7-yl)-methanone 419 (2.65 g, 7.19 mmol) and 10% Pd—C (153 mg) in THF (80 ml) gave the title compound (1.41 g, 58%) after purification by column chromatography with heptane/EtOAc (70:30) as the eluent.
MW: 338.33
HPLCMS (Method B): [m/z]: 339.45

1-(3-[1,3]Dioxolan-2-yl-4-fluoro-phenyl)-2-methyl-1,4-dihydro-2H-3-thia-2,4,5-triaza-phenanthrene 3,3-dioxide (Intermediate 421)

In a similar fashion using route 27 general procedure 70, (8-amino-quinolin-7-yl)-(3-[1,3]dioxolan-2-yl-4-fluoro-phenyl)-methanone 420 (500 mg, 1.48 mmol), N-methylsulfamoyl chloride 213 (574 mg, 4.43 mmol) and NaBH4 (56 mg, 1.48 mmol) in pyridine (10 ml) gave the title compound (442 mg, 72%) after purification by column chromatography with heptane/EtOAc (50:50) as the eluent.
MW: 415.44
HPLCMS (Method B): [m/z]: 416.85

General Procedure 87: 2-Fluoro-5-(2-methyl-3,3-dioxo-1,2,3,4-tetrahydro-3λ*6*-thia-2,4,5-triaza-phenanthren-1-yl)-benzaldehyde (Intermediate 422)

6 M HCl (5 ml) was added dropwise to a solution of 1-(3-[1,3]dioxolan-2-yl-4-fluoro-phenyl)-2-methyl-1,4-dihydro-2H-3-thia-2,4,5-triaza-phenanthrene 3,3-dioxide 421 (390 mg, 0.94 mmol) in THF (10 ml) and the mixture was heated at 70° C. for 3 h. After cooling, the mixture was neutralised with sat K2CO3 and the aqueous phase was extracted with EtOAc (30 ml). The organic phase was washed with brine (10 ml), dried (Na2SO4) and concentrated in vacuo. The crude residue was purified by column chromatography with DCM/MeOH (95:5) as the eluent to give the title compound (180 mg, 52%).
MW: 371.39
HPLCMS (Method B): [m/z]: 372.35

General Procedure 88: 2-Fluoro-5-(2-methyl-3,3-dioxo-1,2,3,4-tetrahydro-3λ*6*-thia-2,4,5-triaza-phenanthren-1-yl)-benzoic acid methyl ester (Intermediate 423)

AcOH (23.1 μl, 0.4 mmol) was added dropwise to a solution of 2-fluoro-5-(2-methyl-3,3-dioxo-1,2,3,4-tetrahydro-3λ*6*-thia-2,4,5-triaza-phenanthren-1-yl)-benzaldehyde 422 (50 mg, 0.13 mmol), MnO2 (176 mg, 2.02 mmol), and sodium cyanide (66 mg, 1.35 mmol) in MeOH (10 ml). The mixture was stirred at room temperature for 3 h. The mixture was filtered and the filtrate was diluted with water (10 ml). The mixture was extracted with EtOAc (15 ml, ×2) and DCM (15 ml). The combined organic phases were concentrated in vacuo to give the title compound (50 mg, 93%) which was used in the next step without further purification.
MW: 401.41
HPLCMS (Method B): [m/z]: 402

General Procedure 89: 2-Fluoro-5-(2-methyl-3,3-dioxo-1,2,3,4-tetrahydro-3λ*6*-thia-2,4,5-triaza-phenanthren-1-yl)-benzoic acid (Example Compound 424)

LiOH (10 mg, 0.25 mmol) in water (0.5 ml) was added to a solution of 2-fluoro-5-(2-methyl-3,3-dioxo-1,2,3,4-tetrahydro-3λ*6*-thia-2,4,5-triaza-phenanthren-1-yl)-benzoic acid methyl ester 423 (50 mg, 0.12 mmol) in THF:MeOH (1:1; 2 ml) and the mixture was stirred at room temperature for 1 h. The mixture was concentrated in vacuo, the residue was diluted in the minimum amount of water and acidified to pH=3-4 with 2 M HCl. The resulting precipitate was collected by filtration and dried. The crude solid was purified by preparative HPLC (acidic conditions 1) to give the title compound (8 mg, 17%).
EOAI3362467 VIT-2203
MW: 387.39
HPLCMS (Method A): [m/z]: 387.95

General Procedure 90: N'-[2-Fluoro-5-(2-methyl-3,3-dioxo-1,2,3,4-tetrahydro-3λ*6*-thia-2,4,5-triaza-phenanthren-1-yl)-benzyl]-N,N-dimethyl-ethane-1,2-diamine (Example Compound 425)

Sodium triacetoxyborohydride (40 mg, 0.19 mmol) was added to a solution of 2-fluoro-5-(2-methyl-3,3-dioxo-1,2,3, 4-tetrahydro-3λ*6*-thia-2,4,5-triaza-phenanthren-1-yl)-benzaldehyde 422 (50 mg, 0.13 mmol) and N,N-dimethyl-ethane-1,2-diamine (12.9 µl, 0.16 mmol) in DCE (2 ml) and the mixture was stirred at room temperature for 18 h. The reaction was quenched with sat. NaHCO3 solution (1 ml) and the mixture was extracted with EtOAc (5 ml). The organic phase was concentrated in vacuo. The crude residue was triturated from chloroform/MeOH to give the title compound (20 mg, 34%).

EOAI3361314 VIT-2184
MW: 443.54
HPLCMS (Method A): [m/z]: 444.15

[2-Fluoro-5-(2-methyl-3,3-dioxo-1,2,3,4-tetrahydro-3λ*6*-thia-2,4,5-triaza-phenanthren-1-yl)-benzyl]-(2-morpholin-4-yl-ethyl)-amine (Example Compound 426)

In a similar fashion, using route 37 general procedure 90, 2-fluoro-5-(2-methyl-3,3-dioxo-1,2,3,4-tetrahydro-3λ*6*-thia-2,4,5-triaza-phenanthren-1-yl)-benzaldehyde 422 (15.9 µl, 0.13 mmol) and sodium triacetoxyborohydride (40 mg, 0.19 mmol) in DCE (2 ml) gave the title compound (22 mg, 34%) after trituration from MeOH.

EOAI3361315 VIT-2185
MW: 485.57
HPLCMS (Method A): [m/z]: 486.40

1-(4-Fluoro-3-piperazin-1-ylmethyl-phenyl)-2-methyl-1,4-dihydro-2H-3-thia-2,4,5-triaza-phenanthrene 3,3-dioxide (Example Compound 427)

In a similar fashion using route 37 general procedure 90, 2-fluoro-5-(2-methyl-3,3-dioxo-1,2,3,4-tetrahydro-3λ*6*-thia-2,4,5-triaza-phenanthren-1-yl)-benzaldehyde 422 (50 mg, 0.13 mmol), piperazine (12 mg, 0.13 mmol) and sodium triacetoxyborohydride (40 mg, 0.19 mmol) in DCE (2 ml) gave the title compound (6 mg, 10%) after purification by preparative HPLC (acidic conditions 1).

EOAI3361316 VIT-2186
MW: 441.52
HPLCMS (Method A): [m/z]: 442.10

General Procedure 91: [2-Fluoro-5-(2-methyl-3,3-dioxo-1,2,3,4-tetrahydro-3λ*6*-thia-2,4,5-triaza-phenanthren-1-yl)-phenyl]-morpholin-4-yl-methanone (Example Compound 428)

TBTU (49.73 mg, 0.15 mmol) was added to a suspension of 2-fluoro-5-(2-methyl-3,3-dioxo-1,2,3,4-tetrahydro-3λ*6*-thia-2,4,5-triaza-phenanthren-1-yl)-benzoic acid 424 (60 mg, 0.15 mmol) in DCM (1 ml) and the mixture was stirred at room temperature for 20 min. Morpholine (13.6 µl, 0.15 mmol) and DIPEA (25.6 µl, 0.15 mmol) were added and the mixture was stirred at room temperature for 3 h. The mixture was diluted with water (1 ml) and the mixture was extracted with DCM (3 ml). The organic phase was concentrated in vacuo. The crude residue was purified by preparative HPLC (acidic conditions 1) to give the title compound (32 mg, 45%).

EOAI3362847 VIT-2220
MW: 456.49
HPLCMS (Method A): [m/z]: 457.10

N-(2-Dimethylamino-ethyl)-2-fluoro-5-(2-methyl-3,3-dioxo-1,2,3,4-tetrahydro-3λ*6*-thia-2,4,5-triaza-phenanthren-1-yl)-benzamide (Example Compound 429)

In a similar fashion, using route 37 general procedure 90, 2-fluoro-5-(2-methyl-3,3-dioxo-1,2,3,4-tetrahydro-3λ*6*-thia-2,4,5-triaza-phenanthren-1-yl)-benzoic acid 424 (60 mg, 0.15 mmol), TBTU (50 mg, 0.15 mmol), N,N-dimethyl-ethane-1,2-diamine (16.9 µl, 0.15 mmol) and DIPEA (25.6 µl, 0.15 mmol) in DCM (1 ml) gave the title compound (10 mg, 14%) after purification by preparative HPLC (acidic conditions 1).

EOAI3362848 VIT-2221
MW: 457.52
HPLCMS (Method A): [m/z]: 458.05
Route 38 (See Above)

General Procedure 92:
4-Benzylsulfanyl-3-nitro-benzoic acid methyl ester (Intermediate 430)

A solution of methyl 4-chloro-3-nitrobenzoate (1 g, 4.65 mmol) in EtOH (13 ml) was added to a solution of benzylmercaptan (0.65 ml, 5.53 mmol), Na2CO3 (0.64 g, 6.1 mmol) and water (3 ml) and the reaction was heated under reflux for 4 h. After cooling, the mixture was diluted with water. The resulting precipitate was collected by filtration, washed with n-hexane and dried to give the title compound (2.5 g, 88%). The structure was confirmed by 1H NMR.

1-Benzylsulfanyl-4-methanesulfonyl-2-nitro-benzene (Intermediate 431)

In a similar fashion using route 38 general procedure 92, 1-chloro-4-methanesulfonyl-2-nitrobenzene (750 mg, 3.19 mmol), benzylmercaptan (450 ml, 3.82 mmol), Na2CO3 (439 mg, 4.14 mmol) and EtOH:water (25 ml: 18 ml) at 90° C. for 4 h gave the title compound (950 mg, 92%) which was used in the next step without further purification. The structure was confirmed by 1H NMR.

2-Benzylsulfanyl-5-methyl-pyridine (Intermediate 432)

In a similar fashion using route 38 general procedure 92, 2-chloro-5-methyl pyridine (200 mg, 1.5 mmol), K2CO3 (325 mg, 2.3 mmol), benzylmercaptan (292 mg, 2.3 mmol) and DMSO (1.5 ml) at 150° C. for 4 h gave the title compound (235 mg, 69%) which was used in the next step without further purification.

MW: 215.32
HPLCMS (Method C):[m/z]: 216

2-Benzylsulfanyl-6-methyl-pyridine (Intermediate 433)

In a similar fashion using route 38 general procedure 92, 2-chloro-6-methylpyridine (1 g, 7.8 mmol), K2CO3 (1.62 g 11.75 mmol), benzylmercaptan (1.46 g 11.8 mmol) and DMSO (7.5 ml) at 150° C. for 4 h in sealed tube gave the title compound (780 mg, 47%) which was used in the next step without further purification.

MW: 215.32
HPLCMS (Method C):[m/z]: 216.32

3-Benzylsulfanyl-5-trifluoromethyl-pyridine (Intermediate 434)

In a similar fashion using route 38 general procedure 92, 3-bromo-5-(trifluoromethyl)pyridine (400 mg, 1.76 mmol), K2CO3 (366 mg, 2.65 mmol), benzylmercaptan (330 mg, 2.65 mmol) and DMSO (3.2 ml) at 150° C. for 4 h in sealed tube gave the title compound (122 mg, 25%) after purification by column chromatography with n-hexane/EtOAc (99:1) as the eluent.
MW: 269.29
HPLCMS (Method C): [m/z]: 269.99

2-Benzylsulfanyl-pyrazine (Intermediate 435)

In a similar fashion using route 38 general procedure 92, 2-chloropyrazine (1 g, 8.73 mmol), K2CO3 (1.80 g 13.1 mmol), benzylmercaptan (1.62 g 13.1 mmol) and DMSO (8 ml) at 150° C. for 4 h in sealed tube gave the title compound (805 mg, 45%) after purification by column chromatography with n-hexane/EtOAc (97:3) as the eluent.
MW: 202.22
HPLCMS (Method C): [m/z]: 203

2-Benzylsulfanyl-thiazole (Intermediate 436)

In a similar fashion using route 38 general procedure 92, 2-bromothiazole (700 mg, 4.2 mmol), K2CO3 (884 mg, 6.4 mmol), benzylmercaptan (795 ml 6.4 mmol) in DMSO (6 ml) at 150° C. for 4 h in sealed tube gave the title compound (740 mg, 83%) after purification by column chromatography with n-hexane/EtOAc (98:2) as the eluent.
MW: 207.32
HPLCMS (Method C): [m/z]: 208

2-Benzylsulfanyl-3-nitro-pyridine (Intermediate 437)

In a similar fashion using route 38 general procedure 92, 2-chloro-3-nitro-pyridine(2 g, 12.7 mmol), Na2CO3 (1.75 g, 16.6 mmol), benzylmercaptan (1.87 g, 15.1 mmol) and EtOH (20 ml) at 90° C. for 4 h gave the title compound (3 g, 96%) which was used in the next step without further purification. The structure was confirmed by 1H NMR.

General Procedure 93: 4-Chlorosulfonyl-3-nitro-benzoic acid methyl ester (Intermediate 438)

Chlorine gas was bubbled through a suspension of 4-benzylsulfanyl-3-nitro-benzoic acid methyl ester 430 (1.5 g, 82.5 mmol) in AcOH (30 ml) and water (20 ml) for 5-6 h at 0 C. The mixture was extracted with DCM and the organic phase was washed with sodium meta-bisulphate, water and brine. The organic phase was dried (Na2SO4) and concentrated in vacuo to give the title compound (1.65 g) which was used in the next step without further purification. The structure was confirmed by 1H NMR.

4-Methanesulfonyl-2-nitro-benzenesulfonyl chloride (Intermediate 439)

In a similar fashion using route 38 general procedure 93, 1-benzylsulfanyl-4-methanesulfonyl-2-nitro-benzene 431 (500 mg, 1.54 mmol) in AcOH:water (2:3, 9 ml) at 0° C. for 6 h gave the title compound (456 mg) which was used in the next step without further purification. The structure was confirmed by 1H NMR.

5-Methyl-pyridine-2-sulfonyl chloride (Intermediate 440)

In a similar fashion using route 38 general procedure 93, 2-benzylsulfanyl-5-methyl-pyridine 432 (100 mg, 0.46 mmol) in chloroform (5 ml) and water (5 ml) gave the title compound (83 mg) which was used in the next step without further purification. The structure was confirmed by 1H NMR.

6-Methyl-pyridine-2-sulfonyl chloride (Intermediate 441)

In a similar fashion using route 38 general procedure 93, 2-benzylsulfanyl-6-methyl-pyridine 433 (500 mg, 2.3 mmol) in chloroform (25 ml) and water (25 ml) gave the title compound (538 mg) which was used in the next step without further purification. The structure was confirmed by 1H NMR.

5-Trifluoromethyl-pyridine-3-sulfonyl chloride (Intermediate 442)

In a similar fashion using route 38 general procedure 93, 3-benzylsulfanyl-5-trifluoromethyl-pyridine 434 (120 mg, 0.44 mmol) in chloroform (5 ml) and water (5 ml) gave the title compound (155 mg) which was used in the next step without further purification. The structure was confirmed by 1H NMR.

Pyrazine-2-sulfonyl chloride (Intermediate 443)

In a similar fashion using route 38 general procedure 93, 2-benzylsulfanyl-pyrazine 435 (600 mg, 2.9 mmol) in chloroform (30 ml) and water (30 ml) gave the title compound (580 mg) which was used in the next step without further purification. The structure was confirmed by 1H NMR.

Thiazole-2-sulfonyl chloride (Intermediate 444)

In a similar fashion using route 38 general procedure 93, 2-benzylsulfanyl-thiazole 436 (500 mg, 2.3 mmol) in chloroform (25 ml) and water (25 ml) gave the title compound (510 mg) which was used in the next step without further purification. The structure was confirmed by 1H NMR.

General Procedure 94: 3-Nitro-pyridine-2-sulfonyl chloride (Intermediate 445)

AcOH (6 ml) and water (12 ml) were added to a solution of 2-benzylsulfanyl-3-nitro-pyridine 437 (3.0 g, 12.2 mmol) in DCM (42 ml) and the mixture was cooled to 0° C. A suspension of 1,3-dichloro-5,5-dimethyl-imidazolidine-2,4-dione (7.20 g, 36.58 mmol) in DCM (24 ml) was added portionwise to the vigorously stirring solution. The mixture was allowed to slowly warm to 25° C. and stirring was continued for 16 h. The mixture was poured into 5% aq. sodium metabisulfite solution (50 ml) and the aqueous phase was extracted with DCM (100 ml). The organic phase was washed with water, sat. NaHCO3 solution and brine, dried (Na2SO4) and concentrated in vacuo to give the title compound (2.7 g) which was used in the next step without further purification. The structure was confirmed by 1H NMR.

Route 39 (See Above)

General Procedure 95:
4-Chloro-2-nitro-benzenesulfonic acid (Intermediate 446)

A suspension of Na2SO3 (3.26 g, 25.9 mmol) in EtOH (32 ml) and water (40 ml) was added to a solution of 5-chloro-2-fluoro nitrobenzene (2.0 g, 11.4 mmol) in EtOH (24 ml) and the mixture was heated at 70° C. for 16 h. After cooling, the mixture was acidified to pH=2 with conc. HCl (2 ml) and the solvent was removed in vacuo. The residue was diluted with brine solution (12 ml) and the mixture was heated under reflux for 2 h. The solution was cooled in ice bath and the resulting precipitate was collected by filtration to give the title compound (1.54 g, 57%) which was used in the next step without further purification.

MW: 237.62
HPLCMS (Method C): [m-z]: 235.90

5-Methoxy-2-nitro-benzenesulfonic acid (Intermediate 447)

In a similar fashion using route 39 general procedure 95, 2-fluoro-4-methoxy-1-nitrobenezene (2 g, 11.7 mmol) in EtOH (24 ml), Na2SO3 (3.34 g, 26.5 mmol) in EtOH:water (32 ml:40 ml) at 70° C. for 16 h gave the title compound (2.4 g, 88%) which was used in the next step without further purification.

MW: 233.20
HPLCMS (Method C): [m/z]: 231.9

4-Methyl-2-nitro-benzenesulfonic acid (Intermediate 448)

In a similar fashion using route 39 general procedure 95, 1-fluoro-4-methyl-2-nitrobenezene (2.0 g 12.9 mmol) in EtOH (24 ml) and Na2SO3 (3.68 g, 29.2 mmol) in EtOH:water (32 ml: 40 ml) at 70° C. for 16 h gave the title compound (6.2 g, as the salt) which was used in the next step without further purification.

MW: 217.20
HPLCMS (Method C): [m/z]: 216

5-Methyl-2-nitro-benzenesulfonic acid (Intermediate 449)

In a similar fashion using route 39 general procedure 95, 2-fluoro-4-methyl-1-nitrobenzene (2 g, 12.9 mmol) in EtOH (24 ml) and Na2SO3 (2.04 g, 16.0 mmol) in EtOH:water (40 ml: 32 ml) at 70° C. for 14 h gave the title compound (7 g) which was used in the next step without further purification.

MW: 217.20
HPLCMS (Method C): [M-H]: 216.0

5-Fluoro-2-nitro-benzenesulfonic acid (Intermediate 450)

In a similar fashion using route 39 general procedure 95, 2,4-difluoronitrobenzene (2.0 g, 12.0 mmol) in EtOH (24 ml) and Na2SO3 (3.6 g, 28 mmol) in EtOH:water (32 ml: 40 ml) at 70° C. for 14 h gave the title compound (0.6 g) which was used in the next step without further purification. The structure was confirmed by 1H NMR.

2-Methyl-6-nitro-benzenesulfonic acid (Intermediate 451)

In a similar fashion using route 39 general procedure 95, 2-fluoro-3-nitrotoluene (2.5 g 16.1 mmol) in EtOH (60 ml) and Na2SO3 (4.61 g, 36.58 mmol) in EtOH: water (40 ml: 50 ml) at 70° C. for 16 h gave the title compound (7.2 g) which was used in the next step without further purification.

MW: 217.20
HPLCMS (Method C): [m/z]: 215.9

4-Fluoro-5-methyl-2-nitro-benzenesulfonic acid (Intermediate 452)

In a similar fashion using route 39 general procedure 95, 1,4-difluoro-2-methyl-5-nitrobenzene (1.2 g, 6.93 mmol) in EtOH (10 ml) and Na2SO3 (1.98 g, 15.7 mmol) in EtOH:water (40 ml:25 ml) at 70° C. for 16 h gave the title compound (1.2 g, 73%) which was used in the next step without purification.

MW: 235.19
HPLCMS (Method C):[m/z]: 234

2-Nitro-5-trifluoromethyl-benzenesulfonic acid (Intermediate 453)

In a similar fashion using route 39 general procedure 95, 2-fluoro-1-nitro-4-(trifluoromethyl)benzene (730 mg 3.4 mmol) in EtOH (10 ml) Na2SO3 (1 g, 7.9 mmol) in EtOH:water (14 ml:15 ml) gave the title compound (700 mg, 73%) which was used in the next step without further purification.

MW: 271.17
HPLCMS (Method C): [m/z]: 270

General Procedure 96:
4-Chloro-2-nitro-benzenesulfonyl chloride (Intermediate 454)

DMF (0.06 ml, cat) was added to a solution of 4-chloro-2-nitro-benzenesulfonic acid (600 mg, 2.5 mmol) in SOCl2 (3.1 ml) and the mixture was heated at 90° C. for 3 h. After cooling, the solvent was removed in vacuo. The mixture was diluted with water and extracted repeatedly with chloroform. The combined organic layers were washed with saturated NaHCO3 solution, dried (Na2SO4) and concentrated in vacuo to give the title compound (560 mg) which was used in the next step without further purification. The structure was confirmed by 1H NMR.

5-Methoxy-2-nitro-benzenesulfonyl chloride (Intermediate 455)

In a similar fashion using route 39 general procedure 96, 5-methoxy-2-nitro-benzenesulfonic acid 447 (2.0 g, 8.58 mmol), SOCl2 (9.4 ml) and (0.2 ml) DMF gave the title compound (2.5 g) which was used in the next step without further purification. The structure was confirmed by 1H NMR.

4-Methyl-2-nitro-benzenesulfonyl chloride (Intermediate 456)

In a similar fashion using route 39 general procedure 96, 4-methyl-2-nitro-benzenesulfonic acid 448 (6.2 g, Salt form), SOCl2 (15 ml) and DMF (0.28 ml) gave the title compound (3.10 g) which was used in the next step without further purification. The structure was confirmed by 1H NMR.

5-Methyl-2-nitro-benzenesulfonyl chloride (Intermediate 457)

In a similar fashion using route 39 general procedure 96, 5-methyl-2-nitro-benzenesulfonic acid 449 (1.8 g, 8.2 mmol), SOCl2 (10 ml) and DMF (0.18 ml) at 90° C. for 3 h gave the title compound (1.2 g) which was used in the next step without further purification. The structure was confirmed by 1H NMR.

5-Fluoro-2-nitro-benzenesulfonyl chloride (Intermediate 458)

In a similar fashion using route 39 general procedure 96, 5-fluoro-2-nitro-benzenesulfonic acid 450 (0.6 g, 2.71 mmol), SOCl2 (3.1 ml) and DMF (0.06 ml) at 90° C. for 3 h gave the title compound (3.4 g) which was used in the next step without further purification. The structure was confirmed by 1H NMR.

2-Methyl-6-nitro-benzenesulfonyl chloride (Intermediate 459)

In a similar fashion using route 39 general procedure 96, 2-methyl-6-nitro-benzenesulfonic acid 451 (7.2 g crude), SOCl2 (16 ml) and DMF (0.35 ml) at 90° C. for 3 h gave the title compound (3.5 g) which was used in the next step without further purification. The structure was confirmed by 1H NMR.

4-Fluoro-5-methyl-2-nitro-benzenesulfonyl chloride (Intermediate 460)

In a similar fashion using route 39 general procedure 96, 4-fluoro-5-methyl-2-nitro-benzenesulfonic acid 452 (1.5 g, 6.38 mmol), SOCl2 (15 ml) and DMF (0.1 ml) gave the title compound (1.6 g, 99%) which was used in the next step without purification. The structure was confirmed by 1H NMR.

2-Nitro-5-trifluoromethyl-benzenesulfonyl chloride (Intermediate 461)

In a similar fashion using route 39 general procedure 96, 2-nitro-5-trifluoromethyl-benzenesulfonic acid 453 (700 mg, 2.58 mmol), thionyl chloride (7 ml) and (0.1 ml) DMF at 90° C. for 3 h gave the title compound (730 mg) which was used in the next step without further purification. The structure was confirmed by 1H NMR.
Route 40 (See Above)

General Procedure X: 4-chloroquinoline (Intermediate 462)

POCl3 (50 ml) was added to quinolin-4-ol (5.0 g, 34.9 mmol) and the mixture was heated at 90° C. for 0.5 h. After cooling, the mixture was concentrated in vacuo. The residue was quenched with cold sat. NaHCO3 solution under cooling and the resulting aqueous phase was extracted with chloroform. The combined organic phases were washed with water, dried (Na2SO4) and concentrated in vacuo to give the title compound (5.0 g, 89%) which was used in the next step without further purification.
MW: 163.61
HPLCMS (Method C): [m/z]: 163.95

4-chloro-8-nitroquinoline (Intermediate 463)

In a similar fashion using route 11 general procedure 57, 4-chloroquinoline 462 (5.0 g, 30.7 mmol), fuming HNO3 (8.3 ml) and concentrated H2SO4 (16.6 ml) to give the title compound (2.3 g, 36%) which was used in the next step without further purification.
MW: 208.61
HPLCMS (Method C): [m/z]: 208.95

4-Chloro-quinolin-8-ylamine (Intermediate 464)

In a similar fashion using route 2 general procedure 4, 4-chloro-8-nitroquinoline 463 (3.3 g, 15.8 mmol), SnCl2 (15 g, 79.1 mmol), conc. HCl (cat.) and MeOH (100 ml) to give the title compound (2.3 g, 36%) which was used in the next step without further purification.
MW: 178.62
HPLCMS (Method C): [m/z]: 178.95
Route 41 (See Above)

General Procedure 98:
4-Trifluoromethyl-1H-quinolin-2-one (Intermediate 465)

Aniline (7.0 g, 75.3 mmol) and trifluoro ethylacetoacetate (15.4 ml, 105 mmol) were heated at 110° C. for 45 min. The excess ester was removed in vacuo. 75% H2SO4 was added and the mixture was heated at 90° C. for 45 min. After cooling, the mixture was poured onto ice and the resulting precipitate was collected by filtration to give title compound (7.0 g, 44%) which was used in the next step without further purification.
MW: 212.15
HPLCMS (Method C): [m/z]: 214

General Procedure 99:
2-Chloro-4-trifluoromethyl-quinoline (Intermediate 466)

DMF (cat.) was added to a solution of 4-trifluoromethyl-1H-quinolin-2-one 465 (160 mg, 0.75 mmol) in POCl3 (2 ml) and the mixture was heated at 90° C. for 1 h. After cooling, the mixture was concentrated in vacuo and the residue was poured into an ice cold solution of NaHCO3 solution. The aqueous phase was extracted with EtOAc. The organic phase was dried (Na2SO4) and concentrated in vacuo to give the title compound (50 mg, 29%) which was used in the next step without further purification.
MW: 231.61
HPLCMS (Method C):[m/z]: 231.96

General Procedure 100: 4-Trifluoromethyl-quinoline (Intermediate 467)

Pd (PPh3)2Cl2 (170 mg, 0.24 mmol) and triethylsilane (5.4 ml, 33.9 mmol) were added to a solution of 2-chloro-4-trifluoromethyl-quinoline 466 (5.60 g, 24.2 mmol) in MeCN (3 ml) and the mixture was heated at 70° C. for 18 h. The solvent was removed in vacuo. The crude residue was purified by column chromatography with n-hexane/EtOAc (95:5) to give the title compound (2.2 g, 47%).
MW: 197
HPLCMS (Method C):[m/z]: 198

8-Nitro-4-trifluoromethyl-quinoline (Intermediate 468)

In a similar fashion using route 11 general procedure 57, 4-trifluoromethyl-quinoline 467 (200 mg, 1.01 mmol) and H2SO4:HNO3 (2:1) gave the title compound (70 mg, 29%) which was used in the next step without further purification.
MW: 242.16
HPLCMS (Method C): [m/z]: 243

4-Trifluoromethyl-quinolin-8-ylamine (Intermediate 469)

In a similar fashion using route 2 general procedure 4, 8-nitro-4-trifluoromethyl-quinoline 468 (900 mg, 4.13 mmol), SnCl2 (3.12 g, 16.5 mmol), 6N HCl (2 drops) and EtOH (20 ml) at 85° C. for 3 h gave the title compound (700 mg, 89%) which was used in the next step without further purification.
MW: 212.18
HPLCMS (Method C): [m/z]: 213
Route 42 (See Above)

General Procedure 101: 5-bromo-8-nitroquinoline (Intermediate 470)

KNO3 (1.58 g, 15.6 mmol) was added portionwise to a solution of 5-bromoquinoline (2.0 g, 12.0 mmol) conc.H2SO4 (7.5 ml) at 0° C. and the mixture was stirred at room temperature for 16 h. The mixture was poured onto ice and the resulting solid was extracted into DCM. The organic phase was washed with brine, dried (Na2SO4) and concentrated in vacuo to give the title compound (2.8 g, 92%) which was used in the next step without further purification.
MW: 253.06
HPLCMS: (Method C): [m/z]:254

General Procedure 102:
8-nitroquinoline-5-carbonitrile (Intermediate 471)

Zn(CN)2 (739 mg, 6.3 mmol), DIPEA (0.41 ml, 2.37 mmol), X-phos (225 mg, 0.47 mmol) and Pd2(dba)2 (90 mg, 0.16 mmol) were added to a degassed (with argon) solution of 5-bromo-8-nitroquinoline 470 (400 mg, 1.58 mmol) in DMF (4 ml) and the mixture was heated at 100° C. in microwave for 20 min. After cooling, the mixture was poured into water and the aqueous phase was extracted with EtOAc. The organic phase was dried (Na2SO4) and concentrated in vacuo. The crude residue was purified by column chromatography with n-hexane/EtOAc (96:4) as the eluent to give the title compound (230 mg, 63%).
MW: 199.17
HPLCMS: (Method C): [m/z]: 200

8-Amino-quinoline-5-carbonitrile (Intermediate 472)

In a similar fashion using route 19 general procedure 29, 8-nitroquinoline-5-carbonitrile 471 (350 mg, 1.7 mmol), SnCl2 (1.3 g, 7.0 mmol), 6N HCl (4 drops) and EtOH (10 ml) gave the title compound (250 mg, 86%) which was used in the next step without further purification.
MW: 169.19
HPLCMS: (Method C): [m/z]: 170.04
Route 43 (See Above)

8-Nitro-quinoline-4-carboxylic acid (Intermediate 473)

In a similar fashion using route 11 general procedure 15, 4-carboxylquinoline (3.0 g, 17.3 mmol) in conc. H2SO4 (0.75 ml), and HNO3:H2SO4 (6 ml, 12 mmol) gave the title compound (3 g, 79%, mixture of 5- and 8-nitro isomers) which was used in the next step without further purification.
MW: 218.17
HPLCMS (Method C): [m/z]: 219.0

General Procedure 100:
8-Nitro-quinoline-4-carboxylic acid methyl ester (Intermediate 474)

SOCl2 (10 ml, 137 mmol) was added slowly to 8-nitro-quinoline-4-carboxylic acid 473 (3.0 g, 13.8 mmol) in MeOH (40 ml) and the mixture was heated at 70° C. for 7 h. After cooling, the solvent was removed in vacuo and the residue was diluted with EtOAc. The organic phase was washed with sat. NaHCO3 solution and brine, dried (Na2SO4) and concentrated in vacuo. The crude residue was purified by column chromatography with n-hexane/EtOAc (95:5) as the eluent to give the title compound (0.70 g, 22%).
MW: 232.20
HPLCMS: (Method C): [m/z]: 233

8-Amino-quinoline-4-carboxylic acid methyl ester (Intermediate 475)

In a similar fashion using route 19 general procedure 29, 8-nitro-quinoline-4-carboxylic acid methyl ester 474 (0.5 g, 2.15 mmol), SnCl2 (1.6 g, 8.6 mmol), 6N HCl (2 drops) and MeOH (10 ml) at 70° C. for 3 h gave the title compound (370 mg, 65%) which was used in the next step without further purification.
MW: 202.21
HPLCMS: (Method C): [m/z]: 203
Route 44 (See Above)

General Procedure 104:
8-Nitro-3H-quinazolin-4-one (Intermediate 476)

Formamide (17.1 g, 380 mmol) was added to a solution of 2-amino-3-nitrobenzoic acid (2.0 g, 11 mmol) in methoxy ethanol (5 ml) and the reaction was heated at 200 C in a sealed tube for 17 h. After cooling, the mixture was concentrated in vacuo. The residue was quenched with sat. aq. NaHCO3 solution and the aqueous phase was extracted with EtOAc (100 ml, ×2). The combined organic phases were dried (Na2SO4) and concentrated in vacuo. The crude residue was purified by column chromatography with DCM as the eluent to give the title compound (300 mg, 14%).
MW: 191.15
HPLCMS (Method C): [m/z]:191

General Procedure 105:
4-Chloro-8-nitro-quinazoline (Intermediate 477)

N, N-dimethylaniline (0.37 ml, 1.23 mmol) was added dropwise to a solution of 8-nitro-3H-quinazolin-4-one 476 (200 mg, 1.04 mmol) in POCl3 (1.25 ml, 10.5 mmol) at 0° C. The mixture was heated at 65° C. for 1.5 h. After cooling, the mixture was concentrated in vacuo. The residue was quenched with sat. NaHCO3 solution and the aqueous phase was extracted with EtOAc (25 ml, ×2). The combined organic phase was dried (Na2SO4) and concentrated in vacuo. The crude residue was purified by column chromatography with n-hexane/DCM (80:20) to give the title compound (130 mg, 59.63%).
MW: 209.59
HPLCMS: (Method C): [m/z]: 210

General Procedure 106: 4-Methyl-N'-(8-nitro-quinazolin-4-yl)benzene-1-sulfonohydrazide (Intermediate 478)

p-Toluene sulphonyl hydrazine hydrate (390 mg, 2.1 mmol) was added to a solution of 4-chloro-8-nitro-quinazoline 477 (400 mg, 1.91 mmol) in DCM at (10 ml) and the mixture was stirred at room temperature for 24 h. The mixture was concentrated in vacuo and washed with Et2O to give the title compound (650 mg, 95%).
MW: 359
HPLCMS: (Method C): [m/z]:360.30

N'-(8-aminoquinazolin-4-yl)-4-methylbenzene-1-sulfonohydrazide (Intermediate 479)

In a similar fashion using route 2 general procedure 4, 4-methyl-N'-(8-nitroquinazolin-4-yl)benzene-1-sulfonohydrazide 478 (100 mg, 0.27 mmol), SnCl2 (310 mg, 1.67 mmol), 6N HCl (1 drop) and EtOH (3 ml) at 80° C. for 3 h gave the title compound (60 mg, 65%) which was used in the next step without further purification.
MW: 329.38
HPLCMS: (Method C): [m/z]: 330

General Procedure 107: Quinazolin-8-ylamine (Intermediate 480)

1N NaOH (9 ml) was added to a solution of N'-(8-aminoquinazolin-4-yl)-4-methylbenzene-1-sulfonohydrazide 479 (300 mg, 9.1 mmol) in EtOH (20 ml) and the mixture was heated under reflux for 3 h. After cooling, the mixture was concentrated in vacuo. The residue was diluted with water (10 ml) and the aqueous phase was extracted with EtOAc. The organic phase was washed with brine, dried (Na2SO4), and concentrated in vacuo to give title compound (140 mg, 76%) which was used in the next step without further purification. The structure was confirmed by 1H NMR.
Route 45 (See Above)

General Procedure 108: 5-Nitroquinoxaline (Intermediate 481)

Oxaldehyde (40% in water; 1.43 ml, 31.3 mmol) was added to a solution of 3-nitro-o-phenylene-diamine (600 mg, 3.9 mmol) in EtOH (15 ml) and the mixture was heated at 85° C. for 2 h. The solvent was removed in vacuo, the residue was diluted in water and the aqueous phase was extracted with DCM. The organic phase was dried (Na2SO4) and concentrated in vacuo. The crude residue was purified by column chromatography with DCM/MeOH (99:1) as the eluent to give the title compound (666 mg, 97%).
MW: 175.15
HPLCMS: (Method C): [m/z]: 176

Quinoxalin-5-ylamine (Intermediate 482)

In a similar fashion using route 2 general procedure 4, 5-nitroquinoxaline 481 (660 mg, 3.76 mmol), SnCl2 (2.14 g, 11.3 mmol), 6N HCl (6 drops) and MeOH (15 ml) for 3 h at 70° C. gave the title compound (540 mg, 98%) which was used in the next step without further purification.
MW: 145.17
HPLCMS: (Method C): [m/z]: 146.0
Route 46 (See Above)

General Procedure 109: [1,5]Naphthyridine 1-oxide (Intermediate 483)

m-CPBA (1.2 g, 6.91 mmol) was added in 3 portions (after every 3 h) to a solution of 1,5-naphthyridine (1.0 g, 7.68 mmol) in dry DCM (60 ml). After completion of the reaction, the mixture was concentrated in vacuo. The crude residue was purified by column chromatography with DCM/MeOH (98:2) as the eluent to get title compound (0.85 g, 76%).
MW: 146.15
HPLCMS: (Method C): [m/z]: 147.10

General Procedure 110: 4-Chloro-[1,5]naphthyridine (Intermediate 484)

POCl3 (8.5 ml) was added to [1,5]naphthyridine 1-oxide 483 (0.85 g, 5.81 mmol) at 0° C. and the mixture was heated at 100° C. for 6 h. After cooling, the mixture was concentrated in vacuo, neutralized with NaHCO3 solution and the aqueous phase was extracted with EtOAc (40 ml). The organic phase was washed with water and brine, dried (Na2SO4) and concentrated in vacuo. The crude residue was purified by column chromatography with n-hexane/EtOAc (88:12) as the eluent to give the title compound (0.35 g, 36%).
MW: 164.60
HPLCMS: (Method C): [m/z]: 165.10

General Procedure 111: (4-Methoxy-benzyl)-[1,5]naphthyridin-4-yl-amine (Intermediate 485)

p-Methoxybenzylamine (1.45 g, 10.6 mmol) was added to a solution of 4-chloro-[1,5]naphthyridine 484 (0.35 g, 2.13 mmol) in n-BuOH (9 ml) and the mixture was heated at 150° C. for 18 h. The solvent was removed in vacuo. The crude residue was purified by column chromatography with n-hexane/EtOAc (80:20) as the eluent to give the title compound (0.5 g, 89%).
MW: 265.32
HPLCMS: (Method C): [m/z]: 266.30

General Procedure 112: [1,5]Naphthyridin-4-ylamine (Intermediate 486)

48% HBr (13 ml) was added to (4-methoxy-benzyl)-[1,5]naphthyridin-4-yl-amine 485 (0.5 g, 1.88 mmol) and the mixture was heated at 80° C. for 2 h. After cooling, the mixture was neutralized with sat. NaHCO3 solution and the aqueous phase was extracted with EtOAc (80 ml). The organic phase was washed with water, dried (Na2SO4) and concentrated in vacuo. The crude residue was purified by column chromatography with DCM/MeOH/Aq. NH3 (97:2:1) as the eluent to give the title compound (0.25 g, 90%).
MW: 145.17
HPLCMS: (Method C): [m/z]: 146.20
Route 47 (See Above)

4-Carboxy-8-nitroquinoline (Intermediate 487)

In a similar fashion using route 11 general procedure 15, 4-carboxyquinoline (1.6 g, 9.0 mmol) in conc. H2SO4 (3 ml) and fuming HNO3/conc. H2SO4 (1:1; 6 ml) to give the title compound and 4-carboxy-5-nitroquinoline (2.1 g, 106%) which was used in the next step without further purification.
MW: 218.17
HPLCMS (Method B):[m/z-ve]: 217

General Procedure 113:
4-Carboxymethyl-8-nitroquinoline (Intermediate 488)

SOCl2 (6 ml, 48 mmol) was added to a solution of 4-carboxy-8-nitroquinoline 487 (2.1 g, 9.6 mmol, as mixture of regioisomers) in DCM (10 ml) and added and the mixture was heated under reflux for 4 h. The solvent was removed in vacuo and MeOH (20 ml) was added. The solvent was again removed in vacuo. The residue was dissolved in EtOAc (150 ml) and the organic phase was washed sat. NaHCO3 solution, dried (MgSO4) concentrated in vacuo. The crude residue was purified by column chromatography with heptane/EtOAc (3:1) to give the title compound (656 mg, 29%).
MW: 232.20
HPLCMS (Method B):[m/z]: 232.90

8-Amino-quinoline-4-carboxylic acid methyl ester (Intermediate 489)

In a similar fashion using route 19 general procedure 29, 4-carboxymethyl-8-nitroquinoline 488 (100 mg, 0.43 mmol), SnCl2 (485 mg, 2.1 mmol), and EtOH (10 ml) gave the title compound (56 mg, 62%) which was used in the next step without further purification.
MW: 202.21
HPLCMS (Method B):[m/z]: 202.95
Route 48 (See Above)

General Procedure 114: N-[4-(2-Dimethylamino-ethylamino)-quinolin-8-yl]-benzenesulfonamide (Example Compound 490)

N,N-dimethylethylenediamine (0.10 ml, 0.95 mmol) and DIPEA (0.11 ml, 0.63 mmol) were added to a solution of N-(4-chloro-quinolin-8-yl)-benzenesulfonamide 224 (100 mg, 0.32 mmol) in n-butanol (1 ml) and the reaction was heated in a sealed tube at 100° C. for 16 h. After cooling, the mixture was concentrated in vacuo. The crude residue was purified by column chromatography with chloroform/MeOH (97:3) as the eluent to give the title compound (40 mg, 34%).
EOAI3351374 VIT-1953
MW: 370.48
HPLCMS (Method C): [m/z]: 371.1

N-(4-Diethylamino-quinolin-8-yl)-benzenesulfonamide (Example Compound 491)

In a similar fashion using route 48 general procedure 114, N-(4-chloro-quinolin-8-yl)-benzenesulfonamide 224 (100 mg, 0.32 mmol), diethyl amine (0.097 ml, 0.94 mmol), DIPEA (0.11 ml, 0.63 mmol) and n-butanol (1 ml) gave the title compound (30 mg, 27%) after purification by column chromatography with chloroform/MeOH (1 drop NH3) (97:3) as the eluent.
EOAI3352365 VIT-1966
MW: 355.46
HPLCMS (Method C): [m/z]: 356.1

N-(4-Dimethylamino-quinolin-8-yl)-benzenesulfonamide (Example Compound 492)

In a similar fashion using route 48 general procedure 114, N-(4-chloro-quinolin-8-yl)-benzenesulfonamide 224 (80 mg, 0.250 mmol) and dimethyl amine (2M in THF; 1.25 ml, 2.50 mmol) gave the title compound (19 mg, 23%) after purification by column chromatography with chloroform/MeOH (1 drop NH3) (98:2) as the eluent followed by recrystallisation from MeOH/DCM.
EOAI3355979 VIT-2005
MW: 327.41
HPLCMS (Method C): [m/z]: 328

N-(4-Methylamino-quinolin-8-yl)-benzenesulfonamide (Example Compound 493)

In a similar fashion using route 48 general procedure 114, N-(4-chloro-quinolin-8-yl)-benzenesulfonamide 224 (80 mg, 0.25 mmol), methyl amine (2M in THF; 1.23 ml, 2.50 mmol) at 100° C. for 48 h gave the title compound (10 mg, 13%) after purification by column chromatography with chloroform/MeOH (1 drop NH3) (98:2) as the eluent followed by recrystallisation from MeOH/DCM.
EOAI3356960 VIT-2031
MW: 313.38
HPLCMS (Method C): [m/z]: 314
Route 49 (See Above)

General Procedure 115: 1-Pyrazol-1-yl-5H-6-thia-4,5-diaza-chrysene 6,6-dioxide (Example Compound 494)

KOtBu (76 mg, 0.68 mmol) was added to a solution of pyrazole (51 mg, 0.76 mmol) in DMSO (1 ml) at 0° C. in a sealed tube and the mixture was stirred at room temperature for 15 min. 1-Chloro-5H-6-thia-4,5-diaza-chrysene 6,6-dioxide 305 (80 mg, 0.252 mmol) was added and the mixture was heated at 100° C. for 4 h. After cooling, the mixture was poured onto ice and the aqueous was extracted with iPA: chloroform (30:70). The organic phase was dried (Na2SO4) and concentrated in vacuo. The crude residue was purified by column chromatography with chloroform/MeOH (98:2) to give the title compound (25 mg, 29%).
EOAI3358945 VIT-2077
MW: 348.39
HPLCMS (Method C): [m/z]: 349.01

6,6-Dioxo-5,6-dihydro-6λ*6*-thia-4,5-diaza-chrysen-1-yl)-diethyl-amine (Example Compound 495

In a similar fashion using route 48 general procedure 114, 1-chloro-5H-6-thia-4,5-diaza-chrysene 6,6-dioxide 305 (85 mg, 0.27 mmol), diethyl amine (0.14 ml, 1.34 mmol), DIPEA (0.093 ml, 0.53 mmol) and n-butanol (1 ml) gave the title compound (25 mg, 26%) after purification by column chromatography with chloroform/MeOH (99:1) as the eluent.
EOAI3354628 VIT-1990
MW: 353.45
HPLCMS (Method C): [m/z]: 354

N'-(6,6-Dioxo-5,6-dihydro-6λ*6*-thia-4,5-diaza-chrysen-1-yl)-N,N-dimethyl-ethane-1,2-diamine (Example Compound 496)

In a similar fashion using route 48 general procedure 114, 1-chloro-5H-6-thia-4,5-diaza-chrysene 6,6-dioxide 305 (75 mg, 0.23 mmol), N,N-dimethylethylenediamine (0.08 ml, 0.71 mmol), DIPEA (0.09 ml, 0.53 mmol) and n-BuOH (1 ml) gave the title compound (23 mg, 26%) after purification by column chromatography with DCM/MeOH (99:1) as the eluent.
EOAI3354629 VIT-1988
MW: 368.46
HPLCMS (Method C): [m/z]: 369.1

6,6-Dioxo-5,6-dihydro-6λ*6*-thia-4,5-diaza-chrysen-1-yl)-dimethyl-amine (Example Compound 497

In a similar fashion using route 48 general procedure 114, 1-chloro-5H-6-thia-4,5-diaza-chrysene 6,6-dioxide 305 (90 mg, 0.28 mmol), dimethyl amine (2M in THF; 0.13 g, 2.84 mmol) gave the title compound (25 mg, 27%) after washing the precipitated product with Et20.
EOAI3355291 VIT-1997
MW: 325.39
HPLCMS (Method C): [m/z]: 326

6,6-Dioxo-5,6-dihydro-6λ*6*-thia-4,5-diaza-chrysen-1-yl)-methyl-amine (Example Compound 498

In a similar fashion using route 48 general procedure 114, 1-chloro-5H-6-thia-4,5-diaza-chrysene 6,6-dioxide 305 (90 mg, 0.28 mmol), methyl amine (2M in THF; 1.42 ml, 2.84 mmol) gave the title compound (30 mg, 34%) after washing the precipitated product with Et20.
EOAI3355292 VIT-1996
MW: 311.36
HPLCMS (Method C): [m/z]: 312

6,6-Dioxo-5,6-dihydro-6λ*6*-thia-4,5-diaza-chrysen-1-ylamine (Example Compound 499)

In a similar fashion using route 48 general procedure 114, 1-chloro-5H-6-thia-4,5-diaza-chrysene 6,6-dioxide 305 (90 mg, 0.28 mmol), 7M NH3 in MeOH (5 ml) gave the title compound (17 mg, 20%) after purification by column chromatography eluting with chloroform/MeOH (98:2:1 drop NH3).
EOAI3358603 VIT-2067
MW: 297.332
HPLCMS (Method C): [m/z]: 297.99
Route 50 (See Above)

General Procedure 116: 4-Dimethylamino-2-nitro-N-quinolin-8-yl-benzenesulfonamide (Intermediate 500)

4-Fluoro-2-nitro-N-quinolin-8-yl-benzenesulfonamide 145 (0.13 g, 0.36 mmol) was dissolved in dimethyl amine (2M in THF; 1.77 ml, 3.59 mmol) and the mixture was heated at 90° C. in a sealed tube for 5 h. After cooling, water was added and the mixture was extracted with EtOAc. The organic phase was dried (Na2SO4) and concentrated in vacuo to give the title compound (0.13 g, 97%) which was used in the next step without further purification.
MW: 372.09
HPLCMS (Method C) [m/z]: 373

2-Amino-4-dimethylamino-N-quinolin-8-yl-benzenesulfonamide (Intermediate 501)

In a similar fashion using route 2 general procedure 4,4-dimethylamino-2-nitro-N-quinolin-8-yl-benzenesulfonamide 500 (140 mg, 0.37 mmol), SnCl2 (210 mg, 1.12 mmol), 6N HCl (1 ml) and EtOH (5 ml) at 80° C. for 6 h gave the title compound (95 mg, 74%) which was used in the next step without further purification.
MW: 342.42
HPLCMS: (Method C): [m/z]: 343.2

6,6-Dioxo-5,6-dihydro-6λ*6*-thia-4,5-diaza-chrysen-9-yl)-dimethyl-amine (Example Compound 502

In a similar fashion using route 20 general procedure 61, 2-amino-4-dimethylamino-N-quinolin-8-yl-benzenesulfonamide 501 (0.11 g, 0.32 mmol), t-butyl nitrite (0.057 ml, 0.48 mmol) and AcOH:THF (1.1 ml: 1.1 ml) to give the title compound after purification by preparative HPLC (acidic conditions 1)
EOAI3361123 VIT-2201
MW: 325.39
HPLCMS (Method A):[m/z]: 325.95
Route 51 (See Above)

General Procedure 117: 12-Chloro-9-fluoro-5H-6-thia-4,5-diaza-chrysene 6,6-dioxide (Intermediate 503)

1,3-dimethyl-5,5-dimethylhydantoin (0.73 g, 36.7 mmol) was added to a solution of 9-fluoro-5H-6-thia-4,5-diaza-chrysene 6,6-dioxide 187 (1.0 g, 33.3 mmol) in chloroform (40 ml) and the reaction was heated at 70° C. until the starting material was consumed (LCMS). After cooling, the mixture was concentrated in vacuo. The residue was dissolved in EtOAc and the organic phase was washed with sodium metabisulfate, water and brine. The organic phase was dried (Na2SO4) and concentrated in vacuo. The crude residue was purified by column chromatography with DCM/MeOH (99:1) as the eluent to give the title compound (0.8 g, 69%).
MW: 334
HPLCMS (Method C): [m/z]: 335.20

General Procedure 118: 1-(12-Chloro-6,6-dioxo-5,6-dihydro-6λ*6*-thia-4,5-diaza-chrysen-9-yl)-piperidin-4-ol (Example Compound 504)

12-Chloro-9-fluoro-5H-6-thia-4,5-diaza-chrysene 6,6-dioxide 503 (100 mg, 0.3 mmol), 4-hydroxy piperidine (121 mg, 1.2 mmol) and NMP (2 ml) were heated in microwave at 180° C. for 4 h. After cooling, the mixture was poured into ice cold water and the resulting precipitate was collected by filtration and dried. The crude residue was purified by column chromatography with DCM/MeOH (99:1) as the eluent to give the title compound (60 mg, 48%).
EOAI3364583 VIT-2267
MW: 415
HPLCMS (Method C): [m/z]: 416.1

12-Chloro-6,6-dioxo-5,6-dihydro-6Iλ*6*-thia-4,5-diaza-chrysen-9-yl)-diethyl-amine (Example Compound 505

In a similar fashion using route 51 general procedure 118, 12-chloro-9-fluoro-5H-6-thia-4,5-diaza-chrysene 6,6-dioxide 503 (100 mg, 0.3 mmol), diethyl amine (87 mg, 1.2 mmol) and NMP (2 ml) gave the title compound (30 mg, 26%) after purification by column chromatography DCM/MeOH (98:2) as the eluent.
EOAI3365395 VIT-2299
MW: 387
HPLCMS (Method F): [m/z]: 388.4

11-(12-Chloro-6,6-dioxo-5,6-dihydro-6λ*6*-thia-4,5-diaza-chrysen-9-yl)-pyrrolidin-3-ol (Example Compound 506)

In a similar fashion using route 51 general procedure 118, 12-chloro-9-fluoro-5H-6-thia-4,5-diaza-chrysene 6,6-dioxide 503 (150 mg, 0.4 mmol) and 3-pyrrolidinol (156 mg, 1.8 mmol) gave the title compound (22 mg, 16%) after purification by column chromatography with DCM/MeOH (99:1) as the eluent.

EOAI3366007 VIT-2341
MW: 367.43
HPLCMS (Method E): [m/z]: 368.3

12-Chloro-6,6-dioxo-5,6-dihydro-6λ*6*-thia-4,5-diaza-chrysen-9-yl)-(2-methoxy-ethyl)-amine (Example Compound 507

In a similar fashion using route 51 general procedure 118, 12-chloro-9-fluoro-5H-6-thia-4,5-diaza-chrysene 6,6-dioxide 503 (120 mg, 0.36 mmol), 2-methoxyethylamine (67 mg, 0.9 mmol) and NMP (7 ml) gave the title compound (60 mg, 43%) after washing the resulting solid with pentane.
EOAI3363430 VIT-2229
MW: 389.86
HPLCMS (Method C): [m/z]: 390.1

12-Chloro-9-(4-methyl-piperazin-1-yl)-5H-6-thia-4,5-diaza-chrysene 6,6-dioxide (Example Compound 508)

In a similar fashion using route 51 general procedure 118, 12-chloro-9-fluoro-5H-6-thia-4,5-diaza-chrysene 6,6-dioxide 503 (100 mg, 0.3 mmol), 1-methyl piperazine (59 mg, 0.6 mmol) and NMP (2 ml) gave title compound (35 mg, 28%) after purification by column chromatography using DCM/MeOH (99.5:0.5) as the eluent.
EOAI3363589 VIT-2247
MW: 414.92
HPLCMS (Method F): [m/z]: 415.1

12-Chloro-9-morpholin-4-yl-5H-6-thia-4,5-diaza-chrysene 6,6-dioxide (Example Compound 509)

In a similar fashion using route 51 general procedure 118, 12-chloro-9-fluoro-5H-6-thia-4,5-diaza-chrysene 6,6-dioxide 503 (100 mg, 0.3 mmol), morpholine (0.052 ml, 0.6 mmol) and NMP (2 ml) gave title compound (50 mg, 41%) after purification by column chromatography using chloroform/MeOH (99.5:0.5) as the eluent.
EOAI3363590 VIT-2248
MW: 401.87
HPLCMS (Method F): [m/z]: 402.1

12-Chloro-9-piperidin-1-yl-5H-6-thia-4,5-diaza-chrysene 6,6-dioxide (Example Compound 510)

In a similar fashion using route 51 general procedure 118, 12-chloro-9-fluoro-5H-6-thia-4,5-diaza-chrysene 6,6-dioxide 503 (200 mg, 0.6 mmol), piperidine (195 mg, 2.3 mmol) and NMP (2 ml) gave title compound (50 mg, 21%) after purification by column chromatography using DCM/MeOH (99.5:0.5) as the eluent.
EOAI3364585 VIT-2265
MW: 399.90
HPLCMS (Method C): [m/z]: 400.1

12-Chloro-6,6-dioxo-5,6-dihydro-6λ*6*-thia-4,5-diaza-chrysen-9-yl)-(2-morpholin-4-yl-ethyl)-amine (Example Compound 511

In a similar fashion using route 51 general procedure 118, 12-chloro-9-fluoro-5H-6-thia-4,5-diaza-chrysene 6,6-dioxide 503 (200 mg, 0.59 mmol), 2-(morpholin-4-yl)ethan-1-amine (280 mg, 2.3 mmol) and NMP (2 ml) gave title compound (80 mg, 30%) after purification by column chromatography using DCM/MeOH (99.5:0.5) as the eluent.

EOAI3364586 VIT-2266
MW: 444.94
HPLCMS (Method F): [m/z]: 445.2

2-(12-Chloro-6,6-dioxo-5,6-dihydro-6λ*6*-thia-4,5-diaza-chrysen-9-ylamino)-propane-1,3-diol (Example Compound 512)

In a similar fashion using route 51 general procedure 118, 12-chloro-9-fluoro-5H-6-thia-4,5-diaza-chrysene 6,6-dioxide 503 (200 mg, 0.59 mmol), serinol (217 mg, 2.3 mmol) and NMP (2 ml) gave title compound (25 mg, 54%) after purification by column chromatography using DCM/MeOH:aq.NH3 (99.5:0.5:1 drop) as the eluent.
EOAI3365971 VIT-2331
MW: 405.86
HPLCMS (Method E): [m/z]:406.4

Benzyl-(12-chloro-6,6-dioxo-5,6-dihydro-6λ*6*-thia-4,5-diaza-chrysen-9-yl)-amine (Intermediate 513)

In a similar fashion using route 51 general procedure 118, 12-chloro-9-fluoro-5H-6-thia-4,5-diaza-chrysene 6,6-dioxide 503 (400 mg, 1.19 mmol), benzyl amine (510 mg, 4.7 mmol) and NMP (2 ml) gave title compound (218 mg, 42%) after purification by column chromatography using DCM/MeOH (95:5) as the eluent.
MW: 421.91
HPLCMS (Method C): [m/z]: 422.3

General Procedure 119: 12-Chloro-9-cyclopentyloxy-5H-6-thia-4,5-diaza-chrysene 6,6-dioxide (Example Compound 514)

NaH (60% in mineral oil; 53 mg, 1.34 mmol) was added to a solution of cyclopentanol (115 mg, 1.34 mmol) in NMP (3 ml) and the mixture was stirred at room temperature for 15 min. 12-chloro-9-fluoro-5H-6-thia-4,5-diaza-chrysene 6,6-dioxide 503 (150 mg, 0.44 mmol) was added and the mixture was heated at 180 C in a microwave for 2 h. After cooling, the mixture was poured into ice cold water and neutralized using sat aq. KHSO4 solution. The resulting precipitate was collected by filtration and dried. The crude solid was purified by column chromatography with n-hexane/DCM (30:70) as the eluent to give the title compound (23 mg, 20%).
EOAI3365514 VIT-2309
MW: 400.89
HPLCMS (Method E): [m/z]: 401.40

12-Chloro-9-ethoxy-5H-6-thia-4,5-diaza-chrysene 6,6-dioxide (Example Compound 515)

In a similar fashion using route 51 general procedure 119, 12-chloro-9-fluoro-5H-6-thia-4,5-diaza-chrysene 6,6-dioxide 503 (0.3 g, 0.89 mmol), EtOH (0.12 g, 2.6 mmol), NaH (60% in mineral oil; 0.1 g, 2.6 mmol) and NMP (2 ml) gave the title compound (30 mg, 9%) after purification by column chromatography with DCM/MeOH (99:1) as the eluent.
EOAI3365513 VIT-2381
MW: 360.82
HPLCMS (Method C): [m/z]: 361.3

12-Chloro-9-(pyrrolidin-3-yloxy)-5H-6-thia-4,5-diaza-chrysene 6,6-dioxide (Example Compound 516)

In a similar fashion using route 51 general procedure 119, 12-chloro-9-fluoro-5H-6-thia-4,5-diaza-chrysene 6,6-dioxide 503 (0.2 g, 0.6 mmol), 1-boc-3-pyrrolidinol (0.45 g, 2.3 mmol), NaH (60% in mineral oil; 57 mg, 2.3 mmol) and NMP (2 ml) gave the title compound (33 mg, 14%) after purification by preparative HPLC (acidic conditions 2). Boc deprotection occurred in situ during heating.
EOAI3366416 VIT-2357
MW: 401.87
HPLCMS (Method E): [m/z]: 402.3

12-Chloro-9-(piperidin-4-yloxy)-5H-6-thia-4,5-diaza-chrysene 6,6-dioxide (Example Compound 517)

In a similar fashion using route 51 general procedure 119, 12-chloro-9-fluoro-5H-6-thia-4,5-diaza-chrysene 6,6-dioxide 503 (0.15 g, 0.5 mmol), 1-Boc-piperidinol (0.36 g, 0.5 mmol), NaH (60% in mineral oil; 43 mg, 1.8 mmol) and NMP (2 ml) gave the title compound (37 mg, 20%) after purification by column chromatography with DCM/MeOH(98:2) as the eluent. Boc deprotection occurred in situ.
EOAI3366689 VIT-2364
MW: 415.90
HPLCMS (Method C): [M/Z]: 416.4

[2-(12-Chloro-6,6-dioxo-5,6-dihydro-6λ*6*-thia-4, 5-diaza-chrysen-9-yloxy)-ethyl]-dimethyl-amine (Example Compound 518)

In a similar fashion using route 51 general procedure 119, 12-chloro-9-fluoro-5H-6-thia-4,5-diaza-chrysene 6,6-dioxide 503 (200 mg, 0.59 mmol), N,N-dimethyl ethanolamine (210 mg, 2.3 mmol), NaH (60% in mineral oil; 71 mg, 1.79 mmol) and NMP (2 ml) gave the title compound (30 mg, 13%) after purification by column chromatography with DCM/MeOH (98:2) elution.
EOAI3365881 VIT-2330
MW: 403.89
HPLCMS (Method F): [M/Z]: 404.4
Route 52 (See Above)

General Procedure 120: 12-Chloro-6,6-dioxo-5,6-dihydro-6λ*6*-thia-4,5-diaza-chrysen-9-ylamine (Example Compound 519)

A solution of benzyl-(12-chloro-6,6-dioxo-5,6-dihydro-6λ*6*-thia-4,5-diaza-chrysen-9-yl)-amine 513 (218 mg, 0.52 mmol) in 48% aq. HBr (5 ml) was heated at 100° C. in a sealed tube for 3 h. After cooling, the mixture was neutralized with sat. NaHCO3 solution and the aqueous phase was extracted with EtOAc. The organic phase was washed with water, brine, dried (Na2SO4) and concentrated in vacuo. The crude residue was purified by column chromatography with DCM as the eluent to give the title compound (50 mg, 77%).
EOAI3365515 VIT-2353
MW: 331.78
HPLCMS (Method A): [m/z]: 331.95
Route 53 (See Above)

General Procedure 121: 6,6-Dioxo-5,6-dihydro-6λ*6*-thia-4,5-diaza-chrysene-9-carboxylic acid (Example Compound 520)

LiOH (9 mg, 0.21 mmol) was added to a solution of 6,6-dioxo-5,6-dihydro-6λ*6*-thia-4,5-diaza-chrysene-9-carboxylic acid methyl ester 307 (33 mg, 0.097 mmol) in MeOH (2 ml) and the mixture was heated at 65° C. for 18 h. After cooling, the pH was adjusted to 7-8 with methanolic HCl. The mixture was concentrated in vacuo. The crude residue was purified by column chromatography with DCM/MeOH (90:10) as the eluent to give the title compound (28 mg, 90%).
EOAI3359233 VIT-2105
MW: 326.33
HPLCMS (Method C): [m/z]: 326.96

General Procedure 122: 6,6-Dioxo-5,6-dihydro-6λ*6*-thia-4,5-diaza-chrysene-9-carboxylic acid amide (Example Compound 521)

A solution of 6,6-dioxo-5,6-dihydro-6λ*6*-thia-4,5-diaza-chrysene-9-carboxylic acid methyl ester 307 (50 mg, 0.15 mmol) in 7M NH3 in MeOH (5 ml) was heated at 90 C in sealed tube for 36 h. After cooling, the mixture was concentrated in vacuo. The crude residue was purified by column chromatography with DCM/MeOH (95:5) as the eluent to give the title compound (8 mg, 17%).
EOAI3360495 VIT-2162
MW: 325.35
HPLCMS: (Method C): [m/z]:325.95

6,6-Dioxo-5,6-dihydro-6λ*6*-thia-4,5-diaza-chrysene-9-carboxylic acid methylamide (Example Compound 522)

In a similar fashion using route 53 general procedure 122, 6,6-dioxo-5,6-dihydro-6λ*6*-thia-4,5-diaza-chrysene-9-carboxylic acid methyl ester 307 (20 mg, 0.058 mmol), methylamine (33% in EtOH; 4 ml, 0.58 mmol) at 100° C. gave the title compound (16 mg 84%) after purification by column chromatography with DCM/MeOH (99:1) as the eluent.
EOAI3359141 VIT-2095
MW: 339.01
HPLCMS (Method C): [m/z]: 340
Route 54 (See Above)

12-Chloro-6,6-dioxo-5,6-dihydro-6λ*6*-thia-4,5-diaza-chrysene-9-carboxylic acid methyl ester (Intermediate 523)

In a similar fashion using route 51 general procedure 117, 6,6-dioxo-5,6-dihydro-6λ*6*-thia-4,5-diaza-chrysene-9-carboxylic acid methyl ester 307 (1.1 g, 3.2 mmol), 1,3-dichloro-5,5-dimethylhydantion (765 mg, 3.8 mmol) in chloroform (40 ml), gave the title compound (1.6 g, 57%) after washing with MeOH/DCM.
MW: 374.81
HPLCMS (Method C): [m/z]: 375

12-Chloro-6,6-dioxo-5,6-dihydro-6λ*6*-thia-4,5-diaza-chrysene-9-carboxylic acid (Intermediate 524)

In a similar fashion using route 53 general procedure 121, 12-chloro-6,6-dioxo-5,6-dihydro-6λ*6*-thia-4,5-diaza-chrysene-9-carboxylic acid methyl ester 523 (0.85 g, 2.2 mmol), LiOH (190 mg, 4.5 mmol), MeOH:H2O:THF (10 ml: 3 ml: 2 ml) gave the title compound (0.74 g, 89%) after washing with MeOH.
MW: 360.78
HPLCMS (Method C): [m/z]: 361

General Procedure 123: 12-Chloro-6,6-dioxo-5,6-dihydro-6λ*6*-thia-4,5-diaza-chrysene-9-carboxylic acid dimethylamide (Example Compound 525)

Dimethyl amine (0.2M in THF, 2.77 ml, 0.69 mmol) was added to a solution of 12-chloro-6,6-dioxo-5,6-dihydro- 6λ*6*-thia-4,5-diaza-chrysene-9-carboxylic acid 524 (100 mg, 0.27 mmol), EDC.HCl (80 mg, 0.41 mmol), HOBt (56 mg, 0.41 mmol) and TEA (0.12 ml, 0.83 mmol) in DMF (1 ml) and the mixture was stirred at room temperature for 12 h. The mixture was diluted with water and DCM. The organic phase was dried (Na2SO4) and concentrated in vacuo. The crude residue was purified by column chromatography with chloroform/MeOH (95:5) as the eluent to give the title compound (45 mg, 42%).

EOAI3365105 VIT-2278
MW: 387.3
HPLCMS (Method C): [m/z]: 388.31

12-Chloro-6,6-dioxo-5,6-dihydro-6λ*6*-thia-4,5-diaza-chrysen-9-yl)-(4-methyl-piperazin-1-yl)-methanone (Example Compound 526

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 1-methyl piperazine (0.06 ml, 0.55 mmol), EDC.HCl (80 mg, 0.41 mmol), HOBt (56 mg, 0.41 mmol), TEA (0.12 ml, 0.83 mmol) and DMF (1 ml) gave title compound (25 mg, 20%) after purification by column chromatography with chloroform/MeOH (95:5) as the eluent.

EOAI3364584 VIT-2270
MW: 442.93
HPLCMS (Method C): [m/z]: 443.1

12-Chloro-6,6-dioxo-5,6-dihydro-6λ*6*-thia-4,5-diaza-chrysen-9-yl)-morpholin-4-yl-methanone (Example Compound 527

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), morpholine (0.05 ml, 0.55 mmol), EDC.HCl (80 mg, 0.41 mmol), HOBt (56 mg, 0.41 mmol), TEA (0.12 ml, 0.83 mmol) and DMF (1 ml) gave the title compound (55 mg, 46%) after purification by column chromatography with chloroform/MeOH (97:3) as the eluent.

EOAI3365102 VIT-2279
MW: 429.89
HPLCMS (Method C): [m/z]: 430.33

12-Chloro-6,6-dioxo-5,6-dihydro-6λ*6*-thia-4,5-diaza-chrysene-9-carboxylic acid (2-methoxy-ethyl)-amide (Example Compound 528)

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 2-methoxyethylamine (0.05 ml, 0.55 mmol), EDC.HCl (80 mg, 0.41 mmol), HOBt (56 mg, 0.41 mmol), TEA (0.12 ml, 0.83 mmol) and DMF (1 ml) gave the title compound (50 mg, 43%) after purification by column chromatography with chloroform/MeOH (98:2) as the eluent.

EOAI3365103 VIT-2281
MW: 417.3
HPLCMS (Method C):[m/z]: 418.31

12-Chloro-6,6-dioxo-5,6-dihydro-6λ*6*-thia-4,5-diaza-chrysene-9-carboxylic acid (2-dimethylamino-ethyl)-amide (Example Compound 529)

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), N,N dimethylethylenediamine (0.06 ml, 0.55 mmol), EDC.HCl (80 mg, 0.41 mmol), HOBt (56 mg, 0.41 mmol), TEA (0.12 ml, 0.83 mmol) and DMF (1 ml) gave the title compound (60 mg, 50%) after trituration from MeOH.

EOAI3365104 VIT-2280
MW: 430.4
HPLCMS (Method E): [m/z]: 431.38

12-Chloro-6,6-dioxo-5,6-dihydro-6λ*6*-thia-4,5-diaza-chrysen-9-yl)-(4-hydroxy-piperidin-1-yl)-methanone (Example Compound 530

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 4-hydroxy piperidine (56 mg, 0.55 mmol), EDC.HCl (80 mg, 0.41 mmol), HOBt (56 mg, 0.41 mmol), TEA (0.12 ml, 0.83 mmol) and DMF (1 ml) gave the title compound (30 mg, 24%) after column purification with DCM/MeOH (95:5) as the eluent.

EOAI3365511 VIT-2365
MW: 443.9
HPLCMS (Method E): [m/z]: 444.3

12-Chloro-6,6-dioxo-5,6-dihydro-6lambda*6*-thia-4,5-diaza-chrysen-9-yl)-(3-hydroxy-pyrrolidin-1-yl)-methanone (Example Compound 531

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 3-pyrrolidinol (50 mg, 0.55 mmol), EDC.HCl (80 mg, 0.41 mmol), HOBt (56 mg, 0.41 mmol), TEA (0.12 ml, 0.11 mmol) and DMF (1 ml) gave the title compound (52 mg, 43%) after purification by column chromatography with chloroform/MeOH (98:2) as the eluent.

EOAI3365512 VIT-2345
MW: 429.89
HPLCMS (Method C): [m/z]: 430.3

12-Chloro-6,6-dioxo-5,6-dihydro-6λ*6*-thia-4,5-diaza-chrysene-9-carboxylic acid (2-hydroxy-1-hydroxymethyl-ethyl)-amide (Example Compound 532)

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), serinol (50 mg, 0.55 mmol), EDC.HCl (80 mg, 0.41 mmol), HOBt (56 mg, 0.41 mmol), TEA (0.12 ml, 0.11 mmol) and DMF (1 ml) gave the title compound (40 mg, 33%) after purification by column chromatography with chloroform/MeOH (90:10) as the eluent.

EOAI3365878 VIT-2324
MW: 433.3
HPLCMS (Method E): [m/z]: 434.3

12-Chloro-6,6-dioxo-5,6-dihydro-6λ*6*-thia-4,5-diaza-chrysene-9-carboxylic acid cyclopentyl ester (Example Compound 533)

In a similar fashion using route 54 general procedure 123, 12-chloro-6,6-dioxo-5,6-dihydro-6λ*6*-thia-4,5-diaza-chrysene-9-carboxylic acid 524 (150 mg, 0.41 mmol), cyclopentanol (0.19 ml, 2.0 mmol), EDC.HCl (88 mg, 0.45 mmol), DMAP (6 mg, 0.04 mmol) and DMF (1 ml) gave the title compound (50 mg, 28%) after purification by column chromatography with DCM as the eluent.
EOAI3365235 VIT-2289
MW: 428.90
HPLCMS (Method C): [m/z]: 429.36

12-Chloro-6,6-dioxo-5,6-dihydro-6λ*6*-thia-4,5-diaza-chrysene-9-carboxylic acid 1-tert-butoxycarbonyl-piperidin-4-yl ester (Intermediate 534)

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 1-Boc-4-piperidinol (0.11 g, 0.55 mmol), EDC.HCl (80 mg, 0.41 mmol), HOBt (56 mg, 0.41 mmol), TEA (0.12 ml, 0.11 mmol) and DMF (1 ml) gave the title compound (70 mg, 46%) after purification by column chromatography with DCM as the eluent.
MW: 544.03
HPLCMS (Method C): [m/z]: 544.4

12-Chloro-6,6-dioxo-5,6-dihydro-6λ*6*-thia-4,5-diaza-chrysene-9-carboxylic acid 1-tert-butoxycarbonyl-pyrrolidin-3-yl ester (Intermediate 535)

In a similar fashion using route 54 general procedure 123, 12-chloro-6,6-dioxo-5,6-dihydro-6λ*6*-thia-4,5-diaza-chrysene-9-carboxylic acid 524 (100 mg, 0.27 mmol), 1-Boc-3-pyrrolidinol (0.11 g, 0.55 mmol), EDC.HCl (80 mg, 0.41 mmol), HOBt (56 mg, 0.41 mmol) and DMF (1 ml) gave the title compound (70 mg, 47%) after purification by column chromatography with DCM as the eluent.
MW: 530.0
HPLCMS (Method C): [m/z]: 530.4
Route 55 (See Above)

General procedure 124: 12-Chloro-6,6-dioxo-5,6-dihydro-6λ*6*-thia-4,5-diaza-chrysene-9-carboxylic acid piperidin-4-yl ester (Example Compound 536)

A solution of 12-chloro-6,6-dioxo-5,6-dihydro-6λ*6*-thia-4,5-diaza-chrysene-9-carboxylic acid 1-tert-butoxycarbonyl-piperidin-4-yl ester 534 (70 mg, 0.12 mmol) in 4M HCl in dioxane (3 ml) was stirred at room temperature for 12 h. The solvent was removed in vacuo and the residue was washed with MeOH to give the title compound (27 mg, 47%).
EOAI3365879 VIT-2332
MW: 442.30
HPLCMS (Method C): [m/z]: 444.3

12-Chloro-6,6-dioxo-5,6-dihydro-6λ*6*-thia-4,5-diaza-chrysene-9-carboxylic acid pyrrolidin-3-yl ester (Example Compound 537)

In a similar fashion using route 55 general procedure 124, 12-chloro-6,6-dioxo-5,6-dihydro-6λ*6*-thia-4,5-diaza-chrysene-9-carboxylic acid 1-tert-butoxycarbonyl-pyrrolidin-3-yl ester (70 mg, 0.13 mmol) and 4M HCl in dioxane (3 ml) gave the title compound (41 mg, 73%) after washing with MeOH.
EOAI3365880 VIT-2325
MW: 429.89
HPLCMS (Method C):[m/z]: 430.3
Route 56 (See Above)

8-Benzenesulfonylamino-quinoline-4-carboxylic acid methylamide (Example Compound 538)

In a similar fashion using route 53 general procedure 122, 8-benzenesulfonylamino-quinoline-4-carboxylic acid methyl ester 225 (50 mg, 0.15 mmol) and methyl amine (33% in EtOH, 3 ml) gave the title compound (23 mg, 50%) after purification by column chromatography with DCM/MeOH (95:5) as the eluent.
EOAI3357158 VIT-2053
MW: 341.39
HPLCMS (Method C): [m/z]: 342

8-Benzenesulfonylamino-quinoline-4-carboxylic acid amide (Example Compound 539)

In a similar fashion using route 53 general procedure 122, 8-benzenesulfonylamino-quinoline-4-carboxylic acid methyl ester 225 (25 mg, 0.073 mmol) and NH3 in MeOH (7M; 3 ml) gave the title compound (13 mg, 50%) after purification by recrystallisation from DCM.
EOAI3355290 VIT-2001
MW: 327.36
HPLCMS (Method C): [m/z]: 328.30
Route 57 (See Above)

6,6-Dioxo-5,6-dihydro-6λ*6*-thia-4,5-diaza-chrysene-1-carboxylic acid (Intermediate 540)

In a similar fashion using route 53 general procedure 121, 6,6-dioxo-5,6-dihydro-6λ*6*-thia-4,5-diaza-chrysene-1-carboxylic acid methyl ester 319 (114 mg, 0.33 mmol), LiOH (28 mg, 0.66 mmol) and MeOH (3 ml) gave the title compound (150 mg, crude) which was used in the next step without further purification.
MW: 326.33
HPLCMS (Method C): [m/z]:325

6,6-Dioxo-5,6-dihydro-6λ*6*-thia-4,5-diaza-chrysene-1-carboxylic acid dimethylamide (Example Compound 541)

In a similar fashion using route 54 general procedure 123, 6,6-dioxo-5,6-dihydro-6λ*6*-thia-4,5-diaza-chrysene-1-carboxylic acid 540 (75 mg, 0.23 mmol), dimethyl amine (2M in THF; 0.15 ml, 0.92 mmol), EDC.HCl (57 mg, 0.29 mmol), HOBt (34 mg, 0.25 mmol), DIPEA (0.12 ml, 0.69 mmol) and DMF (3.5 ml) at room temperature for 48 h gave the title compound (21 mg, 26%) after purification by column chromatography with DCM/MeOH (99:1) as the eluent.
EOAI3359536 VIT-2118
MW: 353.40
HPLCMS (Method C): [m/z]: 354.2

6,6-Dioxo-5,6-dihydro-6λ*6*-thia-4,5-diaza-chrysene-1-carboxylic acid methylamide (Example Compound 542)

In a similar fashion using route 53 general procedure 122, 6,6-dioxo-5,6-dihydro-6λ*6*-thia-4,5-diaza-chrysene-1-carboxylic acid methyl ester 319 (45 mg, 0.10 mmol) and methyl amine (33% in EtOH; 3 ml) at 80° C. for 16 h gave the title compound (22 mg, 50%) after purification by column chromatography with DCM/MeOH (97:2) as the eluent.
EOAI3358598 VIT-2064
MW: 339.38
HPLCMS (Method C): [m/z]: 339.98

6,6-Dioxo-5,6-dihydro-6λ*6*-thia-4,5-diaza-chrysene-1-carboxylic acid amide (Example Compound 543)

In a similar fashion using route 53 general procedure 122, 6,6-dioxo-5,6-dihydro-6λ*6*-thia-4,5-diaza-chrysene-1- carboxylic acid methyl ester 319 (45 mg, 0.10 mmol) and NH3 in MeOH (7M; 3 ml) at 80° C. for 24 h gave the title compound (25 mg, 59%) after recrystallisation from MeOH/DCM/pentane.
EOAI3358599 VIT-2065
MW: 325.35
HPLCMS (Method C): [m/z]: 325.95

6,6-Dioxo-5,6-dihydro-6λ*6*-thia-4,5-diaza-chrysene-1-carboxylic acid (2-piperidin-1-yl-ethyl)-amide (Example Compound 544)

In a similar fashion using route 53 general procedure 123, 6,6-dioxo-5,6-dihydro-6λ*6*-thia-4,5-diaza-chrysene-1-carboxylic acid 540 (55 mg, 0.16 mmol), 1-2(aminoethyl)piperidine (0.053 ml, 0.35 mmol), EDC.HCl (42 mg, 0.21 mmol), HOBt (25 mg, 0.18 mmol), DIPEA (0.086 ml, 0.5 mmol) and DMF (3 ml) at room temperature for 12 h gave title compound (15 mg, 21%) after purification by column chromatography with chloroform/MeOH (95:5) as the eluent followed by preparative HPLC (acidic conditions 1).
EOAI3360202 VIT-2173
MW: 436.54
HPLCMS (Method A):[m/z]: 437.10
Route 58 (See Above)

General Procedure 125: 12-Bromo-5H-6-thia-4,5-diaza-chrysene 6,6-dioxide (Example Compound 545)

Bromine (170 μl, 3.30 mmol) was added dropwise to a solution of 5H-6-thia-4,5-diaza-chrysene 6,6-dioxide 184 (467 mg, 1.65 mmol) in 1,4-dioxane/chloroform (1:1, 124 ml) at 0° C. After 2 h, chloroform (30 ml) was added and the resulting precipitate was collected by filtration. The solid was triturated from MeOH to give the title compound (385 mg, 64%).
EOAI3360272 VIT-2139
MW: 360.80
HPLCMS (Method A):[m/z]: 360.95/362.90

General procedure 126: N'-(6,6-Dioxo-5,6-dihydro-6*6*-thia-4,5-diaza-chrysen-12-yl)-N,N-dimethyl-ethane-1,2-diamine (Example Compound 546)

Toluene was de-gassed for 15 min. Toluene (2 ml) and N*1*,N*1*-dimethyl-ethane-1,2-diamine (33 I, 0.42 mmol) was added to a mixture of Pd2(dba)3 (3 mg, 3.0 mol), X-Phos (7 mg, 14.0 μmol), NaOtBu (67 mg, 0.69 mmol), 12-bromo-5H-6-thia-4,5-diaza-chrysene 6,6-dioxide 545 (100 mg, 0.28 mmol), under nitrogen. After heating for 18 h at 90° C., the mixture was re-treated with N*1*,N*1*-dimethyl-ethane-1,2-diamine (33 I, 0.42 mmol), Pd2(dba)3 (3 mg, 3.0 mol), X-Phos (7 mg, 14.0 μmol) and NaOtBu (67 mg, 0.69 mmol) twice a day until the starting material was less than 30% by LCMS analysis. After cooling, the mixture was diluted with MeOH and concentrated in vacuo. The residue was dissolved in MeOH (2 ml), filtered and purified by preparative HPLC (acidic conditions 1) to give the title compound (12 mg, 12%).
EOAI3360688 VIT-2159
MW: 368.45
HPLCMS (Method A):[m/z]: 369.00

6,6-Dioxo-5,6-dihydro-6*6*-thia-4,5-diaza-chrysen-12-yl)-(2-morpholin-4-yl-ethyl)-amine (Example Compound 547

In a similar fashion using route 58 general procedure 126, 2-morpholin-4-yl-ethylamine (55 I, 0.42 mmol), Pd2(dba)3 (3 mg, 3 μmol), X-Phos (7 mg, 14 μmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (25 mg, 22%) after purification by preparative HPLC (acidic conditions 1).
EOAI3360689 VIT-2160
MW: 410.49
HPLCMS (Method A):[m/z]: 411.05

6,6-Dioxo-5,6-dihydro-6*6*-thia-4,5-diaza-chrysen-12-yl)-(2-methoxy-ethyl)-amine (Example Compound 548

In a similar fashion using route 58 general procedure 126, 2-methoxyethylamine (37 I, 0.42 mmol), Pd2(dba)3 (3 mg, 3 μmol), X-Phos (7 mg, 14 μmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (12 mg, 10%) after purification by preparative HPLC (acidic conditions 1).
EOAI3361416 VIT-2191
MW: 355.41
HPLCMS (Method A):[m/z]: 355.95

12-Morpholin-4-yl-5H-6-thia-4,5-diaza-chrysene 6,6-dioxide (Example Compound 549)

In a similar fashion using route 58 general procedure 126, morpholine (37 μl, 0.42 mmol), Pd2(dba)3 (3 mg, 3 μmol), X-Phos (7 mg, 14 μmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (28 mg, 28%) after purification by preparative HPLC (acidic conditions 1).
EOAI3361311 VIT-2182
MW: 367.42
HPLCMS (Method A):[m/z]: 367.95

{2-[4-(6,6-Dioxo-5,6-dihydro-6*6*-thia-4,5-diaza-chrysen-12-yl)-piperazin-1-yl]-ethyl}-dimethyl-amine (Example Compound 550)

In a similar fashion using route 58 general procedure 126, dimethyl-(2-piperazin-1-yl-ethyl)-amine (66 μl, 0.42 mmol), Pd2(dba)3 (3 mg, 3 μmol), X-Phos (7 mg, 14 μmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (11 mg, 9%) after purification by preparative HPLC (acidic conditions 1).
EOAI3361312 VIT-2183
MW: 437.56
HPLCMS (Method A):[m/z]: 438.10

12-Piperidin-1-yl-5H-6-thia-4,5-diaza-chrysene 6,6-dioxide (Example Compound 551)

In a similar fashion using route 58 general procedure 126, piperidine (41 μl, 0.42 mmol), Pd2(dba)3 (3 mg, 3 μmol), X-Phos (7 mg, 14 μmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (19 mg, 19%) after purification by preparative HPLC (acidic conditions 1).
EOAI3361417 VIT-2192
MW: 365.45
HPLCMS (Method A):[m/z]: 365.95

N-(6,6-Dioxo-5,6-dihydro-6*6*-thia-4,5-diaza-chrysen-12-yl)-N,N',N'-trimethyl-ethane-1,2-diamine (Example Compound 552)

In a similar fashion using route 58 general procedure 126, N,N,N'-trimethyl-ethane-1,2-diamine (43 µl, 0.42 mmol), Pd2(dba)3 (3 mg, 3 µmol), X-Phos (7 mg, 14 µmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (19 mg, 19%) after purification by preparative HPLC (acidic conditions 1).
EOAI3361418 VIT-2193
MW: 382.48
HPLCMS (Method A):[m/z]: 383.05

General procedure 127: 12-Pyrrolidin-1-yl-5H-6-thia-4,5-diaza-chrysene 6,6-dioxide (Example Compound 553)

Toluene was de-gassed for 15 min. Toluene (2 ml) and pyrrolidine (30 µl, 0.42 mmol) were added to a mixture of Pd2(dba)3 (25 mg, 28 µmol), X-Phos (66 mg, 0.14 mmol), NaOtBu (67 mg, 0.69 mmol), 12-bromo-5H-6-thia-4,5-diaza-chrysene 6,6-dioxide 545 (100 mg, 0.28 mmol), under nitrogen and the mixture was heated at 90° C. for 18 h. After cooling, the mixture was diluted with MeOH (3 ml), filtered and concentrated in vacuo. The residue was purified by preparative HPLC (acidic conditions 1) to give the title compound (33 mg, 34%).
EOAI3366361 VIT-2343
MW: 351.42
HPLCMS (Method A):[m/z]: 351.95

6,6-Dioxo-5,6-dihydro-6λ*6*-thia-4,5-diaza-chrysen-12-yl)-(2-methoxy-ethyl)-methyl-amine (Example Compound 554)

In a similar fashion using route 58 general procedure 127, (2-methoxy-ethyl)-methyl-amine (45 µl, 0.42 mmol), Pd2(dba)3 (25 mg, 28 µmol), X-Phos (66 mg, 0.14 mmol), NaOtBu (67 mg, 0.69 mmol), 12-bromo-5H-6-thia-4,5-diaza-chrysene 6,6-dioxide 545 (100 mg, 0.28 mmol) and toluene (2 ml) gave the title compound (10 mg, 10%) after purification by preparative HPLC (acidic conditions 1).
EOAI3366362 VIT-2344
MW: 369.44
HPLCMS (Method A):[m/z]: 370.10

General Procedure 128: (6,6-Dioxo-5,6-dihydro-6λ*6*-thia-4,5-diaza-chrysen-12-yl)-morpholin-4-yl-methanone (Example Compound 555)

Morpholine was added to a suspension of 12-bromo-5H-6-thia-4,5-diaza-chrysene 6,6-dioxide 545 (100 mg, 0.28 mmol), Hermann's palladacycle (13 mg, 14 µmol), Mo(CO)6 (73 mg, 0.28 mmol), DBU (126 mg, 0.83 mmol) and THF (2 ml) in a microwave vessel. The vessel was sealed under air and the mixture was heated in the microwave at 150° C. for 15 min. After cooling, the mixture was concentrated in vacuo. The residue was diluted with MeOH (2 ml), filtered and the filtrate was purified by preparative HPLC (acidic conditions 1) to give the title compound (6 mg, 6%).
EOAI3362739 VIT-2214
MW: 395.43
HPLCMS (Method A):[m/z]:396.05

6,6-Dioxo-5,6-dihydro-6λ*6*-thia-4,5-diaza-chrysene-12-carboxylic acid (2dimethylamino-ethyl)-amide (Example Compound 556)

In a similar fashion using route 58 general procedure 128, N*1*,N*1*-dimethyl-ethane-1,2-diamine (73 mg, 0.83 mmol), 12-bromo-5H-6-thia-4,5-diaza-chrysene 6,6-dioxide 545 (100 mg, 0.28 mmol), Hermann's palladacycle (13 mg, 14 µmol, Mo(CO)6 (73 mg, 0.28 mmol), DBU (126 mg, 0.83 mmol) and THF (2 ml) gave the title compound (43 mg, 39%).
EOAI3362740 VIT-2215
MW: 396.46
HPLCMS (Method A):[m/z]: 397.10

6,6-Dioxo-5,6-dihydro-6λ*6*-thia-4,5-diaza-chrysene-12-carboxylic acid (2-piperidin-1-yl-ethyl)-amide (Example Compound 557)

In a similar fashion using route 58 general procedure 128, 2-piperidin-1-yl-ethylamine (106 mg, 0.83 mmol), 12-bromo-5H-6-thia-4,5-diaza-chrysene 6,6-dioxide 545 (100 mg, 0.28 mmol), Hermann's palladacycle (13 mg, 14 µmol, Mo(CO)6 (73 mg, 0.28 mmol), DBU (126 mg, 0.83 mmol) and THF (2 ml) gave the title compound (42 mg, 35%).
EOAI3362741 VIT-2216
MW: 436.53
HPLCMS (Method A):[m/z]: 437.10
Route 59 (See Above)

General Procedure 129: 1-(6,6-Dioxo-5,6-dihydro-6λ*6*-thia-4,5-diaza-chrysen-12-yl)-ethanone (Intermediate 558)

A solution of DMF/H$_2$O (4:1) was de-gassed for 15 min. DMF/H$_2$O (4:1, 6 ml) and 1-vinyloxy-butane (0.59 ml, 4.53 mmol) were added to a mixture of Pd(OAc)2 (6 mg, 26 µmol), 1,3-bis(diphenylphosphino)propane (24 mg, 57 K2CO3 (150 mg, 1.01 mmol), 12-bromo-5H-6-thia-4,5-diaza-chrysene 6,6-dioxide 545 (370 mg, 0.91 mmol), under nitrogen. The mixture was heated at 90° C. for 2.5 h in the microwave. After cooling, the reaction was diluted with THF (2 ml) and 1M HCl (2 ml) and the mixture was stirred for 18 h. The mixture was further diluted with EtOAc (10 ml) and washed with water (10 ml, x3). The precipitate formed during work-up was collected by filtration of the organic and aqueous phases and was found to be the title compound (140 mg, 40%). The organic phase was dried (Na2SO4) and concentrated in vacuo. The residue was triturated from MeOH to give the title compound (90 mg, 24%) which was used in the next step without further purification.
MW: 324.35
HPLCMS (Method B):[m/z]: 324.90

General Procedure 130: 2-Bromo-1-(6,6-dioxo-5,6-dihydro-6λ*6*-thia-4,5-diaza-chrysen-12-yl)-ethanone (Intermediate 559)

Bromine (22 µl, 0.43 mmol) and HBr (33% solution in AcOH; 1.1 ml) were added to a suspension of 1-(6,6-dioxo-5,6-dihydro-6*6*-thia-4,5-diaza-chrysen-12-yl)-ethanone 558 (140 mg, 0.43 mmol) in AcOH (1.1 ml). The mixture was stirred at 0° C. for 1 h and stirring was continued at room temperature for 16 h. The mixture was diluted with water (5 ml) and the resulting solid was collected by filtration to give the title compound (162 mg, 41%) which was used in the next step without further purification.
MW: 403.25
HPLCMS (Method B):[m/z]: 402.95/404.75

General Procedure 131: 1-(6,6-Dioxo-5,6-dihydro-6λ*6*-thia-4,5-diaza-chrysen-12-yl)-2-morpholin-4-yl-ethanone (Example Compound 560)

Morpholine (104 mg, 1.19 mmol) was added to a suspension of 2-bromo-1-(6,6-dioxo-5,6-dihydro-6*6*-thia-4,5-diaza-chrysen-12-yl)-ethanone 559 (160 mg, 0.40 mmol) in THF (2 ml) and the mixture was stirred at room temperature for 16 h. The reaction was concentrated in vacuo and the residue was diluted with sat. NaHCO3 solution (3 ml) and the aqueous phase was extracted with DCM. The organic phase was dried (Na2SO4) and concentrated in vacuo. The crude residue was purified by preparative HPLC (acidic conditions 1) to give the title compound (7 mg, 4%).
EOAI3364709 VIT-2264
MW: 409.46
HPLCMS (high pH*):[m/z]: 410.10

General Procedure 132: 1-(6,6-Dioxo-5,6-dihydro-6*6*-thia-4,5-diaza-chrysen-12-yl)-ethanol (Example Compound 561)

NaBH4 (7 mg, 0.18 mmol) was added to a stirred solution of 1-(6,6-dioxo-5,6-dihydro-6*6*-thia-4,5-diaza-chrysen-12-yl)-ethanone 558 (30 mg, 92 µmol) in EtOH (1 ml) at 0° C. The mixture was allowed to warm to room temperature and was stirred at room temperature for 18 h. The reaction was re-treated with NaBH4 (7 mg, 0.18 mmol) and stirring was continued for a further 18 h. The mixture was concentrated in vacuo. The crude residue was purified by preparative HPLC (acidic conditions 1) to give the title compound (2 mg, 7%).
EOAI3362849 VIT-2219
MW: 326.37
HPLCMS (Method A):[m/z]: 327.00
Route 60 (See Above)

General Procedure 133: [2-(6,6-Dioxo-5,6-dihydro-6*6*-thia-4,5-diaza-chrysen-12-yloxy)-ethyl]-dimethyl-amine (Example Compound 562)

Toluene was de-gassed for 15 min. Toluene (1 ml) and 2-dimethylamino-ethanol (56 µl, 0.55 mmol) were added to a mixture of 12-bromo-5H-6-thia-4,5-diaza-chrysene 6,6-dioxide 545 (100 mg, 0.28 mmol), Pd(OAc)2 (3 mg, 14 µmol), di-tert-butyl-(2',4',6'-triisopropyl-biphenyl-2-yl)-phosphane (9 mg, 22 µmol) and Cs2CO3 (135 mg, 0.42 mmol), under nitrogen. After heating at 90° C. for 18 h, the reaction was re-treated with Pd(OAc)2 (3.1 mg, 14 µmol), di-tert-butyl-(2',4',6'-triisopropyl-biphenyl-2-yl)-phosphane (9.4 mg, 22 µmol) and Cs2CO3 (135 mg, 0.42 mmol). The reaction was heated for a further 18 h. After cooling, the mixture was diluted with MeOH and concentrated in vacuo. The crude residue was dissolved in MeOH (2 ml), filtered and purified by preparative HPLC (acidic conditions 1) to give the title compound (12 mg, 12%).
EOAI3365970 VIT-2314
MW: 369.44
HPLCMS (Method A):[m/z]: 370.05
Route 61 (See Above)

General Procedure 134: 8-Nitro-quinolin-5-ol (Intermediate 563)

KOH (2.69 g, 47.9 mmol) was added to a solution of 5-chloro-8-nitro-quinoline 27 (1.0 g, 4.79 mmol) in EtOH (20 ml) and water (30 ml) and the mixture was heated at 100° C. for 2 h. The reaction mixture was cooled in the fridge for 18 h and the resulting crystals were collected by filtration and dried to give the title compound (616 mg, 68%).
MW: 190.16
HPLCMS (Method B):[m/z]: 191.15

General Procedure 135: 5-Benzyloxy-8-nitro-quinoline (Intermediate 564)

Bromomethyl-benzene (424 µl, 3.57 mmol) and K2CO3 (493 mg, 3.57 mmol) were added to a solution of 8-nitro-quinolin-5-ol 563 (566 mg, 2.98 mmol) in DMF (5 ml) and the mixture was heated at 90° C. for 6 h. After cooling, the mixture was diluted with water (25 ml) and the aqueous phase was extracted with EtOAc. The combined organic phases were washed with brine (25 ml), dried (Na2SO4) and concentrated in vacuo to give the title compound (572 mg, 69%) which was used in the next step without further purification.
MW: 280.29
HPLCMS (Method B):[m/z]: 281.40

5-Benzyloxy-quinolin-8-ylamine (Intermediate 565)

In a similar fashion using route 19 general procedure 29, 5-benzyloxy-8-nitro-quinoline 564 (572 mg, 2.04 mmol), SnCl2 (1.84 g, 8.16 mmol), and EtOH (15 ml) gave the title compound (336 mg, 66%) which was used in the next step without further purification.
MW: 250.30
HPLCMS (Method B):[m/z]: 251.40

N-(5-Benzyloxy-quinolin-8-yl)-2-nitro-benzene-sulfonamide (Intermediate 566)

In a similar fashion using route 18 general procedure 26, 5-benzyloxy-quinolin-8-ylamine 565 (336 mg, 1.34 mmol), 2-nitrobenzenesulfonyl chloride (357 mg, 1.61 mmol), and pyridine (3 ml) gave the title compound (519 mg, 89%) which was used in the next step without further purification.
MW: 435.45
HPLCMS (Method B):[m/z]: 436.35

2-Amino-N-(5-benzyloxy-quinolin-8-yl)-benzene-sulfonamide (Intermediate 567)

In a similar fashion using route 19 general procedure 29, N-(5-benzyloxy-quinolin-8-yl)-2-nitro-benzenesulfonamide 566 (519 mg, 1.19 mmol), SnCl2 (1.08 g, 4.77 mmol), and EtOH (10 ml) gave the title compound (417 mg, 86%) which was used in the next step without further purification.
MW: 405.47
HPLCMS (Method B):[m/z]: 406.35

N-(5-Benzyloxy-quinolin-8-yl)-benzenesulfonamide (Example Compound 568)

In a similar fashion using route 20 general procedure 36, 2-amino-N-(5-benzyloxy-quinolin-8-yl)-benzenesulfonamide 567 (417 mg, 1.03 mmol), t-butyl nitrite (209 µl, 1.75 mmol), AcOH (4 ml) and THF (10 ml) gave the title compound (22 mg, 5%) after purification by preparative HPLC (acidic conditions 1).
EOAI3361313 VIT-2181
MW: 390.46
HPLCMS (Method A):[m/z]: 391.05
Route 62 (See Above)

N-(7-Chloro-4-methoxy-quinolin-8-yl)-2-nitro-benzenesulfonamide (Intermediate 569)

In a similar fashion using route 18 general procedure 26, 8-amino-7-chloro-4-methoxyquinoline 70 (550 mg, 2.6 mmol), 2-nitrobenzenesulphonylchloride (642 mg, 2.9 mmol) in pyridine (10 ml) gave the title compound (580 mg, 55%) which was used in the next step without further purification.
MW: 393.81
HPLCMS (Method B):[m/z]: 393.90

2-Amino-N-(7-chloro-4-methoxy-quinolin-8-yl)-benzenesulfonamide (Intermediate 570)

In a similar fashion using route 19 general procedure 29, N-(7-chloro-4-methoxy-quinolin-8-yl)-2-nitro-benzenesulfonamide 569 (580 mg, 1.4 mmol), SnCl2 (1.66 g, 7.3 mmol) in EtOH (20 ml) gave the title compound (470 mg, 92%) which was used in the next step without further purification.
MW: 363.83
HPLCMS (Method B):[m/z]: 363.90

General Procedure 136: 2-Amino-N-(4-methoxy-quinolin-8-yl)-benzenesulfonamide (Intermediate 571)

10% Pd—C (97 mg) was added to a solution of 2-amino-N-(7-chloro-4-methoxy-quinolin-8-yl)-benzenesulfonamide 570 (470 mg, 1.8 mmol), ammonium formate (571 mg, 9.2 mmol) in 50% AcOH (10 ml) and the mixture was heated to 70° C. for 15 h. After cooling, the solvent was removed in vacuo. The residue was dissolved in EtOAc (100 ml) and the organic phase was washed with sat. NaHCO3 solution (50 ml), dried (MgSO4) concentrated in vacuo. The crude residue was purified by column chromatography DCM/MeOH (99:1) as the eluent to give the title compound (191 mg, 32%).
MW: 329.38
HPLCMS (Method A):[m/z]: 330.30

General Procedure 137: 1-Methoxy-5H-6-thia-4,5-diaza-chrysene 6,6-dioxide (Example Compound 572)

t-Butyl nitrite (120 µl, 1.1 mmol) added was added to a solution of 2-amino-N-(4-methoxy-quinolin-8-yl)benzenesulfonamide 571 (254 mg, 0.77 mmol) in AcOH/THF (1:1; 10 ml) at 0° C. and the mixture was stirred at 5° C. for 2 h. The crude residue was purified by column chromatography with DCM/MeOH (99:1) as the eluent followed by preparative HPLC (acidic conditions 1) to give the title compound (16 mg, 6%).
EOAI3349155 VIT-1855
MW: 312.35
HPLCMS (Method A):[m/z]: 313
Route 63 (See Above)

General Procedure 138: 7-Chloroquinoline (Intermediate 573)

4,7 Dichloroquinoline (10 g, 50 mmol) in THF (100 ml) was degassed with N2 for 5 min. PdCl2dppf (1.2 g, 2 mmol), TMEDA (9.97 g, 86 mmol), and NaBH4 (3.24 g, 86 mmol) were added and the mixture was stirred at room temperature for 5 h. Brine (20 ml) was added dropwise and the solvent was removed in vacuo. The residue dissolved in EtOAc (200 ml), dried (MgSO4) and concentrated in vacuo. The crude residue was purified by column chromatography with heptane/EtOAC (4:1-1:1 gradient) as the eluent to give the title compound (5.4 g, 65%).
MW: 163.61
HPLCMS (Method B):[m/z]: 163.90

8-Nitro-7-chloroquinoline (Intermediate 40)

In a similar fashion using route 11 general procedure 15, 7-chloro quinoline 573 (3.5 g, 21 mmol) and fuming HNO3/conc. H2SO4 (4.5 ml:9 ml) gave the title compound 1.24 g, 78%) after purification by column chromatography with heptane/EtOAc (2:1) as the eluent.
MW: 208.61
HPLCMS (Method B):[m/z]: 208.85

General Procedure 139: (8-Nitro-quinolin-7-yl)-phenyl-amine (Intermediate 574)

Aniline (2 ml, 21 mmol) was added to a solution of 8-nitro-7-chloroquinoline 40 (200 mg, 0.96 mmol) in pyridine (1 ml) and the mixture was heated in a microwave at 170° C. under nitrogen for 3 h. The residue was dissolved in EtOAc (50 ml) and the organic phase was washed with sat. NaHCO3 (30 ml) and concentrated in vacuo to give the title compound (230 mg, 89%) which was used in the next step without further purification.
MW: 265.27
HPLCMS (Method B):[m/z]: 266.25

8-Nitro-quinolin-7-yl)-4-Trifluoromethyl-benzylamine (Intermediate 575

In a similar fashion using route 63 general procedure 139, 8-nitro-7-chloroquinoline 40 (800 mg, 4.0 mmol), 4-trifluoromethylbenzylamine (1.34 ml, 8.0 mmol) and pyridine (1 ml) gave the title compound (437 mg, 15%) after purification by column chromatography with heptane/EtOAc (2:1) as the eluent.
MW: 347.30
HPLCMS (Method B):[m/z]: 348

N*7*-Phenyl-quinoline-7,8-diamine (Intermediate 576)

In a similar fashion using route 19 general procedure 29, (8-nitro-quinolin-7-yl)-phenyl-amine 574 (100 mg, 0.37 mmol), SnCl2 (425 mg, 1.8 mmol) and EtOH (10 ml) gave the title compound (56 mg, 62%) which was used in the next step without further purification.
MW: 235.29
HPLCMS (Method B):[m/z]: 236

N*7*-(4-Trifluoromethyl-benzyl)-quinoline-7,8diamine (Intermediate 577)

In a similar fashion using route 19 general procedure 29, (8-nitro-quinolin-7-yl)-phenyl-amine 575 (437 mg, 1.26 mmol), SnCl2 (425 mg, 1.8 mmol) and EtOH (10 ml) gave the title compound (332 mg, 83%) which was used in the next step without further purification.
MW: 317.32
HPLCMS (Method B):[m/z]: 318.05

General Procedure 140: Phenyl-1,3-dihydro-2-thia-1,3,9-triaza-cyclopenta[a]naphthalene 2,2-dioxide (Example Compound 578)

Sulfamide (34 mg, 0.35 mmol) was added to a solution of N*7*-phenyl-quinoline-7,8-diamine 576 (56 mg, 0.23 mmol) in pyridine (2 ml) and the mixture was heated in a microwave at 115° C. for 2 h. After cooling, the solvent was removed in vacuo. The residue was dissolved in EtOAc (50 ml) and the organic phase was washed with sat. NaHCO3 solution (30 ml), dried (Na2SO4) and concentrated in vacuo. The crude residue was purified by column chromatography DCM/MeOH/TEA (98:2:0.5-90:10:0.5 gradient) followed by preparative HPLC (acidic conditions 1) to give the title compound (12.3 mg, 17%).
EOAI3352800 VIT-1975
MW: 297.34
HPLCMS (Method B):[m/z]: 297.95

3-(4-Trifluoromethyl-benzyl)-1,3-dihydro-2-thia-1,3,9-triaza-cyclopenta[a]naphthalene 2,2-dioxide (Example Compound 579)

In a similar fashion using route 63 general procedure 140, N*7*-(4-trifluoromethyl-benzyl)-quinoline-7,8-diamine 577 (334 mg, 1.0 mmol), sulfamide (154 mg, 1.5 mmol) and pyridine (5 ml) gave the title compound (48 mg, 12%) after purification by preparative HPLC (acidic conditions 1).
EOAI3355148 VIT-1982
MW: 379.36
HPLCMS (Method A):[m/z]: 380
Route 64 (See Above)

General Procedure 141: 5-Morpholin-4-yl-8-nitro-quinoline (Intermediate 580)

Morpholine (251.6 µl, 2.88 mmol) was added to a solution of 5-chloro-8-nitro-quinoline 27 (200 mg, 0.96 mmol) in DMSO (2 ml) and the mixture was heated at 100° C. in a sealed tube for 18 h. After cooling, the mixture was diluted with water (10 ml) and the resulting precipitate was collected by filtration. The solid was dried in vacuo to give the title compound (200 mg, 81%) which was used in the next step without further purification.
MW: 259.26
HPLCMS (Method B):[m/z]: 260.35

5-Morpholin-4-yl-quinolin-8-ylamine (Intermediate 581)

In a similar fashion using route 19 general procedure 29, 5-morpholin-4-yl-8-nitro-quinoline 580 (200 mg, 0.77 mmol), SnCl2 (696 mg, 3.09 mmol) and EtOH (5 ml) gave the title compound (154 mg, 87%) which was used in the next step without further purification.
MW: 229.28
HPLCMS (Method B):[m/z]: 230.35

N-(5-Morpholin-4-yl-quinolin-8-yl)-2-nitro-benzenesulfonamide (Intermediate 582)

In a similar fashion using route 18 general procedure 26, 5-morpholin-4-yl-quinolin-8-ylamine 581 (154 mg, 0.67 mmol), 2-nitrobenzenesulfonyl chloride (148.86 mg, 0.67 mmol), and pyridine (1 ml) gave the title compound (216 mg, 78%) after purification by column chromatography with DCM/MeOH (100%-98:2 gradient) as the eluent.
MW: 414.44
HPLCMS (Method B):[m/z]: 414.95

2-Amino-N-(5-morpholin-4-yl-quinolin-8-yl)-benzenesulfonamide (Intermediate 583)

In a similar fashion using route 19 general procedure 29, N-(5-morpholin-4-yl-quinolin-8-yl)-2-nitro-benzenesulfonamide 582 (216 mg, 0.52 mmol), SnCl2 (470 mg, 2.09 mmol), and EtOH (5 ml) gave the title compound (151 mg, 75%) which was used in the next step without further purification.
MW: 384.45
HPLCMS (Method B):[m/z]: 385.35

N-(5-Morpholin-4-yl-quinolin-8-yl)-benzenesulfonamide (Example Compound 584)

In a similar fashion using route 20 general procedure 36, 2-amino-N-(5-morpholin-4-yl-quinolin-8-yl)-benzenesulfonamide 583 (150 mg, 0.39 mmol), tert-butyl nitrite (79.53 µl, 0.66 mmol), AcOH (1.5 ml) and THF (3 ml) gave the title compound (10 mg, 7%) after purification by preparative HPLC (acidic conditions 1).
EOAI3361152 VIT-2174
MW: 369.44
HPLCMS (Method A):[m/z]: 370.05
Route 65 (See Above)

General Procedure 142: 5-methoxy-8-nitroquinoline (Intermediate 585)

NaOMe (570 mg, 10.5 mmol) was added to a solution of 5-chloro-8-nitroquinoline 27 (550 mg, 2.64 mmol) in MeOH (15 ml) and the mixture was heated at 80° C. for 2 h. The solvent was removed in vacuo and the residue was diluted with water and the aqueous phase was extracted with DCM. The organic phase was washed with brine and concentrated in vacuo to give the title compound (500 mg, 93%) which was used in the next step without further purification.
MW: 204.19
HPLCMS (Method C): [m/z]: 205

5-Methoxy-quinolin-8-ylamine (Intermediate 586)

In a similar fashion using route 2 general procedure 4, 5-methoxy-8-nitroquinoline 585 (550 mg, 2.69 mmol), SnCl2 (1.53 g, 8.08 mmol), 6N HCl (3 drops) and MeOH (15 ml) for 1.3 h at 70° C. for 4 h gave the title compound (430 mg, 91%) which was used in the next step without further purification.
MW: 174.20
HPLCMS (Method C): [m/z]: 175

N-(5-Methoxy-quinolin-8-yl)-2-nitro-4-trifluoromethyl-benzenesulfonamide (Intermediate 587)

In a similar fashion using route 18 general procedure 27, 5-methoxy-quinolin-8-ylamine 586 (280 mg, 1.6 mmol), 2-nitro-4-(trifluoromethyl) benzenesulfonyl chloride (600 mg, 2.0 mmol), pyridine (0.39 ml, 4.8 mmol) DMAP (cat.) and DCM (15 ml) gave the title compound (500 mg, 73%) after purification by column chromatography with DCM as the eluent.
MW: 427.36
HPLCMS (Method C): [m/z]: 428

2-Amino-N-(5-methoxy-quinolin-8-yl)-4-trifluoromethyl-benzenesulfonamide (Intermediate 588)

In a similar fashion using route 2 general procedure 4 N-(5-methoxy-quinolin-8-yl)-2-nitro-4-trifluoromethyl-benzenesulfonamide 587 (500 mg, 1.17 mmol), SnCl2 (0.9 g, 4.6 mmol), 6N HCl (2 drops) and EtOH (10 ml) at 85° C. for 48 h gave the title compound (440 mg, 92%) which was used in the next step without further purification.
MW: 397.38
HPLCMS (Method C): [m/z]: 398

12-Methoxy-9-trifluoromethyl-5H-6-thia-4,5-diazachrysene 6,6-dioxide (Example Compound 589)

In a similar fashion using route 20 general procedure 61, 2-amino-N-(5-methoxy-quinolin-8-yl)-4-trifluoromethyl-benzenesulfonamide 588 (440 mg, 1.1 mmol), t-butyl nitrite (0.2 ml, 1.6 mmol), AcOH (4.4 ml) and THF (4.4 ml) gave the title compound (19 mg, 5%) after preparative HPLC (neutral conditions).
EOAI3359234 VIT-2104
MW: 380.35
HPLCMS (Method C): [m/z]: 381

Commercial Compounds

5-Bromo-thiophene-2-sulfonic acid naphthalene-1-yl-amide (Example Compound 1)

VIT-1008
MW:
Supplier: Chembridge

N-Quinolin-8-yl-benzenesulfonamide (Example Compound 4)

EOAI3333821 VIT-1228
MW: 284.33
Supplier: Chembridge
HPLCMS (Method A):[m/z]: 284.9
The result is shown in FIG. 4

N-(5,7-Dichloro-quinolin-8-yl)-4-methyl-benzenesulfonamide (Example Compound 51)

EOAI3335553 VIT-1392
MW: 367.25
Supplier: Chembridge
HPLCMS (Method A):[m/z]: 368
The result is shown in FIG. 51

N-(5,7-Dichloro-quinolin-8-yl)-2,4,6-trimethyl-benzenesulfonamide (Example Compound 52)

EOAI3335554 VIT-1393
MW: 395.30
Supplier: Chembridge
HPLCMS (Method A):[m/z]: 396
The result is shown in FIG. 52

N-Quinolin-8-yl-benzenesulfonamide (Intermediate 217)

EOAI3333821 VIT-1228
MW: 284.33
Supplier: Chembridge
HPLCMS (Method A):[m/z]: 284.9

4-Chloro-N-quinolin-8-yl-benzamide (Intermediate 218)

EOAI3334004 VIT-1232
MW: 282.72
Supplier: Enamine
HPLCMS (Method A):[m/z]: 283

N-(5,7-Dichloro-quinolin-8-yl)-4-methyl-benzenesulfonamide (Intermediate 219)

EOAI3335553 VIT-1392
MW: 367.25
Supplier: Chembridge
HPLCMS (Method A):[m/z]: 368

N-(5,7-Dichloro-quinolin-8-yl)-2,4,6-trimethyl-benzenesulfonamide (Intermediate 220)

EOAI3335554 VIT-1393
MW: 395.30
Supplier: Chembridge
HPLCMS (Method A):[m/z]: 396

DESCRIPTION OF THE FIGURES

FIG. 3: Chromatogramm of Example Compound 3

Figure 1:
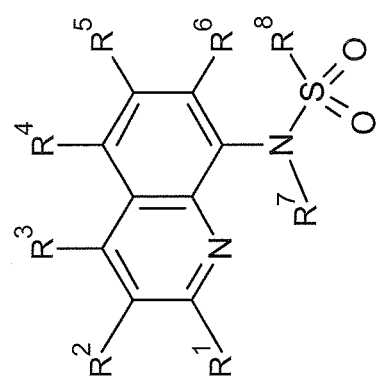
FIG. 1: General Formula (I)
Figure 2:
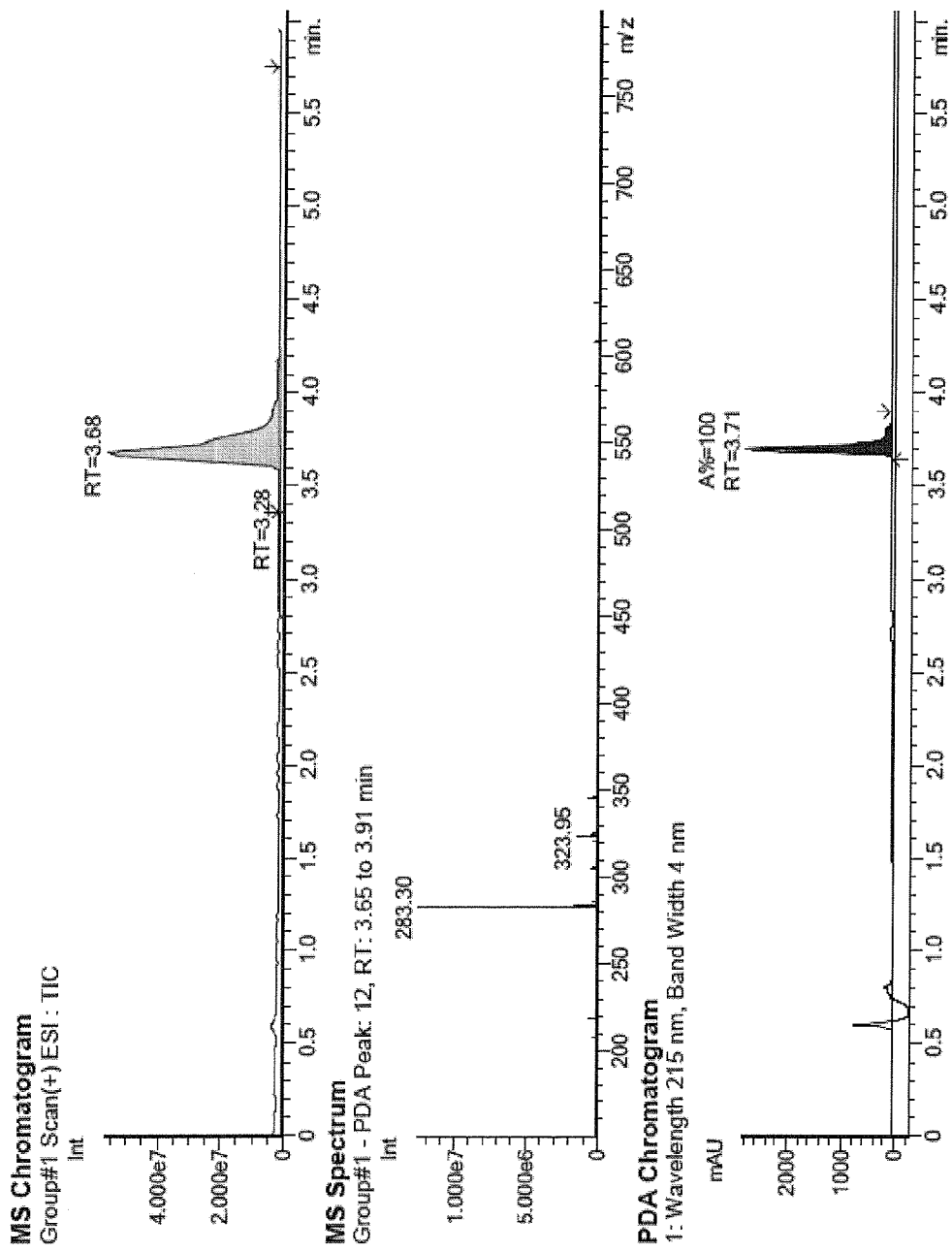
FIG. 2: Chromatogramm of Example Compound 2
Figure 4:
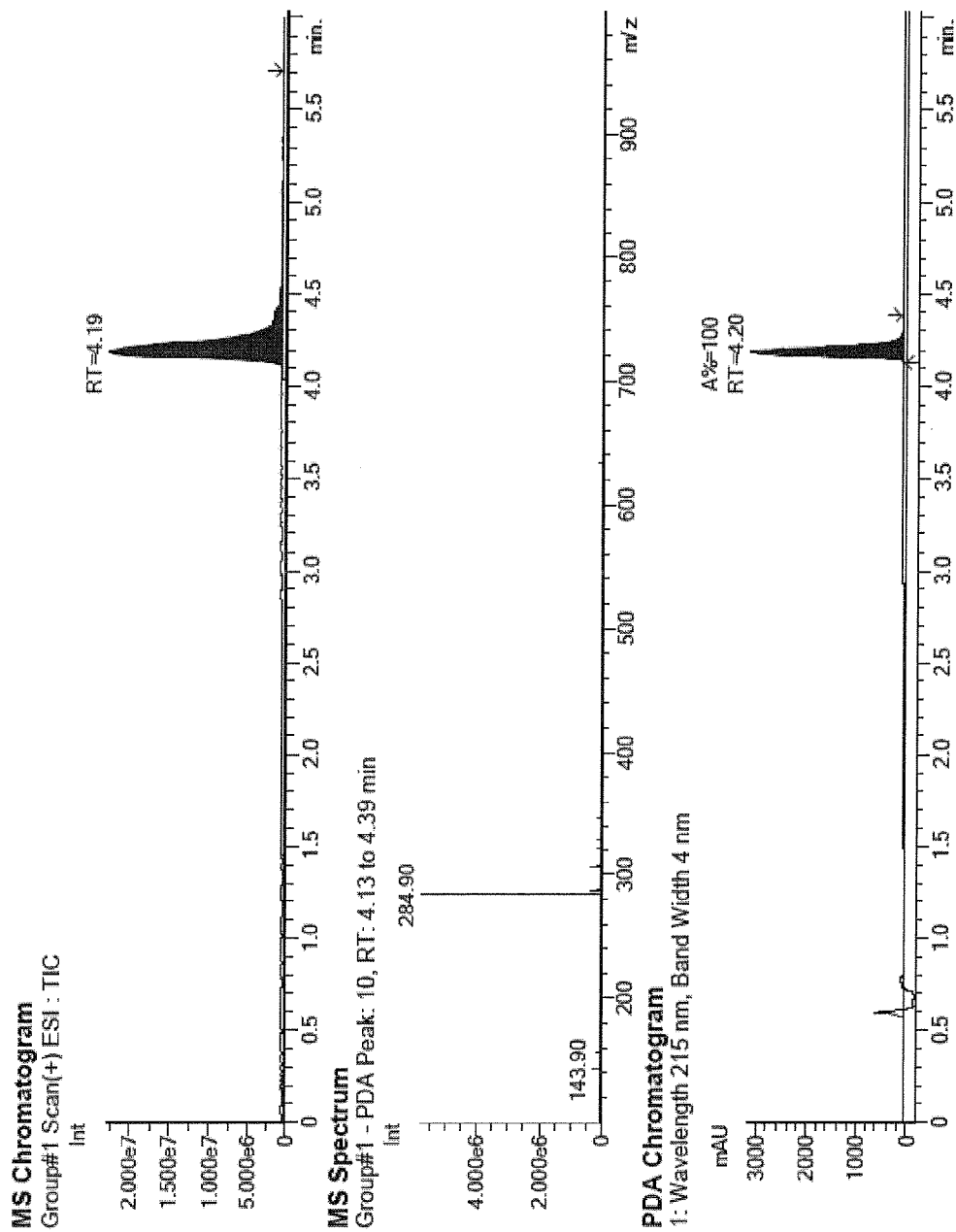
FIG. 4: Chromatogramm of Example Compound 4
Figure 5:
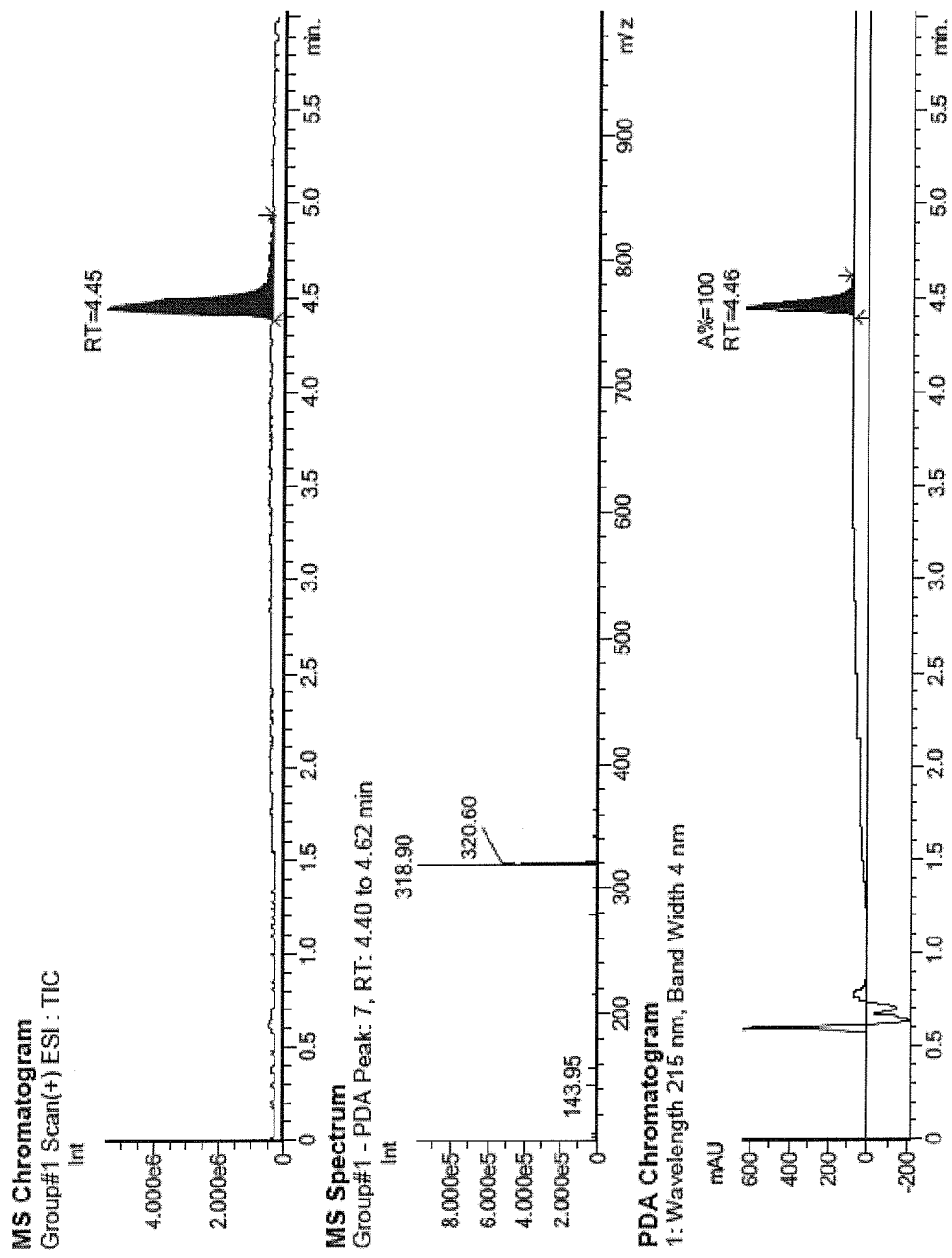
FIG. 5: Chromatogramm of Example Compound 5
Figure 6:
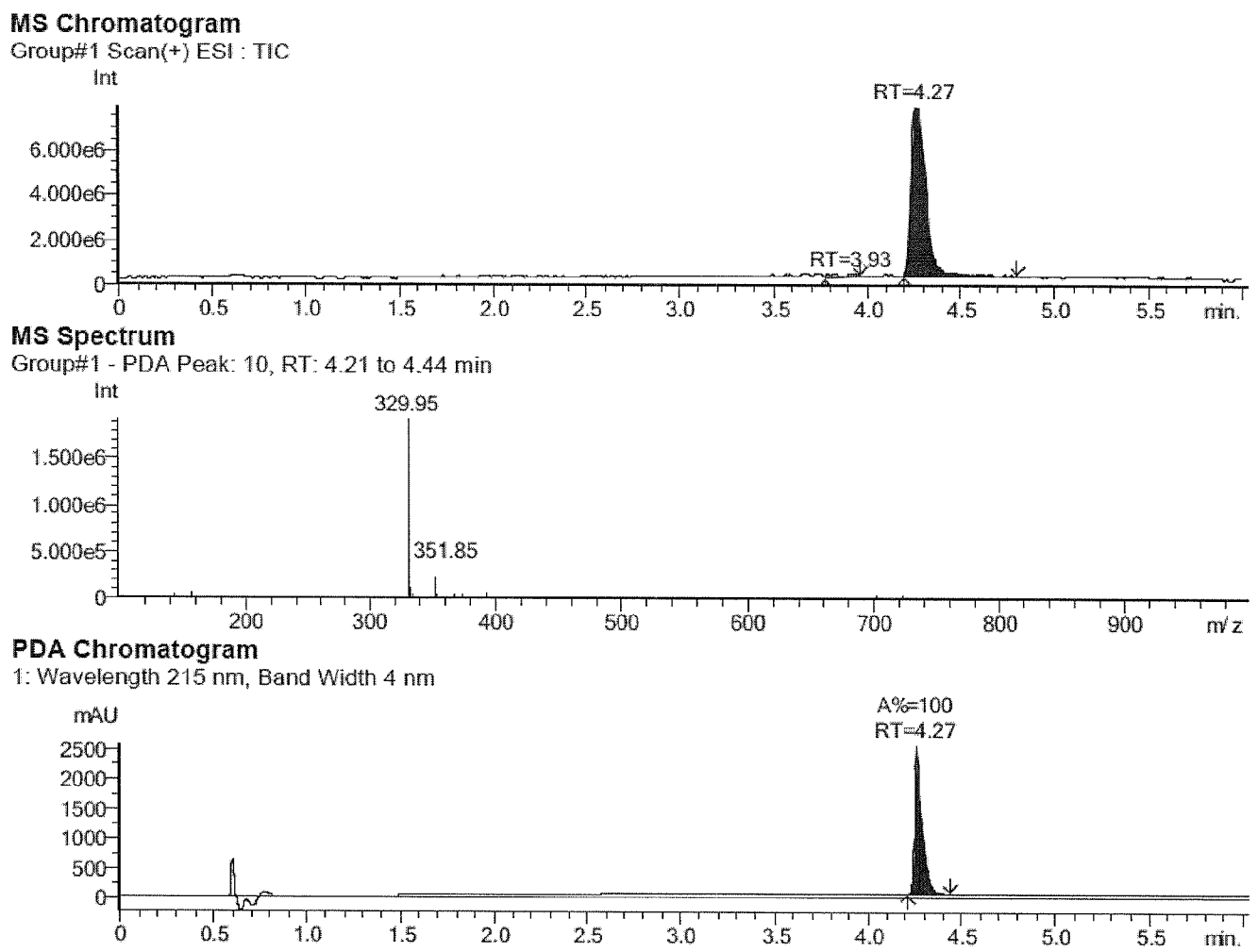
FIG. 6: Chromatogramm of Example Compound 6
Figure 7:
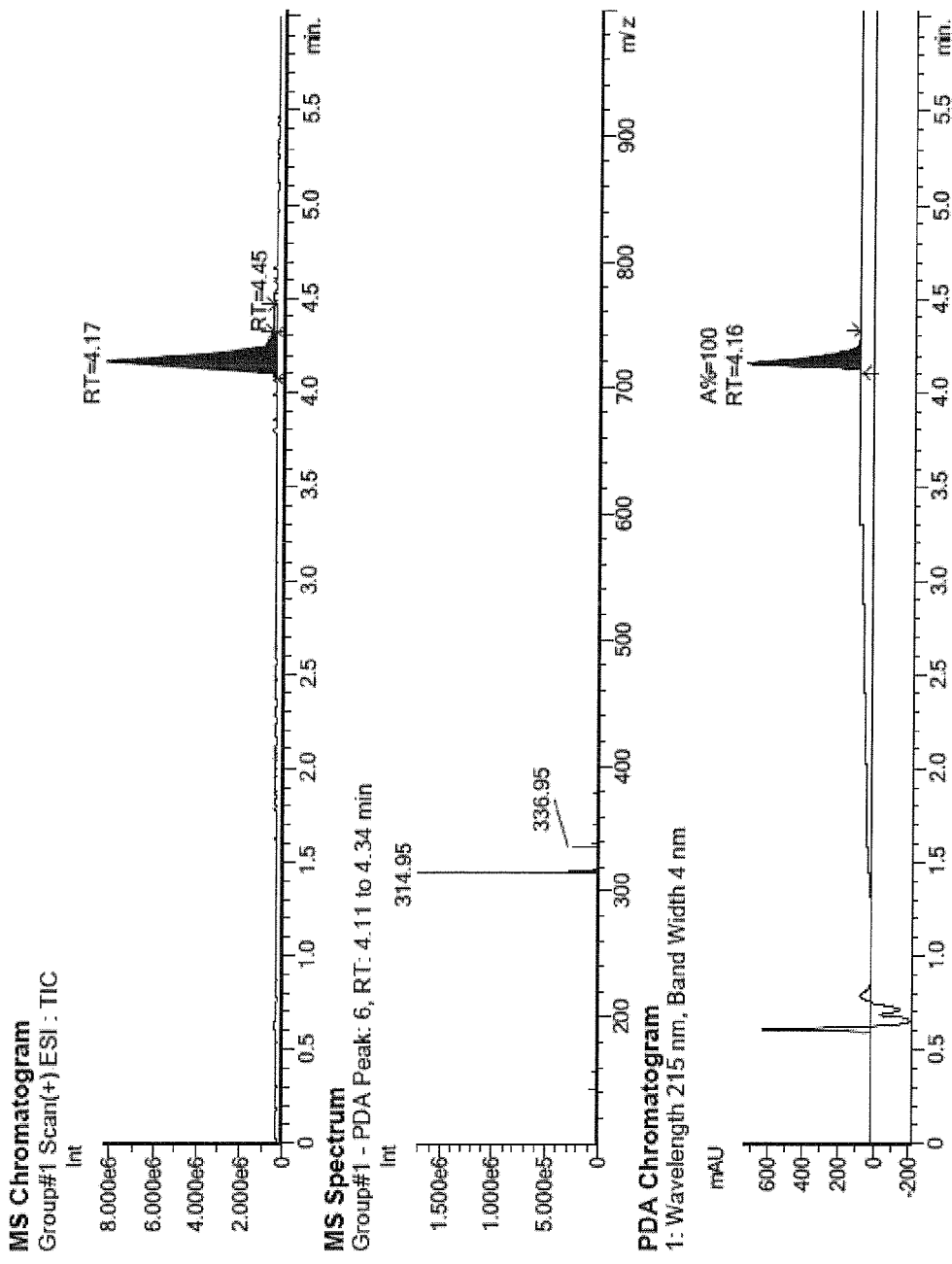
FIG. 7: Chromatogramm of Example Compound 7
Figure 8:
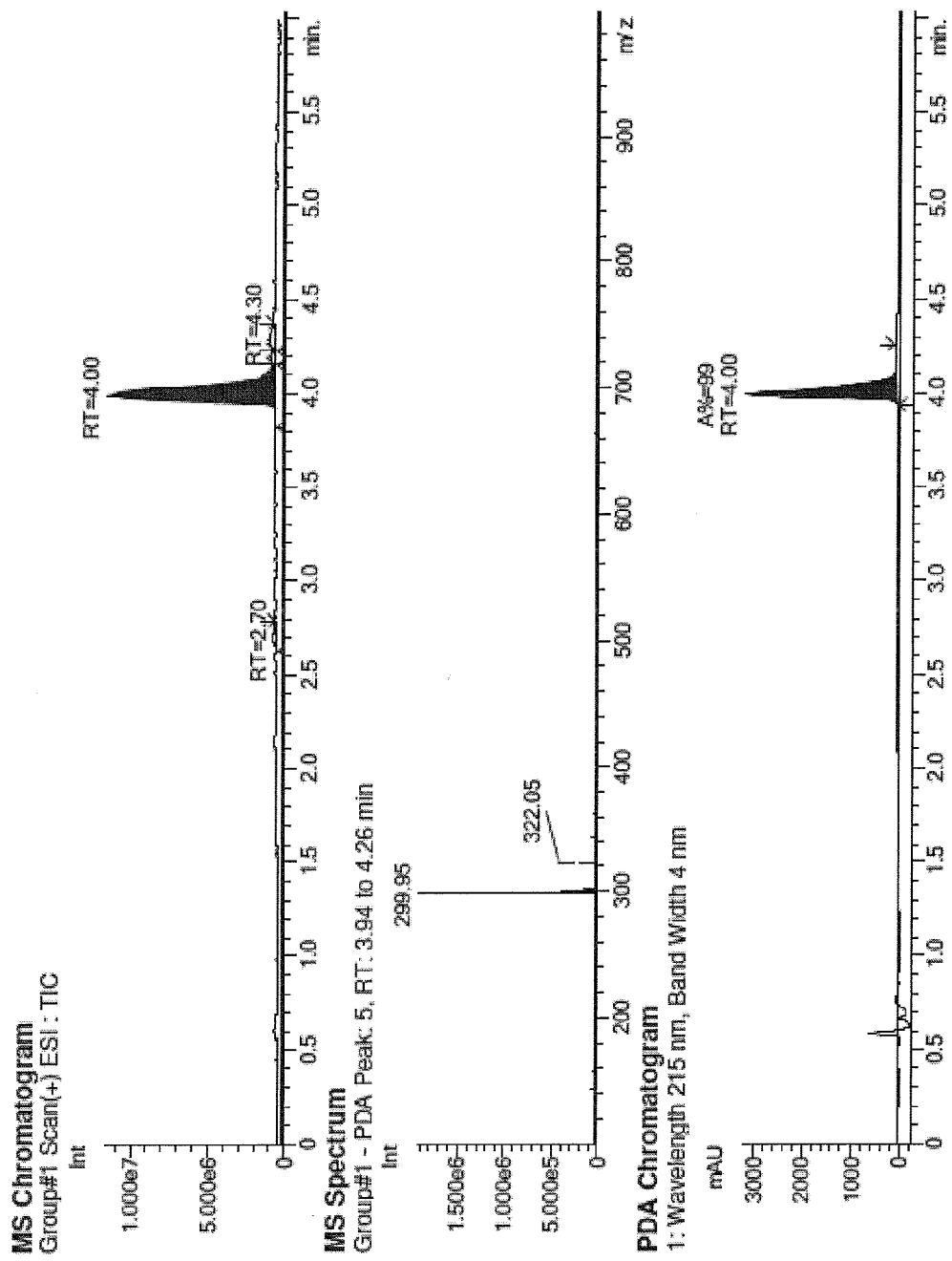
FIG. 8: Chromatogramm of Example Compound 8
Figure 9:
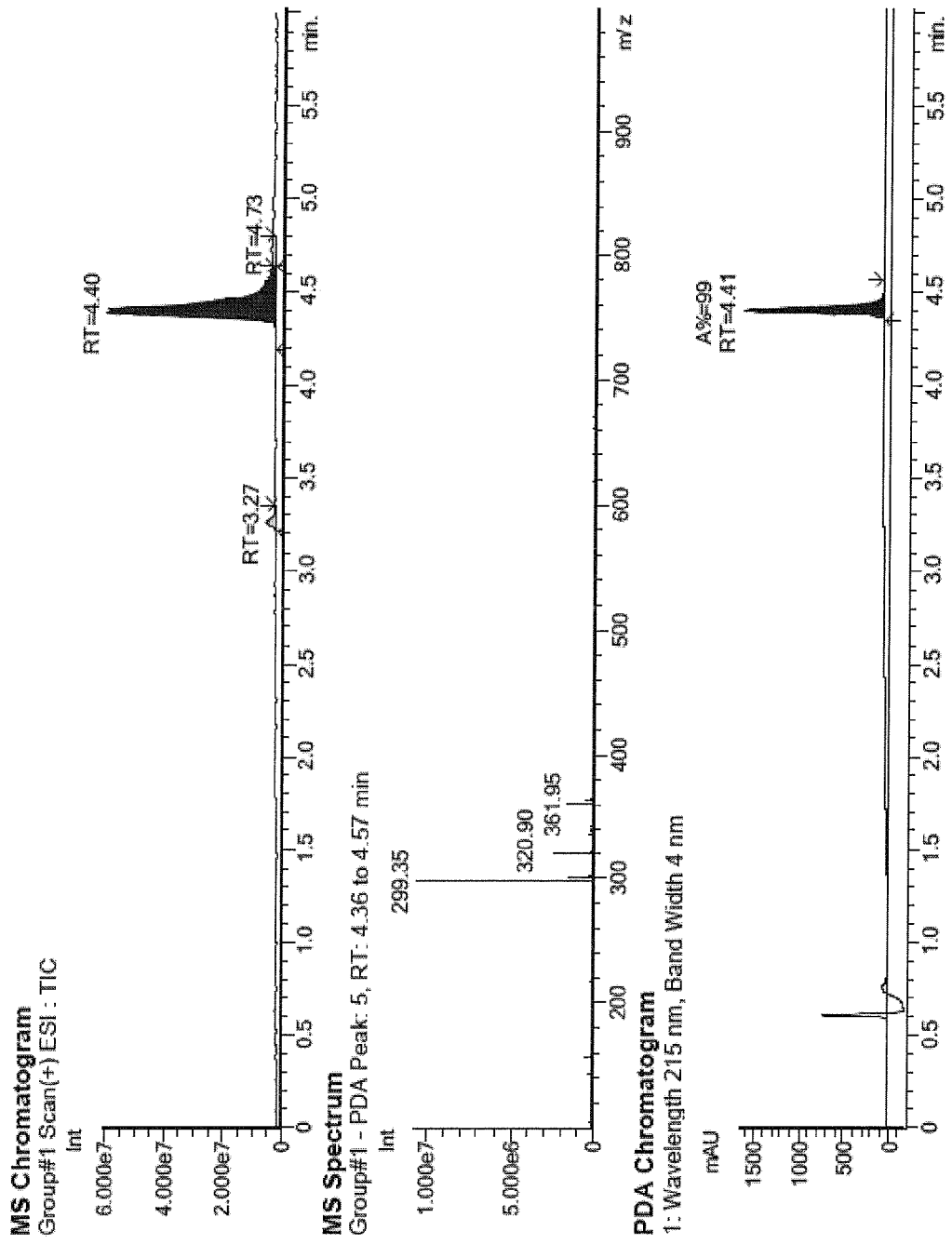
FIG. 9: Chromatogramm of Example Compound 9
Figure 10:
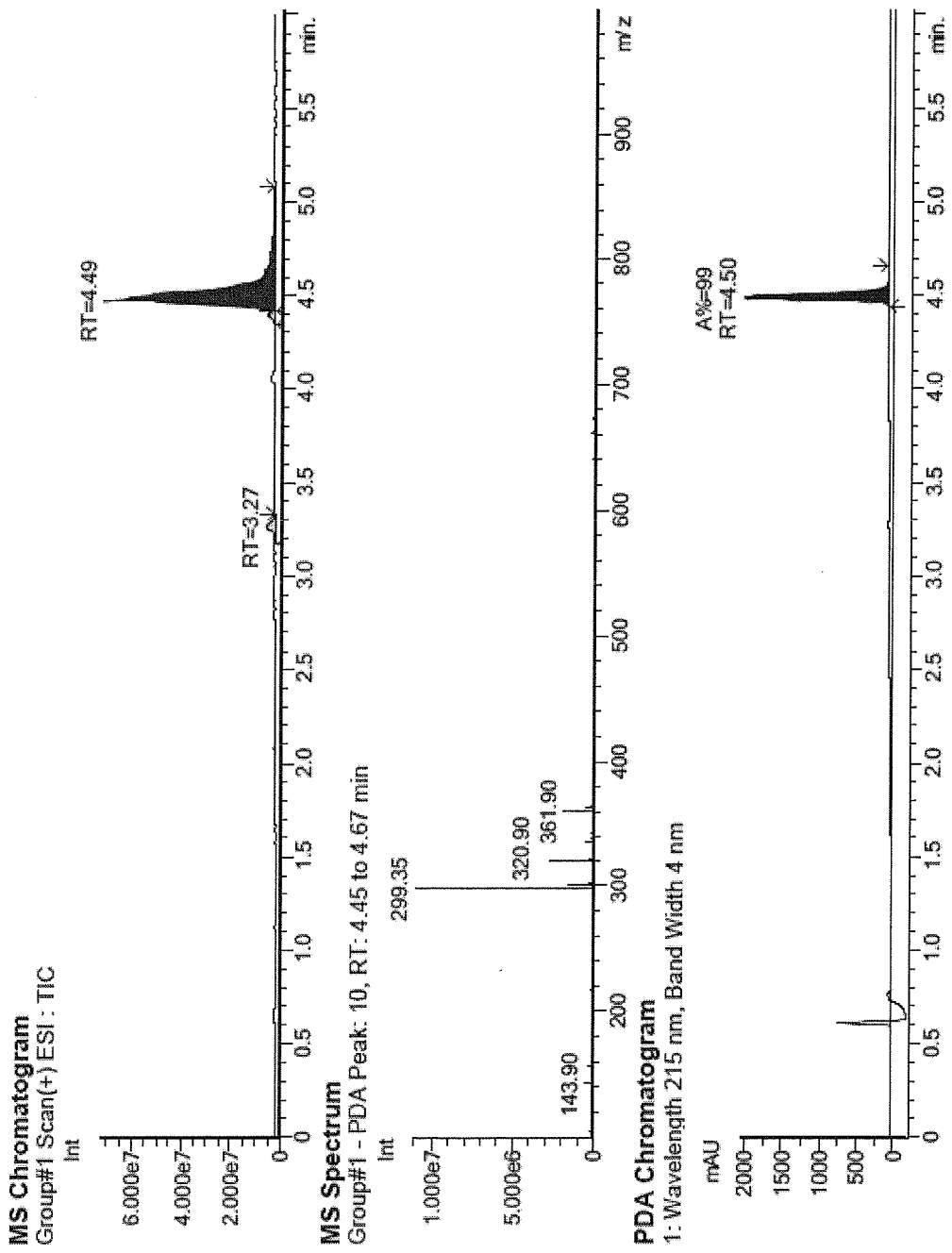
FIG. 10: Chromatogramm of Example Compound 10
Figure 11:
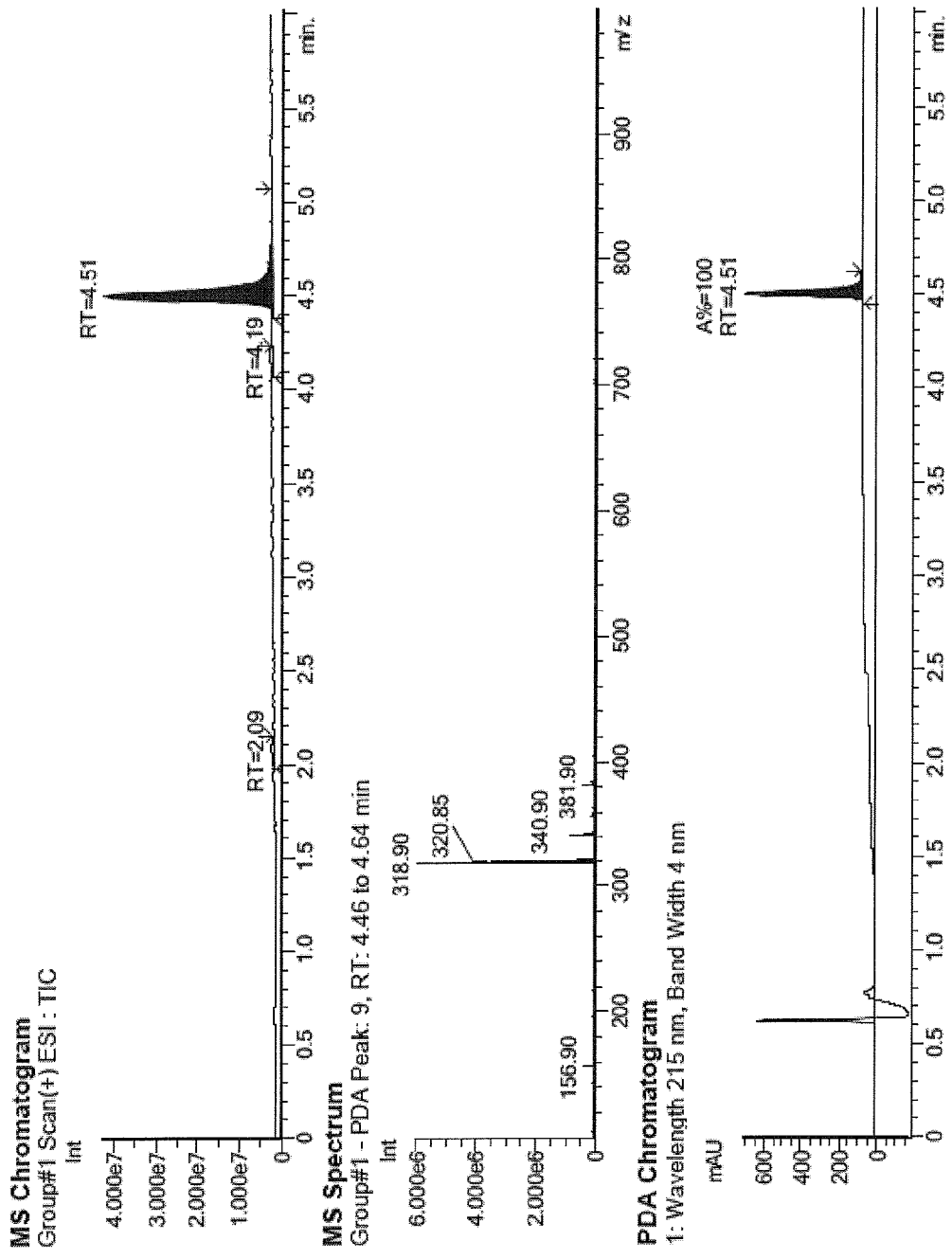
FIG. 11: Chromatogramm of Example Compound 11
Figure 12:
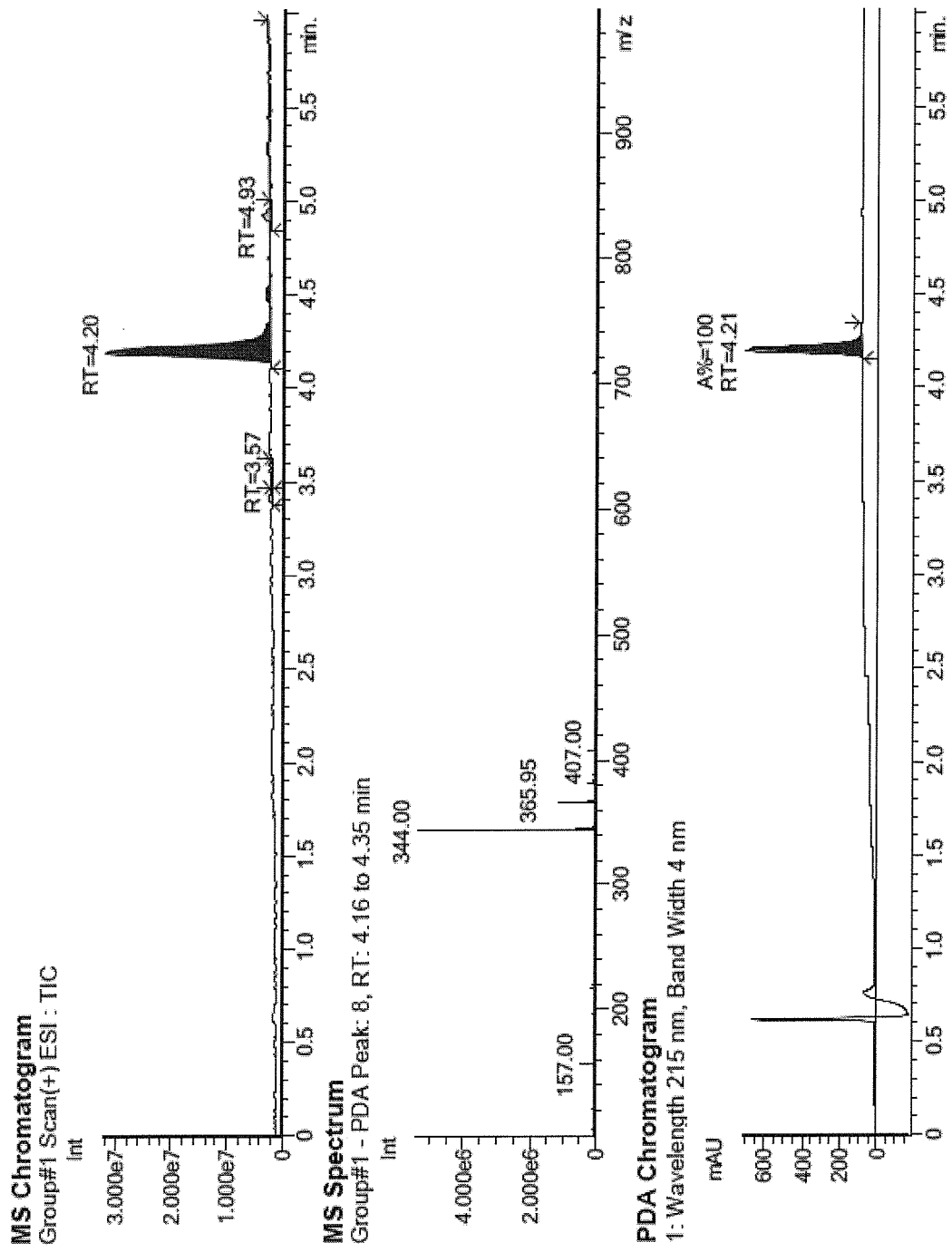
FIG. 12: Chromatogramm of Example Compound 12
Figure 13:
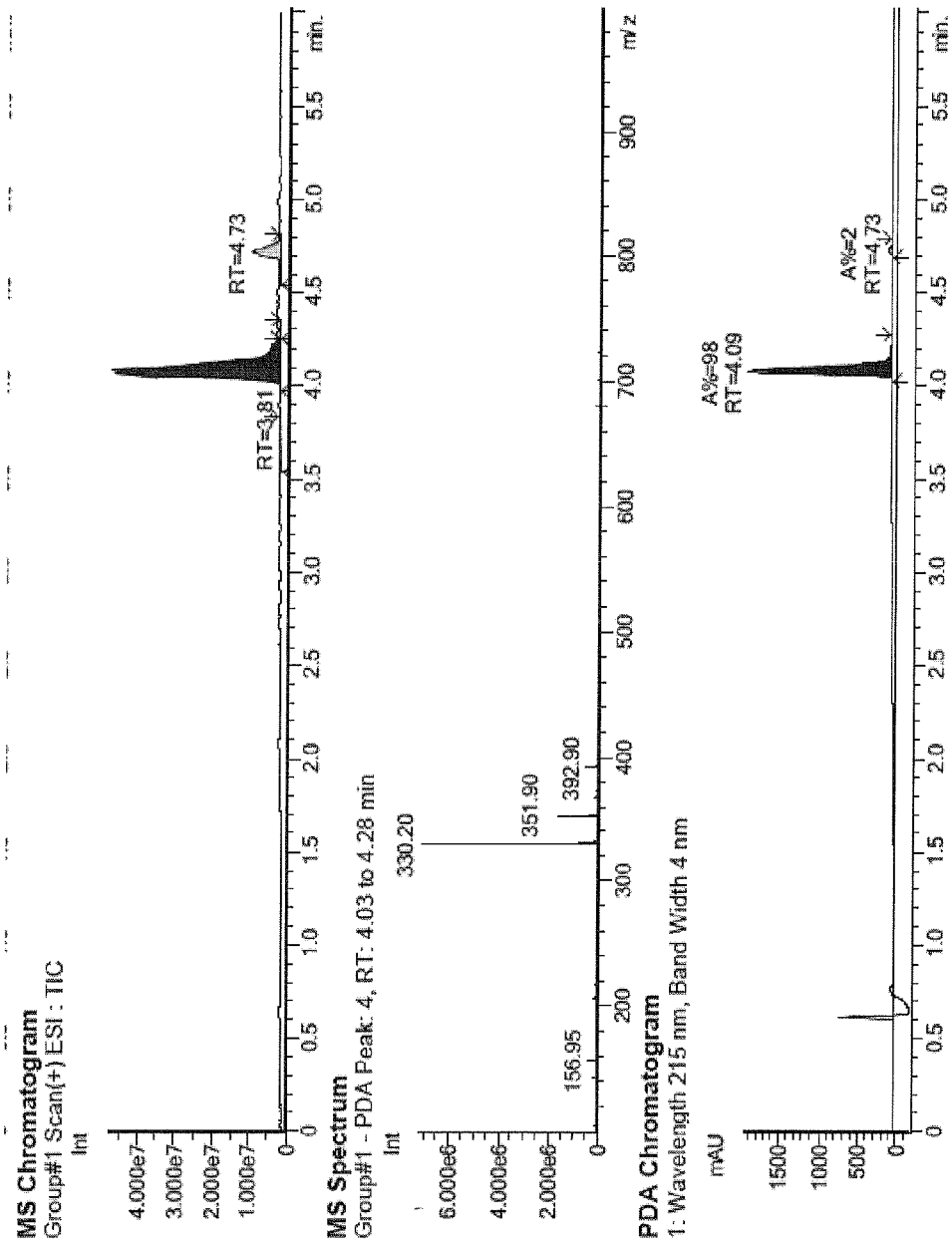
FIG. 13: Chromatogramm of Example Compound 13
Figure 14:
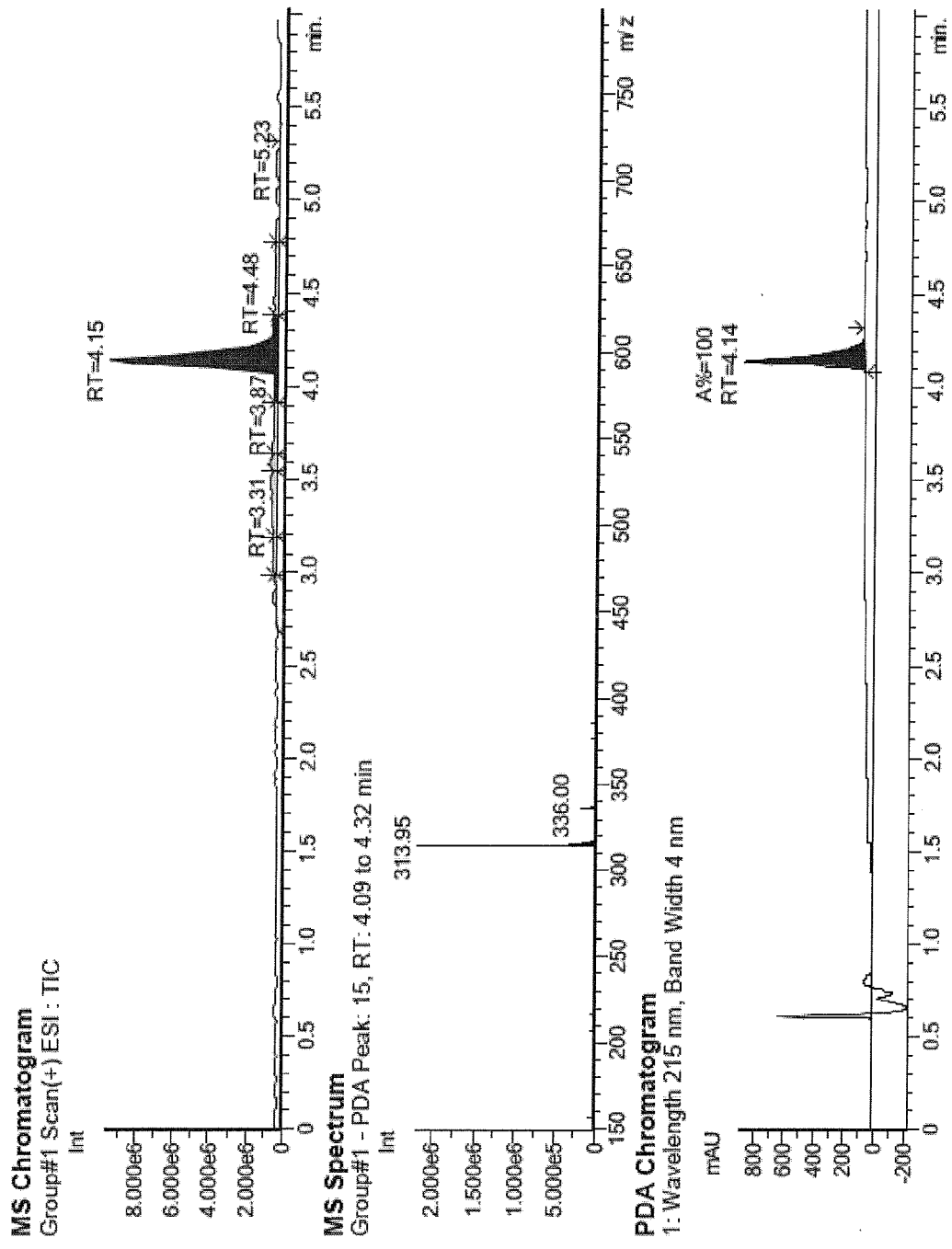
FIG. 14: Chromatogramm of Example Compound 14
Figure 15:
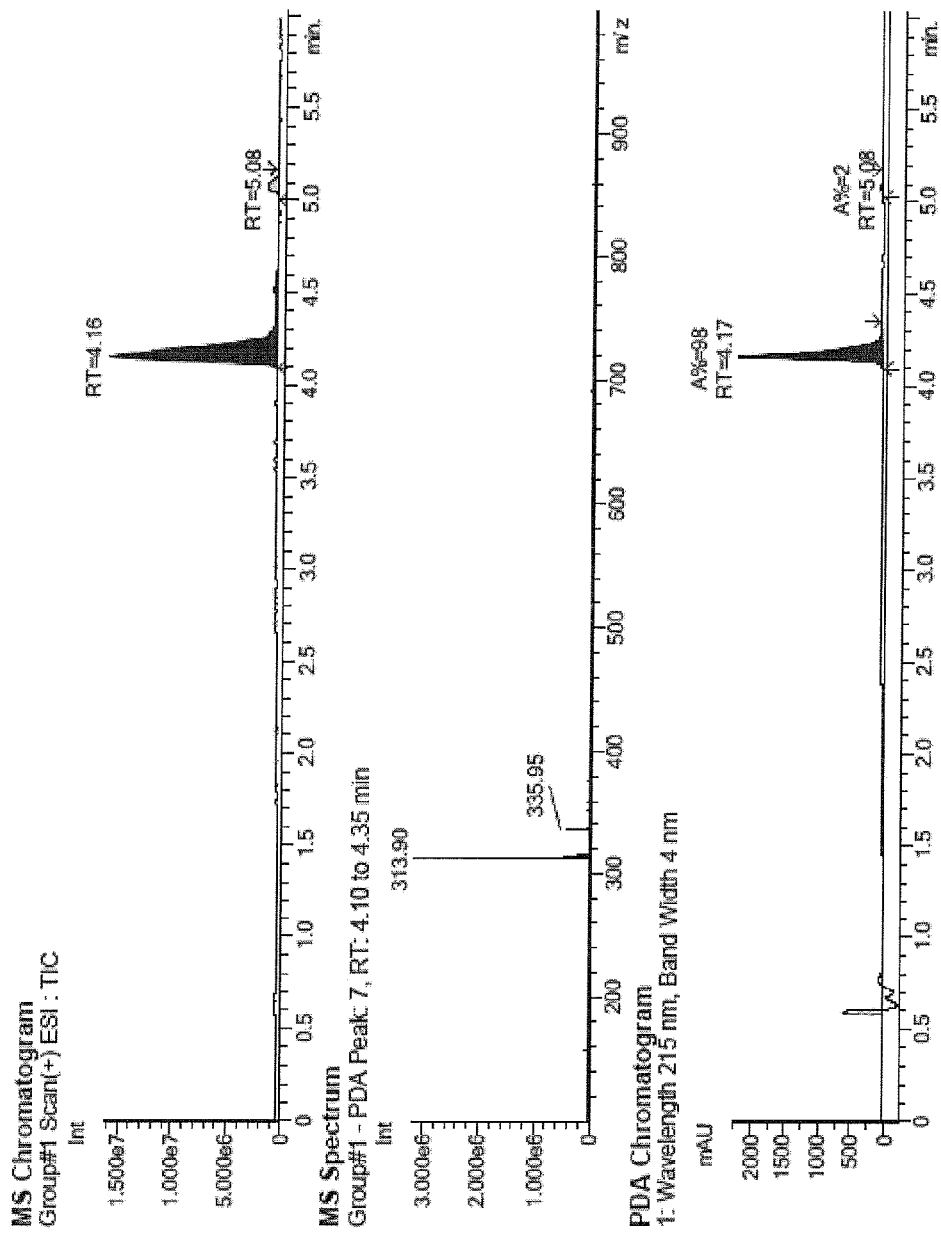
FIG. 15: Chromatogramm of Example Compound 15
Figure 16:
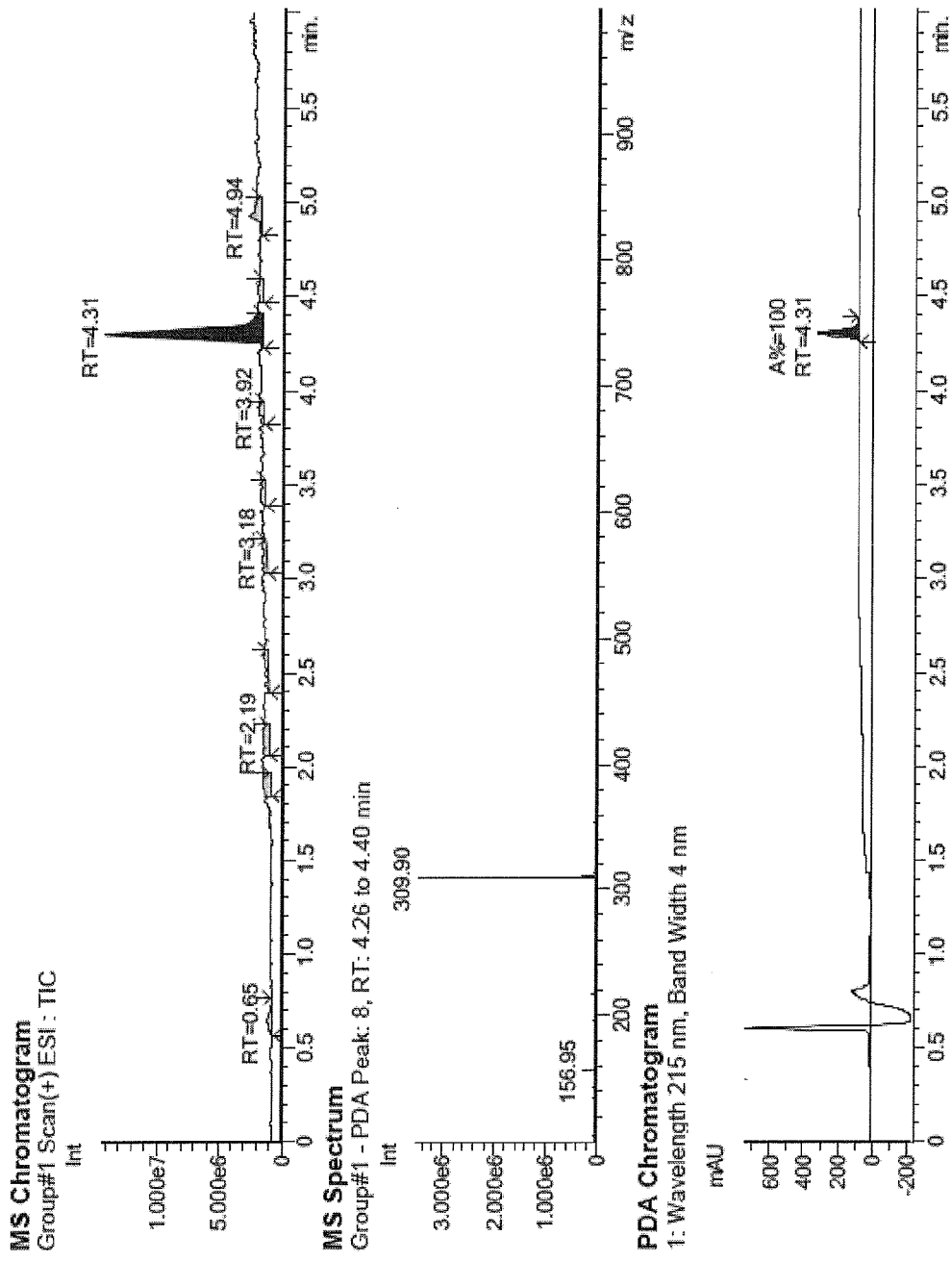
FIG. 16: Chromatogramm of Example Compound 16
Figure 17:
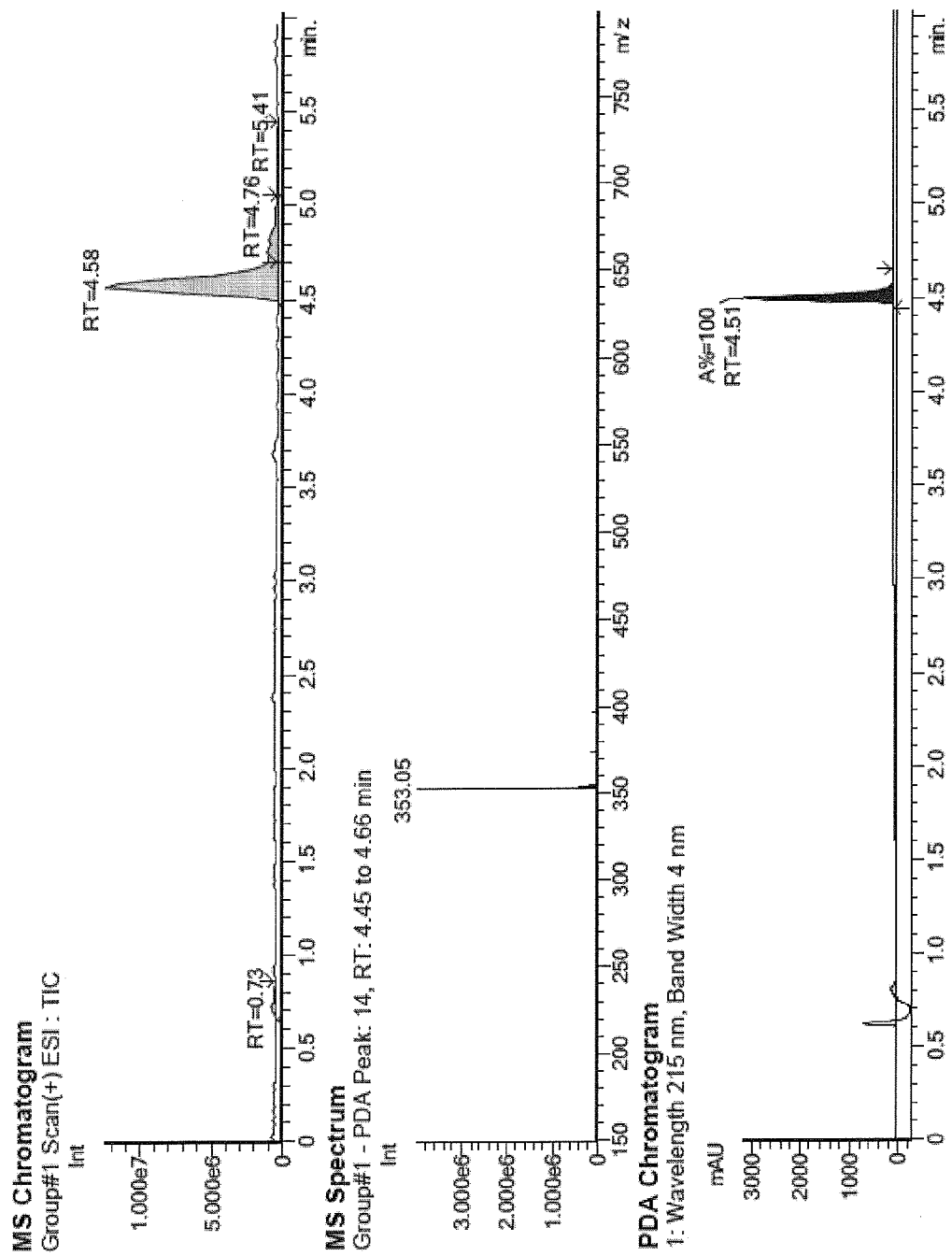
FIG. 17: Chromatogramm of Example Compound 17
Figure 18:
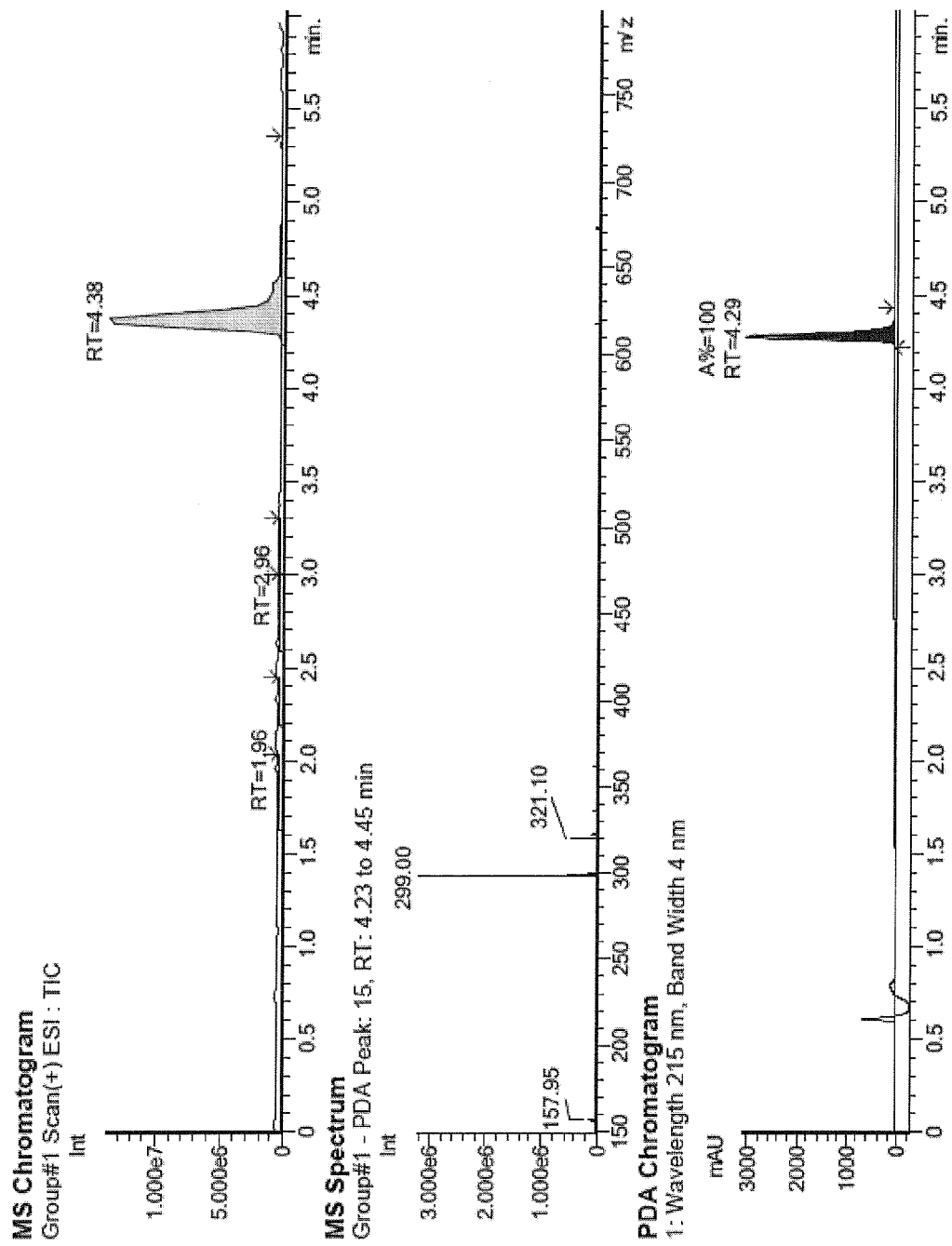
FIG. 18: Chromatogramm of Example Compound 18
Figure 19:
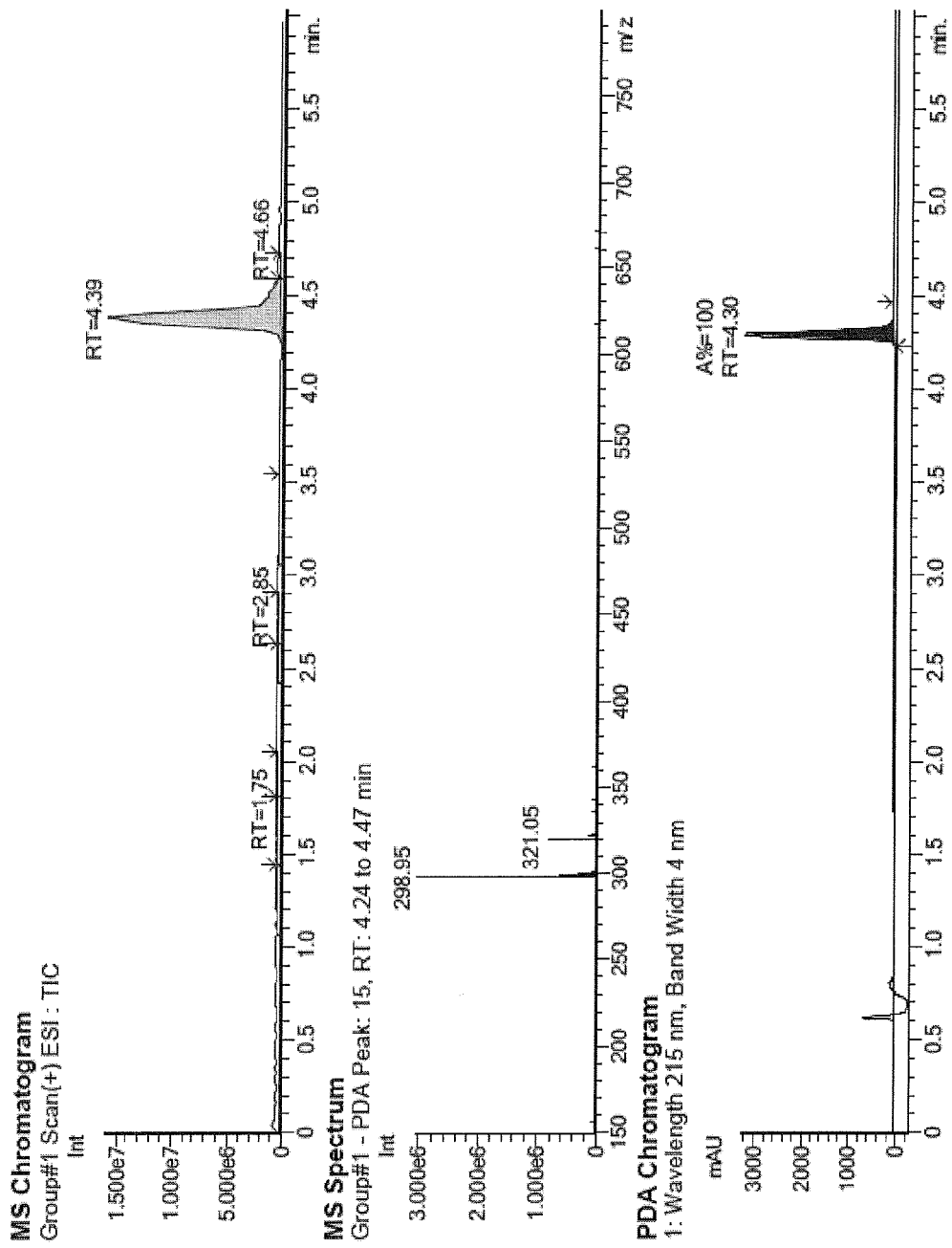
FIG. 19: Chromatogramm of Example Compound 19
Figure 20:
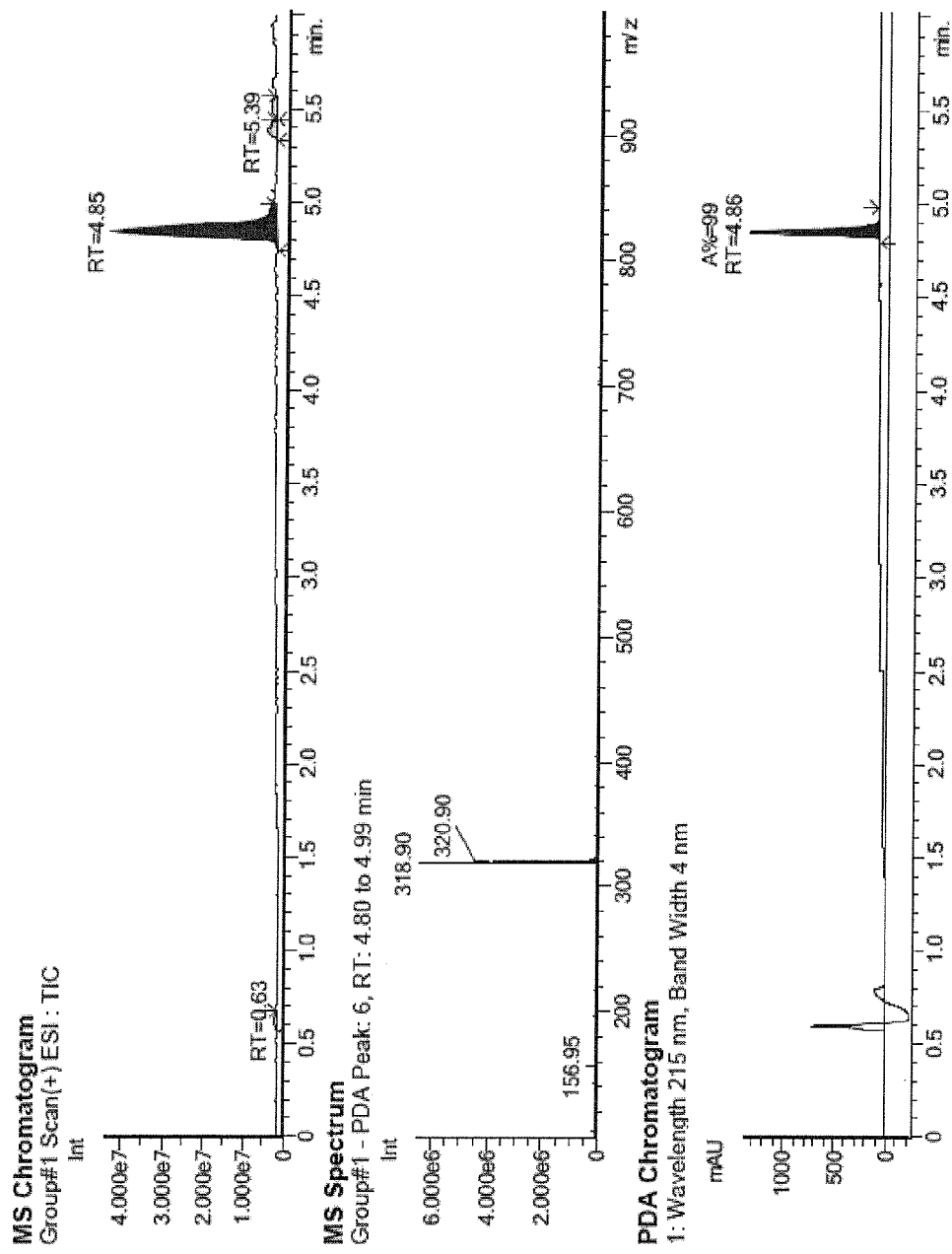
FIG. 20: Chromatogramm of Example Compound 20
Figure 21:
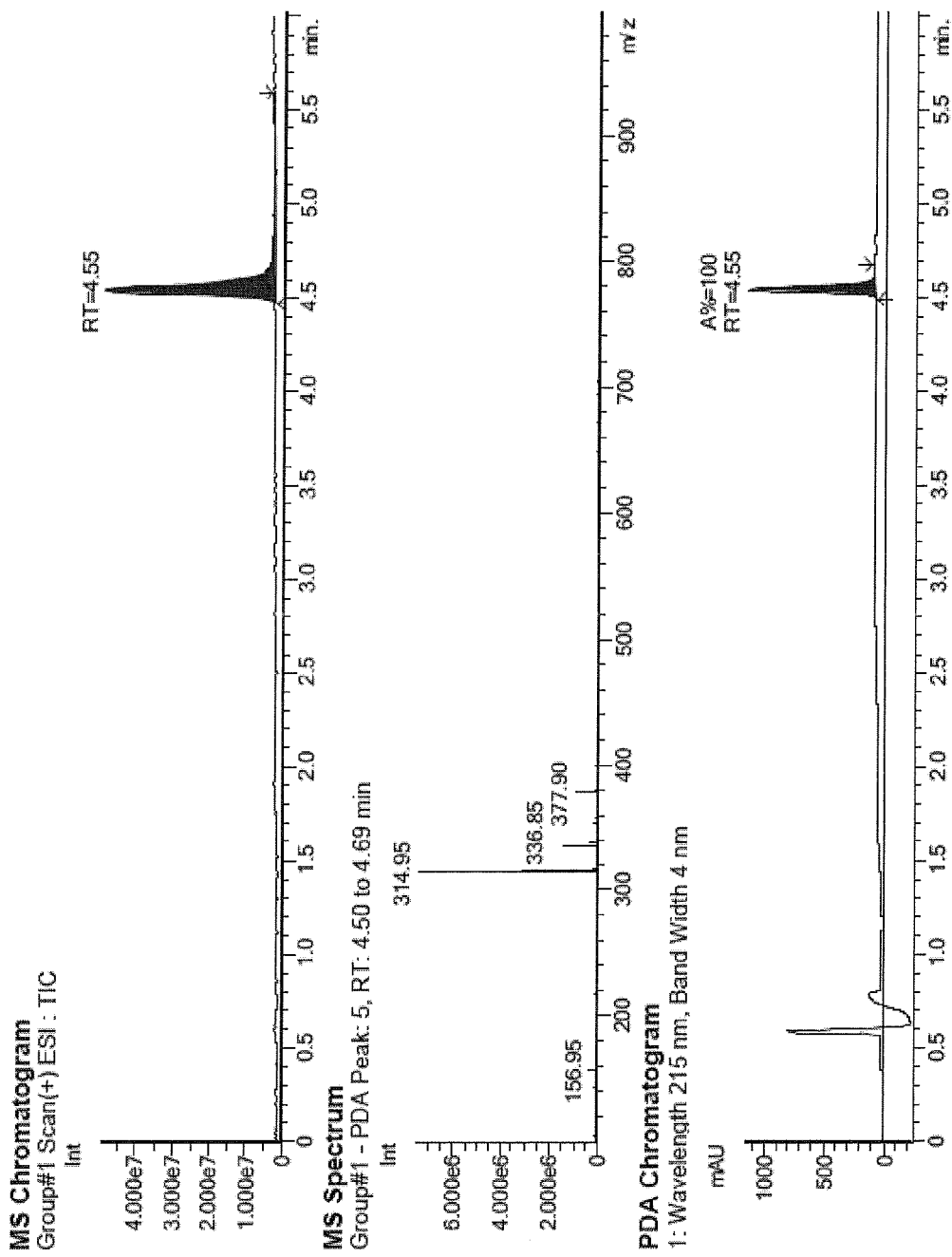
FIG. 21: Chromatogramm of Example Compound 21
Figure 22:
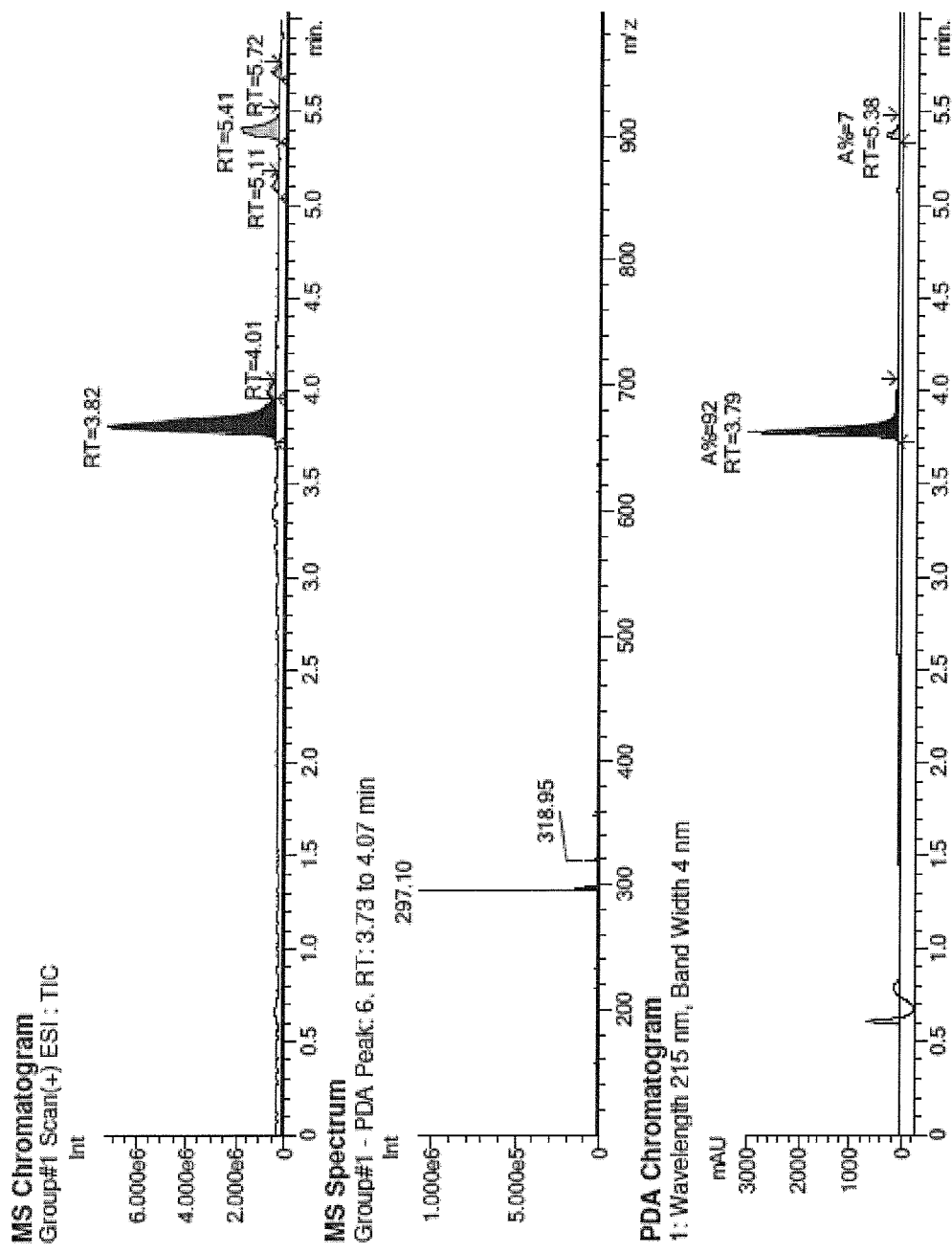
FIG. 22: Chromatogramm of Example Compound 22
Figure 23:
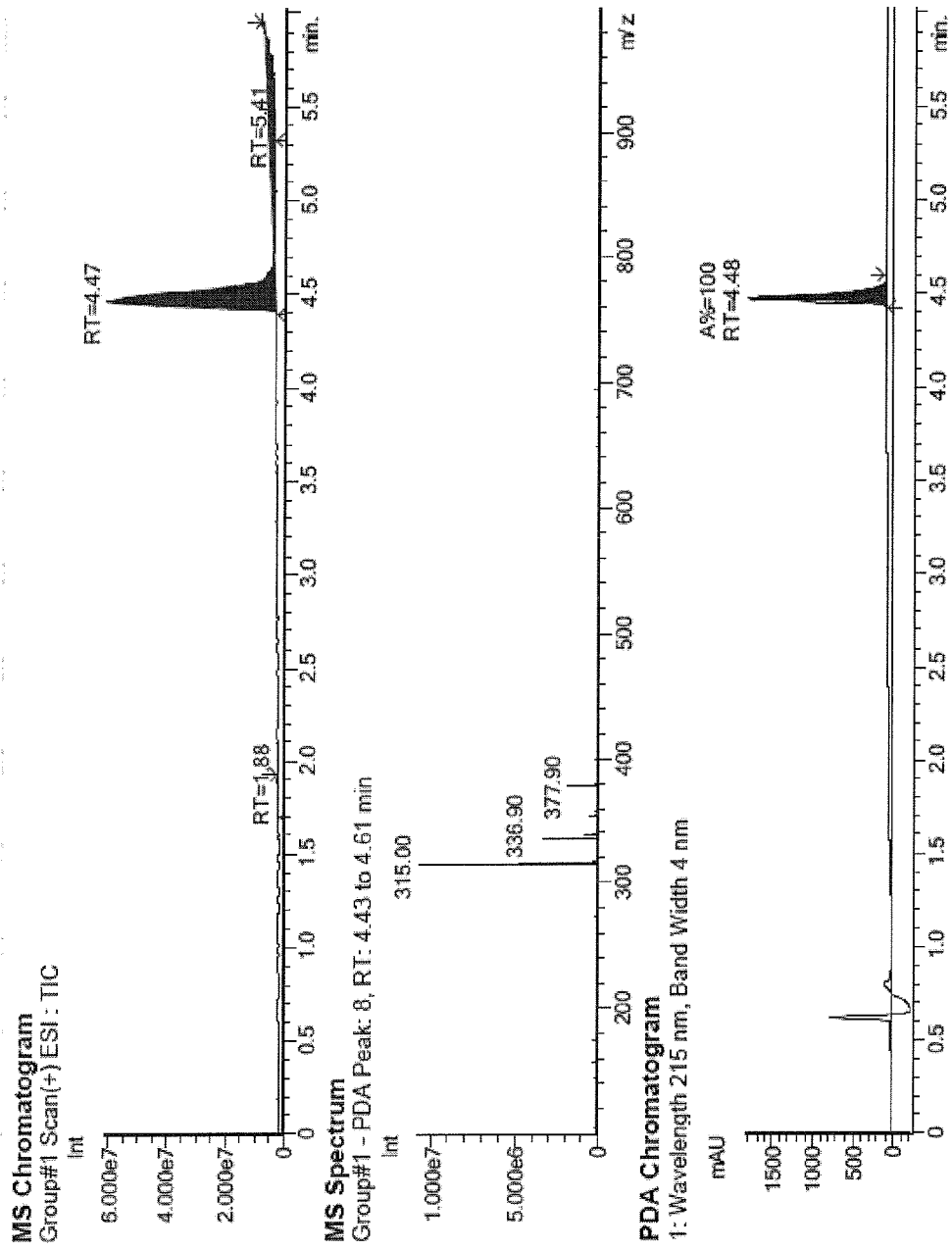
FIG. 23: Chromatogramm of Example Compound 23
Figure 24:
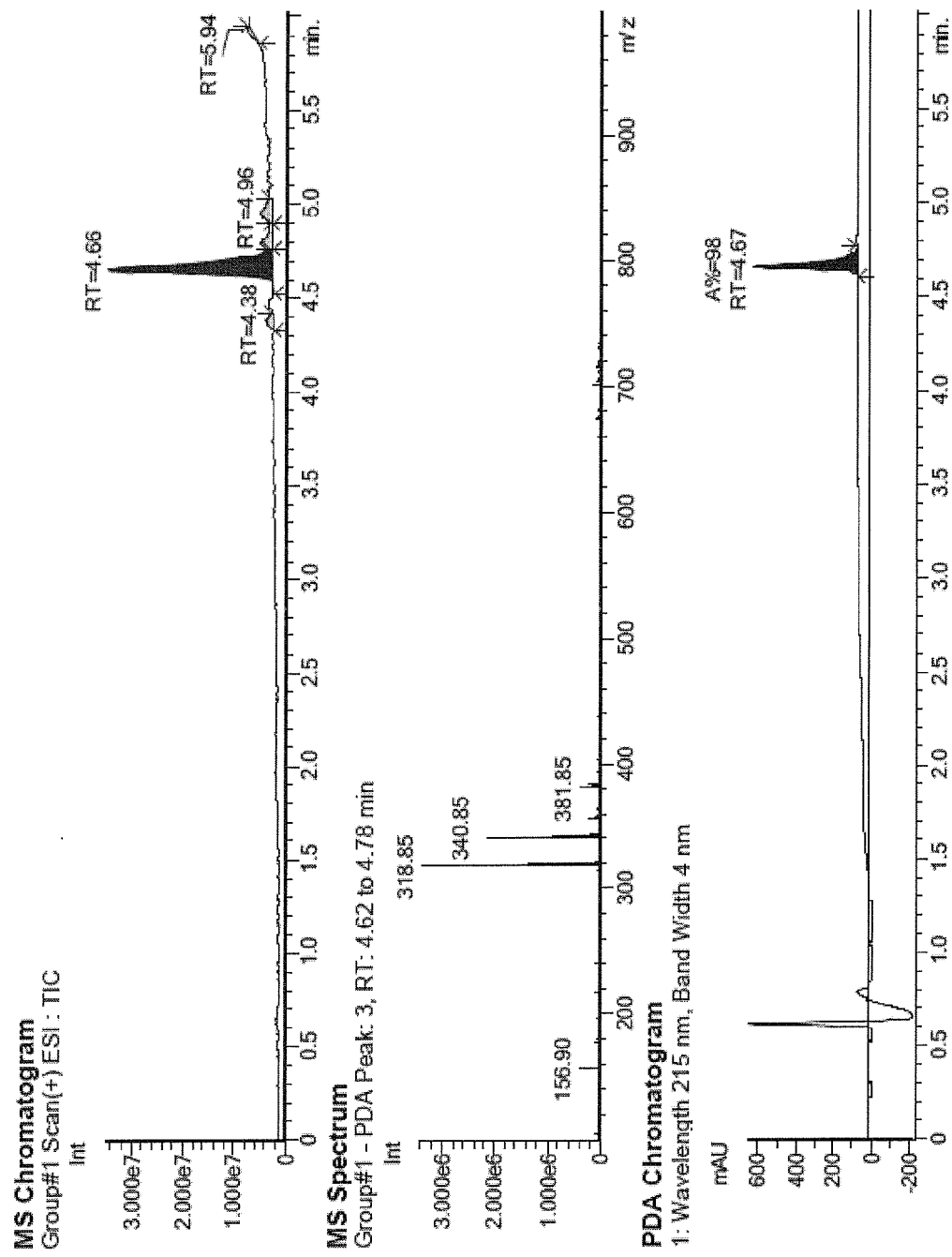
FIG. 24: Chromatogramm of Example Compound 24
Figure 25:
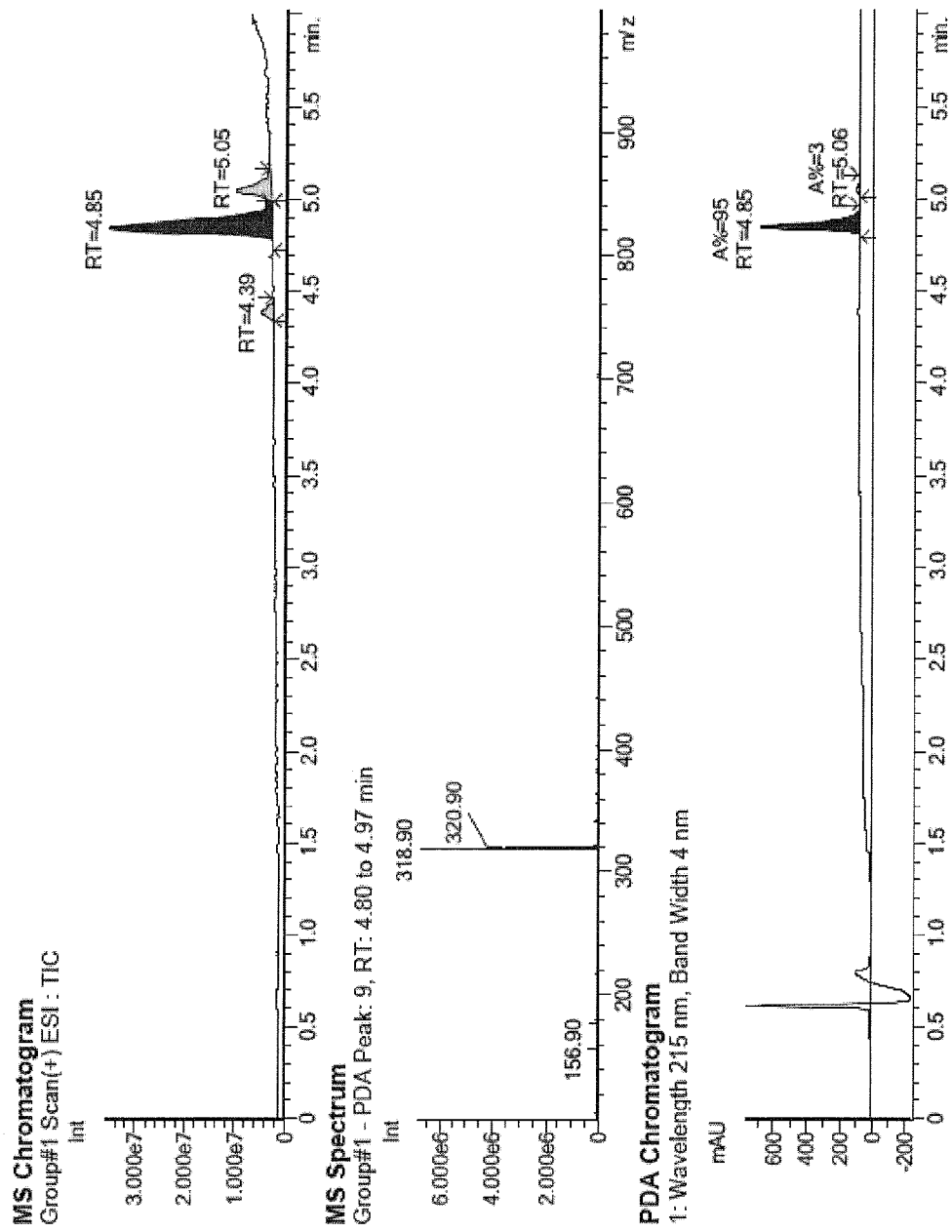
FIG. 25: Chromatogramm of Example Compound 25
Figure 26:
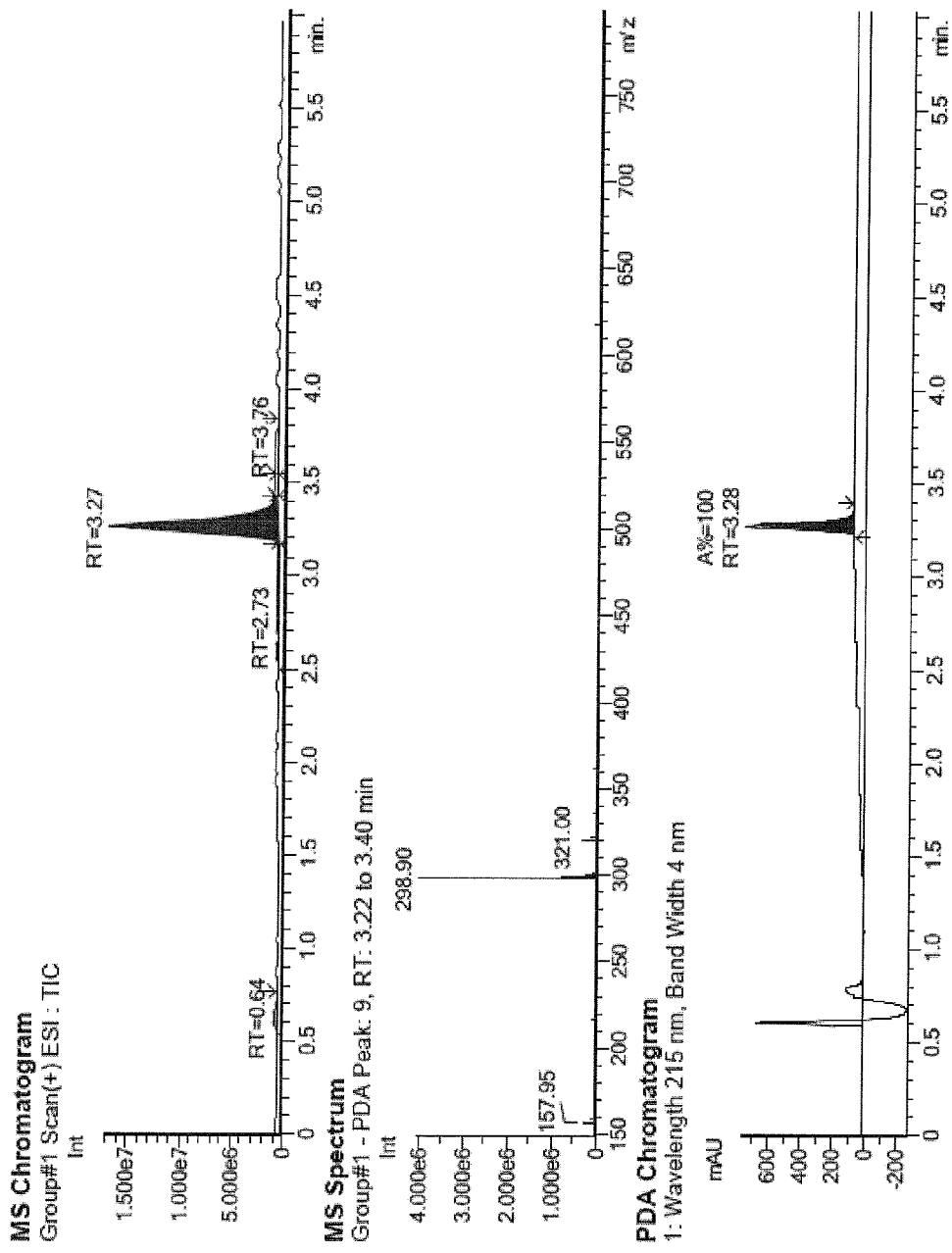
FIG. 26: Chromatogramm of Example Compound 26
Figure 27:
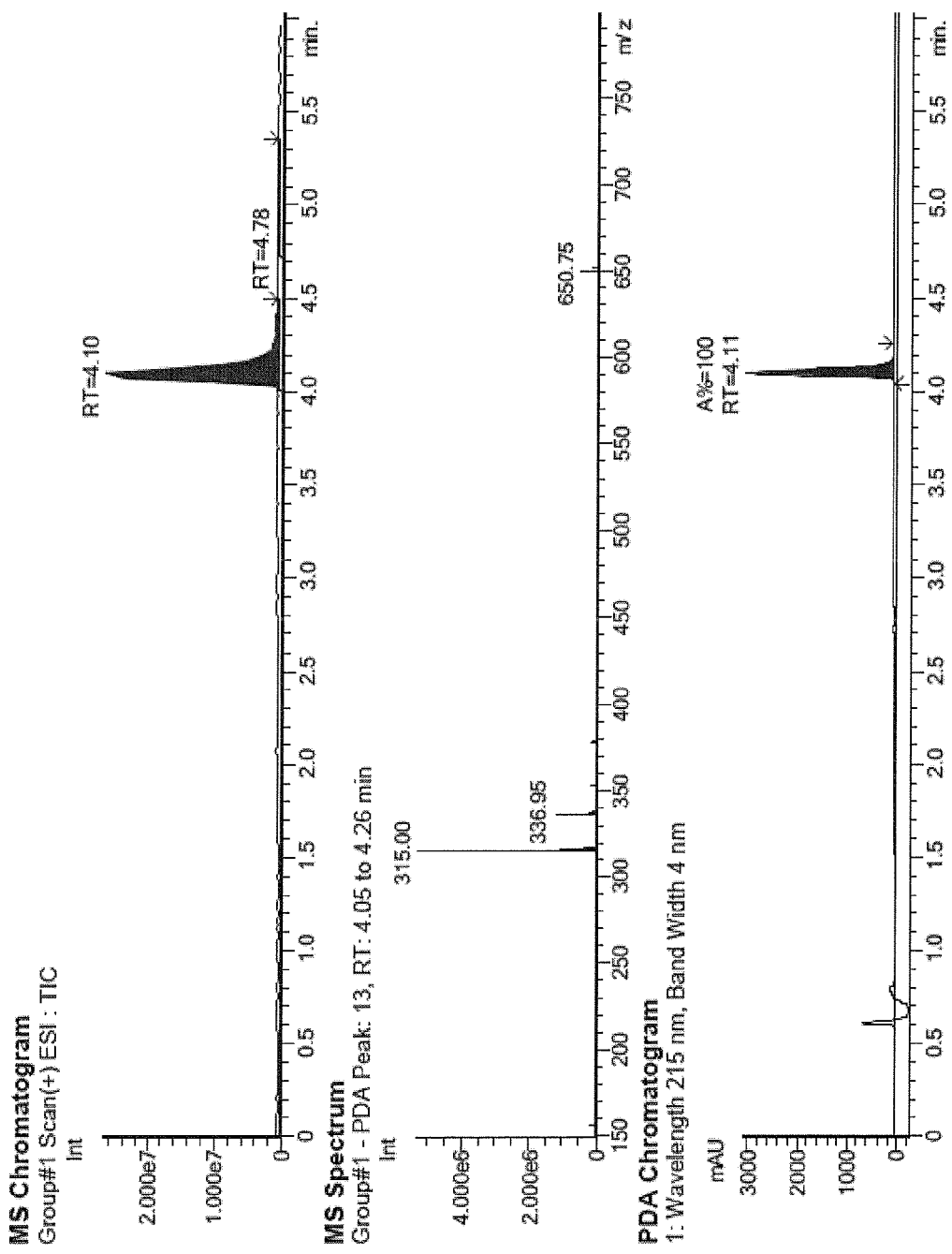
FIG. 27: Chromatogramm of Example Compound 27
Figure 28:
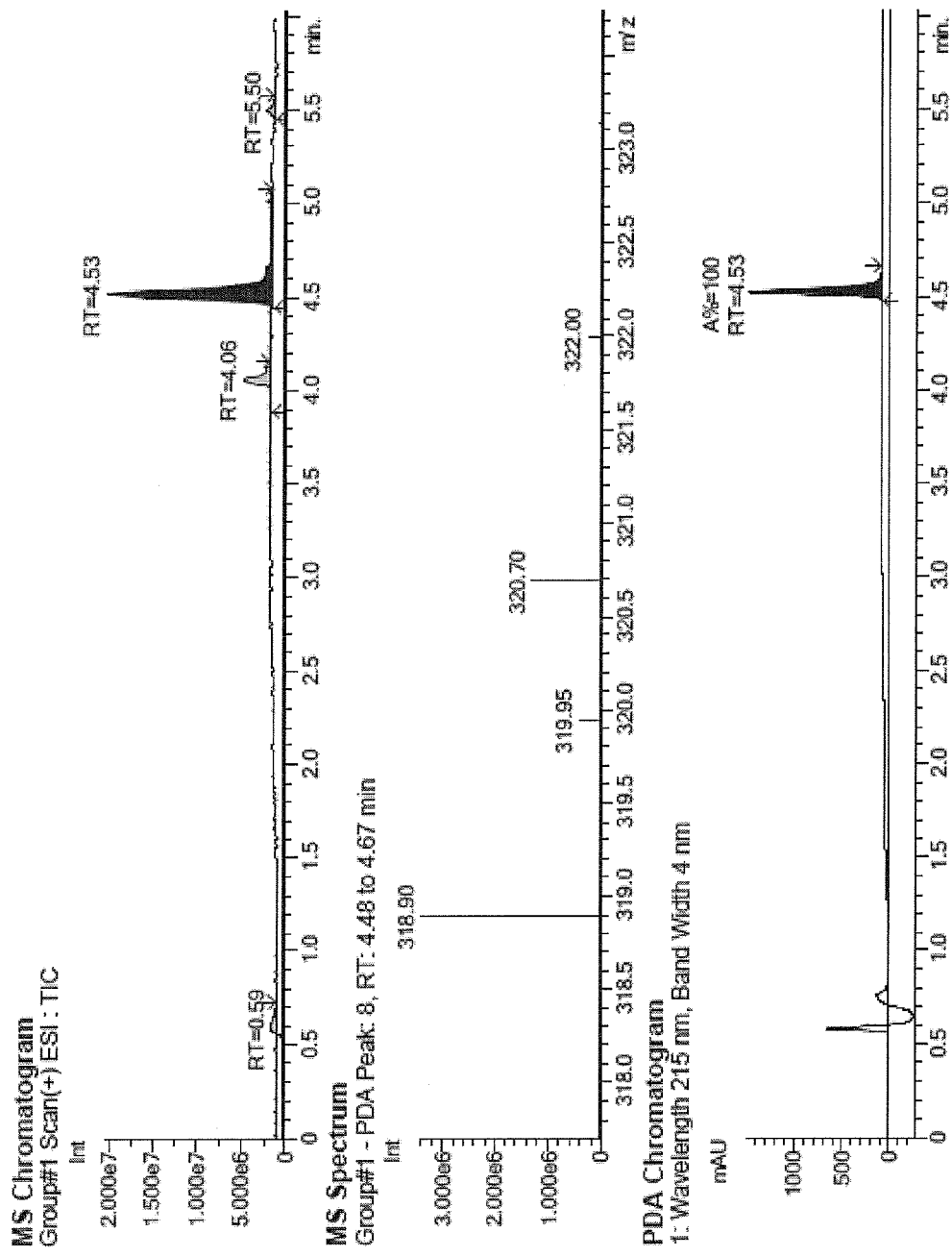
FIG. 28: Chromatogramm of Example Compound 28
Figure 29:
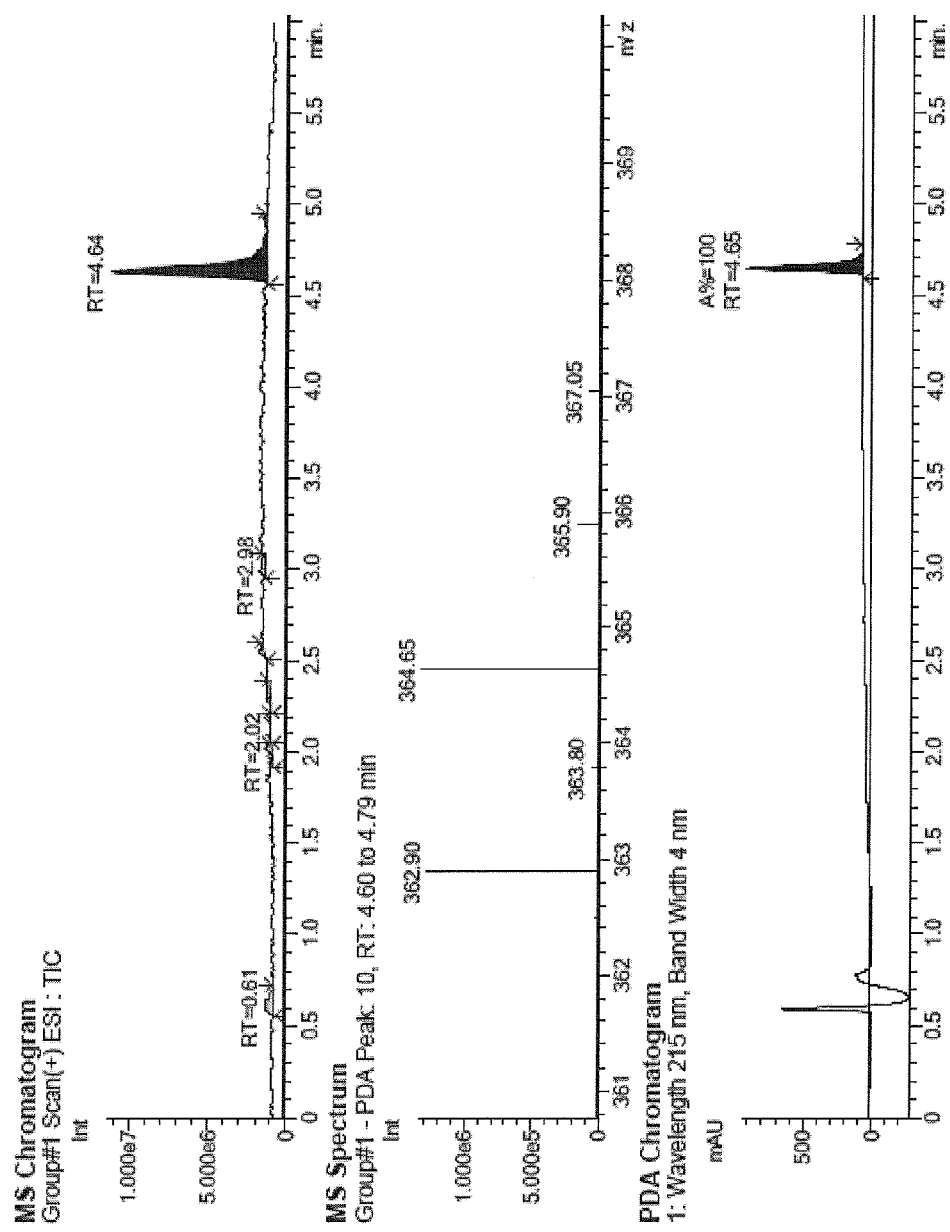
FIG. 29: Chromatogramm of Example Compound 29
Figure 30:
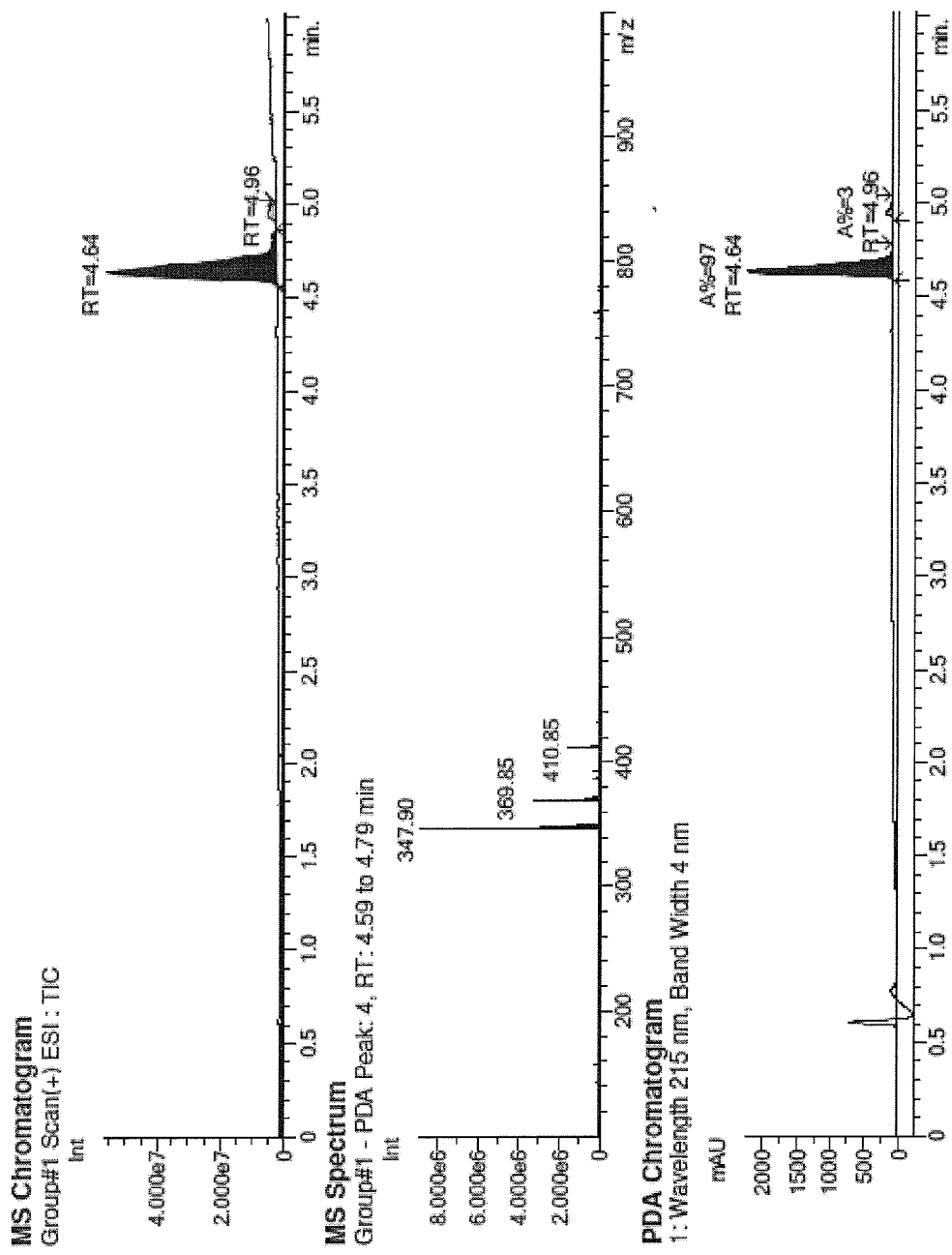
FIG. 30: Chromatogramm of Example Compound 30
Figure 31:
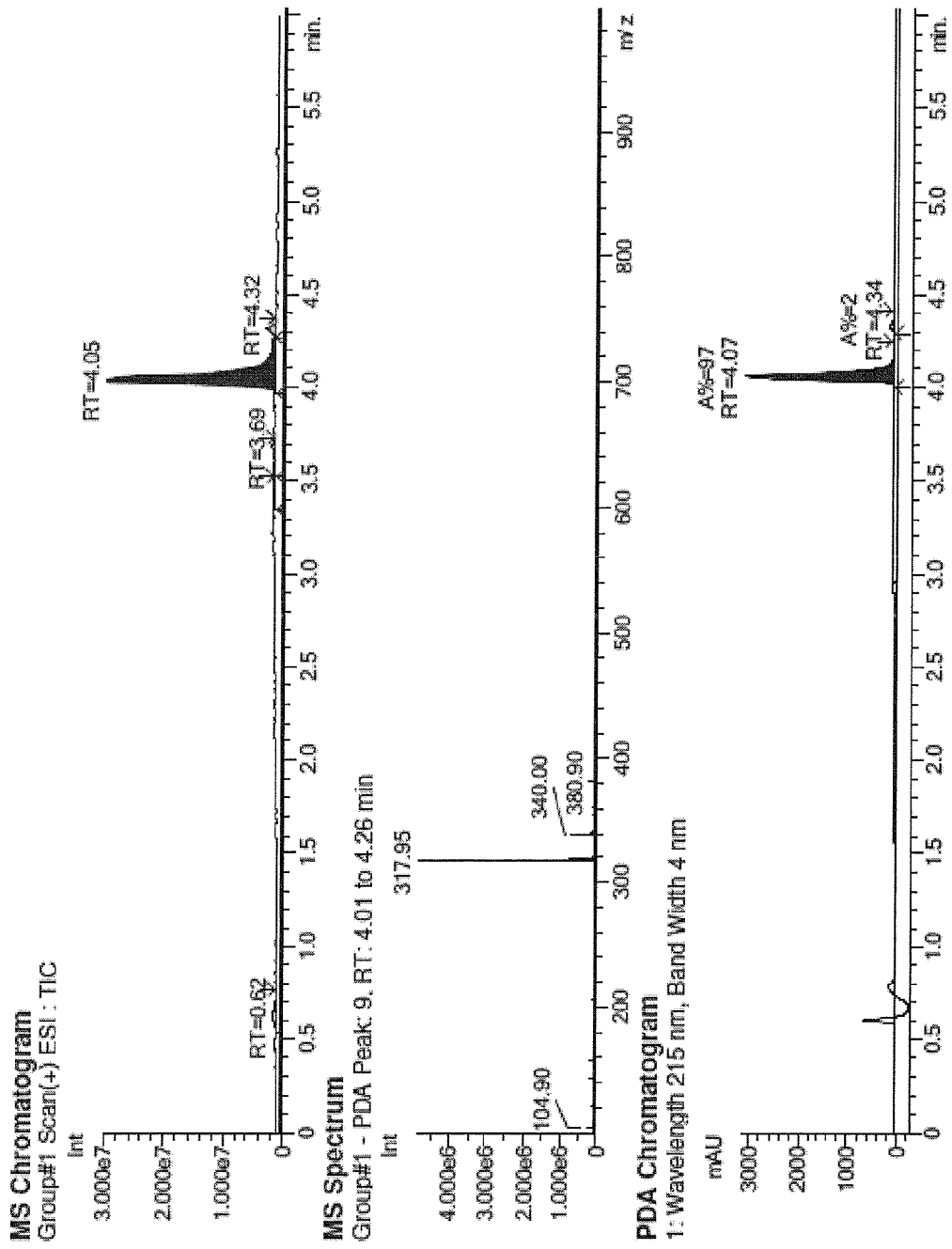
FIG. 31: Chromatogramm of Example Compound 31
Figure 32:
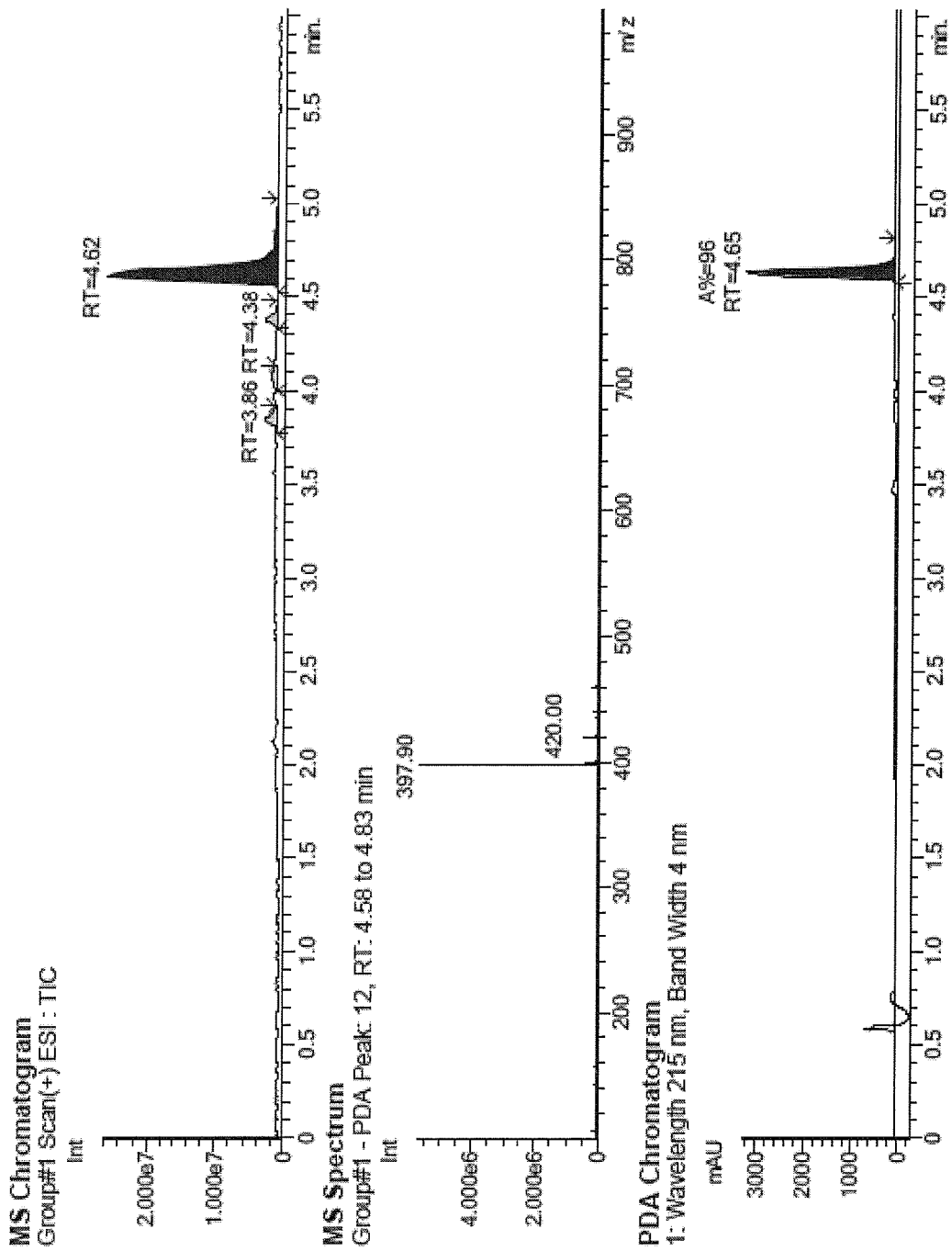
FIG. 32: Chromatogramm of Example Compound 32
Figure 33:
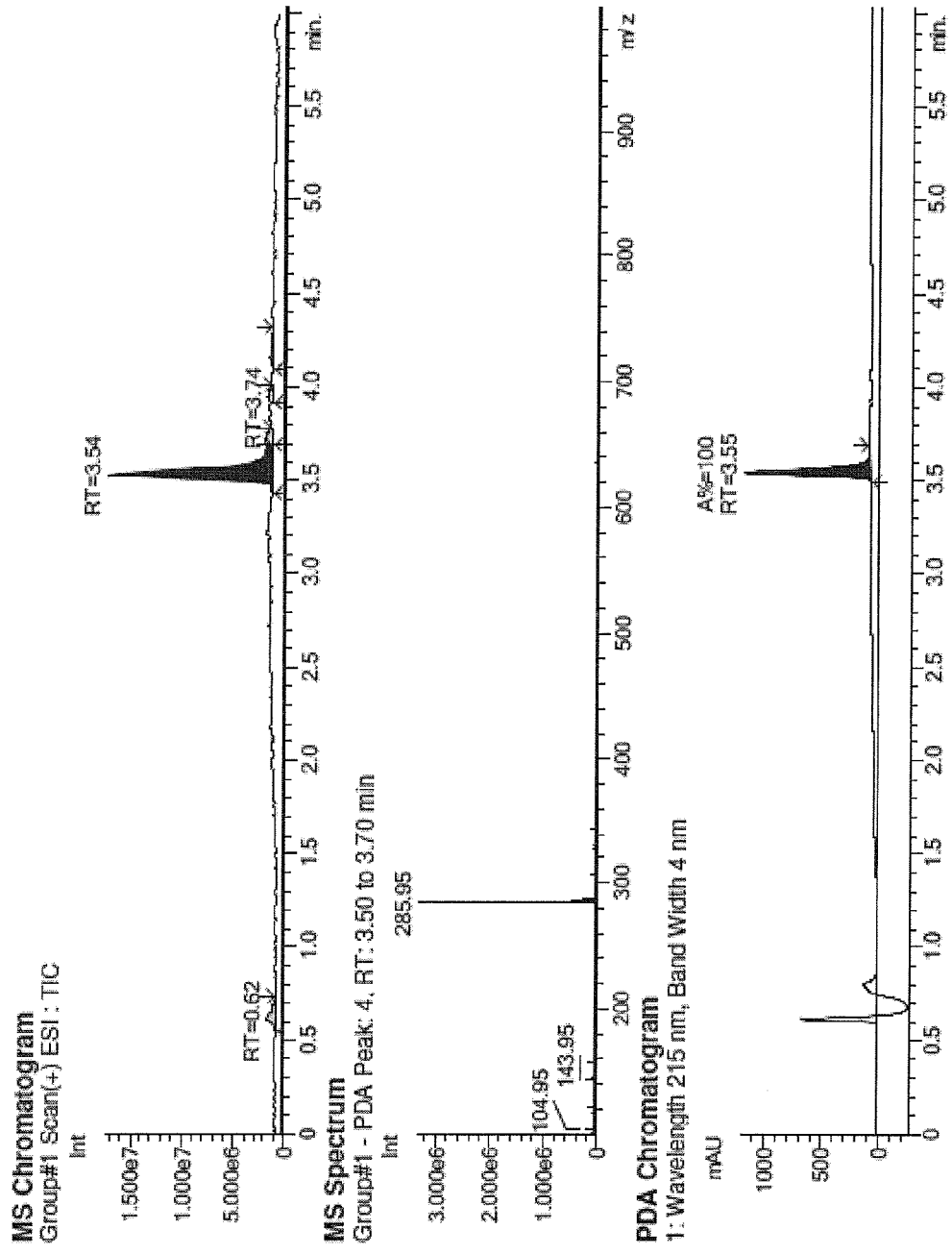
FIG. 33: Chromatogramm of Example Compound 33
Figure 34:
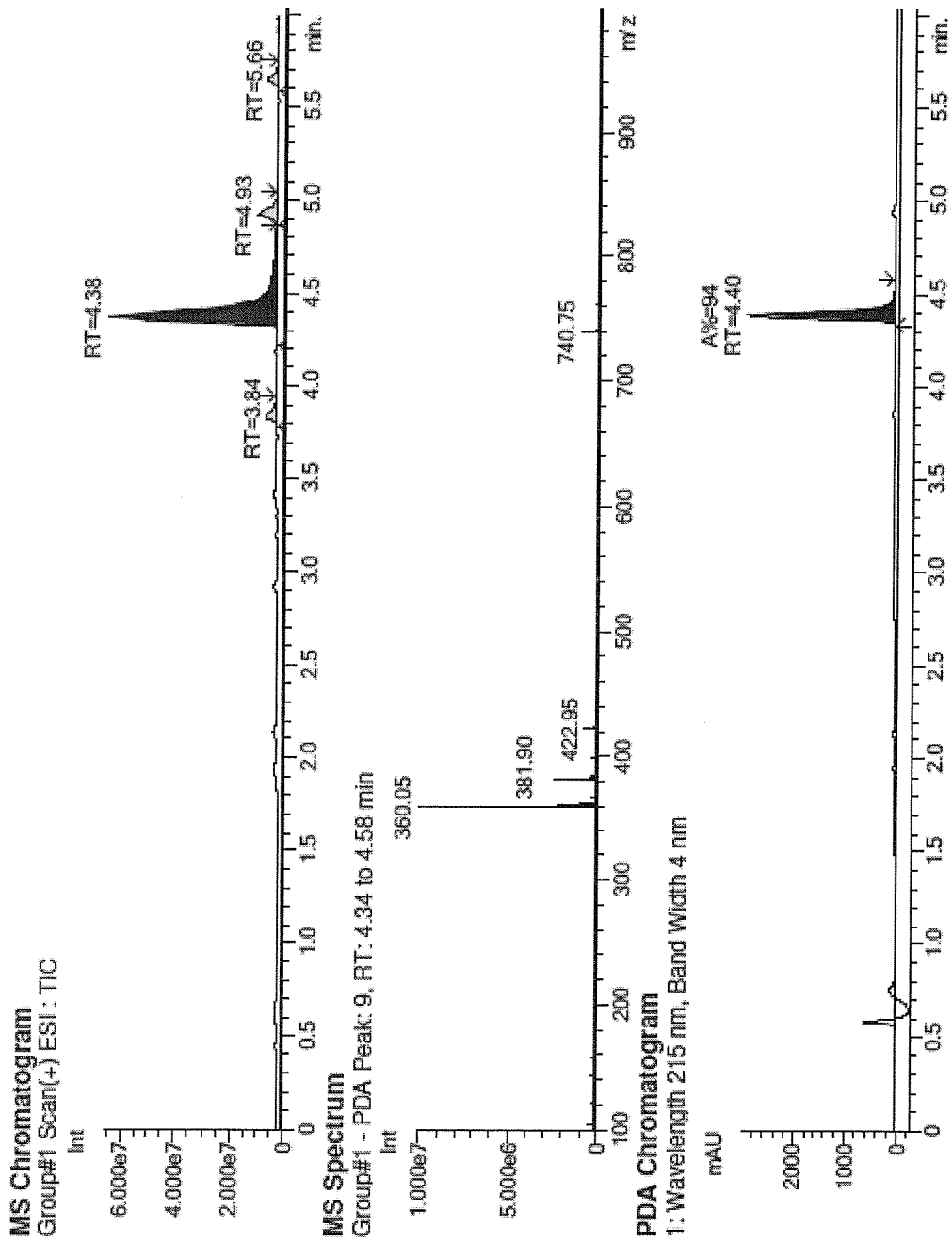
FIG. 34: Chromatogramm of Example Compound 34
Figure 35:
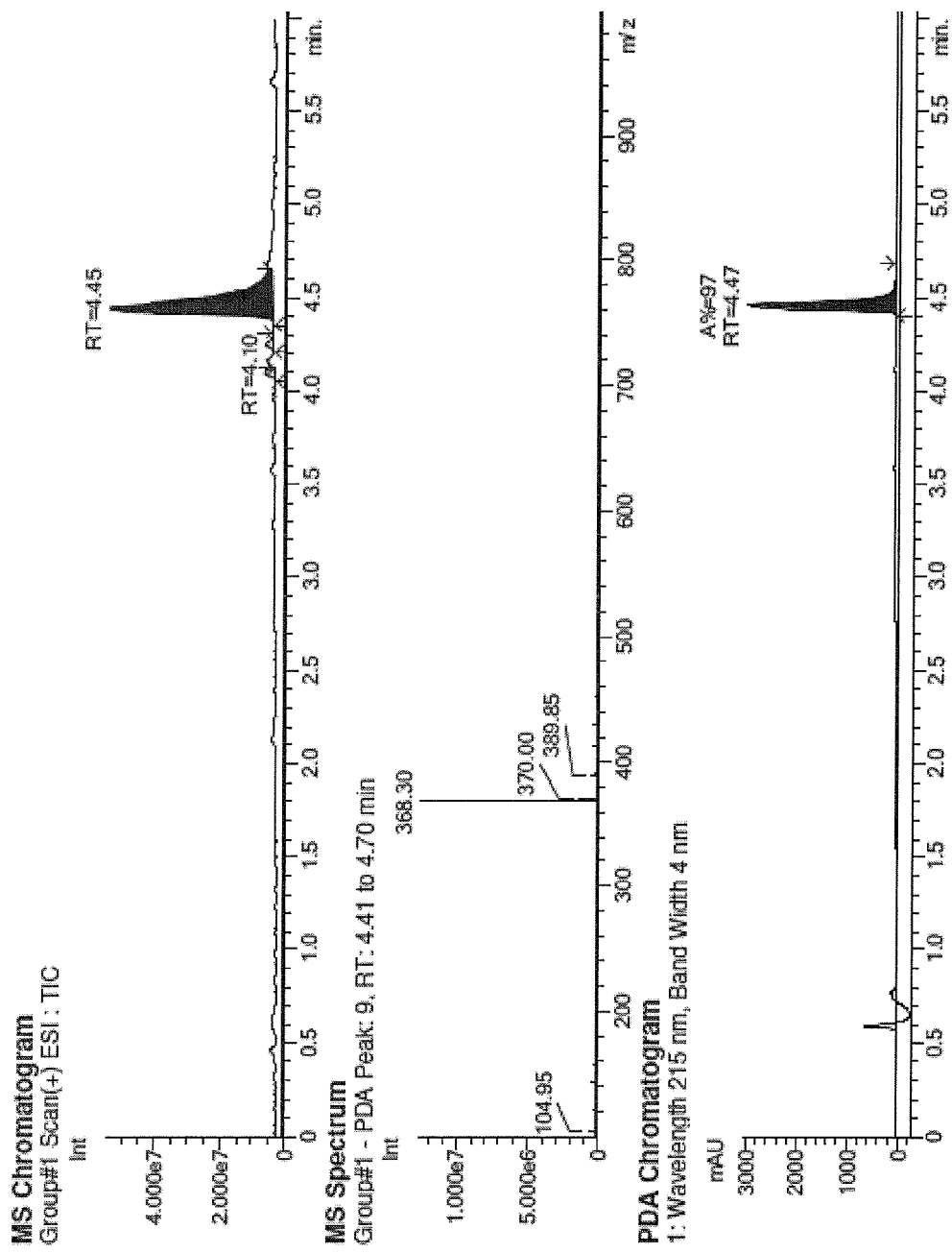
Figure 36:
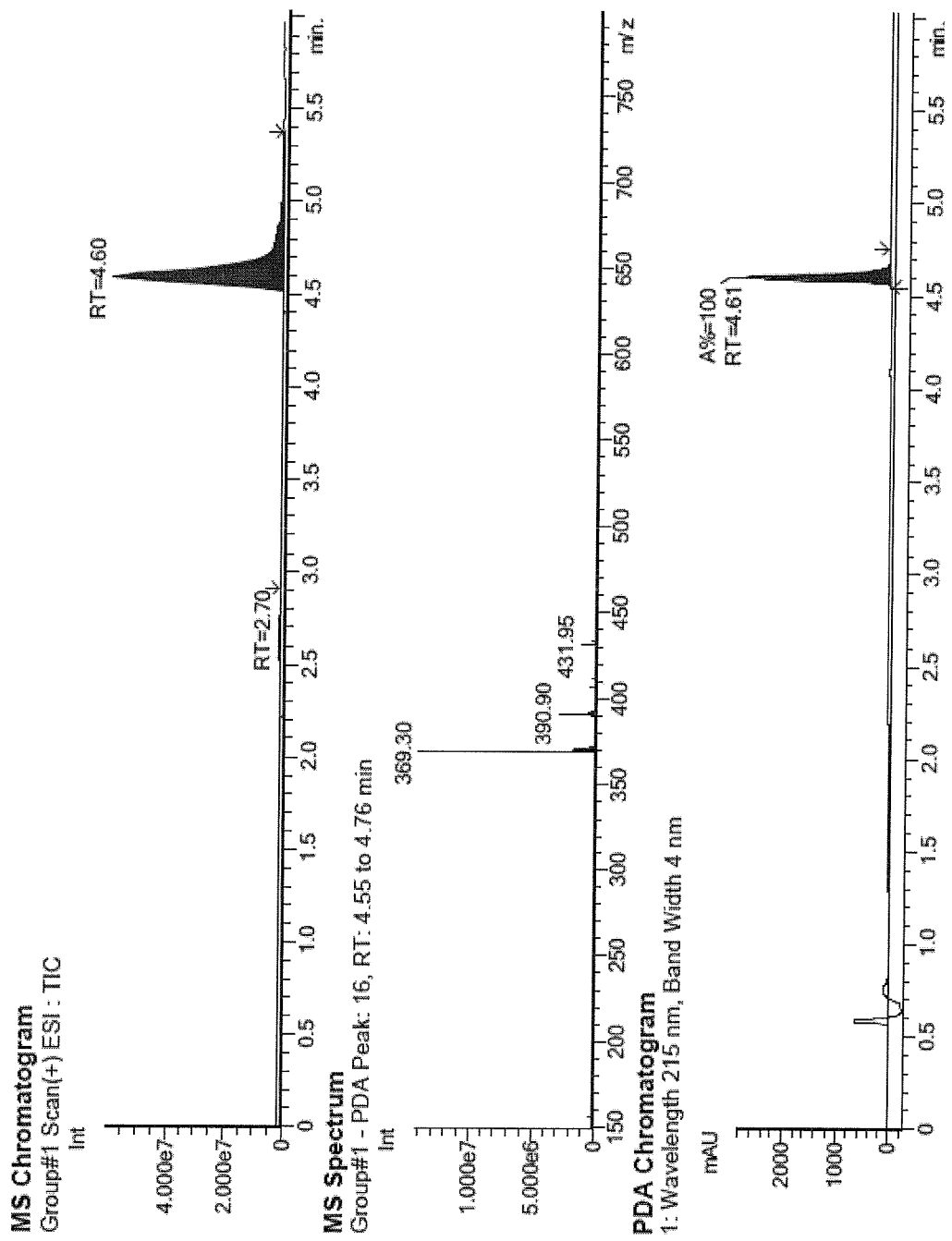
FIG. 36: Chromatogramm of Example Compound 36
Figure 37:
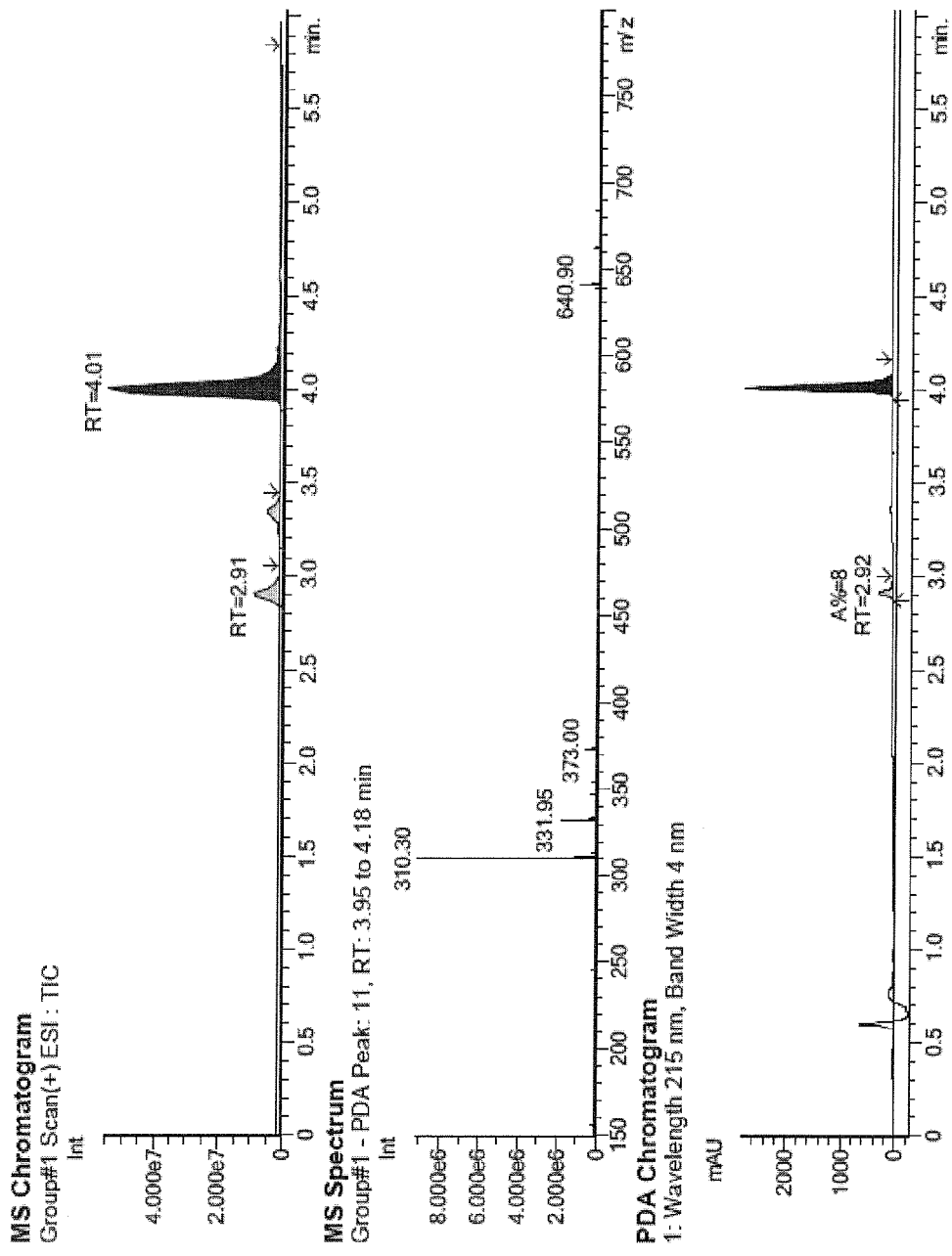
FIG. 37: Chromatogramm of Example Compound 37
Figure 38:
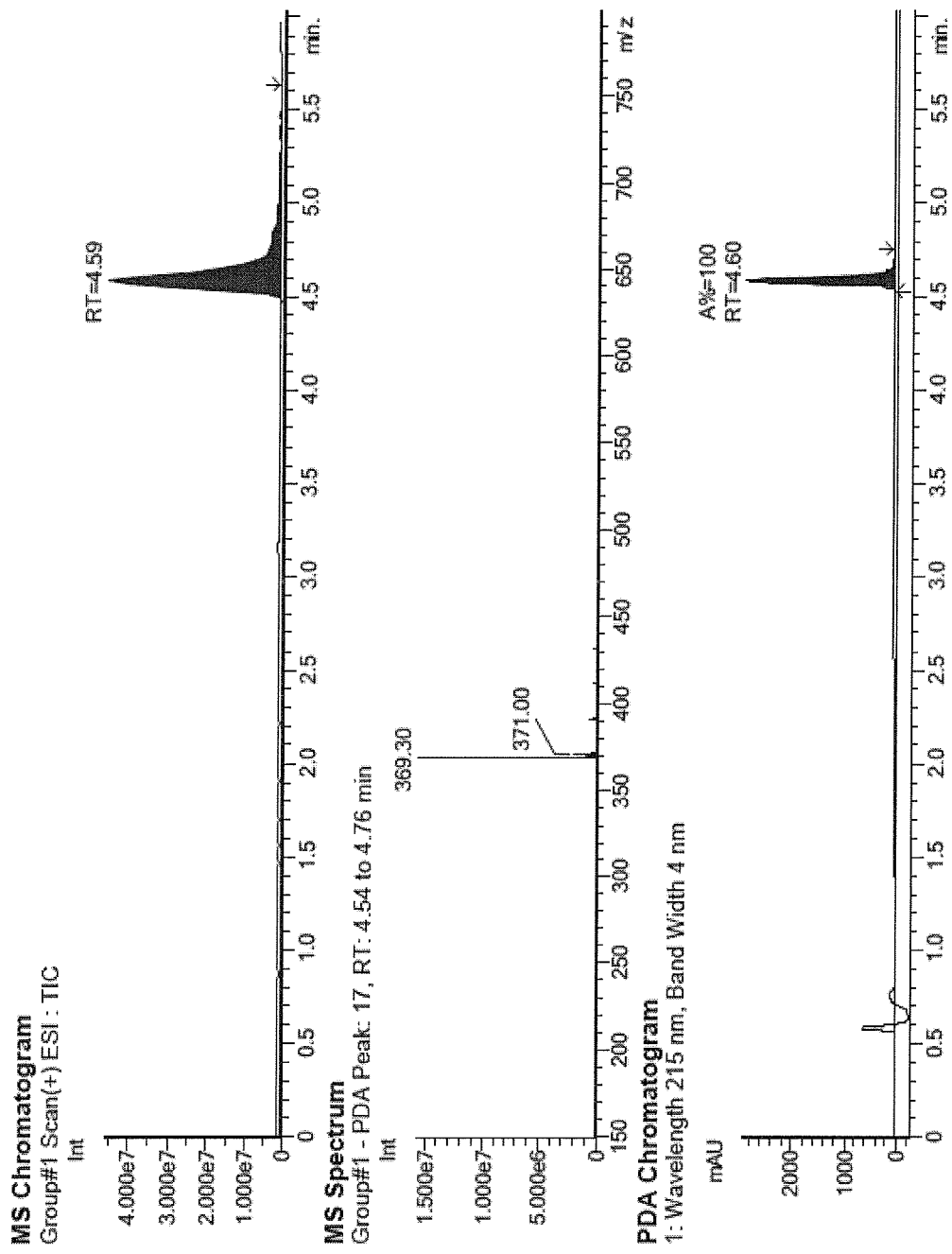
FIG. 38: Chromatogramm of Example Compound 38
Figure 39:
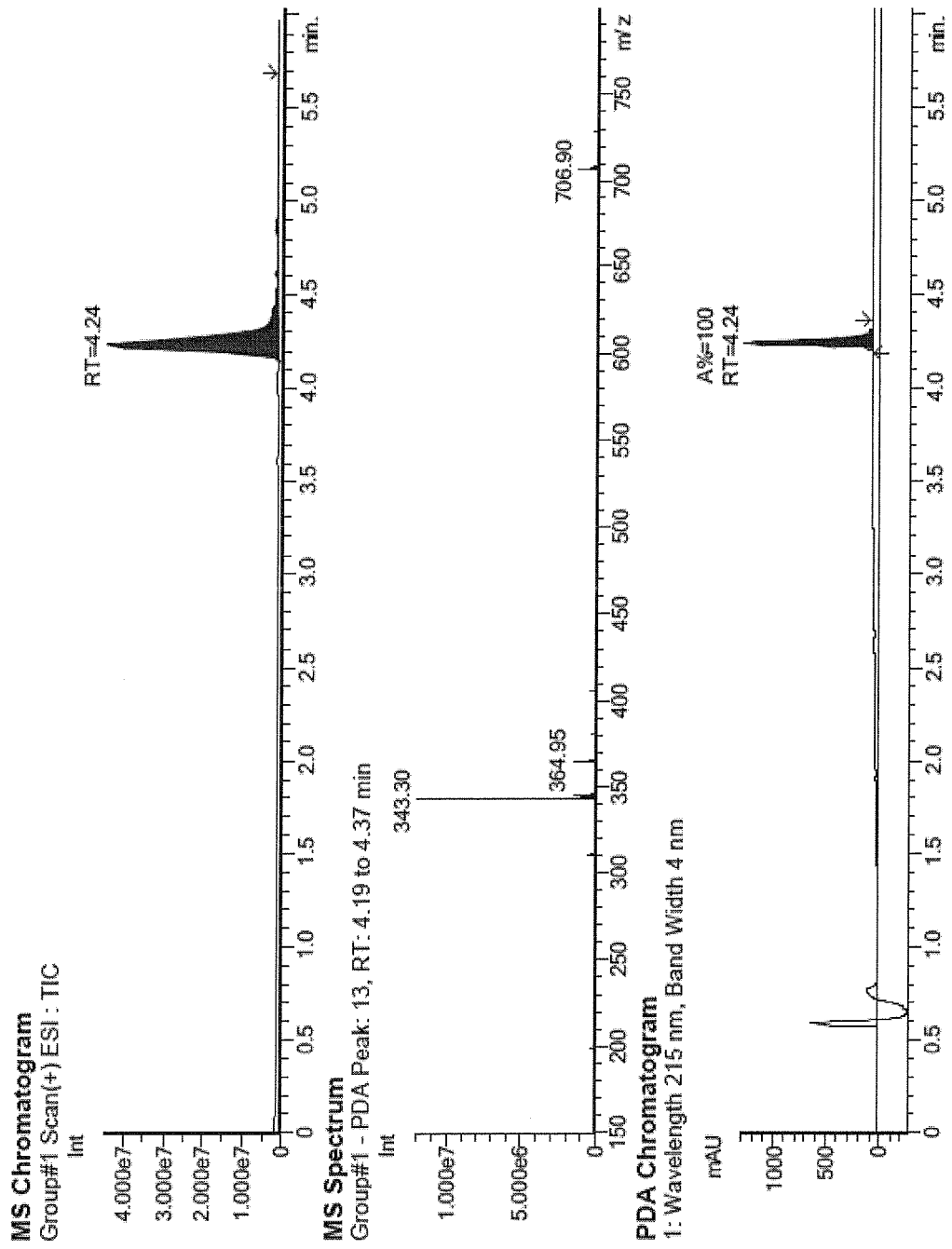
FIG. 39: Chromatogramm of Example Compound 39
Figure 40:
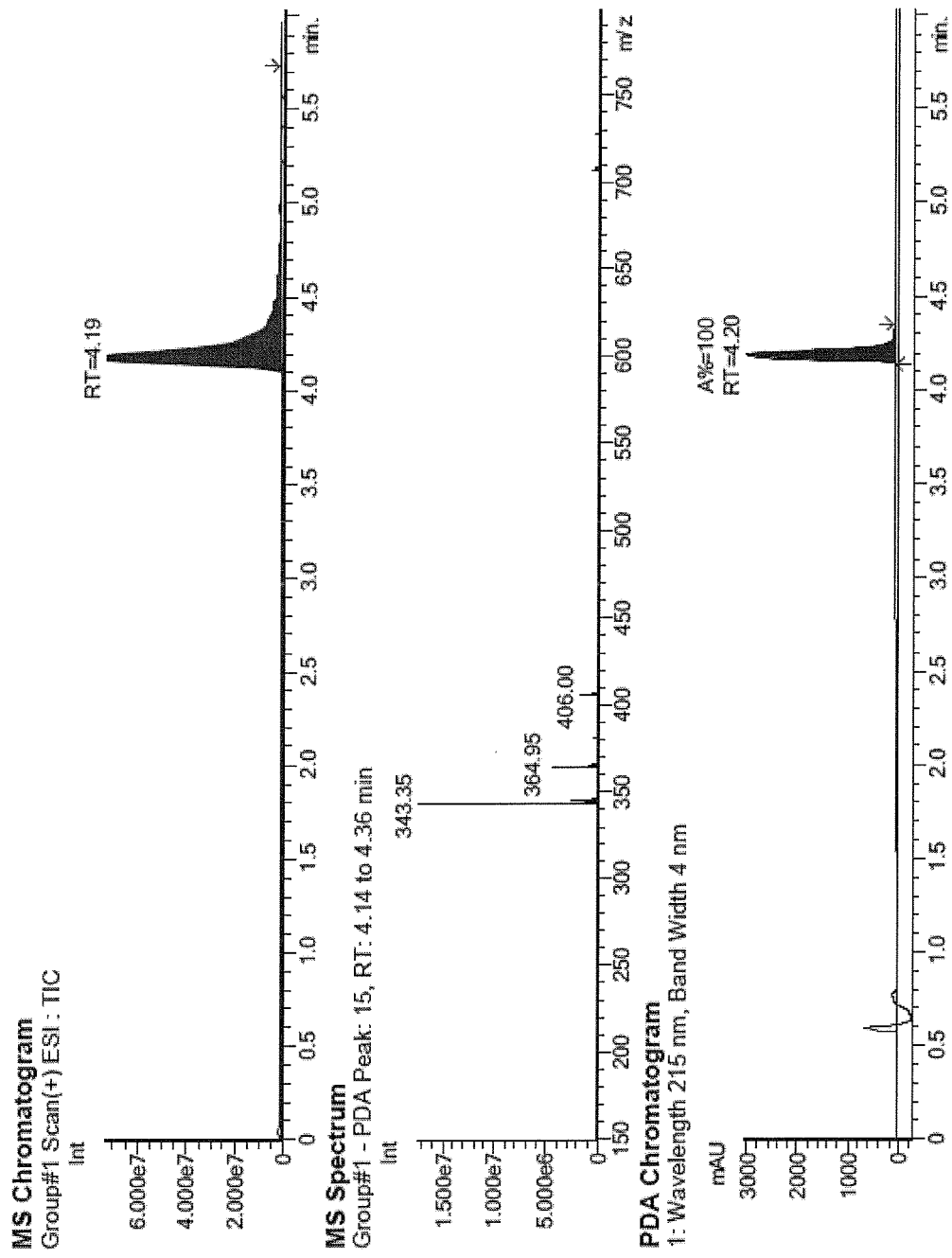
FIG. 40: Chromatogramm of Example Compound 40
Figure 41:
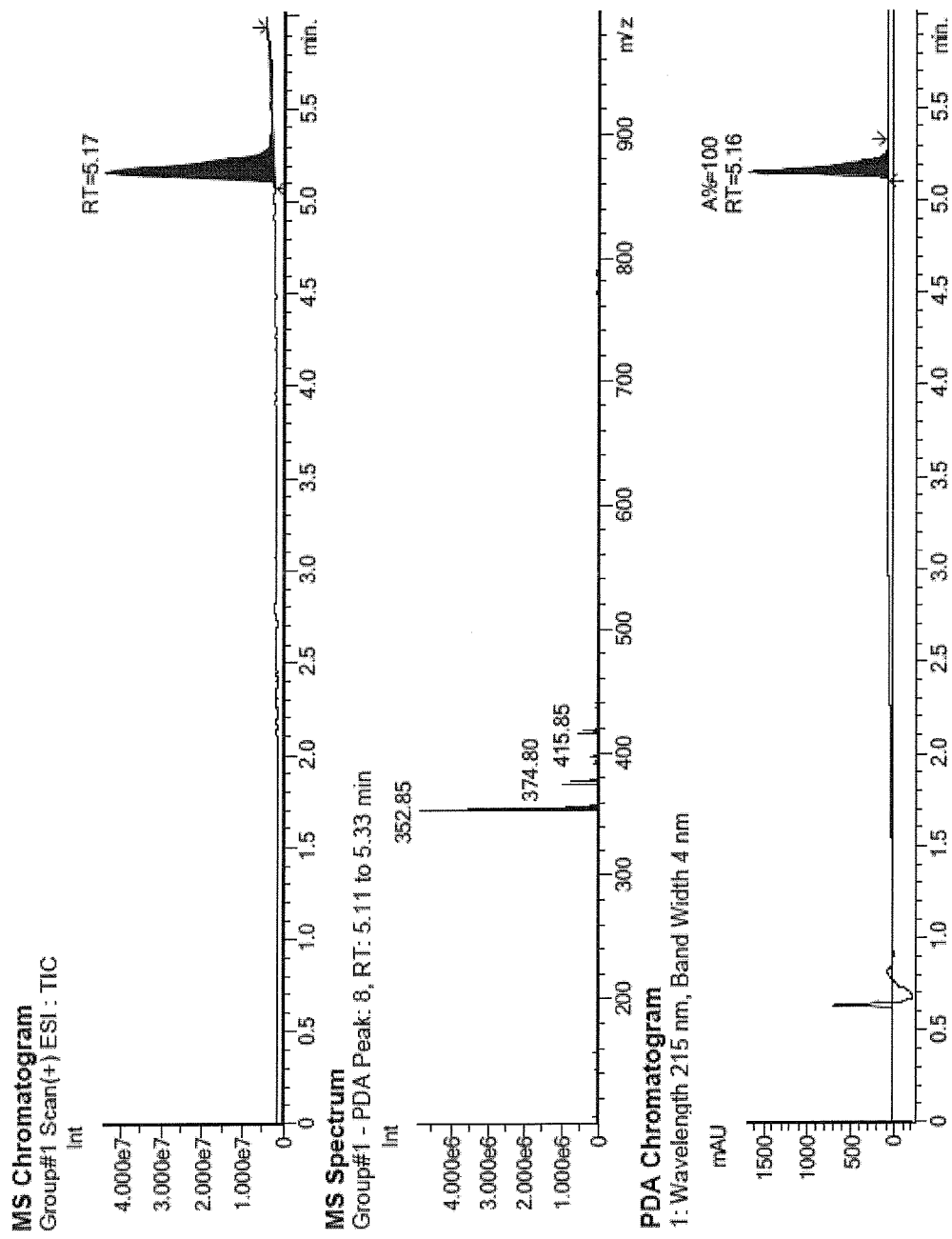
FIG. 41: Chromatogramm of Example Compound 41
Figure 42:
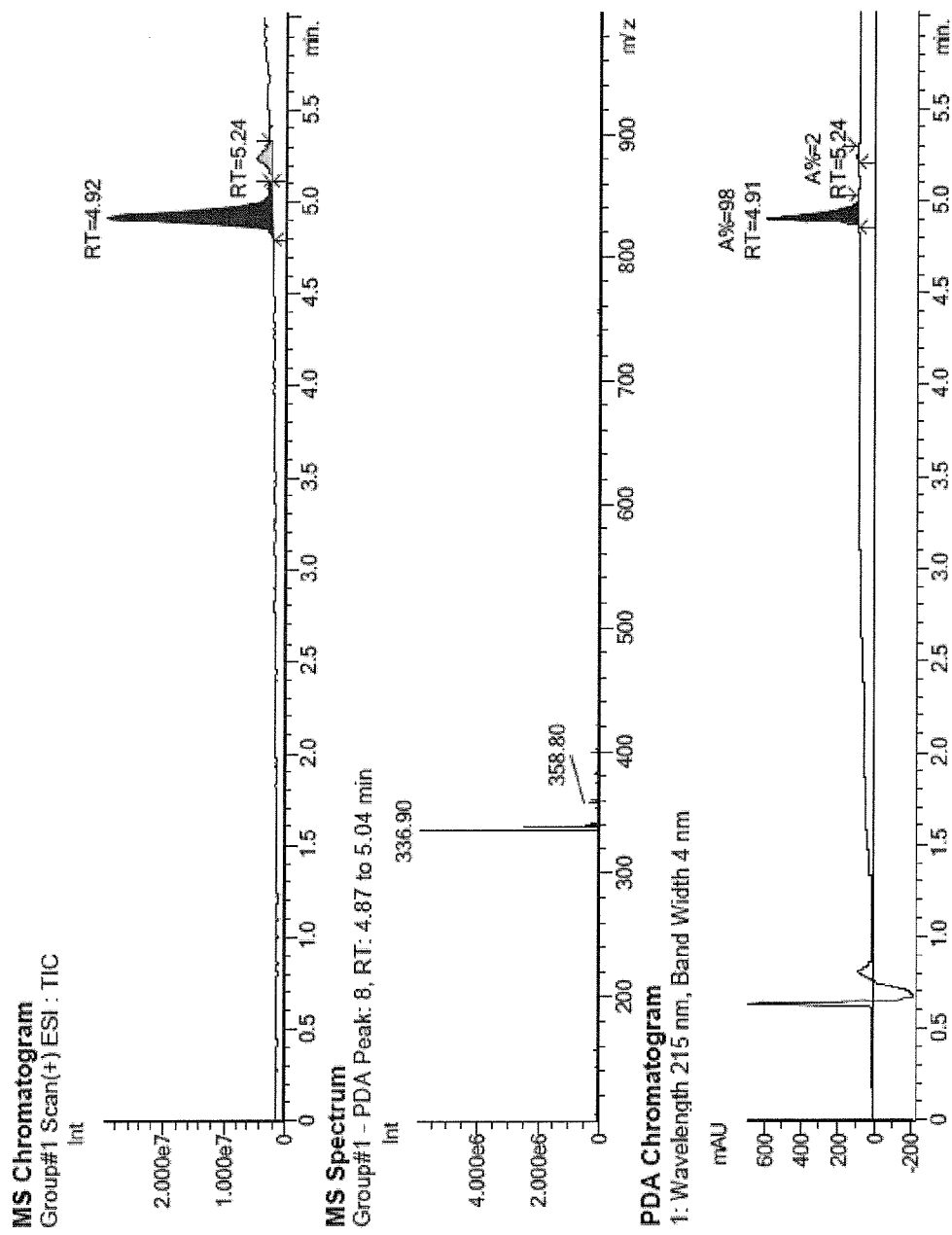
FIG. 42: Chromatogramm of Example Compound 42
Figure 43:
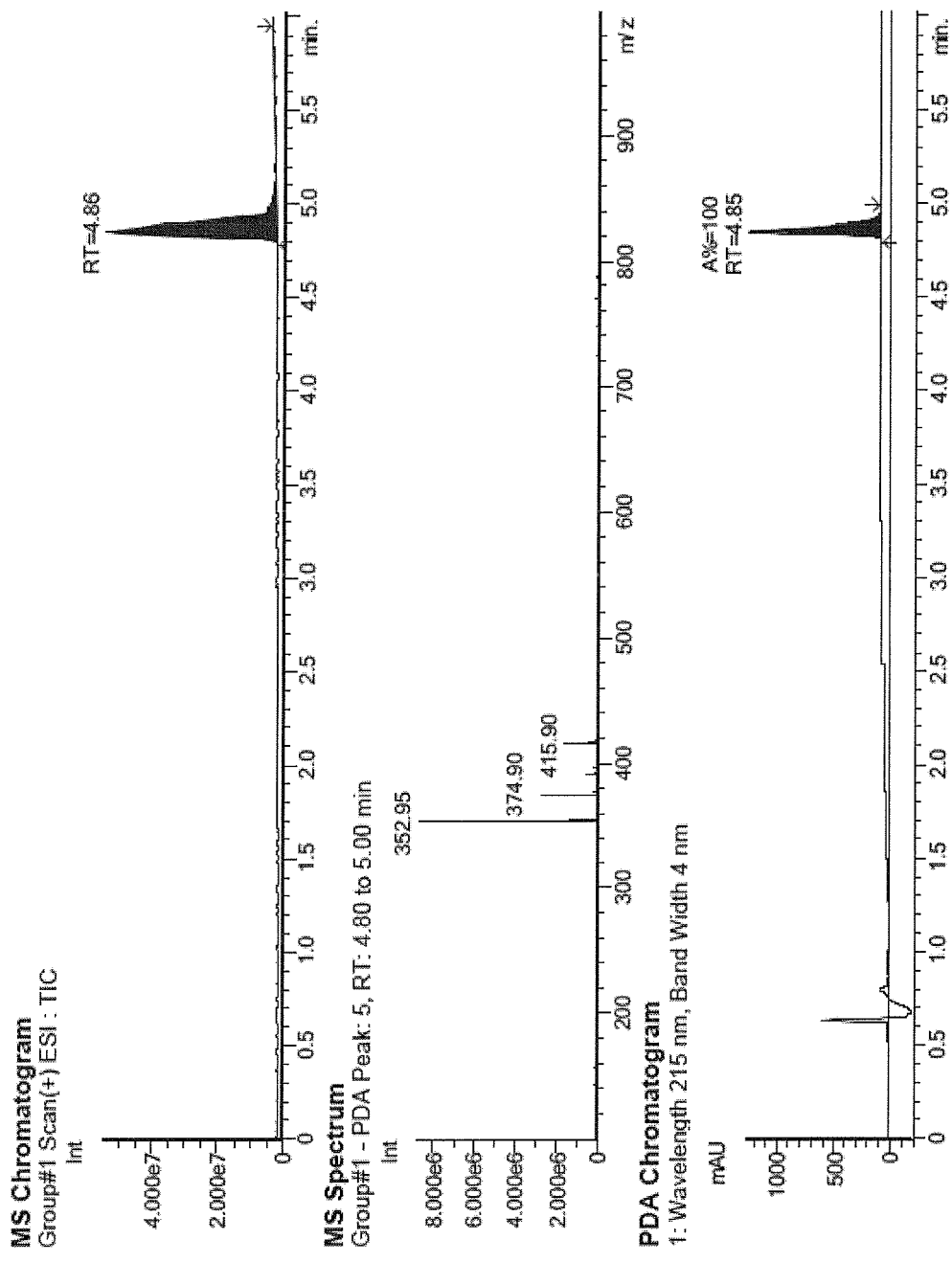
FIG. 43: Chromatogramm of Example Compound 43
Figure 44:
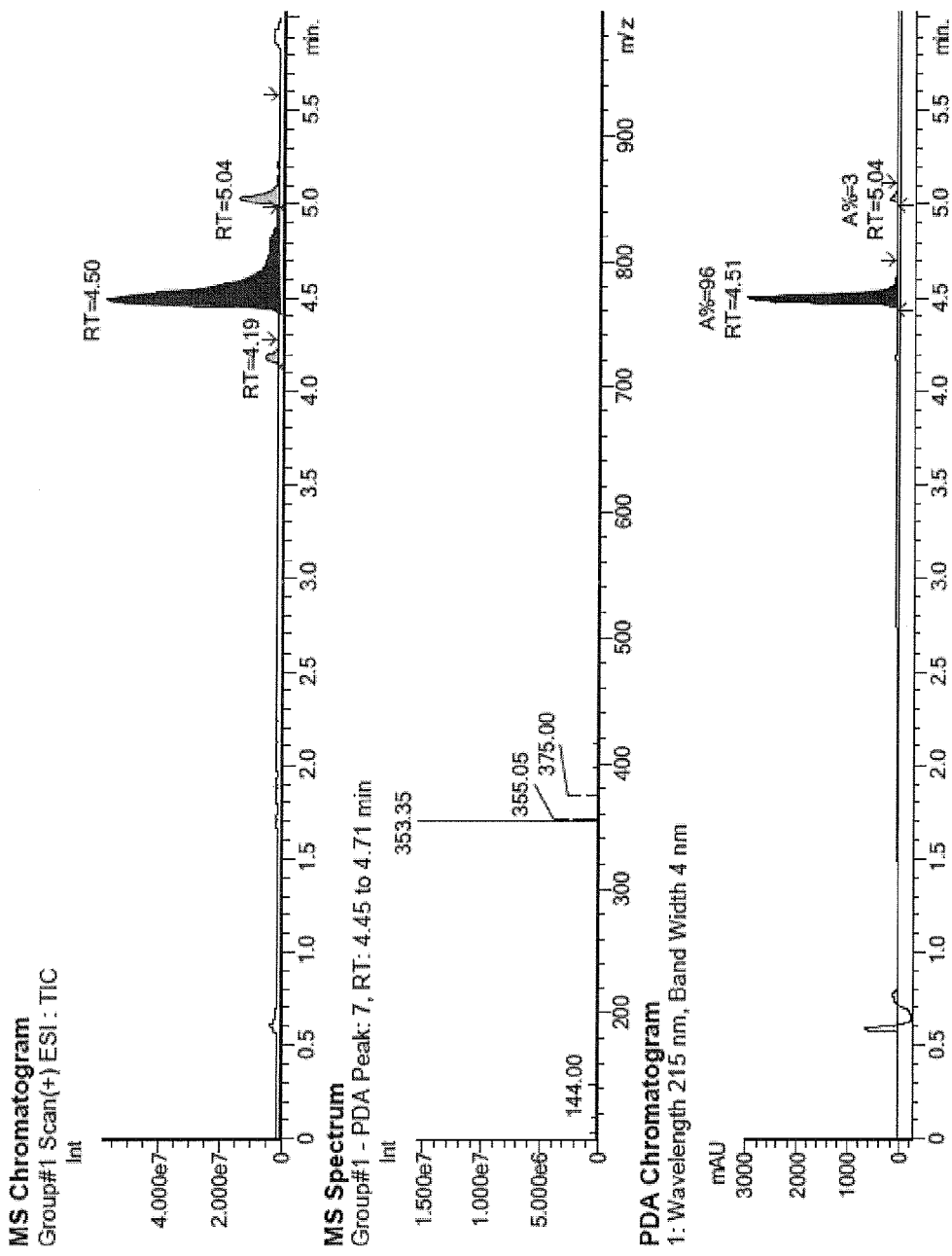
FIG. 44: Chromatogramm of Example Compound 44
Figure 45:
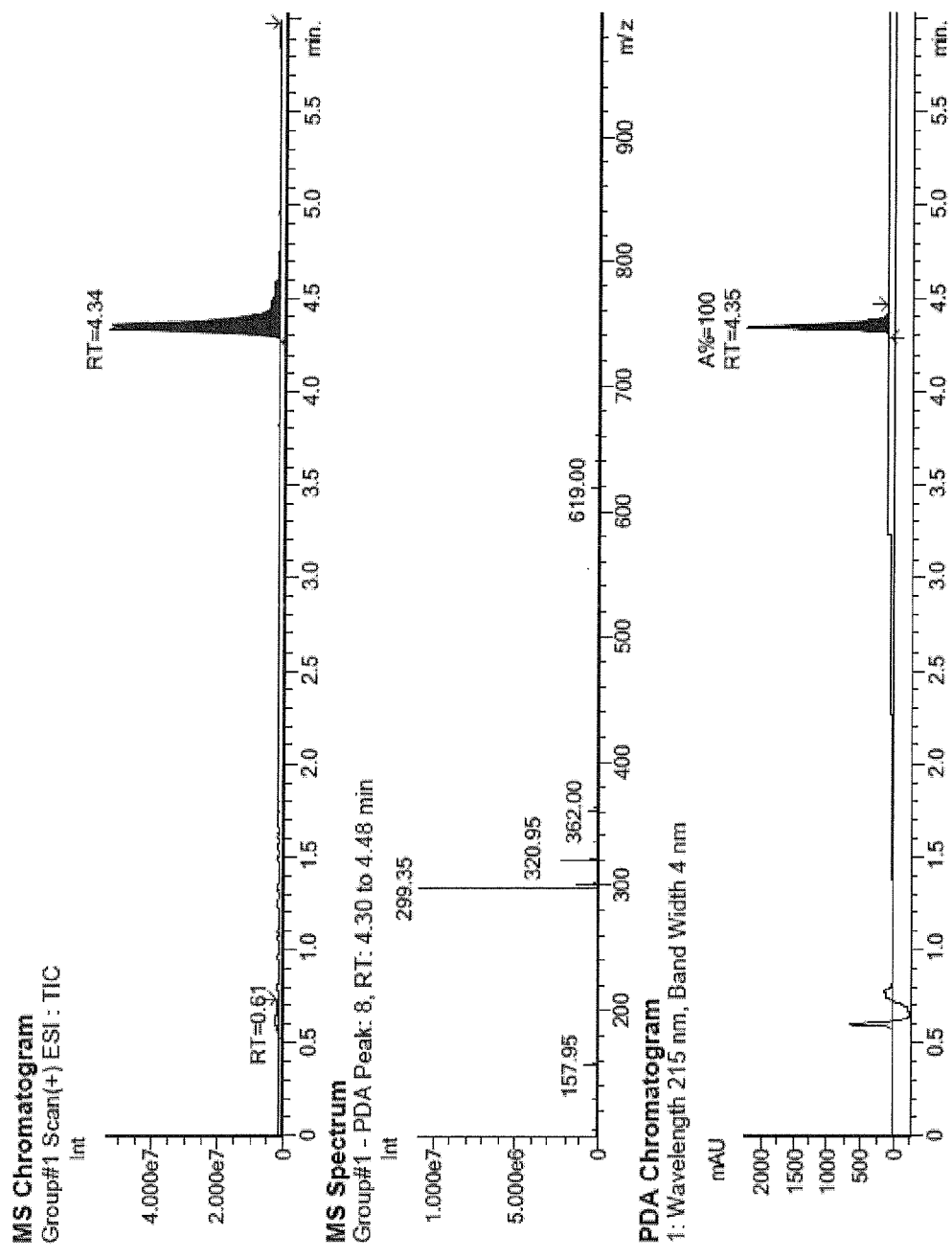
FIG. 45: Chromatogramm of Example Compound 45
Figure 46:
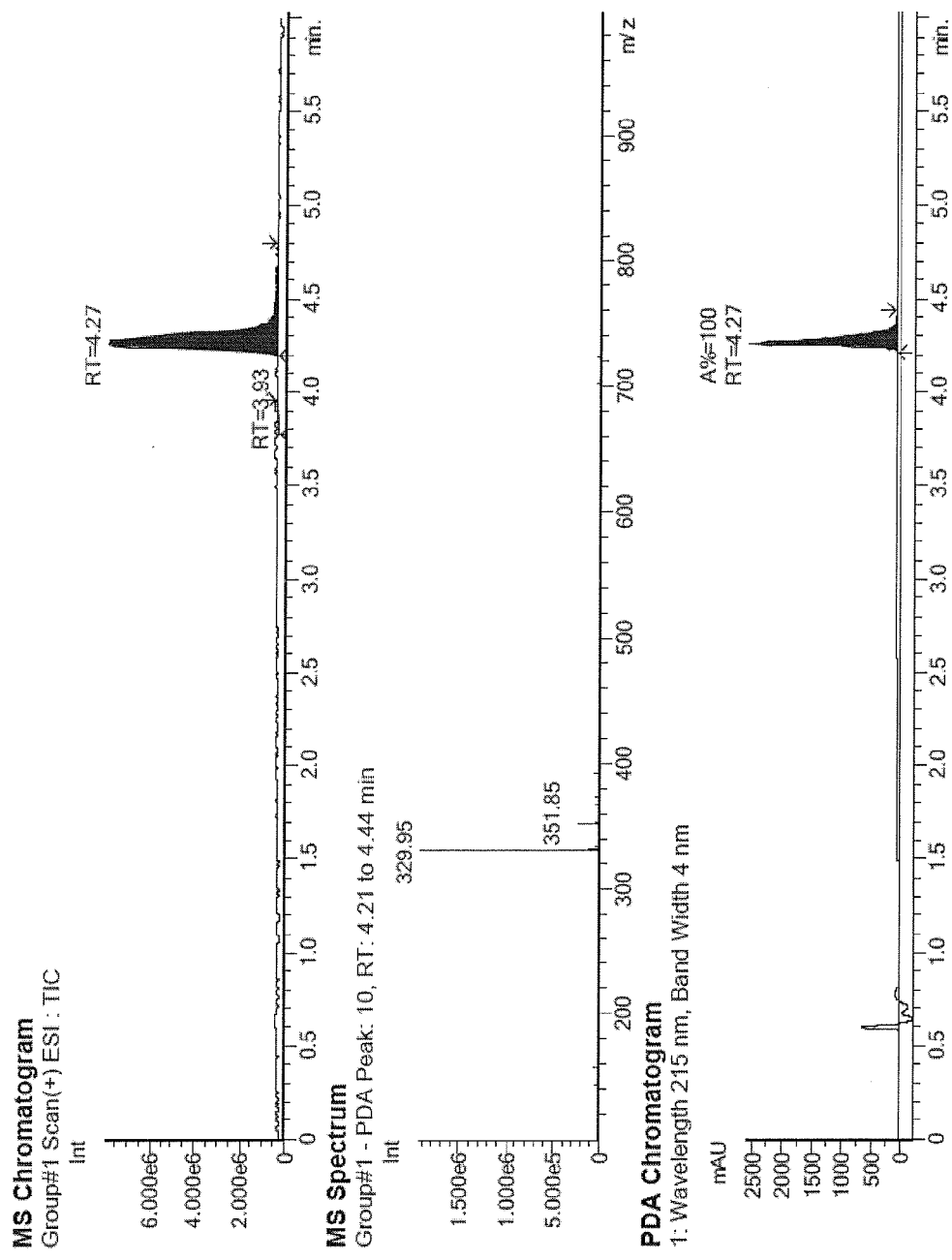
FIG. 46: Chromatogramm of Example Compound 46
Figure 47:
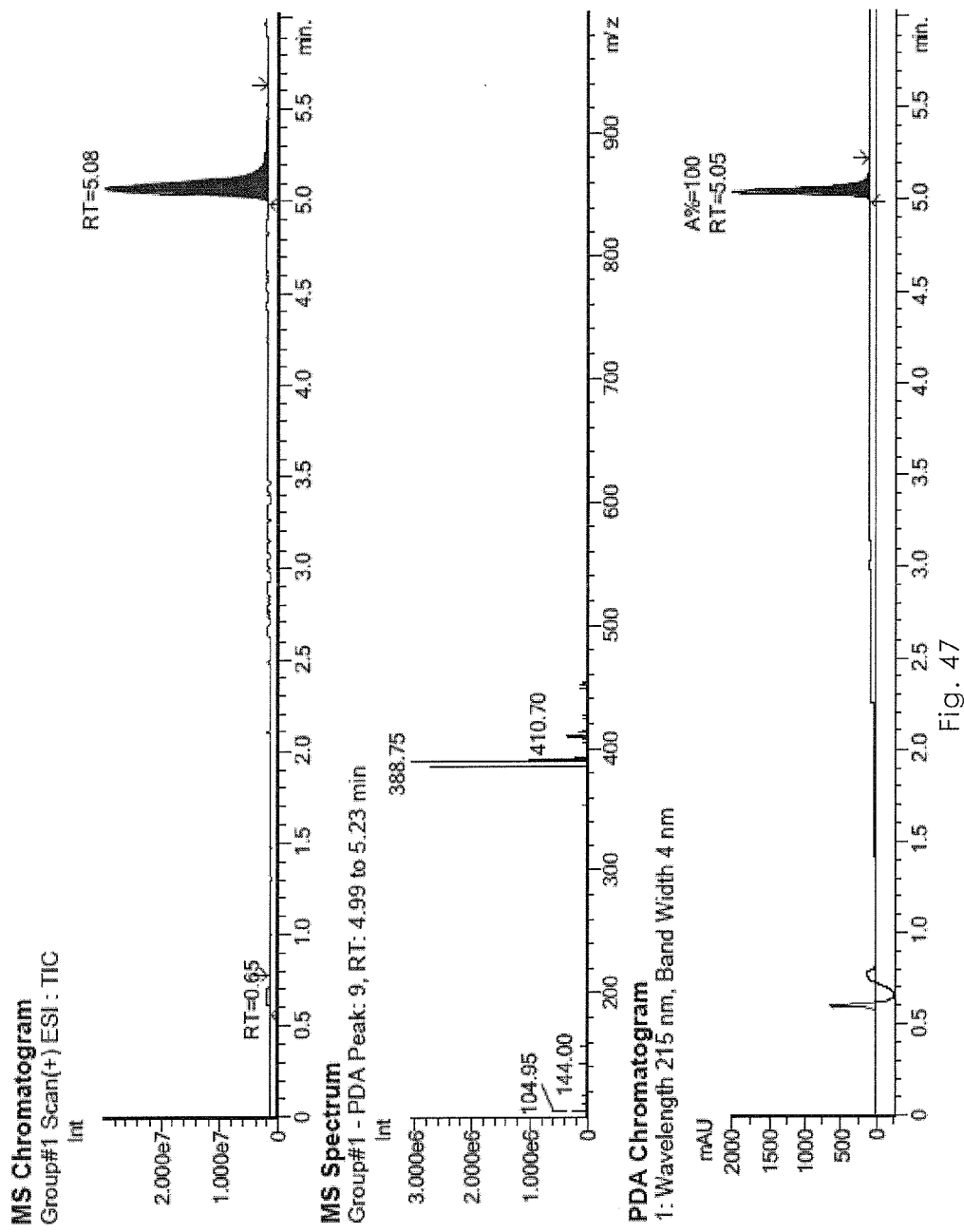
FIG. 47: Chromatogramm of Example Compound 47
Figure 48:
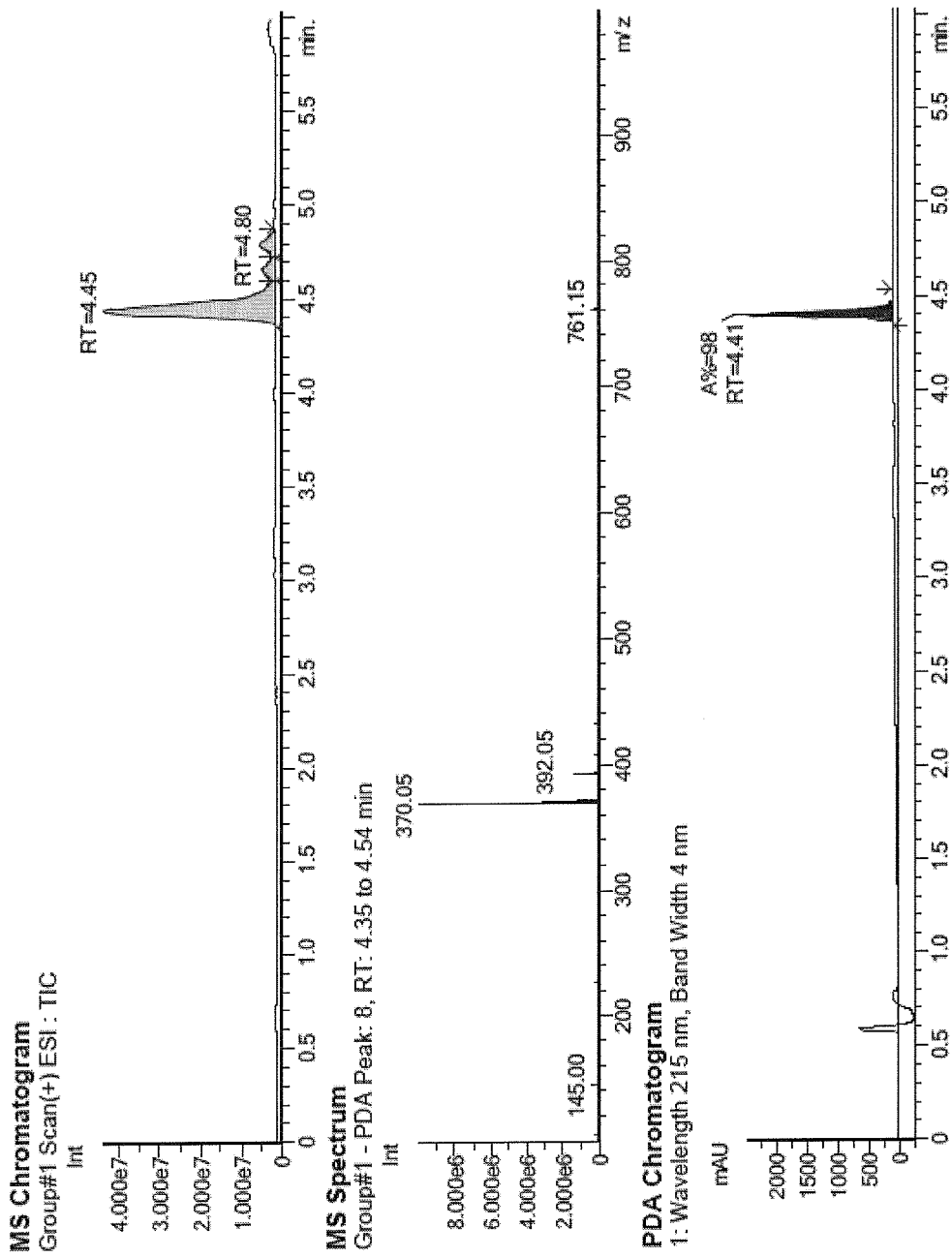
FIG. 48: Chromatogramm of Example Compound 48
Figure 49:
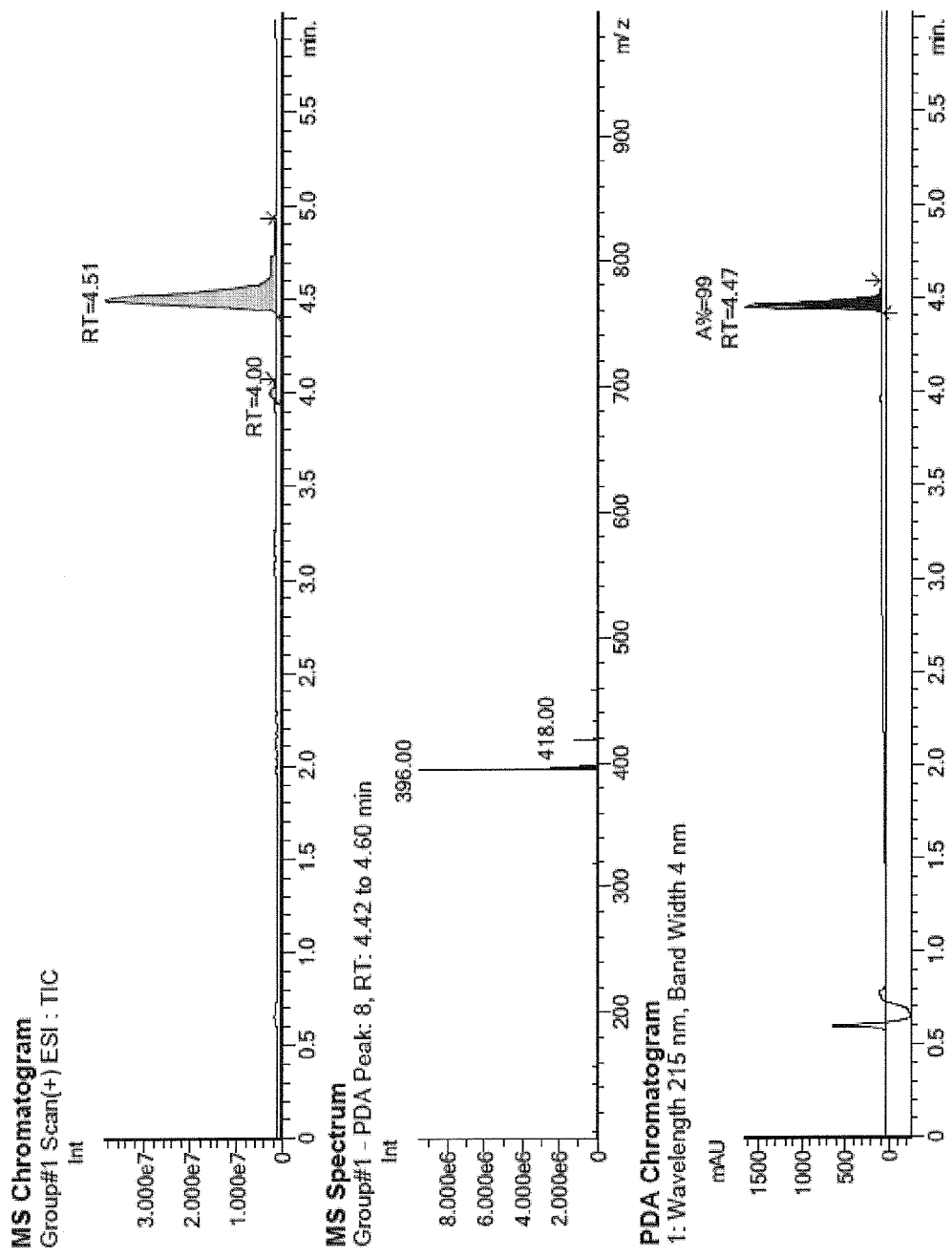
FIG. 49: Chromatogramm of Example Compound 49
Figure 50:
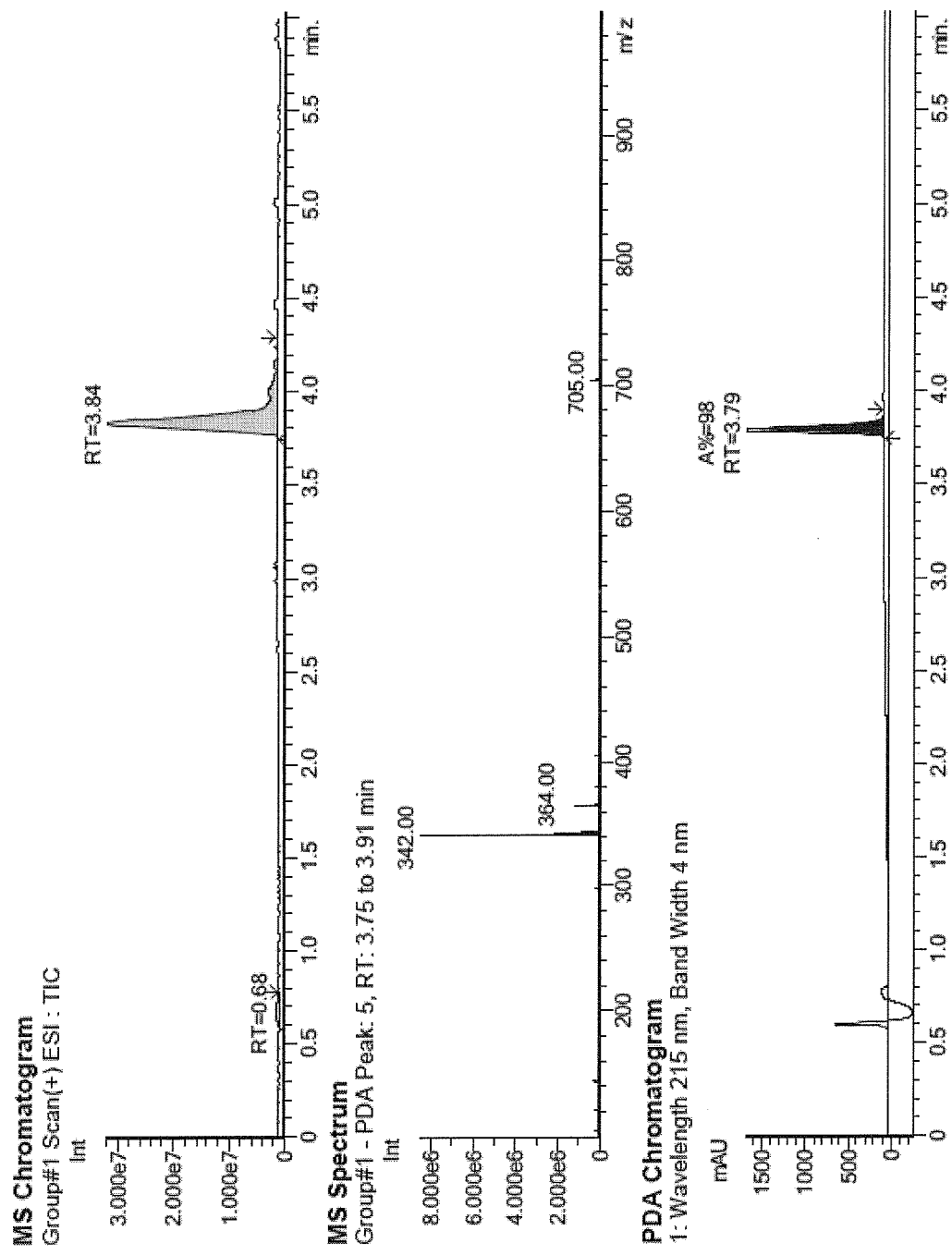
FIG. 50: Chromatogramm of Example Compound 50
Figure 51:
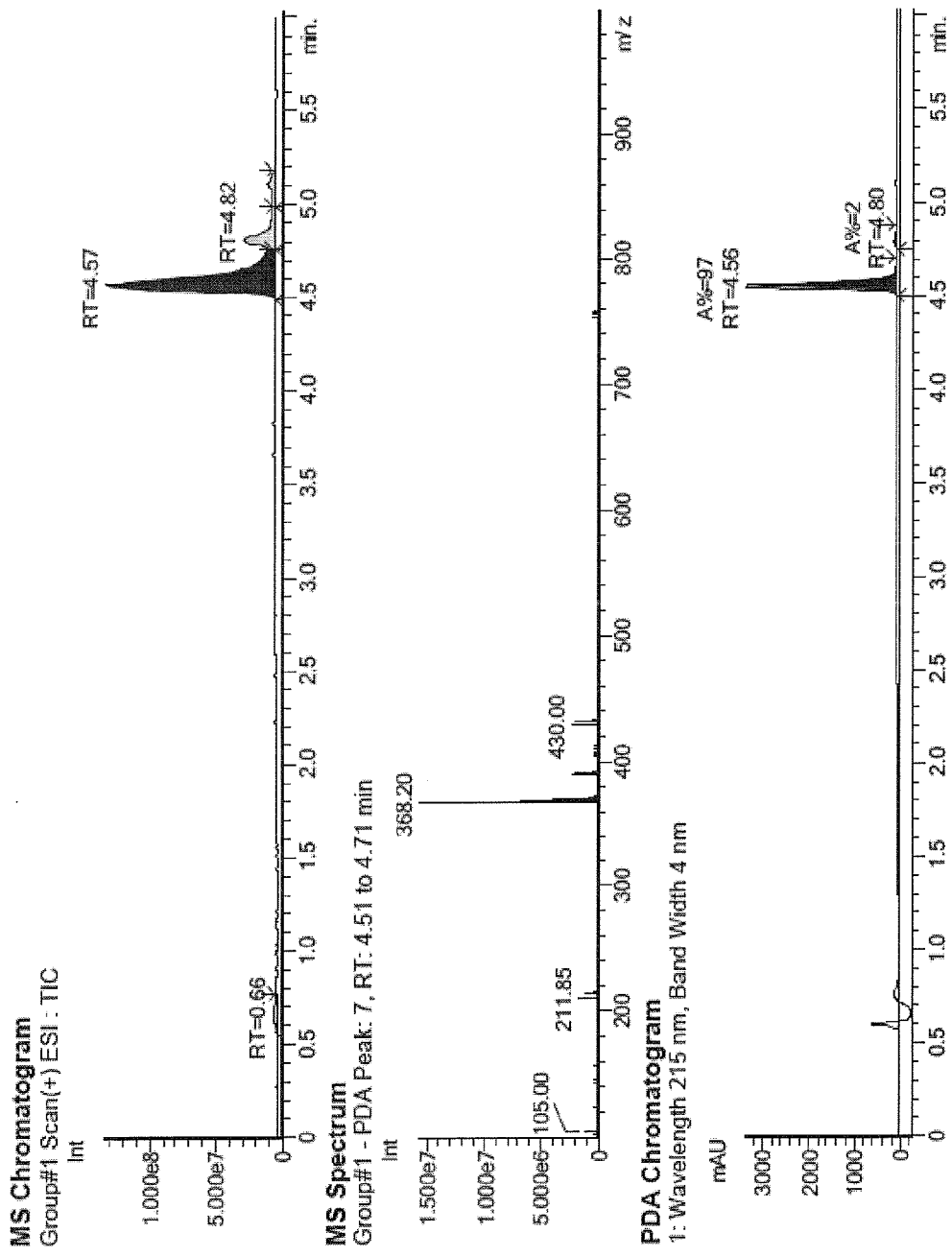
FIG. 51: Chromatogramm of Example Compound 51
Figure 52:
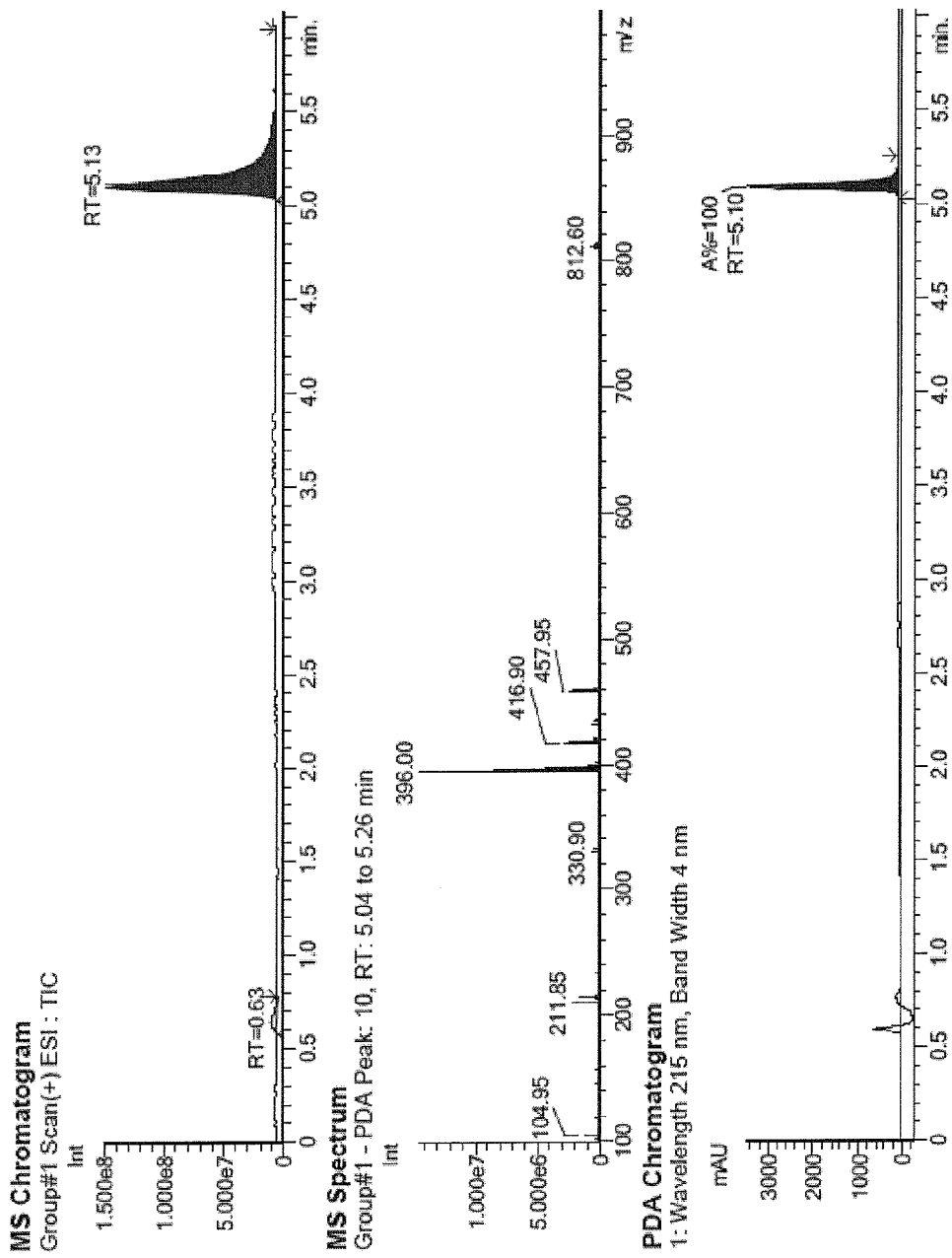
FIG. 52: Chromatogramm of Example Compound 52
Figure 53:
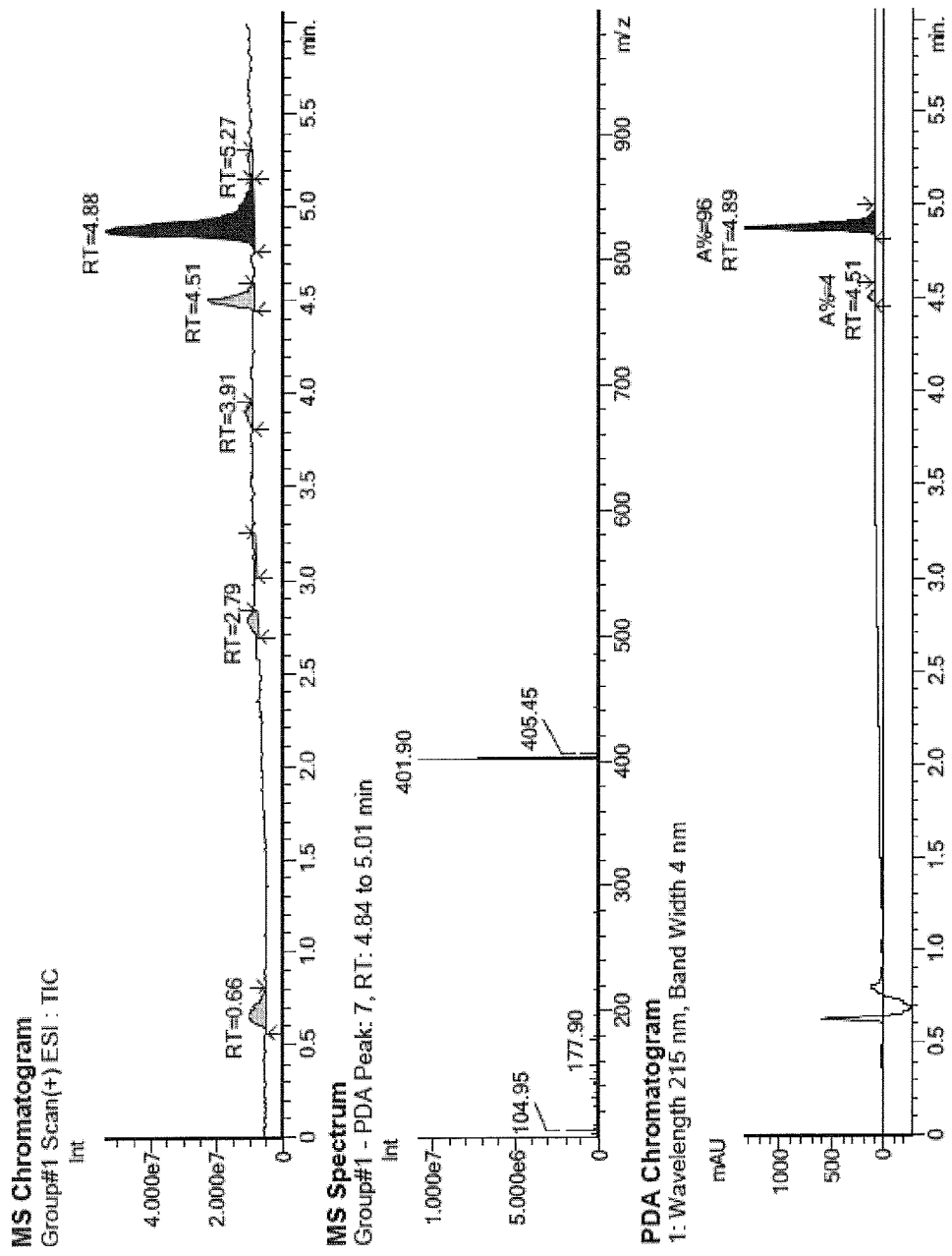
FIG. 53: Chromatogramm of Example Compound 53
Figure 54:
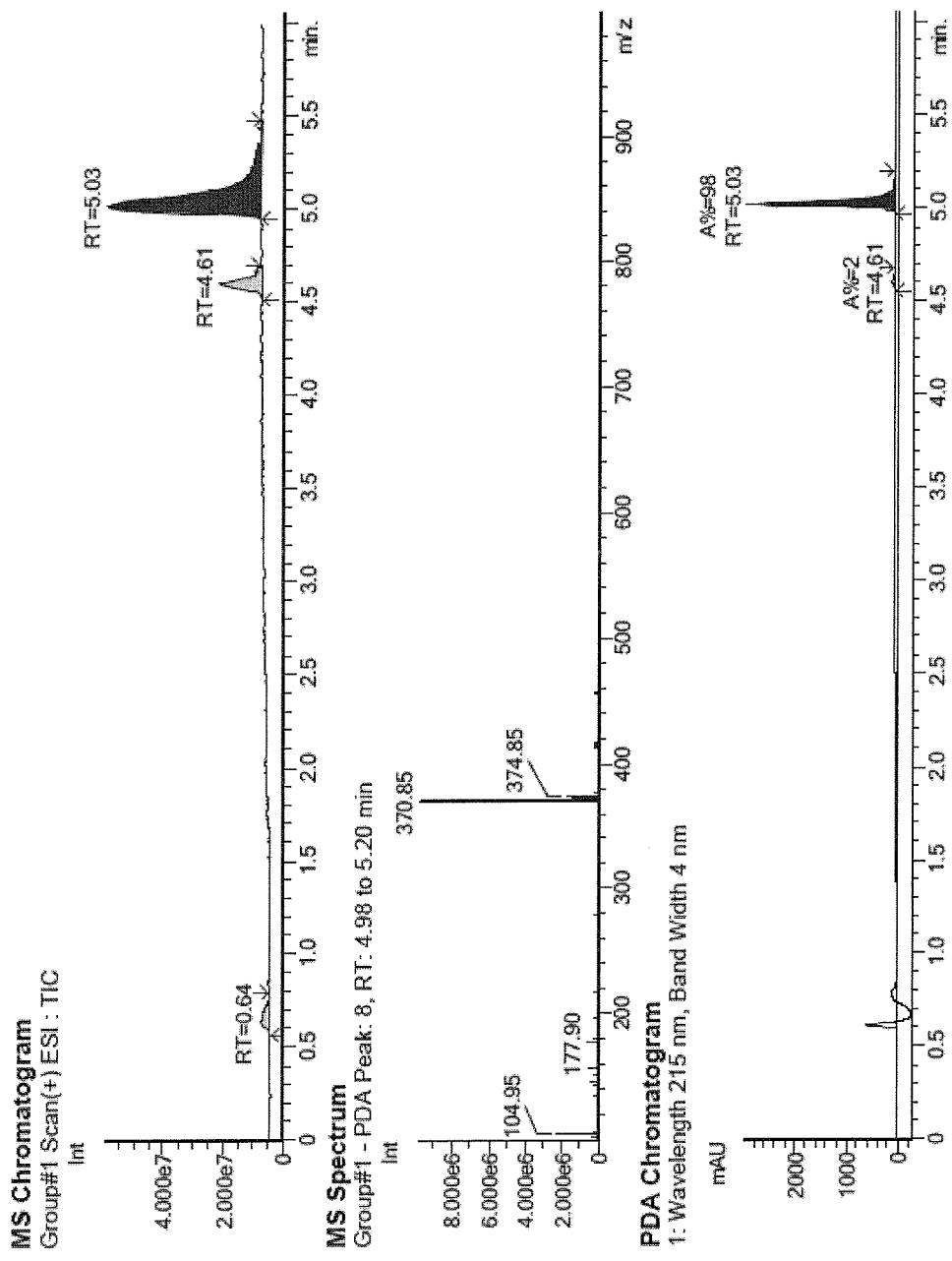
FIG. 54: Chromatogramm of Example Compound 54
Figure 55:
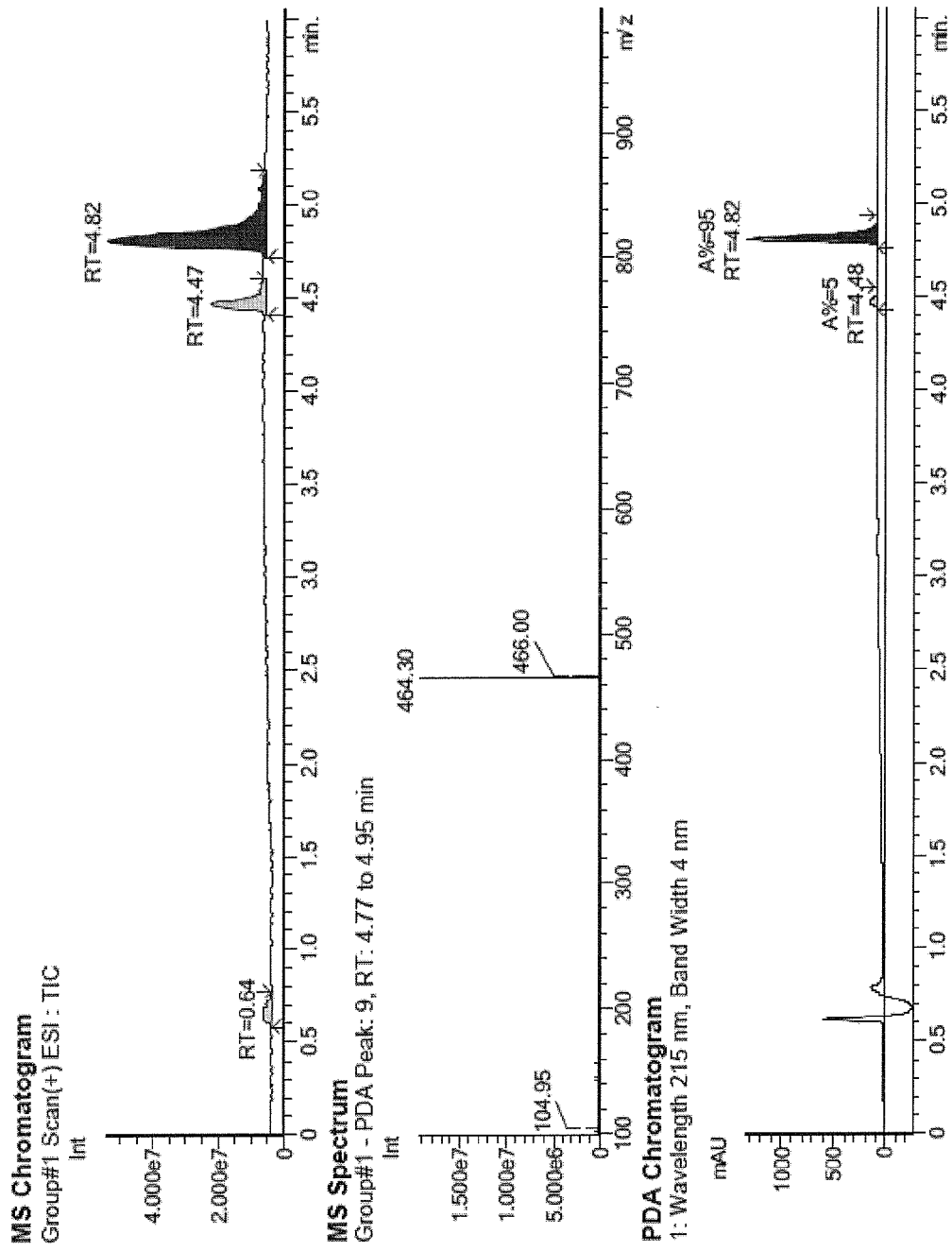
FIG. 55: Chromatogramm of Example Compound 55
Figure 56:
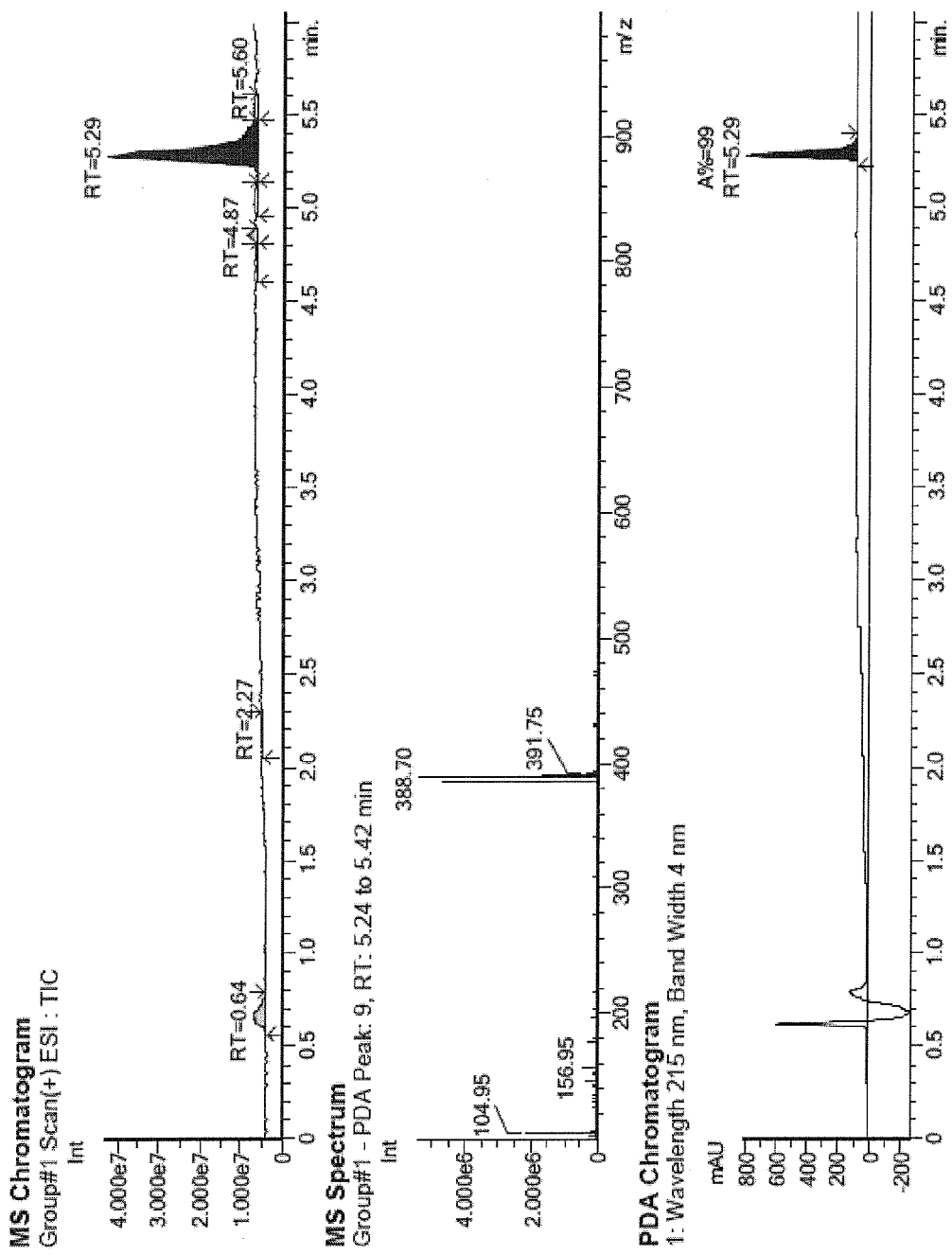
FIG. 56: Chromatogramm of Example Compound 56
Figure 57:
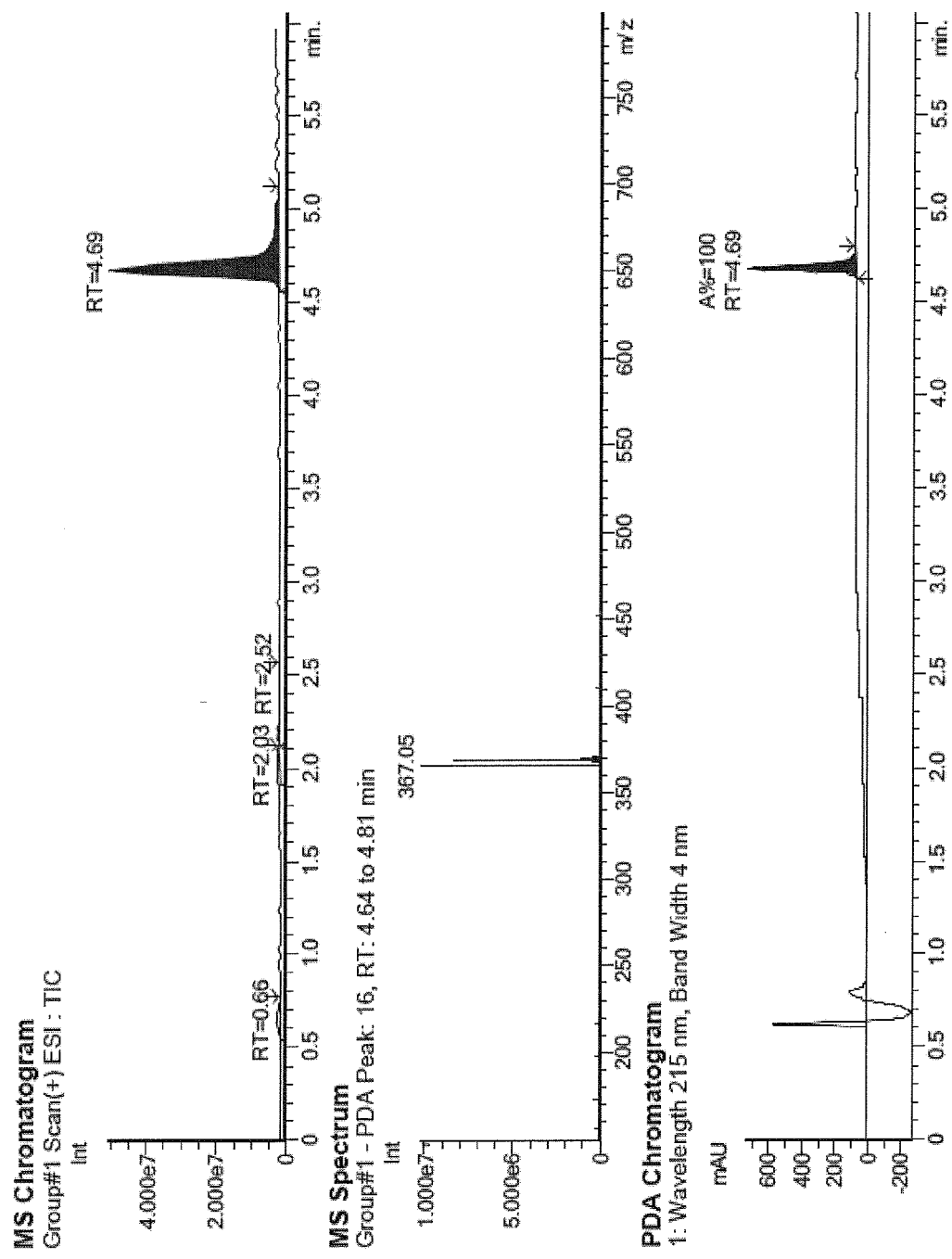
FIG. 57: Chromatogramm of Example Compound 57
Figure 58:
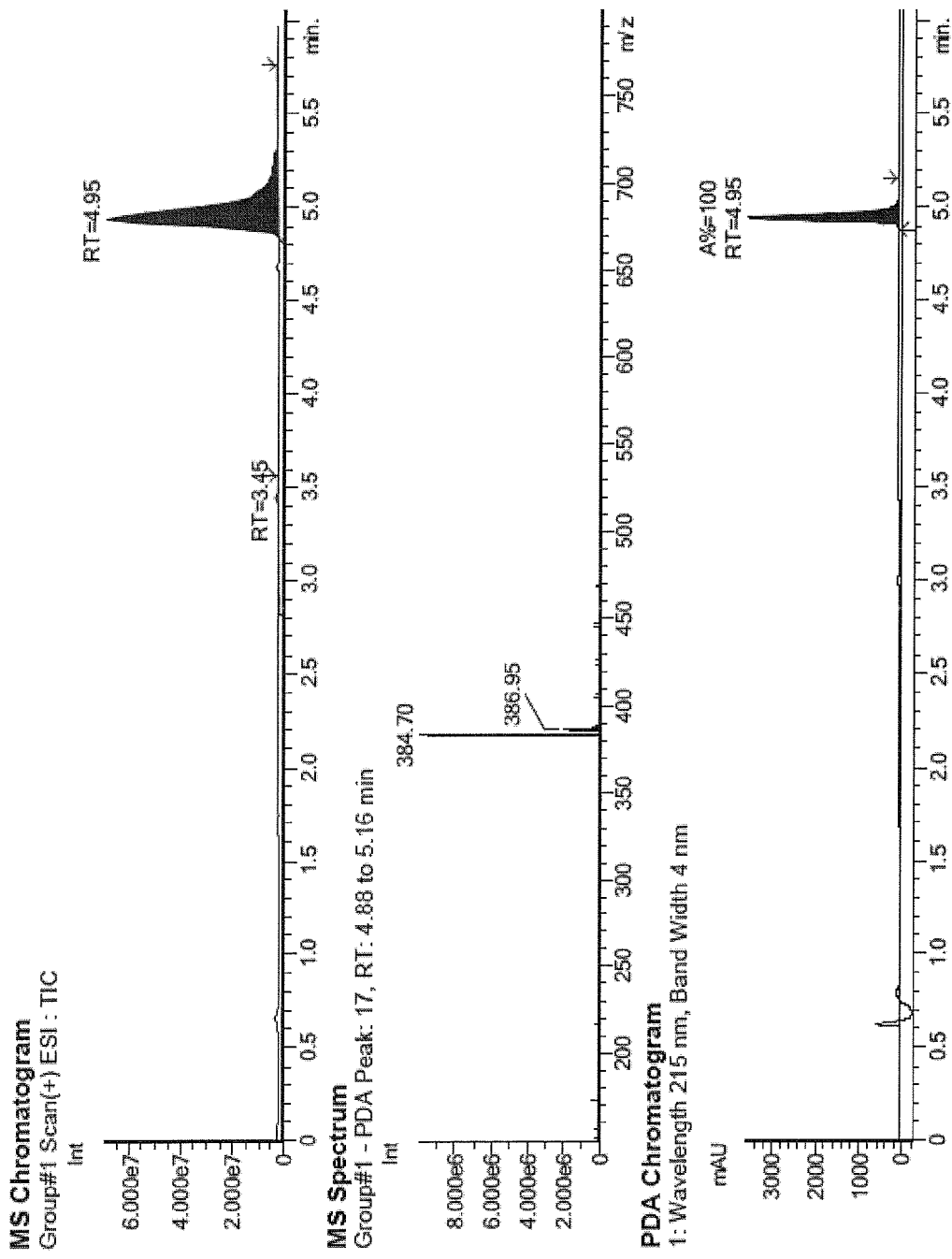
FIG. 58: Chromatogramm of Example Compound 58
Figure 59:
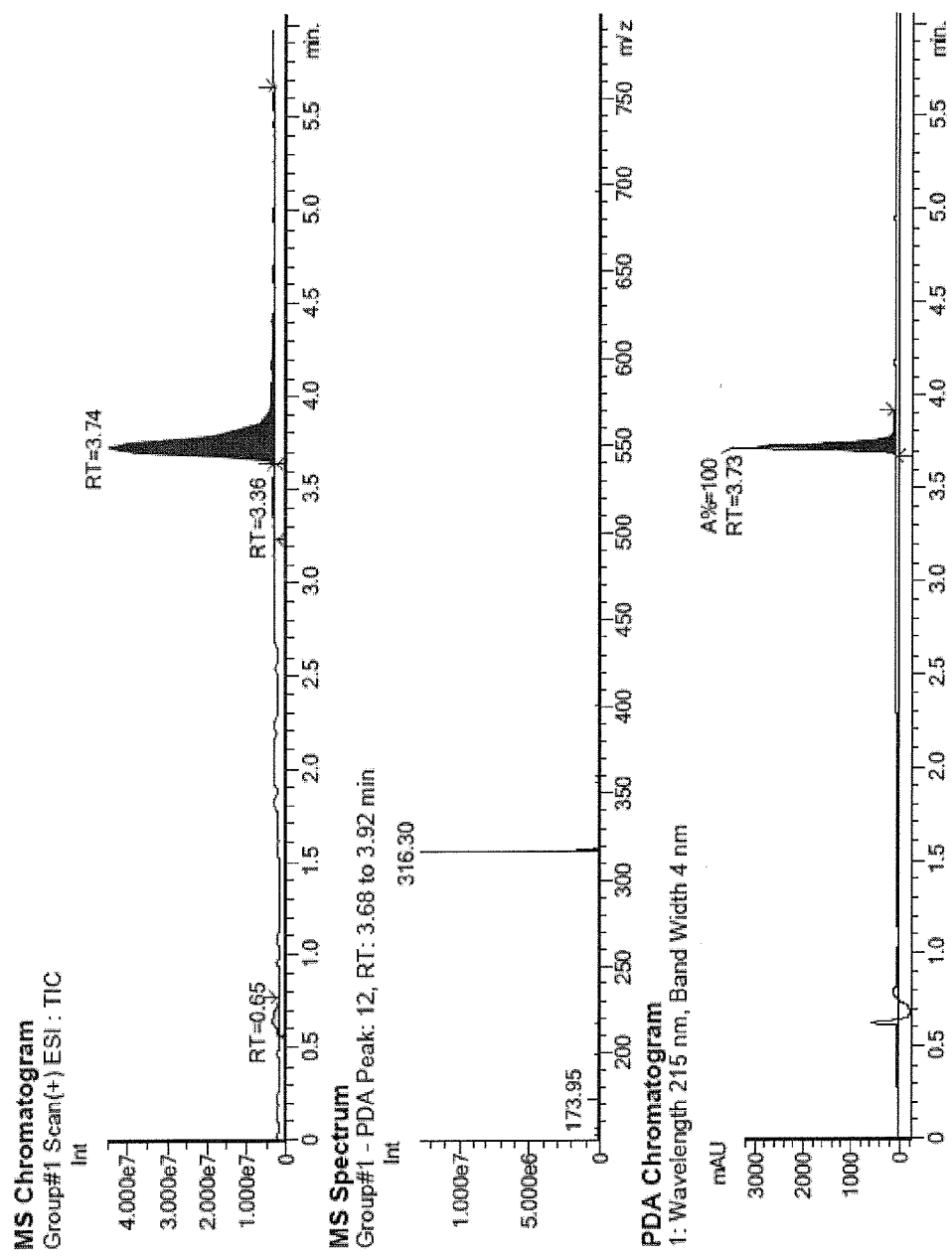
FIG. 59: Chromatogramm of Example Compound 59
Figure 60:
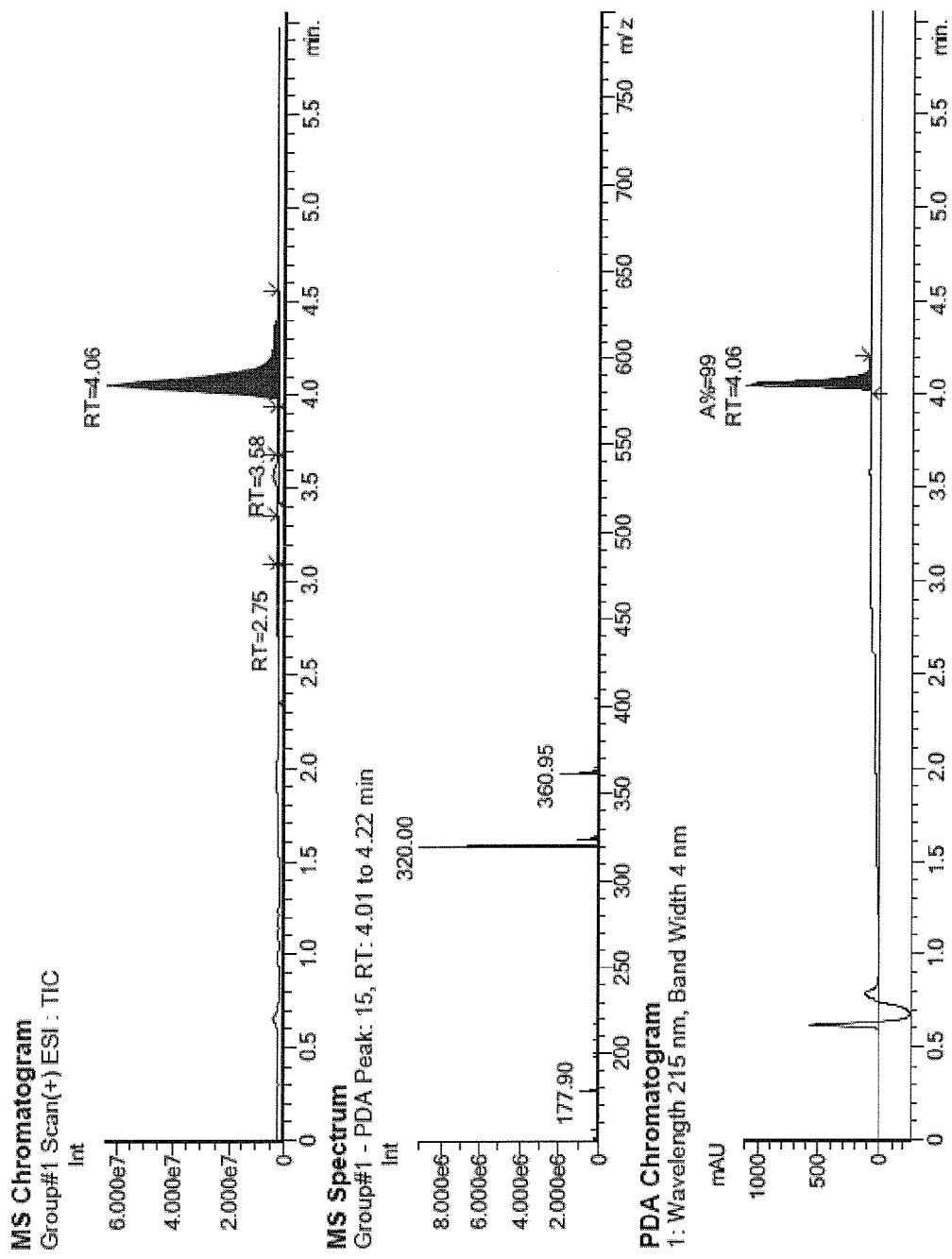
FIG. 60: Chromatogramm of Example Compound 60
Figure 61:
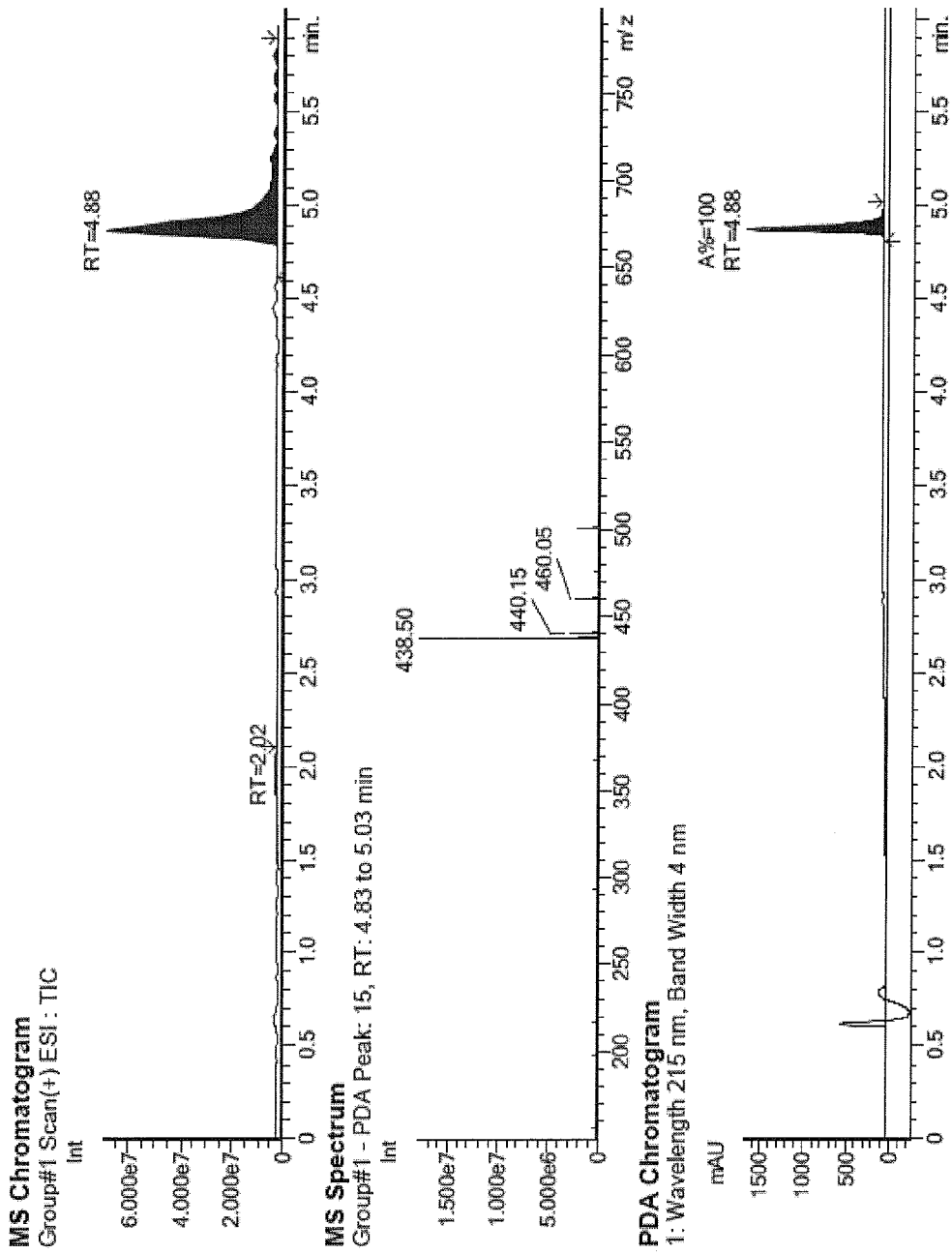
FIG. 61: Chromatogramm of Example Compound 61
Figure 62:
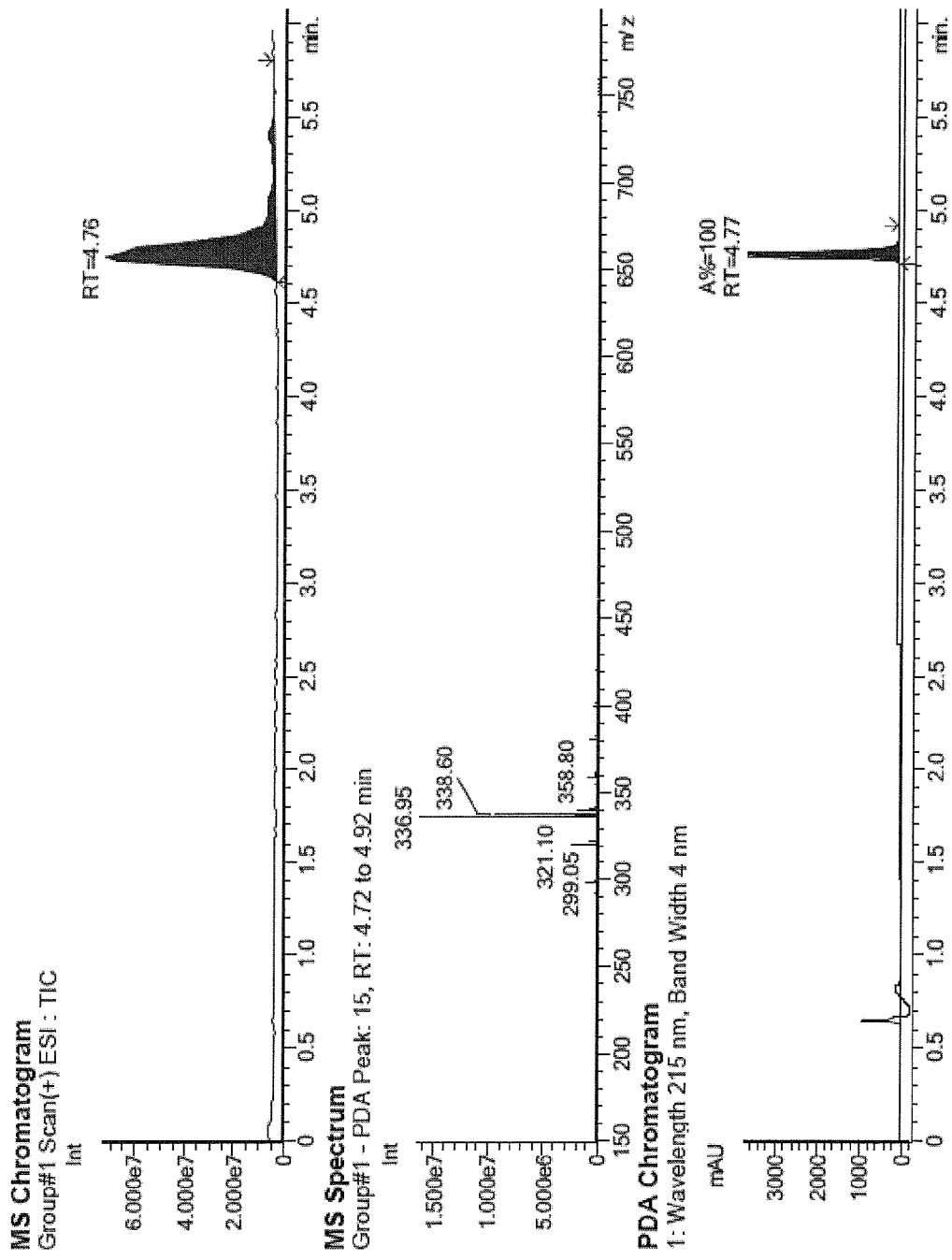
FIG. 62: Chromatogramm of Example Compound 62
Figure 63:
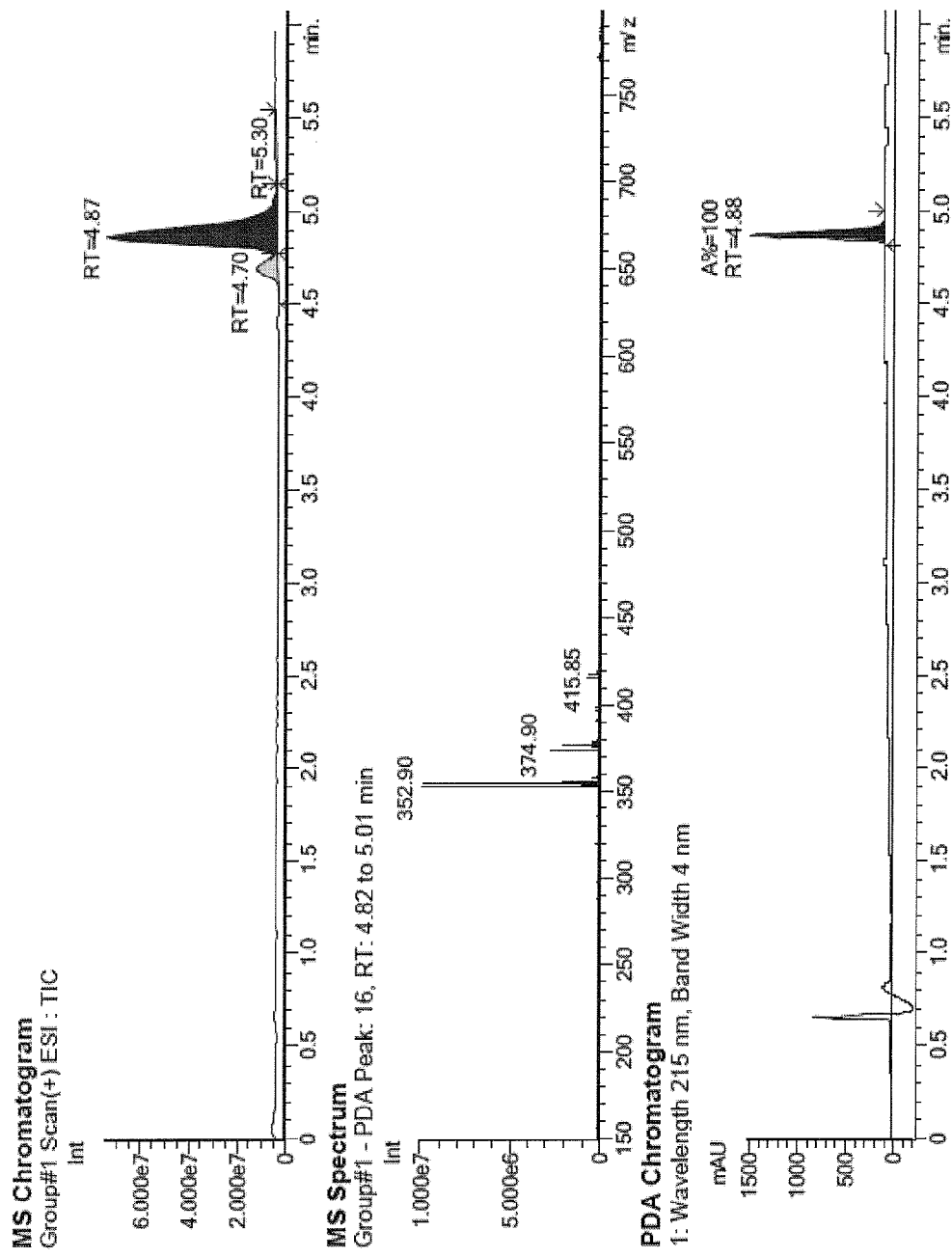
FIG. 63: Chromatogramm of Example Compound 63
Figure 64:
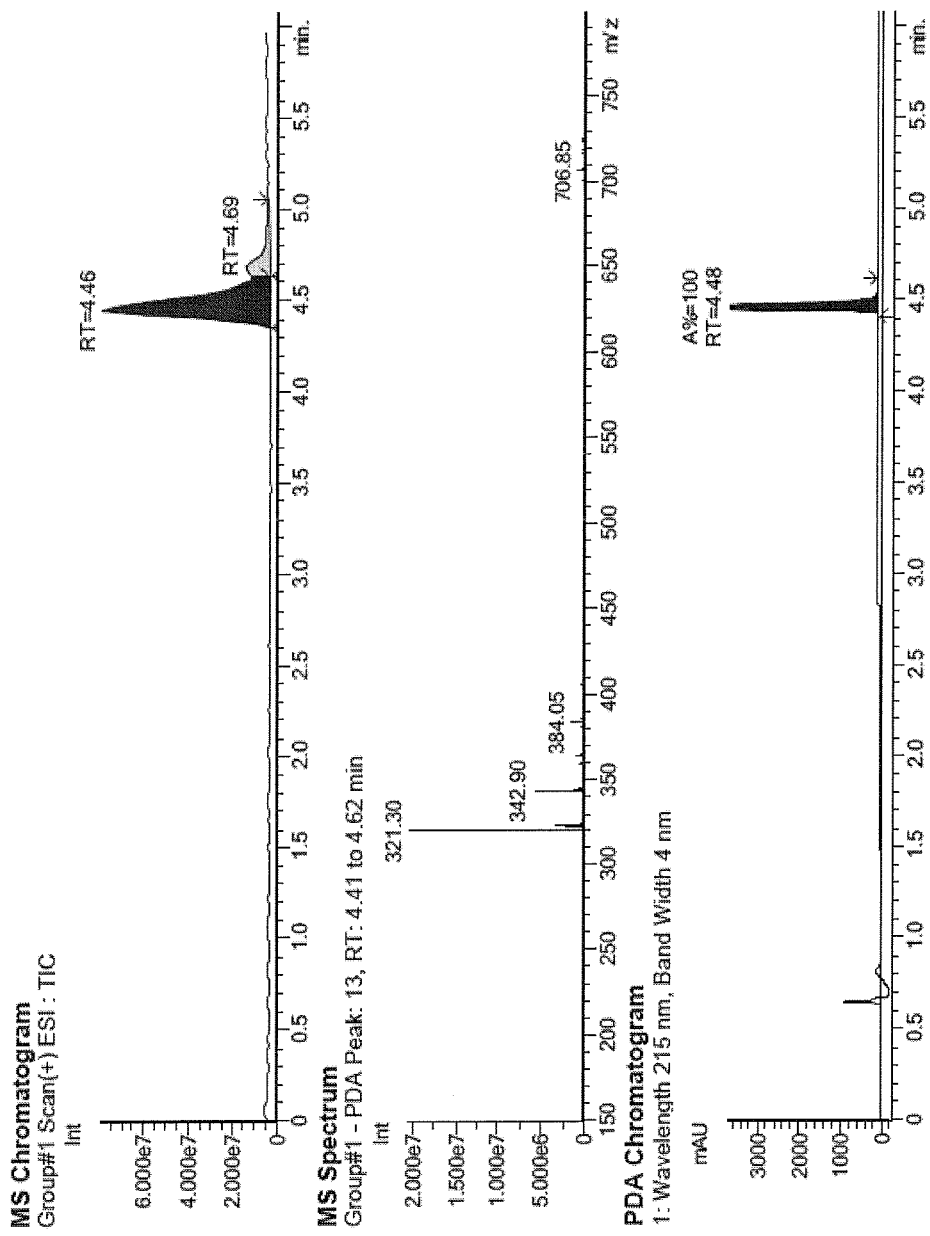
FIG. 64: Chromatogramm of Example Compound 64
Figure 65:
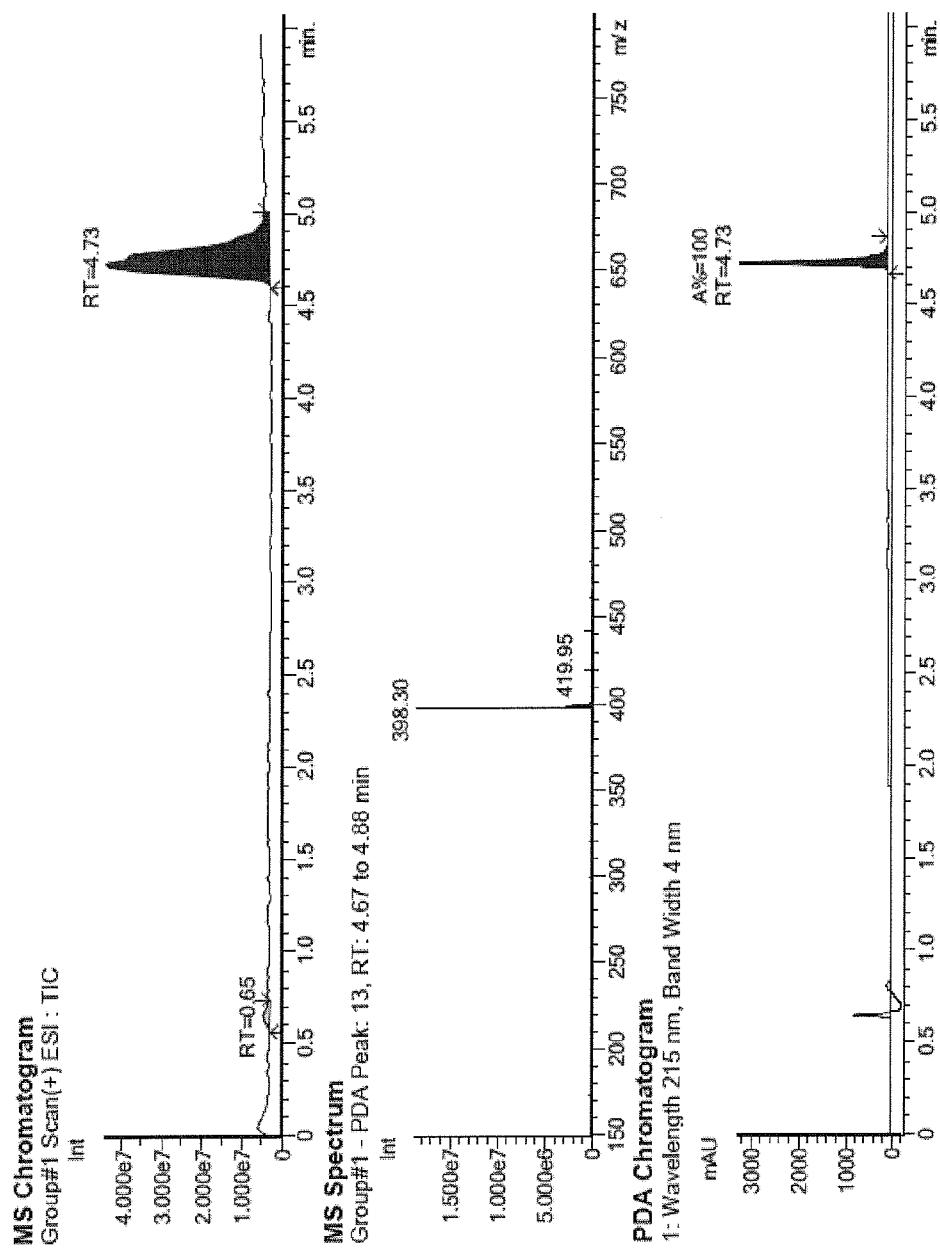
FIG. 65: Chromatogramm of Example Compound 65
Figure 66:
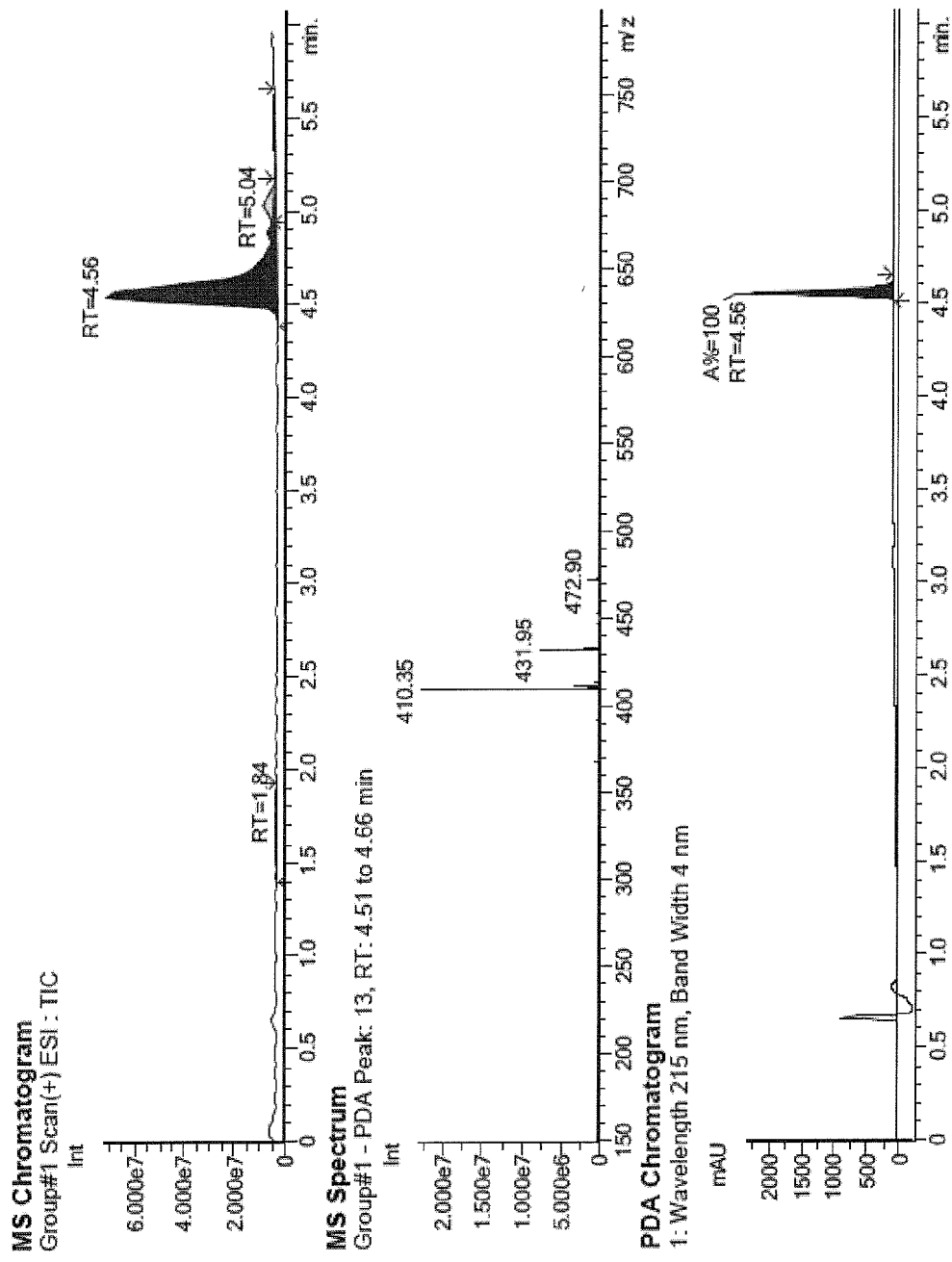
FIG. 66: Chromatogramm of Example Compound 66
Figure 67:
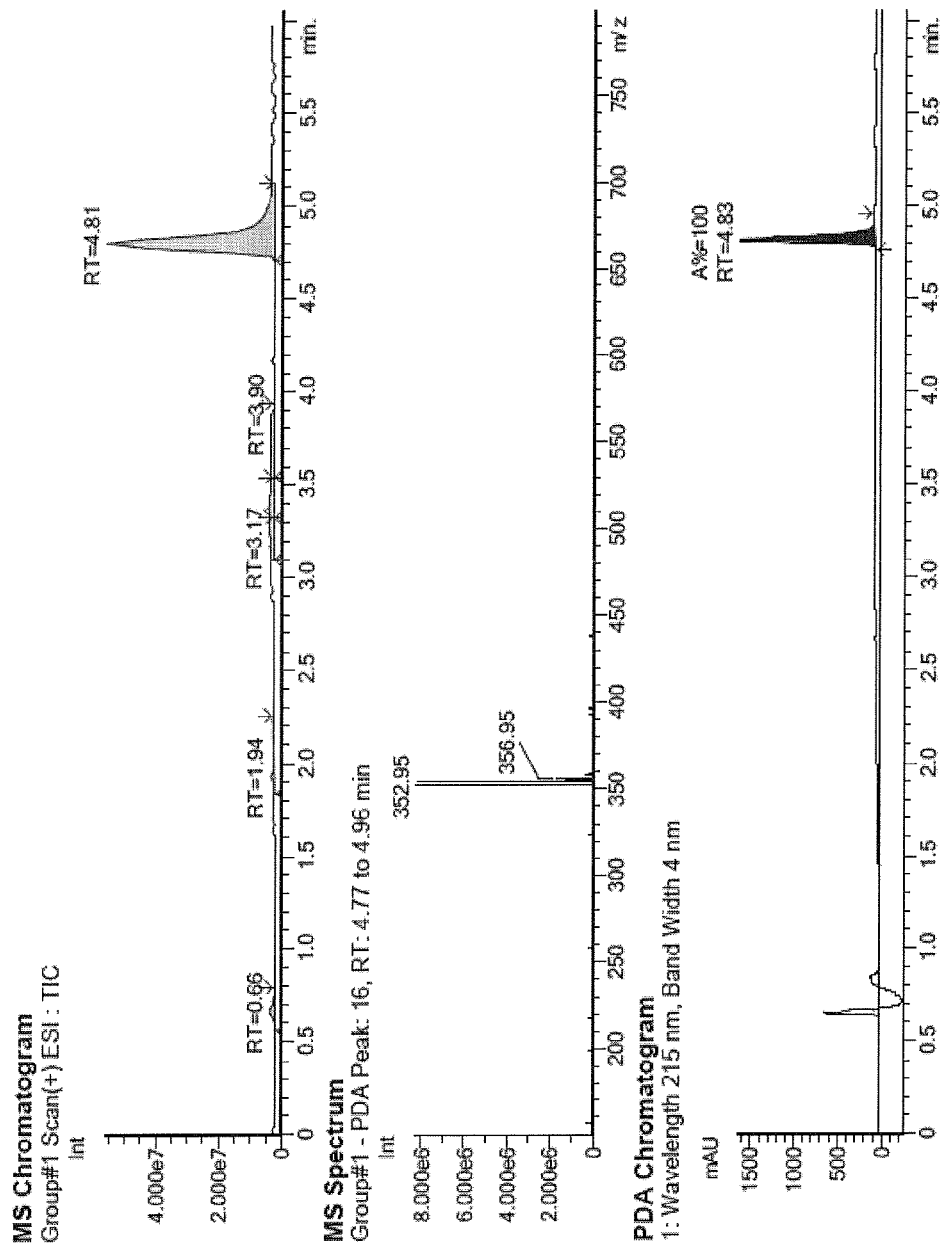
FIG. 67: Chromatogramm of Example Compound 67
Figure 68:
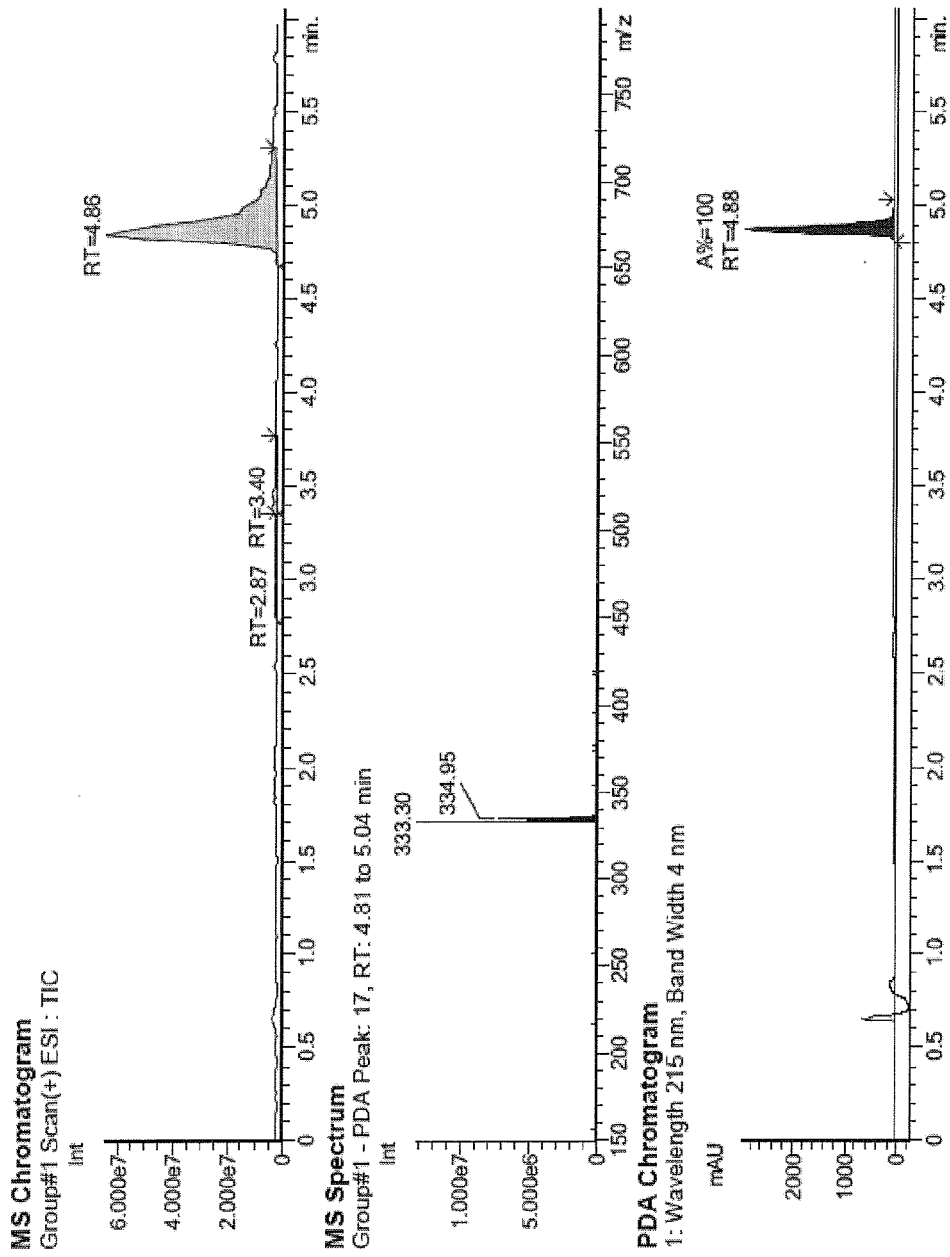
FIG. 68: Chromatogramm of Example Compound 68
Figure 69:
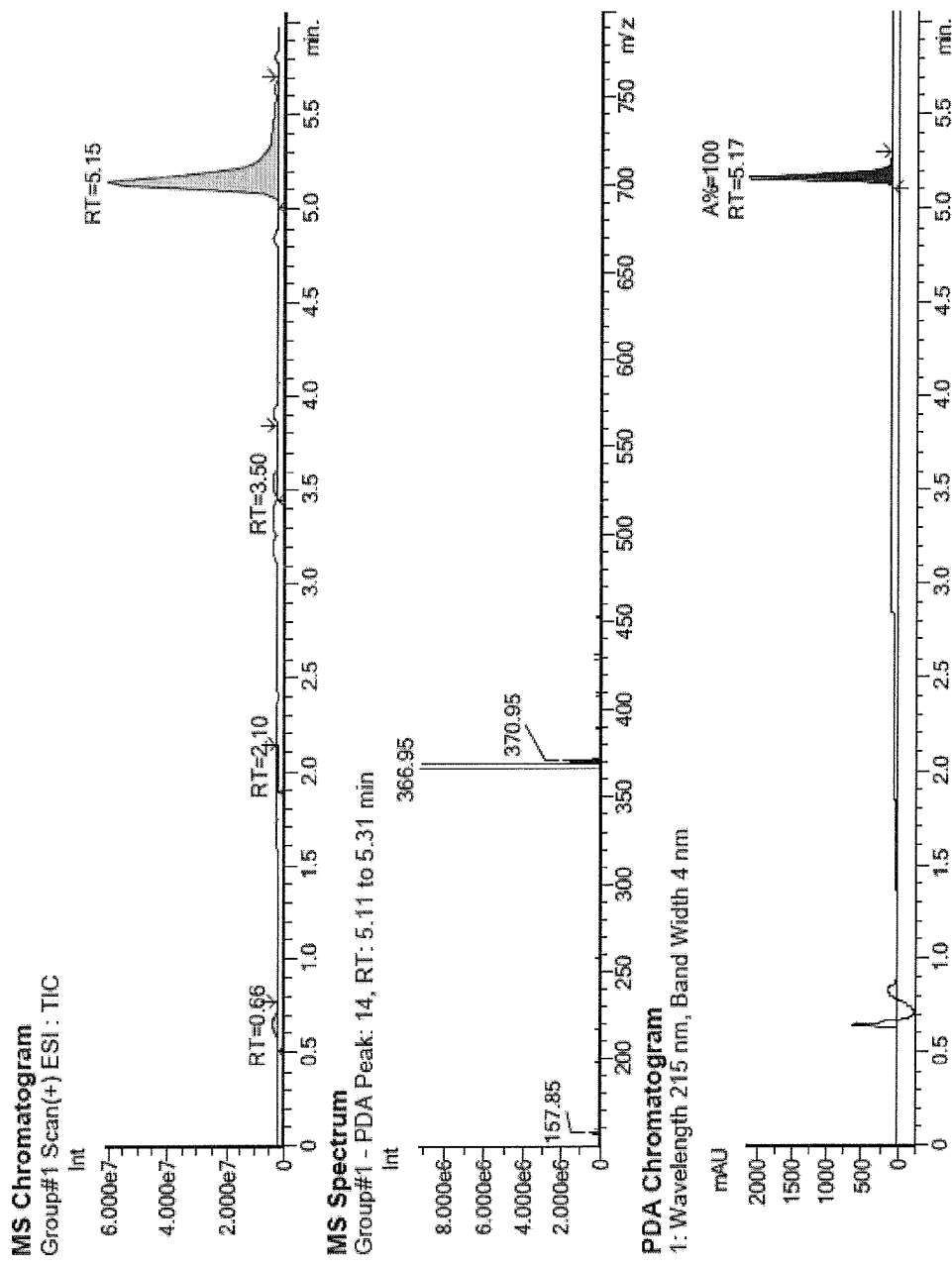
FIG. 69: Chromatogramm of Example Compound 69
Figure 70:
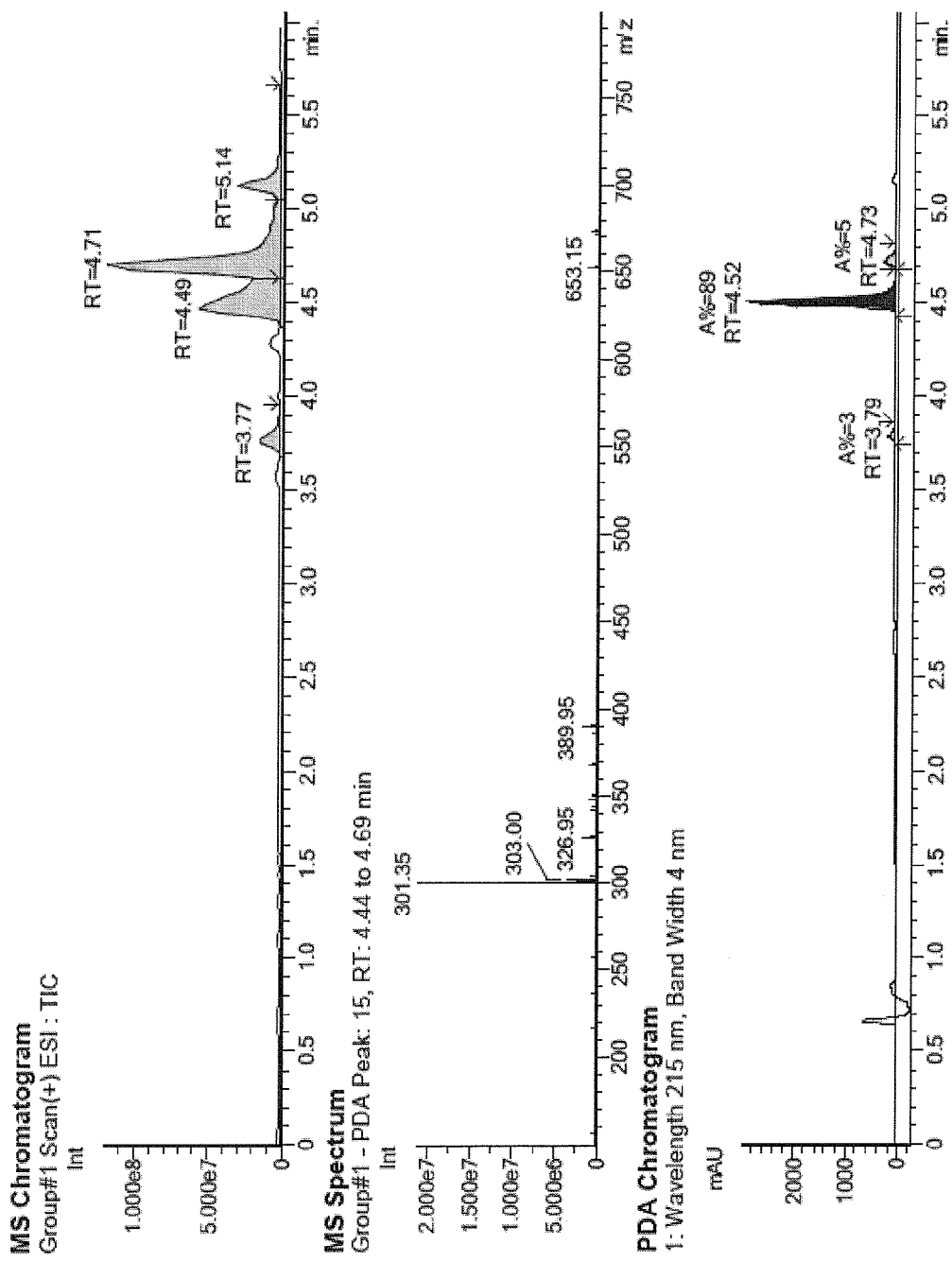
FIG. 70: Chromatogramm of Example Compound 70
Figure 71:
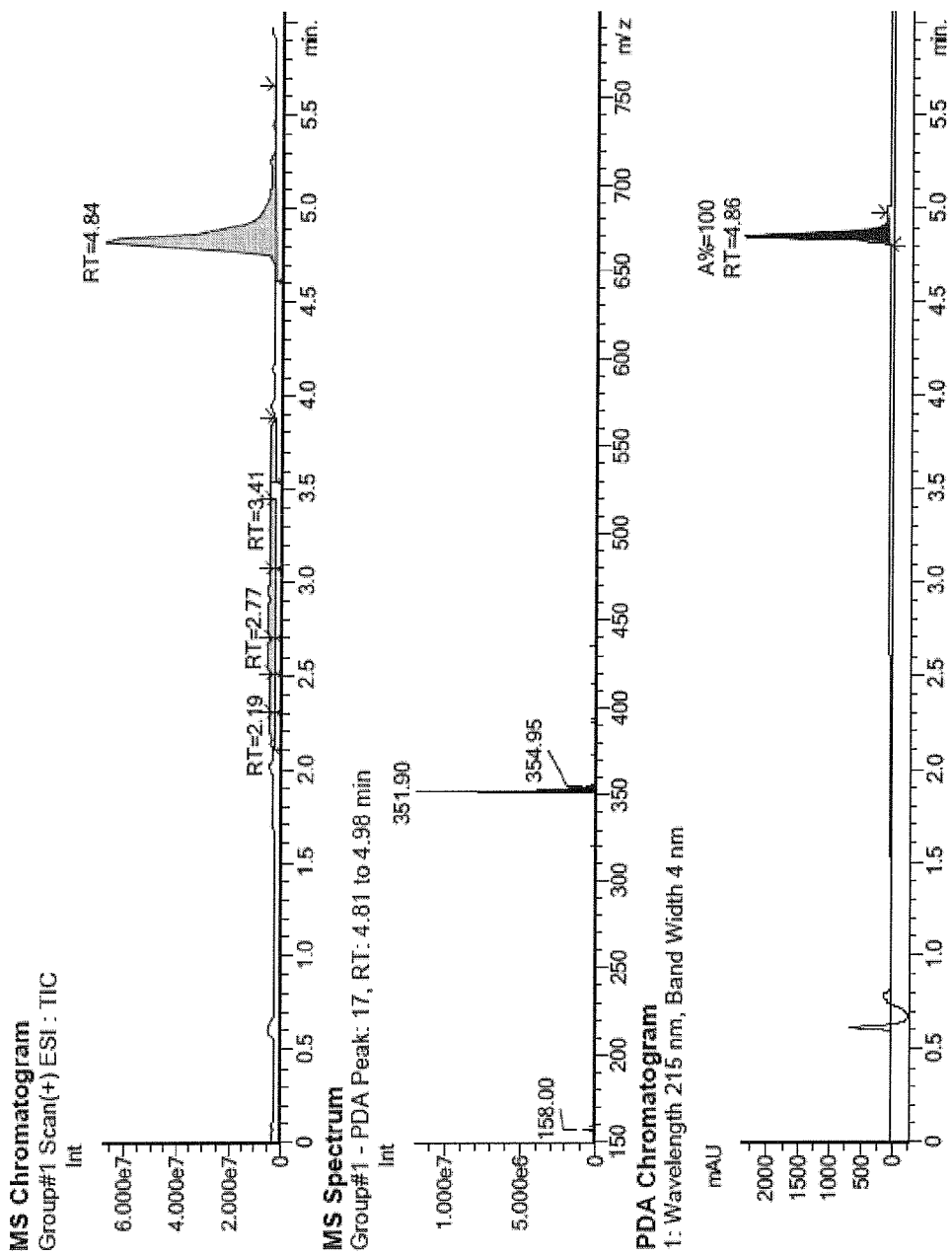
FIG. 71: Chromatogramm of Example Compound 71
Figure 72:
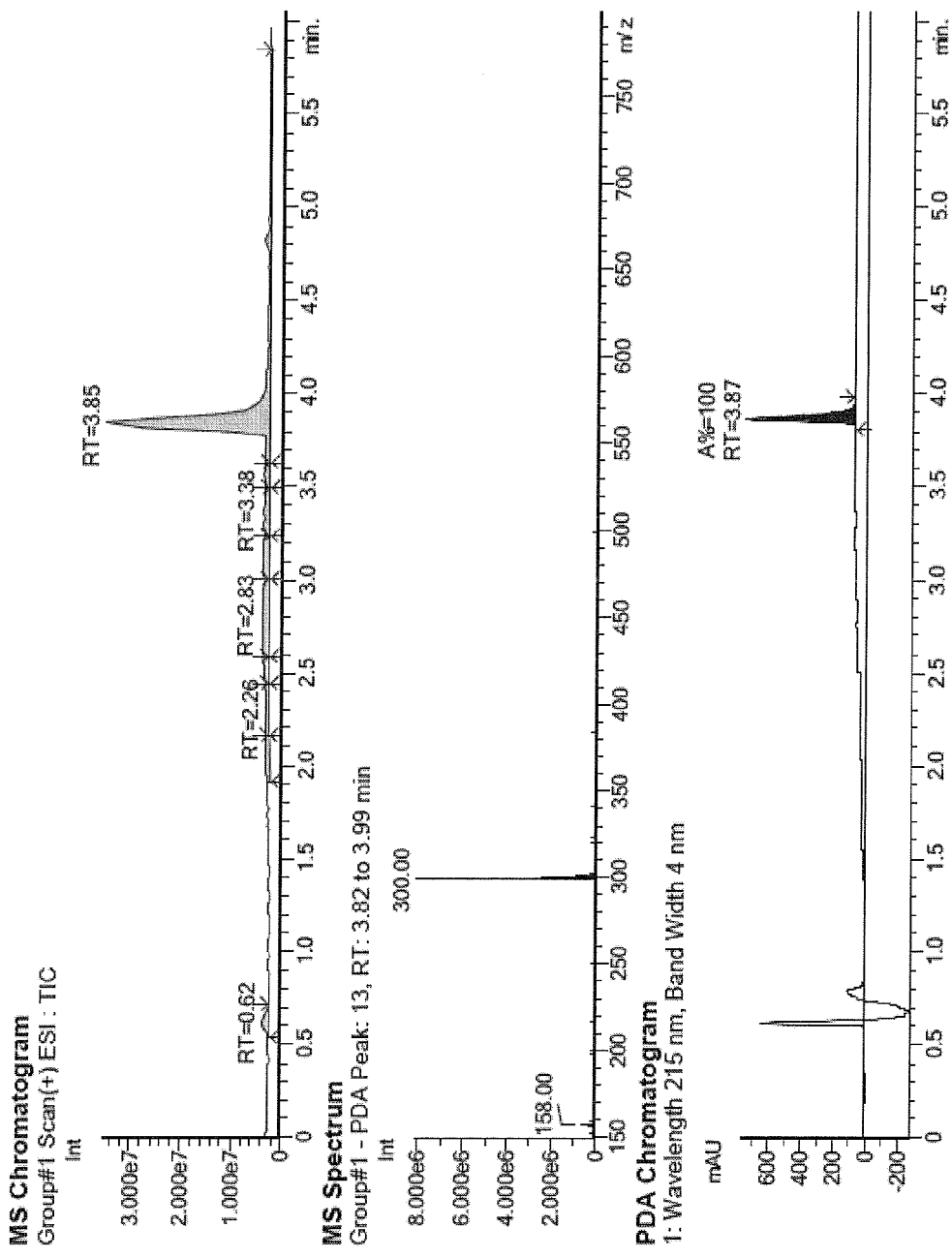
Figure 73:
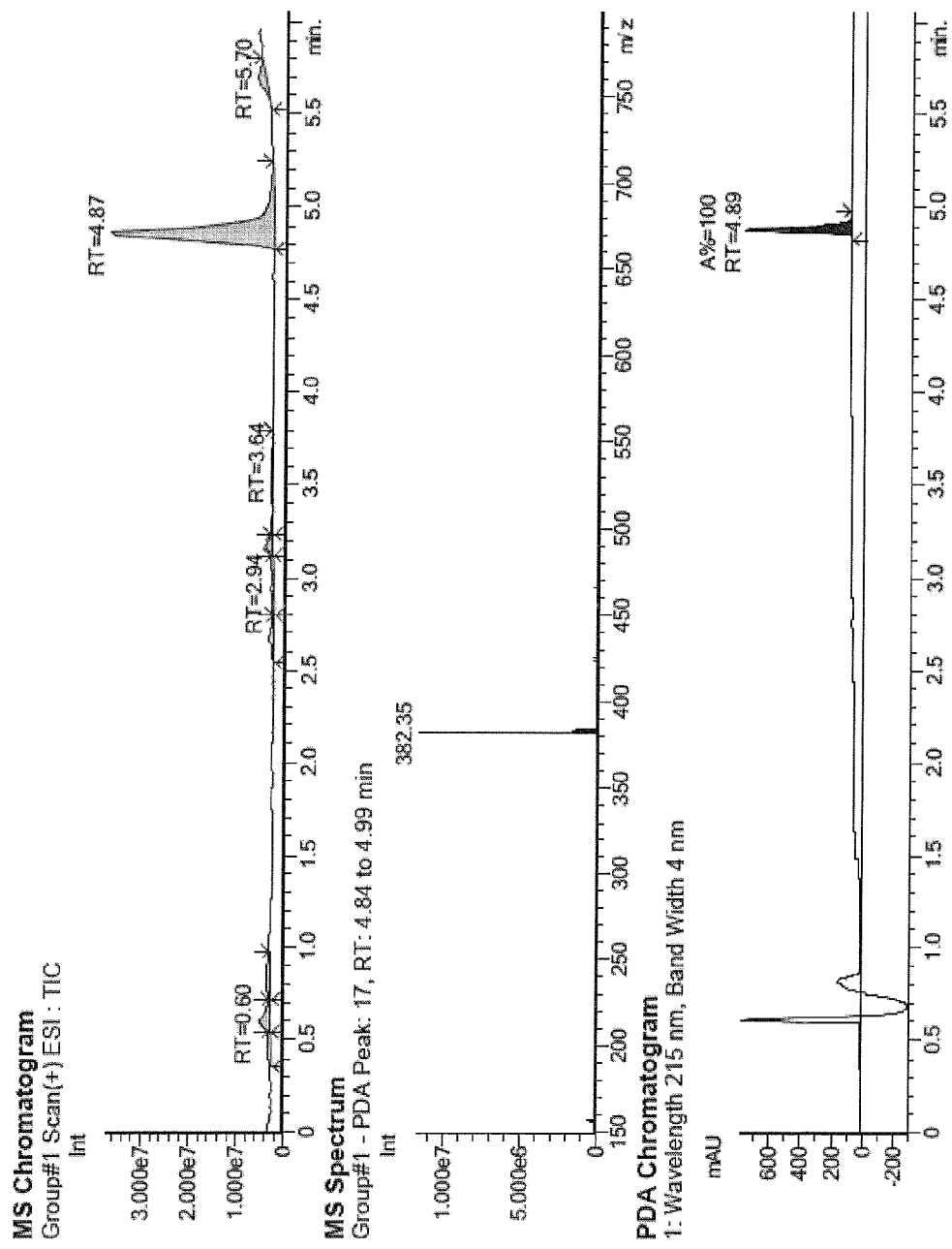
FIG. 73: Chromatogramm of Example Compound 73
Figure 74:
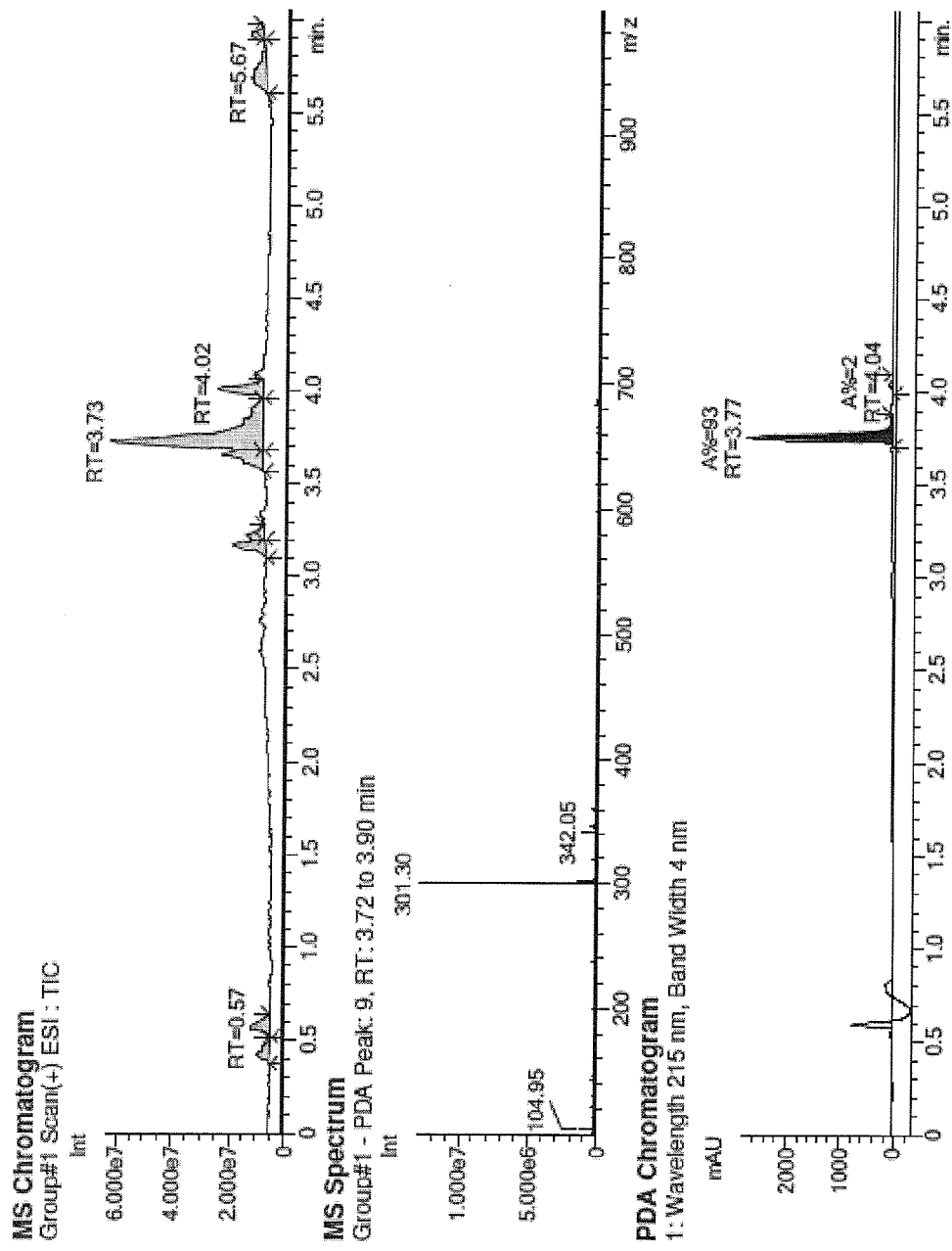
FIG. 74: Chromatogramm of Example Compound 74
Figure 75:
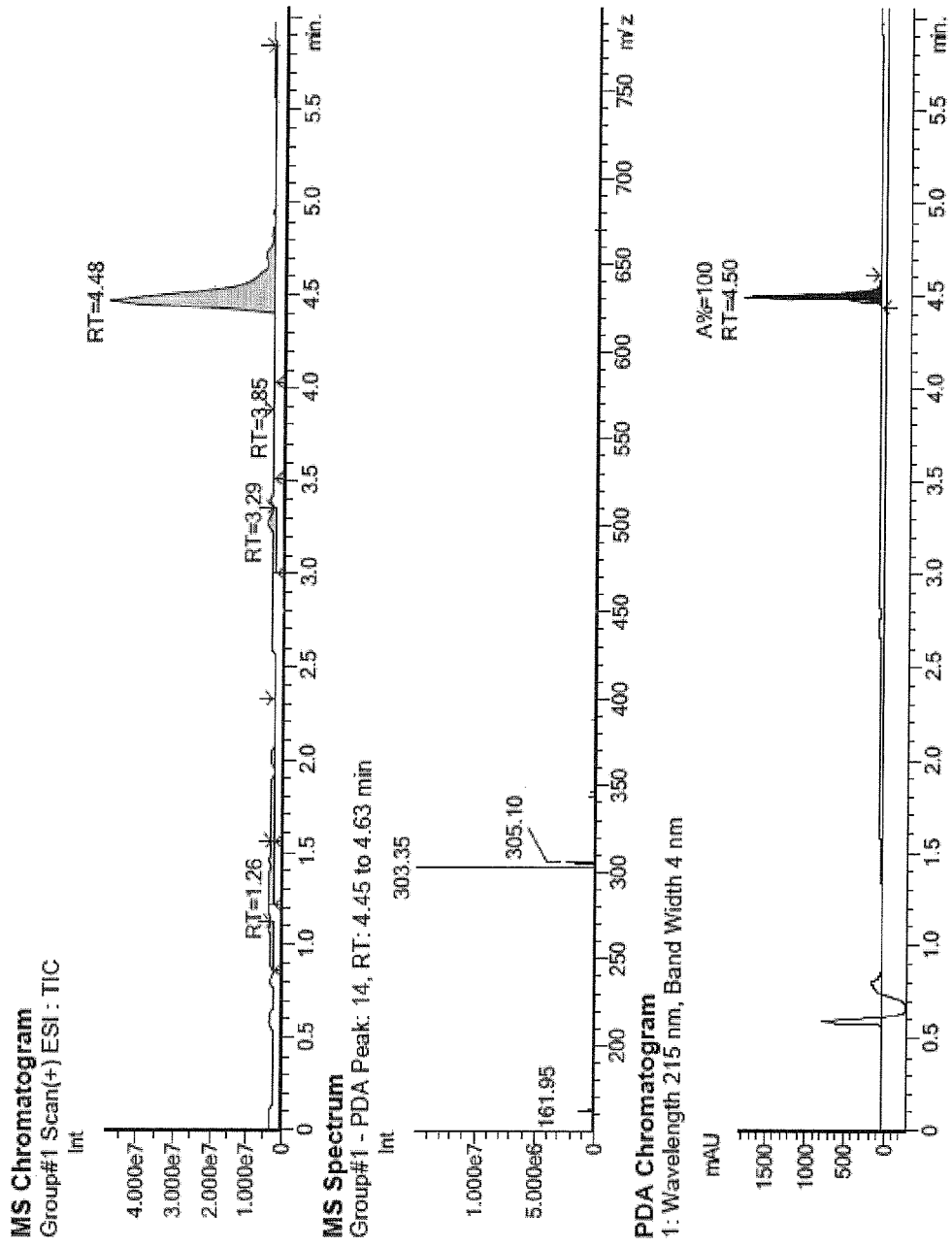
FIG. 75: Chromatogramm of Example Compound 75
Figure 76:
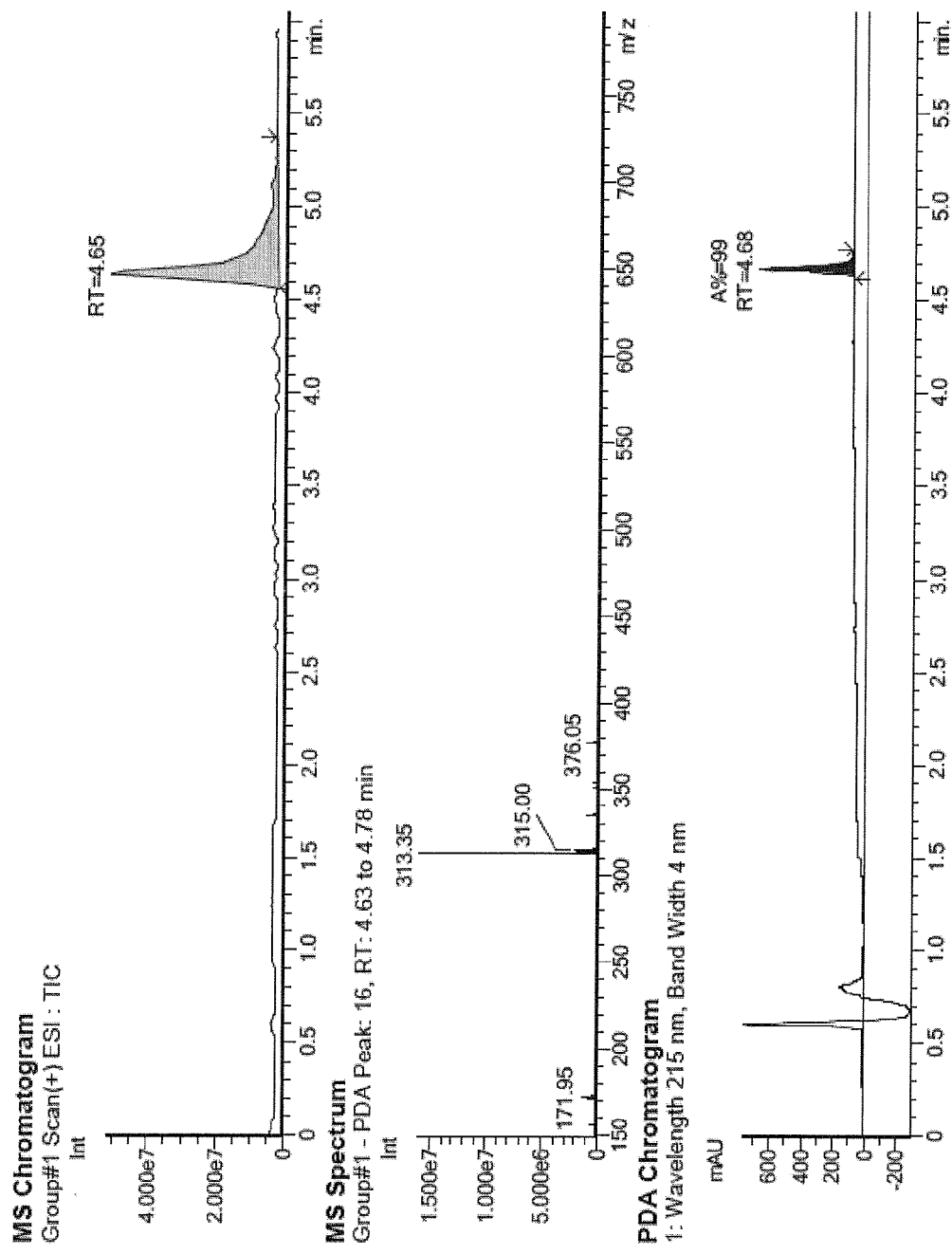
FIG. 76: Chromatogramm of Example Compound 76
Figure 77:
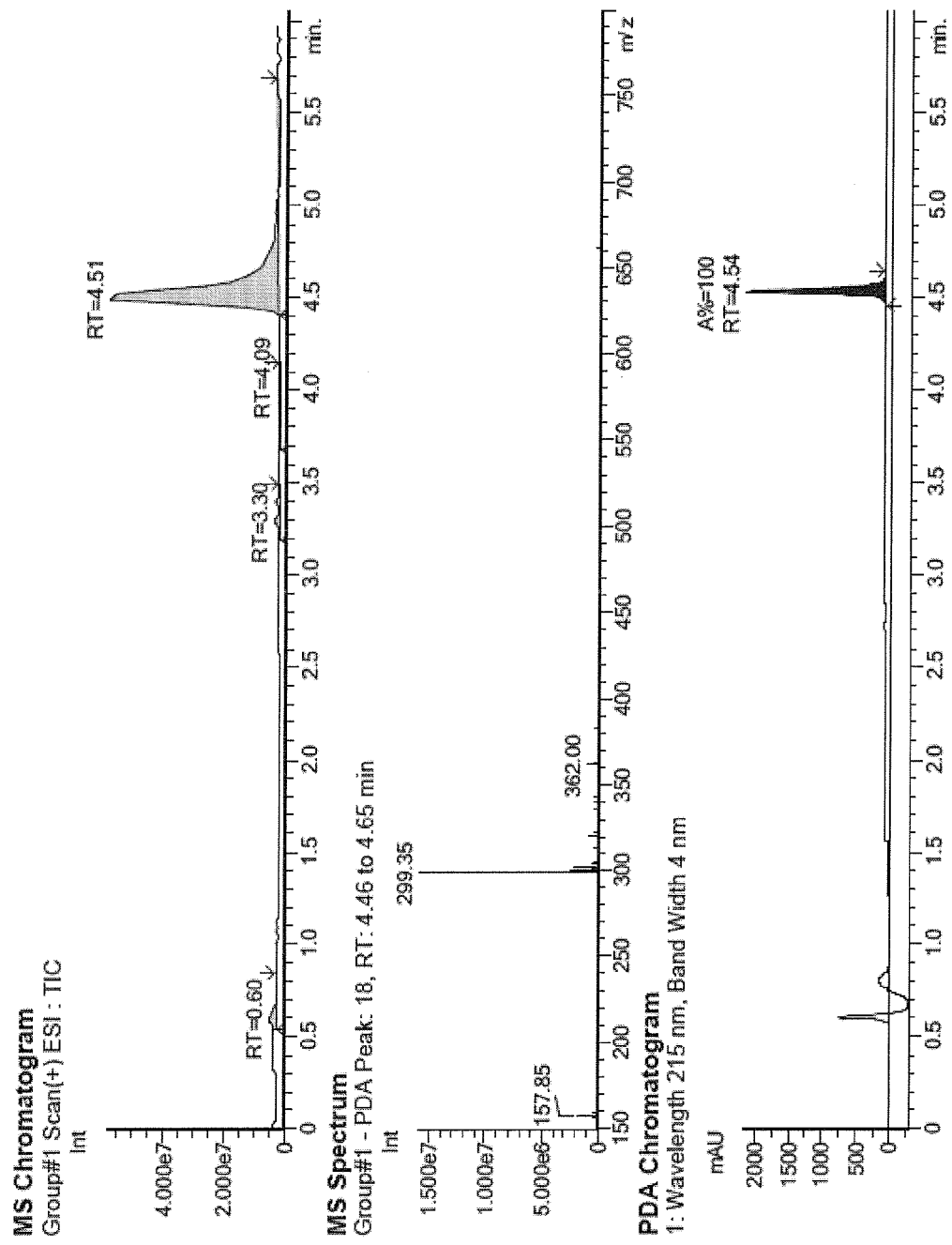
FIG. 77: Chromatogramm of Example Compound 77
Figure 78:
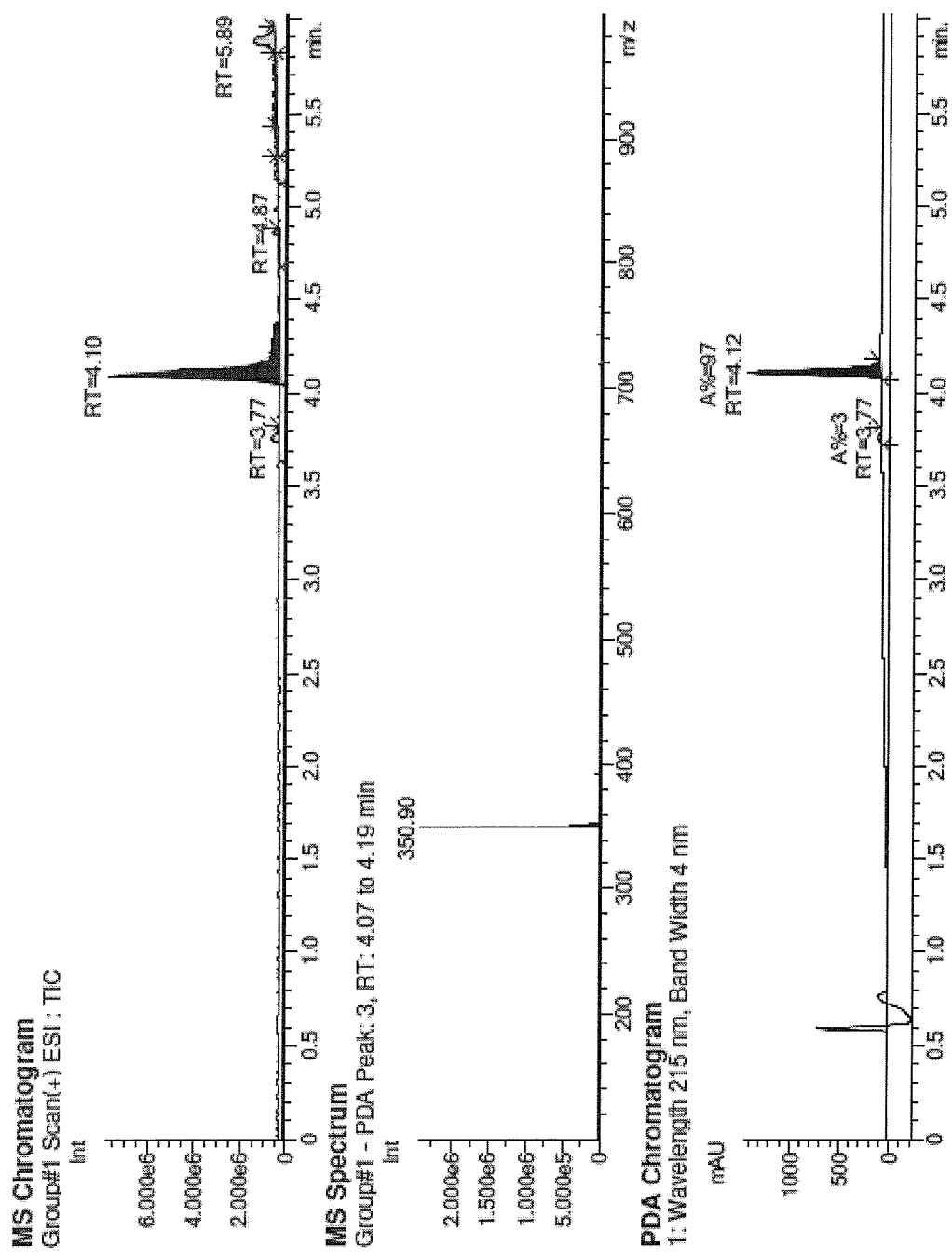
FIG. 78: Chromatogramm of Example Compound 78
Figure 79:
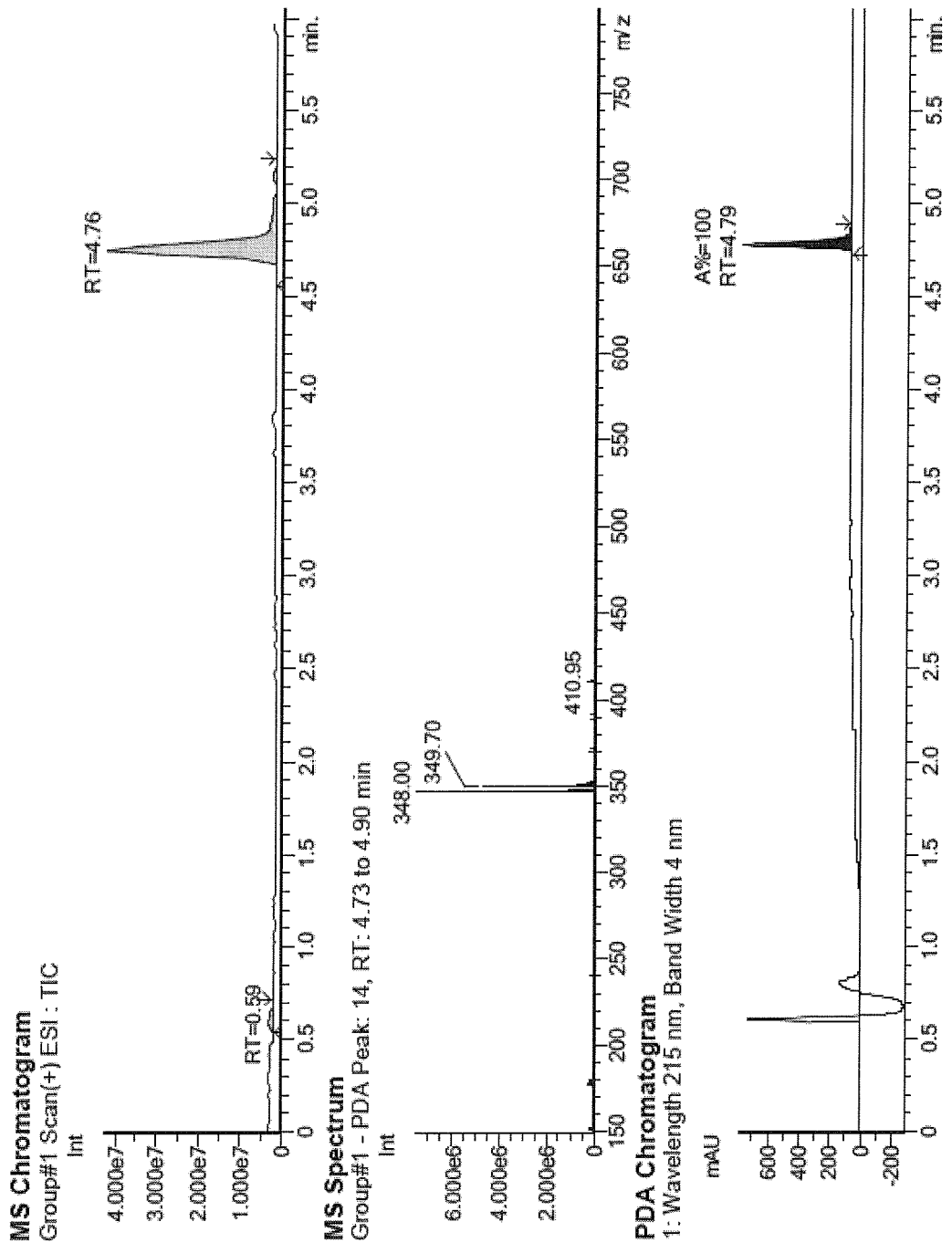
FIG. 79: Chromatogramm of Example Compound 79
Figure 80:
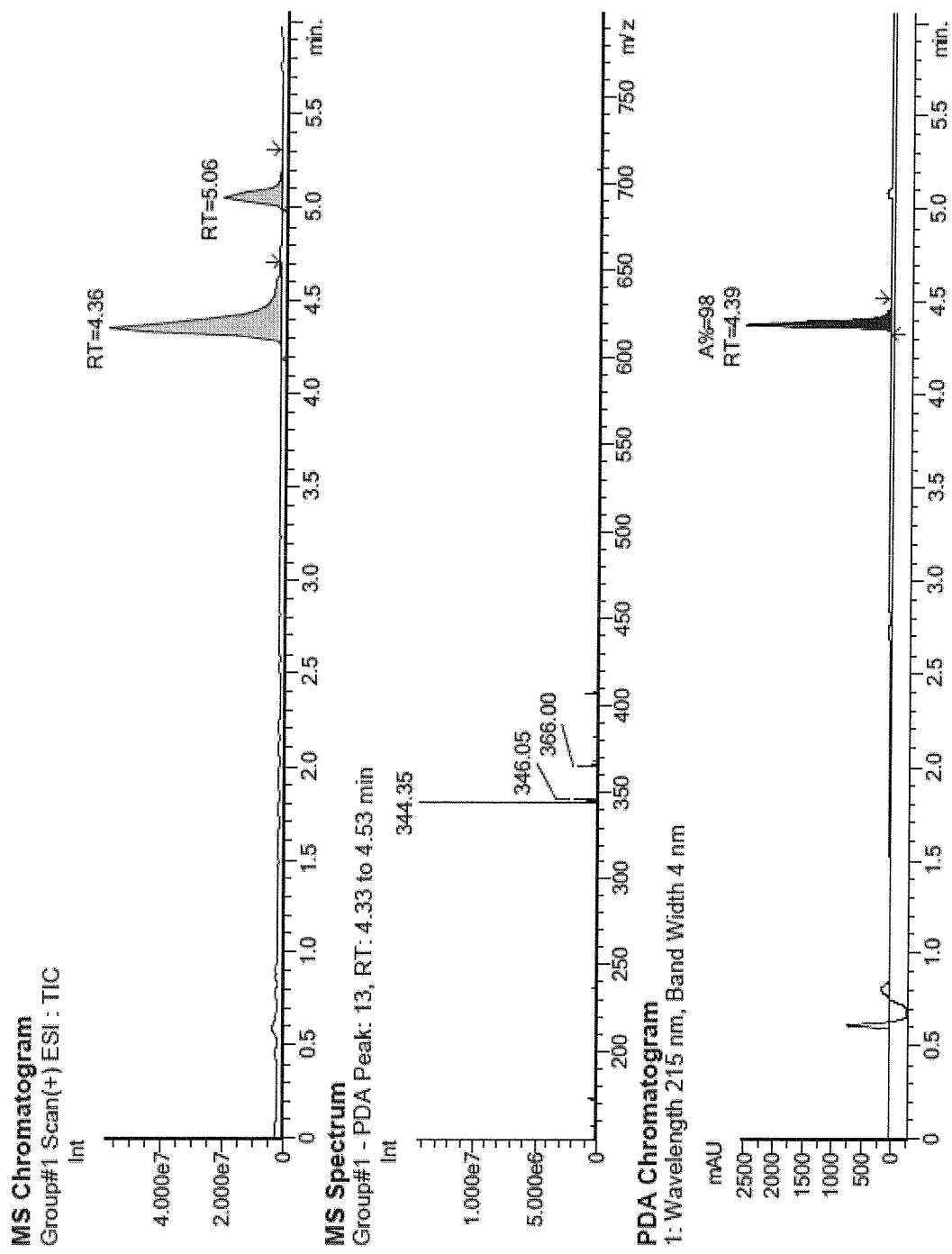
FIG. 80: Chromatogramm of Example Compound 80
Figure 81:
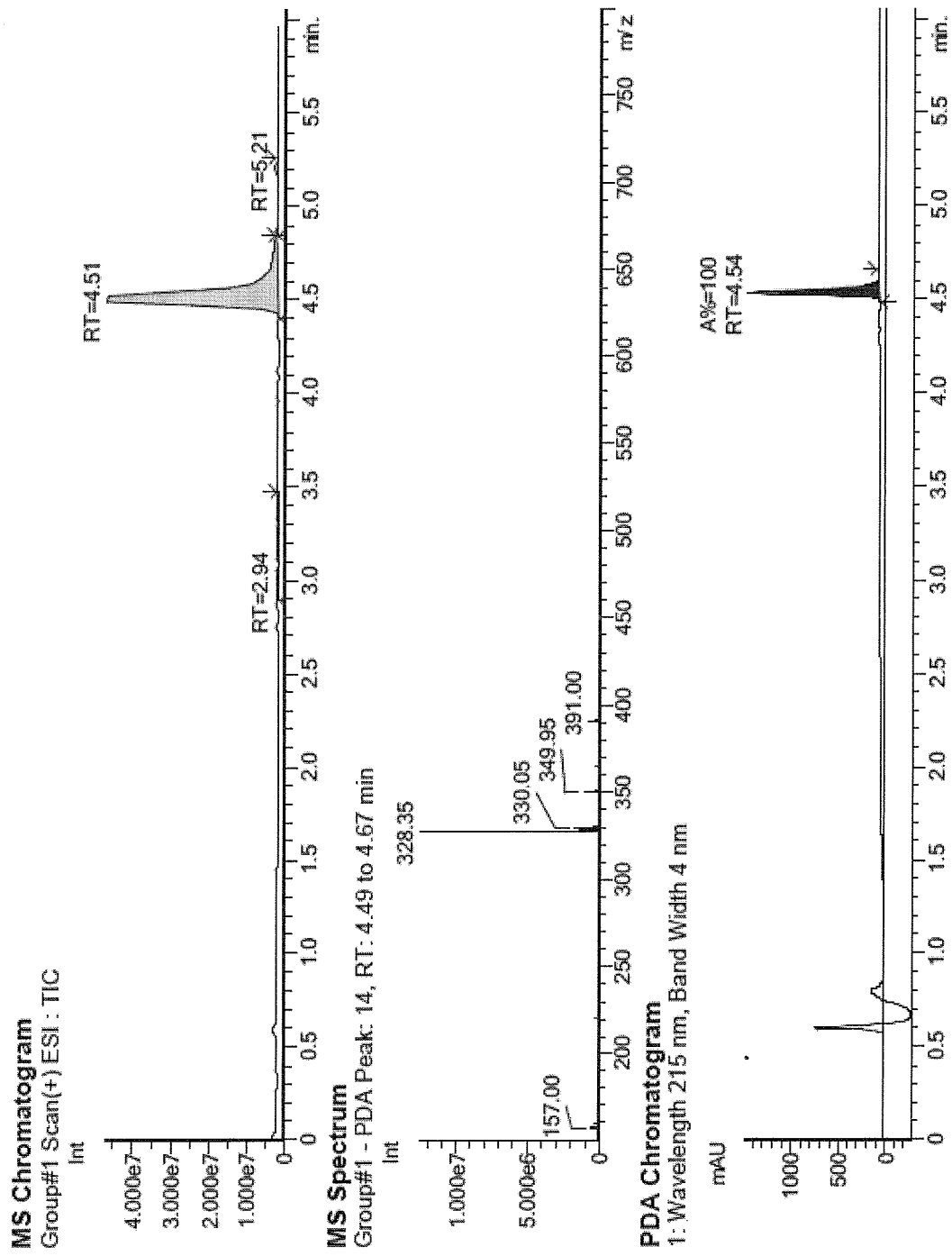
FIG. 81: Chromatogramm of Example Compound 81
Figure 82:
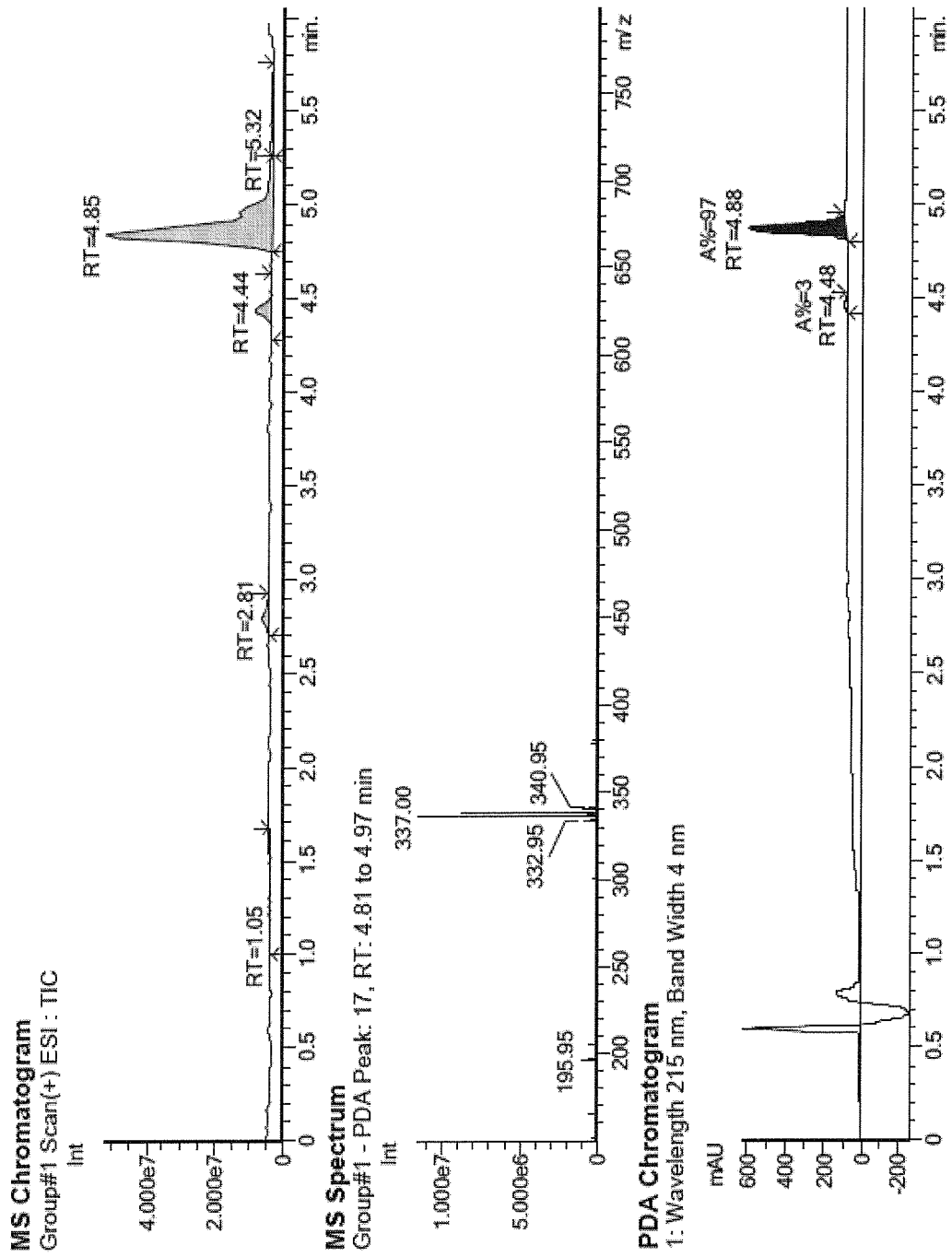
FIG. 82: Chromatogramm of Example Compound 82
Figure 83:
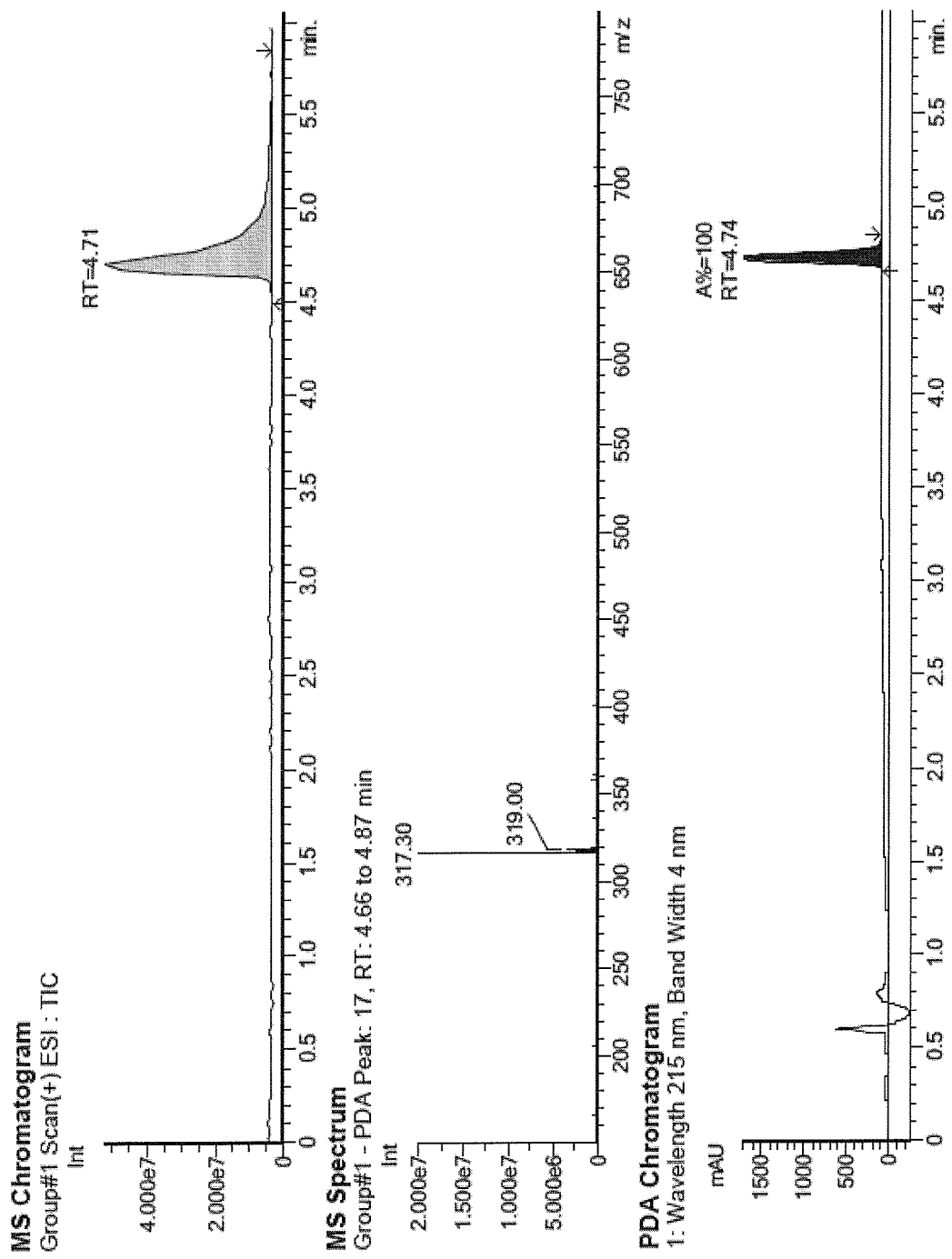
FIG. 83: Chromatogramm of Example Compound 83
Figure 84:
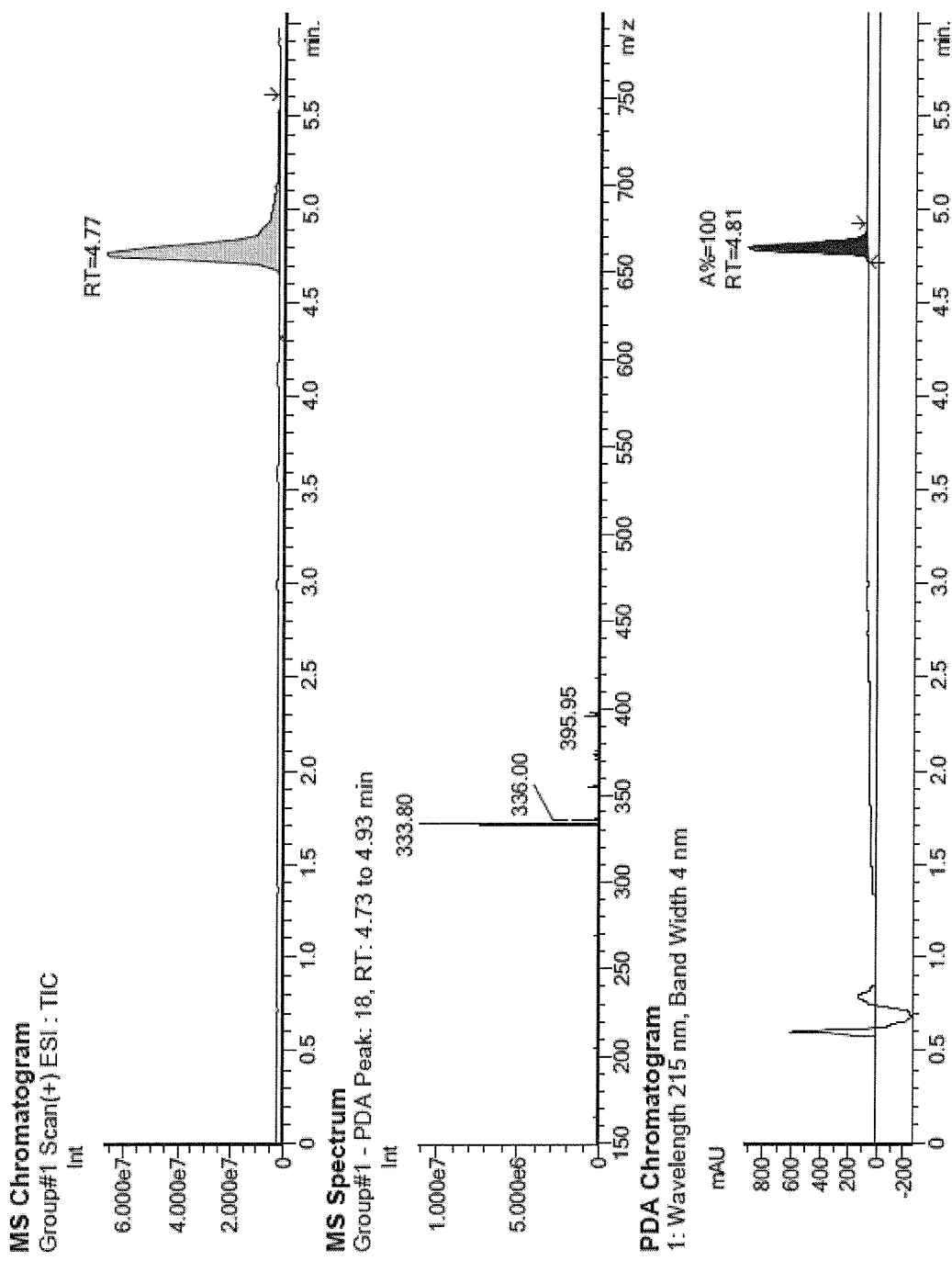
FIG. 84: Chromatogramm of Example Compound 84
Figure 85:
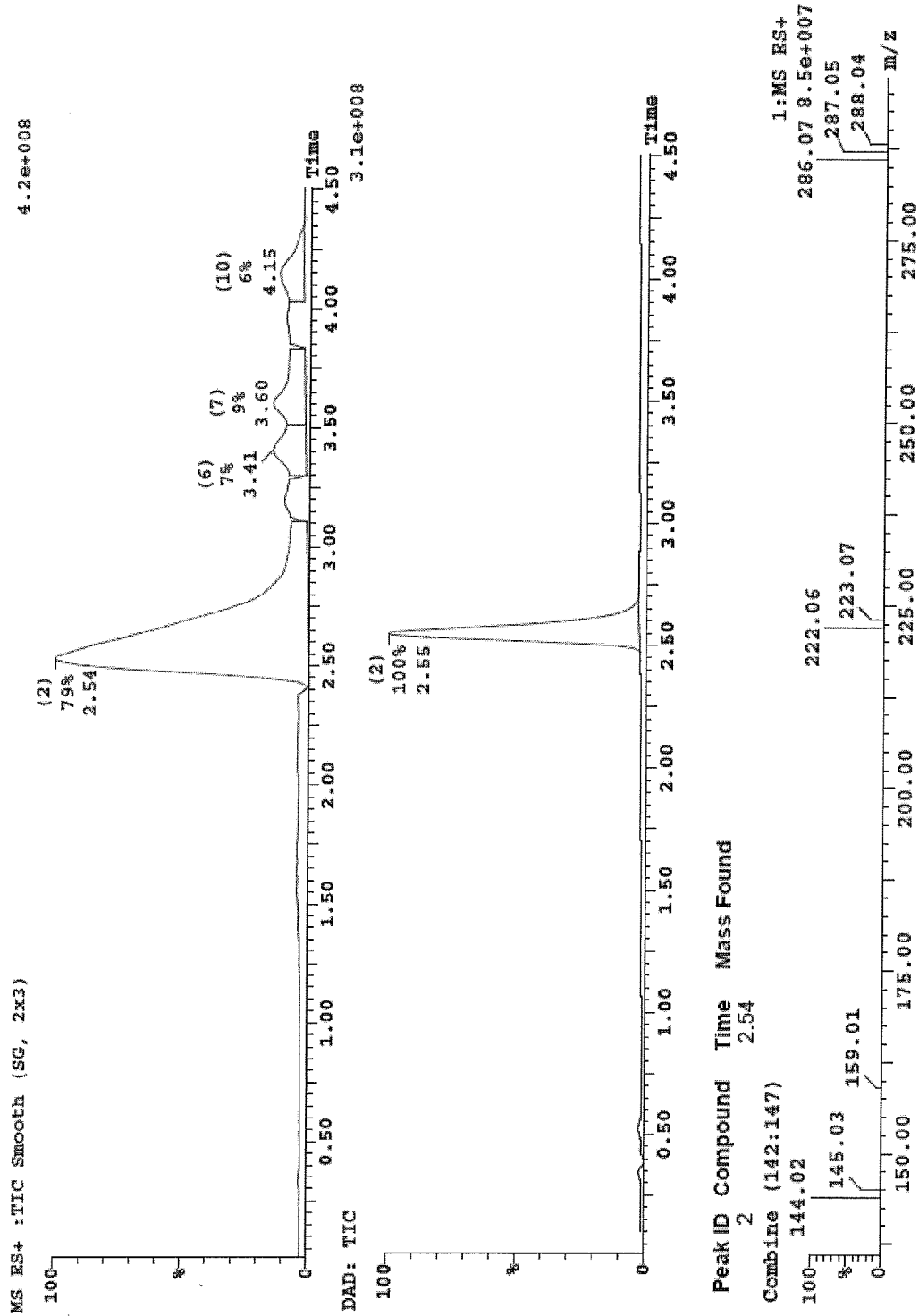
FIG. 85: Chromatogramm of Example Compound 85
Figure 86:
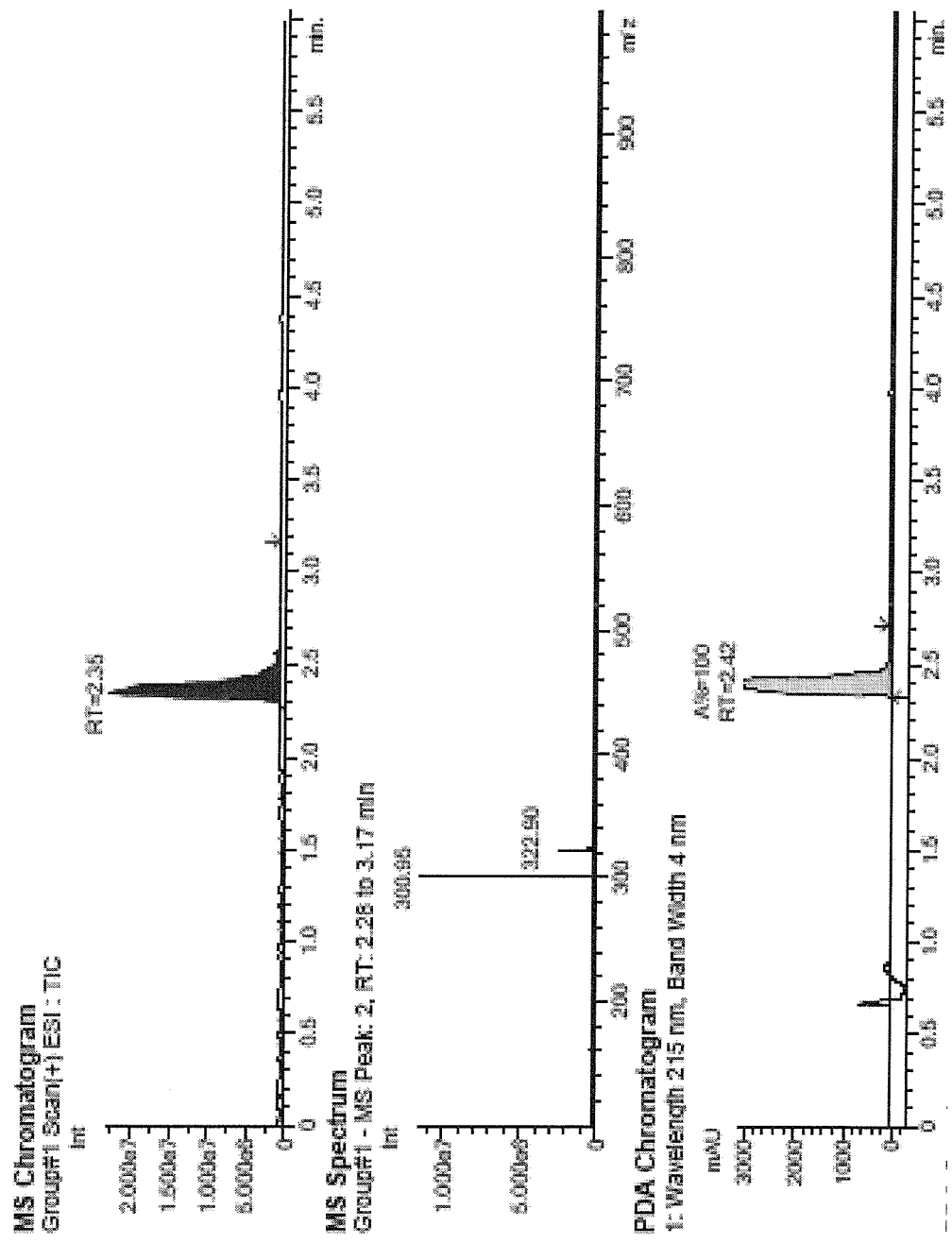
FIG. 86: Chromatogramm of Example Compound 86
Figure 87:
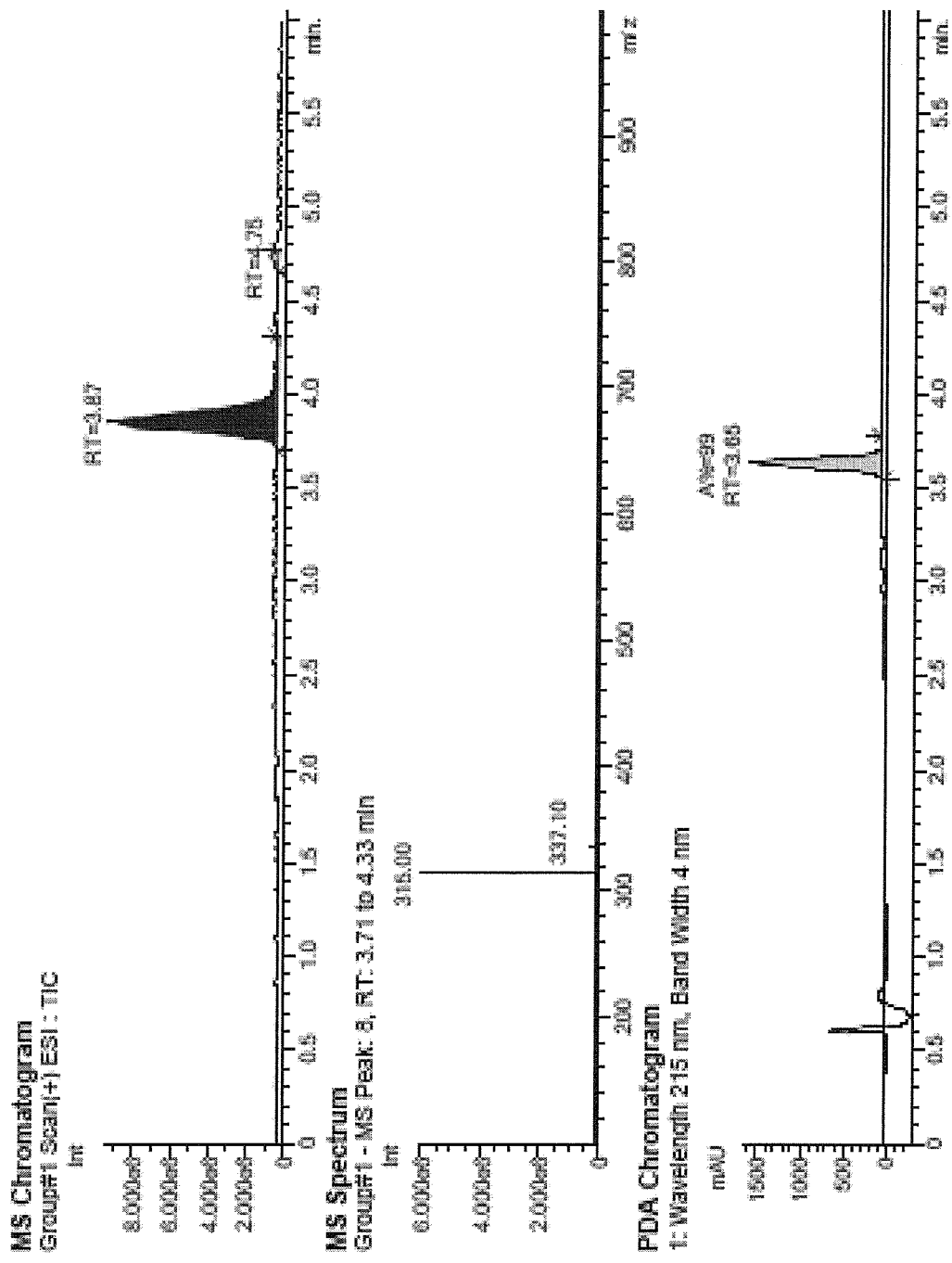
FIG. 87: Chromatogramm of Example Compound 87
Figure 88:
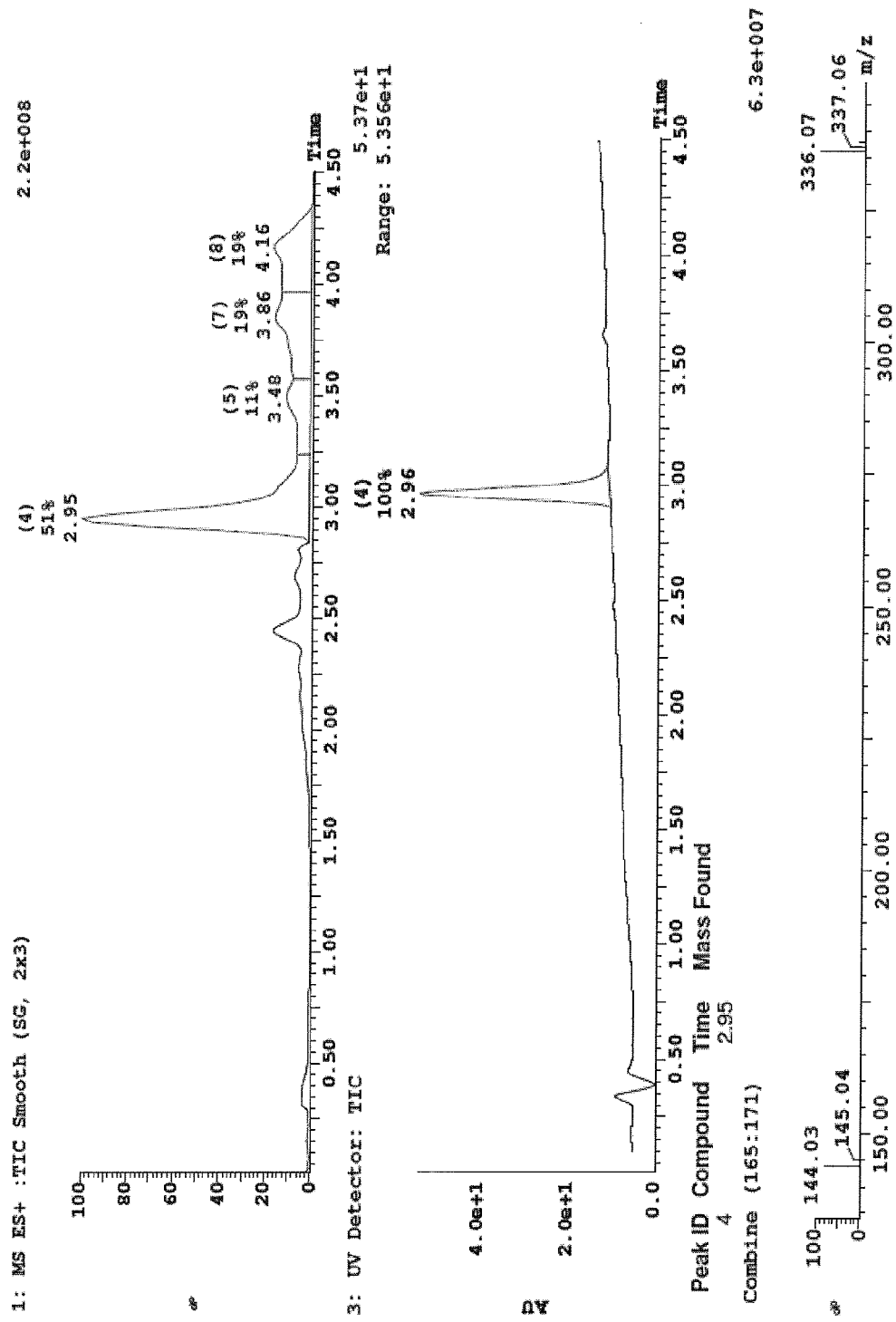
FIG. 88: Chromatogramm of Example Compound 88
Figure 89:
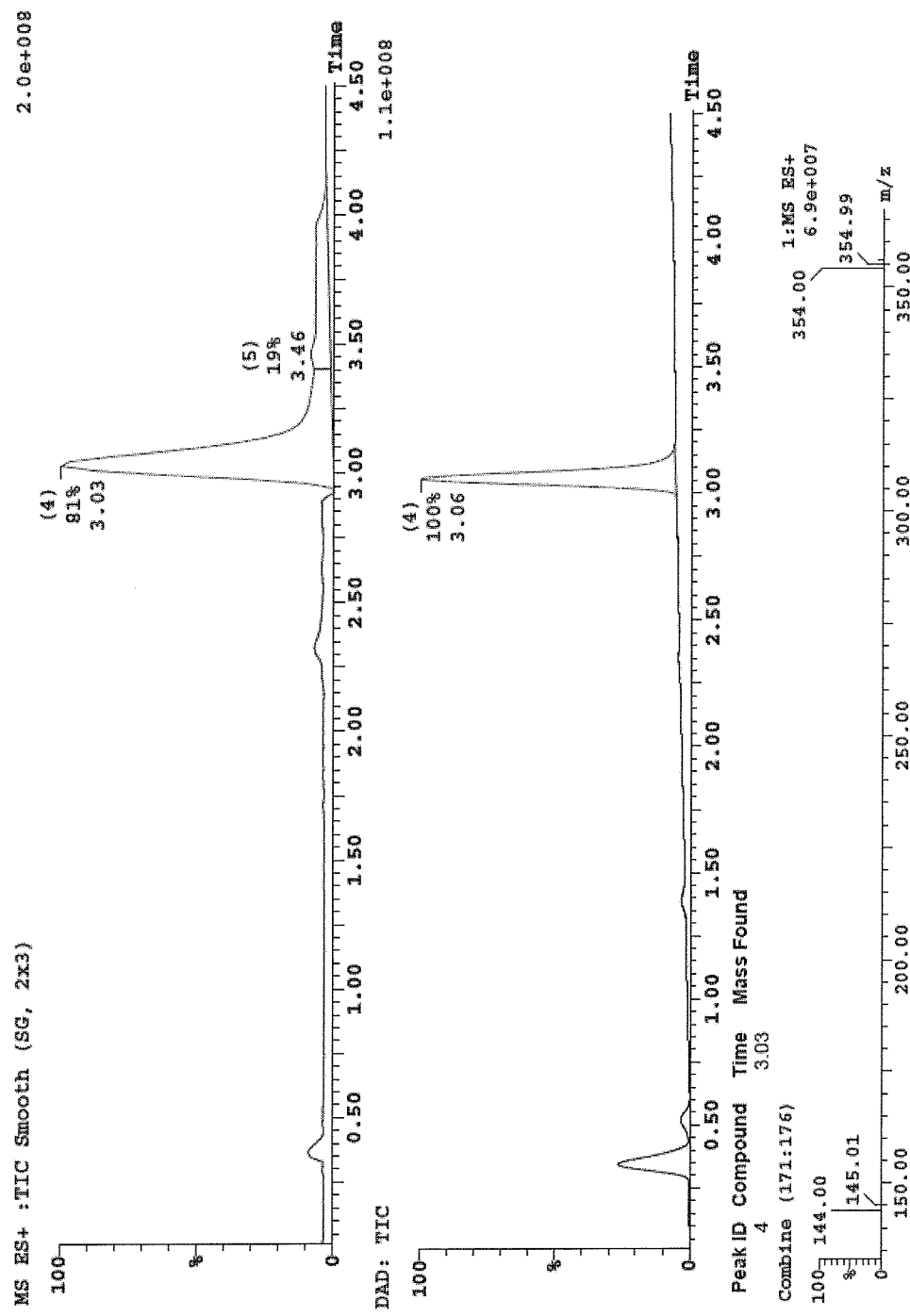
FIG. 89: Chromatogramm of Example Compound 89
Figure 90:
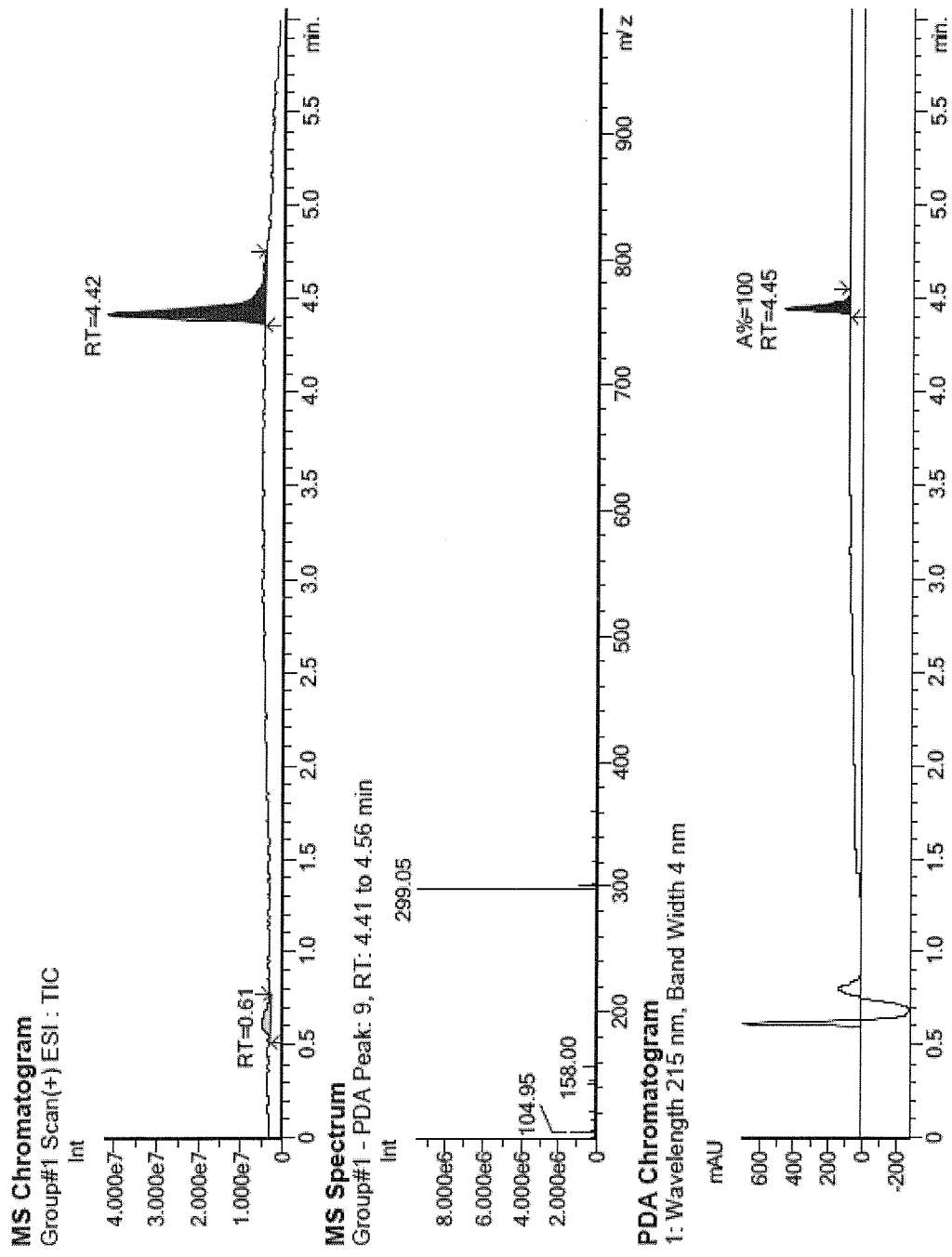
FIG. 90: Chromatogramm of Example Compound 90
Figure 91:
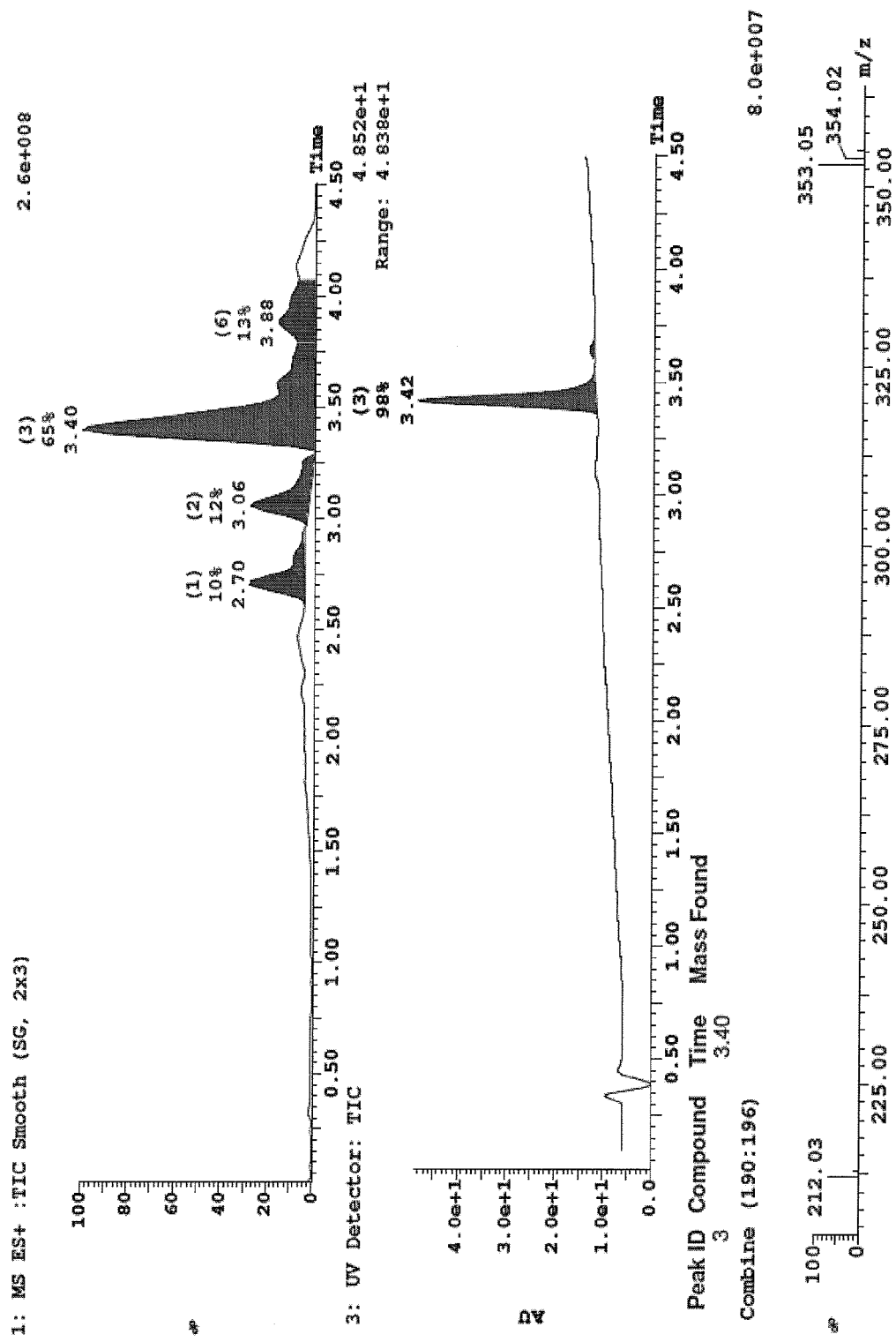
FIG. 91: Chromatogramm of Example Compound 91
Figure 92:
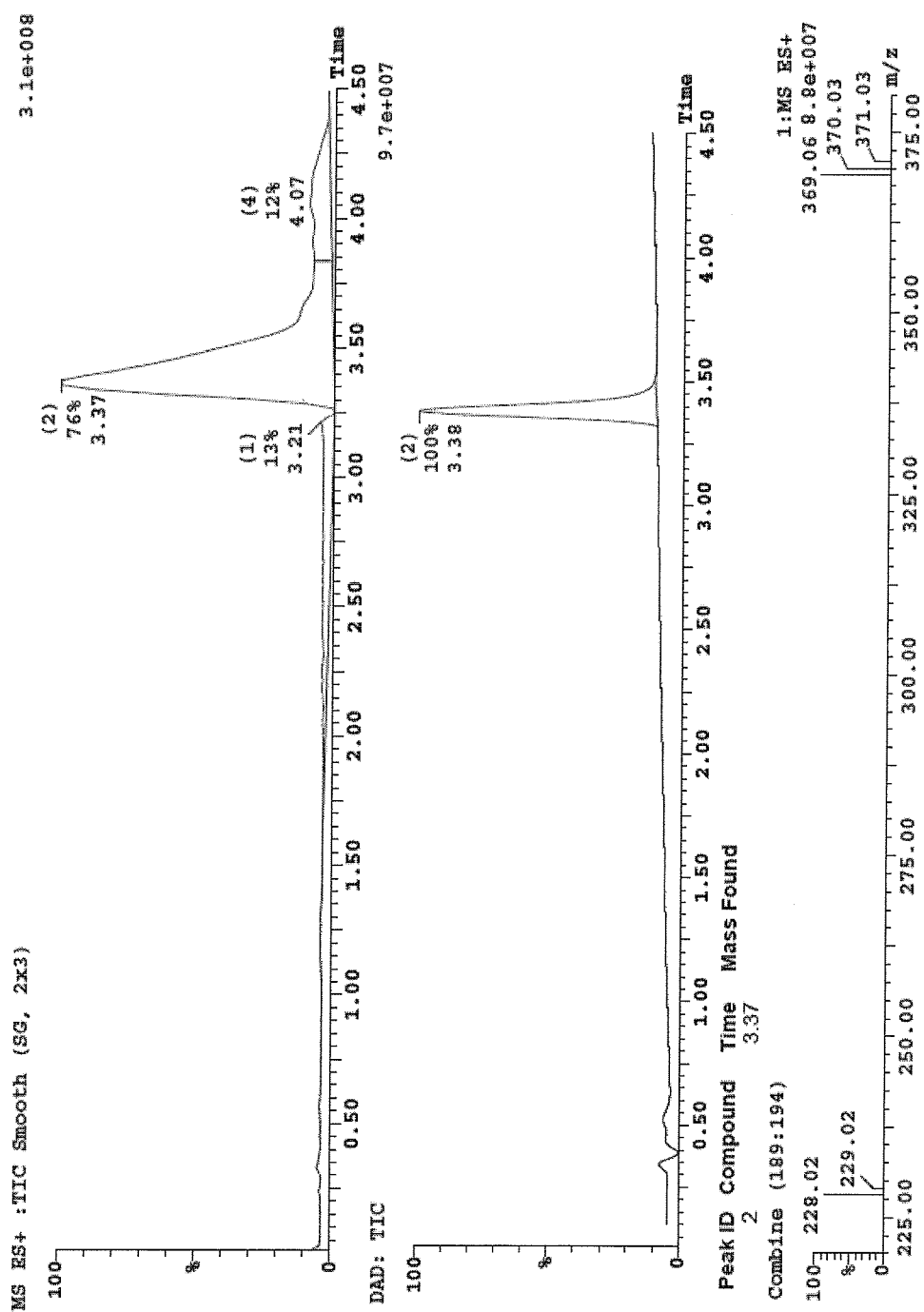
FIG. 92: Chromatogramm of Example Compound 92
Figure 93:
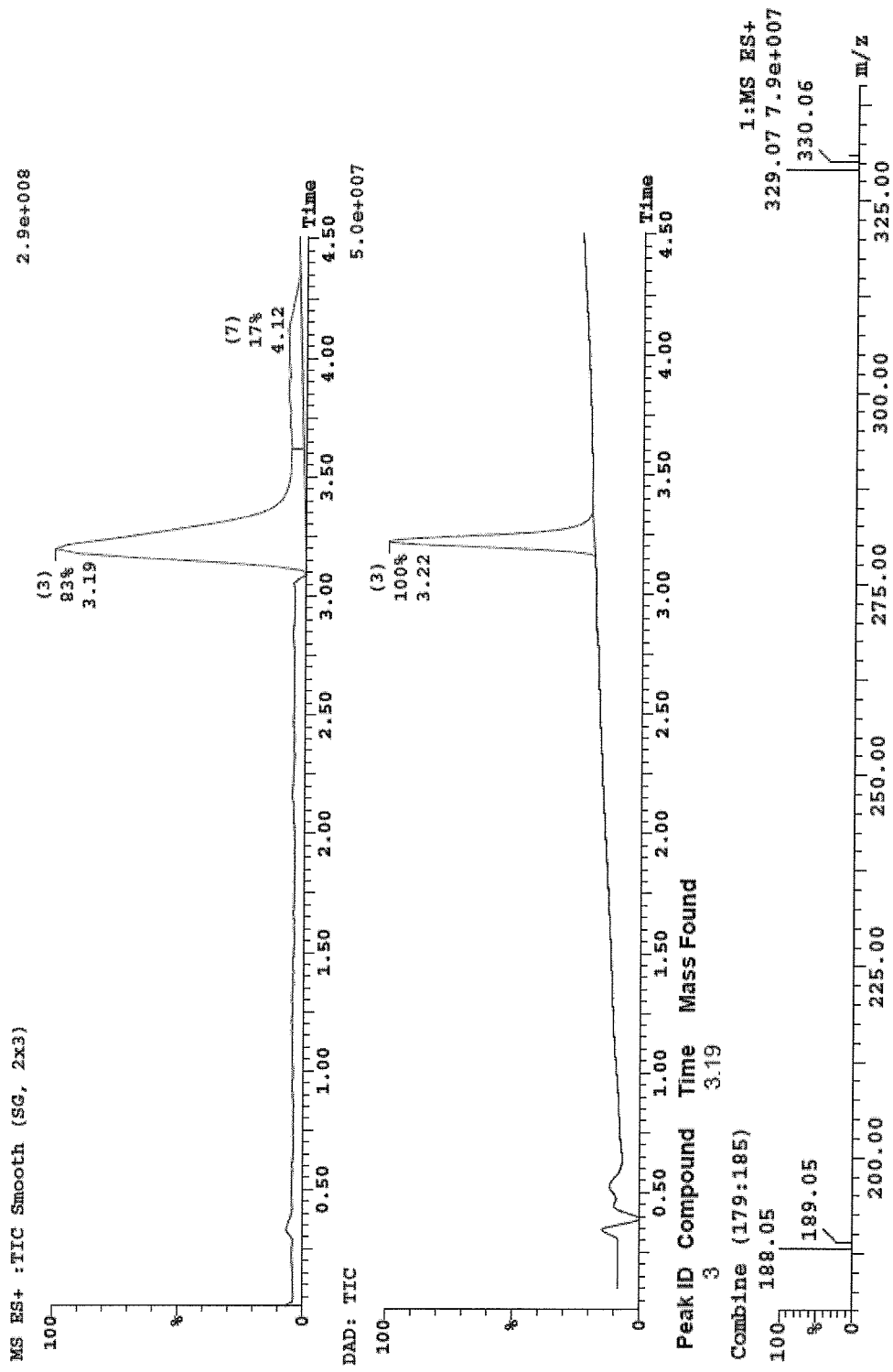
FIG. 93: Chromatogramm of Example Compound 93
Figure 94:
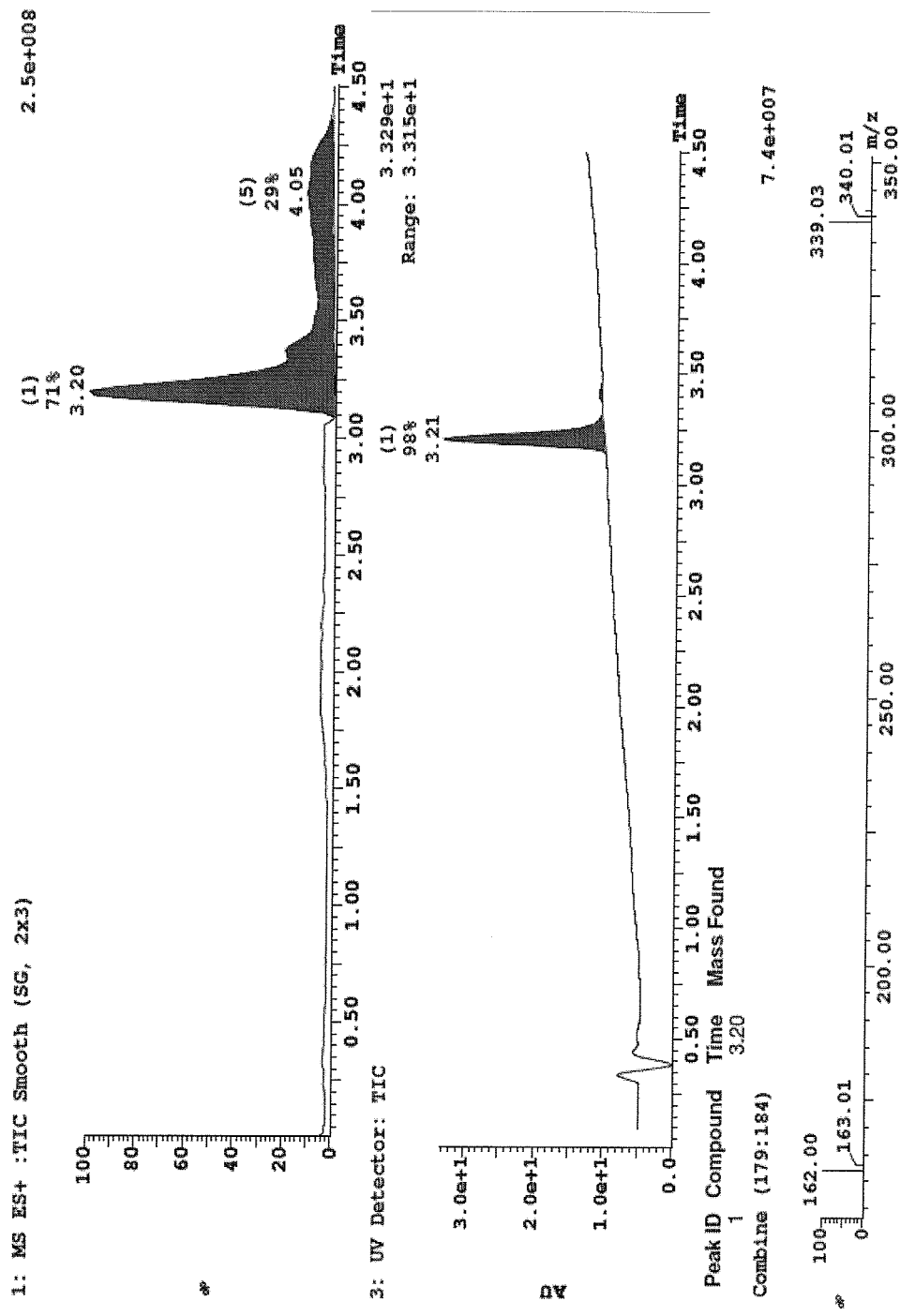
FIG. 94: Chromatogramm of Example Compound 94
Figure 95:
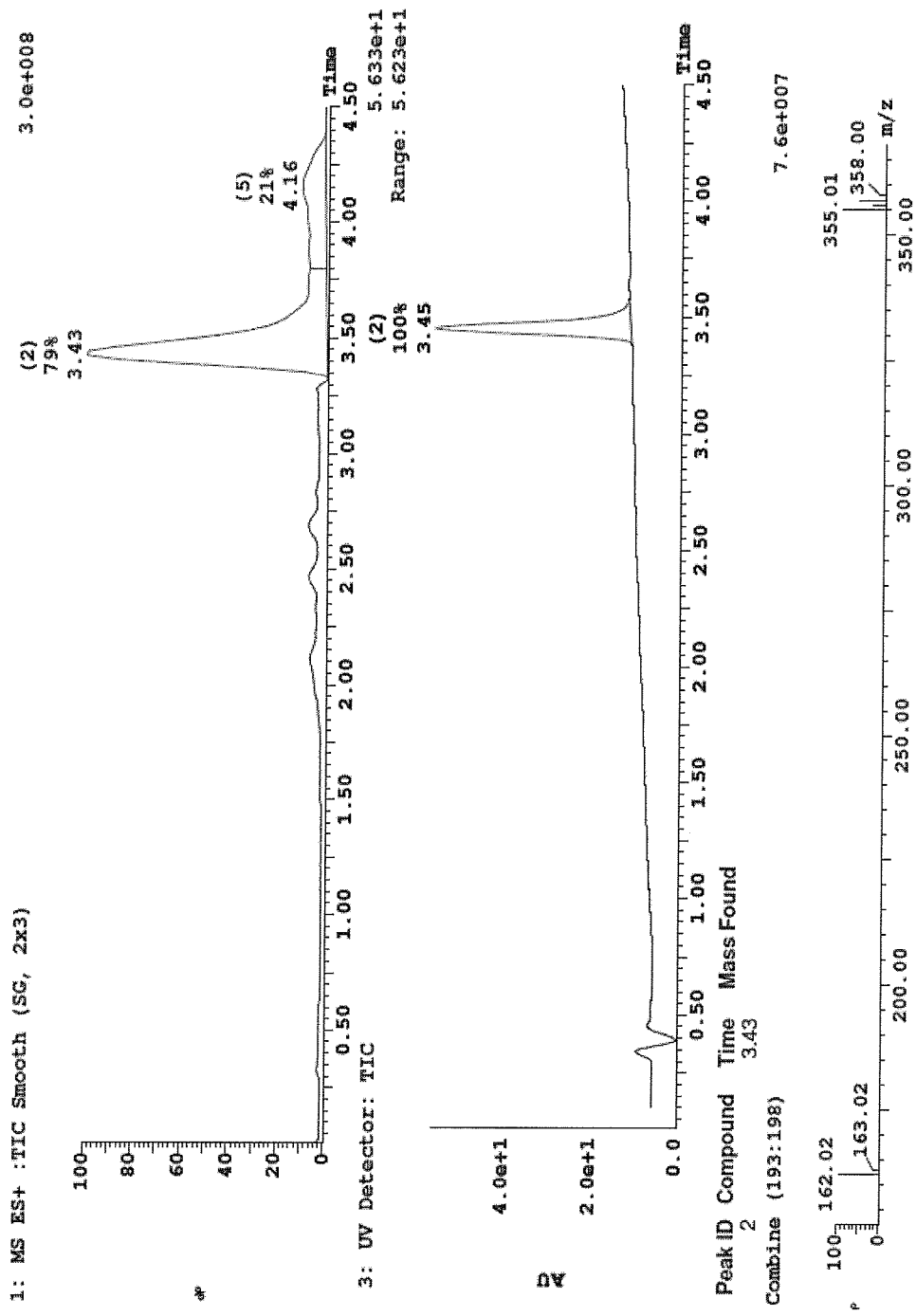
FIG. 95: Chromatogramm of Example Compound 95
Figure 96:
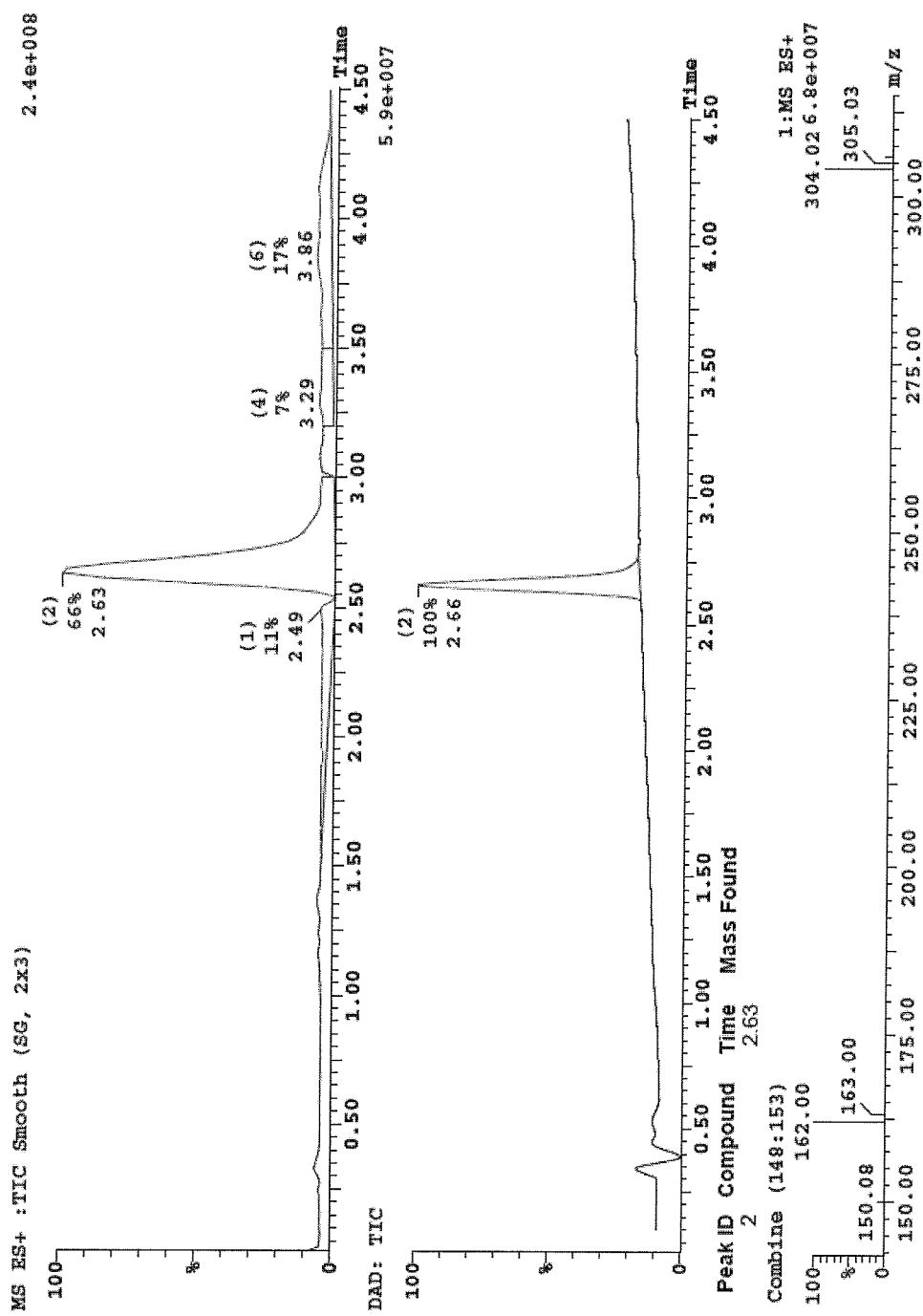
FIG. 96: Chromatogramm of Example Compound 96
Figure 97:
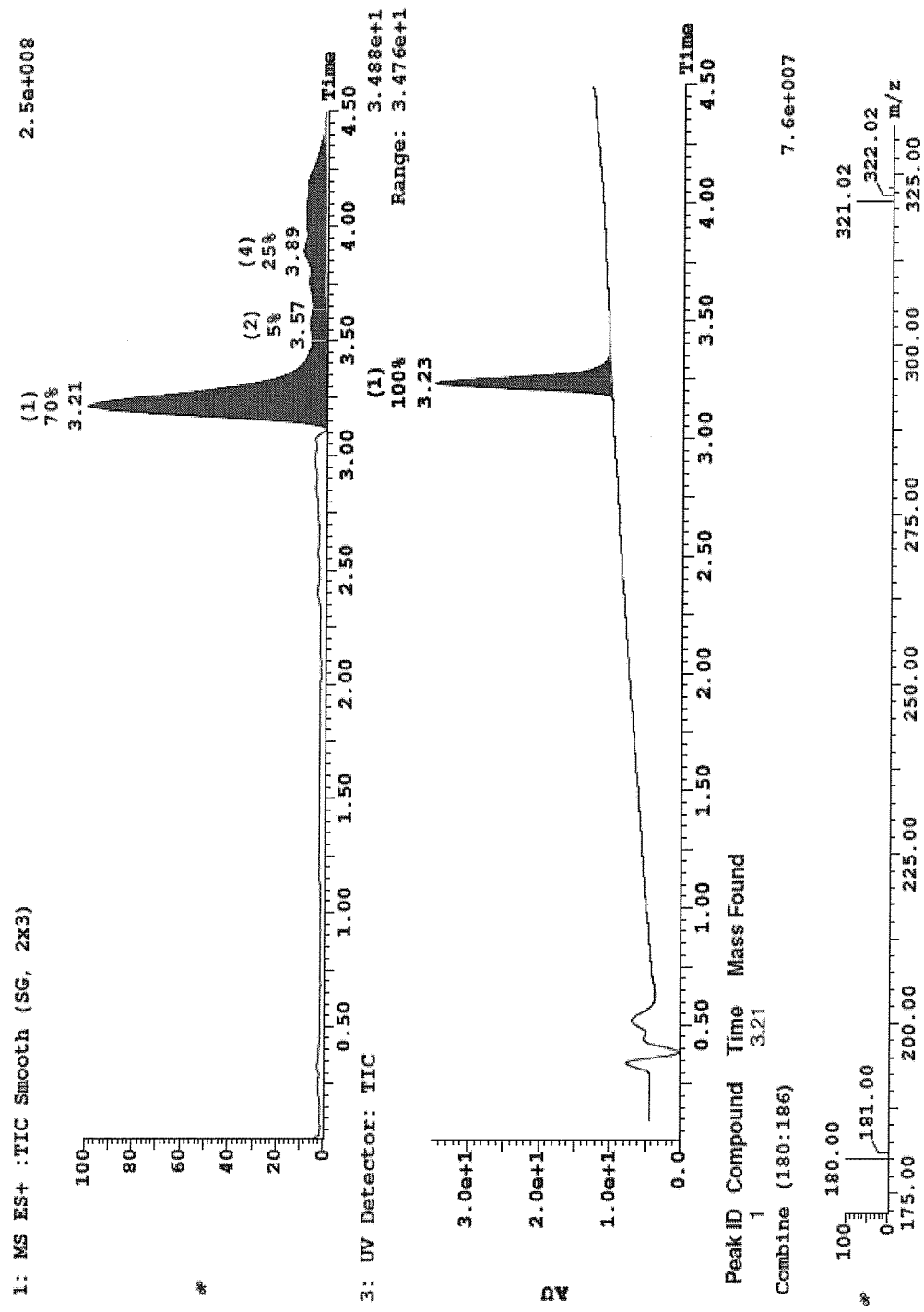
FIG. 97: Chromatogramm of Example Compound 97
Figure 98:
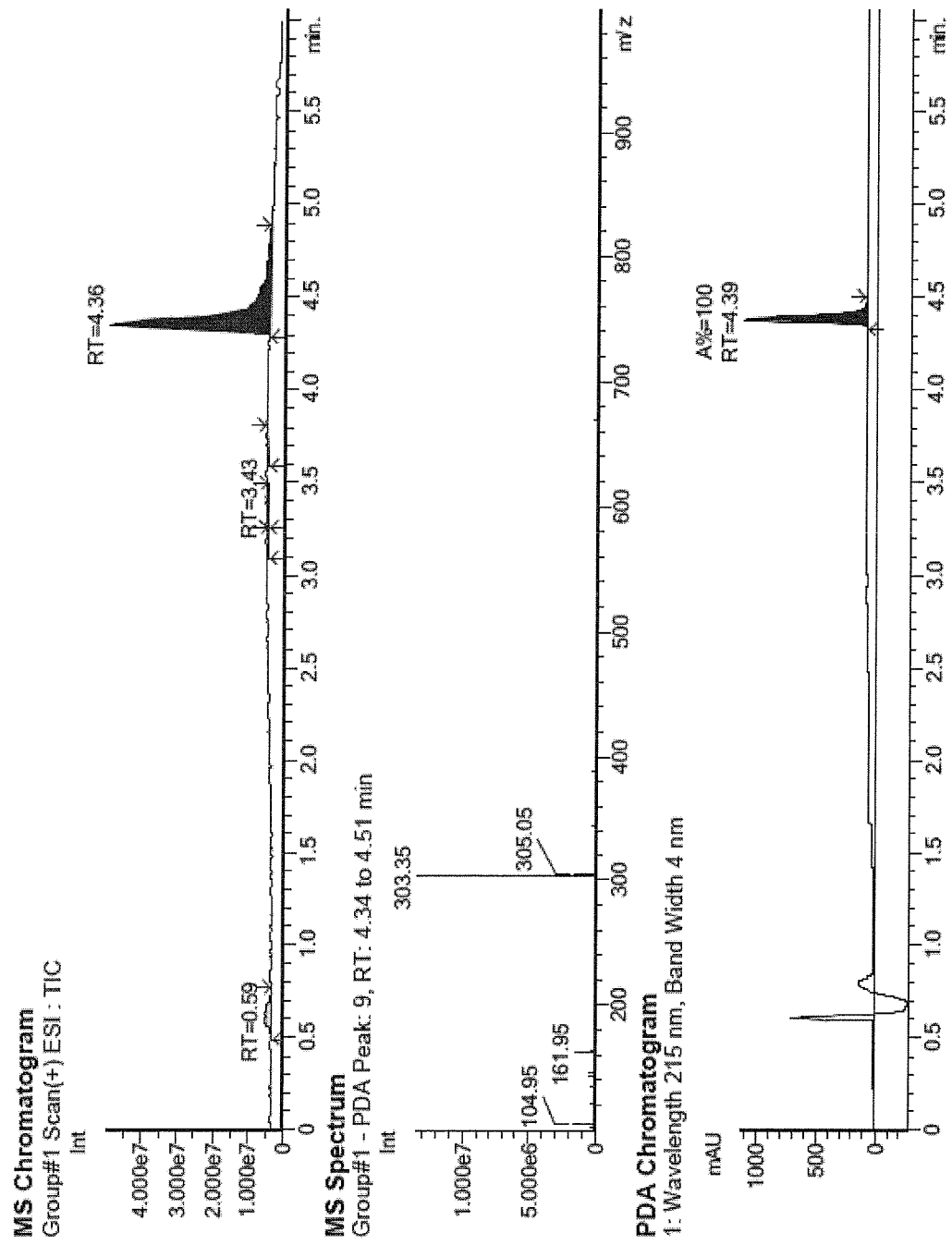
FIG. 98: Chromatogramm of Example Compound 98
Figure 99:
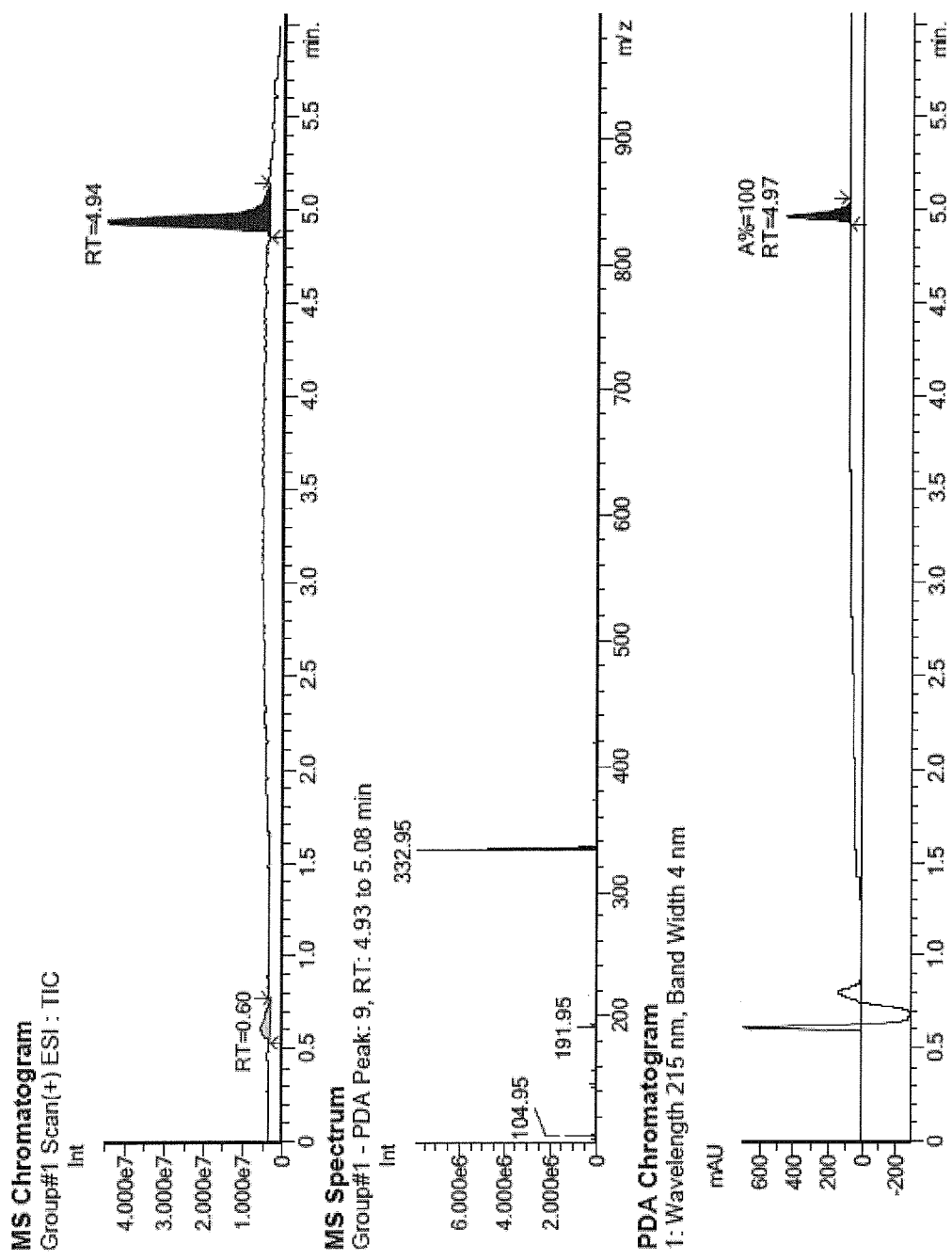
FIG. 99: Chromatogramm of Example Compound 99
Figure 100:
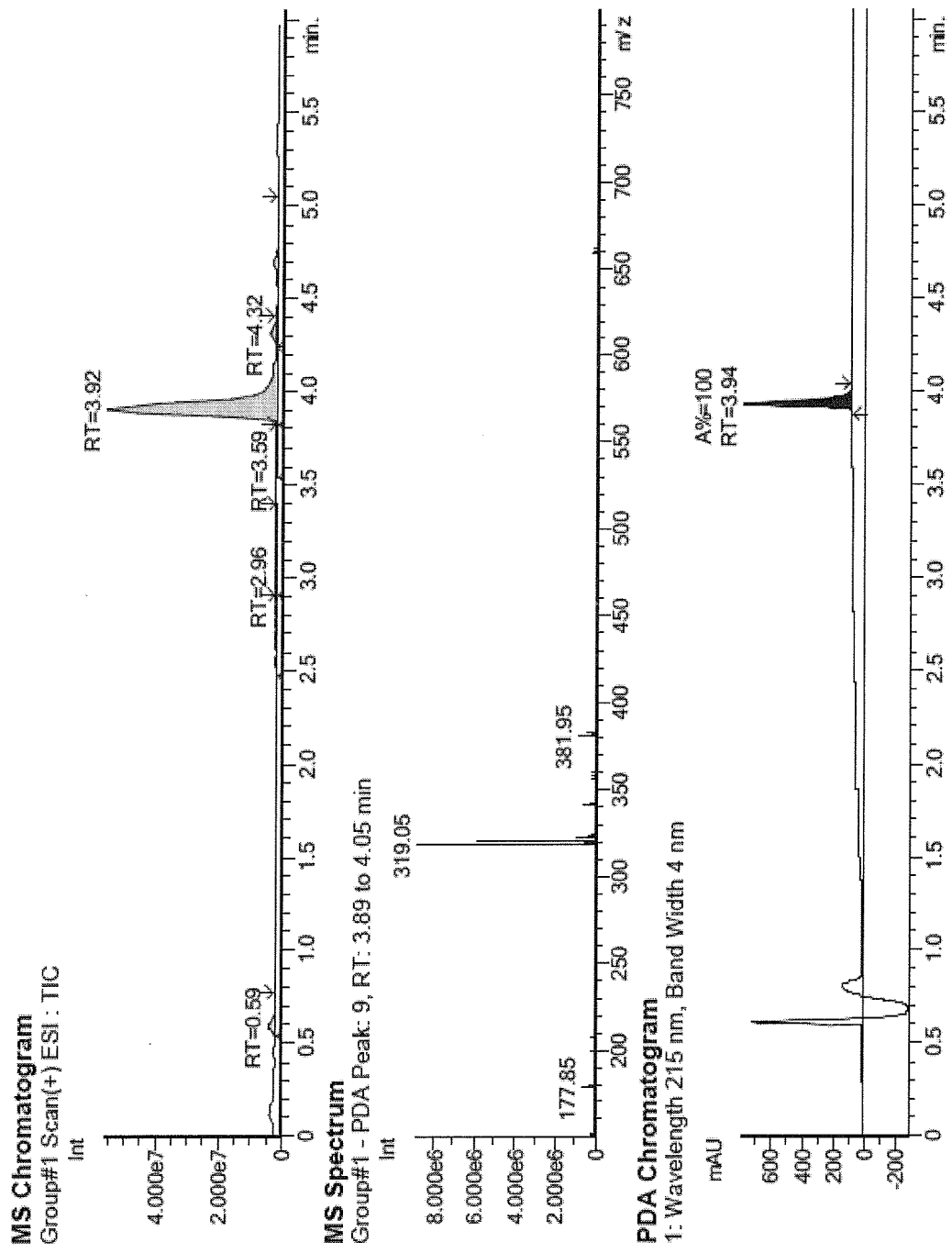
FIG. 100: Chromatogramm of Example Compound 100
Figure 101:
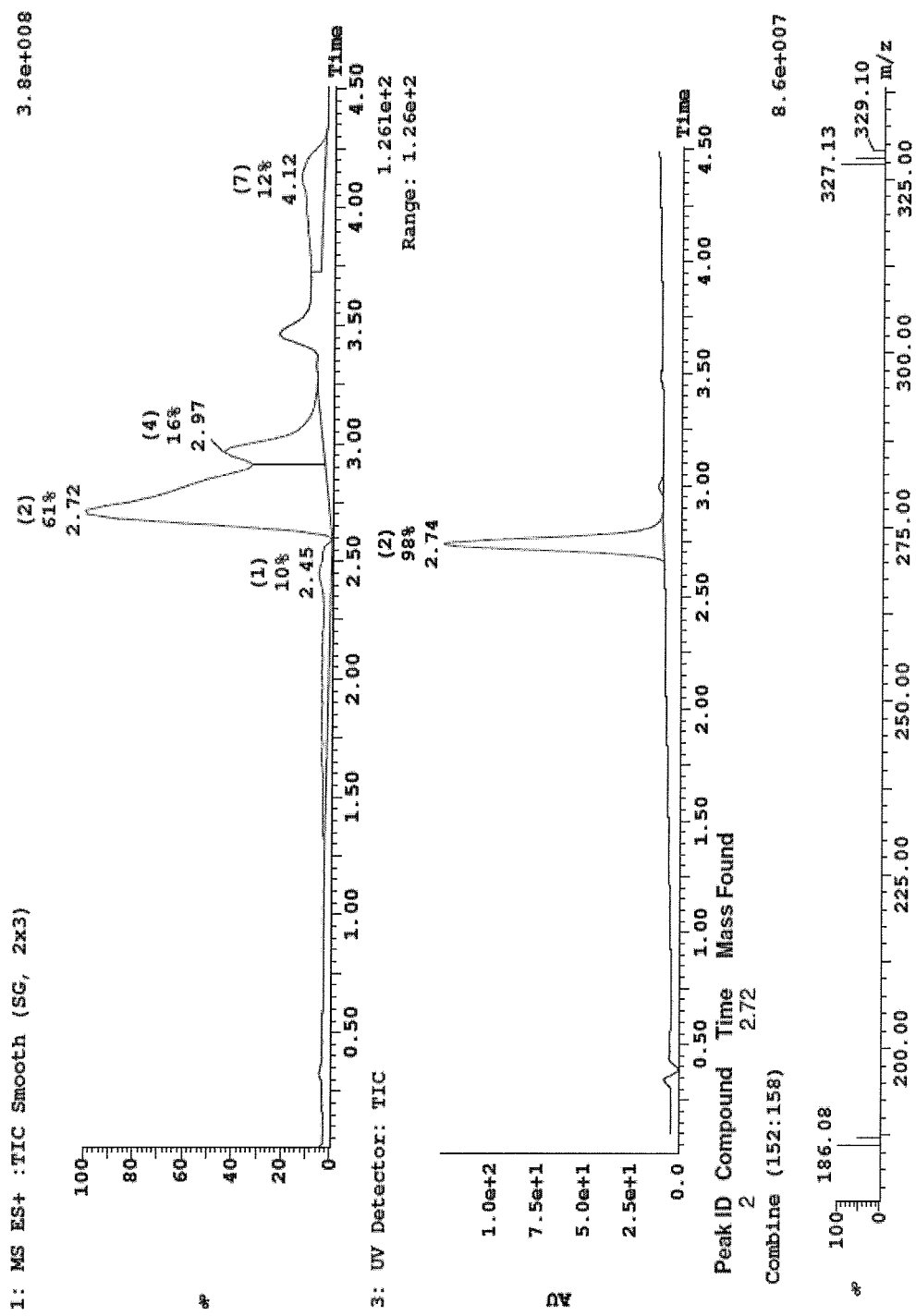
FIG. 101: Chromatogramm of Example Compound 101
Figure 102:
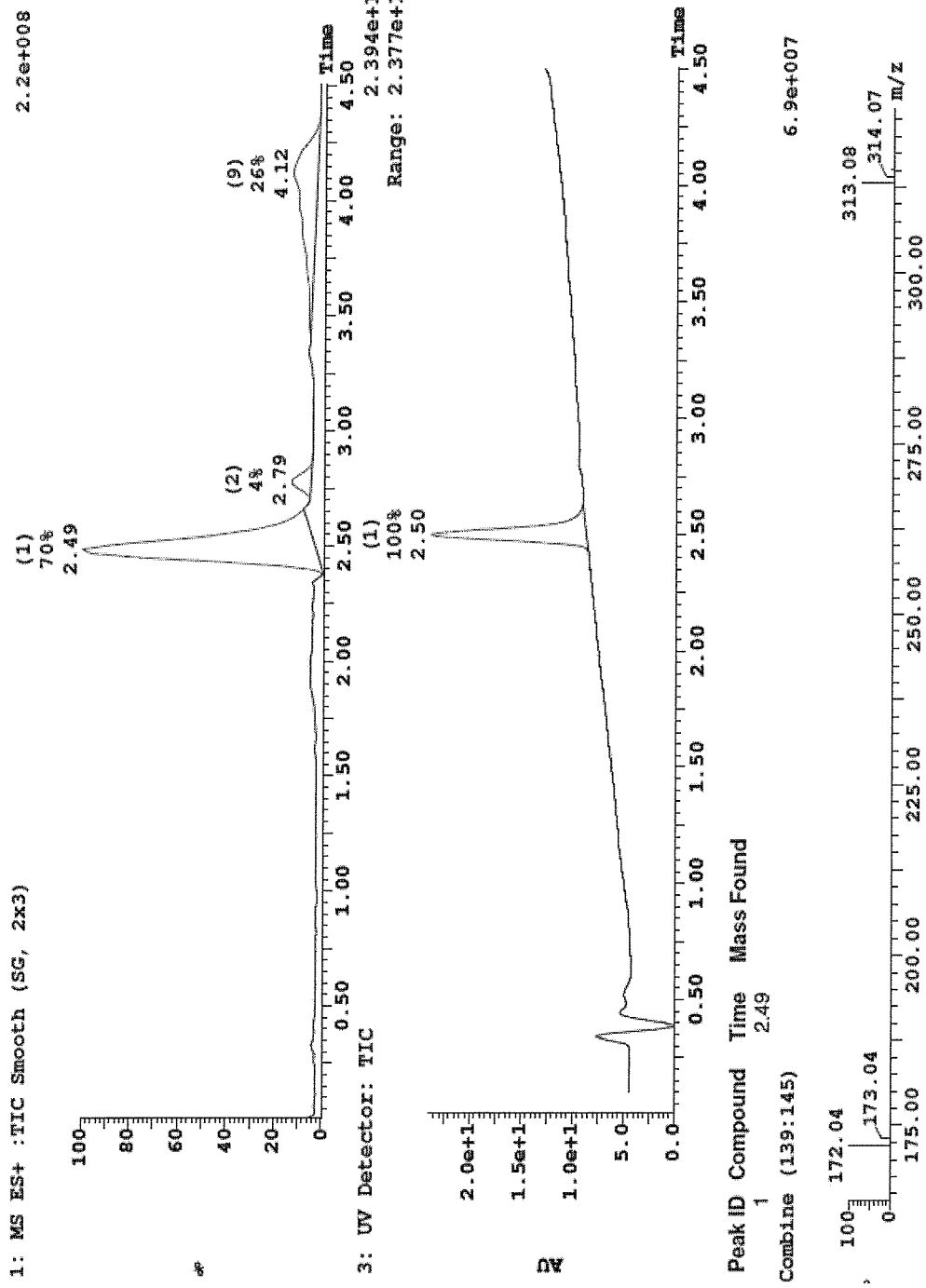
FIG. 102: Chromatogramm of Example Compound 102
Figure 103:
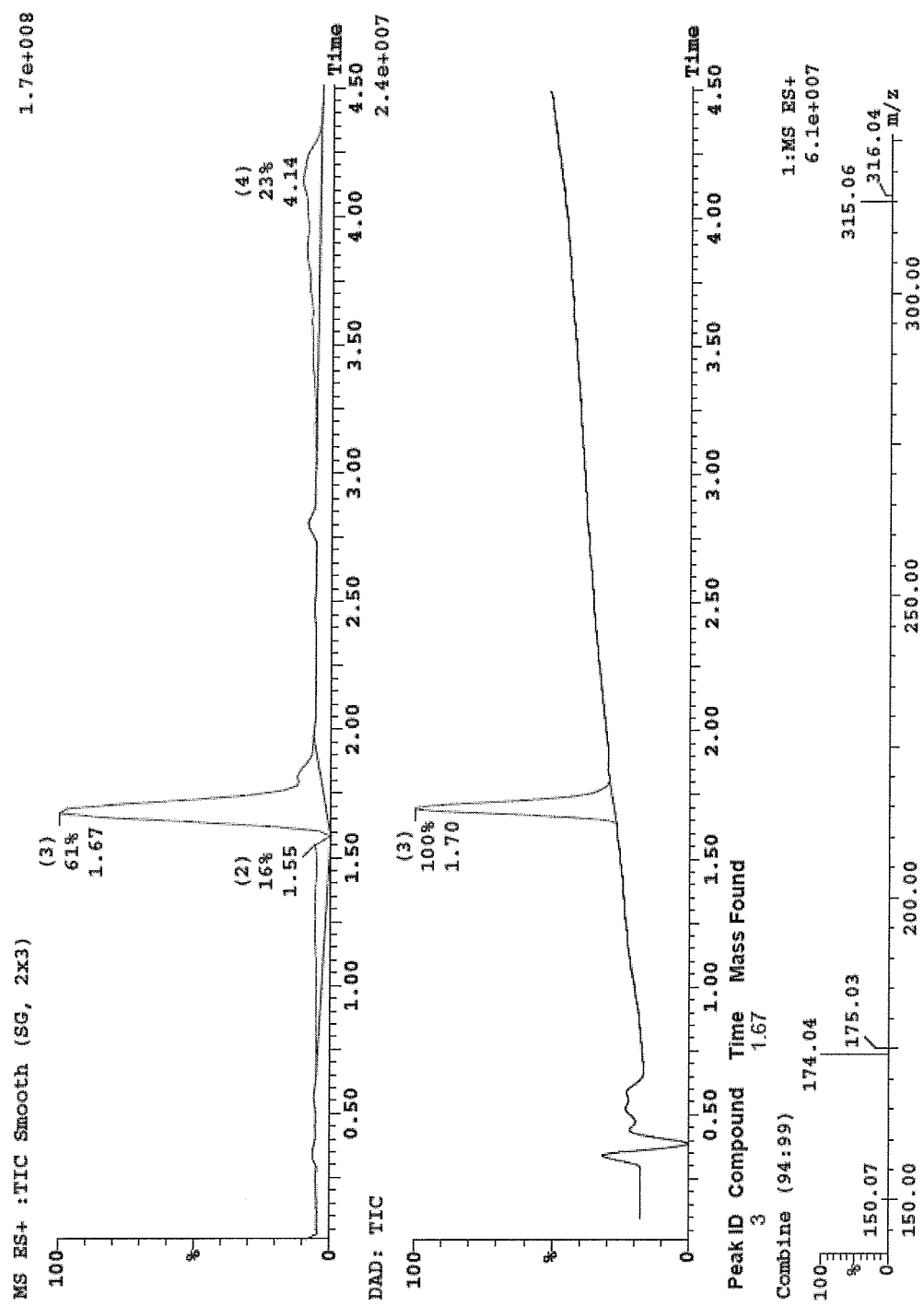
FIG. 103: Chromatogramm of Example Compound 103
Figure 104:
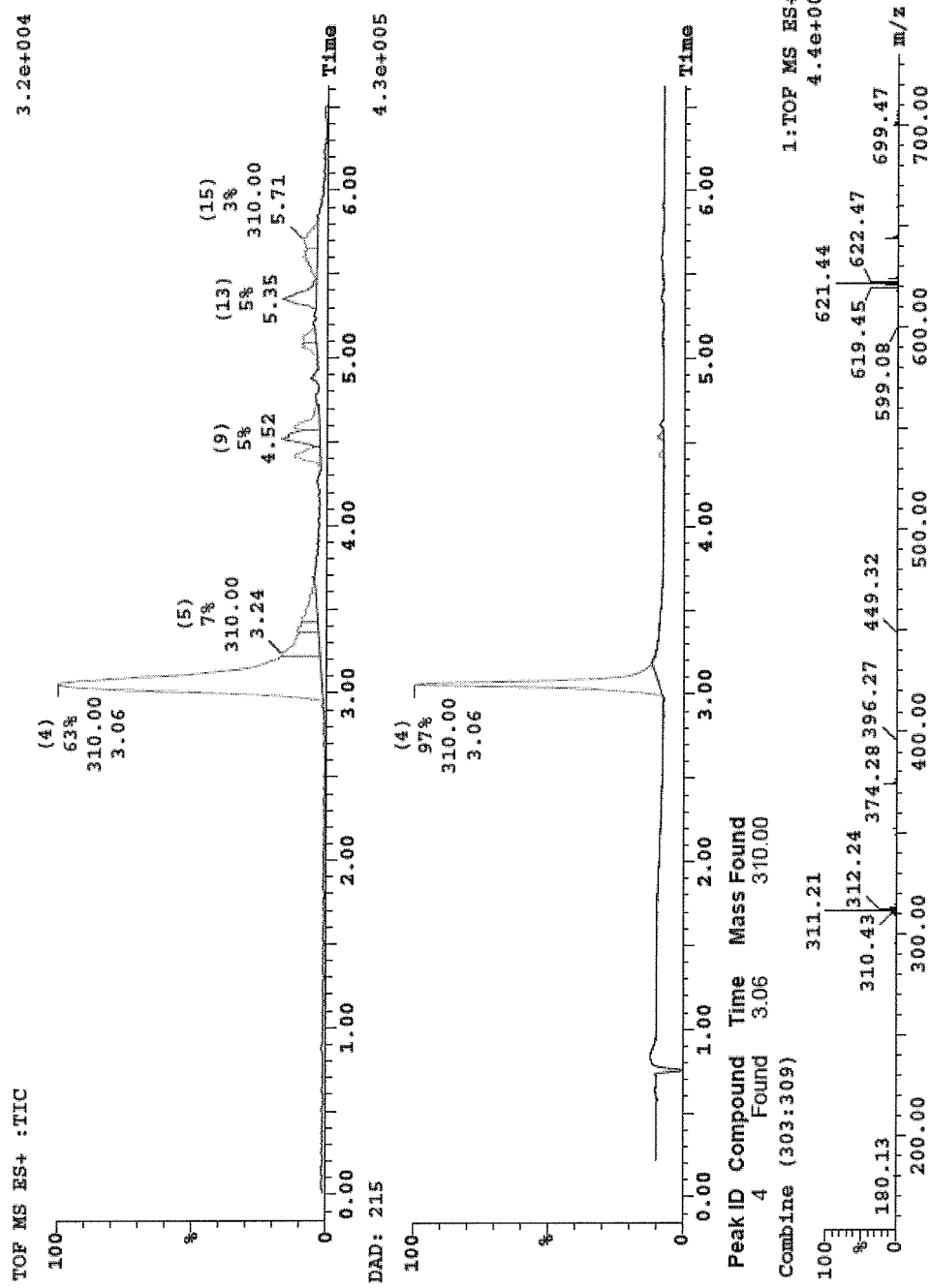
FIG. 104: Chromatogramm of Example Compound 104
Figure 105:
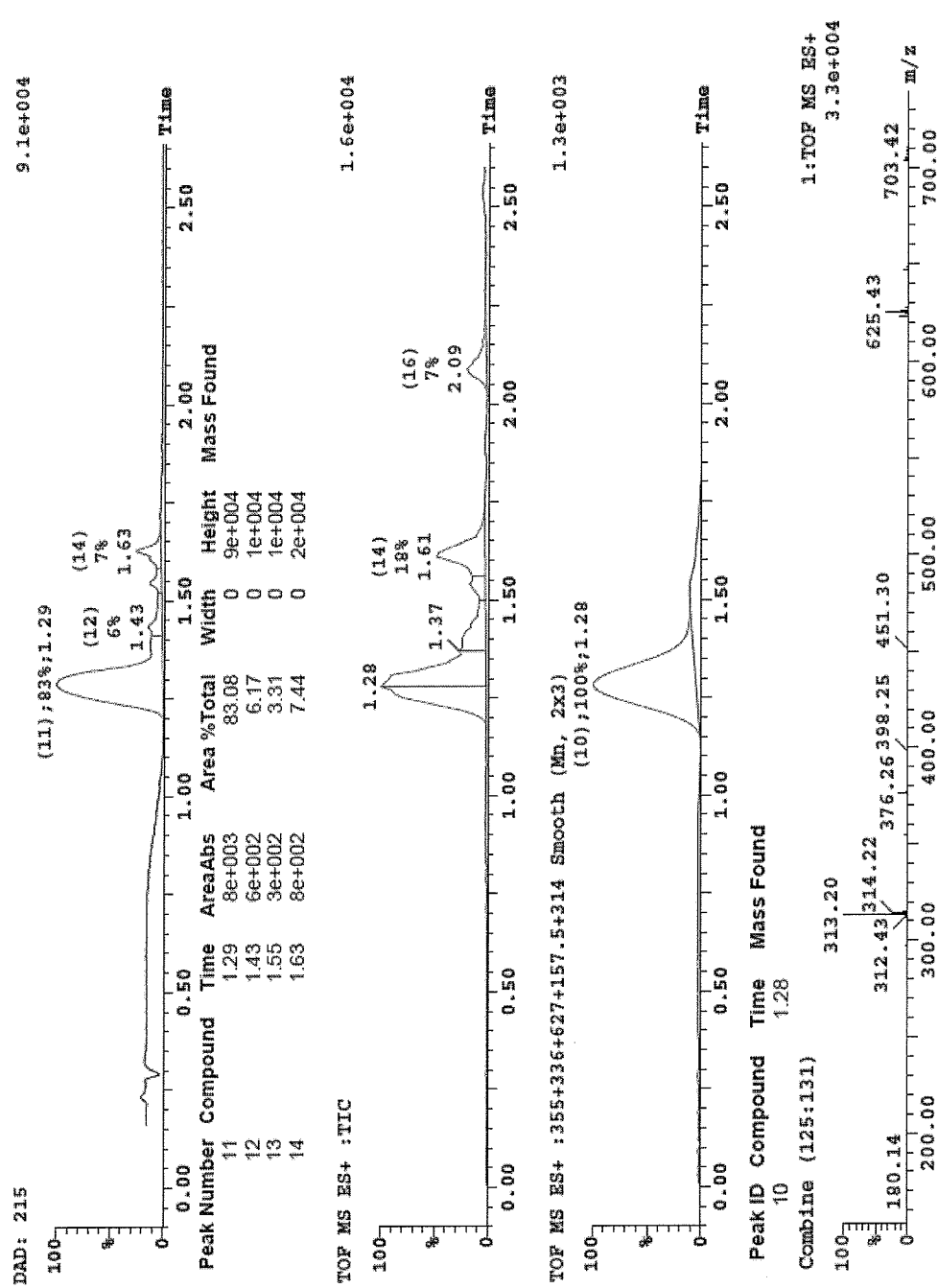
FIG. 105: Chromatogramm of Example Compound 105
Figure 106:
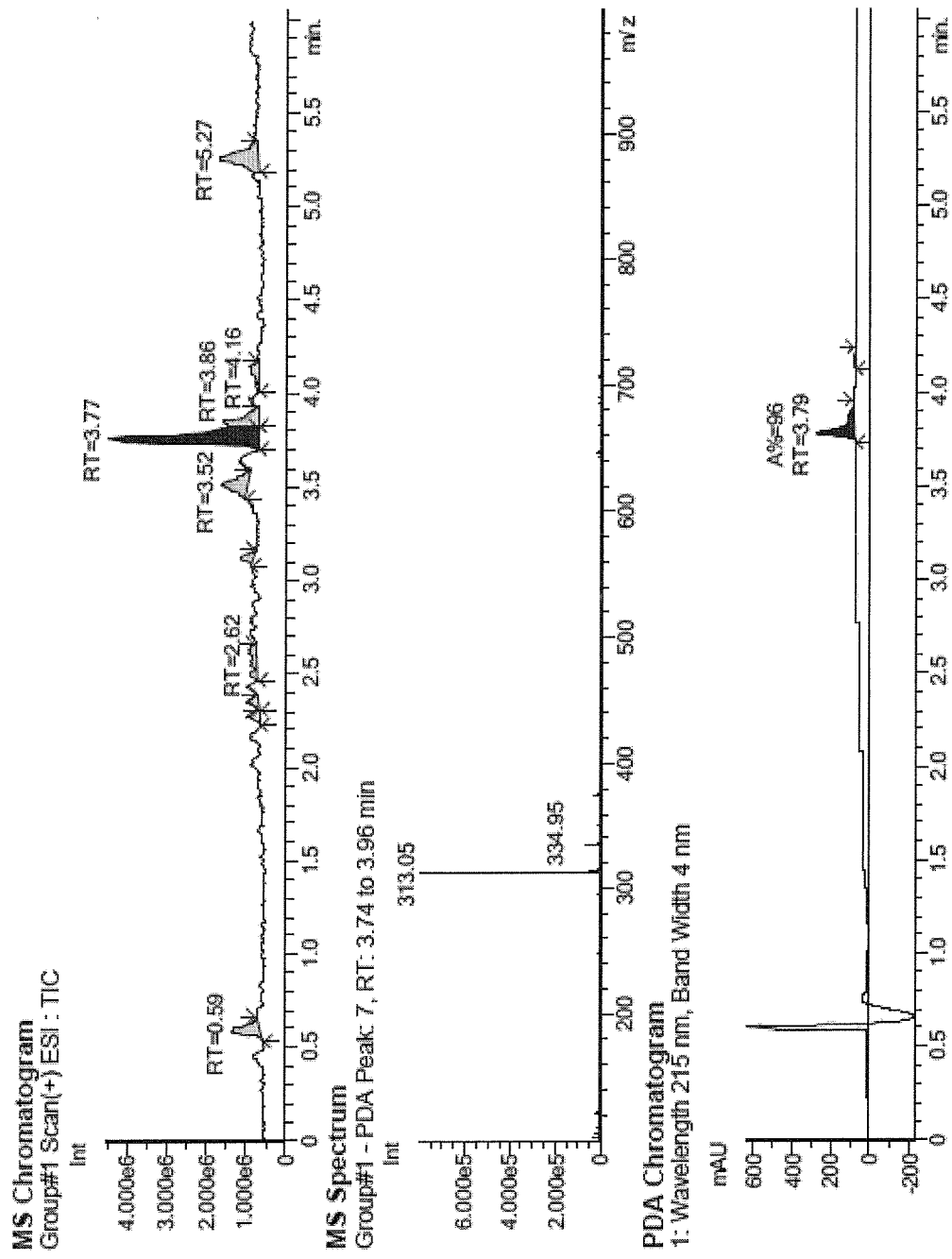
FIG. 106: Chromatogramm of Example Compound 106
Figure 107:
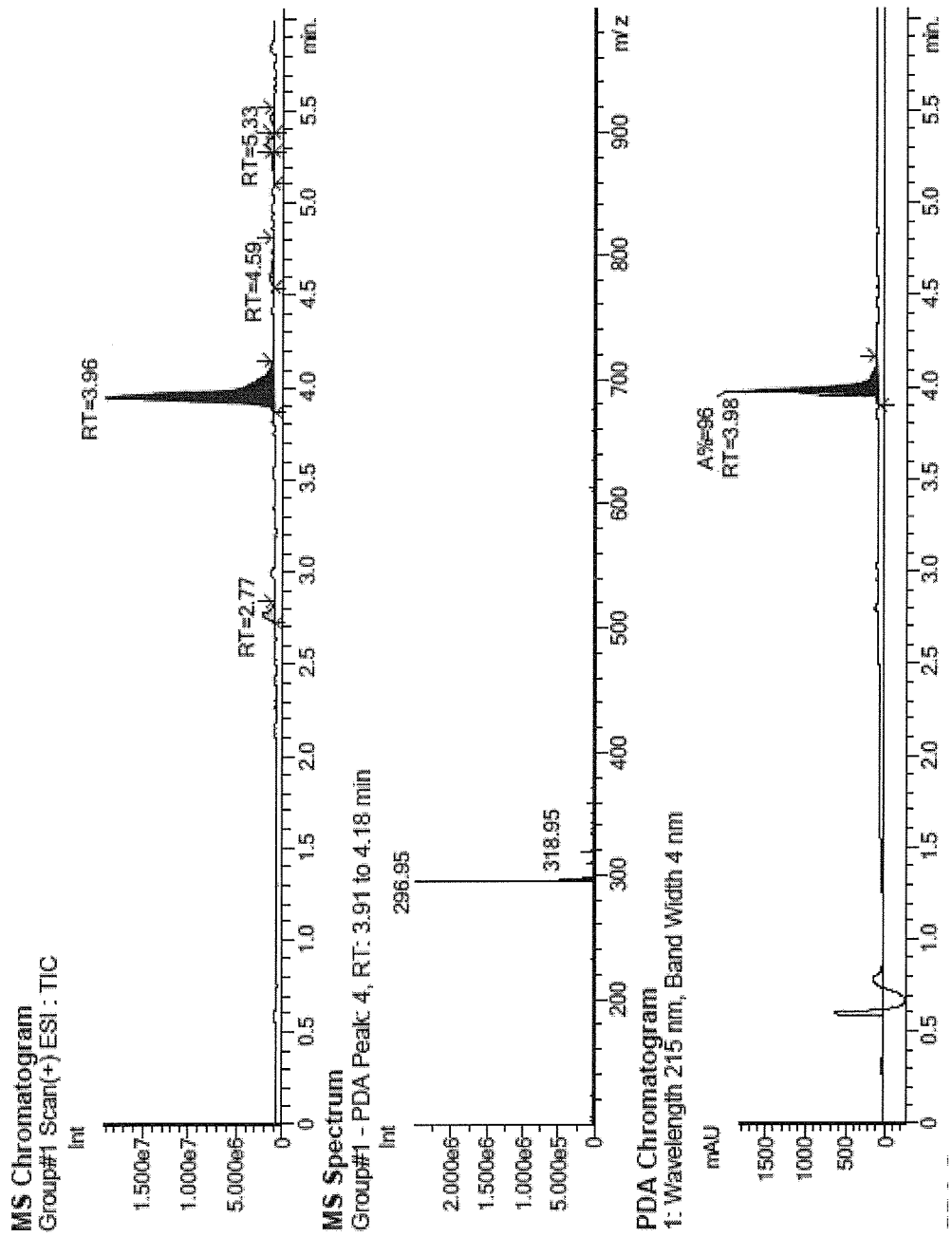
FIG. 107: Chromatogramm of Example Compound 107
Figure 108:
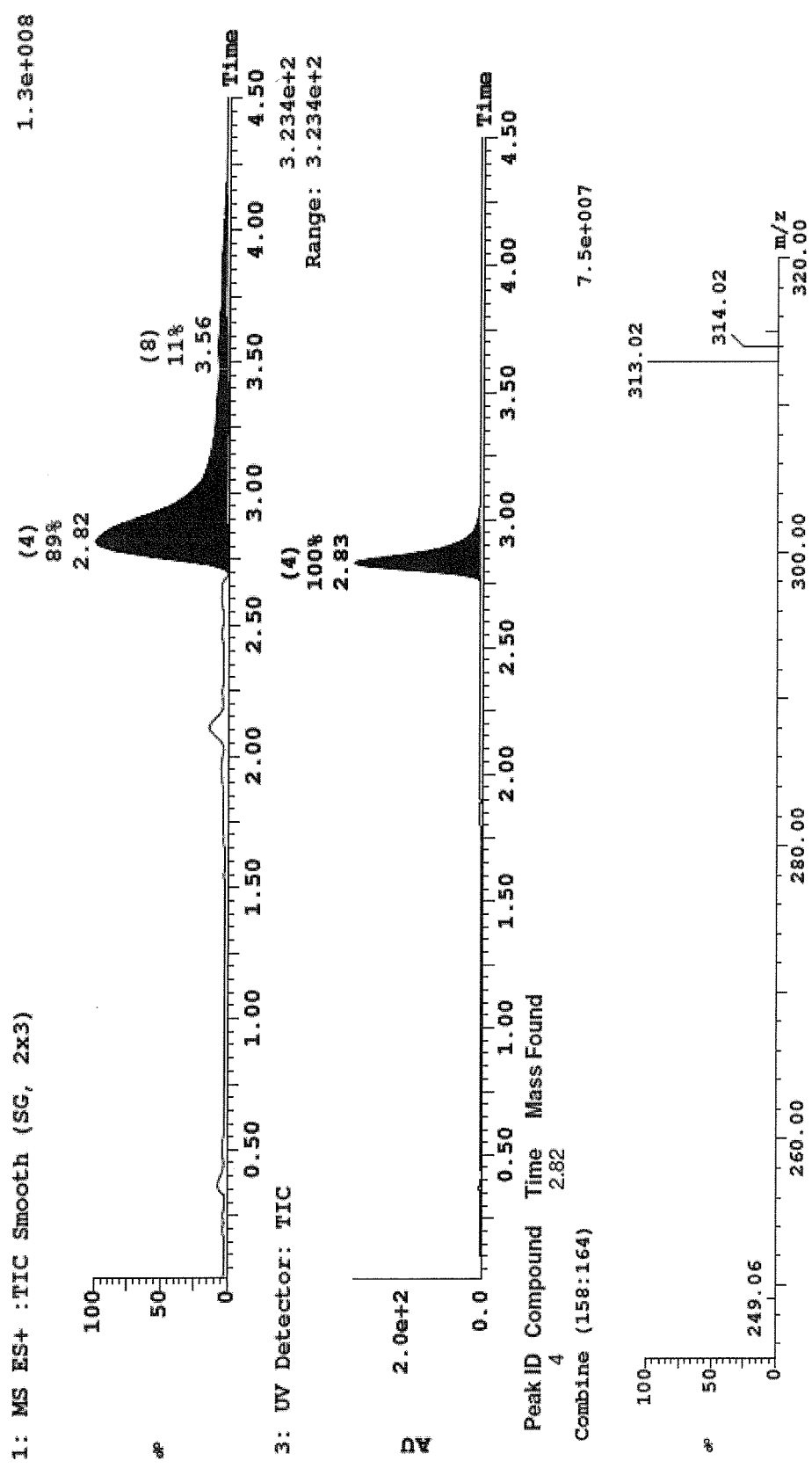
FIG. 108: Chromatogramm of Example Compound 108
Figure 109:
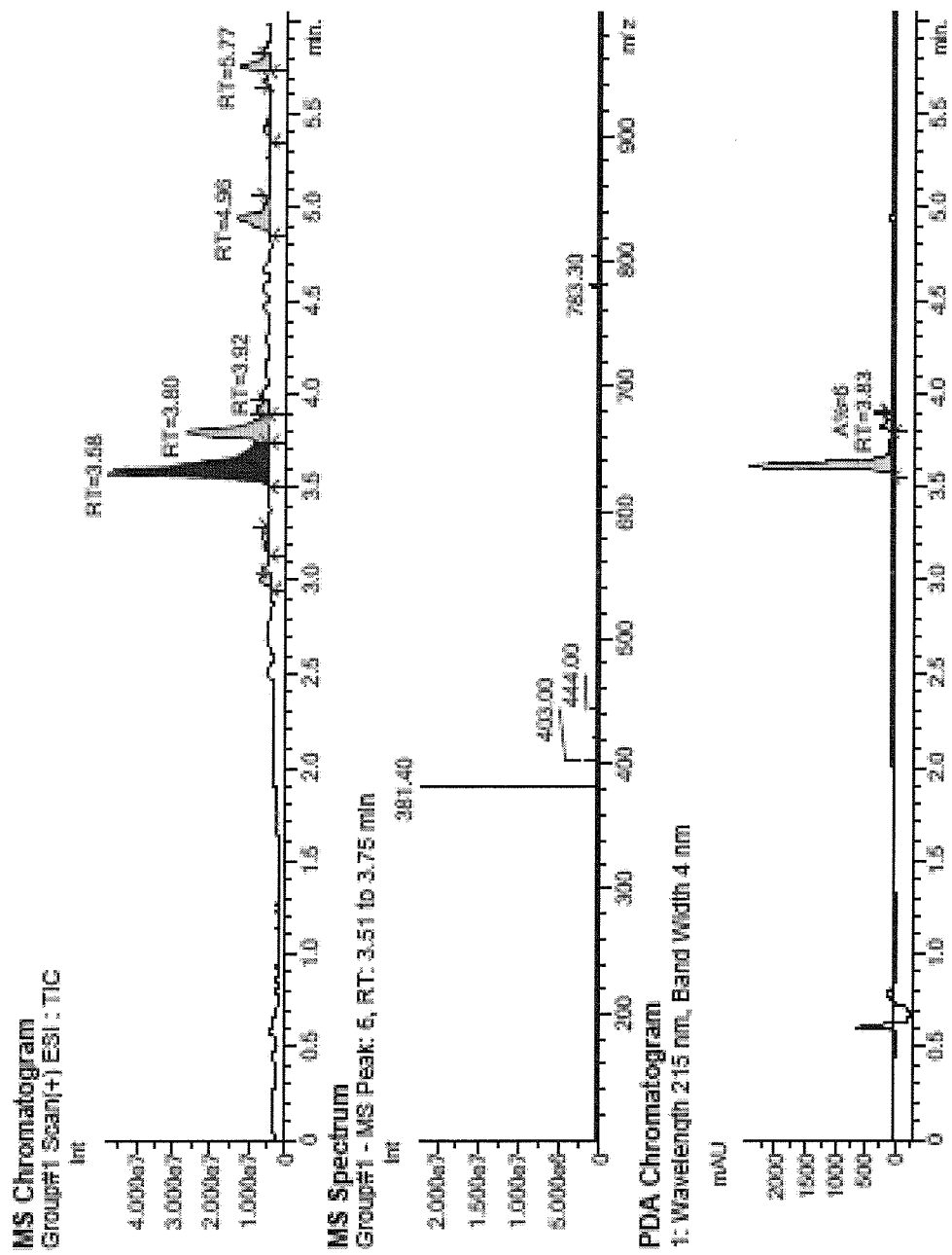
Figure 110:
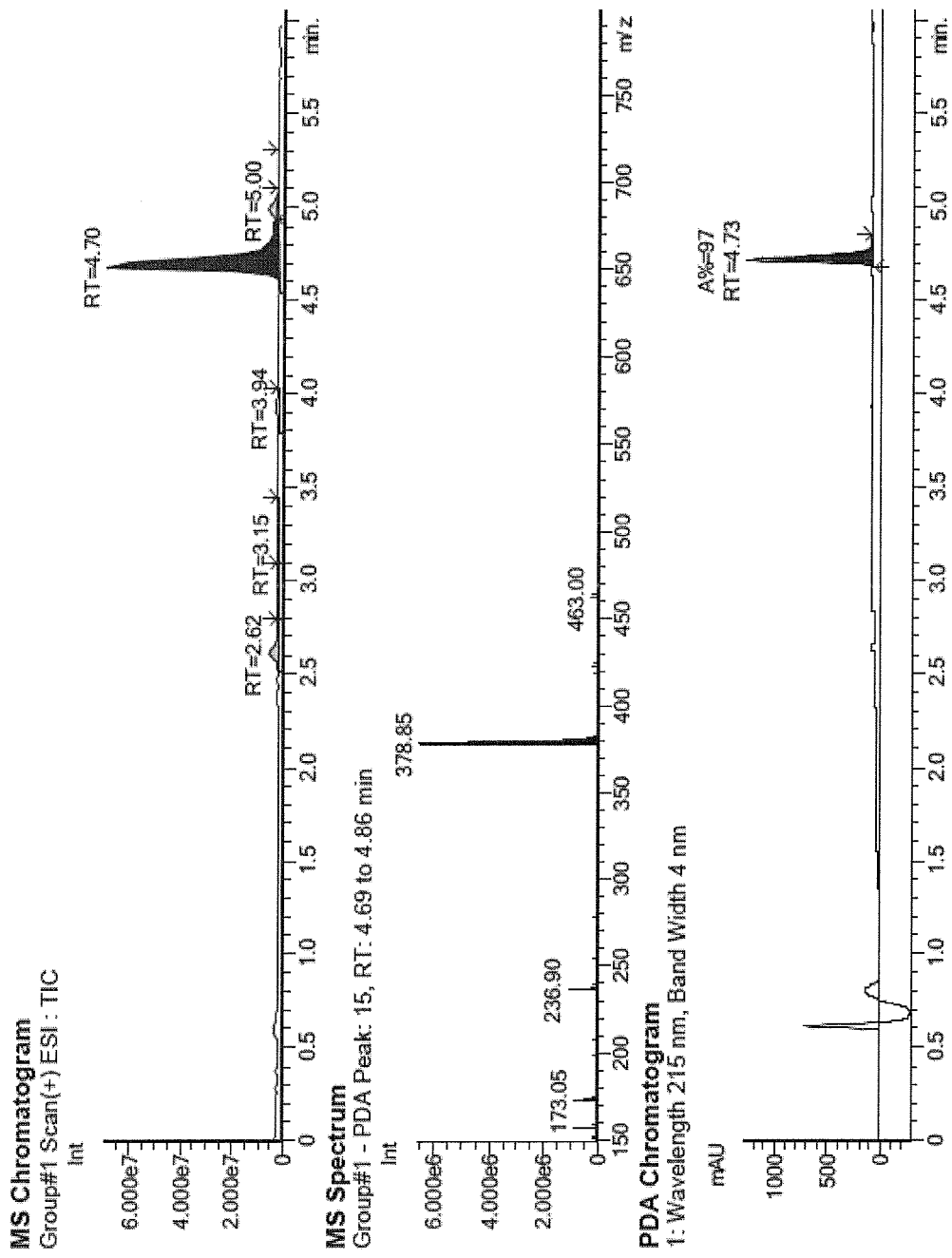
FIG. 110: Chromatogramm of Example Compound 110
Figure 111:
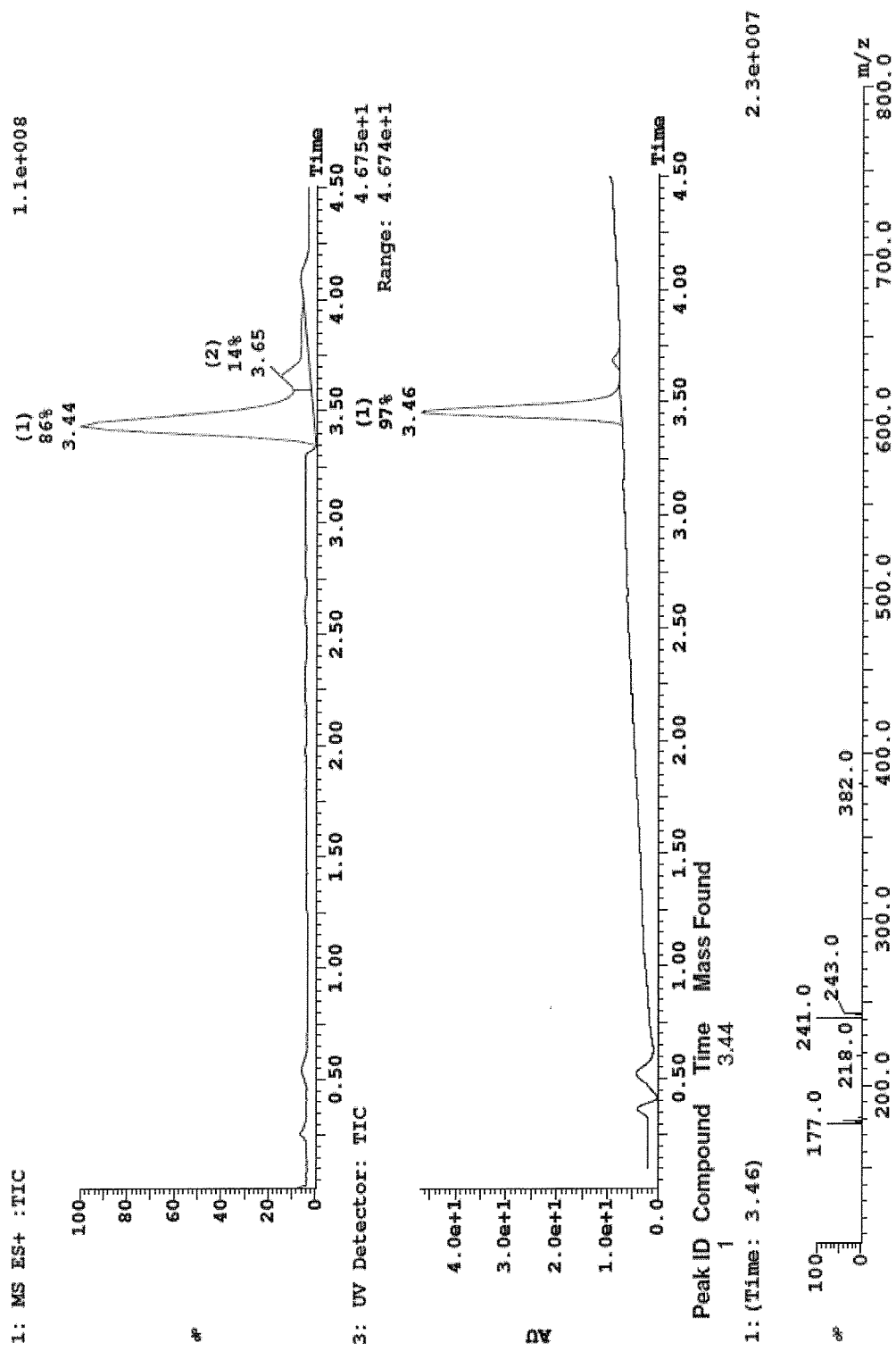
FIG. 111: Chromatogramm of Example Compound 111
Figure 112:
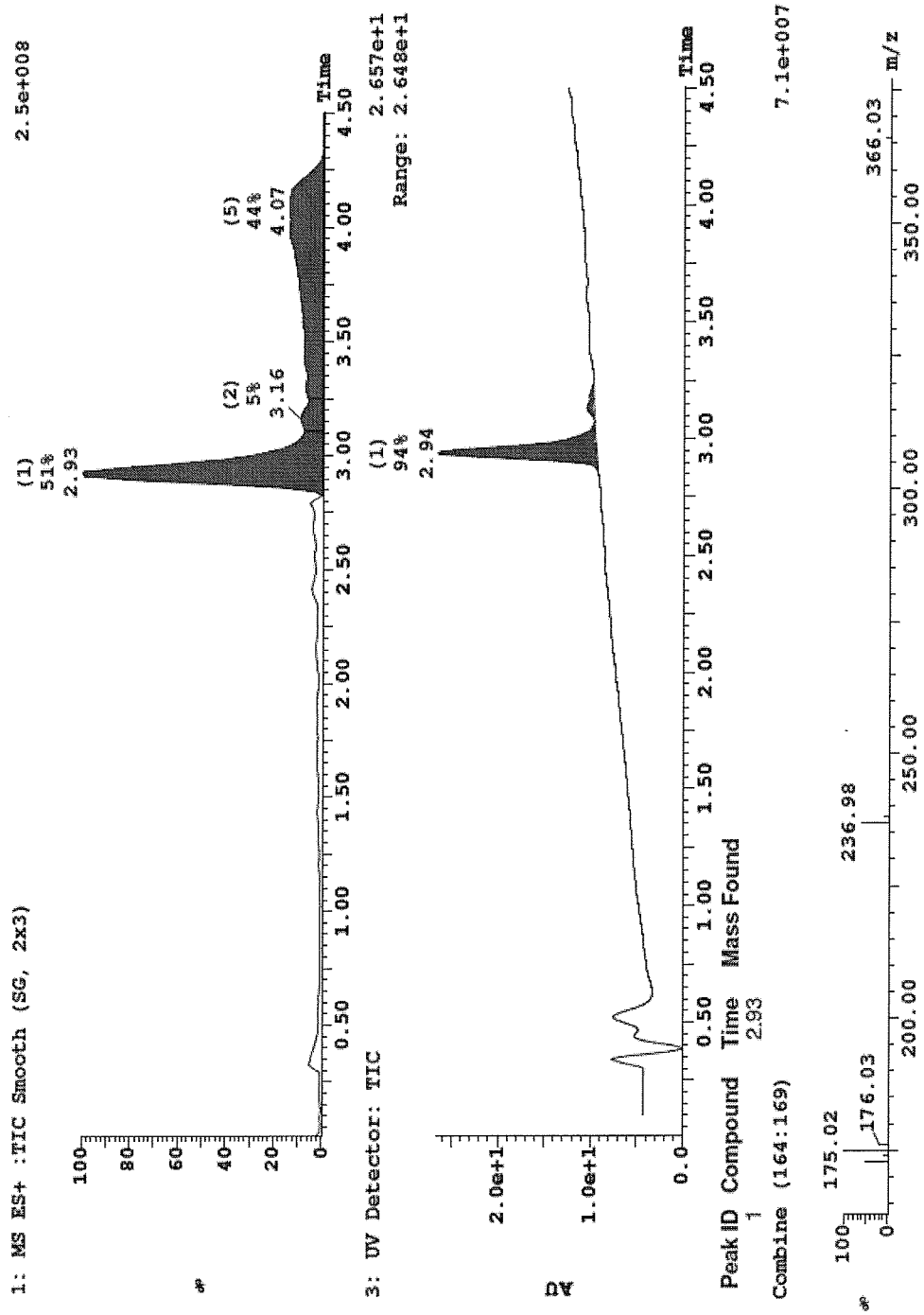
FIG. 112: Chromatogramm of Example Compound 112
Figure 113:
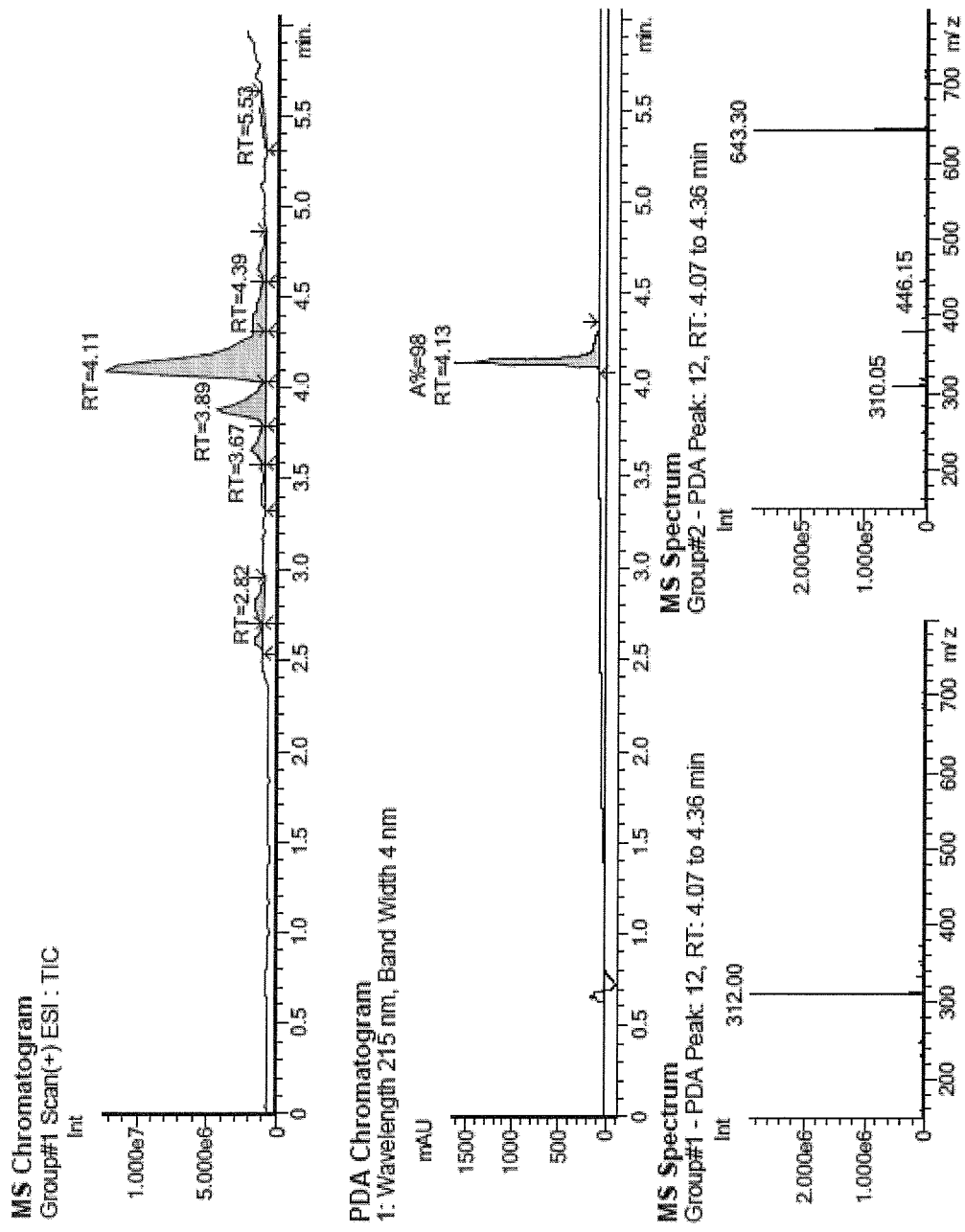
FIG. 113: Chromatogramm of Example Compound 113
Figure 114:
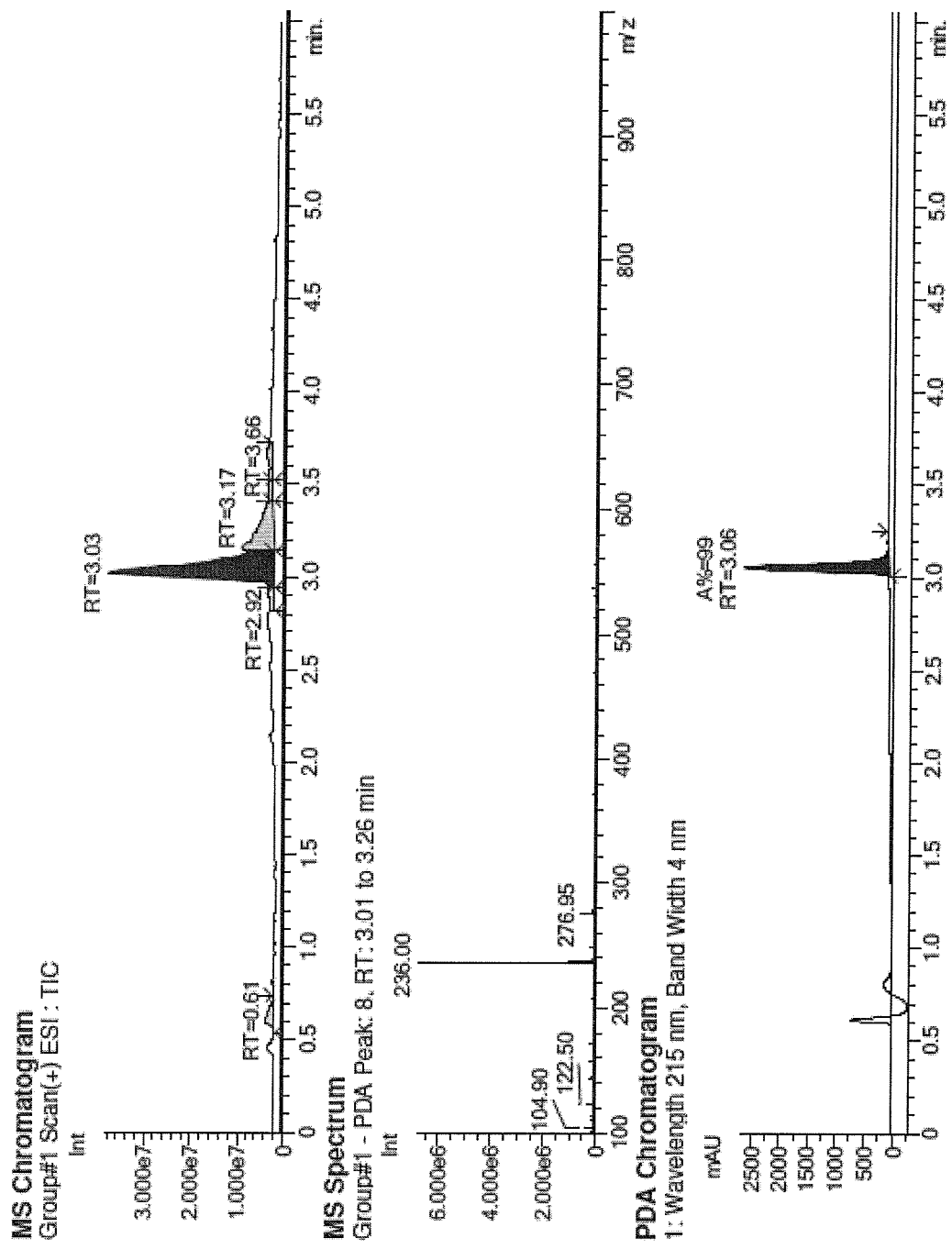
FIG. 114: Chromatogramm of Example Compound 114
Figure 115:
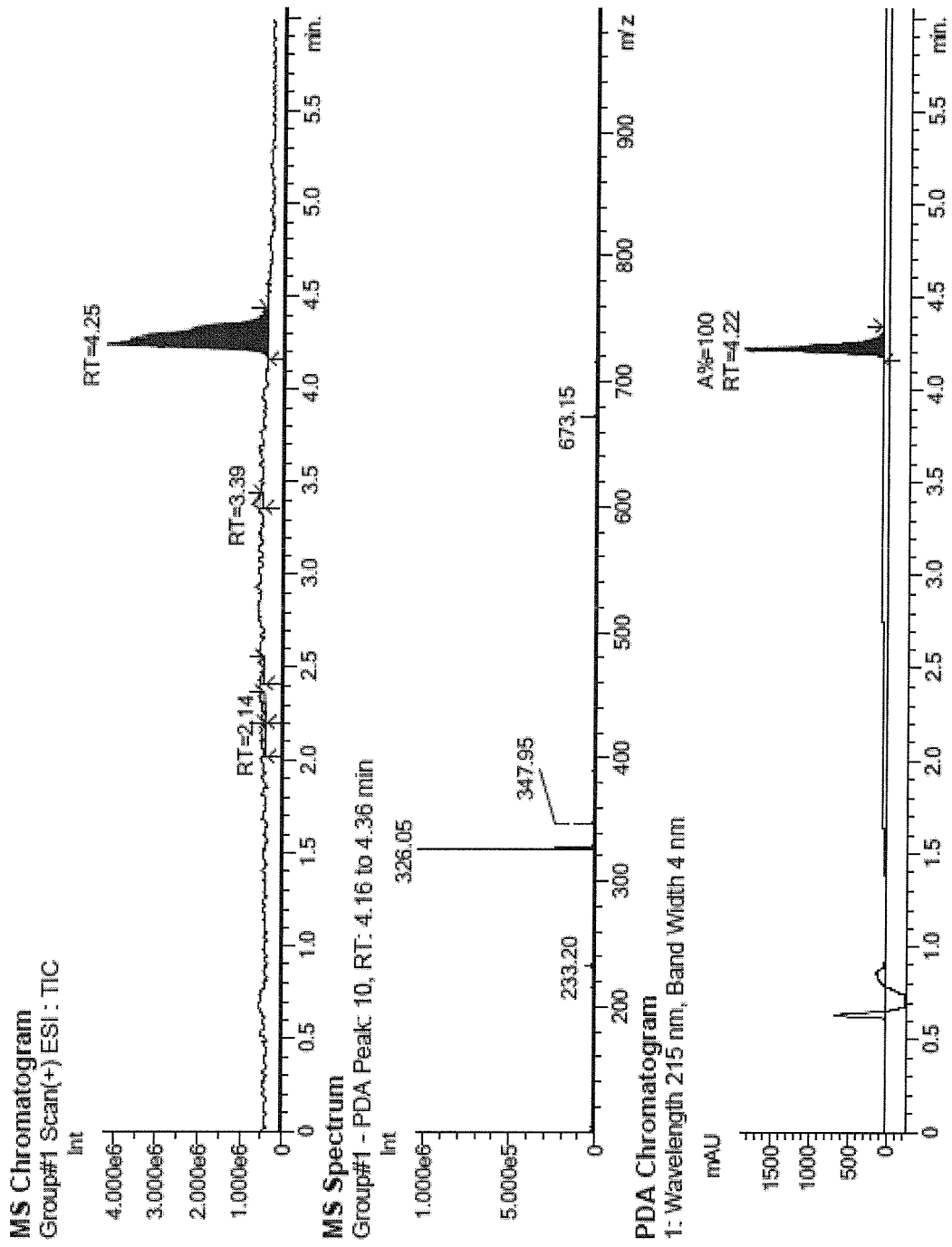
FIG. 115: Chromatogramm of Example Compound 115
FIG. 116 Chromatogramm of Example Compound 116
FIG. 117 Chromatogramm of Example Compound 225
FIG. 118 Chromatogramm of Example Compound 226
FIG. 119 Chromatogramm of Example Compound 227
FIG. 120 Chromatogramm of Example Compound 228
FIG. 121 Chromatogramm of Example Compound 229
FIG. 122 Chromatogramm of Example Compound 230
FIG. 123 Chromatogramm of Example Compound 231
FIG. 124 Chromatogramm of Example Compound 232
FIG. 125 Chromatogramm of Example Compound 233
Figure 116:
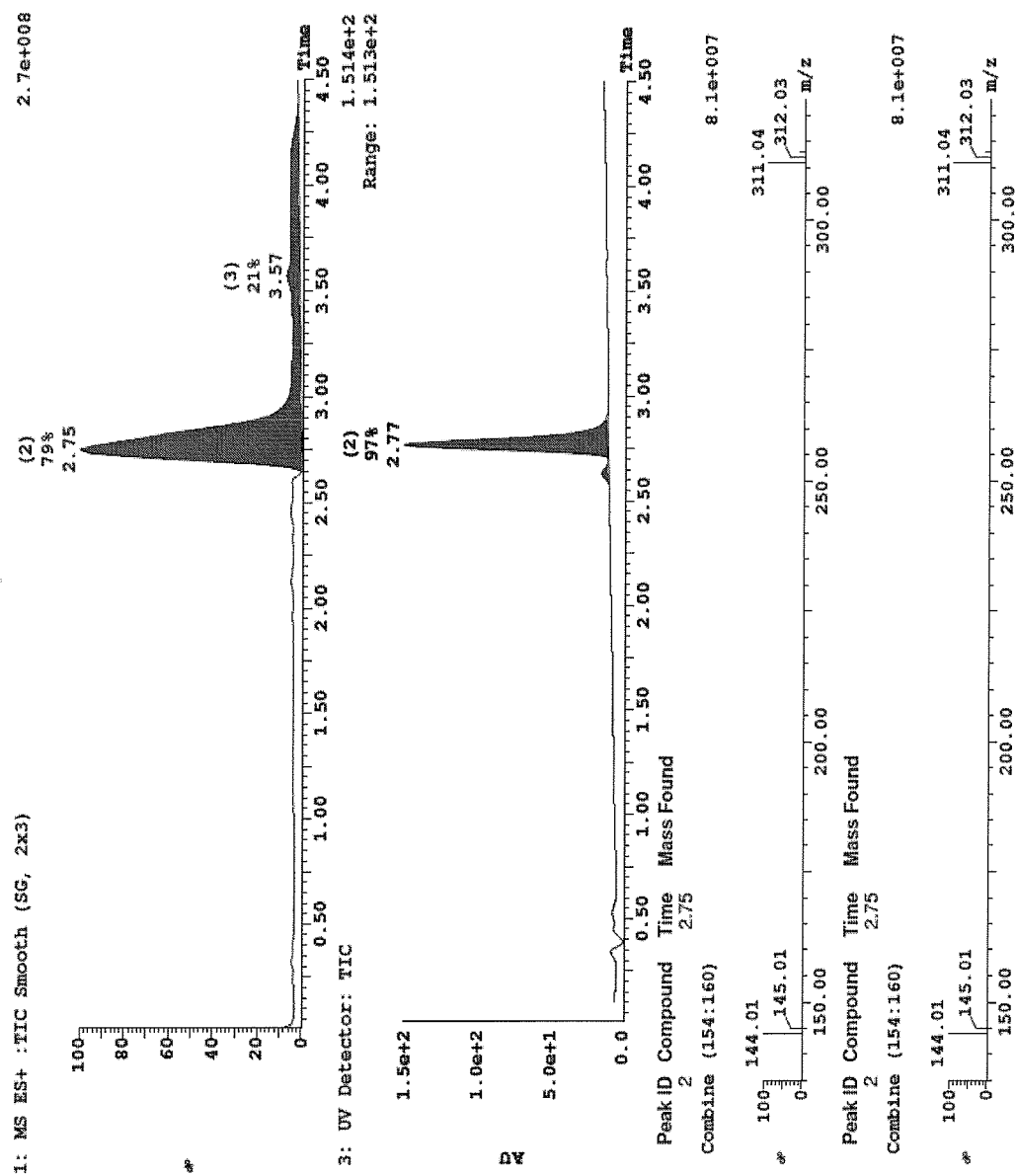
Figure 117:
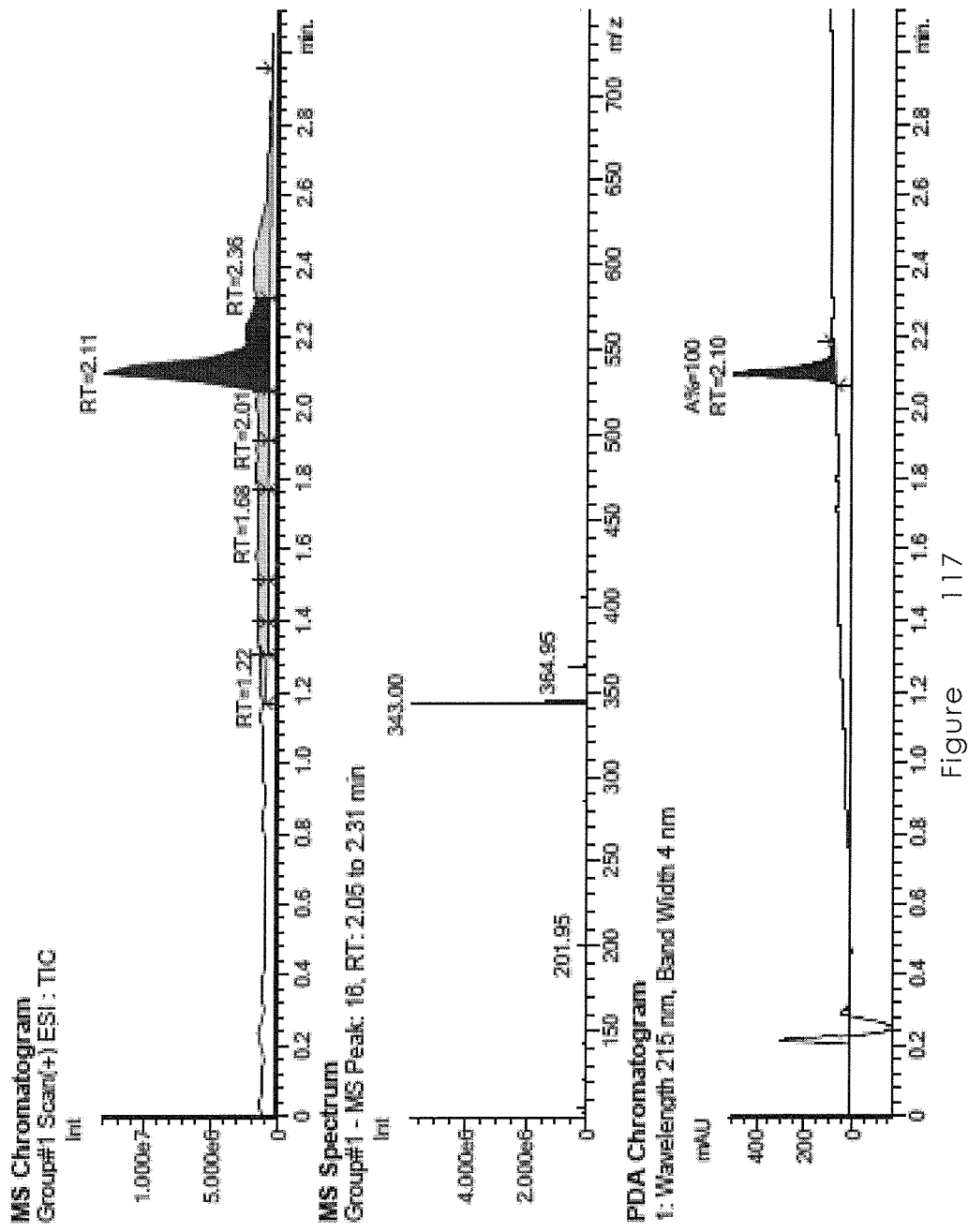
Figure 118:
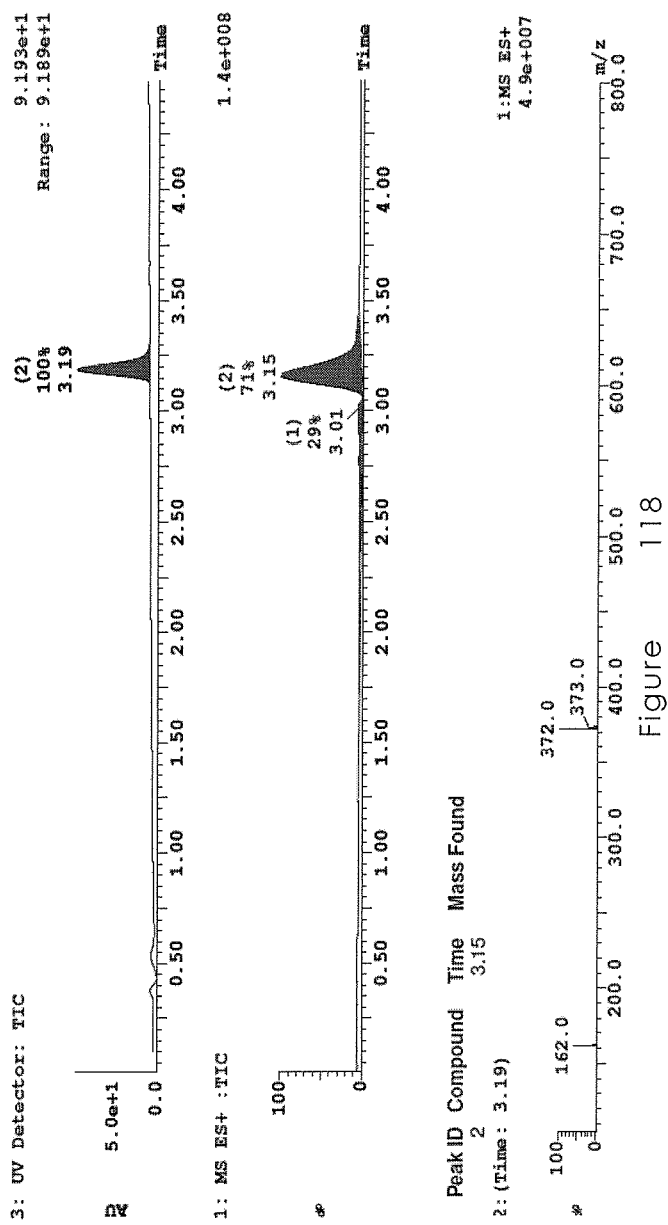
Figure 119:
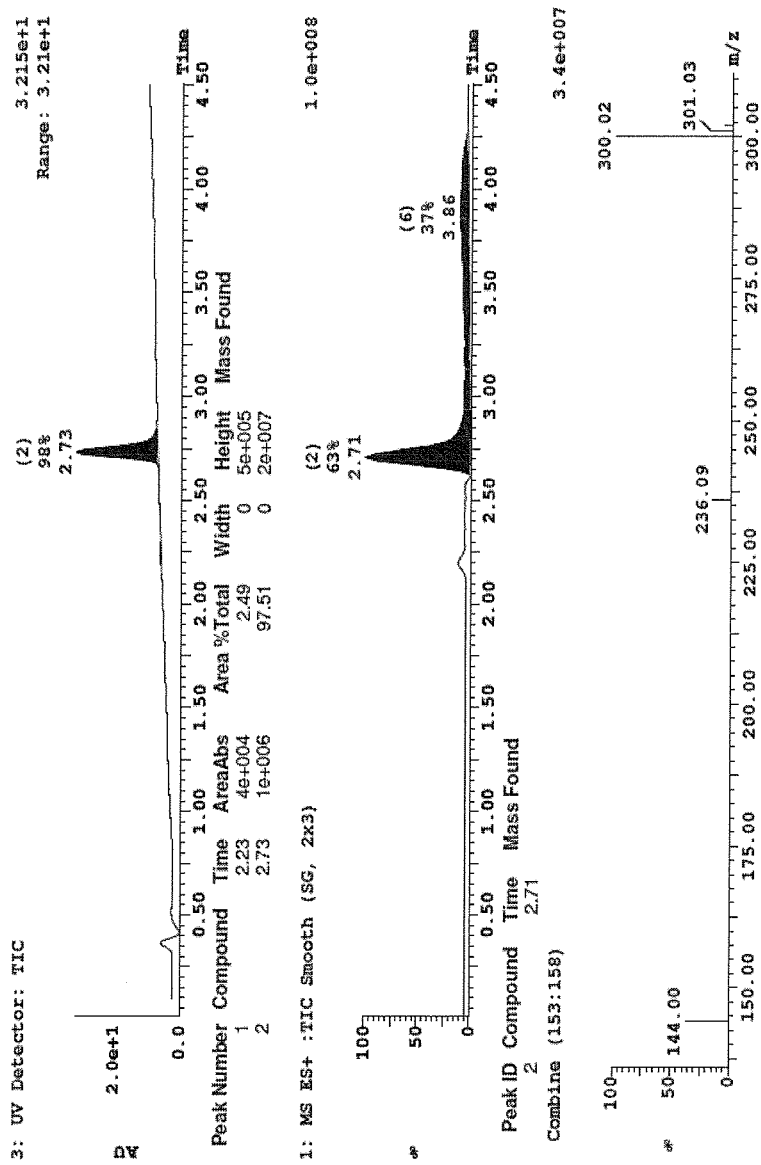
Figure 120:
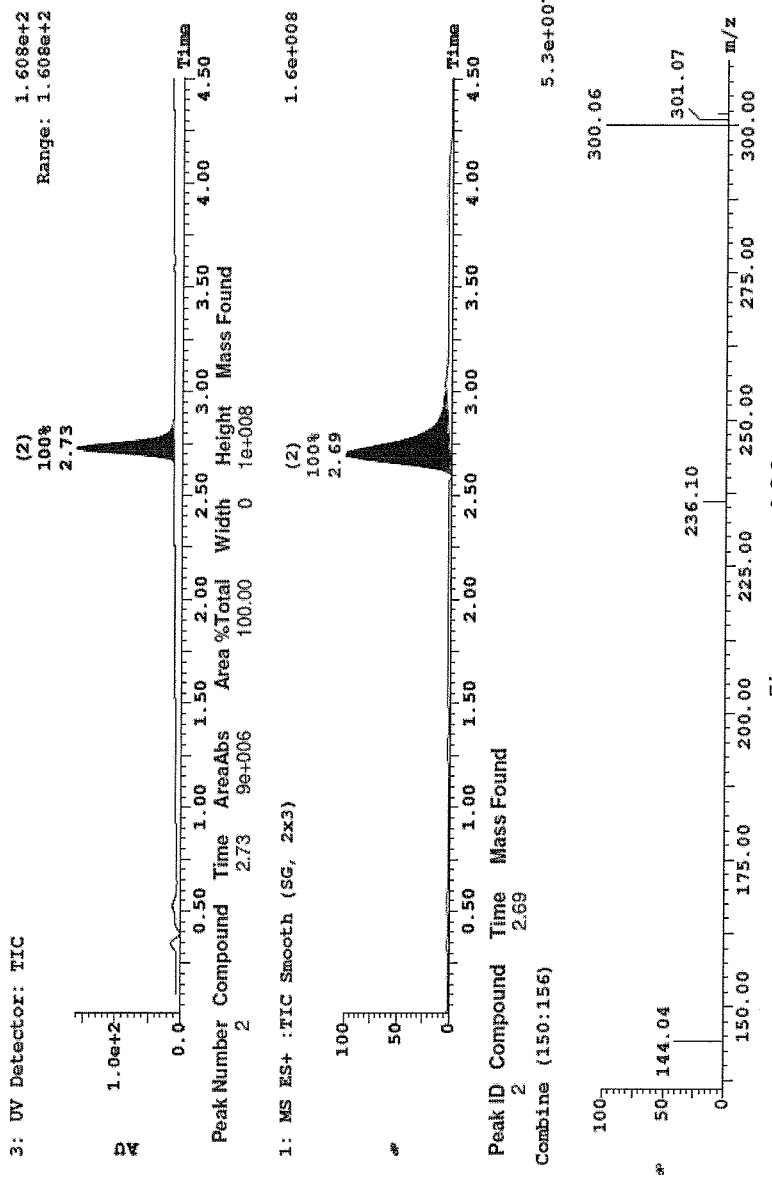
Figure 121:
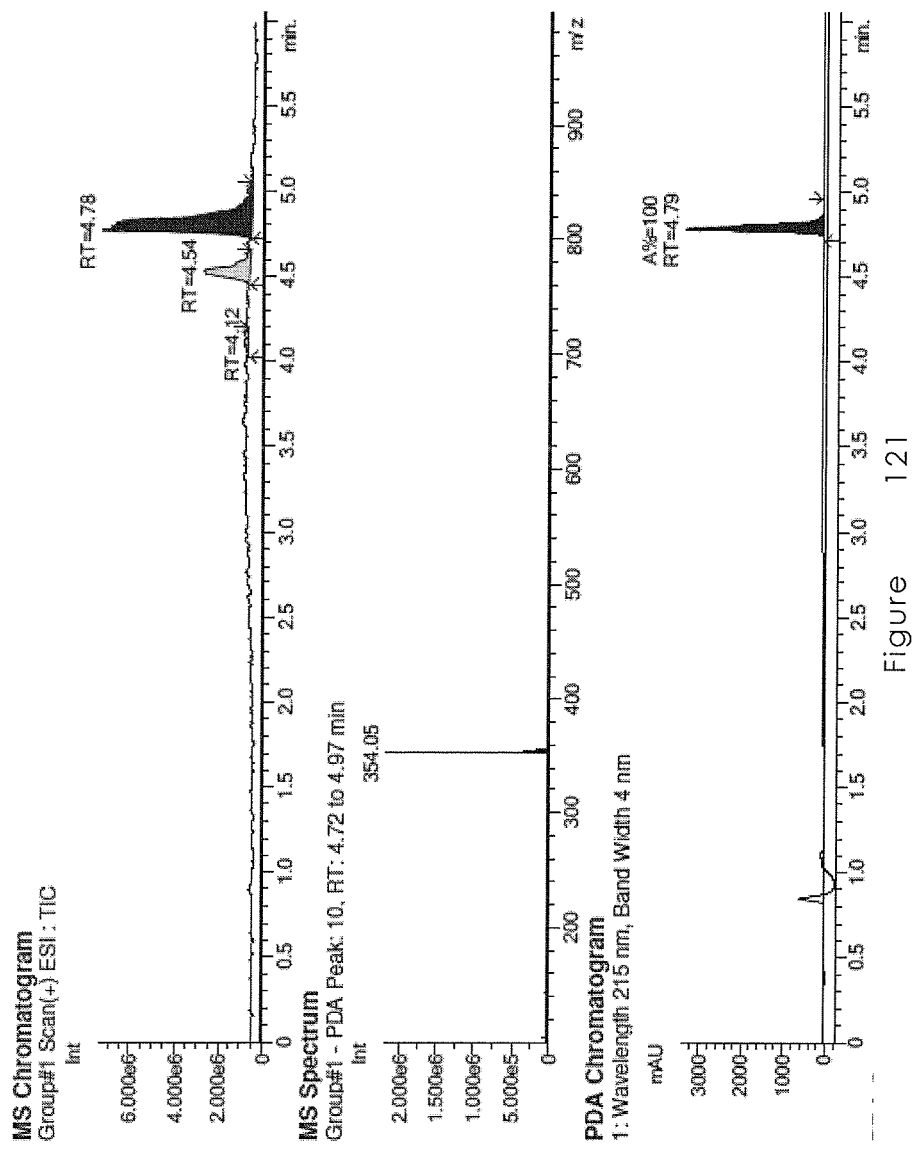
Figure 122:
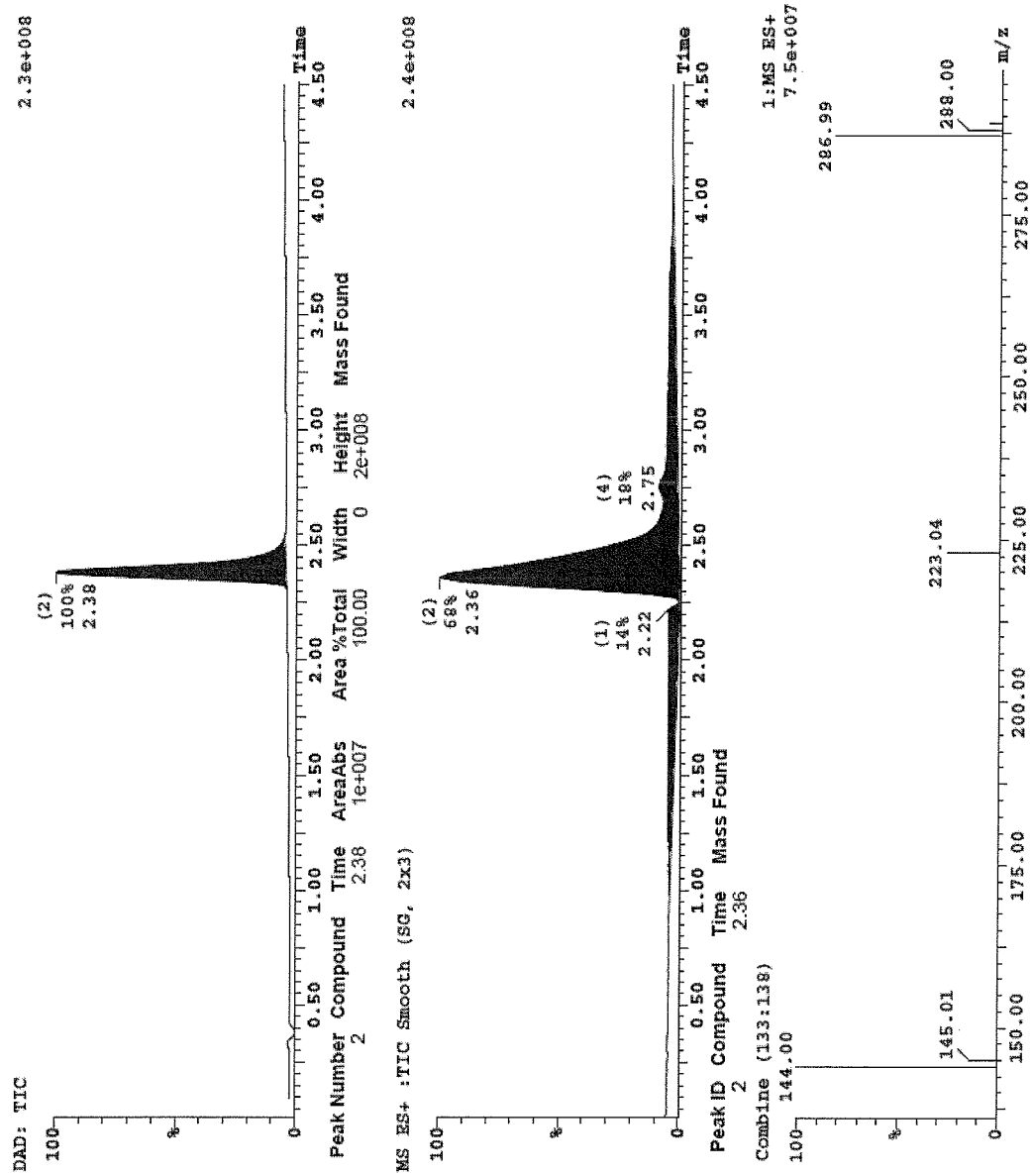
Figure 123:
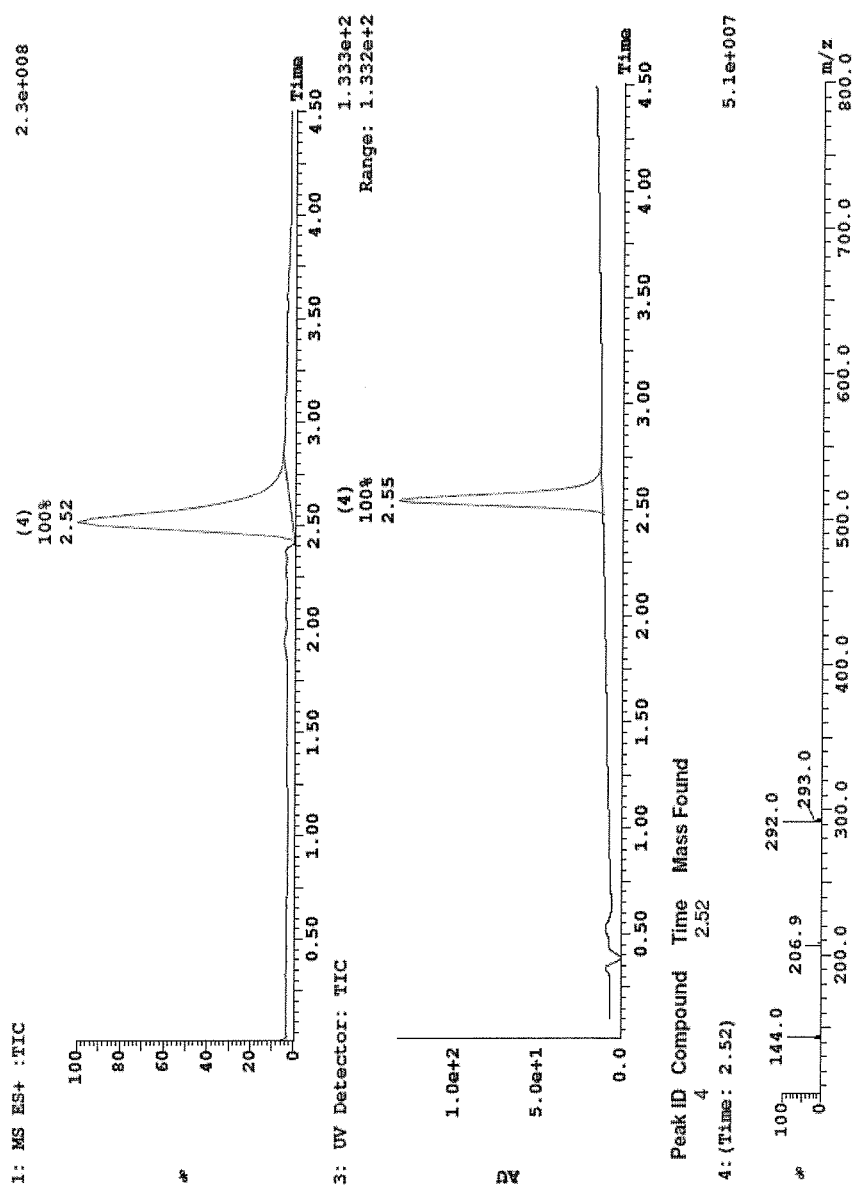
Figure 124:
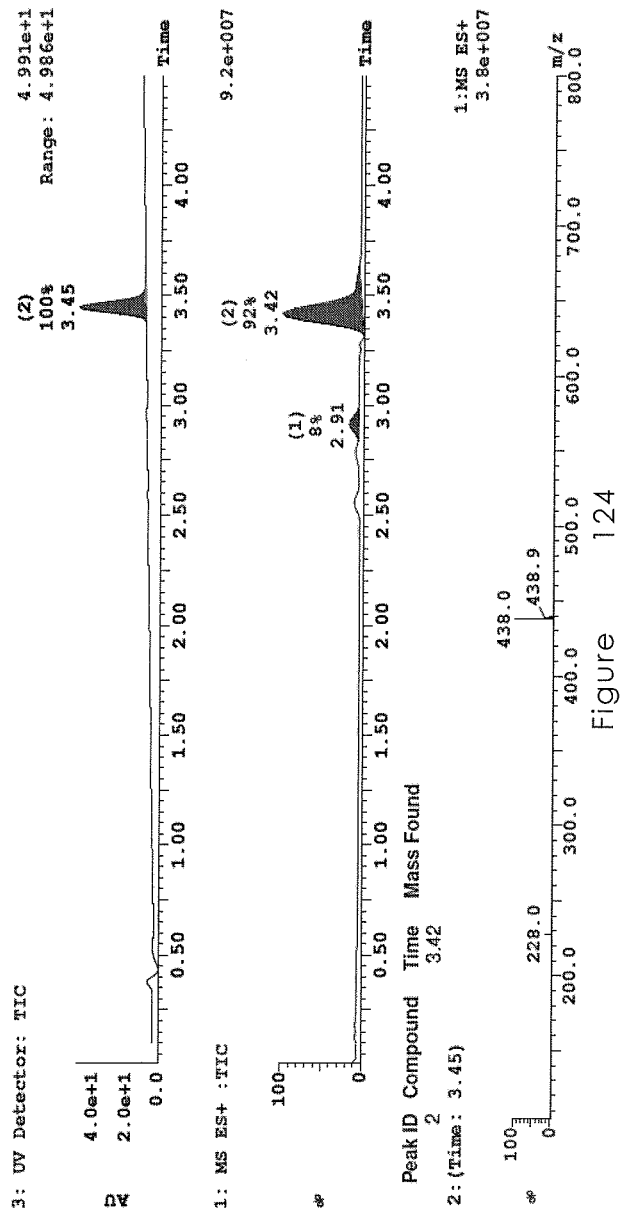
Figure 125:
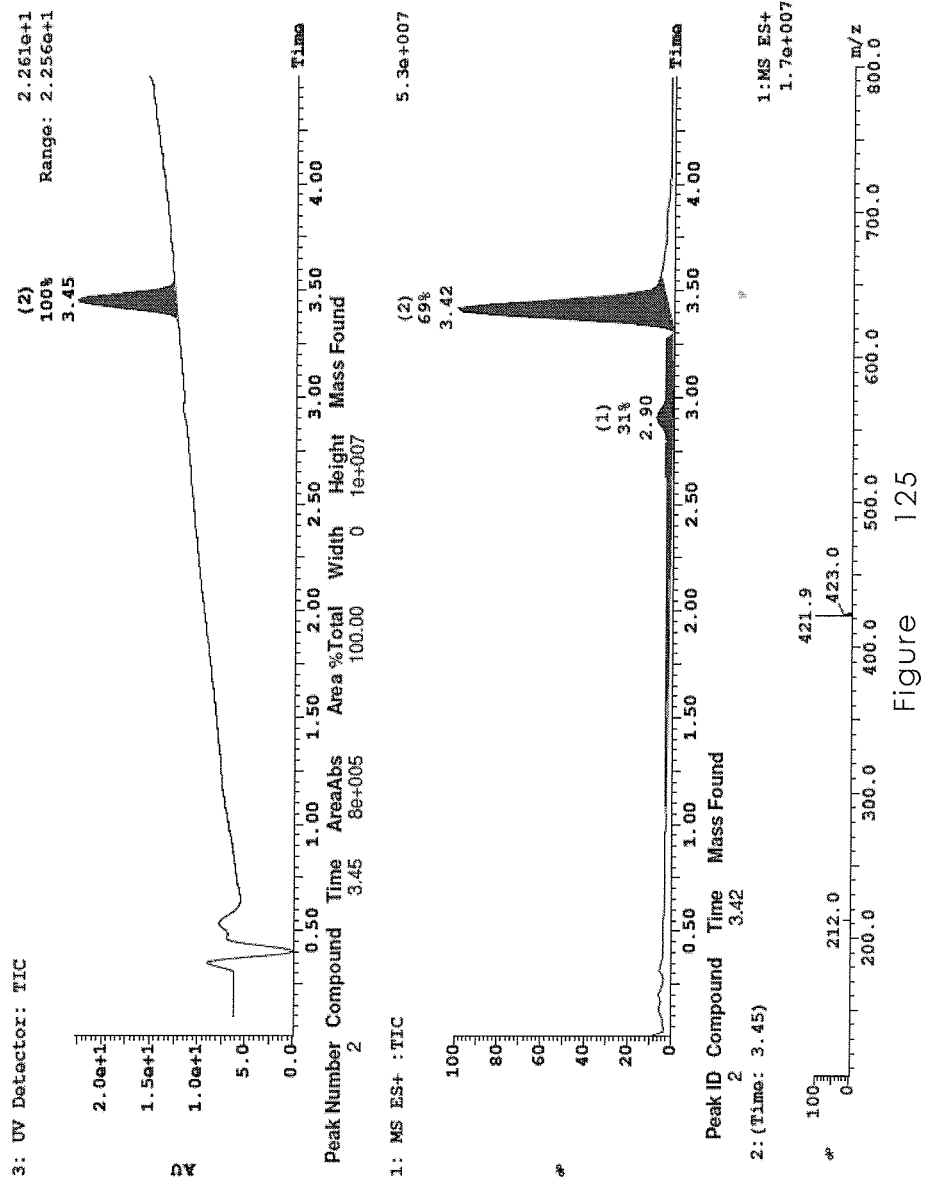

The invention claimed is:
1. A method for treating iron metabolism disorders selected from the group consisting of iron deficiency diseases and iron deficiency anemias, the method comprising administering to a patient in need thereof compounds of the formula (I)

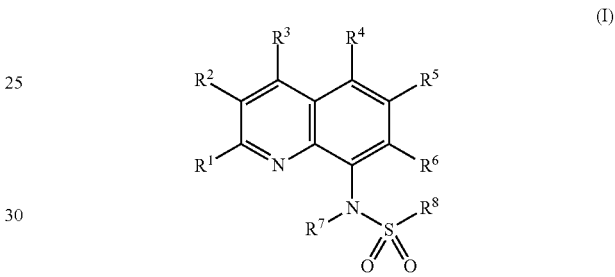

wherein $R^6$ and $R^8$ together define a residue of the formula

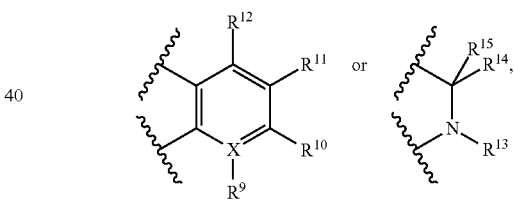

defining compounds according to the formula (Ia)

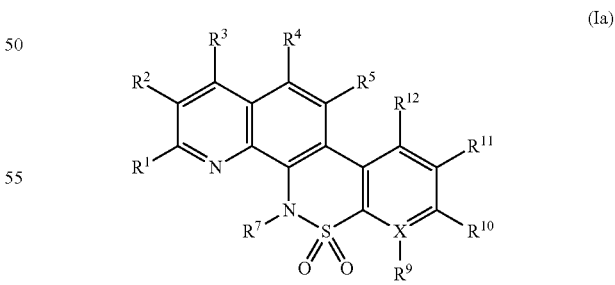

wherein
$R^1$ is selected from
hydrogen,
halogen and
alkyl, which may be substituted with 1 to 3 identical or different substituents, selected from the group consisting of:

hydroxyl,
halogen,
cyano,
alkoxy,
heterocyclyloxy,
carboxyl,
aryl, which may be substituted with 1 to 3 identical or different substituents selected from
hydroxyl,
halogen,
nitro,
cyano,
amino,
mercapto,
alkyl,
acyl,
alkoxy,
aryloxy,
heterocyclyloxy,
alkoxycarbonyl
aryl,
heterocyclyl, and
heterocyclyl, which may be substituted with 1 to 3 substituents as defined for aryl,
acyl, including aliphatic acyl (alkanoyl=alkyl-CO—), with alkyl as defined above, aromatic acyl (aroyl=aryl-CO—) with aryl as defined above, and heterocyclic acyl (heterocycloyl=heterocyclyl-CO—), with heterocyclyl as defined above,
aryloxy, (aryl-O) with aryl as defined above,
amino, which may be substituted with one or two selected from alkyl, as defined above, aryl, heterocyclyl and acyl, each as defined above, to include
amino,
mono- or dialkylamino,
mono- or diarylamino,
(N-alkyl)(N-aryl)amino,
mono- or diheterocyclylamino,
(N-alkyl)(N-heterocyclyl)amino,
(N-aryl)(N-heterocyclyl)amino,
mono- or diacylamino,
mercapto,
alkyl-, aryl- or heterocyclylsulfonyl (R—SO$_2$—) with R being alkyl, aryl or heterocyclyl, each as defined above;
$R^2$ is selected from
hydrogen and
alkyl as defined for $R^1$;
$R^3$ is selected from
hydrogen,
halogen,
aminocarbonyl, wherein the amino group may be substituted as defined for $R^1$,
amino, as defined for $R^1$
alkyl as defined for $R^1$,
alkoxycarbonyl (—(C=O)—O-alkyl), with alkyl as defined for $R^1$,
alkoxy (alkyl-O), with alkyl as defined for $R^1$, and
heterocyclyl, which may be substituted with 1 to 3 substituents as defined as aryl for $R^1$;
$R^4$ is selected from
hydrogen,
halogen,
cyano,
aminocarbonyl, as defined for $R^3$,
amino, as defined for $R^1$,
alkyl, as defined for $R^1$,
acyl, including aliphatic acyl (alkanoyl=alkyl-CO—), with alkyl as defined for $R^1$, aromatic acyl (aroyl=aryl-CO—) with aryl as defined for $R^1$, and heterocyclic acyl (heterocycloyl=heterocyclyl-CO—), with heterocyclyl as defined for $R^1$,
alkoxy, as defined for $R^1$e, and
heterocyclyl, as defined for $R^1$;
$R^5$ is selected from
hydrogen,
halogen,
alkyl, as defined for $R^1$, and
alkoxy, as defined for $R^1$; and
$R^7$ is selected from
hydrogen and
alkyl, as defined for $R^1$;
wherein
X is C or N;
$R^9$, $R^{10}$, $R^{11}$ and $R^{12}$ are the same or different and are independently selected from the group consisting of:
hydrogen,
hydroxyl,
carboxyl,
halogen,
cyano,
nitro,
amino, as defined for $R^1$,
alkyl, as defined for $R^1$,
acyl, as defined for $R^1$,
alkoxycarbonyl, as defined for $R^1$,
acyloxy (—O—(C=O)-alkyl, —O—(C=O)-aryl, —O—(C=O)-heterocyclyl) with acyl as defined for $R^1$,
alkoxy, as defined for $R^1$,
aryloxy (aryl-O), with aryl as defined for $R^1$,
aryl, as defined for $R^1$, and
heterocyclyl, as defined for $R^1$;
and defining compounds according to the formula (Ib)

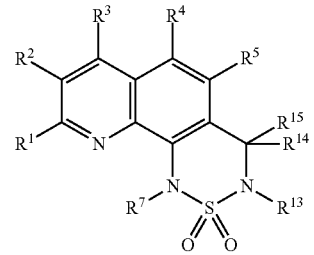

(Ib)

wherein
$R^{13}$ is selected from the group consisting of:
hydrogen,
sulfonyl (—SO$_2$R), with R being hydroxyl (—OH), alkyl, aryl or heterocyclyl, each as defined for $R^1$;
alkyl, as defined for $R^1$,
acyl, as defined for $R^1$,
alkoxycarbonyl, as defined for $R^1$,
aryl, as defined for $R^1$, and
heterocyclyl, as defined for $R^1$; and
$R^{14}$ and $R^{15}$ are the same or different and are respectively selected from the group consisting of:
hydrogen,
hydroxyl,
halogen,
cyano,
carboxyl, amino, as defined for R¹,
alkyl, as defined for
acyl, as defined for R¹,
alkoxycarbonyl, as defined for R¹,
acyloxy, as defined for R¹,
alkoxy, as defined for R¹,
aryloxy, as defined for R¹,
alkenyl, which may be substituted with 1 to 3 identical or different substituents, selected from hydroxyl, halogen and alkoxy,
aryl, as defined for R¹, and
heterocyclyl, as defined for R¹;
or pharmaceutically acceptable salts thereof.

2. The method according to claim 1, wherein
R⁹, R¹⁰, R¹¹ and R¹² are the same or different and are respectively selected from the group consisting of:
hydrogen,
halogen,
alkyl,
alkoxy, each as defined in claim 1;
or pharmaceutically acceptable salts thereof.

3. The method according to claim 1, wherein
R¹³ is selected from the group consisting of:
hydrogen,
alkyl, and
aryl, each as defined in claim 1; and
R¹⁴ and R¹⁵ are the same or different and are respectively selected from the group consisting of:
hydrogen,
alkyl,
aryl and
heterocyclyl, each as defined in claim 1;
or pharmaceutically acceptable salts thereof.

4. The method according to claim 1, wherein the compounds are selected from:

2
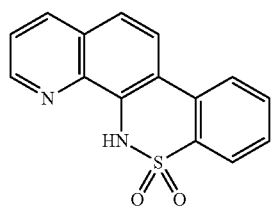

3
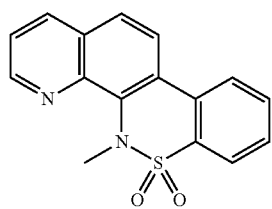

22
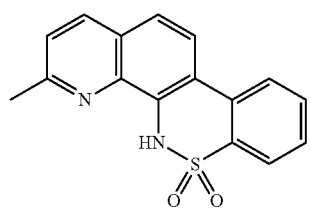

-continued

74
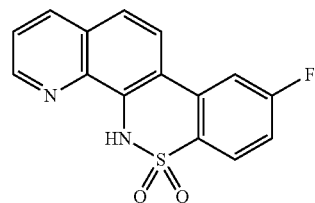

78
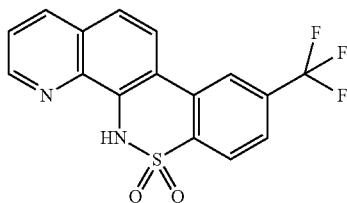

104
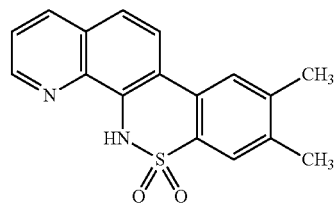

105
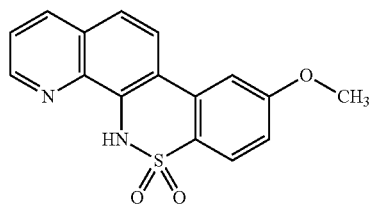

106
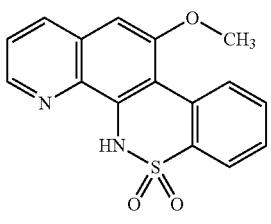

107
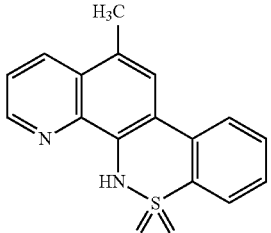

108
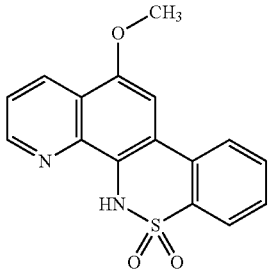

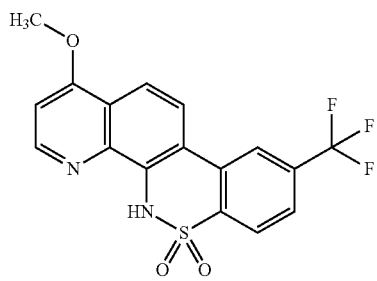
109
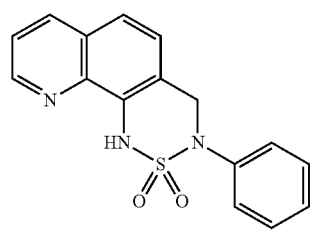
113
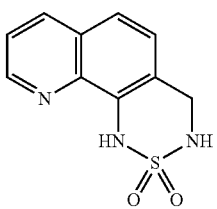
114
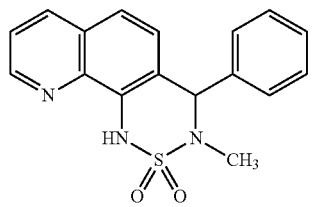
115
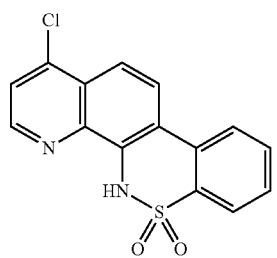
305
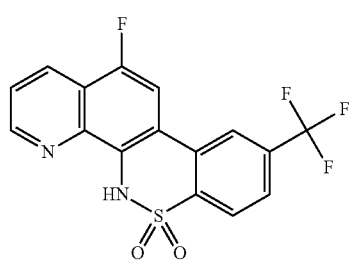
306
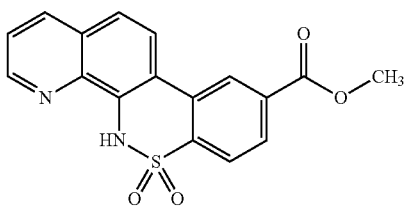
307
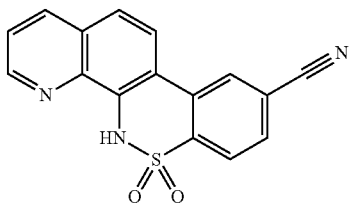
308
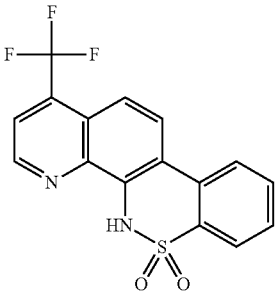
309
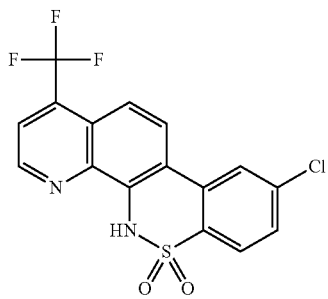
310
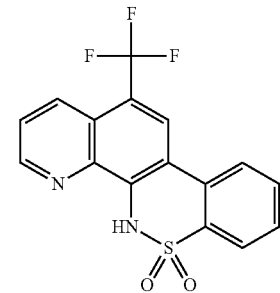
311
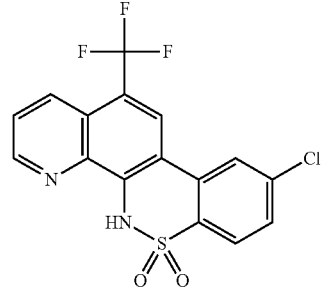
312

| | |
|---|---|
| 313 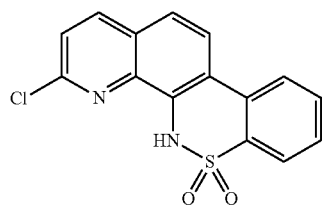 | 319 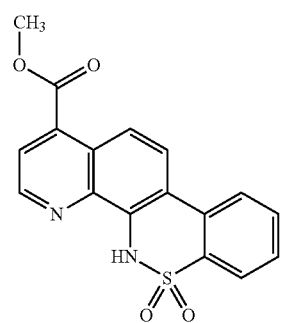 |
| 314 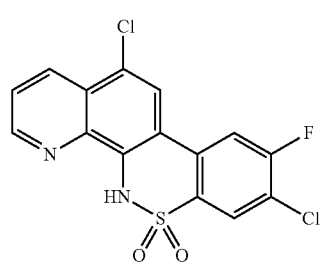 | 321 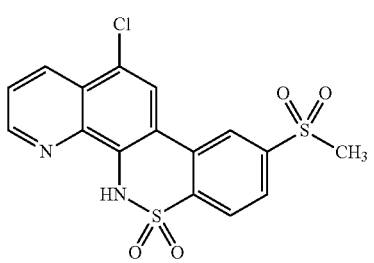 |
| 315 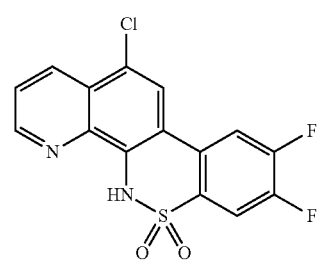 | 323 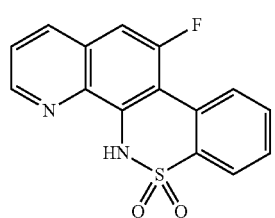 |
| 316 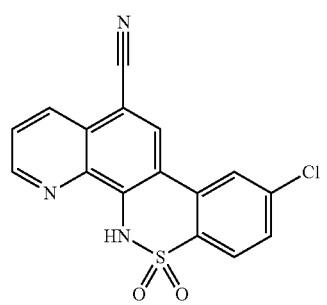 | 324 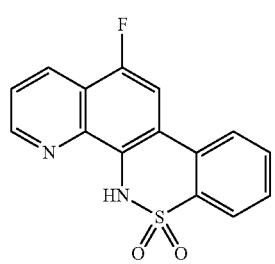 |
| 317 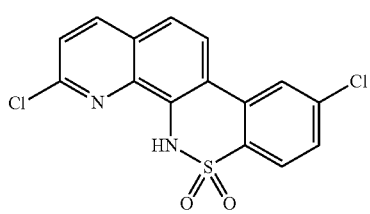 | 325 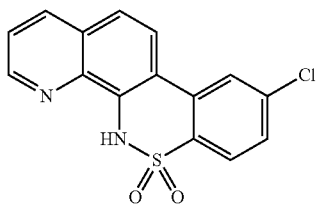 |
| 318 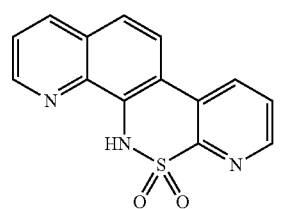 | 326 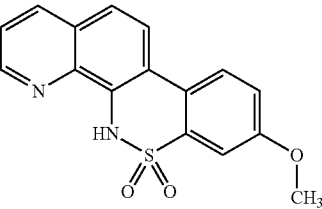 |

| | |
|---|---|
| 327 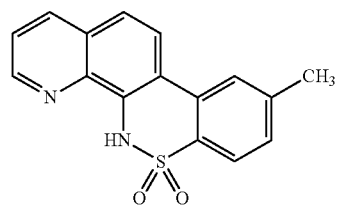 | 334 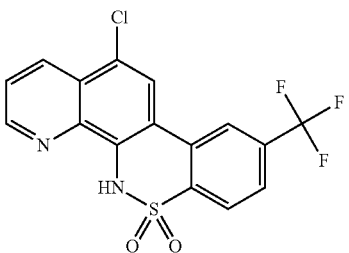 |
| 328 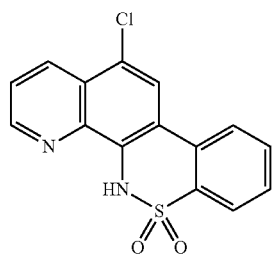 | 335 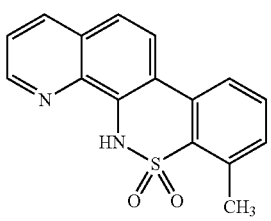 |
| 329 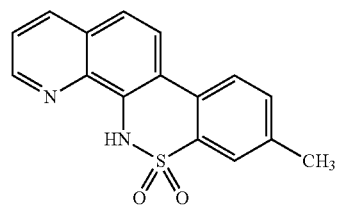 | 382 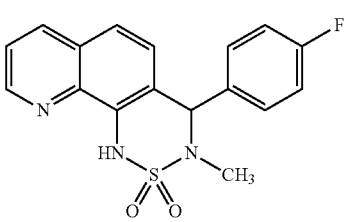 |
| 330 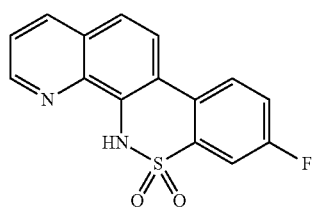 | 383 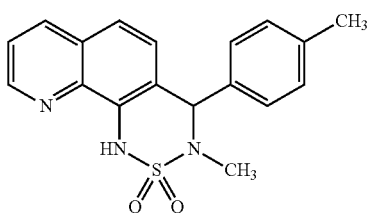 |
| 331 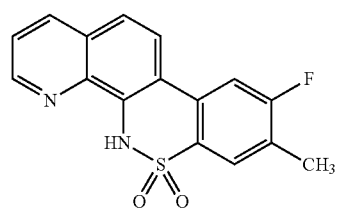 | 384 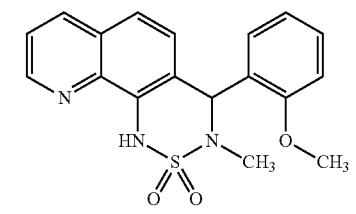 |
| 332 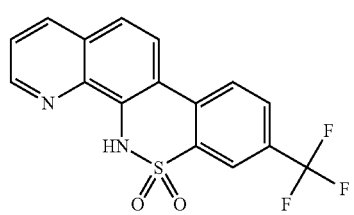 | 385 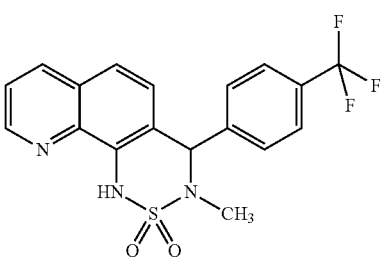 |
| 333 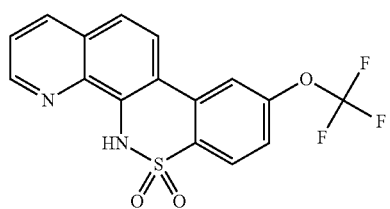 | 386 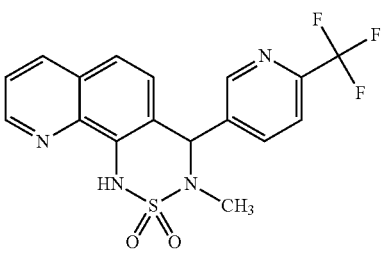 |

387 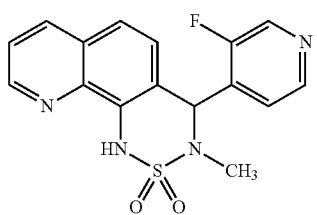
388 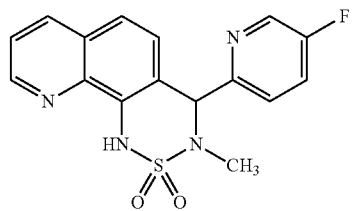
389 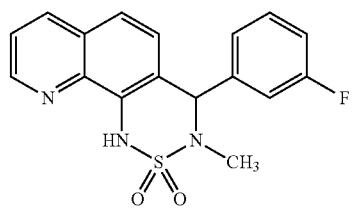
390 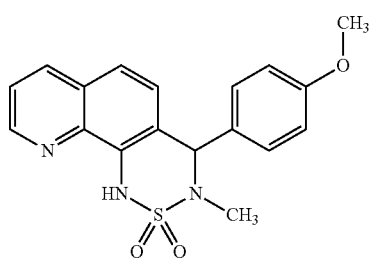
391 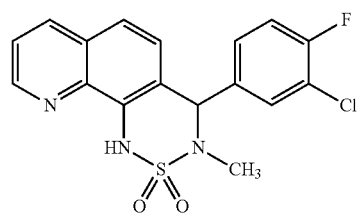
392 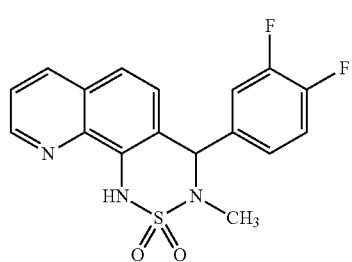
393 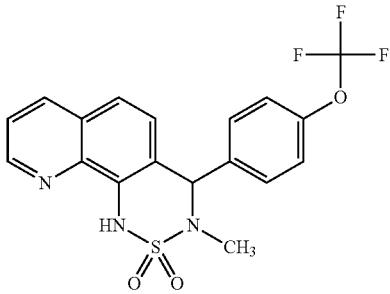
394 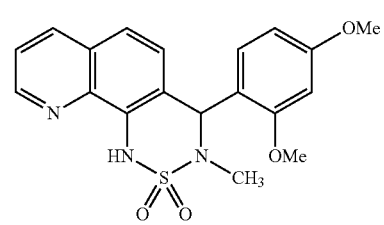
395 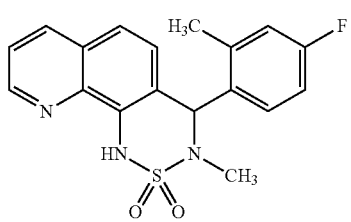
396 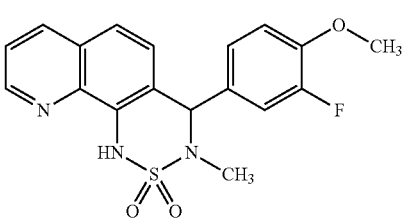
398 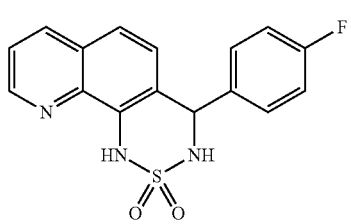
399 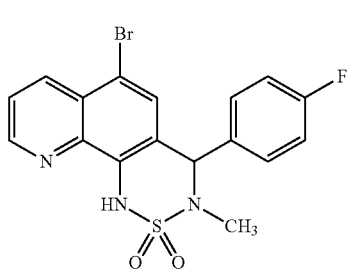

369
-continued
401 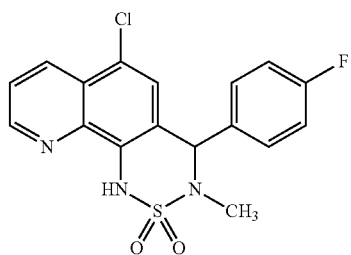
402 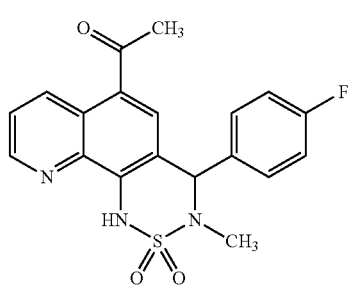
403 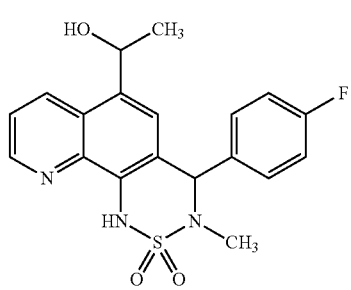
405 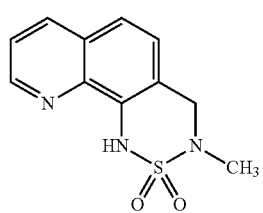
407 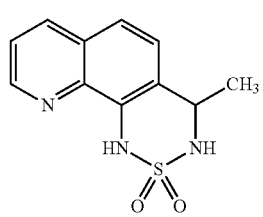
412 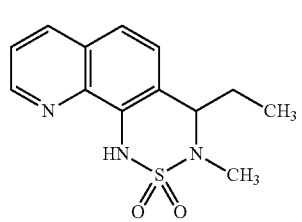
370
-continued
413 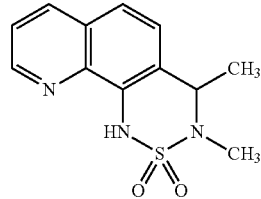
416 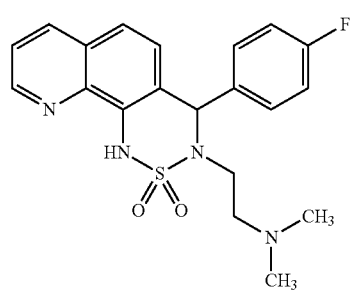
424 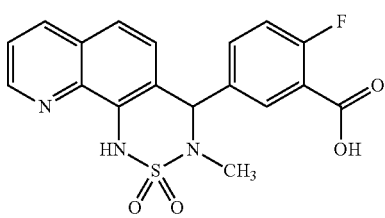
425 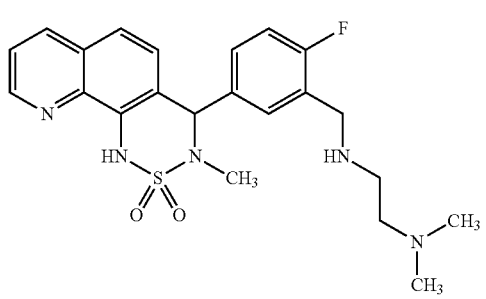
426 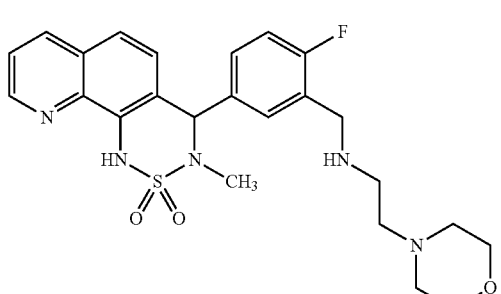
427 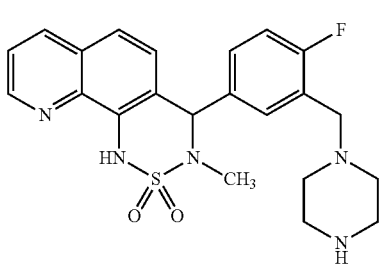

428 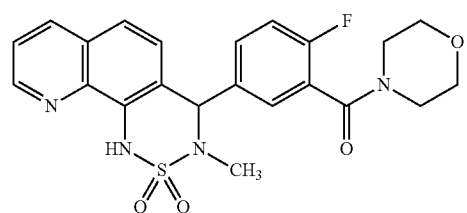
429 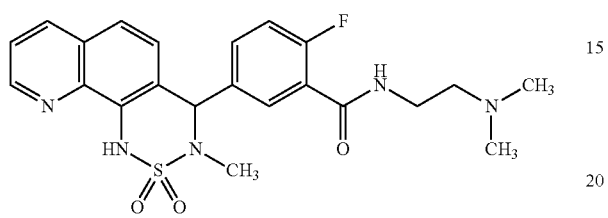
494 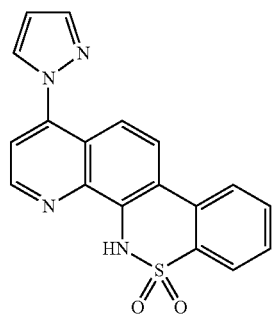
495 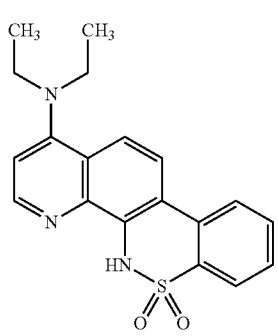
496 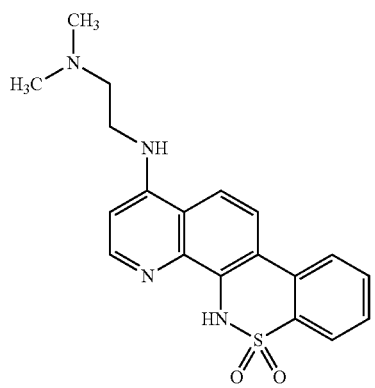
497 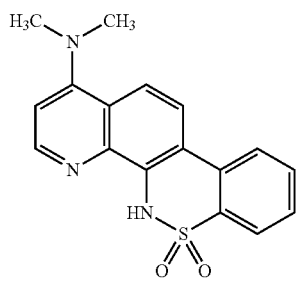
498 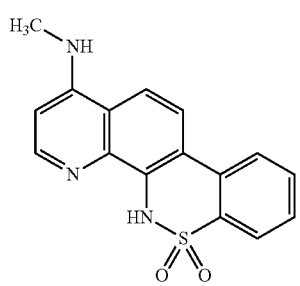
499 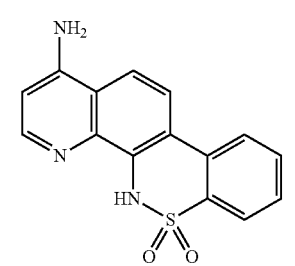
502 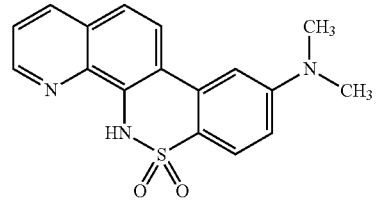
504 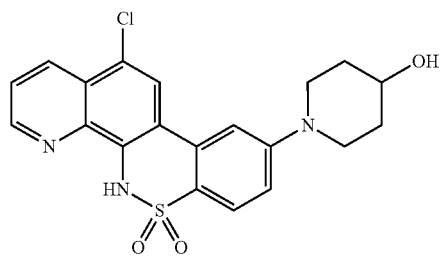
505 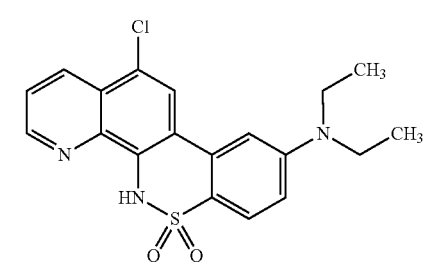

506
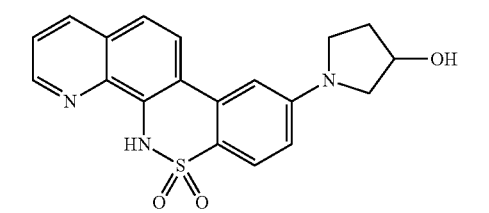
507
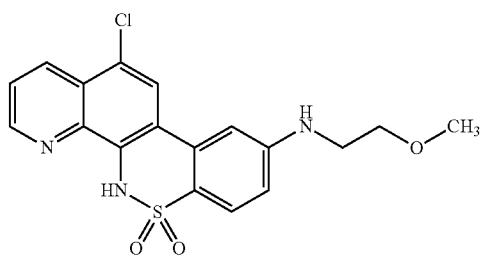
508
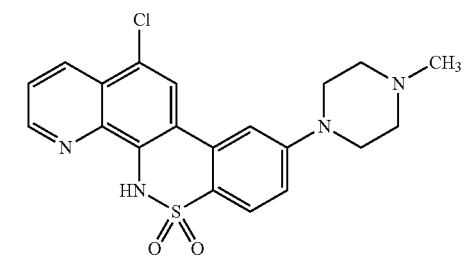
509
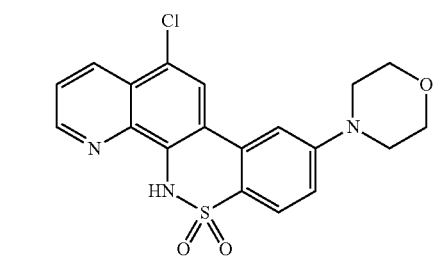
510
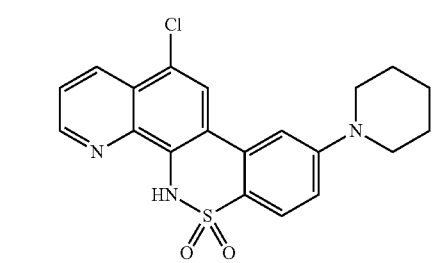
511
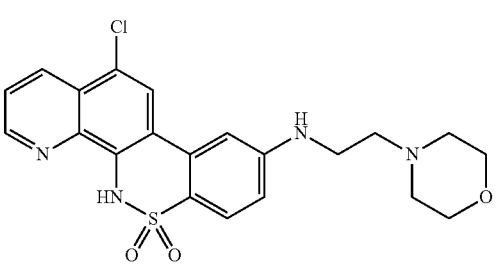
512
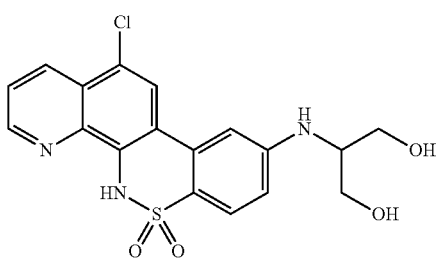
514
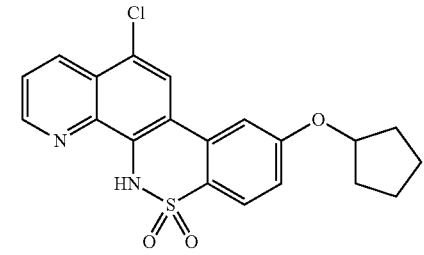
515
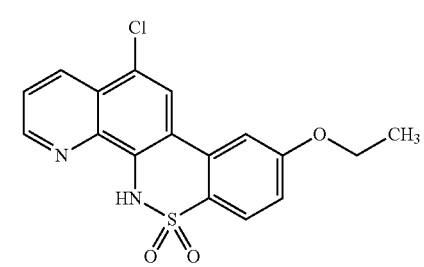
516
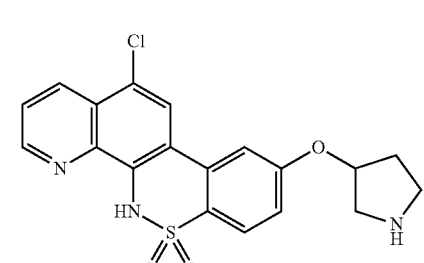
517
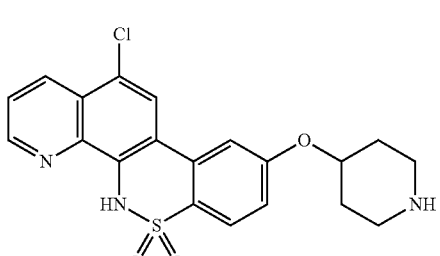
518
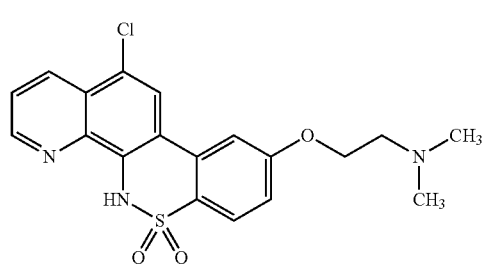

375
-continued
519
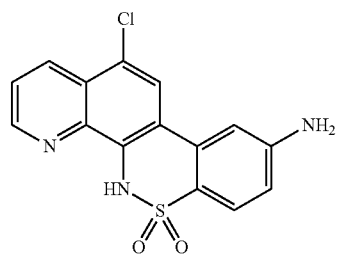
520
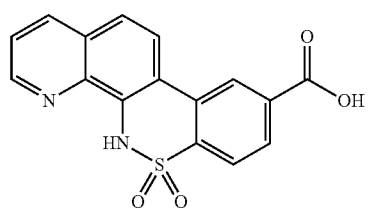
521
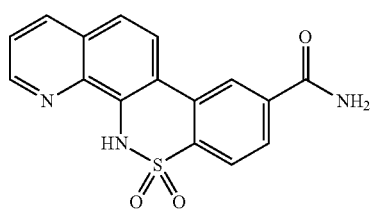
522
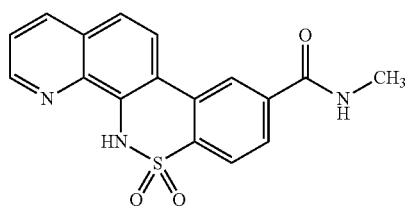
525
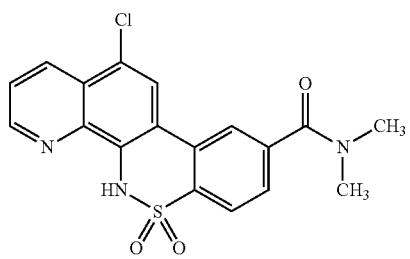
526
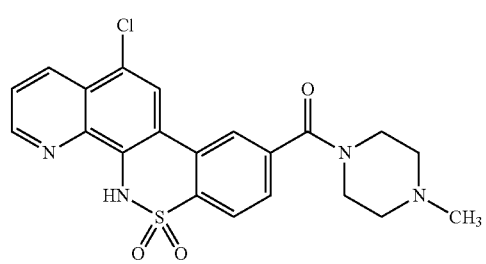
376
-continued
527
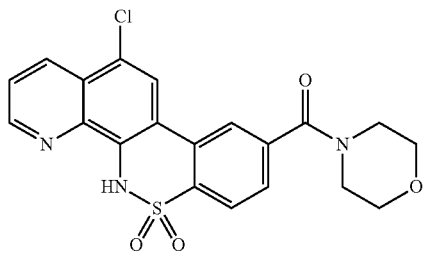
528
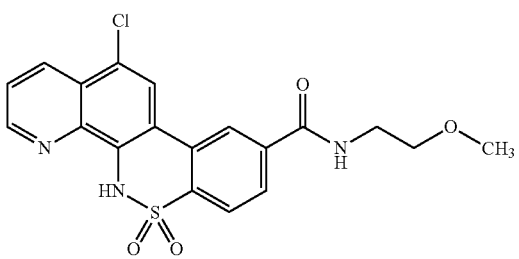
529
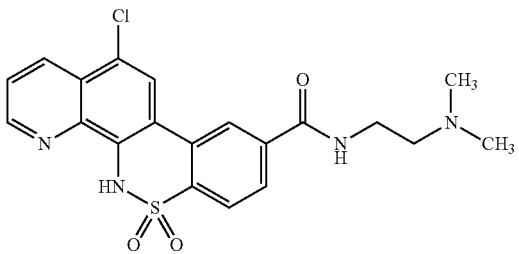
530
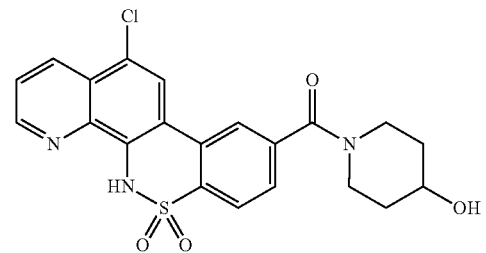
531
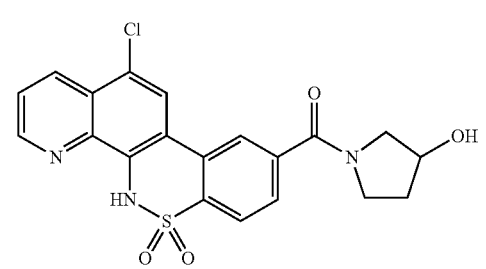

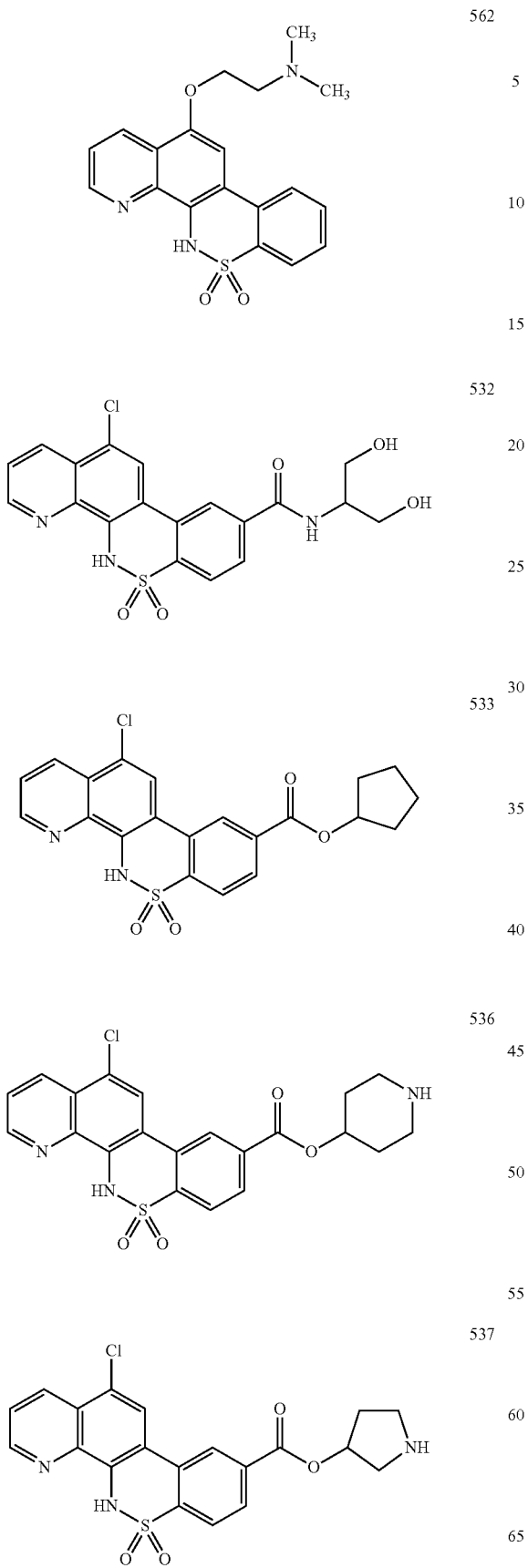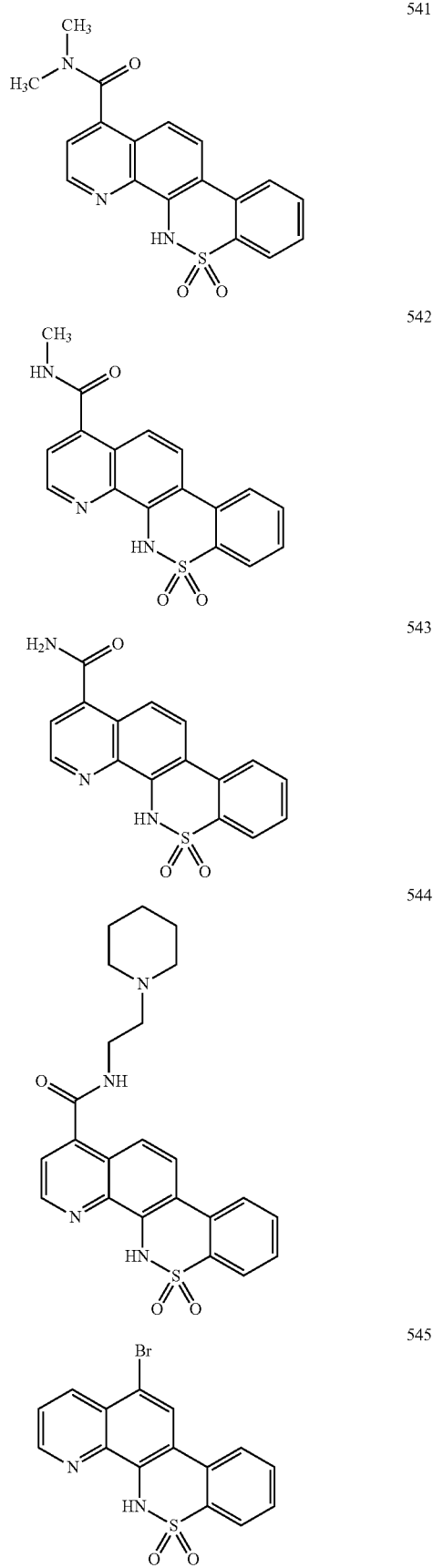

| 546 | 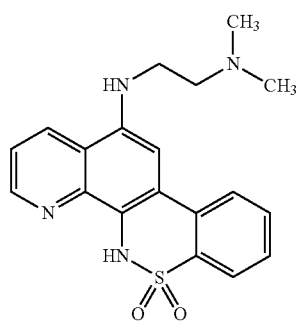 |
| 547 | 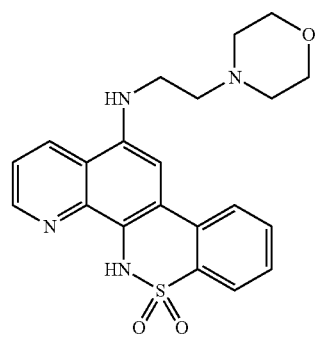 |
| 548 | 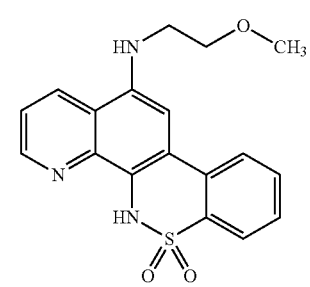 |
| 549 | 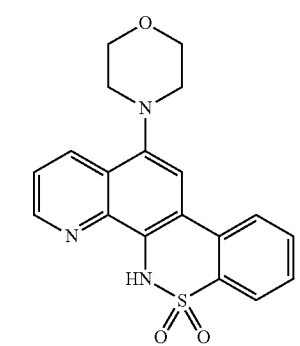 |
| 550 | 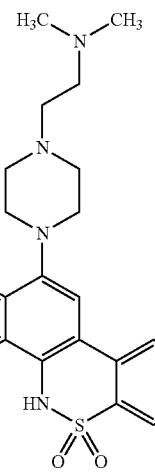 |
| 551 | 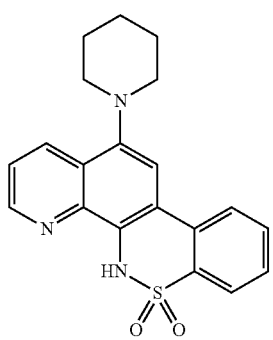 |
| 552 | 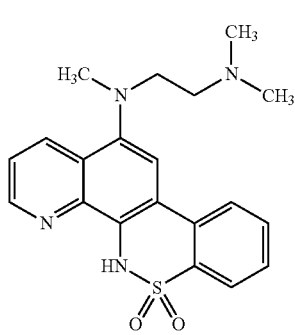 |
| 553 | 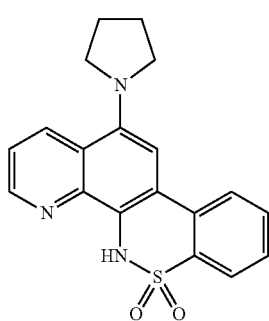 |

554

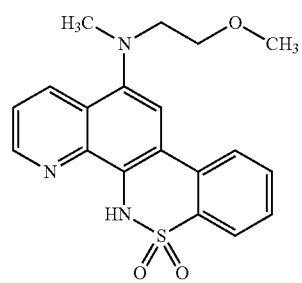

555

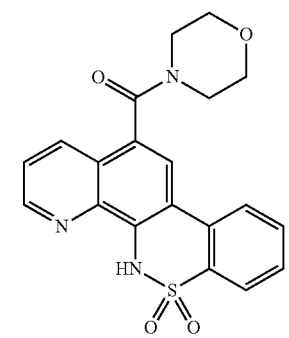

556

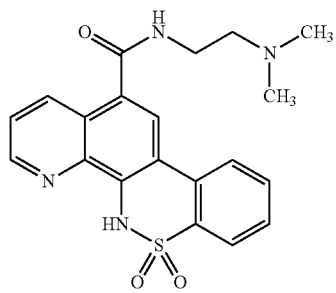

557

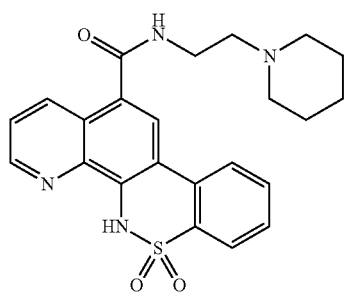

560

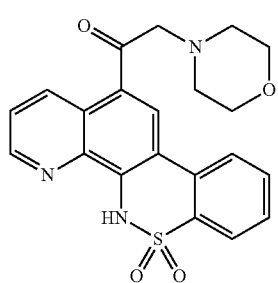

561

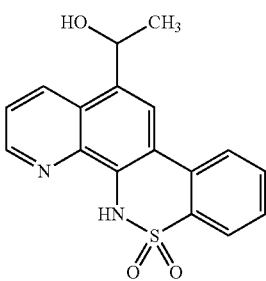

572

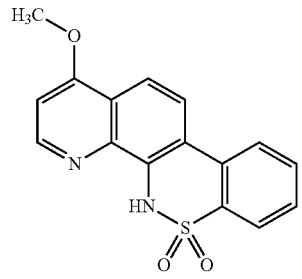

589

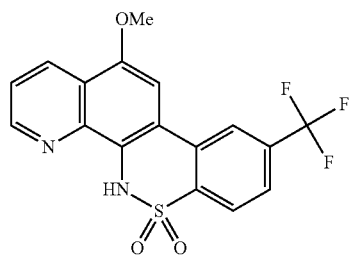

or pharmaceutically acceptable salts thereof.

5. The method according to claim 1, wherein the iron deficiency diseases and/or iron deficiency anemias are selected from the group consisting of anemias in the case of cancer, anemia triggered by chemotherapy, anemia triggered by inflammation, anemias in the case of congestive cardiac insufficiency, anemia in the case of congestive heart failure, anemia in the case of chronic renal insufficiency stage 3-5, anemia in the case of chronic kidney diseases stage 3-5, anemia triggered by chronic inflammation, anemia in the case of rheumatoid arthritis, anemia in the case of systemic lupus erythematosus and anemia in the case of inflammatory bowel diseases.

6. The method according to claim 1, wherein the compounds of Formula (Ia) are administered together with one or more selected from the group consisting of pharmaceutical carriers, auxiliary substances and solvents.

7. The method according to claim 6, further comprising administering at least one further pharmaceutically active compound for the treatment of iron deficiency diseases and/or iron deficiency anemias and the symptoms associated therewith.

8. The method according to claim 7, wherein the at least one further pharmaceutically active compound is an iron-containing compound.

9. The method according to claim 1, further comprising administering at least one further pharmaceutically active compound for the treatment of iron deficiency diseases and/or iron deficiency anemias and the symptoms associated therewith.

10. The method according to claim 9, wherein the at least one further pharmaceutically active compound is an iron-containing compound.

11. The method according to claim 2, further comprising administering at least one further pharmaceutically active compound for the treatment of iron deficiency diseases and/or iron deficiency anemias and the symptoms associated therewith.

12. The method according to claim 11, wherein the at least one further pharmaceutically active compound is an iron-containing compound.

13. The method according to claim 3, further comprising administering at least one further pharmaceutically active compound for the treatment of iron deficiency diseases and/or iron deficiency anemias and the symptoms associated therewith.

14. The method according to claim 13, wherein the at least one further pharmaceutically active compound is an iron-containing compound.

15. The method according to claim 4, further comprising administering at least one further pharmaceutically active compound for the treatment of iron deficiency diseases and/or iron deficiency anemias and the symptoms associated therewith.

16. The method according to claim 15, wherein the at least one further pharmaceutically active compound is an iron-containing compound.

* * * * *